US012415836B2

(12) United States Patent
Screaton et al.

(10) Patent No.: US 12,415,836 B2
(45) Date of Patent: Sep. 16, 2025

(54) ANTI-DENGUE VACCINES AND ANTIBODIES

(71) Applicants: OXFORD UNIVERSITY INNOVATION LIMITED, Oxford (GB); UNIVERSITÉ PARIS-SACLAY, Saint Aubin (FR)

(72) Inventors: Gavin Screaton, London (GB); Juthathip Mongkolsapaya, London (GB); Alexander Rouvinski, Paris (FR); Pablo Guardado-Calvo, Paris (FR); Giovanna Barba-Spaeth, Paris (FR); Stéphane Duquerroy, Paris (FR); Marie-Christine Vaney, Paris (FR); Felix Augusto Rey, Paris (FR)

(73) Assignees: OXFORD UNIVERSITY INNOVATION LIMITED, Oxford (GB); Universite Paris-Saclay, Saint Aubin (FR)

( * ) Notice: Subject to any disclaimer, the term of this patent is extended or adjusted under 35 U.S.C. 154(b) by 0 days.

(21) Appl. No.: 17/510,930

(22) Filed: Oct. 26, 2021

(65) Prior Publication Data

US 2022/0127307 A1 Apr. 28, 2022

Related U.S. Application Data

(62) Division of application No. 15/328,441, filed as application No. PCT/GB2015/052139 on Jul. 23, 2015, now Pat. No. 11,198,706.

(30) Foreign Application Priority Data

Jul. 23, 2014 (GB) ..................................... 1413086

(51) Int. Cl.

| | |
|---|---|
| ***C07K 14/005*** | (2006.01) |
| ***A61K 39/12*** | (2006.01) |
| ***A61K 47/68*** | (2017.01) |
| ***C07K 14/18*** | (2006.01) |
| ***C07K 16/10*** | (2006.01) |
| *A61K 39/00* | (2006.01) |

(52) U.S. Cl.

CPC ............ *C07K 14/005* (2013.01); *A61K 39/12* (2013.01); *A61K 47/6841* (2017.08); *C07K 14/1825* (2013.01); *C07K 16/1081* (2013.01); *A61K 2039/5258* (2013.01); *A61K 2039/545* (2013.01); *C07K 2317/21* (2013.01); *C07K 2317/33* (2013.01); *C07K 2317/34* (2013.01); *C07K 2317/56* (2013.01); *C07K 2317/76* (2013.01); *C12N 2770/24122* (2013.01); *C12N 2770/24134* (2013.01); *Y02A 50/30* (2018.01)

(58) Field of Classification Search

None

See application file for complete search history.

(56) References Cited

U.S. PATENT DOCUMENTS

| | | | | |
|---|---|---|---|---|
| 2003/0175304 | A1* | 9/2003 | Peters | A61P 31/14 435/235.1 |
| 2009/0311225 | A1 | 12/2009 | Koduri | |
| 2013/0316944 | A1 | 11/2013 | Volkman | |

FOREIGN PATENT DOCUMENTS

| | | |
|---|---|---|
| WO | 99/006068 | 2/1999 |
| WO | 2002/077199 | 10/2002 |
| WO | 2005/003316 | 1/2005 |
| WO | 2006/033679 | 3/2006 |
| WO | 2005/056600 | 5/2006 |
| WO | 2009/098450 | 8/2009 |

(Continued)

OTHER PUBLICATIONS

Allison, et al., "Oligomeric rearrangement of tick-borne encephalitis virus envelope proteins induced by an acidic pH", *J Virol.*, 69:695-700 (1995).

Allison, et al., "Mutational Evidence for an Internal Fusion Peptide in Flavivirus Envelope Protein E", *J. of Virology*, 4268-4275 (2001).

Balakrishnan, et al., "Dengue virus activates polyreactive, natural IgG B cells after primary and secondary infection", *PLoS One*, 6: e29430 (2011).

Beltramello, et al., "The human immune response to Dengue virus is dominated by highly cross-reactive antibodies endowed with neutralizing and enhancing activity", *Cell Host Microbe*, 8:271-83(2010).

(Continued)

*Primary Examiner* — Benjamin P Blumel
(74) *Attorney, Agent, or Firm* — Pabst Patent Group LLP

(57) ABSTRACT

A Dengue virus Envelope Dimer Epitope (EDE) wherein the EDE: c) spans the polypeptides of a Dengue virus Envelope polypeptide dimer; and/or d) is presented on a dimer of Envelope proteins; and/or c) is formed from consecutive or nonconsecutive residues of the envelope polypeptide dimer, wherein the dimer is a homodimer or heterodimer of native and/or mutant envelope polypeptides, from any one or two of DENV-1, DENV-2, DENV-3 and DENV-4. The EDE may be a stabilized recombinant dengue virus envelope glycoprotein E ectodomain (sE) dimer, wherein the dimer is: covalently stabilized with at least one disulphide inter-chain bond between the two sE monomers, and/or covalently stabilized with at least one sulfhydryl-reactive crosslinker between the two sE monomers, and/or covalently stabilized by linking the two sE monomers through modified sugars; and/or, covalently stabilised by being formed as a single polypeptide chain, optionally with a linker region, optionally a Glycine Serine rich linker region, separating the sE sequences, and/or non-covalently stabilized by substituting at least one amino acid residue in the amino acid sequence of at least one sE monomer with at least one bulky side chain amino acid, at the dimer interface or in domain 1 (D1)/domain 3 (D3) linker of each monomer. A compound, for example an antibody or antibody fragment that can neutralise more than one Dengue virus serotype, for example an antibody that can bind to an EDE of the invention.

12 Claims, 122 Drawing Sheets

Figure 1A:
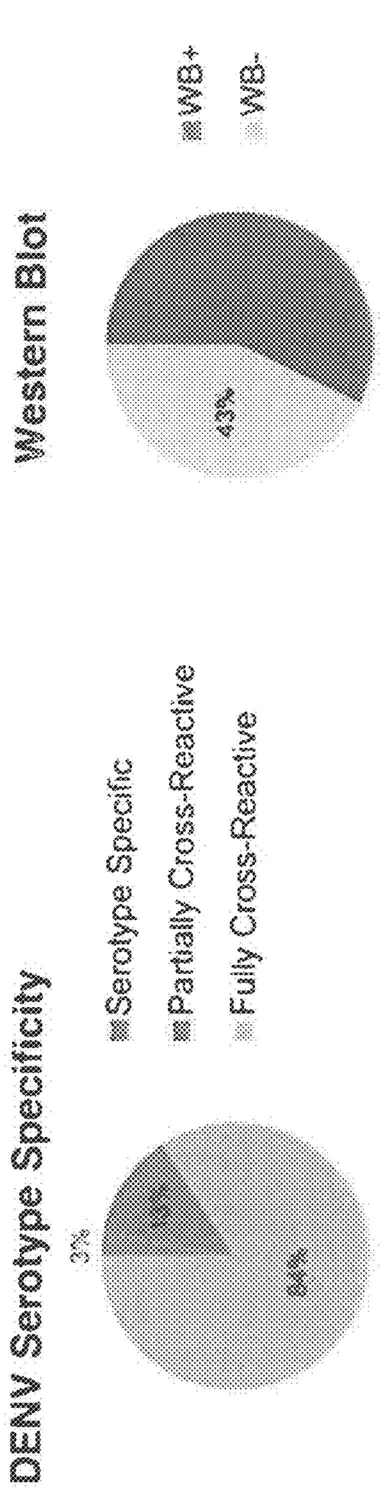

Specification includes a Sequence Listing.

(56) References Cited

FOREIGN PATENT DOCUMENTS

| | | |
|---|---|---|
| WO | 2011/050168 | 6/2011 |
| WO | 2012/154202 | 11/2012 |
| WO | 2013/151764 | 10/2013 |
| WO | 2014/074535 | 5/2014 |

OTHER PUBLICATIONS

Bommakanti, et al., "Design of an HA2-based *Escherichia coli* expressed influenza immunogen that protects mice from pathogenic challenge", *PNAS*, 107:13701-6 (2010).
Bowie, et al., "Deciphering the Message in Protein Sequences: Tolerance to Amino Acid Substitutions", *Science*, 247:1306-1310 (1990).
Bressanelli, et al., "Structure of a flavivirus envelope glycoprotein in its low-pH-induced membrane fusion conformation", *EMBO J*, 23:728-38 (2004).
Burton, "Scaffolding to build a rational vaccine design strategy", *PNAS*, 107:17859-60 (2010).
Cherrier, et al., "Structural basis for the preferential recognition of immature flaviviruses by a fusion-loop antibody", *EMBO J.*, 28:3269-76 (2009).
Cockburn, et al., "Mechanism of dengue virus broad cross-neutralization by a monoclonal antibody", *Structure*, 20:303-14 (2012).
Cockburn, et al., "Structural insights into the neutralization mechanism of a higher primate antibody against dengue virus", *Embo J.*, 31:767-79 (2012b).
Coller and Clements, "Dengue vaccines: progress and challenges", *Current Opinion Immunology*, 23:391-8 (2011).
Costin, et al., "Mechanistic Study of Broadly Neutralizing Human Monoclonal Antibodies against Dengue Virus That Target the Fusion Loop", *J Virol.*, 87:52-66 (2013).
De Alwis, et al., "Identification of human neutralizing antibodies that bind to complex epitopes on dengue virions", *PNAS*, 109:7439-44 (2012).
Dejnirattisai, et al., "A complex interplay among virus, dendritic cells, T cells, and cytokines in dengue virus infections", *J. Immunol.*, 181:5865-74 (2008).
Dejnirattisai, et al., "Corrigendum: A new class of highly potent, broadly neutralizing antibodies isolated from viremic patients infected with dengue virus", *Nature Immunol*, 16:170-7 (2015).
Dejnirattisai, et al., "Enhancing cross-reactive anti-prM dominates the human antibody response in dengue infection", *Science*, 328(5979):745-8 (2010).
Ekiert, et al., "A highly conserved neutralizing epitope on group 2 influenza A viruses", *Science*, 333:843-50 (2011).
Fibriansah, et al., "Structural Changes in Dengue Virus When Exposed to a Temperature of 37C", *J. Virol.*, 87:7585-92 (2012).
Goncalvez, et al., "Epitope determinants of a chimpanzee Fab antibody that efficiently cross-neutralizes dengue type 1 and type 2 viruses map to inside and in close proximity to fusion loop of the dengue type 2 virus envelope glycoprotein", *J Virol.*, 78:12919-28 (2004).
Gromowski, et al., "Characterisation of Dengue virus complex-specific neutralizing epitopes on envelope protein domain III of dengue 2 virus", *J Virol*, 82:8828-37 (2008).
Halstead, "Neutralization and antibody-dependent enhancement of dengue viruses", *Advances in virus research*, 60:421-67 (2003).
Junjhon, et al., "Influence of pr-M cleavage on the heterogeneity of extracellular dengue virus particles", *J. Virol.*, 84:8353-8 (2010).
Kabsch, "XDS", *Acta Crystallogr. D Biol Crystallogr.*, 66:125-132 (2010).
Kaufmann, et al., "Neutralization of West Nile virus by cross-linking of its surface proteins with Fab fragments of the human monoclonal antibody CR4354", *PNAS*, 107:18950-5 (2010).
Kuhn, et al., "Structure of dengue virus: implications for flavivirus organization, maturation, and fusion", *Cell*, 108:717-25 (2002).
Lai, et al., "Antibodies to envelope glycoprotein of dengue virus during the natural course of infection are predominantly cross-reactive and recognize epitopes containing highly conserved residues at the fusion loop of domain II", *J Virol.*, 82:6631-43 (2008).
Lee, et al., "New vaccines against influenza virus", *Clin. Exper. Vac Res.*, 3:12-28 (2014).
Li, et al., "Click Chemistry in Peptide-Based Drug Design", *Molecules*, 18:9797-9817 (2013).
Li, et al., "The flavivirus precursor membrane-envelope protein complex: structure and maturation", *Science*, 319:1830-4 (2008).
Lin, et al., "Analysis of epitopes on dengue virus envelope protein recognized by monoclonal antibodies and polyclonal human sera by a high throughput assay", *PLoS NTD*, 6: e1447 (2012).
Lok, et al., "Binding of a neutralizing antibody to dengue virus alters the arrangement of surface glycoproteins", *Nat Struct Mol Biol.*, 15:312-7 (2008).
Mantel, et al., "Genetic stability of a dengue vaccine based on chimeric yellow fever/dengue viruses", *Vaccine*, 29:6629-35 (2011).
Matsui, et al., "Characterization of dengue complex-reactive epitopes on dengue 3 virus envelope protein domain III", *Virology*, 384(1):16-20 (2009).
McLellan, et al., "Structure of RSV fusion glycoprotein trimer bound to a prefusion-specific neutralizing antibody", *Science*, 340:1113-7 (2013a).
Modis, et al., "Structure of the dengue virus envelope protein after membrane fusion", *Nature*, 427:313-9 (2004).
Mongkolsapaya, et al., "Original antigenic sin and apoptosis in the pathogenesis of dengue hemorrhagic fever", *Nat Med.*, 9:921-7 (2003).
Mukhopadhyay, et al., "A structural perspective of the flavivirus life cycle", *Nat Rev Micro Biol.*, 3:13-22 (2005).
Murphy and Whitehead, "Immune response to dengue virus and prospects for a vaccine", *Ann Rev Immunol.*, 29:587-619 (2011).
Nelson, et al., "Maturation of West Nile virus modulates sensitivity to antibody-mediated neutralization", *PLoS Pathog.*, 4: e1000060 (2008).
Ofek, et al., "Elicitation of structure-specific antibodies by epitope scaffolds", *PNAS*, 107: 17880-7 (2010).
Oliphant, et al., "Antibody recognition and neutralization determinants on domains I and II of West Nile Virus envelope protein", *J Virol.*, 80:12149-59 (2006).
Osorio, et al., "Development of DENVax: A chimeric dengue-2 PDK-53-based tetravalent vaccine for protection against dengue fever", *Vaccine*, 29:7251-60 (2011).
Plevka, et al., "Maturation of flaviviruses starts from one or more icosahedrally independent nucleation centres", *EMBO Reports*, 12:602-6 (2011).
Pokidysheva, et al., "Cryo-EM reconstruction of dengue virus in complex with the carbohydrate recognition domain of DC-SIGN", *Cell*, 124:485-93 (2006).
Punna, et al., "Head-to-Tail Peptide Cyclodimerization by Copper-Catalyzed zide-Alkyne Cycloaddition", *Angew. Chem. Int. Ed.*, 44:2215-2220 (2005).
Reeck, et al., ""Homology" in Proteins and Nucleic Acids: A Terminology Muddle and a Way out of It", *Cell*, 50: 667 (1987).
Rey, "Two hosts, two structures", *Nature*, 375:291-8 (1995).
Rey, et al., "The envelope glycoprotein from tick-borne encephalitis virus at 2 A resolution", *Nature*, 497:443-4 (2013).
Rodenhuis-Zybert, et al., "A fusion-loop antibody enhances the infectious properties of immature flavivirus particles", *J. Virol.*, 85:11800-8 (2011).
Rodenhuis-Zybert, et al., "Immature dengue virus: a veiled pathogen", *PLoS Pathog*, 6: e1000718 (2010).
Rouvinski, et al., "Recognition determinants of broadly neutralizing human antibodies against dengue viruses", *Nature*, 520:109-13 (2015).
Sabchareon, et al., "Protective efficacy of the recombinant, live-attenuated, CYD tetravalent dengue vaccine in Thai schoolchildren: a randomised, controlled phase 2b trial", *Lancet*, 380:1559-67 (2012).

(56) References Cited

OTHER PUBLICATIONS

Sasaki, et al., "Dengue virus neutralization and antibody-dependent enhancement activities of human monoclonal antibodies derived from dengue patients at acute phase of secondary infection", *Antiviral Res.*, 98(3):423-31 (2013).
Simmons, et al. "Dengue", *N Engl J Med.*, 366:1423-32 (2012).
Sittisombut, et al., "Lack of augmenting effect of interferon-gamma on dengue virus multiplication in human peripheral blood monocytes", *J Med Virol.*, 45:43-9 (1995).
Smith, et al., "The potent and broadly neutralizing human dengue virus-specific monoclonal antibody 1C19 reveals a unique cross-reactive epitope on the bc loop of domain II of the envelope protein", *mBio*, 4:e00873-13 (2013).
Sukupolvi-Petty, et al., "Structure and function analysis of therapeutic monoclonal antibodies against dengue virus type 2", *J Virol.*, 84:9227-39 (2010).
Teoh, et al., "The structural basis for serotype-specific neutralization of Dengue virus by a human antibody", *Sci Transl Med.*, 139:189-97 (2012).
Thirumurugan, et al., "Click Chemistry for Drug Development and Diverse Chemical-Biology Applications", *Chemical Reviews*, A-BW (2013).
Tsai, et al., "High-avidity and potently neutralizing cross-reactive human monoclonal antibodies derived from secondary dengue virus infection", *J. Virol.*, 87:12562-75 (2013).
Wengler, et al., "The isolation of the ectodomain of the alphavirus E1 protein as a soluble hemagglutinin and its crystallization", *Virology*, 257:472-82 (1999).
Whittle, et al., "Broadly neutralizing human antibody that recognizes the receptor-binding pocket of influenza virus hemagglutinin", *PNAS*, 108:14216-21 (2011).
Wrammert, et al., "Rapid and massive virus-specific plasma blast responses during acute dengue virus infection in humans", *Virol.*, 86:2911-8 (2012).
Wu and Kabat, "An analysis of the sequences of the variable regions of Bence Jones proteins and myeloma light chains and their implications for anti-body complementarity", *J Exper. Med.*, 132: 211-50 (1970).
Wu, et al., "Human skin Langerhans cells are targets of dengue virus infection", *Nat Med.*, 6: 816-20 (2000).
Yu, et al., "Structure of the immature dengue virus at low pH primes proteolytic maturation", *Science*, 319:1834-7 (2008).
Zhang, et al., "Conformational changes of the flavivirus E glycoprotein", *Structure*, 12:1607-18 (2004).
Zhang, et al., "Cryo-EM structure of the mature dengue virus at 3.5-A resolution", *Nat Struct Mol Biol.*, 20: 105-10 (2013b).
Zhang, et al., "Dengue structure differs at the temperatures of its human and mosquito hosts", *PNAS*, 110:6795-9 (2013a).
Zhou, et al., "Structural basis for broad and potent neutralization of HIV-1 by antibody VRC01", *Science*, 329:811-7 (2010).
Zhou, et al., "Structural definition of a conserved neutralization epitope on HIV1 gp120", *Nature*, 44:732-7 (2007).
Zidane, et al., "Cross-reactivities between human IgMs and the four serotypes of dengue virus as probed with artificial homodimers of domain-III from the envelope proteins", *BMC Infect. Dis.*, 13: 302 (2013).
Allison, et al., "Mutational Evidence for an Internal Fusion Peptide in Flavivirus Envelope Proetin E", J. of Virology, 4268-4275 (2001).
Zhang et al., "Molecular manipulation associated with disulphide bond formation to enhance the stability of recombinant therapeutic protein." Protein Expression and Purification, 75:28-39(2011).

* cited by examiner a b

Table 1: Germline analysis of VDE1 and VDE2 BNAs.

| BNA Group | BNA name | V-H allele | V-H divergence (288nt) | V-H aa changes/total | J-H allele | D-H allele | H-CDR length [H1.H2.H3] |
|---|---|---|---|---|---|---|---|
| VDE2 | B7 | IGHV3-74*01 | 6,94% | 9/98 | IGHJ6*02 | IGHD3-22*01 | [8.8.26] |
| VDE2 | A11 | IGHV3-74*01(#) | 8.68% | 14/98 | IGHJ6*02 | IGHD3-22*01 | [8.8.26] |
| VDE1 | C8 | IGHV3-64D*06 | 6.94% | 12/97 | IGHJ6*02 | IGHD2-21*01 | [8.8.15] |
| VDE1 | C10 | IGHV1-3*01 | 2.78% | 4/98 | IGHJ4*02 | IGHD4-17*01(&) | [8.8.21] |

| V-L allele | V-L divergence (288nt) | V-L aa changes/total | J-L allele | L-CDR length [L1.L2.L3] |
|---|---|---|---|---|
| IGLV2-23*01(#) | 4.51% | 10/98 | IGLJ3*02(#) | [9.3.10] |
| IGLV2-23*01(#) | 6.94% | 14/98 | IGLJ3*02(#) | [9.3.10] |
| IGKV3-11*01 | 5.02%($) | 9/95 | IGKJ2*01 | [6.3.10] |
| IGLV2-14*01 | 3.82% | 10/98 | IGLJ3*02 | [9.3.10] |

V-H, J-H, D-H, V-L, J-L represent the putative genes and alleles corresponding to the given Ab, predicted by IMGT analysis (see methods). 'Homsap' precedes gene/allele names.
(#) Additional possibilities were also predicted by IMGT; (&)ORF2; ($)279nt.
CDR lengths are indicated in square brackets for HCDRs and LCDRs : [CDR1.CDR2.CDR3].

Figure 7

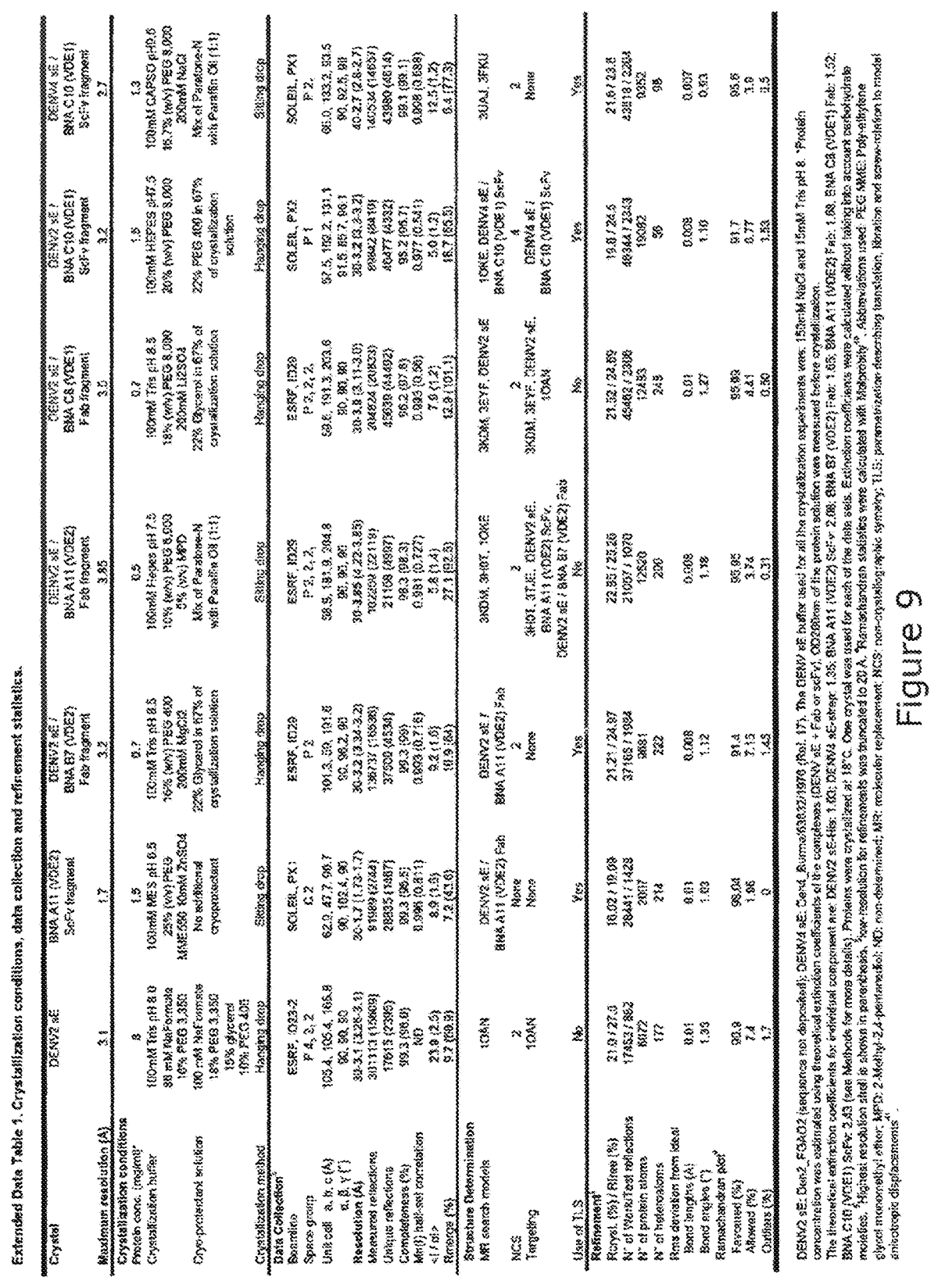

Extended Data Table 1. Crystallization conditions, data collection and refinement statistics.

| Crystal | DENV2 sE | BNA A11 (VDE2) ScFv fragment | DENV2 sE / BNA B7 (VDE2) Fab fragment | DENV2 sE / BNA A11 (VDE2) Fab fragment | DENV2 sE / BNA C8 (VDE1) Fab fragment | DENV2 sE / BNA C10 (VDE1) ScFv fragment | DENV4 sE / BNA C10 (VDE1) ScFv fragment |
|---|---|---|---|---|---|---|---|
| **Maximum resolution (Å)** | 3.1 | 1.7 | 3.2 | 3.85 | 3.5 | 3.2 | 2.7 |
| **Crystallization conditions** | | | | | | | |
| Protein conc. (mg/ml)* | 8 | 1.5 | 0.7 | 0.5 | 0.7 | 1.5 | 1.3 |
| Crystallization buffer | 100mM Tris pH 8.0 88 mM NaFormate 16% PEG 3,350 | 100mM MES pH 6.5 25% (v/v) PEG MME550 10mM ZnSO4 | 100mM Tris pH 8.5 16% (w/v) PEG 400 300mM MgCl2 | 100mM Hepes pH 7.5 10% (w/v) PEG 8,000 5% (v/v) MPD | 100mM Tris pH 8.5 18% (w/v) PEG 8,000 200mM Li2SO4 | 100mM HEPES pH7.5 20% (w/v) PEG 8,000 | 100mM CAPSO pH9.6 15.7% (w/v) PEG 8,000 200mM NaCl |
| Cryo-protectant solution | 100 mM NaFormate 18% PEG 3,350 15% glycerol 10% PEG 400 | No additional cryoprotectant | 22% Glycerol in 67% of crystallization solution | Mix of Paratone-N with Paraffin Oil (1:1) | 22% Glycerol in 67% of crystallization solution | 22% PEG 400 in 67% of crystallization solution | Mix of Paratone-N with Paraffin Oil (1:1) |
| Crystallization method | Hanging drop | Sitting drop | Hanging drop | Sitting drop | Hanging drop | Hanging drop | Sitting drop |
| **Data Collection**§ | | | | | | | |
| Beamline | ESRF, ID23-2 | SOLEIL, PX1 | ESRF, ID29 | ESRF, ID29 | ESRF, ID29 | SOLEIL, PX2 | SOLEIL, PX1 |
| Space group | F 4₁ 3 2 | C 2 | P 2 | P 2₁ 2₁ 2₁ | P 2₁ 2₁ 2₁ | P 1 | P 2₁ |
| Unit cell a, b, c (Å) | 105.4, 105.4, 165.8 | 62.9, 47.7, 96.7 | 101.3, 59, 191.8 | 58.5, 181.9, 204.8 | 58.6, 191.3, 203.6 | 97.5, 100.2, 131.1 | 65.0, 133.2, 93.5 |
| α, β, γ (°) | 90, 90, 90 | 90, 102.4, 90 | 90, 98.2, 90 | 90, 90, 90 | 90, 90, 90 | 91.5, 85.7, 96.1 | 90, 92.5, 90 |
| **Resolution (Å)** | 30-3.1 (3.28-3.1) | 30-1.7 (1.73-1.7) | 30-3.2 (3.34-3.2) | 30-3.85 (4.22-3.85) | 30-3.8 (3.11-3.0) | 30-3.2 (3.2-3.2) | 40-2.7 (2.8-2.7) |
| Measured reflections | 301113 (15609) | 91989 (2744) | 136737 (16538) | 102209 (22118) | 304824 (20823) | 89842 (8419) | 140534 (14657) |
| Unique reflections | 17615 (2395) | 28835 (1487) | 37500 (4534) | 21108 (4997) | 45639 (4492) | 46477 (4332) | 43980 (4814) |
| Completeness (%) | 99.3 (98.8) | 99.3 (95.5) | 99.3 (99) | 98.3 (98.3) | 96.2 (97.8) | 95.2 (95.7) | 99.1 (99.1) |
| Mn(I) half-set correlation | ND | 0.996 (0.811) | 0.993 (0.716) | 0.981 (0.727) | 0.993 (0.56) | 0.977 (0.541) | 0.998 (0.688) |
| <I / σI> | 23.8 (2.5) | 8.9 (1.5) | 9.2 (1.6) | 5.8 (1.4) | 7.9 (1.2) | 5.0 (1.2) | 12.5 (1.2) |
| Rmerge (%) | 9.7 (69.9) | 7.2 (43.6) | 10.9 (64) | 27.1 (92.5) | 12.8 (101.1) | 16.7 (65.5) | 6.4 (77.3) |
| **Structure Determination** | | | | | | | |
| MR search models | 1OAN | DENV2 sE / BNA A11 (VDE2) Fab | DENV2 sE / BNA A11 (VDE2) Fab | 3NDM, 3H0T, 1OKE | 3KDM, 3EYF, DENV2 sE | 1OKE, DENV4 sE / BNA C10 (VDE1) ScFv | 3UAJ, 3FKU |
| NCS | 2 | None | 2 | 3 | 2 | 4 | 2 |
| Targeting | 1OAN | None | None | 3H0T, 3TJE, DENV2 sE, BNA A11 (VDE2) ScFv, DENV2 sE / BNA B7 (VDE2) Fab | 3KDM, 3EYF, DENV2 sE, 1OAN | DENV4 sE / BNA C10 (VDE1) ScFv | None |
| Use of TLS | No | Yes | Yes | No | No | Yes | Yes |
| **Refinement**† | | | | | | | |
| Rcryst. (%) / Rfree (%) | 21.9 / 27.0 | 16.02 / 19.08 | 21.21 / 24.87 | 22.85 / 25.26 | 21.52 / 24.69 | 19.8 / 24.5 | 21.6 / 23.8 |
| N° of Work/Test reflections | 17453 / 862 | 28441 / 1428 | 37165 / 1984 | 21007 / 1070 | 45482 / 2308 | 48344 / 2343 | 43818 / 2284 |
| N° of protein atoms | 6072 | 2007 | 9681 | 12520 | 12483 | 19082 | 9352 |
| N° of heteroatoms | 177 | 214 | 222 | 200 | 245 | 56 | 98 |
| Rms deviation from ideal | | | | | | | |
| Bond lengths (Å) | 0.01 | 0.01 | 0.008 | 0.008 | 0.01 | 0.008 | 0.007 |
| Bond angles (°) | 1.33 | 1.03 | 1.12 | 1.18 | 1.27 | 1.10 | 0.93 |
| Ramachandran plot¶ | | | | | | | |
| Favoured (%) | 90.8 | 98.04 | 91.4 | 95.95 | 95.89 | 91.7 | 95.6 |
| Allowed (%) | 7.4 | 1.96 | 7.15 | 3.74 | 4.41 | 6.77 | 3.9 |
| Outliers (%) | 1.7 | 0 | 1.45 | 0.31 | 0.50 | 1.53 | 0.5 |

DENV2 sE: Den2_FGA02 (sequence not deposited); DENV4 sE: Den4_Burma/63632/1976 (Ref. 17). The DENV sE buffer used for all the crystallization experiments was: 150mM NaCl and 15mM Tris pH 8. *Protein concentration was estimated using theoretical extinction coefficients of the complexes (DENV sE + Fab or scFv), OD280nm of the protein solution was measured before crystallization.
The theoretical extinction coefficients for individual component are: DENV2 sE-His: 1.60; DENV4 sE-strep: 1.35; BNA A11 (VDE2) ScFv: 2.08; BNA B7 (VDE2) Fab: 1.65; BNA A11 (VDE2) Fab: 1.68, BNA C8 (VDE1) Fab: 1.52; BNA C10 (VDE1) ScFv: 2.43 (see Methods for more details). Proteins were crystallized at 18°C. One crystal was used for each of the data sets. Extinction coefficients were calculated without taking into account carbohydrate moieties. §Highest resolution shell is shown in parenthesis. †low-resolution for refinements was truncated to 20 Å. ¶Ramachandran statistics were calculated with Molprobity[40]. Abbreviations used: PEG MME: Poly-ethylene glycol monomethyl ether; MPD: 2-Methyl-2,4-pentanediol; ND: non-determined; MR: molecular replacement; NCS: non-crystallographic symetry; TLS: parametrization describing translation, libration and screw-rotation to model anisotropic displacements[41].

Figure 9

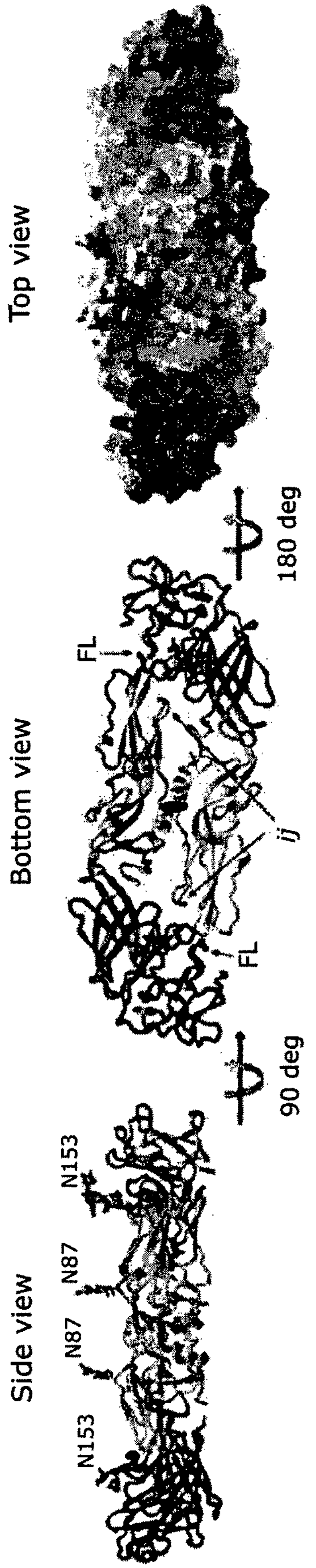
Figure 12a DENV2 sE
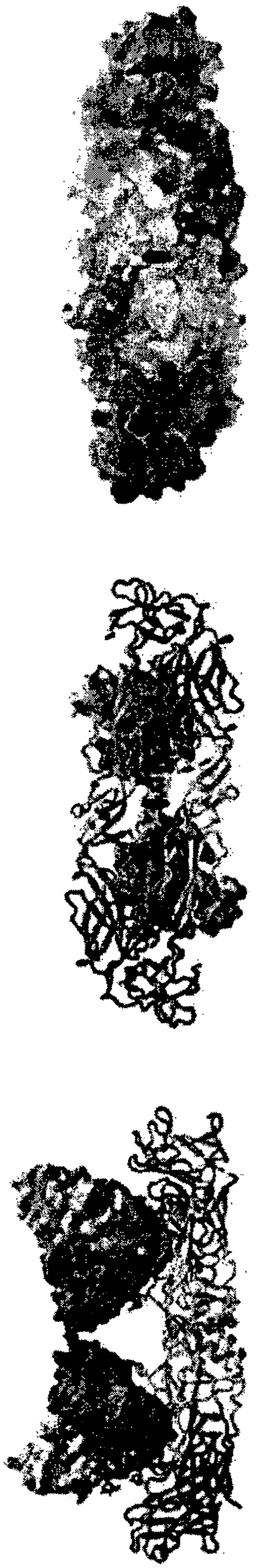
Figure 12b DENV2 sE/87 (VDE2 BNA)

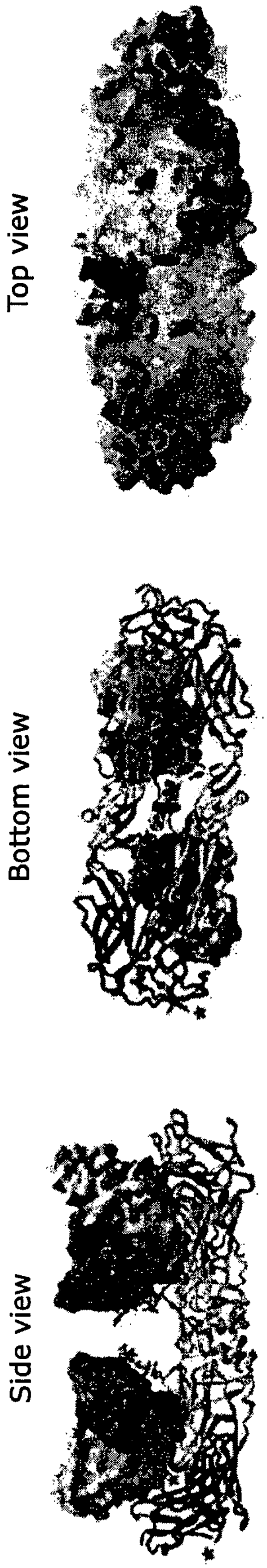
Figure 12c DENV2 sE/C8 (VDE 1 BNA)
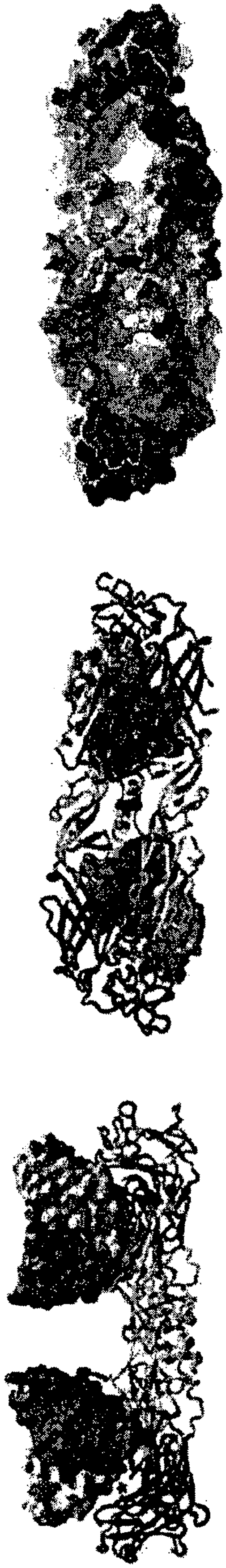
Figure 12d DENV2 sE/C10 (VDE1 BNA)
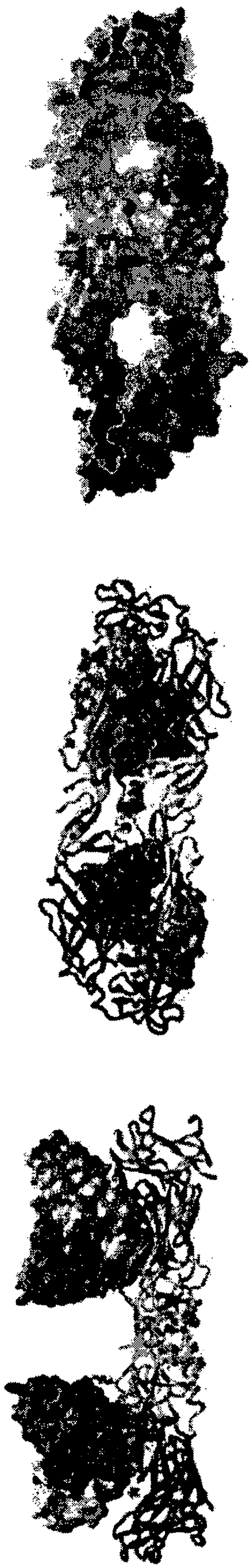
Figure 12e DENV4 sE/C10 (VDE1 BNA)

Extended Data Table 2. Buried surface areas and surface complementarity in the various BNA complexes.

| | BSA BNA | | | BSA sE dimer | | | | | Complex | |
|---|---|---|---|---|---|---|---|---|---|---|
| | VH | VL | Total | Reference subunit (glycans[#]) | Opposite subunit (glycans[#]) | Total ($Å^2$) | Main[+] chain atoms ($Å^2$) | Total glycan BSA ($Å^2$) | BSA / molecule ($Å^2$) | SC |
| **DENV2 sE / VDE2 B7** | | | | | | | | | | |
| Epitope A | 992.1 | 180.8 | 1172.9 | 621.1 (83.6) | 478.4 (358.0) | 1099.5 | 233 (21.2%) | 442 (40%) | 1136.2 | 0.728 |
| Epitope B | 1010.4 | 181.5 | 1191.9 | 501.8 (358.0) | 604.1 (68.2) | 1105.9 | 234 (21.2%) | 426 (39%) | 1148.9 | 0.721 |
| **DENV2 sE / VDE2 A11** | | | | | | | | | | |
| Epitope A | 945.1 | 199.4 | 1144.5 | 544.2 (17.80) | 491.9 (359.1) | 1036.1 | 224 (21.6) | 377 (36%) | 1090.3 | 0.706 |
| Epitope B | 984.8 | 183.2 | 1168.0 | 473.4 (351.4) | 587.5 (64.4) | 1060.9 | 221 (20.8%) | 416 (39%) | 1114.5 | 0.668 |
| **DENV2 sE / VDE1 C8** | | | | | | | | | | |
| Epitope A | 744.2 | 492.3 | 1236.5 | 944.9 (204.9) | 234.6 | 1197.6 | 362 (30.2%) | 234 (19.5%) | 1217.1 | 0.693 |
| Epitope B | 855.7 | 559.2 | 1414.9 | 366.4 | 963.3 (239.2) | 1329.4 | 352 (26.5%) | 239.2 (18%) | 1372.2 | 0.687 |
| **DENV2 sE / VDE1 C10 *** | | | | | | | | | | |
| Epitope A | 706.6 | 623.3 | 1329.9 | 781.3 (84.5) | 366.9 | 1148.2 | 351 (31%) | 84.5 (7.3%) | 1239.1 | 0.681 |
| Epitope B | 706.0 | 644.4 | 1350.4 | 373.2 | 778.3 (94.20) | 1151.5 | 320 (28%) | 94.2 (8.2%) | 1251.0 | 0.681 |
| Epitope C | 823.7 | 562.6 | 1386.3 | 717.8 (90.6) | 465.6 | 1183.4 | 374 (32%) | 90.6 (7.6%) | 1284.9 | 0.742 |
| Epitope D | 718.1 | 635.5 | 1353.6 | 374.9 | 788.7 (99.1) | 1163.6 | 341 (29%) | 99.1 (8.5%) | 1258.6 | 0.668 |
| **DENV4 sE / VDE1 C10** | | | | | | | | | | |
| Epitope A | 765.5 | 565.1 | 1330.6 | 719.5 (81.60) | 461.4 | 1180.9 | 374 (31.7%) | 81.6 (6.9%) | 1255.8 | 0.595 |
| Epitope B | 636.7 | 526.8 | 1163.5 | 395.9 | 666.0 (59.20) | 1061.9 | 324 (30.5%) | 59.2 (5.6%) | 1112.7 | 0.582 |

BSA: Buried Surface Area ($Å^2$) of sE protein by the Fabs or ScFv (calculated with program 'areaimol' in CCP4)
H is for heavy chain; L is for light chain
SC: Surface Complementarity coefficient (calculated with program 'sc' in CCP4)
[#] Glycan chain contribution to BSA in $Å^2$ and (%)
[+] Main chain atoms contribution to BSA in $Å^2$ and (%)
* There are two sE dimer-(C10 ScFv)$_2$ complexes in the asymmetric unit.

Figure 13 scFv C10 epitope A
DEN2_FGA02
Fab C8 epitope A
red
yellow
blue

DENV2 sE / BNA VDE2 A11

DENV2 sE / BNA VDE1 C8

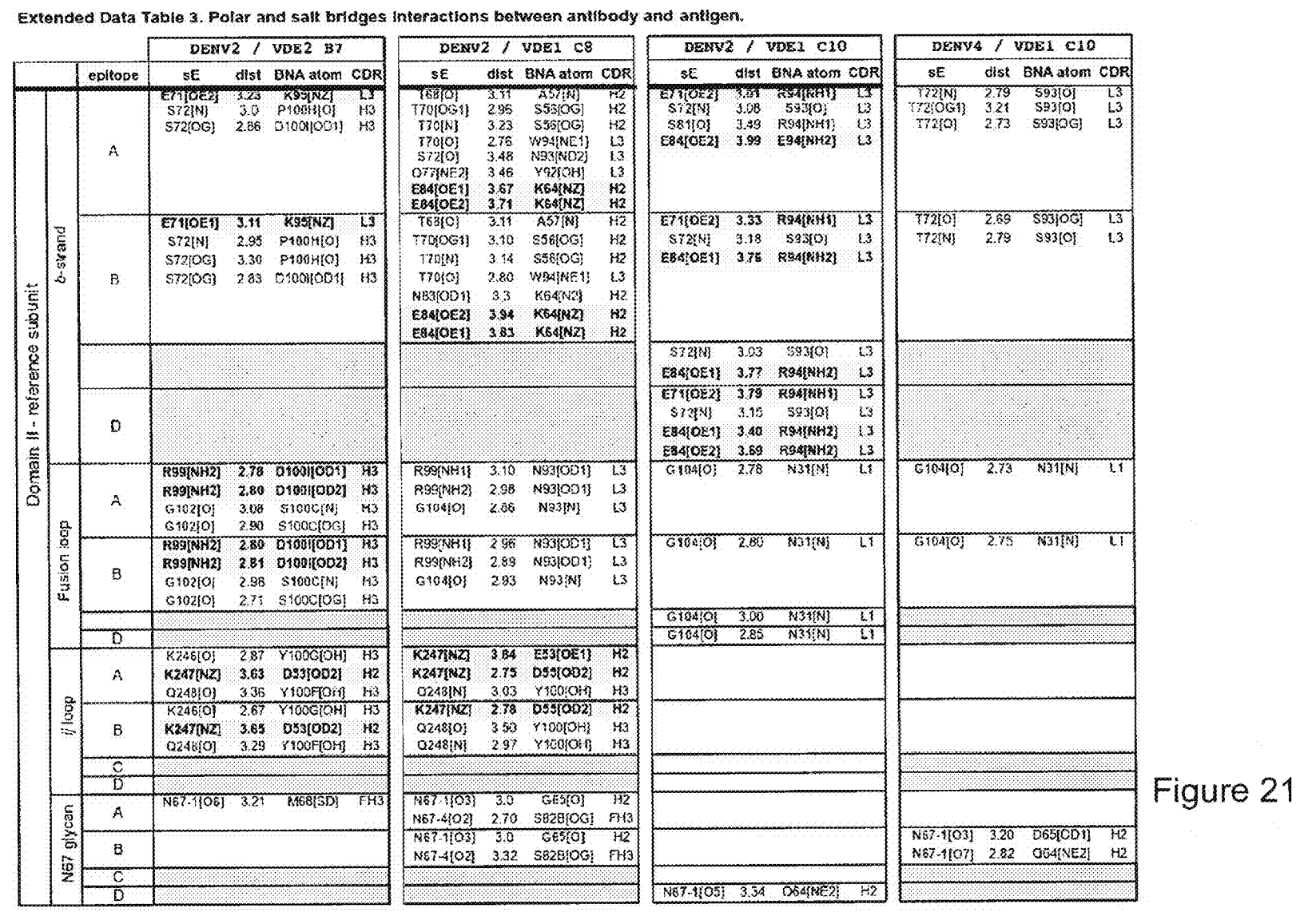

Extended Data Table 3. Polar and salt bridges interactions between antibody and antigen.

| | | | DENV2 / VDE2 B7 | | | | DENV2 / VDE1 C8 | | | | DENV2 / VDE1 C10 | | | | DENV4 / VDE1 C10 | | | |
|---|---|---|---|---|---|---|---|---|---|---|---|---|---|---|---|---|---|---|
| | | epitope | sE | dist | BNA atom | CDR | sE | dist | BNA atom | CDR | sE | dist | BNA atom | CDR | sE | dist | BNA atom | CDR |
| Domain II - reference subunit | b-strand | A | E71[OE2] | 3.23 | K95[NZ] | L3 | T68[O] | 3.11 | A57[N] | H2 | E71[OE2] | 3.81 | R94[NH1] | L3 | T72[N] | 2.79 | S93[O] | L3 |
| | | | S72[N] | 3.0 | P100H[O] | H3 | T70[OG1] | 2.96 | S56[OG] | H2 | S72[N] | 3.08 | S93[O] | L3 | T72[OG1] | 3.21 | S93[O] | L3 |
| | | | S72[OG] | 2.86 | D100I[OD1] | H3 | T70[N] | 3.23 | S56[OG] | H2 | S81[O] | 3.49 | R94[NH1] | L3 | T72[O] | 2.73 | S93[OG] | L3 |
| | | | | | | | T70[O] | 2.76 | W94[NE1] | L3 | **E84[OE2]** | **3.99** | **E94[NH2]** | L3 | | | | |
| | | | | | | | S72[O] | 3.48 | N93[ND2] | L3 | | | | | | | | |
| | | | | | | | Q77[NE2] | 3.46 | Y92[OH] | L3 | | | | | | | | |
| | | | | | | | **E84[OE1]** | **3.67** | **K64[NZ]** | **H2** | | | | | | | | |
| | | | | | | | **E84[OE2]** | **3.71** | **K64[NZ]** | **H2** | | | | | | | | |
| | | B | **E71[OE1]** | **3.11** | **K95[NZ]** | L3 | T68[O] | 3.11 | A57[N] | H2 | **E71[OE2]** | **3.33** | **R94[NH1]** | L3 | T72[O] | 2.69 | S93[OG] | L3 |
| | | | S72[N] | 2.95 | P100H[O] | H3 | T70[OG1] | 3.10 | S56[OG] | H2 | S72[N] | 3.18 | S93[O] | L3 | T72[N] | 2.79 | S93[O] | L3 |
| | | | S72[OG] | 3.30 | P100H[O] | H3 | T70[N] | 3.14 | S56[OG] | H2 | **E84[OE1]** | **3.76** | **R94[NH2]** | L3 | | | | |
| | | | S72[OG] | 2.83 | D100I[OD1] | H3 | T70[O] | 2.80 | W94[NE1] | L3 | | | | | | | | |
| | | | | | | | N83[OD1] | 3.3 | K64[NZ] | H2 | | | | | | | | |
| | | | | | | | **E84[OE2]** | **3.94** | **K64[NZ]** | **H2** | | | | | | | | |
| | | | | | | | **E84[OE1]** | **3.83** | **K64[NZ]** | **H2** | | | | | | | | |
| | | | | | | | | | | | S72[N] | 3.03 | S93[O] | L3 | | | | |
| | | | | | | | | | | | **E84[OE1]** | **3.77** | **R94[NH2]** | L3 | | | | |
| | | D | | | | | | | | | **E71[OE2]** | **3.79** | **R94[NH1]** | L3 | | | | |
| | | | | | | | | | | | S72[N] | 3.15 | S93[O] | L3 | | | | |
| | | | | | | | | | | | **E84[OE1]** | **3.40** | **R94[NH2]** | L3 | | | | |
| | | | | | | | | | | | **E84[OE2]** | **3.69** | **R94[NH2]** | L3 | | | | |
| | Fusion loop | A | **R99[NH2]** | **2.78** | **D100I[OD1]** | **H3** | R99[NH1] | 3.10 | N93[OD1] | L3 | G104[O] | 2.78 | N31[N] | L1 | G104[O] | 2.73 | N31[N] | L1 |
| | | | **R99[NH2]** | **2.80** | **D100I[OD2]** | **H3** | R99[NH2] | 2.98 | N93[OD1] | L3 | | | | | | | | |
| | | | G102[O] | 3.08 | S100C[N] | H3 | G104[O] | 2.66 | N93[N] | L3 | | | | | | | | |
| | | | G102[O] | 2.90 | S100C[OG] | H3 | | | | | | | | | | | | |
| | | B | **R99[NH2]** | **2.80** | **D100I[OD1]** | **H3** | R99[NH1] | 2.96 | N93[OD1] | L3 | G104[O] | 2.80 | N31[N] | L1 | G104[O] | 2.75 | N31[N] | L1 |
| | | | **R99[NH2]** | **2.81** | **D100I[OD2]** | **H3** | R99[NH2] | 2.89 | N93[OD1] | L3 | | | | | | | | |
| | | | G102[O] | 2.98 | S100C[N] | H3 | G104[O] | 2.93 | N93[N] | L3 | | | | | | | | |
| | | | G102[O] | 2.71 | S100C[OG] | H3 | | | | | | | | | | | | |
| | | | | | | | | | | | G104[O] | 3.00 | N31[N] | L1 | | | | |
| | | D | | | | | | | | | G104[O] | 2.85 | N31[N] | L1 | | | | |
| | ij loop | A | K246[O] | 2.87 | Y100G[OH] | H3 | **K247[NZ]** | **3.84** | **E53[OE1]** | **H2** | | | | | | | | |
| | | | **K247[NZ]** | **3.63** | **D53[OD2]** | **H2** | **K247[NZ]** | **2.75** | **D55[OD2]** | **H2** | | | | | | | | |
| | | | Q248[O] | 3.36 | Y100F[OH] | H3 | Q248[N] | 3.03 | Y100[OH] | H3 | | | | | | | | |
| | | B | K246[O] | 2.67 | Y100G[OH] | H3 | **K247[NZ]** | **2.78** | **D55[OD2]** | **H2** | | | | | | | | |
| | | | **K247[NZ]** | **3.65** | **D53[OD2]** | **H2** | Q248[O] | 3.50 | Y100[OH] | H3 | | | | | | | | |
| | | | Q248[O] | 3.29 | Y100F[OH] | H3 | Q248[N] | 2.97 | Y100[OH] | H3 | | | | | | | | |
| | | C | | | | | | | | | | | | | | | | |
| | | D | | | | | | | | | | | | | | | | |
| | N67 glycan | A | N67-1[O6] | 3.21 | M68[SD] | FH3 | N67-1[O3] | 3.0 | G65[O] | H2 | | | | | | | | |
| | | | | | | | N67-4[O2] | 2.70 | S82B[OG] | FH3 | | | | | | | | |
| | | B | | | | | N67-1[O3] | 3.0 | G65[O] | H2 | | | | | N67-1[O3] | 3.20 | D65[CD1] | H2 |
| | | | | | | | N67-4[O2] | 3.32 | S82B[OG] | FH3 | | | | | N67-1[O7] | 2.82 | Q64[NE2] | H2 |
| | | C | | | | | | | | | | | | | | | | |
| | | D | | | | | | | | | N67-1[O5] | 3.34 | Q64[NE2] | H2 | | | | |

Figure 21

| | | | | | | | | | | | | | | | | | | |
|---|---|---|---|---|---|---|---|---|---|---|---|---|---|---|---|---|---|---|
| Domain I - across dimer interface | | A | | | | | | | | | R2[NH2] | 3.27 | D99[OD1] | H3 | R2[NH2] | 3.39 | D99[OD1] | H3 |
| | | | | | | | | | | | R2[NH2] | 3.19 | D99[OD2] | H3 | R2[NH1] | 3.33 | D99[OD2] | H3 |
| | | | | | | | | | | | E44[OE2] | 3.34 | Y100[OH] | H3 | R2[NH2] | 2.80 | D99[OD2] | H3 |
| | | | | | | | | | | | | | | | G28[N] | 2.92 | Y100[OH] | H3 |
| | | | | | | | | | | | | | | | E44[OE2] | 3.46 | Y100[OH] | H3 |
| | | B | | | | | | | | | R2[NH2] | 3.53 | D99[OD1] | H3 | R2[NH2] | 3.50 | D99[OD2] | H3 |
| | | | | | | | | | | | R2[NH2] | 3.64 | D99[OD2] | H3 | R2[NH1] | 3.11 | D99[OD2] | H3 |
| | | | | | | | | | | | E44[OE2] | 3.37 | Y100[OH] | H3 | | | | |
| | | C | | | | | | | | | R2[NH2] | 3.07 | D99[OD2] | H3 | | | | |
| | | | | | | | | | | | E44[OE1] | 2.73 | Y100[OH] | H3 | | | | |
| | | D | | | | | | | | | R2[NH2] | 3.20 | D99[OD1] | H3 | | | | |
| | | | | | | | | | | | R2[NH2] | 3.11 | D99[OD2] | H3 | | | | |
| | | | | | | | | | | | E44[OE2] | 2.70 | Y100[OH] | H3 | | | | |
| | | | | | | | | | | | L45[O] | 3.49 | Y100[OH] | H3 | | | | |
| | 150 loop | A | D154[N] | 3.07 | S100C[OG] | H3 | | | | | | | | | | | | |
| | | | T155[OG1] | 2.86 | Y99[OH] | H3 | | | | | | | | | | | | |
| | | | T155[OG1] | 3.03 | S100C[O] | H3 | | | | | | | | | | | | |
| | | | T155[OG1] | 3.35 | S31[OG] | H1 | | | | | | | | | | | | |
| | | B | G152[O] | 3.50 | S100C[OG] | H3 | | | | | | | | | | | | |
| | | | T155[OG1] | 3.11 | S31[OG] | H1 | | | | | | | | | | | | |
| | | | T155[OG1] | 2.87 | Y99[OH] | H3 | | | | | | | | | | | | |
| | | | T155[OG1] | 2.89 | S100C[O] | H3 | | | | | | | | | | | | |
| | | | D154[N] | 3.04 | S100C[OG] | H3 | | | | | | | | | | | | |
| | 153 glycan | A | N153-1[N2] | 3.0 | Y99[O] | H3 | | | | | | | | | | | | |
| | | | N153-4[O4] | 3.20 | S56[OG] | L2 | | | | | | | | | | | | |
| | | | N153-4[O4] | 3.0 | S56[N] | L2 | | | | | | | | | | | | |
| | | B | N153-1[N2] | 3.0 | Y99[O] | H3 | | | | | | | | | | | | |
| | | | N153-4[O4] | 3.10 | S56[OG] | L2 | | | | | | | | | | | | |
| | | | N153-4[O4] | 3.0 | S56[N] | L2 | | | | | | | | | | | | |
| | | | N153-5[O2] | 2.90 | D101[OD1] | H3 | | | | | | | | | | | | |
| | *fg* | A | | | | | | | | | | | | | K203[NZ] | 2.88 | N56[OD1] | H2 |
| | | B | | | | | | | | | | | | | | | | |
| | *kl* | A | | | | | | | | | | | | | | | | |
| | | B | | | | | S274[N] | 3.30 | E53[OE2] | H2 | | | | | D274[OD2] | 2.68 | R71[NH2] | FH3 |

Figure 21 (continued)

| | | | | | |
|---|---|---|---|---|---|
| Domain III - across dimer interface | A | | K310[NZ] 3.69 D50[OD1] L2<br>E311[OE1] 3.94 R66[NH1] FL3<br>E311[OE2] 2.74 R66[NH1] FL3<br>E311[OE2] 3.28 R66[NH2] FL3<br>E311[OE1] 3.28 S30[OG] L1<br>D362[OD2] 3.69 R54[NH1] L2 | K310[NZ] 3.40 N31[OD1] L1<br>K310[NZ] 3.49 D50[OD1] L2<br>K310[NZ] 3.35 D50[OD2] L2<br>R323[NH1] 3.01 S53[OG] L2<br>R323[NH1] 3.18 D50[OD1] L2<br>R323[NH2] 3.05 D50[OD1] L2<br>D362[O] 2.71 R54[NH2] L2<br>D362[OD2] 3.16 S60[OG] FL3 | D309[OD1] 2.80 T52[OG1] L2<br>K310[NZ] 3.66 D50[OD2] L2<br>N362[O] 3.11 R54[NH1] L2 |
| | B | | K310[NZ] 3.62 D50[OD1] L2<br>E311[OE1] 3.35 R66[NH1] FL3<br>E311[OE1] 3.85 R66[NH2] FL3<br>E311[OE2] 2.80 R66[NH1] FL3 | K310[NZ] 3.60 D50[OD1] L2<br>K310[NZ] 3.23 D50[OD2] L2<br>K310[NZ] 2.89 N31[OD1] L1<br>R323[NH1] 3.19 D50[OD1] L2<br>R323[NH2] 3.67 D50[OD1] L2<br>R323[NH1] 3.28 S53[OG] L2<br>D362[O] 3.02 R54[NH2] L2 | K310[NZ] 3.36 D50[OD2] L2 |
| | C | | | K310[NZ] 3.33 D50[OD2] L2<br>K310[NZ] 3.33 D50[OD1] L2<br>R323[NH1] 2.89 S53[OG] L2<br>R323[NH1] 3.41 D50[OD1] L2<br>R323[NH2] 2.99 D50[OD1] L2<br>D362[O] 3.04 R54[NH2] L2 | |
| | D | | | K310[NZ] 3.47 D50[OD2] L2<br>K310[NZ] 3.12 D50[OD1] L2<br>R323[NH1] 3.77 D50[OD1] L2<br>K310[NZ] 3.2 N31[OD1] L1<br>D362[O] 3.36 R54[NH2] L2 | |

In black: Hydrogen bonds (d ≤ 3.5 Å). In bold black and yellow background : Salt bridges (d ≤ 4 Å).
In bold red: Main chain atoms involved in contacts. In bold blue: Sugar atoms involved in contacts.
In grey background : the epitopes C and D do not exist in the corresponding stuctures. Distances (dist) are reported in Å.

shaded

Figure 21 (continued)

a - DENV2 sE / BNA VDE1 C8 Complex

I - 3D structure diagram with localization of epitopes

II – Histogram of number of atomic contacts of the BNA per sE residue on epitopes A and B b - DENV2 sE / BNA VDE1 C10 Complex I - 3D structure diagram with localization of epitopes II – Histogram of number of atomic contacts of the BNA per sE residue on epitopes A and B b (continued) - DENV2 sE / BNA VDE1 C10 Complex III - 3D structure diagram with localization of epitopes (second complex in the asymmetric unit of the crystal)

IV – Histogram of number of atomic contacts of the BNA per sE residue on epitopes C and D C- DENV2 sE / BNA VDE2 A11 Complex I - 3D structure diagram with localization of epitopes II – Histogram of number of atomic contacts of the BNA per sE residue on epitopes A and B d- DENV2 sE / BNA VDE2 B7 Complex I – 3D structure diagram with localization of epitopes II – Histogram of number of atomic contacts of the BNA per sE residue on epitopes A and B II – Histogram of number of atomic contacts of the BNA per sE residue on epitopes A and B b (continued) BNA VDE1 C10 residues in contact with DENV2 sE
(second complex in the asymmetric unit of the crystal)

I - 3D diagram

C BNA VDE2 A11 residues in contact with DENV2 sE

I - 3D diagram

II – Linear diagram with histogram of contacts.

e BNA VDE1 C10 residues in contact with DENV4 sE

I - 3D diagram

Extended Data Table 4. Comparative BSA and germline analysis of Dengue VDE BNAs with RSV, Influenza and HIV BNAs.

| BNA Type | Fab/ ScFv | BSA | BSA MC (%) | V-H allele | V-H nt diverg | V-H aa diverg | J-H allele | D-H allele | HCDR length [H1.H2.H3] | V-L allele | V-L nt diverg | V-L aa diverg | J-L allele | LCDR length [L1.L2.L3] | PDB access |
|---|---|---|---|---|---|---|---|---|---|---|---|---|---|---|---|
| VDE2 | B7 | 1103 | 234 (21%) | IGHV3-74 | 7% | 9% | IGHJ6 | IGHD3-22 | [8.8.26] | IGLV2-23 | 5% | 10% | IGLJ3 | [9.3.10] | This work |
| VDE2 | A11 | 1049 | 222 (21%) | IGHV3-74 | 9% | 14% | IGHJ6 | IGHD3-22 | [8.8.26] | IGLV2-23 | 7% | 14% | IGLJ3 | [9.3.10] | - |
| VDE1 | C8 | 1263 | 357 (28%) | IGHV3-64D | 7% | 12% | IGHJ6 | IGHD2-21 | [8.8.15] | IGKV3-11 | 5% | 10% | IGKJ2 | [6.3.10] | - |
| VDE1 | C10 | 1162 | 347 (30%) | IGHV1-3 | 3% | 4% | IGHJ4 | IGHD4-17 | [8.8.21] | IGLV2-14 | 4% | 10% | IGLJ3 | [9.3.10] | - |
| RSV | D25 (Ref. 24) | 859 | 250 (29%) | IGHV1-69 | - | 21% | IGHJ4 | - | [8.8.19] | IGKV1-33 | - | 6% | IGKJ4 | [6.3.9] | 4JHW |
| Influenza | CH65 (Ref. 25) | 775 | 226 (29%) | IGHV1-2 | 5% | 12% | IGHJ6 | IGHD1-1 | [8.8.19] | IGLV3-21 | 4% | 5% | IGLJ2 | [6.3.11] | 3SM5 |
| Influenza | CR8020 (Ref. 26) | 772 | 216 (28%) | IGHV1-18 | 4% | 13% | IGHJ4 | - | [8.8.15] | IGKV3-20 | 2% | 8% | IGKJ1 | [7.3.9] | 3DSY |
| HIV | B12 (Ref. 27) | 935 | 341 (36%) | IGHV1-03 | 13% | 20% | IGHJ6 | IGHD3-10 | [8.8.20] | IGKV3-20 | 16% | 23% | IGKJ2 | [7.3.9] | 2NY7 |
| HIV | VRC01 (Ref. 28) | 1156 | 380 (33%) | IGHV1-02 | 32% | 42% | IGHJ1 | IGHD3-16 | [8.8.14] | IGKV3-11 | 17% | 28% | IGKJ2 | [4.3.5] | 3NGB |

V-H, J-H, D-H, V-L, J-L represent the putative genes and alleles corresponding to the given Ab, predicted by IMGT analysis (see methods). 'Homsap' precedes gene/allele names
CDR lengths are indicated in square brackets for HCDRs and LCDRs: [CDR1.CDR2.CDR3]
Germlines for D25 were predicted from amino acid sequence.

Figure 27

>DENV1 strain Hawaii
MRCVGIGNRDFVEGLSGGTWVDVVLEHGSCVTTMAKDKPTLDIELLKTEVTNPAVLRKLCIEAK
ISNTTTDSRCPTQGEATLVEEQDANFVCRRTFVDRGWGNGCGLFGKGSLITCAKFKCVTKLEGK
IVQYENLKYSVIVTVHTGDQHQVGNETTEHGTIATITPQAPTSEIQLTDYGALTLDCSPRTGLD
FNEMVLLTMKEKSWLVHKQWFLDLPLPWTSGASTPQETWNREDLLVTFKTAHAKKQEVVVLGSQ
EGAMHTALTGATEIQTSGTTKIFAGHLKCRLKMDKLTLKGMSYVMCTGSFKLEKEVAETQHGTV
LVQVKYEGTDAPCKIPFSTQDEKGVTQNGRLITANPIVTDKEKPVNIEAEPPFGESYIVVGAGE
KALKLSWFKKGSSIGKMLEATARGARRMAILGDTAWDFGSIGGVFTSVGKLVHQIFGTAYGVLF
SGVSWTMKIGIGILLTWLGLNSRSTSLSMTCIAVGMVTLYLGVMVQA >DENV2 strain 16681
MRCIGMSNRDFVEGVSGGSWVDIVLEHGSCVTTMAKNKPTLDFELIKTEAKQPATLRKYCIEAK
LTNTTTESRCPTQGEPSLNEEQDKRFVCKHSMVDRGWGNGCGLFGKGGIVTCAMFRCKKNMEGK
VVQPENLEYTIVITPHSGEEHAVGNDTGKHGKEIKITPQSSITEAELTGYGTVTMECSPRTGLD
FNEMVLLQMENKAWLVHRQWFLDLPLPWLPGADTQGSNWIQKETLVTFKNPHAKKQDVVVLGSQ
EGAMHTALTGATEIQMSSGNLLFTGHLKCRLRMDKLQLKGMSYSMCTGKFKVVKEIAETQHGTI
VIRVQYEGDGSPCKIPFEIMDLEKRHVLGRLITVNPIVTEKDSPVNIEAEPPFGDSYIIIGVEP
GQLKLNWFKKGSSIGQMFETTMRGAKRMAILGDTAWDFGSLGGVFTSIGKALHQVFGAIYGAAF
SGVSWTMKILIGVIITWIGMNSRSTSLSVTLVLVGIVTLYLGVMVQA >DENV3 stain H87
MRCVGVGNRDFVEGLSGATWVDVVLEHGGCVTTMAKNKPTLDIELQKTEATQLATLRKLCIEGK
ITNITTDSRCPTQGEAILPEEQDQNYVCKHTYVDRGWGNGCGLFGKGSLVTCAKFQCLESIEGK
VVQHENLKYTVIITVHTGDQHQVGNETQGVTAEITSQASTAEAILPGYGTLGLECSPRTGLDFN
EMILLTMKNKAWMVHRQWFFDLPLPWTSGATTETPTWNRRELLVTFKNAHAKKQEVVVLGSQEG
AMHTALTGATEIQTSGGTSIFAGHLKCRLKMDKLELKGMSYAMCLNTFVLKKEVSETQHGTILI
KVEYKGEDAPCKIPFSTEDGQGKAHNGRLITANPVVTKKEEPVNIEAEPPFGESNIVIGIGDKA
LKINWYRKGSSIGKMFEATARGARRMAILGDTAWDFGSVGGVLNSLGKMVHQIFGSAYTALFSG
VSWIMKIGIGVLLTWIGLNSKNTSMSFSCIAIGIITLYLGVVVQA >DENV4 strain 241
MRCVGVGNRDFVEGVSGGAWVDLVLEHGGCVTTMAQGKPTLDFELIKTTAKEVALLRTYCIEAS
ISNITTATRCPTQGEPYLKEEQDQQYICRRDVVDRGWGNGCGLFGKGGVVTCAKFSCSGKITGN
LVQIENLEYTVVVTVHNGDTHAVGNDIPNHGVTATITPRSPSVEVKLPDYGELTLDCEPRSGID
FNEMILMKMKKKTWLVHKQWFLDLPLPWAAGADTSEVHWNYKERMVTFKVPHAKRQDVIVLGSQ
EGAMHSALTGATEVDSGDGNHMFAGHLKCKVRMEKLRIKGMSYTMCSGKFSIDKEMAETQHGTT
VVKVKYEGAGAPCKVPIEIRDVNKEKVVGRIISSTPFAEYTNSVTNIELEPPFGDSYIVIGVGD
SALTLHWFRKGSSIGKMLESTYRGVKRMAILGETAWDFGSVGGLFTSLGKAVHQVFGSVYTTMF
GGVSWMVRILIGFLVLWIGTNSRNTSMAMTCIAVGGITLFLGFTVHA underline: Extracellular domain
Highlight: 150 loop sequences.

Figure 28

| Sequence ID | epitope | SEQ ID NO: | Sequence AA (H chain) | SEQ ID NO: | Sequence AA (L chain) |
|---|---|---|---|---|---|
| 747(4) B3 | EDE1 | 40 | QVQLQESGPGLMKPSETLSLTCSVSGVSISTHYWSWIRQPPGKGLEWIGFIYNSGGTHYNPSLKSRVTISADTSKNQFALTLSSVTAADTAVYYCARGRRAYDSSGYVKYYYFYGVDVWGQGTTVTVSS | 86 | QTVVTQEPSLTVSPGGTVTLTCGSNTGPVTNGHYPYWFQQKSGQAPRTLIYDTTNRQSWTPVRFSGSLLGGKAALTLSGAQPEDEADYHCLLSYSDGLVFGGGTKLTVL |
| 747 A12 | EDE1 | 41 | EVQLVESGSELKKPGASVKVSCRASGFTFTSYTFNWVRQAPGQGLEWMGWIDTKSGRPTYAQGFTGRFVLSLDTSVSTAYLQINSLKVEDTAMYYCARVHTGGYPPELRYYYYGMDVWGQGTTVTVSS | 87 | CMTPAPSTLAVTPGEPASISCRSTQSLLHSDGYNYLDWYLQKPGQSPHLLIYLGSHRASGVPDRFSGSGSDTDFTLKISRVEAEDVGVYYCMQPLRTPPTFGQGTKLEIK |
| 752 B10 | EDE1 | 42 | EVQLVESGGGLVQPGGSLRLSCSASGFTFSTYSMHWVRQAPGKGLEYVSAITTDGNSAFYADSVKGRFTISRDNSKNTMYFHMNSLRPEDTAVYYCVGGYSSFYYYYTMDVWGQGTTVTVSS | 88 | EIVLTQSPATLSLSAGDRATLSCRASQDISSFLAWYQQKPGQAPRLLMYDTSNRATGVPARFSGSRSGTDFTLTISTLEPEDVAVYYCQHRYNWPPYTFGQGTKVEIK |
| 752 B11 | EDE1 | 43 | QVQLVESGGGLVQPGGSLRLSCSASGFTFSTYSMHWVRQAPGKGLEYVSAITTDGDSAFYADSVKGRFTISRDNSKNTMFFHMSNLRPEDTAVYYCVGGYSSFYYYYTLDVWGQGTTVTVSS | 89 | EIVLTQSPATLSLSPGERATLSCRASQSISSFLAWYQQKPGQAPRLLIYDASNRVTGVPARFSGSRSGTDFTLTISTLEPEDFAVYYCQHRYNWPPYTFGQGTKVEIK |
| 752 C9 | EDE1 | 44 | EVQLVESEGGLVQPGGSLRLSCSASGFTFSTYSMHWVRQAPGKGLEYVSAITTNGDSTFYADSVKGRFTISRDNSKNTLYFQMSSLRAEDTGVYYCVGGYSSFYYYYTMDVWGQGTTVTVSS | 90 | EIVLTQSPATLSLSPGERATLSCRASQSISTYLAWYQQKPGQAPRLLIYDASNRATGVPARFSGSRSGTDFTLTISTLEPEDFAVYYCQQRYNWPPYTFGQGTKVEIK |

Figure 29

| | | | | | |
|---|---|---|---|---|---|
| 752(2) A2 | EDE1 | 45 | EVQLVQSGPEMRKPGASVKVSCKASGYTFTSHGINWVRQVPGQGPEWMGWSSSYTDNTNYAQKFKGRVTMTTDPSTSTAYMELRSLRSDDTAIYFCARGFYSGSYYPTAPFDIWGQGTLVTVSS | 91 | DIQMTQSPSSLSASVGDRVTITCRASQTISGSLSWYQHKPGKAPKLLIYAASSLQSGVPSRFSGSGSGTDFTLTISSLQPEDFATFYCQQSYSTPYTFGQGTKVEIK |
| 752(2) A5 | EDE1 | 46 | EVQLVQSGAEVKKPGASVKVSCKASGYTFTTYGLSWVRQAPGQGLEWMGWCSSYNDNTNYAQKFKGRVTMTTDTSTNTAYMELRSLRSDDTAVYYCARVFYSGSYYPNSPFDYWGQGTLVTVSS | 92 | DIQMTQSPSSLSASIGDRVTITCRASESISSQLHWYQQKPGKAPRLLIYAASSLQGGVPSRFSGSGSGTDFTLTISGLQPEDFATYCCQQSFTTPYTFGQGTKVEIK |
| 752(2) A7 | EDE1 | 47 | QVQLQESGPGLVKPSQTLSLTCTVSGDSISSNNYQWNWIRQPAGKGLEWLGRIDTTGSTNYNPSLKSRISISIDTSKKQFSLRLNSVTAADTAVYYCARSLWSGELWGGPLGYWGQGTLVTVSS | 93 | EIVMTQSPATLSASPGERATLSCRASQDVSTFVAWFQQNPGQAPRLLIYDASTRAPGIPARFSGSRSGTEFTLTINSLQSEDFAVYYCQQYYNWPPWTFGQGTKVEIK |
| 752(2) A8 | EDE1 | 48 | EVQLVESGAEVKNPGASVKVSCKASGYTFIGYYIHWVRQAPGQGLEWMGWINPNSGATYSAQKFQGRVTLTGDASPSTVYMELSSLRSDDTAIYYCAGRSYNWNDVFYYYYMDVWGQGTTVTVSS | 94 | DIQMTQSPSSVSASVGDRVTISCRASQDISASLGWYQQKPGKAPKLLIYRASNLEGGVPSRFRGSGSGTDFTLTISSLQPEDFATYYCLQANSFPLTFGGGTKVEIK |
| 752(2) B10 | EDE1 | 49 | EVQLVESGPGLVKPSETLSLTCTISGVSISDYYWTWIRQPPGKGLEWIGNIYNTGSTNYNPSLKSRVAIWMDTSKNKFSLRLTSVTSADTAVYYCARVEGGPKYYFGSGDFYNLWGRGSLVTVSS | 95 | DIQMTQSPSSLSASVGDSVTVACRASQPIYRNLNWYQQKPGKAPKLLIYDASTLQSGVPARFSGSGSGTDFTLTISSLQAEDFATYYCQQSYSSPRTFGQGTKVEIK |

Figure 29 (continued)

| | | | | | |
|---|---|---|---|---|---|
| 752(2) C2 | EDE1 | 50 | SQVQLVQSGAELKKPGASVKVSCKTSGYTFSYYIHWVRQAPGQGLEWMAMINPTSGSTSYAQRFQGRVTMTRDTPTNTVYMEVRSLRSDDTAVYFCASRGYNWNDVQYYYTMDVWGQGTTVTVSS | 96 | DIQMTQSPSTLSASVGDRVTITCRASQSISTYLAWYQQKPGKAPKLLIYKASSLEIGVPSRFSGSGSGTEFTLTISSLQPDDFAIYYCQQYNNYSPPVTFGGGTKVEIK |
| 752(2) D4 | EDE1 | 51 | SEVQLVQSGAELKKPGASVKVSCKASGYTFSYYIHWVRQAPGQGLEWMAIINPTSGSTSYAQRFQGRVTMTRDTSTNTVYMELSSLISEDTAVYYCASRGYNWNDVHYYYTMDVWGQGTTVTVSS | 97 | DIQMTQSPSTLSASVGDRVTITCRASQSISTYLAWYQQKPGKAPKLLIYKASTLESGVPLRFSGSGSGTEFTLTISSLQPDDFAIYYCQQYNNYSPPVTFGGGTKVEIK |
| 752(2) B11 | EDE1 | 52 | QVQLVESGAEVKKPGSSVKVSCKASGYTFTTYGLSWVRQAPGQGLEWMGWCSSYEDNTNYAPRFKGRVTMTTDTSTNTAYMELRSLRFDDTAVYYCARVFYSGSYYPNSPFDSW | 98 | DIQMTQSPSSLSASVGDAVSITCRASESVSRQLNWYQQKPGKAPNLLIYAASSLQGGVPSRFSGSGSGTDFTLTISGLQPEDFATYYCQQGYSTPYSFGQGTKVEIK |
| 752-2 A2 | EDE1 | 53 | QVQLVESGGGLVQPGGSLRLSCSASGFTFSTYSMHWVRQAPGKGLEYISAITTDGDSAFYADSVKGRFTISRDNSKNTMYFHMNSLRPEDTAVYYCVGGYSSFYYYYTMDVWGQGTTVTVSS | 99 | EIVLTQSPATLSLSAGERATLSCRASQSISSYLAWYQQKPGQAPRLLIYDASNRATGVPARFSGSQSGTDFTLTISTLEPEDFAVYYCQLRYNWPPYTFGQGTKVEIK |
| 752-2 A4 | EDE1 | 54 | EVQLVESGAEVKKPGASVKVSCKASGYTFTSYGINWVRQAPGQGLEWMGWISSDSGHTNYARKLKGRVTMTTDTSTTTAYMELRSLRSDDTAVYYCARGLYSVSYYPTSPFDYWGQGSTVTVSS | 100 | DIQMTQSPSPLSASVGDRVTITCRASQSISSHLNWYQQKSGKVPKLLIYAASSLQSGVPSRFSGSGSGTDFTLTITSLQPEDFATYYCQQSDTTPYTFGQGTKVEIK |
| 752-2 A5 | EDE1 | 55 | QVQLVESGAEVKKPGSSVKVSCRASGYTFTTYGLSWVRQAPGQGLEWMGWCSSYNDNTNYAQKFKGRVTMTTDTSTNTAYMELRSLRSDDTAVYYCARVFYSGSYYPNSPFDSWGQGTLVTVSS | 101 | DIQMTQSPSSLSASVGDAVSITCRASESIARQLNWYQQKPGKAPNLLIYAASSLQGGVPSRFSGSGSGADFTLTISGLQPEDFATYYCQQGYSTPYTFGQGTKVEIK |

Figure 29 (continued)

| | | | | | |
|---|---|---|---|---|---|
| 752-2 A9 | EDE1 | 56 | EVQLVESGGGLVQPGGSLRLSCSASGFTFSTYSMHWVRQAPGKGLEYVSAITTDGDSAFYADSVKGRFTISRDNSKNTMYFHMNSVRPEDTAVYYCVGGYSSFYYYYTMDVWGQGTTVTVSS | 102 | EIVLTQSPATLSLSAGERATLSCRASQDISTFLAWYQQKPGQAPRLLIYDTSTRATGVPARFSGSRSGTDFTLTITTLEPEDFAVYYCQHRYNWPPYTFGQGTKVEIK |
| 752-2 B2 | EDE1 | 57 | EVQLVESGGGLVQPGGSLRLSCSASGFTFSTYSMHWVRQAPGKGLEYVSAITTDGDSAFYADSVKGRFTISRDNSKNTMYFHMNSLRPEDTAVYYCVGGYSSFYYYYTMDVWGQGTTVTVSS | 103 | EIVLTQSPATLSLSAGERATLSCRASQSISSYLAWYQQKPGQAPRLLIYDASNRATGVPARFSGSRSGTDFTLTISTLEPEDFAVYYCQHRYNWPPYTFGQGTKVEIK |
| 752-2 B3 | EDE1 | 58 | EVQLLESGGGLVQPGGSLRLSCSASGFTFSTYSMHWVRQAPGKGLEYVSAISTDGDSAFYADSVKGRFTISRDNSKNTLYFHMSSLRAEDTAVYYCLGGYSTFYYYYTMDVWGQGTTVTVSS | 104 | EIVLTQSPATLSLSPGERATLSCRASHSISTFLAWYQQKPGQAPRLLIYDTSTRATGVPARFSGSRSGTDFTLTINTLEPEDFAVYYCQQRYNWPPYTFGQGTKVEIK |
| 752-2 B4 | EDE1 | 59 | QVQLVESGGGLVQPGGSLRLSCSASGFPFSTYSMHWVRQAPGKGLEYVSAITTNGDSTFYADSVKGRFTISRDNSKNTVYFQLSSLRAEDTAVYYCVGGYSSFYFYYTMDVW | 105 | EIVLTQSPATLSLSPGERATLSCRASQSISSFLAWYQQKPGQAPRLLIYDTSNRATGVPARFSGSRSGTDFTLTISTLEPEDFAIYYCQHRYNWPPYTFGQGTKVEIK |
| 752-2 B7 | EDE1 | 60 | EVQLVQSGAEVKKPGASVKVSCKASGYTYTNYGLSWVRQAPGQGLEWMGWMSSYNDNTNYSQKFKGRVTMTTDPSTTTAYMELRSLRSDDTAVYYCARGLYSGSHYPTSPLDYWGQGTLVTVSS | 106 | DIQMTQSPSSLSASVGDRVTITCRASQSISRSLNWYQQKPGKAPKLLIYAASTLQSGVPSRFSGSGSGTDFALTISSLQPEDFATYSCQQSDRTPYTFGQGTKVEIK |

Figure 29 (continued)

| | | | | | |
|---|---|---|---|---|---|
| 752 -2 B11 | EDE 1 | 61 | EVQLVESGGGLVQPGGSLRLSCSASGFTFTTYSLHWVRQTPGKGLEYVSAITTDGDSAFYADSVKGRFTISRDNSKNTMYFHMSSLRPEDTAVYYCVGGYSSFYYFYTVDVWGQGTTVTVSF | 107 | EIVLTQSPATLSLSPGERATLSCRASQSISTYLVWYQQKPGQAPRLLIYDASTRATGVPARFSGSRSGTDFTLTISTLEPEDFAVYYCQHRYNWPPYTFGRGTKVEIK |
| 752 -2 C4 | EDE 1 | 62 | SQVQLVESGAELKKPGASVKVSCKASGYTFSYYMHWVRQAPGQGLEWMAIINPTSGSTTYAQRFQGRVTMTRDTSTSTVYMELSSLRSEDTAVYYCASRGYNWNDVHYYYTMDVWGQGTTVTVSS | 108 | DIQMTQSPSTLSASVGDRVTITCRASQSISTYLAWYQQKVGKAPKLLIYKASTLEGGVPSRFSGSGSGTEFTLTISSLQPEDFAIYYCQQYNNYSPPVTFGGGTKVEIK |
| 752 -2 C8 | EDE 1 | 1 | EVQLVESGGGLVQPGGSLRLSCSASGFTFSTYSMHWVRQAPGKGLEYVSAITGEGDSAFYADSVKGRFTISRDNSKNTLYFEMNSLRPEDTAVYYCVGGYSNFYYYYTMDVWGQGTTVTVSS | 37 | EIVLTQSPATLSLSPGERATLSCRASQSISTFLAWYQHKPGQAPRLLIYDASTRATGVPARFSGSRSGTDFTLTISTLEPEDFAVYYCQQRYNWPPYTFGQGTKVEIK |
| 753 (3) C10 | EDE 1 | 2 | EVQLVESGAEVKKPGASVKVSCKASGYTFTSYAMHWVRQAPGQRLEWMGWINAGNGNTKYSQKFQDRVTITRDTSASTAYMELSSLRSEDTAIYYCARDKVDDYGDYWFPTLWYFDYWGQGTLVTVSS | 38 | QSALTQPASVSGSPGQSITISCTGTSSDVGGFNYVSWFQQHPGKAPKLMLYDVTSRPSGVSSRFSGSKSGNTASLTISGLQAEDEADYYCSSHTSRGTWVFGGGTKLTVL |
| 753 (3) B10 | EDE 1 | 63 | EVQLVESGPEVKKPGASVKVSCKTSGYTFINYYIHWVRQAPGQGLEWLGLINPRGGNTNYAEKFEDRVTMTRDTSTSTVNMELSSLTSEDTAVYYCARPLAHTYDFWSGYHRATGYGMDVWGQGTTVTVSS | 109 | DIVMTQSPLSLSVTPGEPASISCRSSQSLVYSDGNKYLDWYVQKPGQSPQLLIYLTSTRASGVPDRFSGSASGTDFTLKISRVEAEDVGLYYCMQALQTPFTFGPGTKVDIK |
| 758 P6A 1 | EDE 1 | 64 | EVQLVESGGGLVQPGGSLRLSCAAFGFTFVNYAMNWVRQAPGKGPEWVAVIYAAGDGANYGDSVKGRFTISRDNSRNTLYLQMNSLRAEDTAIYYCAKPAHYDDSGYPYMAYFDSWGQGTLVTVSS | 110 | EIVMTQSPATLSVSPGERATLTCRASQTISTFLAWYQQKPGQPPRLLIYDTSTRATGIPGRFSGSRSGTEFTLTISSLQSEDVAVYYCQHYYNWPPWTFGQGTKVEIK |

Figure 29 (continued)

| | | | | | |
|---|---|---|---|---|---|
| 758 P6A 3 | EDE 1 | 65 | QVQLVQSGAEVKKPGSSVKVSCKASGGFFSSYAITWVRQAPGQGLEWMGGIIPDYDSAKYAQKFQGRVTITADESTSTAYLELRSLRSEDTAVYYCARRHCSSTSCSDPWTFFPSWGQGTLVTSPQ | 111 | QSALTQPPSASGSPGQSVTISCTGSSSDIGGNEYVSWYQLQPGKAPKLMIYEVTKRPSGVPNRFSGSKSGNTASLTVSGLQSEDEGDYYCSSYADNSVLFGGGTTLTVL |
| 758 P6A 12 | EDE 1 | 66 | EVQLVESGAEMKKPGSSVKVSCKASGATFTSFAMYWVRQAPGQGLEWMGRIIPMFASAEYAQKFQGRLTMTADESTTTAYMELSSLRSDDTAVYYCAGRYCSSTSCSDPWTYFPHWGQGTLVTVSS | 112 | QSVLTQPPSASGSPGQSVTISCTGTSSDVGAYYYVSWYQQHPGKAPKLIIYEVNKRPSGVPARFSGSKSGNTASLTVSGLQGEDEADYYCTSYAGSNTVIFGGGTKLTVL |
| 758 P6B 4 | EDE 1 | 67 | EVQLVQSGATVRKPGASVTISCKTSGYTFTDYALHWVRQAPGQRLEWMGWLIPGSGYTKFAENFQGRVTITRATSAHTAYMELSNLRSEDTAVYYCARWGGDCNAGSCYGPYQYRGLDAWGQGTTVTVSS | 113 | EIVLTQSPVTLSLSPGERATLSCRASQTVDSTYLAWYQQKPGRAPRLLIYGASNRAIGVPSRFTGSGSGTDFTLTISRLEPEDFALYYCQQSDGSLFTFGPGTKVDIK |
| 758 P6B 5 | EDE 1 | 68 | EVQLVQSGAEVKKPGASVKVSCKASGYSFIGYYLHWVRQAPGQGLEWMGRINPNSGGIDYGQTFQGRVTMTRDMSSSTVYLELTRLRSDDTARYYCAGRSDNWNDVYYNYALDVWGQGTTVTVSS | 114 | DIQMTQSPASVSASVGDRVTISCRASQGIASWLAWYQQKPGKAPRLLIYGASSLQSGVPSRFRGSGSGTDFTLTISSLQPEDFATYYCQQANSFPFTFGPGTKVDIK |
| 758 P6B 11 | EDE 1 | 69 | EVQLLESGGGVVQPGRSLKLSCAASGFTFSGYAMHWVRQAPGKGLEWLAVISYDATTTYYTPSVKGRFTISRDNSKNTLYLQINSLRAEDAAVYYCAKEISYCGGDCQNFFFYYNMDVWGQGTTVTVSS | 115 | QSALTQPASVSGSPGQSITISCTGTSSDVGRYNVVSWYQQHPGKAPKLIIYGSTKRPSGVSYRFSASKSGNTASLTISGLQAEDEAEYHCCSYASGSVWVFGGGTKLTVL |
| 758 P6C 4 | EDE 1 | 70 | QVQLVQSGAEVKKPGASVKVSCKASGYTFTAYYIHWVRQAPGQGLEWMGSINPNNGGTNYAQGFQGRVTMTRDTSIRTVYMELSKLRSDDTALYYCARDLGAMGYYLCSAGNCPFDYWGQGTLVTVSS | 116 | QSALTQPPSASGSPGQSVTISCTGTSSDVGGYNYVSWYQHHPGKAPKLIIYEVSKRPSGVPHRFSGSKSGNTASLTVSGLQAEDEAEYYCSSYAGSNTFTFGGGTKLTVL |

Figure 29 (continued)

| | | | | | |
|---|---|---|---|---|---|
| 747 B8 | EDE2 | 71 | QVQLVESGGALVKPGGSLRLSCAASGFTFRSHWMHWVRQAPGKGLVWVSRINSDGSSTNYADFVKGRFTTSRDNAENTLYLEMNSLTADDTAVYYCVRDGVRYYYDSSGYYPDSFFKYGMDVWGQGTTVTVSS | 117 | QSALTQTASVSGSPGQSITISCTGTSSDAEIYNLVSWYQQHPGKAPKLIIYEGSKRPSGVSNRFSASKSAGAASLRISGLQPEDEADYYCCSYATSKTLVFGGGTKLTVV |
| 747 C2 | EDE2 | 72 | EVQLVESGGGLVQPGGSLRLSCAASGFTFRSSAMYWVRQAPGKGLEFVSCIRSNGVTHYADSVKGRFTISRDNSKNTLHLQMGGLRPDDMAVYYCTRDDGPYSGYDWPWASSMDVWGQGTTVTVSS | 118 | DVVMTQSPLSLPVTLGQPASISCRSSRSLLNSDGNTYLNWFHQRPGQSPRRLIFKLSNRDSGVPDRFSGSGSGTDFTLKISRVEAEDVGIYYCMQGTHWPVTFGGGTKVEIK |
| 747 D8 | EDE2 | 73 | EVQLVESGGGLVQPGGSLRLSCAASGFIFSNHWMHWVRQAPGKGLVWVSRTNSDGSSTSYADFVKGRFTISRDNAKNTLHLQINSLRADDTAVYYCARDGVRYYYDSTGYYPDSYYEYGLDVWGQGTTVTVSS | 119 | QSALTQPASVSGSPGQSITISCTGTSSGVGSYNLVSWYQQHPGKAPKFIIYEGSKRPSGVSNRFSGSNSGNTASLTISGLQAEDEADYYCCSYAGSKTLVFGGGTKVTVL |
| 747(4) A3 | EDE2 | 74 | EVQLVESGGGLVQPGGSLRLSCAASGFIFNRHWMHWVRQGPGKGLVWVSRINSDGSSTSYADSVKGRFTISRDNAKNTLHLQINSLRAEDTAVYYCARDGVRYYYDSTGYYPDSYYEYGMDVWGQGTTVTVSS | 120 | QSVLTQPASVSGSPGQSITISCTGTSSDVGSYNLVSWYQQHPGKAPKFIIYEGSKRPSGVSNRFSGSNSGNTASLTISGLQAEDEADYYCCSYAGSKTLVFGGGTKVTVL |
| 747(4) A10 | EDE2 | 75 | QVQLVQSGGALVKPGGSLRLSCVASGFTFGSHWMHWVRQAPGKGLVWVSRVNSDGSSTNYADFVKGRFTTSRDNAENTLYLEMNSLTADDTAVYYCVRDGVRYYYDSSGYYPDSFFKYGMDVWGQGTTVTVSS | 121 | QSALTQPASVSGSPGQSITISCTGTSSDIGIYNLVSWYQQHPGKAPKLIIYEGSKRPSGVSNRFSASKSAGAASLTISGLQPEDEADYYCCSYATSKTLVFGGGTKLTVV |
| 747(4) A11 | EDE2 | 3 | EVQLVESGGGLVRPGGSLRLSCAASGFSYSNHWMHWVRQAPGKGLVWVSRINSDGSTRNYADFVKGRFTISRDNAENTLYLEMNSLTADDTAVYYCVRDGVRFYYDSTGYYPDSFFKYGMDVWGQGTTVTVSS | 39 | QSVLTQPASVSGSPGQSITISCTGTSSNADTYNLVSWYQQRPGKAPKLMIYEGTKRPSGVSNRFSASKSATAASLTISGLQPEDEADYYCCSYATSRTLVFGGGTKLTVV |

Figure 29 (continued)

| | | | | | |
|---|---|---|---|---|---|
| 747(4) B4 | EDE2 | 76 | QVQLQESGPGLVRPSETLSLTCTVSGLSVSTYYWSWIRQPPGKGLEWIAYVYSRGGTNYNPSLESRVTISVDTATNQFSLRLRSVTAADTAVYFCARATNYFDSSGYFFAPWFDPWGQGILVTVSS | 122 | EIVMTQSPATLSVSPGERATLSCRASQSVKSNLAWYQQKPGQAPRLLMYGASTRVVTIPARFSGSGSGTEFTLTISSLQSEDFAVYYCQQYNKWPLTFGGGTKVEIK |
| 747(4) B6 | EDE2 | 77 | QVQLVQSGAEVKKPGSSVKVSCKASGGTRSSYAISWVRRAPGRGLEWMGVIIPFFGTANYAQIFQGRLTITADESTSIANMELTSLTPEDTAIYYCASGGGGYAGYNWFDPWGQGTLVTVSS | 123 | QSALTQPASVSGSPGQSITISCTGTSSDIGGFNYVSWYQQHPGKAPKVMIFDVSNRPSGVSNRFSGSKSGNTASLTISGLQAEDEADYYCSSYTTRTTYVFGTGTKVTVL |
| 747(4) B7 | EDE2 | 4 | EVQLVESGGGLVQPGGSLKLSCAASGFTFSSHWMHWVRQAPGKGLVWVSRTNSDGSSTSYADSVKGRFMISRDNSKNTVYLHMNGLRAEDTAVYFCARDGVRYYYDSTGYYPDNFFQYGLDVWGQGTTVTVSS | 40 | QSALTQPASVSGSPGQSITISCTGISSDVETYNLVSWYEQHPGKAPKLIIYEASKRPSGVSNRFSGSKSGNTASLAISGLQAEDEADYYCCSYAGGKSLVFGGGTRLTVL |
| 747(4) D6 | EDE2 | 78 | EVQLVQSGGGLIQPGGSLKLSCAASGFSFRNHWMHWVRQAPGKGLVWVSRVNSDGYSTSYADSVKGRFTISRDNAKNTLYLQMNSLRPEDTAVYFCARDGVRFYSDSTGYYPDNYFPYGMDVWGQGTTVTVSS | 124 | QSALTQPASVSGSPGQSITISCSGFSSDVGGDKVVSWYEQHPGKVPKLIIYEGSKRPSGVSNRFSGSKSGNTASLTISGLQAEDEADYYCCSYAGPKTLVFGGGTKVTVL |
| 747 B2 | EDE2 | 79 | EVQLVESGGGLVQPGGSLRLSCKVSGFTFKAYWMHWVRQAPGKGLVWVSRINGLGSSRDYADSVRGRFTISRDDAENTVYLQMNSLTAEDTAMYYCARDVXFHDSSGYYRXGFXAPWG | 125 | NSPLSLSASVGDRVTITCRASRTIDNFLHWYQQKPGKAPNLLIYAASSLQSGVPSRFRGSGSGTDFTLTINSVQPEDFATYYCQQSYTIPPTFGGGTKVEIR |

Figure 29 (continued)

| | | | | | |
|---|---|---|---|---|---|
| 747 C4 | EDE2 | 80 | EVQLVESGGGLVQPGGSLRLSCAASGFAFSNHWMHWVRQAPGKGLVWVSRINSDGSSTTYADSVKGRFTISRDNAKNTLSLELNSLRAEDTAIYYCARDGVRFYYDSTGYYPDPYFQYGLDVWGQGTTVTVSS | 126 | QSALTQPASVSGSLGQSITISYTGTAIDVGSYNLVSWYQQHPGKVPKLMIYEGSKRPSGVSNRFFGSKSGNTASLTISGLQSEDEAEYYCCSYGGSRTLLFGGGTKLTVL |
| 747 C7 | EDE2 | 81 | EVQLVESGGGLVQPGASLRVSCAASGFTFSTYNMNWVRQAPGKGLEWVSYISSRSSTIYYADSVQGRFTISRDNAKNSLYLQMNSLRAEDTAVYYCARDIGHYYDSSGYFHYSFGMDVWGQGTTVTVSS | 127 | DIVMTQSPLSLPVTLGEPASISCRSSRSLLHSNGYNYLDWYLQKPGQSPQLLIYLGSNRASGVPDRFSGSGSGTDFTLKISRVEAEDVGVYYCMQARQTPVTFGGGTKVEIK |
| 747 D5 | EDE2 | 82 | EVQLVESGGGLVQPGGSLRLSCAASGFIFRNYWMHWVRQAPGKGLVWVSRINGLGSTTTYADSVEGRFTITRDDAKNTIFLQMNSLRAEDTAVYYCARDVNFYDSSGYYREGWFDSWGPGTTVTVSS | 128 | GPFTLSASVGDRVTITCRASRSINTFLNWYQQKTGSAPKLLIYGASTLQSGVPSRFSGSGSGTDFALTITSLQPDDFAAYYCQQSYTTPLTFGGGTRVEIK |

Figure 29 (continued)

| | | | | | |
|---|---|---|---|---|---|
| 747 D11 | EDE2 | 83 | EVQLLESGAEVKKPGSSVKISCKASGGTFSNYAISWVRQAPGRGLEWLGGIIPIFGTPNYAQRFQGRVTITADESTSTAYMELNSLTSDDTAIYYCARDHPTVINPTFVGSWFDPWGQGTLVTVSS | 129 | SYELTQPPSVSVAPGKTATITCGGDNIGSKTVHWYQQKPGQAPLLVIYYNGDRPPGIPERFSGSNSGNTATLTITRVEAGDEADYCCQIWDSRSSHPVFGGGTKLTVL |
| 752 B6 | EDE2 | 84 | QVQLVESGAEVKKPGASVKVSCKASGFTFTSYYIHWVRQAPGQGLEWMGVINPSGGTTIYARNLQGRVTMTRDTSTTTVYMELSSLKSEDTAVYYCARAHSGNYDFWSGSNYHYYYGMDVWGQGTTVTVSS | 130 | DIVMTQSPLSLPVTPGEPASISCRSSQSLLHTNGYNFLDWYVQKPGQSPQLLIYLGSSRASGVPDRFSGSGSGTDFTLKISRVEAEDVGLYYCMQALHTPRTFGQGTKVEIK |
| 752(2) D2 | EDE2 | 85 | EVQLVESGAEVKKPGASVKVSCKASGFTFTSYYIHWVRQAPGQGLEWMGVINPSGGTTIYAQNFQGRVTMTRDTSTTTVYMELSSLKSEDTAVYYCARAHSGNYDFWSGSNYHYYYGMDVWGQGTTVTVSS | 131 | DIVMTQSPLSLPVTPGEPASISCRSSQSLLHTNGYNFLDWYVQKPGQSPQLLIYLGSSRASGVPDRFSGSGSGTDFTLKISRVEAEDVGLYYCMQALQTPRTFGQGTKVEIK |

Figure 29 (continued)

Focus Reduction Neutralization Test (FRNT)

Reagents :
- M3 : MEM containing 3%FCS + L-glutamine and Penicillin/Streptomycin
- Overlayer media : Mix 3% CMC and completed 2xMEM media together in equal volume

Neutralization assay (FACS)

Reagents :

•M3 . MEM containing 3%FCS + L-glutamine and Penicillin/Streptomycin

Focus Reduction Neutralization Test (FRNT)

Reagents :

•M3 · MEM containing 3%FCS + L-glutamine and Penicillin/Streptomycin

•Overlayer media : Mix 3% CMC and completed 2xMEM media together in equal volume

Neutralization assay (FACS)

Reagents :

•M3 : MEM containing 3%FCS + L-glutamine and Penicillin/Streptomycin

| B7_EDE2 (DENV2) | A11_EDE2 (DENV2) | C10_EDE1 (DENV2) | C10_EDE1 (DENV4) | C8_EDE1 (DENV2) |
|---|---|---|---|---|
| N67 | N67 | R2 | R2 | N67 |
| T68 | T68 | H27 | H27 | T68 |
| T69 | T69 | G28 | G28 | T69 |
| T70 | T70 | E44 | G29 | T70 |
| E71 | E71 | L45 | E44 | E71 |
| S72 | S72 | I46 | L45 | S72 |
| R73 | R73 | K47 | T46 | R73 |
| L82 | C74 | N67 | N67 | C74 |
| V97 | E84 | T68 | T69 | Q77 |
| D98 | V97 | T69 | T70 | N83 |
| R99 | D98 | T70 | A71 | E84 |
| W101 | R99 | E71 | T72 | V97 |
| G102 | G102 | S72 | R73 | D98 |
| N103 | N103 | R73 | C74 | R99 |
| G104 | G104 | C74 | Q77 | W101 |
| I113 | C105 | Q77 | V97 | G102 |
| G152 | V114 | S81 | R99 | N103 |
| N153 | N153 | L82 | W101 | G104 |
| D154 | D154 | N83 | G102 | C105 |
| T155 | T155 | E84 | N103 | G106 |
| G156 | G156 | V97 | G104 | L113 |
| K246 | H158 | R99 | C105 | E148 |
| K247 | K246 | W101 | G106 | H158 |
| Q248 | K247 | G102 | V113 | K246 |
| D249 | Q248 | N103 | R247 | K247 |
| | D249 | G104 | Q248 | Q248 |
| | V250 | C105 | D249 | D249 |
| | | G106 | D271 | I308 |
| | | L113 | M278 | K310 |
| | | T115 | D309 | E311 |
| | | K246 | K310 | R323 |
| | | K247 | V324 | D362 |
| | | Q248 | K323 | G374 |
| | | Q271 | K325 | |
| | | V309 | T361 | |
| | | K310 | N362 | |
| | | R323 | | |
| | | Q325 | | |
| | | D362 | | |

Figure 31

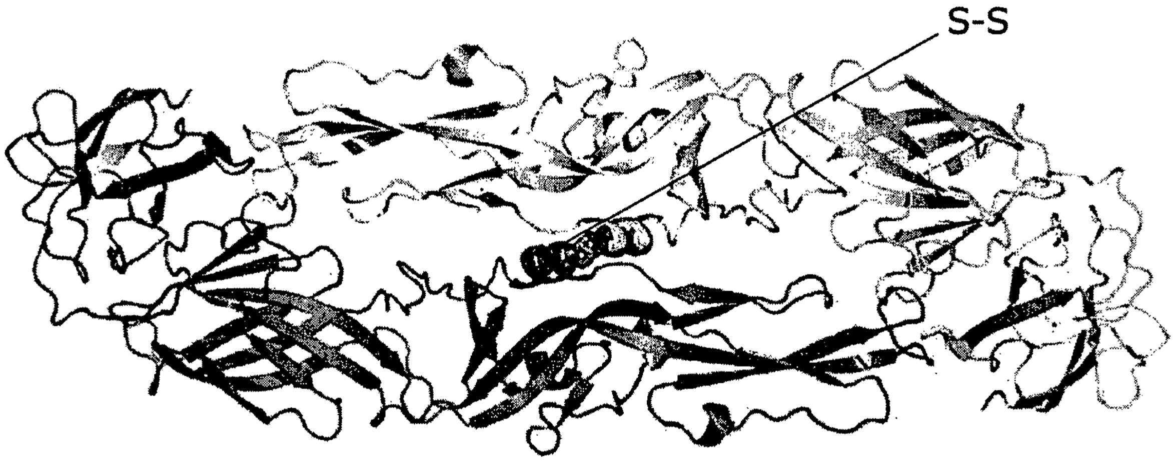
A259C
S255C
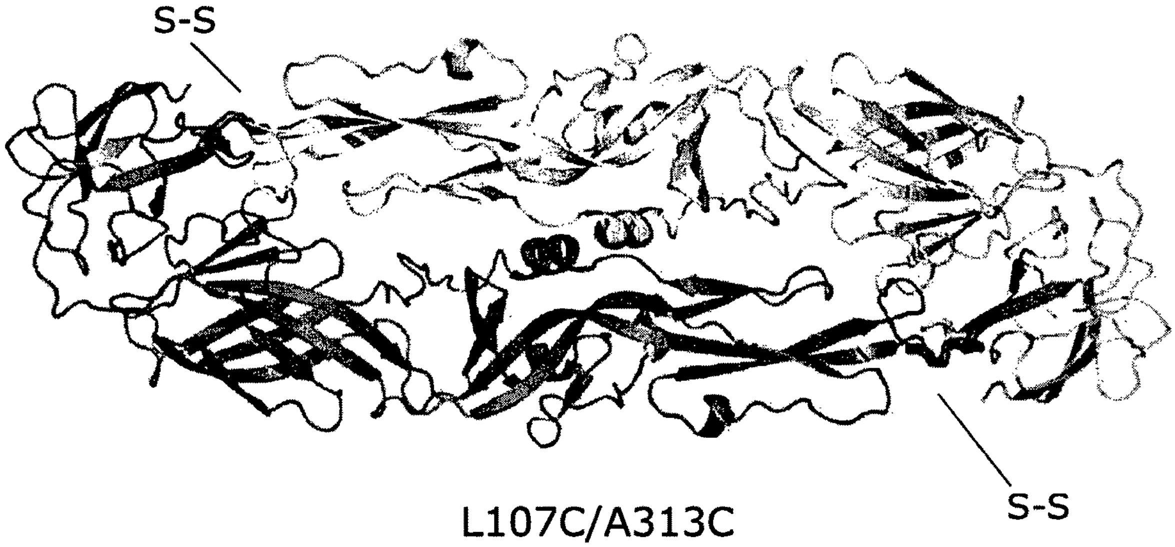
L107C/A313C
Figure 32

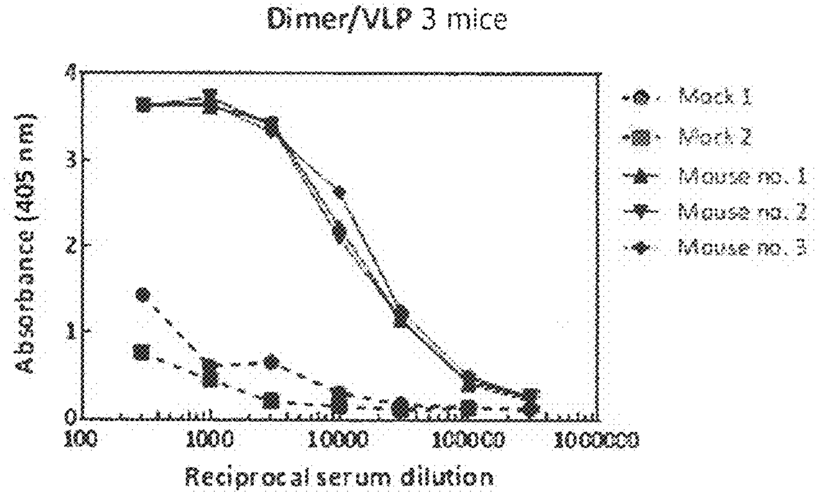
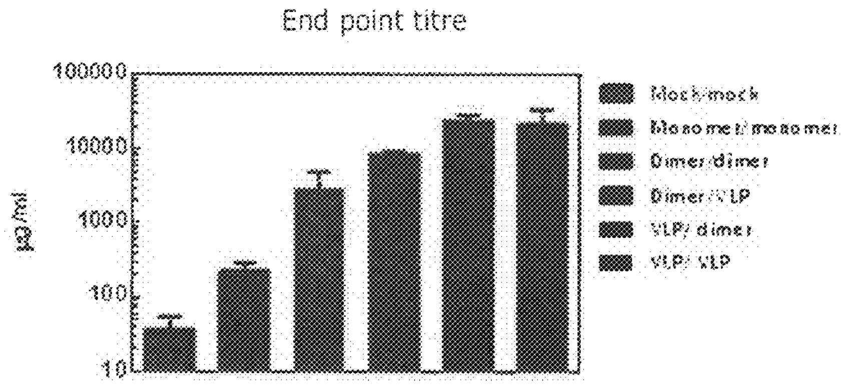
Group 1 monomer/monomer
prime and boost with E WT. E WT
Group 2 dimer/dimer
prime and boost with E A259C mutant
Group 3 VLP/VLP
prime and boost with prM/E viral like particle (VLP)
Group 4 dimer/VLP
prime with E A259C mutant followed by boosting with VLP
Group 5 VLP/dimer
prime with VLP followed by boosting with E A259C mutant
Group 6 mock
non immunisation
Figure 41
(continued)

Figure 42:
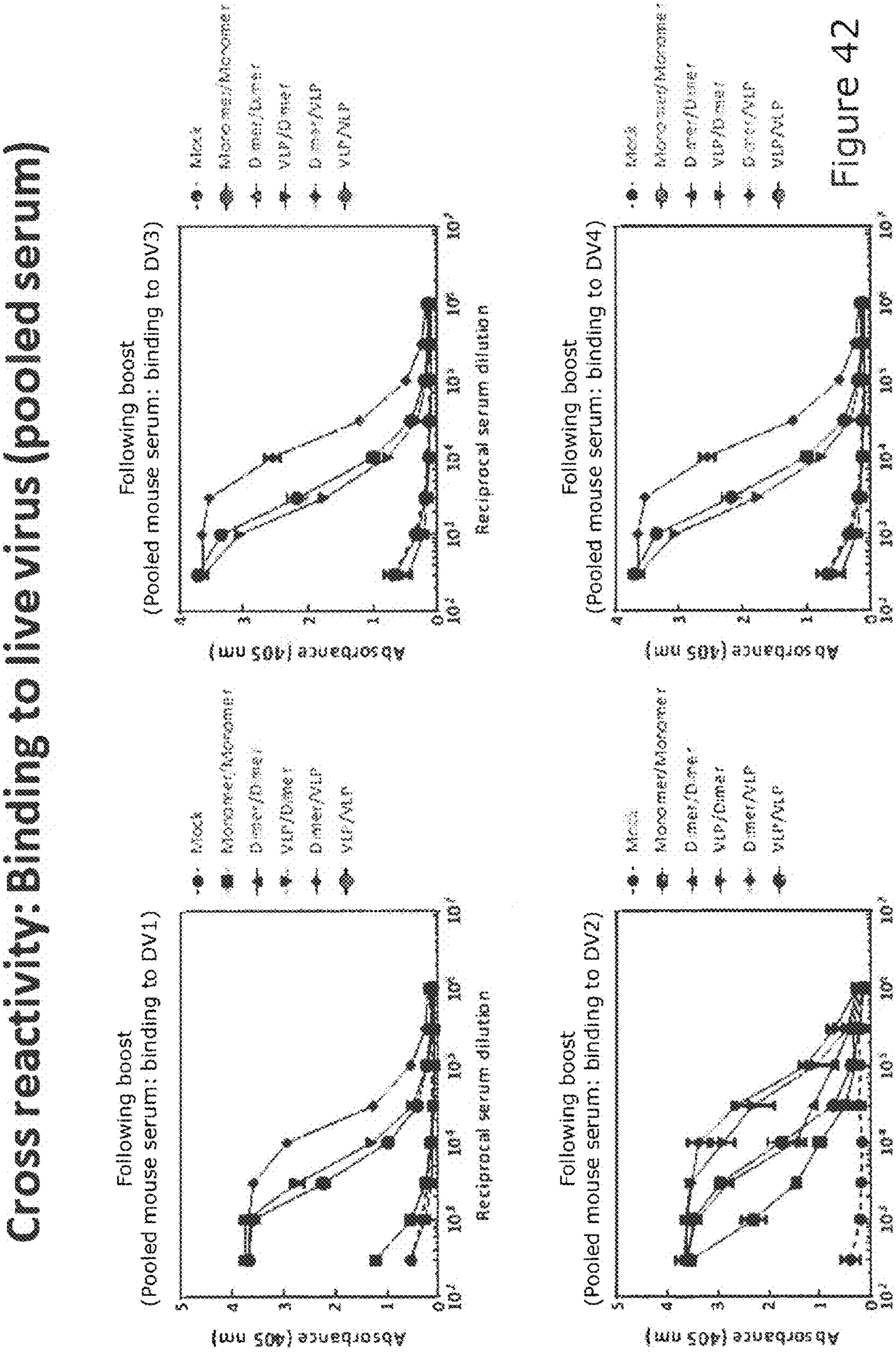

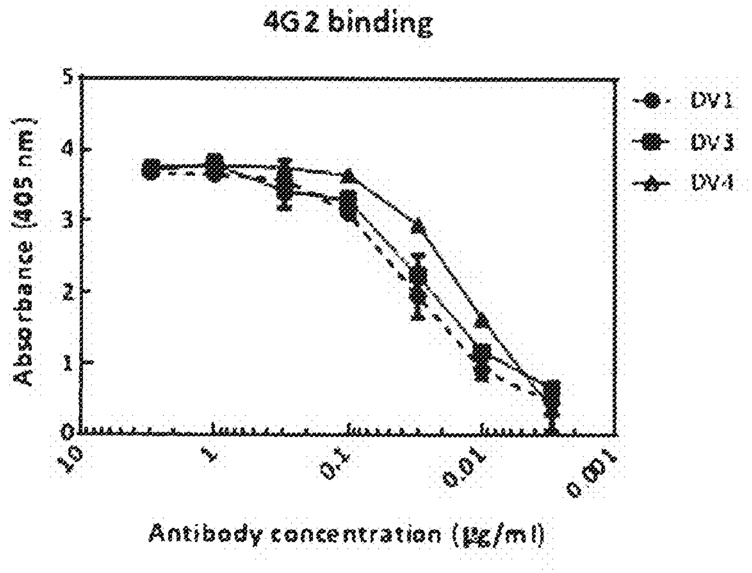
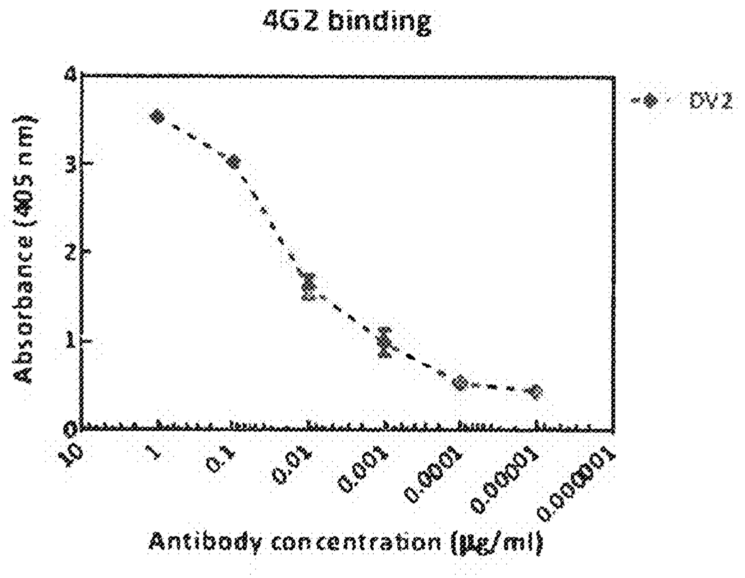
Group 1 monomer/monomer
prime and boost with E WT. E WT
Group 2 dimer/dimer
prime and boost with E A259C mutant
Group 3 VLP/VLP
prime and boost with prM/E viral like particle (VLP)
Group 4 dimer/VLP
prime with E A259C mutant followed by boosting with VLP
Group 5 VLP/dimer
prime with VLP followed by boosting with E A259C mutant
Group 6 mock
non immunisation
Figure 42
(continued)

Figure 43:
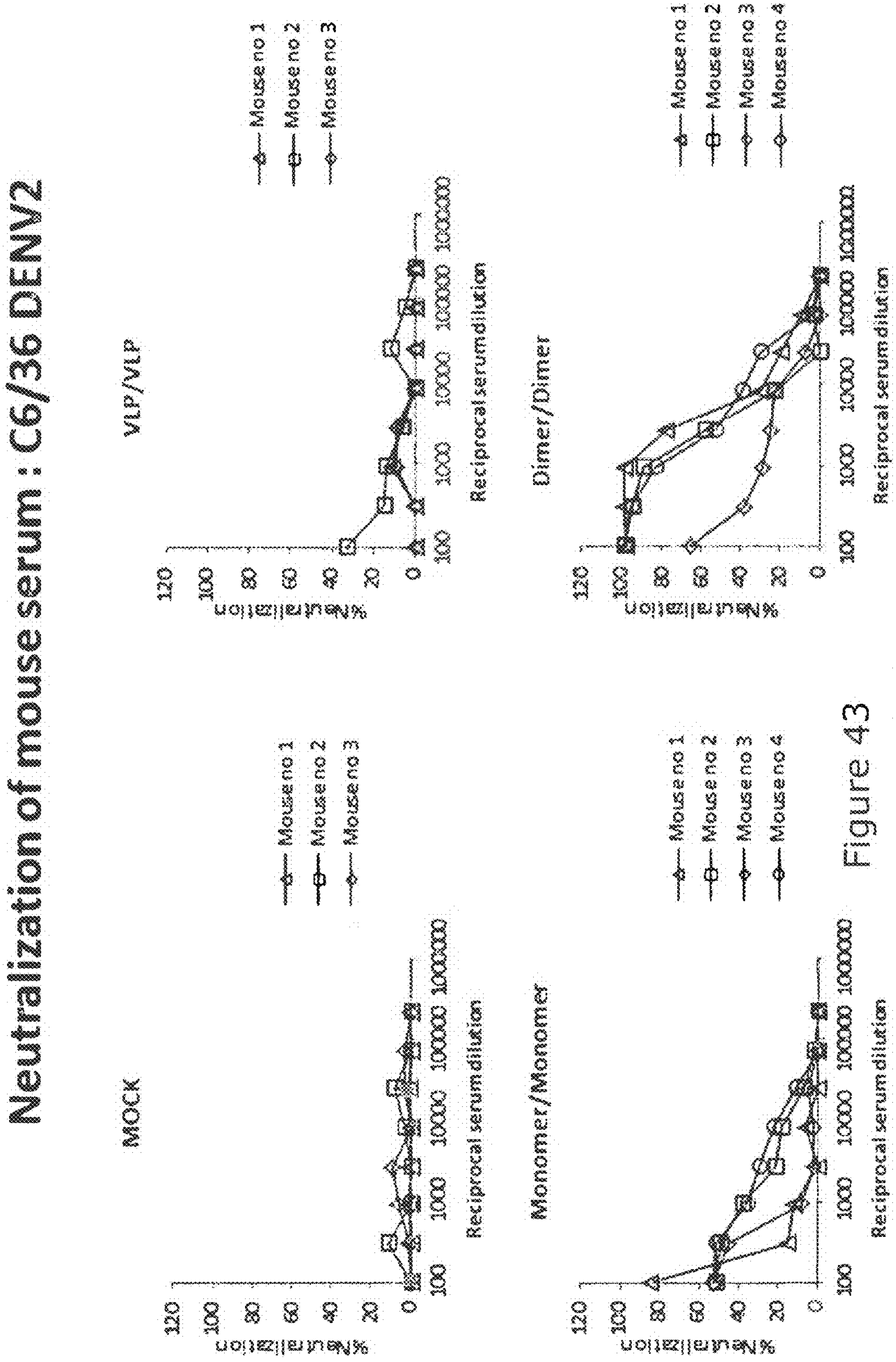

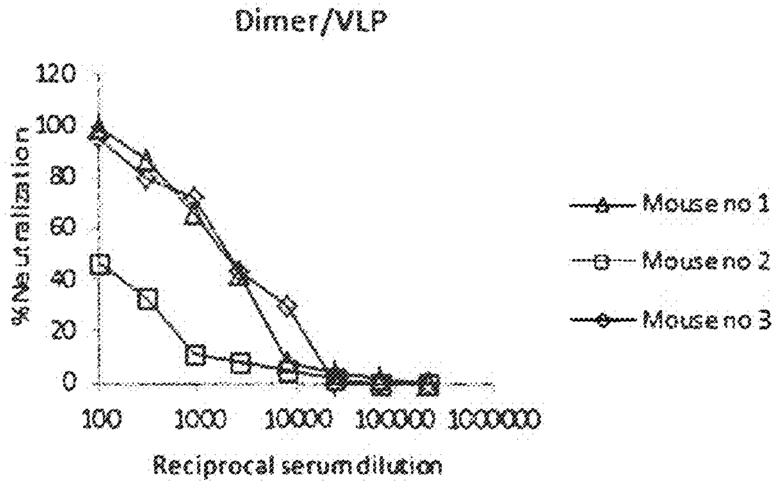
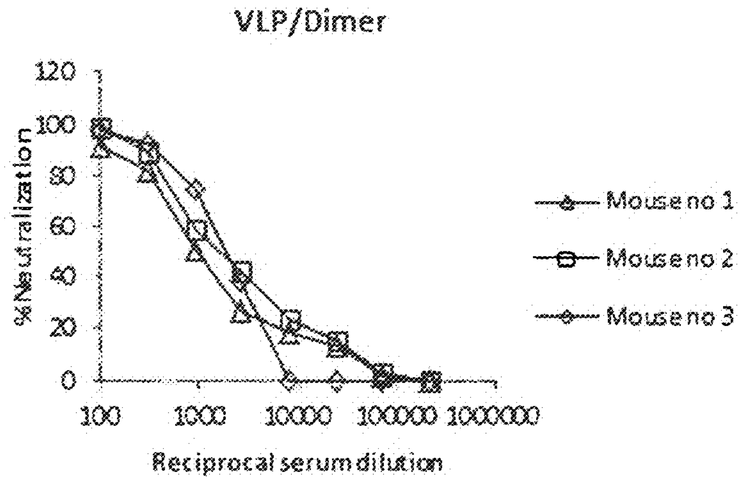
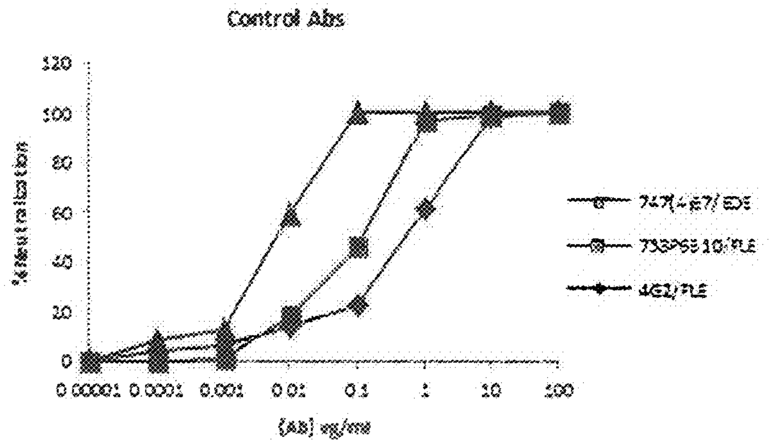
Group1 Monomer/Monomer
prime and boost with E WT
Group2 Dimer/Dimer
prime and boost with E A259C mutant
Group3 VLP/VLP
prime and boost with prM/E virus like particle (VLP)
Group4 Demer/VLP
prime with E A259C mutant followed by boosting with VLP
Group5 VLP/Dimer
prime with VLP followed by boosting with E A259C mutant
Group6 Mock
Non-immunization
Figure 43
(continued)

ADE: Pooled mouse serum: U937
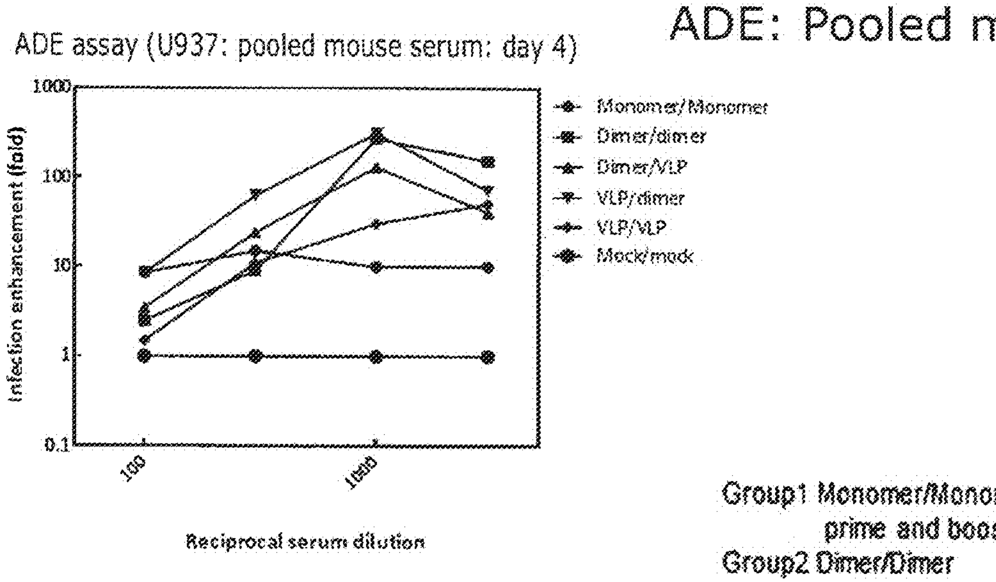
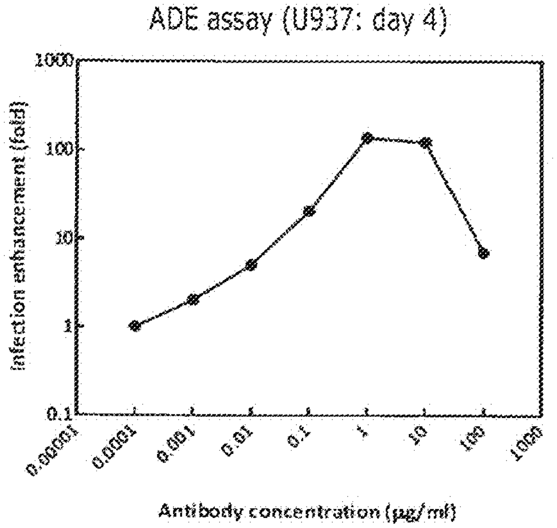
Group1 Monomer/Monomer
prime and boost with E WT
Group2 Dimer/Dimer
prime and boost with E A259C mutant
Group3 VLP/VLP
prime and boost with prM/E virus like particle (VLP)
Group4 Demer/VLP
prime with E A259C mutant followed by boosting with VLP
Group5 VLP/Dimer
prime with VLP followed by boosting with E A259C mutant
Group6 Mock
Non-immunization
Figure 45

ANTI-DENGUE VACCINES AND ANTIBODIES

CROSS-REFERENCE TO RELATED APPLICATIONS

This application is a divisional of U.S. application Ser. No. 15/328,441, filed Aug. 21, 2017, which is a 371 application of International Application No. PCT/GB2015/052139, filed Jul. 23, 2015, which claims priority to and benefit of G.B. Application No. 1413086.8, filed Jul. 23, 2014, the disclosures of which are hereby incorporated herein by reference in their entirety.

STATEMENT REGARDING FEDERALLY SPONSORED RESEARCH OR DEVELOPMENT

This invention was made with government support under grant agreement No. 232378 awarded by the European Union Seventh Framework Programme FP7/2007-2011. The government has certain rights in the invention.

REFERENCE TO SEQUENCE LISTING

The Sequence Listing submitted Oct. 26, 2021, as a text file named "ICOBY_P58870USDIV_ST25.txt," created on Dec. 4, 2019, and having a size of 185,651 bytes is hereby incorporated by reference.

FIELD OF THE INVENTION

The invention relates to the field of treatment and prevention of Dengue virus infection and related compounds and methods.

SUMMARY

Dengue infects nearly 400 million people annually[1], with symptoms in 25% of infections ranging from mild disease (dengue fever) to severe cases such as dengue haemorrhagic fever. The etiological agents are four serologically related viruses from the flavivirus genus[2], termed dengue virus serotypes 1-4 (DENV1-4). Infection with one serotype leads to lifelong protection against that serotype but not against the other serotypes. There is epidemiological evidence that severe disease is more likely to occur during a secondary infection than during the first or primary DENV infection[3-4]. The enhancement of disease upon secondary infection and the need to protect against four diverse serotypes sets a high bar for vaccines, which are urgently needed to protect against the 400 million infections estimated to occur annually[1,5,6].

Most DENV vaccines in development aim to raise virus neutralizing antibodies and the DENV envelope is the main focus of this effort 8,9 The envelope protein is responsible for receptor binding and subsequent receptor-mediated endocytosis. In the acidic environment of the endosome, envelope protein catalyses a membrane fusion reaction between the viral envelope and the endosomal membrane, thereby releasing the viral genomic RNA into the cytoplasm. The envelope protein is about 500 amino acids long, with a large N-terminal ectodomain and two transmembrane (TM) helices at the C-terminal end. Its overall structure is conserved among all flaviviruses, with an amino acid sequence identity of approximately 65% between the most distant viruses within the dengue group, all of which display two conserved N-linked glycosylation sites at positions N67 and N153. The 400 amino terminal residues of the ectodomain of the envelope protein (termed "sE" for "soluble E") fold into a β-sheet rich three-domain structure typical of class II viral fusion proteins, which form head-to-tail homodimers[5-7] that coat the surface of mature virions[8,9]

The crystal structure of the envelope glycoprotein ectodomain from dengue virus serotypes 2, 3 and 4 are available in the PDB (Protein Data Bank) database under the accession numbers 1OAN, 10K8 for dengue virus serotype 2, 1UZG for dengue virus serotype 3 and 3UAJ for dengue virus serotype 4.

However, antibody recognition of DENV particles is complicated by a number of dramatically different compositions and conformations of the virus capsid that are displayed at different phases of the virus life cycle[11,12]. The "immature" virus particle has a full complement of precursor membrane protein (prM) in 1:1 association with envelope and the virion adopts a characteristic spiky appearance where each spike is made up of a trimer of prM/E proteins[11-15].

Following furin-mediated prM cleavage the "mature" virus particle adopts a smooth appearance with 90 closely packed dimers of envelope protein arranged around 2, 3 and 5 fold axes of symmetry; an expansion of these mature particles into a "bumpy" form upon exposure to temperatures above 34° C., in which the envelope protein dimers rearrange with respect to each other, has also been recently described[16, 17]. Following internalization into early endosomes, the acidic environment triggers a major conformational change of the envelope protein, which exposes the fusion loop and then trimerizes irreversibly to induce membrane fusion[18,19].

An important and additional level of complexity is that prM cleavage is frequently incomplete leading to a population of viruses with varying degrees of cleavage[15, 20]. Viruses containing high levels of prM are not infectious whereas viruses with lower levels of prM are still infectious and furthermore it has been demonstrated that high-prM non-infectious particles can be driven to infect by antibody dependent enhancement[21,22].

It is currently unclear as to what the epitope is that most human neutralising antibodies target, for example de Alwis[27] suggests the epitope requires virus assembly for formation, whilst Rey[81] suggests that the envelope dimer itself is the target.

Antibody dependent enhancement of DENV infection (ADE) is one of the mechanisms postulated to increase the severity of disease upon secondary infection 23 Antibody formed to the primary infection is proposed to opsonize but not fully neutralize virus and promote Fc receptor mediated uptake into myeloid cells driving higher virus loads in secondary infection. ADE can be seen at sub-neutralizing concentrations of almost all antibodies and its perceived risk complicates vaccine strategies in DENV.

The leading dengue vaccine candidates currently being tested in clinical trials consist of tetravalent formulations of live attenuated dengue or dengue/yellow fever chimeric viruses 24, 25 Raising balanced tetravalent immunity without unacceptable reactogenicity has proved challenging. The most advanced dengue vaccine candidate returned much lower vaccine efficacy than anticipated in a recent phase II clinical trial 4, and did not protect against DENV-2, whilst in a phase III study the vaccine reduced the incidence of disease by 56% (sanofipasteur.com/en/articles/theworld-s-first-large-scale-dengue-vaccine-efficacy-study-successfully-achieved-its-primary-clinical-endpoint.aspx); Capeding et al (2014) Lancet Published online Jul. 11, 2014 dx.doi.org/10.1016/S0140-6736 (14) 61060-6, leaving approximately half the population exposed to the disease. This disparity creates a pressing need to understand the human antibody response in natural dengue infection and following vaccination, and in particular to identify the epitopes recognized by the most potent cross-reactive antibodies generated in humans and understand the correlates with protection from disease. It is therefore crucial to provide a dengue vaccine including the epitopes recognized by the most potent cross-reactive antibodies generated in humans.

Recent evidence has indicated that the dengue virus (DENV)-specific serum Ab response in humans consists of a large fraction of cross-reactive, poorly neutralizing Abs and a small fraction of serotype-specific, potently inhibitory antibodies[27], which bind to a complex, quaternary structure epitope that is expressed only when envelope proteins are assembled on a virus particle, implying that in order to stimulate an effective immune response, an intact viral particle is required.

In contrast to this recent evidence, the inventors of the present invention have surprisingly identified and characterised human antibodies obtained by isolating rearranged heavy- and light-chain genes from sorted single plasmablasts of patients infected with dengue virus which were found to be potently neutralising cross-reactive antibodies. In addition, the epitope to which these antibodies bind was found to be limited to the envelope protein dimer, and did not require full virus assembly. A subunit vaccine comprising a stabilized soluble protein E dimer is therefore a good candidate for a successful dengue vaccine, avoiding eliciting antibodies against poorly immunogenic regions that are normally not accessible at the surface of an infectious virion.

The invention, as described below, provides compounds, compositions, methods, uses and vaccines in relation to the newly identified antibodies and antigen.

The inventors characterized 145 human monoclonal antibodies from patients with a dengue infection. The acute human antibody response was found to be focused on two major epitopes; one of which is well described on the fusion loop, and a second novel epitope found on intact virions or dimers of envelope protein, which encompasses areas of domains I, II and III. Antibodies reactive with this epitope, the Envelope Dimer Epitope, or EDE, were found to be able to fully neutralise virus made in both insect and primary human cells in the low picomolar range. This novel epitope has wide ranging implications for the treatment and prevention of diseases caused by the dengue virus.

The invention will be described below with reference to various embodiments of different aspects of the invention. It is appreciated that certain features of the invention, which are, for clarity, described in the context of separate embodiments, may also be provided in combination in one or more embodiments or in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

Thus, in a first aspect of the invention, a compound is provided that neutralises dengue virus of more than one serotype of dengue virus.

Preferably the compound neutralises the dengue virus of two serotypes of dengue virus, more preferably three types of dengue virus and most preferably four serotypes of dengue virus ie all serotypes of dengue virus, for example neutralises two or more serotypes of dengue virus from the list comprising DENV-1, DENV-2, DENV-3 and DENV-4.

By a compound we mean any compound that can neutralise more than one serotype of Dengue virus. The compound may, for example, be a small molecule, a polypeptide or protein (which terms are used interchangeably herein), including a glycoprotein, a nucleic acid, a carbohydrate, a fat, an element, for example a metal. In a preferred embodiment the compound is a polypeptide, preferably an antibody or antigen binding portion thereof. The antigen binding portion may be a Fv fragment; a Fab-like fragment (e.g. a Fab fragment, a Fab' fragment, a $F(ab)_2$ fragment, Fv or scFv fragments); or a domain antibody. The antibody binding portion may be derived from the linear amino acid sequence present in an intact antibody, or may comprise a set of non-consecutive amino acids, optionally interspersed with other amino acids, for example may comprise particular amino acids that are required for contact with an epitope, but may for example not comprise the amino acids required for the framework of a native antibody, which, in some cases, may be replaced by a heterologous scaffold protein, for example. An antibody according to the present invention is obtainable by a method comprising a step of immunizing a mammal, such as a human, a monkey, a rabbit or a mouse; and/or by an in vitro method, for example comprising a phage display selection step, as will be well known to those skilled in the art.

By antibody we include the meaning of a substantially intact antibody molecule, as well as a chimeric antibody, humanised antibody (wherein at least one amino acid is mutated relative to a non-human antibody, for example a naturally occurring non-human antibody or antibody assembled from non-human antibody sequences), single chain antibody, bi-specific antibody, antibody heavy chain, antibody light chain, homo-dimer or heterodimer of antibody heavy and/or light chains, and antigen binding portions and derivatives of the same.

When the compound is a protein, for example an antibody or fragment thereof is administered to a human subject and if the antibody is not a human antibody or fragment thereof, then it can be humanized in order to reduce immunogenicity in human. Methods for producing humanized antibodies or fragments thereof are known in the art (Vinckle et al., 2009).

Further, the bioavailability of the antibody or fragment thereof according to the present invention can be improved by conjugating the neutralizing antibody or fragment thereof to inert carriers like albumin (Coppieters et al, 2006) or immunoglobulins (Harmsen et al., 2005).

The term antibody also includes all classes of antibodies, including IgG, IgA, IgM, IdD and IgE. The term antibody also includes variants, fusions and derivatives of any defined antibodies and antigen binding portions thereof.

The compound may alternatively be a cyclic peptide, for example a polycyclic peptide, for example a bicyclic peptide, for example as described in MILLWARD STEVEN W ET AL: “Design of cyclic peptides that bind protein surfaces with antibody-like affinity”, ACS CHEMICAL BIOLOGY, vol. 2, no. 9, 1 Jan. 2007 (2007-01-01), pages 625-634, XP002616292, AMERICAN CHEMICAL SOCIETY, WASHINGTON, DC, US ISSN: 1554-8929, DOI: 10.1021/

CB7001126; HEINIS CHRISTIAN ET AL: "Phage-encoded combinatorial chemical libraries based on bicyclic peptides" NATURE CHEMICAL BIOLOGY, vol. 5, no. 7, July 2009 (2009-07), pages 502-507, XP007913181. See also, for example WO2009098450. Bicyclic peptides with required binding properties can be selected by, for example, phage display techniques. By neutralise we mean reduce the ability of the virus to infect previously uninfected cells.

The person skilled in the art will be well aware of suitable techniques to monitor the viral neutralising ability of a compound. One example of such a method is detailed in Example 3 and involves allowing one or more serotypes of dengue virus to infect a population of potential host cells, wherein the compound under assay is mixed with the virus, and then the mixture is incubated with the potential host cells. The number of cells infected is assayed which gives a measure of the neutralising ability of the compound, i.e. the ability of the compound to prevent infection In one particular example the neutralising potential of a compound, for example an antibody or antigen binding portion thereof can be determined using the Focus Reduction Neutralization Test (FRNT), where the reduction in the number of the infected foci is compared to control (no compound)[22]. Briefly, the compound is mixed with the virus and incubated for 1 hr at 37° C. The mixtures are then transferred to Vero cells (kidney epithelial cell line from the African Green Monkey) and incubated for 3 days. The focus-forming assay can be performed using anti-E mAb (4G2) followed by rabbit anti-mouse IgG, conjugated with HRP. The reaction can be visualized by the addition of DAB substrate. The percentage focus reduction is calculated for each compound. 50% FRNT values can be determined from graphs of percentage reduction versus concentration of compound using the probit program from the SPSS package. Typically the assay may be performed so that there are approximately 100 foci in the absence of the test compound, for example in a 96 well plate well with confluent cells, for example just-confluent cells.

Other such examples will be known to those skilled in the art, for example foci reduction neutralisation testing (FRNT); plaque reduction neutralisation testing (PRNT; see WHO document whqlibdoc.who.int/hq/2007/who_ivb_07.07_eng.pdf; FRNT; techniques using flow cytometry and in vivo such as mice and monkeys. See, for example, FIG. 30 of WO 2016/012800 for examples of FRNT and flow cytometry methods. See also the Examples of the present specification.

In one embodiment, the compound neutralises the virus to at least 80%, preferably 90%, more preferably 95% and most preferably 100%. In a more preferred embodiment, the compound neutralises all serotypes of dengue virus to at least 80%, preferably 90%, more preferably 95% and most preferably 98%, 99% or 100%. The virus may be produced by insect cells or in human cancer cell lines (typically considered to produce high pr-M containing virus, as discussed further below); or alternatively in human primary cells, for example primary human dendritic cells, or in cell lines over-expressing furin (which are considered to make low-pr-M containing virus).

By neutralise to a particular level, we include the meaning of neutralise to a particular level for a given concentration of compound. It will be appreciated that an appropriate concentration of a given compound may depend on the actual compound. For example, the concentration of the given compound, for example as used in the assay above, may be no more than 100 mM, 10 mM, 1 mM, 100 μM, 10 μM, 1 μM, 100 nM, 10 nM or 1 nM; or no more than 0.01 μg/ml, 0.02 μg/ml, 0.04 μg/ml, 0.05 μg/ml, 0.06 μg/ml, 0.075 μg/ml, 0.1 μg/ml, 0.25 μg/ml, 0.5 μg/ml, 0.75 μg/ml, 1 μg/ml, 1.25 μg/ml, 1.5 μg/ml, 1.75 μg/ml, 2 μg/ml, 2.25 μg/ml, 2.5 μg/ml, 2.75 μg/ml, 3 μg/ml, 3.25 μg/ml, 3.5 μg/ml, 3.75 μg/ml, 4 μg/ml, 4.25 μg/ml, 4.5 μg/ml, 4.75 μg/ml, 5 μg/ml, 5.25 μg/ml, 5.5 μg/ml, 5.75 μg/ml, 6 μg/ml, 6.5 μg/ml, 7 μg/ml, 7.5 μg/ml, 8 μg/ml, 8.5 μg/ml, 9 μg/ml, 9.5 μg/ml or 10 μg/ml, or less than 0.01 μg/ml. Typically the concentration of the compound, for example an antibody, may be less than 1 μg/ml, for example.

For example, a compound (for example an antibody) may neutralise the one or more serotypes of the virus to 80% at a compound concentration of 0.1 μg/ml, and may neutralise one or more serotypes of the virus to at least 98%, for example 100%, at a compound concentration of 1 μg/ml. Preferably the compound (for example an antibody) neutralises one or more serotypes of the virus to 80% at a concentration of 0.05 μg/ml, or neutralises one or more serotypes of the virus to at least 98%, for example 100%, at a concentration of 0.5 μg/ml.

It will also be appreciated that the level of neutralisation observed for a given concentration of a compound may depend on the number of viral particles in the assay. For example, it may be expected that for a given concentration of compound, if the number of viral particles in the assay is doubled, then the level of neutralisation may reduce (for a given population of host cells). The number of viral particles in the assay will typically be such as to provide around 100 foci in the absence of the test compound, for example in a 96 well microtire plate well, for example with confluent cells, for example just-confluent cells.

For example, in one embodiment, the compound neutralises one or more serotypes of the virus at a concentration of 1 μg/ml or 0.05 μg/ml or less to a level of at least 80%, or to a level of 100% when the viral concentration is sufficient to produce around 100 foci in the absence of the test compound for example in a 96 well microtire plate well, for example with confluent cells, for example just-confluent cells.

The number of cells in the assay which may be infected by the virus may also influence the apparent level of neutralisation. For example, a small number of cells may exhibit a larger infection rate, expressed per cell, than a large population of cells. Therefore the ratio of compound, virus and host cell number may also be important. The cells used in the assay may be confluent. The assay may be carried out in a microtitre well plate, for example in a 96-well microtitre plate. The cells may be confluent, for example, just-confluent in the container, for example a microtitre plate well, for example a well of a 96-well microtitre plate.

Preferably, the compound is able to neutralise virus made in both insect cells, for example C6/36 insect cells, or human tumour cell lines (which may typically produce high pr-M containing virus) and human cells, for example primary human cells, for example primary human dendritic cells, or cells which overexpress furin (which are considered to make low-pr-M containing virus). The production of a virus particle, sub-viral particle or a virus-like particle in different cell types will be well known to the person skilled in the art. For example The ability of the compound to neutralise the virus can be tested as detailed above and in the examples. In one embodiment the compound is able to neutralise the virus made in primary human cells, for example primary human dendritic cells, or in insect cells. In another embodiment the compound is able to neutralise the virus made in primary human and insect cells to the same level. By to the same level we include the meaning that for a given concentration of compound and/or given concentration of virus and/or given number of potential host cells, the level of neutralisation caused by the compound is not significantly different for virus made in both insect and primary human cells, or that the level of neutralisation caused by the compound is over a particular threshold for example over 80%, 90%, 95% or 98% neutralisation in virus from both insect and primary human cells. For example, for a given concentration of viral particles, and a given number of potential host cells, the 50% FRNT is the same (not significantly different) for virus made in insect and primary human cells, for example is 0.05 μg/ml or lower, or 0.5 μg/ml or lower or 1 μg/ml or lower or 5 μg/ml or lower. In a preferred embodiment, the compound is able to neutralise more than one serotype of dengue virus made in primary human and insect cells, preferably two serotypes, preferably three serotypes, more preferably four serotypes or all serotypes. In a most preferred embodiment the compound is able to fully neutralise (i.e. to 100%) all serotypes of dengue virus made in both insect and primary human cells. For example, the compound can neutralise virus made in both primary human and insect cells to 100%, at a viral concentration sufficient to yield around 100 foci, as discussed above at a compound concentration of 0.05 μg/ml. By made in both primary human and insect cells we include the meaning of virus made independently in primary human cells (for example), and virus made independently in insect cells rather than a particular population of viral particles that have been produced using both primary human and insect cells in the same procedure.

The cross-reactive, highly neutralising compounds identified in the present invention were found to bind to a specific epitope which can be found on both the intact virus and a dimer of envelope protein, independently of virus formation. Thus, the compounds of the present invention can be defined in terms of their ability to bind to this specific epitope.

Thus, in a further aspect of the invention is provided a compound that binds to an Envelope Dimer Epitope (EDE) of a Dengue virus. By EDE we include the meaning of any EDE herein defined.

By a compound that binds to an Envelope Dimer Epitope (EDE) we mean any compound that can bind to the EDE of a Dengue virus, of one or more serotypes. The compound may be a small molecule, a polypeptide, a nucleic acid, a carbohydrate, a fat, an element, for example a metal. In a preferred embodiment the compound is a polypeptide, preferably an antibody or antigen binding portion thereof. Preferences for the compound are as detailed earlier.

There are four serotypes of dengue virus. Thus it will be appreciated that the compound may bind to the EDE of one serotype of dengue virus. In a preferred embodiment, the compound will bind to the EDE of more than one serotype of dengue virus, and will bind to two serotypes of dengue virus, or three serotypes of dengue virus, or four serotypes of dengue virus, ie considered to be all serotypes of dengue virus, as discussed above.

By "bind" we include the meaning of any form of non-covalent bonding between a compound of the invention and an epitope or molecule or macromolecule or compound, and we include the meaning of any significant degree of binding to the EDE as assessed by methods usual in the art. In a preferred embodiment the compound selectively binds the EDE. By selectively binds the EDE we include the meaning that the compound does not, or does not significantly, bind the dengue virus or envelope protein other than on the EDE. We also include the meaning that the compound does not bind to, or does not significantly bind to, another compound or molecule or macromolecule other than one displaying the EDE Determining whether or not the compound binds the EDE will be well within the skill remit of a person skilled in the art. For example, an ELISA-type assay may be used, as well known to those skilled in the art. One non-limiting example of a method to determine whether the compound binds the EDE is as follows: Intact virus, of one or more, preferably of all serotypes of dengue virus, and/or the envelope dimer of one or more, preferably of all serotypes of dengue virus, and/or the EDE according to any of the definitions described herein, for example a stabilised envelope dimer, or an EDE comprising residues from the envelope protein held within a heterologous scaffold; and mock uninfected supernatant are captured separately onto a solid support, for example a MAXISORP immunoplate (NUNC) coated anti-E Abs (4G2). The captured wells are then incubated with the compound, for example an antibody or antigen binding portion thereof, for example a human monoclonal antibody, for example 1 μg/ml of a human mAb, followed by incubation with a secondary antibody (that binds to the compound) conjugated to a reporter, for example ALP-conjugated anti-human IgG. The reaction is visualized by, for example the addition of a suitable substrate, for example PNPP substrate, and stopped with NaOH. For ALP/PNPP the absorbance is measured at 405 nm.

By a compound that binds to the EDE we include the meaning of any compound which binds to the wells containing the virus or EDE, for example stabilised soluble protein E dimer, to any degree above the level of background binding to the wells containing uninfected supernatant. Preferably the level of binding obtained to the virus or EDE, for example stabilised soluble protein E dimer, is 2 times the level of background binding to the uninfected supernatant wells, preferably 4 times, preferably 6 times, more preferably ten times. To determine if the compound binds to the virus or envelope protein at a site other than the EDE, the ability of the compound to bind to the denatured or monomeric or recombinant envelope protein may be assessed. If the compound binds to the denatured or monomeric or recombinant envelope protein to a significant level, it is deemed to bind to the virus or envelope protein at a site other than the EDE. To determine whether the compound selectively binds the EDE rather than any other molecule or macromolecule or compound, the ability of the compound to bind the EDE can be compared to the ability of the compound to bind to a molecule or macromolecule or compound using the above detailed method. A compound selectively binds the EDE if it binds the EDE to a significantly greater extent than it binds to another molecule or macromolecule or compound, for example denatured or monomeric envelope protein, for example if the compound binds to the EDE with at least 2 times, 4 times, 6 times, 8 times or 10 times greater affinity than it binds to another molecule, macromolecule or compound, for example denatured or monomeric or recombinant envelope protein.

The EDE is an epitope which is considered to be formed on an intact viral particle spanning a dimer of envelope proteins, or on a free dimer of envelope proteins, for example on a free dimer of soluble envelope proteins, spanning the two polypeptides. The envelope protein sequence is detailed in FIG. 29 and SEQ ID No: 29, 31, 33 and 35.

In a preferred embodiment, the compound of the invention binds the EDE, either on the intact virus or on the free envelope dimer (ie having a molecular weight of twice that of an envelope polypeptide monomer), or other structure providing the EDE, as indicated above and discussed further below, and does not bind to the monomeric envelope protein, or denatured envelope protein. In one embodiment, if the compound binds to the monomeric envelope protein or denatured envelope protein, it is not considered a useful compound and is not a compound of the invention. Accordingly, one non-limiting method of identifying whether a compound is a compound of this embodiment of the invention is, for example, by assaying a compound, for example an antibody or antigen binding portion thereof, for its ability to bind to denatured envelope protein, for example on a western blot, and/or recombinant (monomeric) envelope protein, for example in an ELISA, and intact virus particles, and/or a dimer of envelope protein (for example a dimer of soluble envelope protein), for example in an ELISA. Preferred compounds of the invention are considered to bind to the intact virus or non-denatured dimer, but not (or to a significantly lesser extent) to denatured or monomeric envelope protein. The degree of binding can be assessed as described above.

A compound which binds to the fusion loop, and not to the EDE is not considered to be a compound of the invention. The fusion loop is a restricted set of residues in and around 101W defining the previously described or classical fusion loop epitope (FL). In the fusion loop, residues 101-WGNG-104 make a distorted $\alpha$-helical turn that projects the W101 side chain towards domain III across the dimer interface. If a compound binds to the envelope monomer or to denatured envelope protein (for example determined as described above), it may be considered to bind to the fusion loop, though it is possible that the antibody may instead bind to a different part of the envelope polypeptide (which could be checked by binding to envelope polypeptide mutated in the fusion loop region).

In another embodiment, a compound which binds the fusion loop is one which is unaffected (or not significantly affected) by mutation at any one or more of the following residues in the envelope protein, particularly DENV-1: E49, Q77, I161, T200, W391 or F392.

A compound of the present invention, in some embodiments, does not bind to the denatured EDE, or denatured envelope protein.

In one embodiment the EDE is considered to span the polypeptides of a dengue virus envelope polypeptide dimer, for example a soluble envelope polypeptide dimer. In a particular embodiment the EDE comprises areas of domains I, II and III of an envelope polypeptide dimer. It will be appreciated that the EDE comprises a quaternary structure dependent epitope at the dimer interface of the envelope proteins of one or more serotypes of the Dengue virus.

It will be appreciated that envelope proteins from different dengue serotypes can dimerise, forming a hybrid dimer. As such, the EDE that the compound binds to in one embodiment is made from envelope monomers derived from different dengue serotypes and as such the EDE may comprise a homodimer or heterodimer.

It will also be appreciated that the EDE could be presented to the compound as part of a virion or a sub-viral particle or a virus-like particle, as the dimer of envelope protein is found on the intact virion or virus like particle. Where the EDE is presented as part of a virion or a sub-viral particle or a virus-like particle, the compound of the present invention is one that binds the intact virion or sub-viral particle or virus-like particle, but does not bind monomeric or denatured envelope protein.

Alternatively, the EDE could be presented to the compound not as part of a virion, for example the EDE which is formed from a dimer of two envelope proteins could be presented to the compound as a free dimer. Thus, in one embodiment, the compound of the invention is a compound which binds to the EDE, when the EDE is a free dimer of envelope or soluble envelope (sE) protein. In another embodiment, the compound of the invention is a compound which binds to the EDE when the EDE is a stabilised dimer of envelope or sE protein.

The free dimer may be presented as part of a composition comprising elements that stabilise the dimerization of the proteins. For example, particular buffer components considered to promote protein association may be used. Alternatively, the envelope protein may be presented at high concentrations which promote dimer formation (see Example 7).

In addition to external agents which stabilise the envelope dimer, the envelope protein may be engineered to have increased stability in the dimer configuration. For example, the dimer may be:

- covalently stabilized with at least one, optionally 2, 3, 4, 5, 6, 7, 8, 9, or 10 or more disulphide inter-chain bond between the two envelope or sE monomers and/or,
- covalently stabilized with at least one, optionally 2, 3, 4, 5, 6, 7, 8, 9, or 10 or more sulfhydryl-reactive cross-linker between the two sE monomers and/or,
- covalently stabilized by linking the two envelope or sE monomers through modified sugars; and/or,
- non-covalently stabilized by substituting at least one amino acid residue in the amino acid sequence of at least one envelope or sE monomer with at least one bulky side chain amino acid, at the dimer interface or in domain 1 (D1)/domain 3 (D3) linker of each monomer.

A dengue virus envelope glycoprotein E ectodomain (sE; soluble envelope polypeptide/glycoprotein) refers to the 1-395 amino acid fragment of the envelope glycoprotein E of the dengue virus serotypes 1, 2 and 4, and to the 1-393 amino acid fragment of the envelope glycoprotein E of the dengue virus serotype 3.

In a preferred embodiment, the compound binds to the EDE wherein the EDE is a stabilised dimer of sE, wherein the recombinant dengue virus envelope glycoprotein E ectodomain (recombinant sE) monomer is selected from the group consisting of: the DENV-1 sE of SEQ ID NO: 132, the DENV-2 sE of SEQ ID NO: 133 the DENV-3 sE of SEQ ID NO: 134, the DENV-4 sE of SEQ ID NO: 135 and a mutant sE thereof having at least one mutation (substitution) selected among H27F, H27W, L107C, F108C, H244F, H244W, S255C, A259C, T/S262C, T/A265C, L278F, L292F, L294N, A313C (S313C in DEN3) and T315C. These mutations are considered to contribute to increased stability in the dimer configuration, as detailed below.

Optionally, said mutant sE thereof has further at least one mutation (substitution) selected among Q227N, E174N and D329N, preferably the three mutations Q227N, E174N and D329N. These mutations are considered to allow masking non appropriate immunogenic regions and allow the stabilized recombinant sE dimer of the invention to preferentially elicit in a subject neutralizing antibodies directed to all four dengue virus serotypes.

The above detailed mutagenesis of the sE dimer introduces mutations that do not interfere with its immunogenicity but provide a higher dimer affinity, including cysteine mutations at the dimer contacts to provide stabilization by cross-links, and/or introduces new glycosylation sites to allow chemical cross-linking between adjacent sugars on the dimer by click chemistry, and/or substitution of at least one amino acid residue in the amino acid sequence of at least one sE monomer with at least one bulky side chain amino acid to allow forming cavities at the dimer interface or in domain 1 (D1)/domain 3 (D3) linker of each monomer.

Figure 15A:
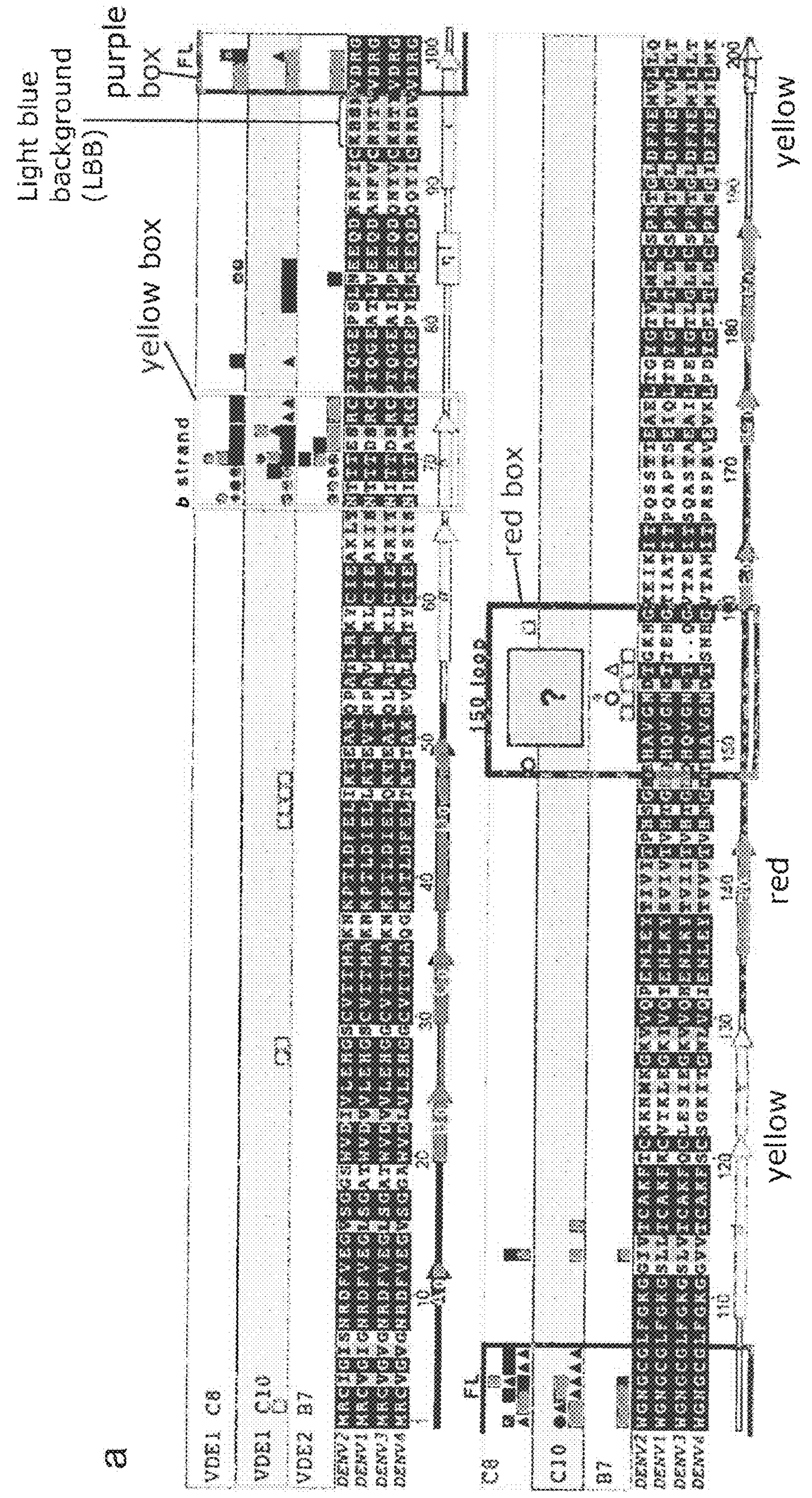
Figure 15A:
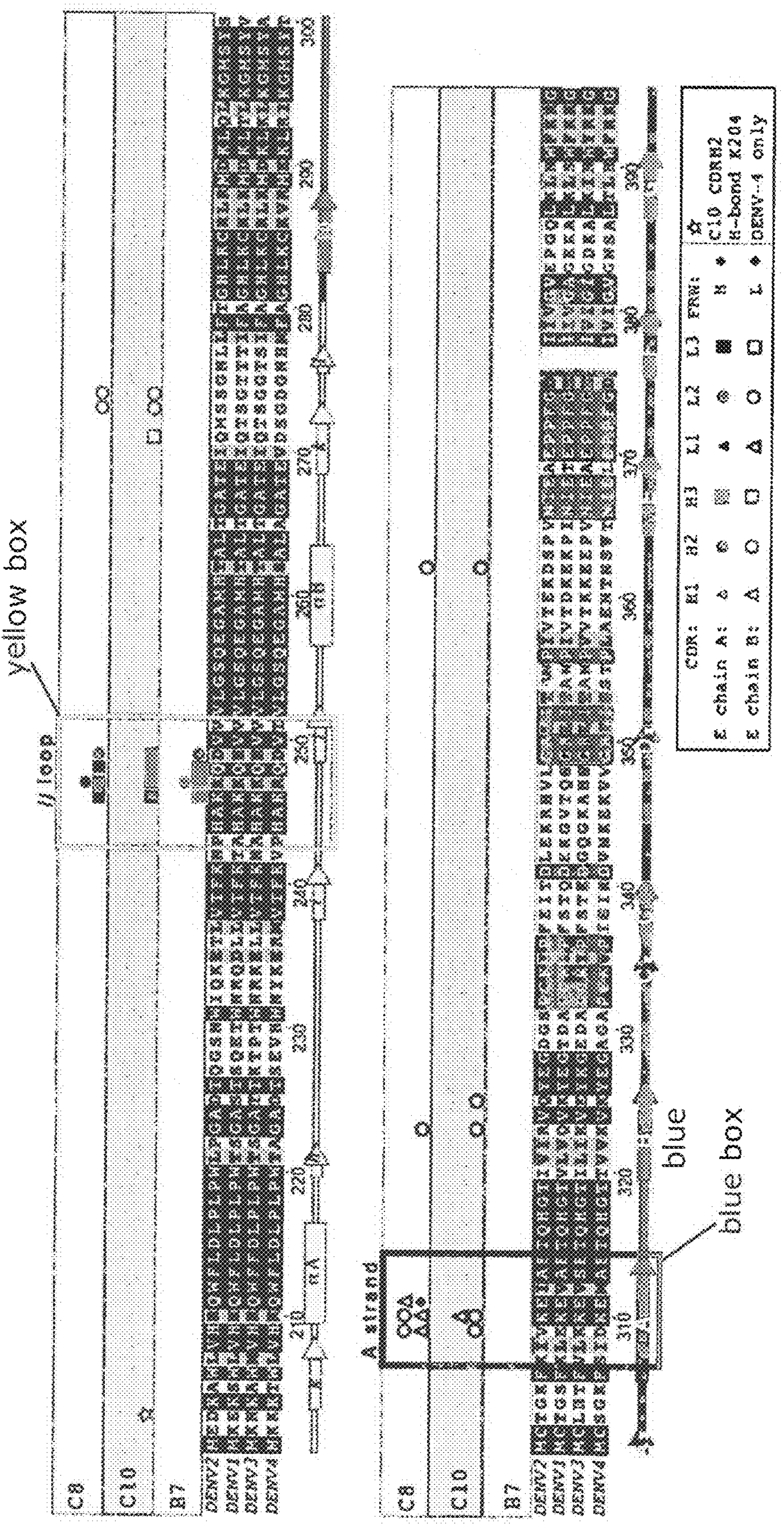

Unless otherwise specified, the amino acid residue position is numbered according to sE amino acid sequence alignment shown in FIGS. 15A and B.

Nucleic acid sequences encoding DENV-1 sE of SEQ ID NO: 132, DENV-2 sE of SEQ ID NO: 133, DENV-3 sE of SEQ ID NO: 134, DENV-4 sE of SEQ ID NO: 135 are respectively represented as SEQ ID NO: 136, 137, 138 and 139.

As used herein, the term "recombinant" refers to the use of genetic engineering methods (cloning, amplification) to produce a dengue virus envelope glycoprotein E ectodomain, an antibody or an antibody fragment of the present invention.

The dimer can be a homodimer of two identical recombinant sE as defined above or a heterodimer of two different recombinant sE as defined above, the dimer being preferably a homodimer.

By way of example, it can be a heterodimer of DENV-1 sE and DENV-2 sE as defined above. It can also be a heterodimer of DENV-1 sE and a mutant sE of DENV-1 sE as defined above.

In one embodiment the compound binds to the EDE wherein the EDE is a stabilised dimer of sE, wherein the stabilised dimer of envelope or recombinant sE is covalently stabilized with at least one, two or three disulphide inter-chain bonds between the two sE monomers.

Advantageously, said stabilized dimer involves single cysteine mutant sE located by the two-fold molecular axis of the dimer, which gives rise to a single inter-chain disulphide bond, or multiple (e.g., double) cysteine mutant sE that can make multiple (e.g., two) disulphide bonds away from the two-fold molecular axis. Said disulphide bonds can be synthetized under oxidative conditions, for example with a DMSO solution (O. Khakshoor et al., 2009) or with oxidative agents such as $CdCl_2$ or $CuSO_4$. Therefore, said stabilized dimer can be composed of monomers wherein one amino acid residue of each monomer by (near) the two-fold molecular axis of the dimer is substituted with a cysteine. Said stabilized dimer can also be composed of monomers wherein two amino acid residues of each monomer away from the two-fold molecular axis of the dimer are substituted with a cysteine. Said stabilized dimer can also be composed of monomers wherein three amino acid residues of each monomer away from the two-fold molecular axis of the dimer are substituted with a cysteine.

It may be desirable for there to be more than one inter-chain disulphide bond, as such an arrangement may limit access to the FLE region and therefore reduce the ability of the molecule to raise anti-FLE responses, as discussed further in Example 17.

In another preferred embodiment, the compound binds to the EDE wherein the EDE is a stabilised dimer of sE, wherein the stabilised dimer of envelope or recombinant sE is a homodimer of mutants sE having each the mutation A259C or S255C as defined above, and wherein the residues 259C or 255C are linked together through a disulphide inter-chain bond.

In another preferred embodiment, wherein the EDE comprises a stabilised dimer of recombinant sE, the stabilized recombinant sE dimer is a heterodimer of a mutant sE having the mutation A259C as defined above and a mutant sE having the mutation S255C as defined above, wherein the residues 259C and 255C are linked together through a disulphide inter-chain bond.

In another preferred embodiment, wherein the EDE comprises a stabilised dimer of recombinant sE, the stabilized recombinant sE dimer is a homodimer of mutant sE having each the mutations F108C and T315C as defined above, or a homodimer of mutants sE having each the mutations L107C and A313C as defined above, wherein the residues 108C and 315C or the residues 107C and 313C are linked together through a disulphide inter-chain bond.

In one embodiment the compound binds to the EDE wherein the EDE is a stabilised dimer of sE, wherein the stabilised dimer of envelope or recombinant sE is a heterodimer of a mutant sE having the mutations F108C and A313C as defined above and a mutant sE having the mutations L107C and T315C as defined above, wherein the residues 108C and 313C are linked respectively to the residues 315C and 107C through a disulphide inter-chain bond between the two sE monomers.

In another preferred embodiment, wherein the EDE comprises a stabilised dimer of recombinant sE, the stabilized recombinant sE dimer is selected from the group consisting of a homodimer of mutants sE having each the mutations A259C, F108C and T315C, a homodimer of mutants sE having each the mutations S255C, F108C and T315C, a homodimer of mutants sE having each the mutations A259C, L107C and A313C, and a homodimer of mutants sE having each the mutations A255C, L107C and A313C as defined above, wherein the residues 259C, 255C, 108C, 315C, 107C and 313C are linked respectively to the residues 259C, 255C, 315C, 108C, 313C and 107C through disulphide inter-chain bonds.

In another preferred embodiment, the compound binds to the EDE wherein the EDE comprises a stabilised dimer of recombinant sE, the stabilized recombinant sE dimer is a heterodimer of a mutant sE having the mutations A259C, F108C and T315C as defined above and a mutant sE having the mutations S255C, F108C and T315C as defined above, wherein the residues 259C, 108C and 315C are linked respectively to the residues 255C, 315C and 108C through disulphide inter-chain bonds.

In another preferred embodiment, wherein the EDE comprises a stabilised dimer of recombinant sE, the stabilized recombinant sE dimer is a heterodimer of a mutant sE having the mutations S255C, L107C and A313C as defined above and a mutant sE having the mutations A259C, L107C and A313C as defined above, wherein the residues 255C, 107C and 313C are linked respectively to the residues 259C, 313C and 107C through disulphide inter-chain bonds.

As well as stabilisation via disulphide bonds, it will be appreciated that stabilisation may also be achieved via sulfhydryl-reactive crosslinkers. Thus, in one embodiment, wherein the EDE comprises a stabilised dimer of recombinant sE, the stabilized recombinant sE dimer of the invention is covalently stabilized with at least one, two or three, sulfhydryl-reactive crosslinkers (also called thiol-reactive crosslinkers) between the sE monomers.

Chemical crosslinking of proteins is well-known in the art (see for review Hemaprabha, 2012).

Naturally, the sE dimer has two difference faces, one exposed to the extracellular medium, where the antibodies bind, and the one exposed to the viral membrane.

Advantageously, said stabilized recombinant sE dimer involves candidate amino acid residues present in the face of sE exposed to the viral membrane and thus are not part of the epitope. One of each candidate amino acid residue of each monomer is mutated (substituted) to cysteine, producing a free sulfhydryl group that is the target of sulfhydryl-reactive crosslinkers of appropriate lengths.

Thr/Ser262 and Thr/Ala265 are candidate residues. The distance between them in the context of the dimer is 12 and 22 Å respectively. Further, these residues (Thr/Ser262, Thr/Ala265) are not fully conserved. Hence, they can tolerate point mutations.

In a preferred embodiment, the compound binds to the EDE wherein the EDE comprises a stabilised dimer of recombinant sE, the stabilized recombinant sE dimer is a homodimer of mutant sE having each the mutation T/S262C or T/A265C as defined above, wherein the residues 262C or 265C are linked together through a sulfhydryl-reactive crosslinker.

In another preferred embodiment wherein the EDE comprises a stabilised dimer of recombinant sE, the stabilized recombinant sE dimer is a heterodimer of a mutant sE having the mutation T/S262C as defined above and a mutant sE having the mutation T/A265C as defined above, wherein the residues 262C and 265C are linked together through a sulfhydryl-reactive crosslinker.

Regions of the recombinant sE which are not considered to be part of the epitope and which can be crosslinked are region A consisting of residues 1-9 of sE, region B consisting of residues 25-30 of sE, region C consisting of residues 238-282 of sE, region D consisting of residues 96-111 of sE and region E consisting of residues 311-318 of sE. Any of the residues of these five regions (A to E) of a monomer is at less than 25-30 Å of other residue of the other monomer in the recombinant sE dimer, and thus these residues can be crosslinked.

Advantageously, one or several of the candidate amino acid residues in these five regions of each monomer is mutated (substituted) to cysteine, producing a free sulfhydryl group that is the target of sulfhydryl-reactive crosslinkers of appropriate lengths as defined above.

In another embodiment, the compound binds to the EDE wherein the EDE comprises a stabilised dimer of recombinant sE, the stabilized recombinant sE dimer is a homodimer or a heterodimer of a mutant sE wherein at least one of the amino acid residues 1-9, 25-30, 238-282, 96-111 311-318 of sE is mutated (substituted) to cysteine and a mutant sE wherein at least one of the amino acid residues 1-9, 25-30, 238-282, 96-111 311-318 of sE is mutated (substituted) to cysteine, and wherein the mutated cysteine residues are linked together through a sulfhydryl-reactive crosslinker.

The sulfhydryl-reactive crosslinkers are preferably homobifunctional reagents with identical or non-identical reactive groups, permitting the establishment of inter-molecular crosslinkages between the two monomers. Homobifunctional crosslinkers have identical reactive groups at either end of a spacer arm, and generally they can be used in one-step reaction procedures. The sulfhydryl-reactive crosslinkers of the invention can be a maleimide, a haloacetyl (preferably a bromo- or iodo-acetyl), a pyridyl disulfide, a vinylsulfone, an alkyl halide or an aziridine compound, an acryloyl derivative, an arylating agent, or a thiol-disulfide exchange reagent (Hermanson, 2010; Hemaprabha, 2012), such as the bis(methanethiosulfonate) (Haberz P. et al., 2006).

Examples of maleimide homo-bifunctional sulfhydryl-reactive crosslinkers according to the invention, with spacer of different lengths, include BMOE (1,2-bis-maleimidoethane), BMB (1,4-bis-maleimidobutane), BMH (1,6-bis-maleimidohexane), TMEA (tris-(2-maleimidoethyl)amine), $BM(PEG)_2$ (1,8-bismaleimidodiethyleneglycol), $BM(PEG)_3$ (1,11-bismaleimidotriethyleneglycol), BMDB (1,4-bismaleimidyl-2,3-dihydroxybutane), DTME (dithio-bis-maleimidoethane), and preferably BMH, $BM(PEG)_2$ and $BM(PEG)_3$.

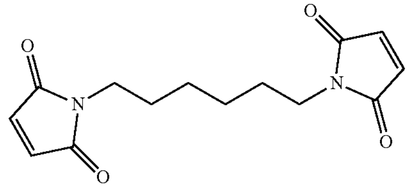

BMH
Bismaleimidohexane
MW 276.29
Spacer Arm 13.0 Å

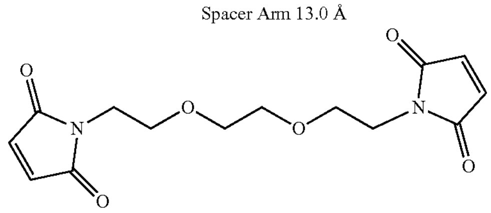

$BM(PEG)_2$
1,8-Bismaleimidodiethyleneglycol
MW 308.29
Spacer Arm 14.7 Å

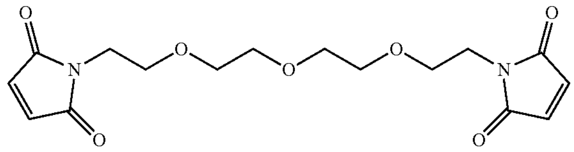

$BM(PEG)_3$
1,11-Bismaleimidotriethyleneglycol
MW 352.34
Spacer Arm 17.8 Å

The maleimide group reacts specifically with the sulfhydryl groups is performed under mild buffer and pH conditions, in order to minimize the degree of structural shift due to crosslinking reactions. Preferably, the pH of the reaction mixture is between 6.5 and 7.5 leading to the formation of a stable thio-ether linkage that is not reversible (the bond cannot be cleaved with reducing agents).

In addition to stabilisation via disulphide bonds and sulfhydryl-reactive crosslinkers, it will be appreciated that stabilisation may be obtained through the linking of the two monomers through modified sugars. To this end, glycosylation sites are inserted on them and are reacted with modified sugars, in order to join them by click-chemistry.

According to this embodiment, the compound binds to the EDE wherein the EDE comprises a stabilised dimer of recombinant sE, the stabilized recombinant sE dimer is a homodimer or heterodimer of mutants sE, wherein:

one sE monomer has at least one mutation which introduces a glycosylation site, and wherein the mutated amino acid residue is glycosylated with a modified sugar bearing an X functional group, and the other sE monomer has at least one mutation which introduces a glycosylation site, and wherein the mutated amino acid residue is glycosylated with a modified sugar bearing a Y functional group, and wherein both mutated residues are joined together through the modified sugars by reacting, specifically by click chemistry, the X functional group of the sugar of the first sE monomer with the Y functional group of the sugar of the other sE monomer.

By X functional group, it is meant a chemical group beared by a sugar which is able to react and form a covalent linking by click chemistry with a Y functional group, said Y functional group being preferably an azide functional group.

By Y functional group, it is meant a chemical group beared by a sugar which is able to react and form a covalent linking by click chemistry with a X functional group, said X functional group being preferably a terminal alkyne functional group.

The modified sugars can be synthesized and introduced in the sE monomers as described by Laughlin et alt, 2007, and joined together as described by Speer et al., 2003.

In addition to the abovementioned covalent methods of stabilising the dimer, non-covalent means may also be used. Thus, in another embodiment wherein the EDE comprises a stabilised dimer of recombinant sE, the dimer is non-covalently stabilized by filling the cavities of said dimer at the dimer interface by substituting at least one amino acid in the amino acid sequence of one or the two monomers, preferably the two monomers, with bulky side chain amino acids. According to this embodiment, cavities unique to the quaternary conformation of the recombinant sE dimer are identified and filled by engineered hydrophobic substitutions in the monomers.

According to this embodiment, the stabilized recombinant sE dimer is non-covalently stabilized by substituting at least one amino acid residue in the amino acid sequence of at least one sE monomer with at least one bulky side chain amino acid within regions forming cavities at the dimer interface or in domain 1 (D1)/domain 3 (D3) linker of each monomer. Such substitutions allow increasing hydrophobic interactions between the two sE monomers.

In a preferred embodiment wherein the EDE comprises a stabilised dimer of recombinant sE, the stabilized recombinant sE dimer is a homodimer or heterodimer, preferably homodimer, of two recombinant sE as defined above, wherein one of the recombinant sE or the two recombinant sE have at least one mutation (substitution) selected from the group consisting of H27F, H27W, H244F, H244W, and L278F. The mutations H27F, H27W, H244F, H244W and L278F allow stabilizing the cavity around F279 of the recombinant sE dimer, strengthening the dimer interface and mimicking the F279 conformation in the virion.

Other means of non-covalently stabilising the dimer include, for example non-covalent stabilisation in domain 1 (D1)/domain 3 (D3) linker of each monomer, by substituting amino acids in the amino acid sequence of one or the two, preferably the two, monomers with at least one bulky side chain amino acid.

In a preferred embodiment the compound binds the EDE wherein the EDE comprises a stabilised dimer of recombinant sE, the stabilized recombinant sE dimer is a homodimer or heterodimer, preferably homodimer, of two recombinant sE as defined above, wherein one of the recombinant sE or the two recombinant sE have at least one mutation (substitution) selected from the group consisting of L292F and L294N. The mutations L292F, L294N are considered to allow stabilizing the D1-D3 linker in sE dimeric conformation.

In a preferred embodiment where the EDE is stabilised in the dimer configuration through engineering, the engineering, such as that described above, does not result in a change in the overall 3D structure of the dimer, or does not substantially change the overall 3D structure and the residues in the native dimer spatially correspond to the engineered dimer. If the native dimer spatially corresponds to the engineered dimer, this means that when a 3D model of the engineered dimer (or part thereof, for example reflecting residues of particular importance in defining the VDR, for example the residues indicated in Table 2 and/or discussed further below) is superimposed on the 3D model of the native dimer, coordinates defining the spatial location of the backbone atoms in the native dimer vary from the coordinates defining the analogous backbone atoms in the engineered dimer by less than about 10 angstroms. Backbone atoms are those atoms in an amino acid that form the peptide backbone, or 3D folding pattern, i.e. does not include the side chain atoms, though the position of some or all of the side chain atoms may similarly not vary significantly. The 3D structure is key to the immunogenicity of the VDE, and as such, in a preferred embodiment, the engineering does not result in a dimer with decreased immunogenicity. In one embodiment the engineering does result in a dimer with a different 3D conformation. Preferably the engineering results in a dimer with increased immunogenicity. Such approaches have been used in ref[84]. Thus in one embodiment, the compound binds to an engineered EDE, such as those described above.

A 3D model of the native dimer may be formed making use of the information on crystal structures for envelope glycoprotein ectodomain from dengue virus serotypes, for example serotypes 2, 3, and 4, available in the Protein Data Bank, for example under accession numbers 1OAN, 10K8, 1UZG and 3UAJ, as noted above.

Whether or not a particular mutation or modification alters or substantially alters the 3D structure could be assessed by different techniques, including monitoring whether the antibodies described herein, which are known to bind to the VDE, can still bind to the engineered version of the VDE.

The skilled person is able to use computer programs to aid in the identification of potential stabilising modifications, for example.

The effect of the engineering on the immunogenicity of the EDE can be assessed by comparing the antibody response in a subject when administered an engineered and non-engineered EDE or by comparing binding to known anti-EDE antibodies.

Alternatively, the modified envelope protein could be expressed in a dengue virus and the ability of the compound to neutralise the virus assessed.

In order to present a stabilised EDE, non-EDE heterologous proteins that have a similar three-dimensional structure to the respective EDE (referred to as scaffold proteins), can be modified to contain the appropriate residues that enable the modified protein to hold the EDE. Thus in one embodiment the compound binds the EDE wherein the EDE is presented as part of an epitope-scaffold protein. An epitope-scaffold protein is a chimeric protein that includes an epitope sequence fused to a heterologous "acceptor" scaffold protein. Design of the epitope-scaffold is performed, for example, computationally in a manner that preserves the native structure and conformation of the epitope when it is fused onto the heterologous scaffold protein. The use of such scaffold proteins is well known in the art and such methods and techniques are described in WO 2011/050168 and refs[54,82,83] and the skilled person can follow methods described therein and apply them to the present invention.

Accordingly, in one embodiment, the EDE comprises part of an epitope-scaffold protein, wherein the scaffold protein comprises a heterologous scaffold protein covalently linked to the Envelope Dimer Epitope. Scaffold proteins are useful for creating the EDE of the present invention in that they hold contact residues of the EDE in the proper spatial orientation to facilitate interaction between such residues and the compound, for example between contact residues of the compound when the compound is a protein, optionally an antibody or antigen binding portion thereof. A contact residue is any amino acid present in a molecule that interacts directly or indirectly (e.g. forms an ionic bond either directly, or indirectly through a salt bridge) with an amino acid in another molecule. Residues of the envelope protein which are considered to be potentially important for compound binding to the EDE, at least for DENV-1, are detailed in Table 2 The scaffold protein may present the entire dimer or may present only the selected residues above. A 3D model of the native dimer or parts thereof may be formed making use of the information on crystal structures for envelope glycoprotein ectodomain from dengue virus serotypes, for example serotypes 2, 3, and 4, available in the Protein Data Bank, for example under accession numbers 1OAN, 10K8, 1UZG and 3UAJ, as noted above.

Mutational analysis revealed particular residues of DENV1 and DENV2 which are important for binding to the antibodies identified in the present invention. These residues are:

DENV1: E49, K64, Q77, W101, V122, N134, N153, T155, I161, A162, P169, T200, K202, E203, L308, K310, Q323, W391, F392;

DENV2: Q77, W101, N153, T155, K310.

All of these residues are considered to be important for binding, and the Q77, W101, N153, T155, K310

Accordingly, in one embodiment, compound binds the EDE wherein the EDE is part of a scaffold protein, wherein the scaffold protein holds at least residues corresponding to one or more of E49, K64, Q77, W101, V122, N134, N153, T155, I161, A162, P169, T200, K202, E203, L308, K310, Q323, W391, F392, of the envelope protein or equivalent residue of a Dengue virus envelope protein, particularly for DENV-1 and DENV-2. Certain residues are considered to be more important, and as such a further embodiment of the EDE comprises a scaffold protein which holds at least one or more of residues corresponding to Q77, W101, N153, T155, K310 of the envelope protein or equivalent residue of a Dengue virus envelope protein, particularly DENV-1 and DENV-2.

Residues of the envelope protein considered to be important for contacting the epitope are given in FIG. 31, for example: the B7 antibody is considered to contact the DENV2 EDE at residues N67, T68, T69, T70, E71, S72, R73, L82, V97, D98, R99, W101, G102, N103, G104, I113, G152, N153, D154, T155, G156, K246, K247, Q248, D249;

the A11 antibody is considered to contact the DENV2 EDE at residues N67, T68, T69, T70, E71, S72, R73, C74, E84, V97, D98, R99, G102, N103, G104, C105, V114, N153, D154, T155, G156, H158, K246, K247, Q248, D249, V250;

the C10 antibody is considered to contact the DENV2 EDE at residues R2, H27, G28, E44, L45, I46, K47, N67, T68, T69, T70, E71, S72, R73, C74, Q77, S81, L82, N83, E84, V97, R99, W101, G102, N103, G104, C105, G106, L113, T115, K246, K247, Q248, Q271, V309, K310, R323, Q325, D362;

the C10 antibody is considered to contact the DENV4 EDE at residues R2, H27, G28, G29, E44, L45, T46, N67, T69, T70, A71, T72, R73, C74, Q77, V97, R99, W101, G102, N103, G104, C105, G106, V113, R247, Q248, D249, D271, M278, D309, K310, V324, K323, K325, T361, N362;

the C8 antibody is considered to contact the DENV2 EDE at residues N67, T68, T 69, T70, E71, S72, R73, C74, Q77, N83, E84, V97, D98, R99, W101, G102, N103, G104, C105, G106, L113, E148, H158, K246, K247, Q248, D249, I308, K310, E311, R323, D362, G374.

Thus residues of the envelope protein that are considered to be important for binding to the compound, particularly for DENV2 and DENV4 are: A71, C105, C74, D154, D249, D271, D309, D362, D98, E148, E311, E44, E71, E84, G102, G104 G106, G152, G156, G28, G29, G374, H158, H27, I113, I308, I46, K246, K247, K310, K323, K325, K47, L113, L45, L82, M278, N103, N153, N362, N67, N83, Q248, Q271, Q325, Q77, R2, R247, R323, R73, R99, S72, S81, T115, T155, T361, T46, T68, T69, T70, T72, V113, V114, V250, V309, V324, V97, W101, or equivalent residue of a Dengue virus envelope protein.

The scaffold protein may present one or more residues selected from both of the sets of residues, for example may present at least one or more, for example, at least 1, 2, 3, 4, 5, 6, 7, 8, 9, or 10 or all of: E49, K64, Q77, W101, V122, N134, N153, T155, I161, A162, P169, T200, K202, E203, L308, K310, Q323, W391, F392, A71, C105, C74, D154, D249, D271, D309, D362, D98, E148, E311, E44, E71, E84, G102, G104, G106, G152, G156, G28, G29, G374, H158, H27, I113, I308, I46, K246, K247, K323, K325, K47, L113, L45, L82, M278, N103, N362, N67, N83, Q248, Q271, Q325, R2, R247, R323, R73, R99, S72, S81, T115, T361, T46, T68, T69, T70, T72, V113, V114, V250, V309, V324, V97, or equivalent residue of a Dengue virus envelope protein.

In addition, the scaffold protein may present any one or more or all of the following sets of residues, which as described earlier are considered to increase stability of the dimer configuration: H27F, H27W, L107C, F108C, H244F, H244W, S255C, A259C, T/S262C, T/A265C, L278F, L292F, L294N, A313C and T315C.

The scaffold protein may hold the dimer, or fragment of dimer, and may comprise any of the described modifications above which are considered essential for immunogenicity, and/or result in increased dimer stability, for example increased disulphide bonds.

Moreover, the scaffold can be such that an improved EDE is presented. In one embodiment, the compound therefore binds an improved EDE. For example, as described below and in Examples 2 and 5, patients with Dengue infection tend to have either antibodies directed towards the VDE, which are considered useful antibodies, or antibodies directed towards the Fusion Loop (anti-FL antibodies) which are not considered to be useful. Thus a scaffold may be engineered such that only the EDE is presented, and is presented in such a way as to exclude the possibility of a compound, for example an antibody or antigen binding portion thereof, being raised to the FL. Therefore, in one preferred embodiment the EDE is capable of raising antibodies to the EDE and not to the FL, optionally by being incorporated into a scaffold protein.

Independently of a scaffold protein, the envelope protein may be engineered such that an improved EDE is generated. As detailed above, an EDE which is incapable of being recognised by the anti-FL antibodies, and incapable of raising such antibodies, is considered to be an improved EDE. This may be accomplished by one or more mutations, deletions or insertions in the envelope protein, or by generating a hybrid protein wherein the specific epitope, without any antigens which would raise anti-FL antibodies, fused to a scaffold protein.

In one embodiment, the envelope protein is engineered by modifying the internal surface of the dimer (projecting to the inside of the virus) with sugars to make it less immunogenic by adding N or O linked glycan sequences.

Extensive mutagenic resurfacing of the dimer may be useful to further reduce the generation of non-ED suboptimal responses by mutation of residues and/or addition of glycan.

As an example, the L278F mutation is considered to re-shape the kl-loop and to mimic the virion-like conformation.

Modelling an optimisation of the core EDE epitopes may also be useful to produce an optimal sequence to induce the desired EDE response to provide binding and neutralising antibodies.

It will be appreciated that the EDE may be the naturally occurring envelope protein held within a scaffold to effect increased dimer stability. The EDE may also be engineered independently of any scaffold to increase dimer stability. The two may be combined such that in one embodiment the EDE comprises a dimer wherein the envelope protein is engineered to have improved stability in the dimer configuration, which is held within a heterologous scaffold protein. Alternatively, the envelope protein may be engineered such that only the relevant portions of the protein are present, and this may then be held in a heterologous scaffold protein.

A dimer conformation may be stabilised by, for example, creating a long linker, for example a glycine-serine-rich liner between two envelope monomers to express as a single polypeptide chain comprising two envelope polypeptide domains. Alternatively or in addition, a dimeric structure may be stabilised by any antibody (for example) which binds to the inner facing surfaces of the dimer or to tags associated with the dimer.

Any reference to the envelope protein, sE, sE dimer or envelope protein dimer also includes within its scope a scaffold protein, or a structure, which comprises the particular residues that make up the EDE, held in a particular conformation so as to present a suitable EDE.

The envelope nucleotide sequence may be engineered such that the envelope protein has any one or more of mutations, insertions or deletions. The nucleotide sequence may be such that it has at least 70%, 80%, 85%, 90%, 95%, 98% or 99% homology to the native sequence of the particular envelope protein (or part thereof).

In a further embodiment the envelope protein may be engineered such that it has at least 70%, 80%, 85%, 90%, 95%, 98% or 99% homology to an envelope protein (or part or parts thereof, for example one or more portions of at least 8, 9 or 10 consecutive amino acids) from another serotype of dengue virus. In a preferred embodiment, the envelope protein is engineered such that it has at least 70%, 80%, 85%, 90%, 95%, 98% or 99% homology to two different envelope proteins (or part or parts thereof, for example one or more portions of at least 8, 9 or 10 consecutive amino acids), more preferably to four different envelope proteins (or part or parts thereof, for example one or more portions of at least 8, 9 or 10 consecutive amino acids), most preferably to all envelope proteins (or part or parts thereof, for example one or more portions of at least 8, 9 or 10 consecutive amino acids) from all serotypes of dengue virus.

As described above, the envelope protein may be engineered such that it actually has very low homology to the native envelope protein, but wherein the integrity and conformation of the EDE is maintained, or is altered in such a way that the EDE is improved, for example, is incapable of raising the anti-FL antibodies. Thus, the level of sequence homology is not necessarily an indication of the 3D structure homology, or functional homology. For example, a particular sequence encoding a structure comprising a EDE may actually have a very low level of homology to the native envelope protein, but may nevertheless be considered a useful compound of the invention. For example, the protein may have 10%, 20%, 30%, 40%, 50% or 60% homology to the native envelope protein, and the nucleotide sequence which encodes this structure may have a correspondingly low sequence identity to the native envelope sequence.

In a preferred embodiment, where the envelope protein, or structure comprising the EDE has at least 70%, 80%, 85%, 90%, 95%, 98% or 99% homology to an envelope protein (or part or parts thereof, for example one or more portions of at least 8, 9 or 10 consecutive amino acids) of a dengue virus, or at least 70%, 80%, 85%, 90%, 95%, 98% or 99% homology to two different envelope proteins (or part or parts thereof, for example one or more portions of at least 8, 9 or 10 consecutive amino acids), more preferably to four different envelope proteins, most preferably to all envelope proteins from all serotypes of dengue virus, or wherein the protein or structure comprising the EDE has at least 10%, 20%, 30%, 40%, 50% or 60% homology to the native envelope protein of one or more serotypes of dengue virus, the protein comprises one or more of, or optionally all of: E49, K64, Q77, W101, V122, N134, N153, T155, I161, A162, P169, T200, K202, E203, L308, K310, Q323, W391, F392, or equivalent residue of a Dengue virus envelope protein.

Some of these residues are considered to be more important than others, as such in a further embodiment of the EDE, the envelope protein, or structure comprising the EDE comprises one or more of, or optionally all of: Q77, W101, N153, T155, K310, or equivalent residue of a Dengue virus envelope protein.

It is considered that one or more of residues E49, K64, Q77, W101, V122, N134, N153, T155, I161, A162, P169, T200, K202, E203, L308, K310, Q323, W391, F392, of the envelope protein, or equivalent residues of a dengue virus protein are required for binding of the compound to the EDE. Thus in one embodiment, the envelope protein or structure comprising the EDE comprises one or more or all of these residues.

Whilst the anti-FL antibodies appear, in most cases, to require only residue W101 out of the residues mutated in the alanine scanning analysis (Example 2) and are not affected by mutation of any of the other residues, the anti-EDE antibodies require a much larger epitope, which requires the presence of residue W101, as does the anti-FL antibodies, but which are also affected by mutations at many of the other residues. As such, in one embodiment the EDE is defined as an epitope in which residues W101 and at least one or more of positions E49, K64, Q77, W101, V122, N134, N153, T155, I161, A162, P169, T200, K202, E203, L308, K310, Q323, W391, F392, or equivalent residue in the Envelope Dimer Epitope are required for binding of the compound.

In a particular embodiment, the Envelope Dimer Epitope comprises the domain III residue K310.

In an embodiment the EDE is glycosylated at position 67 (Asn67 glycan) and/or at position 153 (Asn153 glycan), for example of each envelope, for example sE, monomer, preferably at least at position 67 (Asn67 glycan) of each monomer.

The compound of the invention, according to one embodiment, contacts the N67 glycan chain of the envelope protein dimer, or the N153 glycan chain of the envelope protein dimer. It will be appreciated that the compound can contact both the N67 and N153 glycan chains of the envelope protein dimer.

In a particular example, the compound is an antibody wherein the CDR H2 interacts with the N67 glycan chain of the envelope protein.

In one embodiment, the compound contacts the EDE at any one or more of A71, C105, C74, D154, D249, D271, D309, D362, D98, E148, E311, E44, E71, E84, G102, G104, G106, G152, G156, G28, G29, G374, H158, H27, I113, I308, I46, K246, K247, K310, K323, K325, K47, L113, L45, L82, M278, N103, N153, N362, N67, N83, Q248, Q271, Q325, Q77, R2, R247, R323, R73, R99, S72, S81, T115, T155, T361, T46, T68, T69, T70, T72, V113, V114, V250, V309, V324, V97, W101 in the envelope protein, for example DENV-2 or DENV-4, of one or more serotypes of Dengue virus, where present, preferably all serotypes of dengue virus.

In an embodiment, the Envelope Dimer Epitope comprises a region centred in a valley lined by the b strand on the domain II side, and the "150 loop" (see, for example, FIG. 29) on the domain I side (across from the dimer interface), wherein the 150 loop spans residues 148-159, connecting b-strands E0 and F0 of domain I, and carries the N153 glycan, which covers the fusion loop of the partner subunit in the dimer. The 150 loop is considered to comprise SEQ ID NO: 148 150 loop of Denv-1 QHQVGNETTEHG; SEQ ID NO: 1149 150 loop of Denv 2 EHAVGNDTGKHG; SEQ ID NO: 150 150 loop of Denv 3 QHQVGNETQG; SEQ ID NO: 151 150 loop of Denv 4 THAVGNDIPNHG.

In some cases, the Envelope Dimer Epitope comprises domain II of the envelope protein, optionally further comprising any one or more of the following features of domain II; the b strain (residues 67-74), the fusion loop and residues immediately upstream (residues 97-106) and the ij loop (residues 246-249), and residues 243-251 and residues 307-314.

In one embodiment the EDE comprises the five polypeptide segments of the dengue virus glycoprotein E ectodomain (sE) consisting of the residues 67-74, residues 97-106, residues 148-159, residues 243-251 and residues 307-314.

Thus in one embodiment the invention also provides a compound, for example an isolated neutralizing antibody or antigen binding fragment thereof directed against the stabilized recombinant sE dimer as defined above, wherein said antibody or fragment thereof binds the five polypeptide segments of the dengue virus glycoprotein E ectodomain (sE) consisting of the residues 67-74, residues 97-106, residues 148-159, residues 243-251 and residues 307-314.

The characterization of the binding of an antibody fragment thereof according to the present invention to a polypeptide segment or amino acid residue can be performed by, for example, crystallization trials as describes in the Examples below.

Preferably, in addition to binding to the EDE the compound is capable of neutralising the virus. In a preferred embodiment the compound is capable of neutralising all serotypes of Dengue virus, preferably to at least 90% or at least 98%, for example 100%, and preferably neutralises all serotypes of Dengue virus made in both insect and human cells to at least 90% or at least 98%, for example 100%. Preferences for the neutralisation and neutralisation assay techniques are as described earlier.

In one embodiment the EDE comprises a dimer of full length envelope protein. In another embodiment, the EDE comprises a dimer of the envelope ectodomain (sE). In a further embodiment the envelope protein comprises the (approximately, as discussed above) 400 amino terminal residues of the ectodomain of Envelope protein. See, for example, FIG. 28. The preferences for the stability of a dimer of the full length envelope protein described above also apply to the truncated ectodomain of envelope protein.

Therefore, the dimer of ectodomain of envelope protein may be stabilised through engineering or stabilised by being incorporated into a scaffold protein, or may comprise a hybrid dimer.

In a further embodiment, the compound of the present invention is one which will not bind to dengue virus or virion or sub-viral particle or virus-like particle incubated at acid pH. Acidic pH causes the envelope protein to irreversibly adopt a trimer configuration. The inventors found that the compounds of the present invention do not bind to viral particles incubated at a low pH (see Example 4). Therefore, in one embodiment, the compound, for example and antibody or antigen binding portion thereof, does not bind to dengue virus or virion or sub-viral particle or virus-like particle, incubated at an acidic pH. By an acidic pH we mean any pH below 7, preferably pH 5.5.

As such, the skilled person can readily identify whether a particular compound is a compound of the invention according to this embodiment of the invention, simply by identifying whether the compound cannot bind to one or more than one of: a) a virion or sub-viral particle or a virus-like particle made in cells lacking furin activity; b) a virion or sub-viral particle or a virus-like particle having a high percentage of prM protein, and/or c) a virion or sub-viral particle or a virus-like particle incubated under acidic conditions Methods to assay the binding ability of the compound to the virion, sub-viral particle or virus-like particle detailed above are provided earlier in relation to assaying the ability of the compound to bind to the EDE and is detailed in Example 4 and generally simply involves an ELISA against the particular virion or virus like particle to assay whether or not the compound can bind. The compound is considered useful if it binds to, or significantly binds to, the native EDE or virion or virus like particle, and does not bind to a virion or sub-viral particle or a virus-like particle that: a) is made in cells lacking furin activity; b) have a high percentage of prM protein, and/or c) are incubated under acidic conditions.

The invention further comprises specific compounds. For example, in one embodiment, the compound is an antibody comprising the sequence heavy chain SEQ ID No: 1 and light chain SEQ ID No: 37; or heavy chain SEQ ID No: 2 and light chain SEQ ID No: 38; or heavy chain SEQ ID No: 3 and light chain SEQ ID No: 39; or heavy chain SEQ ID No: 4 and light chain SEQ ID No: 40. It will be appreciated that the invention also includes truncations and mutations of these antibodies, such that the compound is an antigen binding portion thereof. Antibodies with a sequence homology of at least 90% or at least 95% homology to the above sequences are included in the invention. Particular sequences of antibodies, light and heavy chains are given in SEQ ID No's: 1-4, 37-141, 141-147 and, for example, FIG. 29.

In further embodiments, the compound is an antibody and comprises; heavy chain SEQ ID No: 1 and either light chain SEQ ID No: 37, 38, 39 or 40; heavy chain SEQ ID No: 2 and either light chain SEQ ID No: 37, 38, 39 or 40; heavy chain SEQ ID No: 3 and either light chain SEQ ID No: 37, 38, 39 or 40; or heavy chain SEQ ID No: 4 and either light chain SEQ ID No: 37, 38, 39 or 40.

Particular residues of the specific heavy and light chains are considered to be important for binding to the EDE. Thus, in one embodiment, where the sequence homology is at least 90% to the above sequences, where present, the following residues are:

SEQ ID No: 1—T52, E54, D56, S57, A58, K65, G66, T69, E82, N84, S85, Y100, N102, F103, Y104, Y105, Y106;

SEQ ID No: 2—G554, N55, N57, K59, Q62, Q65, G66, R94, R98, F99, Y100, Y101, D102, S103, T104, Y106, Y107, P108, D109, S110, D117, V118;

SEQ ID No: 3—V2, S28, N31, D54, S56, T57, R58, K65, G66, R94, R98, F99, Y100, Y101, D102, S103, T104, Y106, Y107, P108, D109, S110, D117, V118;

SEQ ID No: 4—V2, T28, S31, D54, S56, S57, T58, G66, F68, M69, R94, R98, Y99, Y100, Y101, D102, S103, T104, Y106, Y107, P108, D109, N110, D117, V118;

SEQ ID No: 37—S30, T31, F32, Y49, D50, S52, R54, R66, R91, Y92, N93, W94;

SEQ ID No: 38—S26, S27, G30, G31, F32, N33, Y34, D52, T54, S55, R56, S62, S95, R96, G97;

SEQ ID No: 39—Y51, R56, P57, S58, G59, S96, R97;

SEQ ID No: 40—Y51, R56, P57, S58, K97.

An antibody is composed of a light chain and a heavy chain, and within each light chain and heavy chain are three variable regions. The most variable part of each of these regions is the complementary determining region and is considered to be the most crucial for antigen binding and recognition. Therefore, in one embodiment, the compound comprises one or more of the following amino acid sequences, having no, one or two amino acid substitutions, insertions or deletions:

SEQ ID No: 5 or SEQ ID No: 8 or SEQ ID No: 11 or SEQ ID No: 14 and/or SEQ ID No: 6 or SEQ ID No: 9 or SEQ ID No: 12 or SEQ ID No: 15 and/or SEQ ID No: 7 or SEQ ID No: 10 or SEQ ID No: 13 or SEQ ID No: 16 and/or SEQ ID No: 17 or SEQ ID No: 20 or SEQ ID No: 23 or SEQ ID No: 26 and/or SEQ ID No: 18 or SEQ ID No: 21 or SEQ ID No: 24 or SEQ ID No: 27 and/or SEQ ID No: 19 or SEQ ID No: 22 or SEQ ID No: 25 or SEQ ID No:28.

Particular compounds may comprise the following sequences, having no, one or two amino acid substitutions, insertions or deletions;

Heavy Chain:

SEQ ID No: 5 and SEQ ID No: 6 and SEQ ID No: 7 or SEQ ID No: 8 and SEQ ID No: 9 and SEQ ID No: 10 or SEQ ID No: 11 and SEQ ID No: 12 and SEQ ID No: 13 or SEQ ID No: 14 and SEQ ID No: 15 and SEQ ID No: 16 and/or Light Chain:

SEQ ID No: 17 and SEQ ID No: 18 and SEQ ID No: 19 or SEQ ID No: 20 and SEQ ID No: 21 and SEQ ID No: 22 or SEQ ID No: 23 and SEQ ID No: 24 and SEQ ID No: 25 or SEQ ID No: 26 and SEQ ID No: 27 and SEQ ID No: 28.

In a preferred embodiment, particular compounds may comprise the following sequences, having no, one or two amino acid substitutions, insertions or deletions;

Heavy chain SEQ ID No: 5 and SEQ ID No: 6 and SEQ ID No: 7 and light chain SEQ ID No: 17 and SEQ ID No: 18 and SEQ ID No: 19; or heavy chain SEQ ID No: 8 and SEQ ID No: 9 and SEQ ID No: 10 and light chain SEQ ID No: 20 and SEQ ID No: 21 and SEQ ID No: 22; or heavy chain SEQ ID No: 11 and SEQ ID No: 12 and SEQ ID No: 13 and light chain SEQ ID No: 23 and SEQ ID No: 24 and SEQ ID No: 25; or heavy chain SEQ ID No: 14 and SEQ ID No: 15 and SEQ ID No: 16 and light chain SEQ ID No: 26 and SEQ ID No: 27 and SEQ ID No: 28; or heavy chain SEQ ID NO: 11, 12 and 13 and optionally light chain SEQ ID NO: 25 and optionally the amino acid sequences SEQ ID NO: 23 and 24; or heavy chain SEQ ID NO: 14, 15 and 16 and optionally light chain SEQ ID NO: 28 and optionally the amino acid sequences SEQ ID NO: 26 and 27; or heavy chain SEQ ID NO: 3 and optionally light chain SEQ ID NO: 25, preferably the light chain variable region of SEQ ID NO: 140; or heavy chain variable region of SEQ ID NO: 4 and optionally light chain SEQ ID NO: 28 preferably the light chain variable region of SEQ ID NO: 141.

In a further embodiment, particular residues of the above sequences are considered important for antigen binding. As such, in this embodiment, where present the following residues are:

SEQ ID No: 6 residue 3 is a T, residue 5 is an E, residue 7 is a D, residue 8 is an S, residue 9 is an A, residue 16 is a K and residue 17 is a G SEQ ID No: 7 residue 2 is a Y, residue 4 is an N, residue 5 is an F, residue 6 is a Y, residue 7 is a Y and residue 8 is a Y SEQ ID No: 9 residue 5 is a G, residue 6 is an N, residue 10 is a K, residue 13 is a Q, residue 16 is a Q and residue 17 is a D SEQ ID No: 10 residue 5 is a D, residue 6 is a Y, residue 8 is a D, residue 10 is a W, residue 11 is an F, residue 12 is a P and residue 14 is an L SEQ ID No: 11 residue 1 is an N SEQ ID No: 12 residue 5 is a D, residue 7 is an S, residue 8 is a T, residue 9 is an R, residue 16 is a K and residue 17 is a G SEQ ID No: 13 residue 4 is an R, residue 5 is an F, residue 6 is a Y, residue 7 is a Y, residue 8 is a D, residue 9 is an S, residue 10 is a T, residue 12 is a Y, residue 13 is a Y, residue 14 is a P, residue 15 is a D and residue 16 is an S SEQ ID No: 14 residue 1 is an S SEQ ID No: 15 residue 5 is a D, residue 7 is and S, residue 8 is an S, residue 9 is a T and residue 17 is a G or H SEQ ID No: 16 residue 4 is an R, residue 5 is a Y, residue 6 is a Y, residue 7 is a Y, residue 8 is a D, residue 9 is an S, residue 10 is a T, residue 12 is a Y, residue 13 is a Y, residue 14 is a P, residue 15 is a D and residue 16 is an N SEQ ID No: 17 residue 7 is an S, residue 8 is a T and residue 9 is an F SEQ ID No: 18 residue 1 is a D, residue 3 is an S and residue 5 is an R SEQ ID No: 19 residue 3 is an R, residue 4 is a Y and residue 5 is an N SEQ ID No: 20 residue 4 is an S, residue 5 is an S, residue 8 is a G, residue 9 is a G, residue 10 is an F, residue 11 is an N and residue 12 is a Y SEQ ID No: 21 residue 1 is a D, residue 3 is a T, residue 4 is an S and residue 5 is an R SEQ ID No: 22 residue 5 is an S, residue 6 is an R and residue 7 is a G SEQ ID No: 24 residue 5 is an R, residue 6 is a P and residue 7 is an S SEQ ID No: 25 residue 6 is an S and residue 7 is an R SEQ ID No: 27 residue 5 is an R, residue 6 is a P and residue 7 is an S As described above in relation to the presentation of the antigenic EDE in a protein scaffold, the compound, for example a protein, for example an antibody, may also be part of a larger structure, for example held within a protein scaffold. Preferences for the scaffold are as described earlier. For example, in one embodiment, the antibody or antigen binding portion thereof is within a larger polypeptide.

In a preferred embodiment, the compound that binds to the EDE as defined in any of the embodiments above also neutralises the dengue virus, preferably to at least 80%, preferably 90%, more preferably 95% or 98%, and most preferably 100%. In a more preferred embodiment, the compound neutralises all serotypes of dengue virus to at least 80%, preferably 90%, more preferably 95% or 98% and most preferably 100%. Preferences for neutralisation, including the concentrations of the compound, viral or sub-viral or virus like particles and host cells are as defined earlier in the first aspect of the invention.

As for the first aspect of the invention, it is preferred if the compound that can bind to the EDE is able to neutralise virus made in both insect cells, for example C6/36 insect cells, and human cells, for example primary human cells, for example dendritic cells. Preferably the compound neutralises dengue virus made in both insect cells, for example C6/36 insect cells, and human cells, for example primary human cells, for example dendritic cells to the same level, as discussed above. The ability of the compound to neutralise virus can be tested as detailed above and in the examples. In a most preferred embodiment the compound is able to fully neutralise (i.e. to 100%) all serotypes of dengue virus made in both insect and human cells.

In a preferred embodiment the compound is an antibody or antigen binding portion thereof. The antigen binding portion may be a Fv portion; a Fab-like fragment (e.g. a Fab fragment, a Fab' fragment or a $F(ab)_2$ fragment); or a domain antibody.

In one embodiment the antibody or antigen binding portion thereof is, or is derived from, a monoclonal antibody. In another embodiment the antibody or antigen binding portion thereof is, or is derived from a polyclonal antibody. In a further embodiment, the compound is a composition comprising a mixture of antibodies or antigen binding portions thereof, comprising:

a) a mixture of monoclonal antibodies or antigen binding portion thereof, or
b) a mixture of polyclonal antibodies or antigen binding portion thereof, or
c) a mixture or monoclonal and polyclonal antibodies or antigen binding portion thereof, for example wherein the ratio of monoclonal to polyclonal antibodies or antigen binding portions thereof is 10:1, 8:1, 6:1, 4:1, 2:1, 1:1, 1:2, 1:4, 1:6, 1:8 or 1:10.

It will be appreciated that the compound may be a recombinant protein, for example a recombinant antibody or antigen binding portion thereof. The compound may also be made synthetically. The compound may be a combination of recombinantly and synthetically produced.

The present invention also includes the means of making such a compound, for example a protein, for example an antibody or antigen binding portion thereof.

It will also be appreciated, therefore, that the compound may be produced by recombinant means, for example the compound, for example a polypeptide, for example an antibody or antigen binding portion thereof may be produced and isolated or purified from various organisms, including:

a) a human cell line, optionally CHO cells, or
b) a mammal, optionally a human, or
c) a microorganism, or
d) an insect cell line.

By isolated or purified we mean that the agent has been removed from its natural environment, and does not reflect the extent to which the agent has been purified.

Therefore the invention includes the isolation or purification of a compound of the present invention from various organisms, including from a human cell line, optionally CHO cells, or from a mammal, optionally a human, or from a microorganism, or from an insect cell line.

Where the compound is a polypeptide, for example an antibody or antigen binding portion thereof, or for example included in a protein scaffold, the compound may be encoded by a nucleic acid. By nucleic acid we include the meaning of both DNA and RNA, single or double stranded and in all their various forms. As such the invention includes a nucleic acid encoding any of the proteinaceous compound of the invention. In particular, SEQ ID No: 41-48 are included in the present invention. Any sequence derived from or comprising SEQ ID No: 41-48 which comprises mutations which would result in a silent mutation are included, as are sequences which cover any of the earlier mentioned possibilities, for example a nucleic acid sequence comprising a portion which encodes any of:

SEQ ID No: 1, or a sequence with at least 90% homology to SEQ ID No: 1;

SEQ ID No: 2, or a sequence with at least 90% homology to SEQ ID No: 2;

SEQ ID No: 3, or a sequence with at least 90% homology to SEQ ID No: 3;

SEQ ID No: 4, or a sequence with at least 90% homology to SEQ ID No: 4;

SEQ ID No: 37, or a sequence with at least 90% homology to SEQ ID No: 37;

SEQ ID No: 38, or a sequence with at least 90% homology to SEQ ID No: 38;

SEQ ID No: 39, or a sequence with at least 90% homology to SEQ ID No: 39;

SEQ ID No: 40, or a sequence with at least 90% homology to SEQ ID No: 40;

A sequence with at least 90% homology to SEQ ID No: 1 wherein the following residues are—T52, E54, D56, S57, A58, K65, G66, T69, E82, N84, S85, Y100, N102, F103, Y104, Y105, Y106;

A sequence with at least 90% homology to SEQ ID No: 2 wherein the following residues are—G554, N55, N57, K59, Q62, Q65, G66, R94, R98, F99, Y100, Y101, D102, S103, T104, Y106, Y107, P108, D109, S110, D117, V118;

A sequence with at least 90% homology to SEQ ID No: 3—wherein the following residues are V2, S28, N31, D54, S56, T57, R58, K65, G66, R94, R98, F99, Y100, Y101, D102, S103, T104, Y106, Y107, P108, D109, S110, D117, V118;

A sequence with at least 90% homology to SEQ ID No: 4—wherein the following residues are V2, T28, S31, D54, S56, S57, T58, G66, F68, M69, R94, R98, Y99, Y100, Y101, D102, S103, T104, Y106, Y107, P108, D109, N110, D117, V118;

A sequence with at least 90% homology to SEQ ID No: 37—wherein the following residues are S30, T31, F32, Y49, D50, S52, R54, R66, R91, Y92, N93, W94;

A sequence with at least 90% homology to SEQ ID No: 38—wherein the following residues are S26, S27, G30, G31, F32, N33, Y34, D52, T54, S55, R56, S62, S95, R96, G97;

A sequence with at least 90% homology to SEQ ID No: 39—wherein the following residues are Y51, R56, P57, S58, G59, S96, R97;

A sequence with at least 90% homology to SEQ ID No: 40—wherein the following residues are Y51, R56, P57, S58, K97;

SEQ ID No: 5, or a sequence resulting in the polypeptide having one or two amino acid substitutions, insertions or deletions compared to SEQ ID No: 5;

SEQ ID No: 6 or a sequence resulting in the polypeptide having one or two amino acid substitutions, insertions or deletions compared to SEQ ID No: 6; optionally wherein residue 3 is a T, residue 5 is an E, residue 7 is a D, residue 8 is an S, residue 9 is an A, residue 16 is a K and residue 17 is a G;

SEQ ID No: 7 or a sequence resulting in the polypeptide having one or two amino acid substitutions, insertions or deletions compared to SEQ ID No: 7; optionally wherein residue 2 is a Y, residue 4 is an N, residue 5 is an F, residue 6 is a Y, residue 7 is a Y and residue 8 is a Y;

SEQ ID No: 8 or a sequence resulting in the polypeptide having one or two amino acid substitutions, insertions or deletions compared to SEQ ID No: 8;

SEQ ID No: 9 or a sequence resulting in the polypeptide having one or two amino acid substitutions, insertions or deletions compared to SEQ ID No: 9; optionally wherein residue 5 is a G, residue 6 is an N, residue 10 is a K, residue 13 is a Q, residue 16 is a Q and residue 17 is a D;

SEQ ID No: 10 or a sequence resulting in the polypeptide having one or two amino acid substitutions, insertions or deletions compared to SEQ ID No: 10; optionally wherein residue 5 is a D, residue 6 is a Y, residue 8 is a D, residue 10 is a W, residue 11 is an F, residue 12 is a P and residue 14 is an L;

SEQ ID No: 11 or a sequence resulting in the polypeptide having one or two amino acid substitutions, insertions or deletions compared to SEQ ID No:11; optionally wherein residue 1 is an N;

SEQ ID No: 12 or a sequence resulting in the polypeptide having one or two amino acid substitutions, insertions or deletions compared to SEQ ID No:12; optionally wherein residue 5 is a D, residue 7 is an S, residue 8 is a T, residue 9 is an R, residue 16 is a K and residue 17 is a G;

SEQ ID No: 13 or a sequence resulting in the polypeptide having one or two amino acid substitutions, insertions or deletions compared to SEQ ID No:13; optionally wherein residue 4 is an R, residue 5 is an F, residue 6 is a Y, residue 7 is a Y, residue 8 is a D, residue 9 is an S, residue 10 is a T, residue 12 is a Y, residue 13 is a Y, residue 14 is a P, residue 15 is a D and residue 16 is an S;

SEQ ID No: 14 or a sequence resulting in the polypeptide having one or two amino acid substitutions, insertions or deletions compared to SEQ ID No: 14; optionally wherein residue 1 is an S;

SEQ ID No: 15 or a sequence resulting in the polypeptide having one or two amino acid substitutions, insertions or deletions compared to SEQ ID No: 15; optionally wherein residue 5 is a D, residue 7 is and S, residue 8 is an S, residue 9 is a T and residue 17 is a G or H SEQ ID No: 16 or a sequence resulting in the polypeptide having one or two amino acid substitutions, insertions or deletions compared to SEQ ID No: 16; optionally wherein residue 4 is an R, residue 5 is a Y, residue 6 is a Y, residue 7 is a Y, residue 8 is a D, residue 9 is an S, residue 10 is a T, residue 12 is a Y, residue 13 is a Y, residue 14 is a P, residue 15 is a D and residue 16 is an N;

SEQ ID No: 17 or a sequence resulting in the polypeptide having one or two amino acid substitutions, insertions or deletions compared to SEQ ID No: 17; optionally wherein residue 7 is an S, residue 8 is a T and residue 9 is an F;

SEQ ID No: 18 or a sequence resulting in the polypeptide having one or two amino acid substitutions, insertions or deletions compared to SEQ ID No: 18; optionally wherein residue 1 is a D, residue 3 is an S and residue 5 is an R;

SEQ ID No: 19 or a sequence resulting in the polypeptide having one or two amino acid substitutions, insertions or deletions compared to SEQ ID No: 19; optionally wherein residue 3 is an R, residue 4 is a Y and residue 5 is an N;

SEQ ID No: 20 or a sequence resulting in the polypeptide having one or two amino acid substitutions, insertions or deletions compared to SEQ ID No: 20; optionally wherein residue 4 is an S, residue 5 is an S, residue 8 is a G, residue 9 is a G, residue 10 is an F, residue 11 is an N and residue 12 is a Y;

SEQ ID No: 21 or a sequence resulting in the polypeptide having one or two amino acid substitutions, insertions or deletions compared to SEQ ID No: 21; optionally wherein residue 1 is a D, residue 3 is a T, residue 4 is an S and residue 5 is an R;

SEQ ID No: 22 or a sequence resulting in the polypeptide having one or two amino acid substitutions, insertions or deletions compared to SEQ ID No: 22; optionally wherein residue 5 is an S, residue 6 is an R and residue 7 is a G;

SEQ ID No: 23 or a sequence resulting in the polypeptide having one or two amino acid substitutions, insertions or deletions compared to SEQ ID No: 23;

SEQ ID No: 24 or a sequence resulting in the polypeptide having one or two amino acid substitutions, insertions or deletions compared to SEQ ID No: 24; optionally wherein residue 5 is an R, residue 6 is a P and residue 7 is an S;

SEQ ID No: 25 or a sequence resulting in the polypeptide having one or two amino acid substitutions, insertions or deletions compared to SEQ ID No: 25; optionally wherein residue 6 is an S and residue 7 is an R;

SEQ ID No: 26 or a sequence resulting in the polypeptide having one or two amino acid substitutions, insertions or deletions compared to SEQ ID No: 26;

SEQ ID No: 27 or a sequence resulting in the polypeptide having one or two amino acid substitutions, insertions or deletions compared to SEQ ID No: 27; optionally wherein residue 5 is an R, residue 6 is a P and residue 7 is an S; and SEQ ID No: 28 or a sequence resulting in the polypeptide having one or two amino acid substitutions, insertions or deletions compared to SEQ ID No: 28.

The nucleic acid may or may not contain introns. The nucleic acid may also be modified to enable purification of the subsequently translated polypeptide, for example the open reading frame of the intended polypeptide may be modified to incorporate a tag, for example a myc tag or a his tag, to enable subsequent purification.

The nucleic acid may also be modified, for example codon optimised, to be better translated by the organism which it is to be translated in, without affecting final polypeptide sequence.

Nucleic acids of the present disclosure can be produced or modified using a number of methods known to those skilled in the art for example, classic mutagenesis, chemical treatment, restriction digestion, ligation and PCR.

The nucleic acid of the invention may be incorporated into a vector. Thus the invention also comprises a vector comprising the nucleic acid. By vector we mean vehicle for cloning of amplification of the nucleic acid, or for insertion into a target organism, for example the vector may be a plasmid or may be a nucleic acid used to target the nucleic acid of the invention into a target organism, for example into the genome of a target organism. The vector may further comprise nucleotide sequences required for expression of the polypeptide encoded by the nucleic acid of the invention, for example promoter sequences or termination sequences may be operably linked to the nucleic acid of the invention, and may also include reporter genes, for example antibiotic resistance cassettes. The vector may be single stranded or double stranded, and may be linear or circular. In one embodiment the vector is a plasmid.

In addition to providing a compound which can bind to an EDE as indicated above, a further aspect of the invention also provides an EDE compound as defined below. The invention also provides a nucleic acid, or a vector, which encodes the EDE compound of the invention, in addition to a host cell comprising the nucleic acid or vector. Preferences for a nucleic acid and vector, for example, indicated above may also be relevant to the present aspect of the invention, as will be apparent to the skilled person. Thus the invention provides an EDE compound as defined below, or a nucleic acid encoding such an EDE compound, or a vector comprising said nucleic acid, or a host cell comprising said nucleic acid or vector.

The EDE compound is intended to provide an epitope as described above as a Envelope Dependent Epitope. The EDE compound may bind specifically to one or more EDE-specific antibodies of the invention, for example to a preferred neutralising antibody as discussed above, or as exemplified in the Examples. The EDE compound typically is or comprises a polypeptide. In one embodiment, the EDE compound is a dimer of envelope protein, or envelope ectodomain or the 400 amino terminal residues of the ectodomain of Envelope protein. By "400 amino terminal residues" as used herein is included approximately 400 amino terminal residues, for example between 350 and 450 residues, 320 and 470 residues, or 330 and 480 residues (or combinations thereof), for example between 380 and 420 residues, for example between 390 and 410 residues, for example 395 or 393 residues, as noted above and as will be apparent to those skilled in the art. The envelope protein may be any of the envelope proteins from DENV-1, DENV-2, DENV-3 and DENV-3, and DENV-4, (SEQ ID No's: 29, 31, 33 or 35), or a protein with at least 90% homology to the sequences in SEQ ID No's: 29, 31, 33 or 35. The dimer may be a homodimer or a heterodimer. In a preferred embodiment the dimer is not incorporated into an intact viral particle, or a sub-viral particle, or a virus-like particle, but rather is a free dimer for example with a molecular weight of twice that of the monomeric envelope polypeptide. It will be appreciated that any form of EDE or EDE compound described herein, for example, an engineered envelope protein, for example, as part of a protein scaffold, may potentially be presented as part of a virus, virus-like particle, or sub-viral particle.

In another embodiment, the EDE compound comprises a dimer of envelope protein, or envelope ectodomain or the (approximately) 400 amino terminal residues of the ectodomain of envelope protein which has been engineered to have increased stability in the dimer configuration, for example has been engineered to have increased levels of covalent and/or non-covalent bonds between the dimers;

In a preferred embodiment, the EDE compound is a stabilised recombinant dengue virus envelope glycoprotein E ectodomain (recombinant sE) dimer according to the earlier aspect of the invention, for example, is a stabilised recombinant dengue virus envelope glycoprotein E ectodomain (recombinant sE) dimer wherein the dimer is:
  covalently stabilized with at least one disulphide inter-chain bond between the two sE monomers and/or,
  covalently stabilized with at least one sulfhydryl-reactive crosslinker between the two sE monomers and/or,
  covalently stabilized by linking the two sE monomers through modified sugars; and/or,
  non-covalently stabilized by substituting at least one amino acid residue in the amino acid sequence of at least one sE monomer with at least one bulky side chain amino acid, at the dimer interface or in domain 1 (D1)/domain 3 (D3) linker of each monomer.

A dengue virus envelope glycoprotein E ectodomain (sE) refers to the 1-395 amino acid fragment of the envelope glycoprotein E of the dengue virus serotypes 1, 2 and 4, and to the 1-393 amino acid fragment of the envelope glycoprotein E of the dengue virus serotype 3.

Thus, as described earlier, the EDE compound is a stabilised dimer and may be any one or more of:
  a) A dimer wherein the monomer is selected from the group consisting of: the DENV-1 sE of SEQ ID NO: 132, the DENV-2 sE of SEQ ID NO: 133 the DENV-3 sE of SEQ ID NO: 134, the DENV-4 sE of SEQ ID NO: 135 and a mutant sE thereof having at least one mutation (substitution) selected among H27F, H27W, L107C, F108C, H244F, H244W, S255C, A259C, T/S262C, T/A265C, L278F, L292F, L294N, A313C and T315C; optionally, wherein said mutant sE thereof has further at least one mutation (substitution) selected among Q227N, E174N and D329N, preferably the three mutations Q227N, E174N and D329N;
  b) A dimer wherein the dimer can be a homodimer of two identical recombinant sE as defined above or a heterodimer of two different recombinant sE as defined above, the dimer being preferably a homodimer, for example, it can be a heterodimer of DENV-1 sE and DENV-2 sE as defined above. It can also be a heterodimer of DENV-1 sE and a mutant sE of DENV-1 sE as defined above;
  c) A dimer which is glycosylated at position 67 (Asn67 glycan) and/or at position 153 (Asn153 glycan) of each sE monomer, preferably at least at position 67 (Asn67 glycan) of each monomer;
  d) A dimer which is covalently stabilized with at least one, two or three disulphide inter-chain bonds between the two sE monomers;
  e) A dimer which is a homodimer of mutant sE having each the mutation A259C or S255C as defined above, and wherein the residues 259C or 255C are linked together through a disulphide inter-chain bond f) A dimer which is a heterodimer of a mutant sE having the mutation A259C as defined above and a mutant sE having the mutation S255C as defined above, wherein the residues 259C and 255C are linked together through a disulphide inter-chain bond;

g) A dimer which is a homodimer of mutant sE having each the mutations F108C and T315C as defined above, or a homodimer of mutants sE having each the mutations L107C and A313C as defined above, wherein the residues 108C and 315C or the residues 107C and 313C are linked together through a disulphide inter-chain bond;

h) A dimer which is a heterodimer of a mutant sE having the mutations F108C and A313C as defined above and a mutant sE having the mutations L107C and T315C as defined above, wherein the residues 108C and 313C are linked respectively to the residues 315C and 107C through a disulphide inter-chain bond between the two sE monomers;

i) A dimer which is selected from the group consisting of a homodimer of mutants sE having each the mutations A259C, F108C and T315C, a homodimer of mutants sE having each the mutations S255C, F108C and T315C, a homodimer of mutants sE having each the mutations A259C, L107C and A313C, and a homodimer of mutants sE having each the mutations A255C, L107C and A313C as defined above, wherein the residues 259C, 255C, 108C, 315C, 107C and 313C are linked respectively to the residues 259C, 255C, 315C, 108C, 313C and 107C through disulphide inter-chain bonds;

j) A dimer which is a heterodimer of a mutant sE having the mutations A259C, F108C and T315C as defined above and a mutant sE having the mutations S255C, F108C and T315C as defined above, wherein the residues 259C, 108C and 315C are linked respectively to the residues 255C, 315C and 108C through disulphide inter-chain bonds;

k) A dimer which is a heterodimer of a mutant sE having the mutations S255C, L107C and A313C as defined above and a mutant sE having the mutations A259C, L107C and A313C as defined above, wherein the residues 255C, 107C and 313C are linked respectively to the residues 259C, 313C and 107C through disulphide inter-chain bonds;

l) A dimer which is covalently stabilized with at least one, two or three, sulfhydryl-reactive crosslinkers (also called thiol-reactive crosslinkers) between the sE monomers;

m) A dimer which is a homodimer of mutant sE having each the mutation T/S262C or T/A265C as defined above, wherein the residues 262C or 265C are linked together through a sulfhydryl-reactive crosslinker;

n) A dimer which is a heterodimer of a mutant sE having the mutation T/S262C as defined above and a mutant sE having the mutation T/A265C as defined above, wherein the residues 262C and 265C are linked together through a sulfhydryl-reactive crosslinker;

o) A dimer which is a homodimer or a heterodimer of a mutant sE wherein at least one of the amino acid residues 1-9, 25-30, 238-282, 96-111 311-318 of sE is mutated (substituted) to cysteine and a mutant sE wherein at least one of the amino acid residues 1-9, 25-30, 238-282, 96-111 311-318 of sE is mutated (substituted) to cysteine, and wherein the mutated cysteine residues are linked together through a sulfhydryl-reactive crosslinker;

p) A dimer which is covalently stabilized by linking the two monomers through modified sugars.

q) A dimer which is a homodimer or heterodimer of mutant sE, wherein:

one sE monomer has at least one mutation which introduces a glycosylation site, and wherein the mutated amino acid residue is glycosylated with a modified sugar bearing an X functional group, and the other sE monomer has at least one mutation which introduces a glycosylation site, and wherein the mutated amino acid residue is glycosylated with a modified sugar bearing a Y functional group, and wherein both mutated residues are joined together through the modified sugars by reacting, specifically by click chemistry, the X functional group of the sugar of the first sE monomer with the Y functional group of the sugar of the other sE monomer. By X functional group, it is meant a chemical group beared by a sugar which is able to react and form a covalent linking by click chemistry with a Y functional group, said Y functional group being preferably an azide functional group. By Y functional group, it is meant a chemical group beared by a sugar which is able to react and form a covalent linking by click chemistry with a X functional group, said X functional group being preferably a terminal alkyne functional group;

r) A dimer which is non-covalently stabilized by filling the cavities of said dimer at the dimer interface by substituting at least one amino acid in the amino acid sequence of one or the two monomers, preferably the two monomers, with bulky side chain amino acids;

s) A dimer which is non-covalently stabilized by substituting at least one amino acid residue in the amino acid sequence of at least one sE monomer with at least one bulky side chain amino acid within regions forming cavities at the dimer interface or in domain 1 (D1)/domain 3 (D3) linker of each monomer. Such substitutions allow increasing hydrophobic interactions between the two sE monomers;

t) A dimer which is a homodimer or heterodimer, preferably homodimer, of two recombinant sE as defined above, wherein one of the recombinant sE or the two recombinant sE have at least one mutation (substitution) selected from the group consisting of H27F, H27W, H244F, H244W, and L278F;

u) A dimer which is non-covalently stabilized in domain 1 (D1)/domain 3 (D3) linker of each monomer, by substituting amino acids in the amino acid sequence of one or the two, preferably the two, monomers with at least one bulky side chain amino acid;

v) A dimer which is a homodimer or heterodimer, preferably homodimer, of two recombinant sE as defined above, wherein one of the recombinant sE or the two recombinant sE have at least one mutation (substitution) selected from the group consisting of L292F and L294N.

In yet another embodiment, the EDE compound presents an improved epitope over the naturally occurring envelope dimer within a virus, virus-like particle or sub-viral particle. By improved epitope we include the meaning of improved over any epitope naturally displayed on an intact viral particle. By improved we include the meaning of being capable of eliciting a more beneficial immune response than the native intact dengue virus particle. An EDE compound which has increased stability in the dimer configuration, for example via the modifications described in a)-v) above, is considered to be an improved epitope. The EDE may be improved in other ways, for example, the EDE compound may be an EDE which has been engineered, or inserted into a scaffold, such that the FL is incapable of being recognised by a compound, for example a polypeptide, for example an antibody or antigenic portion thereof, on its own, for example where the EDE is engineered such that the FL cannot be recognised by an antibody in isolation from the immediate neighbours of the fusion loop, i.e. the fusion loop cannot be recognised in a context independent of the quaternary organisation.

In another embodiment, the EDE compound is incorporated into a heterologous protein scaffold which conserves the dimer configuration, by, for example, increasing the level of covalent and/or non-covalent bonds between the dimers, as described above. Further, the VDE compound may comprises a heterologous protein scaffold which may present only a portion of the dimer of envelope protein, or envelope ectodomain or the (approximately) 400 amino terminal residues of the ectodomain of the envelope protein, wherein the portion is a sequential portion of the dimer of envelope protein, or envelope ectodomain or the (approximately) 400 amino terminal residues of the ectodomain of the envelope protein, or wherein the portion comprises select, non-contiguous residues of the dimer of envelope protein, or envelope ectodomain or the (approximately) 400 amino terminal residues of the ectodomain of the envelope protein, as described above.

For example, in one embodiment, the EDE compound comprises one or more of positions E49, K64, Q77, W101, V122, N134, N153, T155, I161, A162, P169, T200, K202, E203, L308, K310, Q323, W391, F392, A71, C105, C74, D154, D249, D271, D309, D362, D98, E148, E311, E44, E71, E84, G102, G104, G106, G152, G156, G28, G29, G374, H158, H27, I113, I308, I46, K246, K247, K310, K323, K325, K47, L113, L45, L82, M278, N103, N153, N362, N67, N83, Q248, Q271, Q325, Q77, R2, R247, R323, R73, R99, S72, S81, T115, T155, T361, T46, T68, T69, T70, T72, V113, V114, V250, V309, V324, V97, W101; or equivalent residue of a Dengue virus envelope polypeptide in a substantially similar spatial configuration as the residues adopt in the native the dimer of envelope protein, or envelope ectodomain or the (approximately) 400 amino terminal residues of the ectodomain of envelope protein. These residues may be within the naturally occurring envelope protein, or in an alternate embodiment, they are held within a scaffold protein in the appropriate configuration. In a preferred embodiment, the EDE compound comprises position W101 and at least one other residue described above. In a more preferred embodiment, the EDE compound comprises all of the above residues. In one embodiment the EDE compound comprises a N153 glycan. In an alternate embodiment, the EDE does not comprise a N153 glycan.

In a more preferred embodiment, the EDE compound comprises residues that are conserved in both amino acid and spatial position across more than one serotype of dengue virus, preferably residues that are conserved in both amino acid and spatial position across all serotypes of dengue virus, that is, across four serotypes of dengue virus.

The EDE compound may comprise the dimer of envelope protein, or envelope ectodomain or the (approximately) 400 amino terminal residues of the ectodomain of the envelope protein which has been engineered to have increased stability in the dimer configuration, and also be held within a protein scaffold as described above.

The inventors have found that particular regions of the envelope dimer are important for contact with a compound of the invention, for example an antibody or antigen binding portion thereof. Therefore, in some embodiments, the VDE compound comprises a particular antigenic portion of a dimer of envelope protein, or envelope ectodomain or the 400 amino terminal residues of the ectodomain of envelope protein.

The EDE compound may be a particular fragment comprising particular residues of the dimer of envelope protein, or envelope ectodomain or the (approximately) 400 amino terminal residues of the ectodomain of the envelope protein which comprises regions deemed to be required for antigenicity. This fragment may also have been engineered to maintain a particular conformation, or may be held within a protein scaffold, or may both be engineered and held within a protein scaffold.

For example, in one embodiment, the EDE compound comprises a region centred in a valley lined by the b strand on the domain II side, and the "150 loop" on the domain I side (across from the dimer interface), wherein the 150 loop spans residues 148-159, connecting b-strands E0 and F0 of domain I, and carries the N153 glycan, which covers the fusion loop of the partner subunit in the dimer. In one embodiment this region comprises three polypeptide segments of domain II of the reference subunit, which is defined as the subunit which contributes the FL to the epitope. These three segments are: the b strand (resides 67-74 which bears the N67 glycan), the fusion loop and residues immediately upstream (residues 97-106) and the ij loop (residues 246-249).

In another embodiment, in addition to the region described above, (the region which comprises the three polypeptide segments of domain II of the reference subunit), the EDE compound further comprises the 150 loop and the N153 glycan chain of the second subunit.

A further embodiment of the EDE compound comprises the region described above, (the region which comprises the three polypeptide segments of domain II of the reference subunit), and the 150 loop and the A strand of domain III of the second subunit, in particular residue K310. The inventors have found that a subset of the useful compounds defined here in cause disorder in the 150 loop of the second subunit upon binding to the EDE. Thus, in one embodiment the 150 loop may be in the natural configuration found in the natural dimer of envelope protein, or envelope ectodomain or the 400 amino terminal residues of the ectodomain of the envelope protein, or in another embodiment the 150 loop may be in the disordered configuration that the 150 loop adopts on binding to one of the compounds of the invention.

It is considered that the N67 glycan is particularly important for dengue infection of dendritic cells. Thus an EDE compound comprising this residue in the correct epitopic environment, as described herein, is considered to be a preferred embodiment.

In a preferred embodiment, the EDE compound is such that it may raise antibodies once administered to a subject, preferably a human, wherein the antibodies are preferably capable of binding to all four serotypes of dengue virus, and optionally are capable of neutralising all four serotypes of dengue virus, preferably capable of neutralising all four serotypes of dengue virus to 100%, and optionally are capable of neutralising virus made in both human and insect cells, preferably capable of neutralising all four serotypes of dengue virus made in both human and insect cells to 100%.

The VDE compound may be an anti-idiotypic antibody (or fragment thereof or molecule sharing the binding specificity, as discussed above), as well known to those skilled in the art, developed against one or more of the high affinity/neutralising antibodies provided herein, for example as indicated in the Examples.

The present invention also provides a method for the synthesis of the EDE wherein the EDE is a stabilized recombinant sE dimer of the present invention, comprising at least one of the following steps:

a) contacting two single or multiple cysteine mutant sE as defined above, under oxidative conditions, and/or,
b) contacting two sE monomers with at least one, two or three, sulfhydryl-reactive crosslinkers as defined above, and/or,
c) contacting two sE monomers having glycosylation sites as defined above, by click chemistry and/or
d) contacting two sE monomers wherein at least one amino acid residue in the amino acid sequence of at least one sE monomer is substituted with a bulky side chain amino acid as defined above.

The present invention also provides a stabilized recombinant sE dimer obtainable by the method as defined above.

To ensure the proper formation of the stabilized recombinant sE dimer according to the present invention the affinity for the antibodies as described below can be measured by ELISA (for the covalently and non-covalently stabilized dimer) or by Surface Plasmon Resonance (for the covalently stabilized dimer).

The invention also includes a host cell comprising any of the nucleic acids of the invention or the vector of the invention, for example a nucleic acid or vector comprising a portion of nucleic acid that encodes the EDE compound or the compound of the invention. For example the invention comprises any host cell known to be useful for the expression of heterologous proteins, for example a C6/36 insect cell, human dendritic cell, CHO cell, or a microorganism, for example a *Pichia pastoris* cell, which comprises the vector, for example a plasmid. The host cell may also comprise a nucleic acid of the invention which has been incorporated into the genome of the host cell, optionally by the use of a viral vector to target the nucleic acid of the invention to the genome, for example adenovirus, adeno-associated virus, cytomegalovirus, herpes virus, poliovirus, retrovirus, sindbis virus, vaccinia virus, or any other DNA or RNA virus vector.

The invention further comprises a non-human transgenic animal comprising at least one cell transformed by a nucleic acid of the invention or the vector of the invention, or the host cell of the invention, for example by a nucleic acid or vector comprising a portion of nucleic acid that encodes the VDE compound or the compound of the invention.

A process for the production of the compound of the invention, preferably a polypeptide, preferably an antibody or antigen binding portion thereof, or the EDE compound of the invention, is provided herein. The process comprises the following stages:

i) Culture in the appropriate medium of a host cell of the invention,
ii) Recovery of said compound, preferably an antibody or antigen binding portion thereof produced, or said EDE compound, wherein said recovery is either from the culture medium or said cultured cells.

It will be appreciated that for the purification or isolation of polypeptides, for example wherein the compound is a polypeptide, or the EDE compound is a polypeptide, the skilled person would readily engineer the nucleotide coding sequence to include nucleotides which aid in purification, for example the inclusion of affinity tags, of epitope tags. Thus in one embodiment, the process for the production of the compound of the invention, or the EDE compound, involves culture of a host cell which comprises the nucleotide sequence encoding the compound or the EDE compound, and further comprising nucleotides that encode a portion useful in the purification of the compound or EDE compound, or vector comprising the nucleotide sequence encoding the compound or the EDE compound, and further comprising nucleotides that encode a portion useful in the purification of the compound or EDE compound.

It will be appreciated that where the compound is a polypeptide, for example an antibody or antigen binding portion thereof, as well as being made by recombinant means, polypeptide production can be triggered by the administration of a EDE as defined in any of the above embodiments, optionally an EDE compound as defined above, to a subject. Following EDE (optionally EDE compound) administration, the natural host response would produce the antibodies which can be recovered from the subject's blood. Preferably the EDE is not presented as part of an intact virus, or virus like particle or sub-viral particle. Preferably the EDE is an envelope polypeptide dimer, as discussed above, or other EDE compound as discussed above or below.

For example, the present invention provides a method of producing a compound of the present invention, where the compound is an antibody of the present invention, comprising the steps of:

a) contacting a mammal with a stabilized recombinant sE dimer of the present invention, or an immunogenic composition of the present invention,
b) detecting the presence of an antibody directed to said sE dimer in one or more serum samples derived from said mammal,
c) harvesting spleen cells from said mammal,
d) fusing said spleen cells with myeloma cells to produce hybridoma cells,
e) identifying hybridoma cells capable of producing said antibody,
f) culturing said hybridoma cells capable of producing said antibody, and
g) optionally, isolating said antibody.

The present invention also provides an antibody obtainable by any of the methods defined above.

The present invention also provides a hybridoma cell obtainable by the method defined above.

The present invention also provides the use of a stabilized recombinant sE dimer of the present invention for the preparation of hybridoma cells capable of producing a neutralizing antibody directed to said dimer as defined above.

In a preferred embodiment the EDE or EDE compound is such that it is has already been determined to be capable of raising highly cross reactive and potently neutralising antibodies. The antibodies identified in the Examples (Examples 1-6) were raised to the intact virus in a natural infection of dengue virus. It is considered that more specific and improved antibodies can be raised by the administration of a specific EDE antigen, which may be a EDE compound of the invention. For example, in the natural infection, some patients did not raise anti-EDE antibodies, and instead produced anti-FL antibodies which are considered to be less useful and are less cross-reactive and are less neutralising. It is considered that administration of a EDE antigen is more likely to raise the anti-EDE useful antibodies. As described earlier, in some embodiments the EDE or EDE compound is engineered to have increased stability in the dimer formation, which is considered to increase the chances of anti- VDE antibodies being made within the subject. In addition, the EDE or EDE compound in some embodiments is engineered, for example mutations within the envelope protein itself, or by the use of a scaffold protein, to present an improved epitope, for example by hiding the fusion loop so that anti-FL antibodies are less likely to be made. Administration of an EDE or EDE compound which is common to all serotypes of dengue virus is likely to raise highly cross-reactive and potently neutralising antibodies. These antibodies can be recovered from the subject and used for further analysis or used in treatment of dengue fever, or in dengue fever clinical trials.

Therefore one embodiment provides a process for the production of a compound according to the invention wherein the compound is a polypeptide, or an antibody or antigen binding portion thereof, wherein said process comprises the following stages:

a. administration to a subject a Envelope Dimer Epitope or EDE compound as defined in any of the preceding embodiments,
b. recovery and isolation of said antibody or antigen binding portion thereof from the subject's blood.

It will be appreciated that the above method of producing compounds, for example antibodies or antigen binding portions thereof, of the invention comprising administering to a subject an EDE or EDE compound, can also be used as part of a method of selecting a suitable antigen for a vaccine. Current vaccines utilise attenuated versions of all four serotypes of dengue, and are not particularly effective. Such a vaccine would also be capable of triggering the production of the non-useful anti-FL antibodies. A preferred vaccine would comprise a single antigen capable of eliciting an immune response to all serotypes of dengue virus, wherein the immune response is capable of neutralising all serotypes of dengue virus ie considered to be four serotypes of dengue virus.

The inventors of the present invention have, for the first time, identified highly cross-reactive and potently neutralising antibodies, and the particular epitope (EDE) to which they bind. Thus, the use of this epitope in a vaccine is likely to be preferable to the current vaccine strategies.

The present invention thus provides a method of selecting a suitable antigen for a vaccine against dengue virus wherein said method comprises characterisation of one or more antibodies made in a subject in response to said antigen, optionally wherein said antigen has previously been found to bind to a panel of antibodies known to bind the Envelope Dimer Epitope as defined in any of the preceding embodiments.

The identification of highly cross-reactive and potently neutralising antibodies in a subject which has been administered a dengue antigen is indicative of that antigens likelihood of being useful in a vaccine. In one embodiment, the antigen is not presented as part of an intact virus. In a preferred embodiment the antigen is an EDE compound as described in any of the earlier embodiments, preferably a dimer of envelope protein, preferably a stabilised dimer, optionally as part of a scaffold protein. In a preferred embodiment, the antigen is such that it has already been determined to be able to bind to highly cross-reactive and potently neutralising antibodies that can bind the EDE, for example the antibodies of this present invention, for example as identified in the Examples.

By administering such an antigen, known to be able to bind to highly useful antibodies, the antibodies made in response to the antigen in the subject can be characterised. It is likely that such an antigen will cause the production of such useful antibodies within the subject and therefore be a suitable candidate antigen for use in vaccine composition. By characterisation we include the meaning of determining whether the antibodies are considered to bind the fusion loop, by, for example, determining the ability of the antibody to bind to linear or denatured or recombinant envelope protein, for example the ability to bind to the envelope protein on a western blot or ELISA, and the ability of the antibody to bind to a dimer of envelope protein, or an EDE or EDE compound as described earlier in previous embodiments. The ability of the antibody to bind to all four serotypes of dengue virus may also be assessed, as may the ability of the antibody to neutralise all four types of dengue virus. Methods for determining the neutralising ability of an antibody are detailed earlier. The ability of the antibody to neutralise dengue virus made in both human and insect cells may also be determined, as described earlier and in the examples.

In one embodiment, an antigen is not considered to be useful as a vaccine if it raises predominantly anti-FL antibodies. For example, the antigen is considered useful if the ratio of antibodies raised against the FL and antibodies raised against the EDE is no more than 1:2, 1:4, 1:5, 1:10, 1:50, 1:100, 1:500, 1:1000. The relative amount of anti-FL antibodies and anti-EDE antibodies can be determined by methods well known to those skilled in the art, for example using ELISA based techniques. The antigen is considered to be useful if it raises antibodies capable of binding to the EDE of more than one serotype of dengue virus, preferably all 4 types of dengue virus. The antigen is considered to be useful if it raises antibodies capable of neutralises more than one serotype of dengue virus, preferably capable of neutralising all 4 types of dengue virus, preferably to 100%. The antigen is also considered useful if it raises antibodies that are capable of neutralising dengue virus made in both human and insect cells, preferably to the same level (as discussed above), preferably neutralises the virus to at least 95% or at least 98%, for example 100%. The antigen is considered most useful if it:

a) Does not raise, or does not significantly raise anti-FL antibodies, and
b) Binds, to some significant degree, to all 4 serotypes of dengue virus, and
c) Neutralises, to some significant degree, all 4 serotypes of dengue virus made in both human and insect cells to 100%.

Further, in another embodiment, the antigen is considered to be suitable for use in a vaccination if the antibodies raised are capable of binding to the EDE as defined in the earlier embodiments.

In a further embodiment, the antigen administered to the subject may comprise an additional agent to help prevent antibodies being raised to the fusion loop.

The antibodies produced by a subject exposed to the antigen may be obtained from sorted single plasma cells of a subject.

It will be appreciated that the identification, for the first time, or highly cross-reactive and potently neutralising antibodies against dengue virus presents a unique opportunity to be able to treat or prevent this viral disease. In addition, it will allow clinical trials comprising live dengue virus to be performed, as until the present invention, there was no reliable way to treat the infection caused during the trial. Therefore a further aspect of the present invention provides a method of treating or preventing Dengue virus infection in a subject.

The method comprises the administration of one or more compounds according to the present invention, preferably a polypeptide, preferably an antibody or fragment thereof. The invention also provides one or more compounds according to the present invention, preferably a polypeptide, preferably an antibody or fragment thereof, for use in the prevention or the treatment of dengue virus infection. The invention also provides the use of a compound of the invention in the manufacture of a medicament for the treatment or prevention of dengue infections.

It will be appreciated that for administration, the compound of the invention may be part of a composition, for example and pharmaceutical composition. The composition may further comprise one or more other therapeutic agents deemed to be useful in either treating the infection itself, for example further anti-viral agents, or one or more agents deemed to be useful in treating a symptom of dengue infection, for example.

The term "treating" includes the administration of any of the compounds of the invention, for example compound of the invention, EDE compound, vaccine composition, antibody, a stabilized recombinant sE dimer or an immunogenic composition of the present invention to a patient who has a dengue virus infection or a symptom of dengue virus infection, with the purpose to cure, heal, alleviate, relieve, alter, remedy, ameliorate, improve, or affect the dengue virus infection and/or the symptoms of the dengue infection. We include the meaning of treating of alleviating any one or more of symptoms of dengue infection. Treating also includes the meaning of preventing new cells from being infected. Whether or not a patient has been successfully treated will be apparent to one skilled in the art. For example, viral load may be reduced.

The term "preventing" means that the progression of a dengue virus infection is reduced and/or eliminated, or that the onset of a dengue virus infection is delayed or eliminated.

Symptoms of dengue virus infection and Dengue fever are set out in WHO Fact sheet no 117, for example. As noted therein, Dengue fever is a severe, flu-like illness that affects infants, young children and adults, but seldom causes death. Dengue should be suspected when a high fever (40° C./104° F.) is accompanied by two of the following symptoms: severe headache, pain behind the eyes, muscle and joint pains, nausea, vomiting, swollen glands or rash. Symptoms usually last for 27 days, after an incubation period of 4-10 days after the bite from an infected mosquito. Severe dengue is a potentially deadly complication due to plasma leaking, fluid accumulation, respiratory distress, severe bleeding, or organ impairment. Warning signs occur 37 days after the first symptoms in conjunction with a decrease in temperature (below 38° C./100° F.) and include: severe abdominal pain, persistent vomiting, rapid breathing, bleeding gums, fatigue, restlessness, blood in vomit. The next 24-48 hours of the critical stage can be lethal; proper medical care is needed to avoid complications and risk of death.

Administration of the compound, or a composition comprising the compound is of an amount, for example a therapeutically effective amount, which causes the inhibition of infection of cells, when the compound is used prophylactically, or inhibition of further infection of cells and/or reduces signs and/or symptoms of the disease when used for therapeutic purposes.

A therapeutically effective amount is that which provides subjective relief of a symptom(s) or an objectively identifiable improvement as noted by a clinician or other qualified observer.

By preventing dengue infection we include the meaning of reducing the level of infection by any significant degree. In one embodiment the compound of the present invention prevents infection by one serotype of dengue virus to 30%, 50%, 70%, 80%, 90%, 95%, preferably 100%. In a preferred embodiment the compound of the present invention prevents infection by two serotypes of dengue virus, by three serotypes of dengue virus, by all four serotypes of dengue virus, to 30%, 50%, 70%, 80%, 90%, 95%, preferably 100%. In the most preferred embodiment the compound of the present invention totally prevents infection by all found serotypes of dengue virus. This may be assessed by techniques well known to those skilled in the art, for example by measuring viral load.

The present invention provides the use of an EDE, preferably of a stabilized recombinant sE dimer, or an immunogenic composition according to the present invention for immunizing an animal (non human), preferably a mammal, such as a monkey, a rabbit, a mouse or a camelid (e.g., Llama pacos).

A further embodiment provides one or more compounds according to the present invention, preferably a polypeptide, preferably an antibody or fragment thereof for use in live Dengue vaccine trials, for example with the intention of terminating infection.

Preferably the compound of the invention is one that is capable of neutralising all four serotypes of dengue virus to at least 95% or at least 98%, for example 100%, made in both insect and human cells. It is considered that prior administration of the compound before exposure to the virus will prevent viral infection.

The compound according to the present invention, for example an antibody or fragment thereof, for example that is capable of neutralising all four serotypes of dengue virus as noted above may be administered before exposure to the virus, as noted above, for example may be used as a prophylactic either in travellers or in outbreaks or in close contacts of one more infected people, for example in the neighbourhood or home, who are likely also to be bitten. Alternatively or in addition, the compound may be administered when a patient first presents with fever; or when symptoms become severe.

All preferences for the compound are as described earlier in the embodiments of the invention.

It will be appreciated that the compound of the invention, for example an antibody or antigen binding portion thereof may be administered with further therapeutic agents, for example one or more T cell vaccines, or other anti-viral agents. These may be administered as part of the same composition as the compound of the invention, or may be administered separately. For example, T cell vaccines are proposed for protection against influenza[85].

The compound of the invention may be administered once, twice or several times. Administration may occur over 1 day, 2 days, 1 week, 2 weeks, 1 month, 6 months, 1 year or more. For treatment after infection, a shorter period, for example up to one month, may be appropriate. For prophylaxis, a longer period, for example 6 months of 1 year or more may be appropriate.

The compound, for example an antibody or antigen binding portion thereof for use in the prevention or treatment of dengue infection may be selected using methods of the invention. Thus the invention provides a method of selecting a suitable antibody or fragment thereof for use in the prevention or treatment of Dengue virus wherein said method comprises characterisation of an antibody or fragment thereof made in a subject in response to an antigen comprising a Envelope dimer Epitope as defined in any earlier embodiment.

The EDE compound as defined in any of the earlier embodiments is likely to be capable of raising suitable antibodies following administration of the EDE to a subject. Thus, antibodies made in such a subject are likely to be useful in the treatment or prevention of dengue infection.

In a preferred embodiment the EDE is an EDE compound of the invention, for example a dimer of envelope protein, preferably a stabilised dimer, optionally as part of a scaffold protein. In a preferred embodiment, the antigen/EDE compound is such that it is already known to be able to bind to highly cross-reactive and potently neutralising antibodies that can bind the EDE, for example the antibodies of this present invention. In a preferred embodiment the antigen is deemed to be improved over the natural envelope dimer, for example by comprising residues in a particular conformation required to raise anti-EDE antibodies that are cross-reacting and potently neutralising, but not comprising residues, or particular conformations of residues, which raise anti-FL antibodies.

In another embodiment, as well as administration of the EDE, optionally EDE compound, the subject is administered a compound or agent which blocks the formation of anti-FL antibodies, for example. A stabilised sE dimer may be useful, for example.

By characterisation we include the meaning of determining whether the antibodies are considered to bind the fusion loop, by, for example, determining the ability of the antibody to bind to linear or denatured or recombinant envelope protein, for example the ability to bind to the envelope protein on a western blot or ELISA, and the ability of the antibody to bind to a dimer of envelope protein, or an EDE or EDE compound as described earlier in previous embodiments. The ability of the antibody to bind to all four serotypes of dengue virus may also be assessed, as may the ability of the antibody to neutralise all four types of dengue virus. Methods for determining the neutralising ability of an antibody are detailed earlier and in the examples. The ability of the antibody to neutralise dengue virus made in both human and insect cells may also be determined.

In one embodiment, an antibody is not considered to be useful if it binds to the FL. The antibody is considered to be useful if it is capable of binding to more than one serotype of dengue virus, preferably all 4 types of dengue virus, or of binding to more than one serotype of EDE as defined in any of the earlier embodiments. The antibody is considered to be useful if it is capable of neutralising more than one serotype of dengue virus, optionally two serotypes of dengue virus, optionally three serotypes of dengue virus, preferably capable of neutralising all 4 types of dengue virus, preferably to at least 95% or at least 98%, for example 100%. The antibody is also considered useful if it is capable of neutralising dengue virus made in both human cells, optionally dendritic cells, and insect cells, optionally C6/36 cells, preferably to the same level, preferably neutralises the virus to at least 95% or at least 98%, for example 100%. The antibody is considered most useful if it:

a) Does not raise, or does not significantly raise anti-FL antibodies, and
b) Binds, to some significant degree, to all 4 serotypes of dengue virus, and
c) Neutralises, to some significant degree, all 4 serotypes of dengue virus made in both human and insect cells to 100%.

As the present inventors found that patients with dengue infection either produce the useful anti-EDE antibodies, or the non-useful anti-FL antibodies, a further method of identifying antibodies that would be useful to treat or prevent dengue infection is to simply identify those antibodies which cannot bind to the envelope protein in its denatured or linear form. Any antibodies which cannot do this are likely to be useful compounds of the invention.

It should be appreciated that the patient may also be treated with a nucleic acid, vector, or host cell expressing the polypeptide, preferably an antibody or antigen binding portion thereof. For example, a nucleic acid encoding the polypeptide may be inserted into a suitable delivery system, for example a viral vector, for example adenovirus, adeno-associated virus, cytomegalovirus, herpes virus, poliovirus, retrovirus, sindbis virus, vaccinia virus, or any other DNA or RNA virus vector, such that the compound of the invention is expressed endogenously within the patient to be treated.

The present invention also provides a method for stratifying patients according to their likely need to receive treatment or prophylactic treatment with one or more compounds of the present invention. Therefore, herein is provided a method for identifying patients suffering from Dengue virus infection as likely to require treatment with, or an elevated dose of, the compound or composition according to any one of the preceding embodiments, wherein the method involves the determination of the levels of anti-Envelope Dimer Epitope antibodies and anti-Fusion Loop antibodies in the subject, wherein the Envelope Dimer Epitope is as defined in any of the preceding embodiments.

As identified by the present inventors, patients with dengue infection produce predominantly anti-EDE antibodies or anti-FL antibodies. The anti-FL antibodies are not considered to be useful, whilst the anti-EDE antibodies are considered to be useful. If a subject has anti-EDE antibodies, whilst it may still require some additional therapy with the compounds of the present invention, a subject with mainly anti-FL antibodies is likely to require a higher dose as they have no innate useful antibodies. Thus, a patient with only anti-FL antibodies is deemed to be one which is likely to require treatment with the compound of the invention. A patient who is already producing the anti-EDE antibodies may not require treatment. In addition a patient who does not produce anti-EDE antibodies and only produces anti-FL antibodies is likely to require a higher dose of the treatment than patients with anti-EDE antibodies. Also, a patient may make anti-EDE antibodies but only to a low level, and may thus require a higher dose of compound.

By a higher dose we mean the patient requires 2, 3, 4, 5, 10, 20, 50 times the dose of the compound of the present invention than a patient who produces anti-EDE antibodies requires.

By "make anti-VDE antibodies to a low level" we mean that the patient, in comparison to other patients which make anti-EDE antibodies, has a lower than average level of anti-EDE antibodies.

Means to identify whether or not the antibodies bind to the EDE are as described earlier and in the Examples, for example determine whether the antibody binds to an intact dengue virus, or the EDE, and not to the denatured or linear envelope protein. Where the envelope protein has been engineered to have increased dimer stability, or where the envelope protein, or residues thereof, are presented as part of a scaffold, the ability of the antibodies to bind to that protein can be assessed.

The level of anti-FL and anti-EDE antibodies within a subject can also be used to assess the need of that subject for a dengue virus vaccination. Thus in a further embodiment is provided a method for assessing the need of a patient for a Dengue virus vaccination, said method comprising the identification of the levels of anti-Envelope Dimer Epitope antibodies and anti-Fusion Loop antibodies in the subject, wherein the Envelope Dimer Epitope is as defined in any of the preceding embodiments. Similar to the criteria for a patient requiring treatment with a compound of the invention, or a higher dose of the compound, if a patient is determined to have anti-Envelope Dimer Epitope antibodies, vaccination is likely unnecessary.

Further, if the patient is determined to have anti-Envelope Dimer Epitope antibodies the patient may subjected to a boost dose.

In another embodiment, if the patient does not have anti-Envelope Dimer Epitope antibodies, full vaccination is required.

The present invention also provides the use of a stabilized recombinant sE dimer (used as an antigen) as defined above, for preparing a preventive or therapeutic immunogenic (or vaccine) composition intended for the prevention and/or the treatment of a dengue virus infection in a sensitive mammal subject, such as in human.

Significantly, the inventors, as described above, have identified for the first time a specific epitope that is recognised by previously unknown highly cross-reactive and potently neutralising antibodies. This epitope is considered to provide a particularly effective antigen for vaccination against dengue virus. Methods to select a suitable antigen for use in a vaccination against dengue virus are described in earlier embodiments. The invention therefore provides a composition presenting a Envelope Dimer Epitope of Dengue virus, optionally EDE compound for use in for preparing a preventive or therapeutic immunogenic (or vaccine) composition intended for the prevention and/or the treatment of a dengue virus infection in a sensitive mammal subject, such as in human, wherein the Envelope Dimer Epitope and EDE compound are as defined in any of the preceding embodiments or identified according to the preceding methods, for example the EDE or EDE compound could be identified in the earlier embodiment setting out a method of selecting a suitable antigen for use in a vaccine, for example by characterising the antibodies made following administration of the potential vaccine candidate EDE/EDE compound to a subject. This would be well within the skilled person's remit. Alternatively, the EDE or EDE compound may be as set out in the earlier embodiments, for example in one embodiment, the EDE or EDE compound is a dimer of envelope protein, or envelope ectodomain or the (approximately) 400 amino terminal residues of the ectodomain of Envelope protein. The envelope protein may be any of the envelope proteins from DENV-1, DENV-2, DENV-3 and DENV-3, and DENV-4, (SEQ ID No's: 29, 31, 33 or 35), or a protein with at least 90% homology to the sequences in SEQ ID No's: 29, 31, 33 or 35. The dimer may be a homodimer or a heterodimer. In a preferred embodiment the dimer is not incorporated into an intact viral particle, or a sub-viral particle, or a virus-like particle, but rather is a free dimer. It will be appreciated that any form of EDE or EDE compound described herein, for example, an engineered envelope protein, for example, as part of a protein scaffold, may be presented as part of a virus, virus-like particle, or sub-viral particle. In a preferred embodiment the EDE compound is a stabilized recombinant sE dimer as described in the earlier embodiments.

In yet another embodiment, the EDE or EDE compound for use in a vaccine composition presents an improved epitope over the naturally occurring envelope dimer. For example, an EDE/EDE compound which has been engineered, or inserted into a scaffold, such that the FL is incapable of being recognised by a compound, for example a polypeptide, for example an antibody or antigenic portion thereof, on its own, for example where the EDE/EDE compound is engineered such that the FL cannot be recognised by an antibody in isolation from the immediate neighbours of the fusion loop, i.e. the fusion loop cannot be recognised in a context independent of the quaternary organisation.

In another embodiment, the EDE or EDE compound for use in a vaccine composition comprises a dimer of envelope protein, or envelope ectodomain or the (approximately) 400 amino terminal residues of the ectodomain of envelope protein which has been engineered to have increased stability in the dimer configuration, for example has been engineered to have increased levels of covalent and/or non-covalent bonds between the dimers, as detailed above; or has been incorporated into a heterologous protein scaffold which conserves the dimer configuration, by, for example, increasing the level of covalent and/or non-covalent bonds between the dimers, as described above. Further, the EDE/EDE compound may comprise a heterologous protein scaffold which may present only a portion of the dimer of envelope protein, or envelope ectodomain or the (approximately) 400 amino terminal residues of the ectodomain of the envelope protein, wherein the portion is a sequential portion of the dimer of envelope protein, or envelope ectodomain or the (approximately) 400 amino terminal residues of the ectodomain of the envelope protein, or wherein the portion comprises select, non-contiguous residues of the dimer of envelope protein, or envelope ectodomain or the 400 amino terminal residues of the ectodomain of the envelope protein, as described above.

For example, in one embodiment, the EDE/EDE compound comprises one or more of positions E49, K64, Q77, W101, V122, N134, N153, T155, I161, A162, P169, T200, K202, E203, L308, K310, Q323, W391, F392, A71, C105, C74, D154, D249, D271, D309, D362, D98, E148, E311, E44, E71, E84, G102, G104, G106, G152, G156, G28, G29, G374, H158, H27, I113, I308, I46, K246, K247, K310, K323, K325, K47, L113, L45, L82, M278, N103, N153, N362, N67, N83, Q248, Q271, Q325, Q77, R2, R247, R323, R73, R99, S72, S81, T115, T155, T361, T46, T68, T69, T70, T72, V113, V114, V250, V309, V324, V97, W101; or equivalent residue of a Dengue virus envelope polypeptide in a substantially similar spatial configuration as the residues adopt in the native the dimer of envelope protein, or envelope ectodomain or the (approximately) 400 amino terminal residues of the ectodomain of envelope protein. These residues may be within the naturally occurring envelope protein, or in an alternate embodiment, they are held within a scaffold protein in the appropriate configuration. In a preferred embodiment, the EDE/EDE compound comprises position W101 and at least one other residue described above. In a more preferred embodiment, the EDE/EDE compound comprises all of the above residues. In one embodiment the EDE/EDE compound comprises a N153 glycan. In an alternate embodiment, the EDE/EDE compound does not comprise a N153 glycan.

In a more preferred embodiment, the EDE/EDE compound for use in a vaccine composition comprises residues that are conserved in both amino acid and spatial position across more than one serotype of dengue virus, preferably residues that are conserved in both amino acid and spatial position across all serotypes of dengue virus, that is, across four serotypes of dengue virus.

The EDE/EDE compound may comprise the dimer of envelope protein, or envelope ectodomain or the (approximately) 400 amino terminal residues of the ectodomain of the envelope protein which has been engineered to have increased stability in the dimer configuration, and also be held within a protein scaffold as described above.

The inventors have found that particular regions of the envelope dimer are important for contact with a compound of the invention, for example an antibody or antigen binding portion thereof. Therefore, in some embodiments, the EDE/EDE compound comprises a particular antigenic portion of a dimer of envelope protein, or envelope ectodomain or the (approximately) 400 amino terminal residues of the ectodomain of envelope protein.

The EDE/EDE compound for use in a vaccine composition may be a particular fragment comprising particular residues of the dimer of envelope protein, or envelope ectodomain or the (approximately) 400 amino terminal residues of the ectodomain of the envelope protein which comprises regions deemed to be required for antigenicity. This fragment may also have been engineered to maintain a particular conformation, or may be held within a protein scaffold, or may both be engineered and held within a protein scaffold.

For example, in one embodiment, the EDE/EDE compound for use in a vaccine composition comprises a region centred in a valley lined by the b strand on the domain II side, and the "150 loop" on the domain I side (across from the dimer interface), wherein the 150 loop spans residues 148-159, connecting b-strands E0 and F0 of domain I, and carries the N153 glycan, which covers the fusion loop of the partner subunit in the dimer. In one embodiment this region comprises three polypeptide segments of domain II of the reference subunit, which is defined as the subunit which contributes the FL to the epitope. These three segments are: the b strand (resides 67-74 which bears the N67 glycan), the fusion loop and residues immediately upstream (residues 97-106) and the ij loop (residues 246-249).

In another embodiment, in addition to the region described above, (the region which comprises the three polypeptide segments of domain II of the reference subunit), the EDE/EDE compound further comprises the 150 loop and the N153 glycan chain of the second subunit.

A further embodiment of the EDE/EDE compound comprises the region described above, (the region which comprises the three polypeptide segments of domain II of the reference subunit), and the 150 loop and the A strand of domain III of the second subunit, in particular residue K310. The inventors have found that a subset of the useful compounds defined here in cause disorder in the 150 loop of the second subunit upon binding to the VDE. Thus, in one embodiment the 150 loop may be in the natural configuration found in the natural dimer of envelope protein, or envelope ectodomain or the (approximately) 400 amino terminal residues of the ectodomain of the envelope protein, or in another embodiment the 150 loop may be in the disordered configuration that the 150 loop adopts on binding to one of the compounds of the invention.

It is considered that the N67 glycan is particularly important for dengue infection of dendritic cells. Thus an EDE/EDE compound comprising this residue in the correct epitopic environment, as described herein, is considered to be a preferred embodiment.

In a preferred embodiment, the EDE/EDE compound is such that it may raise antibodies once administered to a subject, preferably a human, wherein the antibodies are preferably capable of binding to all four serotypes of dengue virus, and optionally are capable of neutralising all four serotypes of dengue virus, preferably capable of neutralising all four serotypes of dengue virus to 100%, and optionally are capable of neutralising virus made in both human and insect cells, preferably capable of neutralising all four serotypes of dengue virus made in both human and insect cells to 100%.

An immunogenic composition comprising an EDE wherein the EDE comprises the stabilized recombinant sE dimer as described above is particularly suitable for eliciting in said subject neutralizing antibodies:

which recognize exclusively envelope dimer epitopes (EDE) (which show no binding to recombinant E protein monomer in ELISA tests), are cross-reactive, and neutralize dengue viruses from the four serotypes (DENV1-4).

The present invention also provides a dengue virus immunogenic composition comprising a therapeutically effective amount of a stabilized recombinant sE dimer (used as an antigen) as defined above.

It will be appreciated that the composition may include the EDE/EDE compound itself, or it may include the means to express the EDE/EDE compound within the subject to be vaccinated. For example, the invention includes a nucleic acid encoding the Envelope Dimer Epitope or EDE compound, for use in vaccination against Dengue virus infections, wherein the Envelope Dimer Epitope or EDE compound is as defined in any of the preceding embodiments. Additionally, the nucleic acid may be part of a vector. Preferences for the vector and vector components are as detailed above.

For example it is well known in the art that vaccination can be carried out using a nucleic acid encoding a particular antigen, for example via direct immunisation with plasmid DNA. Such nucleic acids can be delivered via liposomes and immune-stimulating constructs. Alternatively, attenuated viral hosts or vectors or bacterial vectors can be used, for example adenovirus, adeno-associated virus, cytomegalovirus, herpes virus, poliovirus, retrovirus, sindbis virus, vaccinia virus, or any other DNA or RNA virus vector.

Where the composition for use in vaccination against dengue virus infection is a nucleic acid, the nucleic acid can be delivered to the patient in a viral vector for example adenovirus, adeno-associated virus, cytomegalovirus, herpes virus, poliovirus, retrovirus, sindbis virus, vaccinia virus, or any other DNA or RNA virus vector.

A composition comprising any one or more of the:

a) Envelope Dimer Epitope or EDE compound, b) nucleic acid encoding the EDE or EDE compound, c) vector comprising the nucleic acid, for use in vaccination against Dengue virus infection, wherein the Envelope Dimer Epitope or EDE compound is as defined in any of the preceding embodiments is also part of the invention.

In one embodiment, the:

a) Envelope Dimer Epitope or EDE compound, b) nucleic acid encoding the EDE or EDE compound, c) vector comprising the nucleic acid, are, or encode, more than one, optionally 2, optionally 3, optionally 4 serotypes of Dengue virus.

In a preferred embodiment, the:

a) Envelope Dimer Epitope or EDE compound, b) nucleic acid encoding the EDE or EDE compound, c) vector comprising the nucleic acid, are, or result in the production of a single epitope which can raise antibodies capable of neutralising all four serotypes of dengue virus, preferably neutralise all four serotypes to 100%.

The use of the composition of the present invention in a vaccination against dengue virus is intended to reduce or prevent infection with dengue virus.

By reducing or preventing dengue infection we include the meaning of reducing the level of infection by any degree. In one embodiment the compound of the present invention reduces infection by one serotype of dengue virus by 30%, 50%, 70%, 80%, 90%, 95%, preferably 100%. In a preferred embodiment the compound of the present invention reduces infection by two serotypes of dengue virus, by three serotypes of dengue virus, by all four serotypes of dengue virus, by 30%, 50%, 70%, 80%, 90%, 95%, preferably 100%. In the most preferred embodiment the compound of the present invention totally prevents infection by all found serotypes of dengue virus.

The EDE or EDE compound, for example stabilized recombinant sE dimer of the present invention, which induces neutralizing antibodies against dengue virus infection, is administered to a mammal subject, preferably a human, in an amount sufficient to prevent or attenuate the severity, extent of duration of the infection by dengue virus.

The therapeutically effective amount varies depending on the subject being treated, the age and general condition of the subject being treated, the capacity of the subject's immune response to synthesize antibodies, the degree of protection desired, the severity of the condition to be treated, the particular VDE compound, for example the particular stabilized recombinant sE dimer selected and its mode of administration, among other factors. An appropriate effective amount can be readily determined by one of skill in the art. A therapeutically effective amount will fall in a relatively broad range that can be determined through routine trials.

More particularly the EDE compound, for example stabilized recombinant sE dimer of the invention is administered in a therapeutically effective amount that comprises from 1 to 1000 μg of dimer, preferably 1 to 50 μg.

An optimal amount for a particular vaccine can be ascertained by standard studies involving measuring the anti-sE dimer antibody titers in subjects.

The immunogenic composition of the invention may be administered with or without adjuvant. Adjuvants can be added directly to the immunogenic composition or can be administered separately, either concurrently with or shortly after, administration of the vaccine. Such adjuvants include but are not limited to aluminium salts (aluminium hydroxide), oil-in-water emulsion formulations with or without specific stimulating agents such as muramyl peptides, saponin adjuvants, cytokines, detoxified mutants of bacteria toxins such as the cholera toxin, the pertussis toxin, or the *E. coli* heat-labile toxin.

The immunogenic composition of the invention may be administered with other immunogens or immunoregulatory agents, for example, immunoglobulins, cytokines, lymphokines and chemokines.

Vaccination programmes often include a boost strategy. Following an initial vaccination, subjects may receive one or two booster injections at an appropriate interval determined by one of skill in the art. In one embodiment, the vaccination can comprise a prime followed by one or more boosts. The antigen, composition, nucleic acid or vector which result in the expression of an antigen are included in the present invention for use in a boost strategy for vaccination against Dengue virus infection, optionally wherein the antigen, compound, nucleic acid, vector or composition is for administration before (prime) or after (boost) administration of Dengue virus, optionally attenuated Dengue virus, and/or Dengue virus like particle, wherein the Dengue virus or Dengue virus like particle can be a collection of one or more serotypes of Dengue virus, and may comprise or present a EDE, for example a non-native EDE or EDE compound, as described above. As a further example, heterologous flavivirus such as the chimerivax with yellow fever may be used, for example followed by one or more of dimer, DNA, vaccinia, adeno virus, Different orders and timings of administration of different antigen and/or antigen-encoding nucleic acid may be possible, as will be apparent to those skilled in the art, and the present invention is not limited to any particular combination or order of administration.

The invention also comprises a vaccination strategy to provide protection against Dengue virus wherein the vaccination strategy comprises, for example:

a) A single time administration of a Envelope Dimer Epitope or EDE compound as defined in any of the preceding embodiments, capable of raising antibodies to all four serotypes, or the vaccine composition according to the preceding embodiments, or the nucleic acid for use in vaccination, or the vector for use in vaccination, optionally followed by administration of the attenuated Dengue virus, or
b) Administration of two Envelope Dimer Epitopes or EDE compounds from two serotypes, as defined in any of the preceding embodiments, followed by administration of Envelope Dimer Epitopes or EDE compounds from the other two serotypes, optionally followed by administration of the attenuated Dengue virus, or
c) Administration of the attenuated Dengue virus followed by administration of an Envelope Dimer Epitope as defined in any of the preceding embodiments, capable of raising antibodies to all four serotypes, or
d) Administration of the attenuated Dengue virus followed by administration of two Envelope Dimer Epitopes or EDE compounds from two serotypes, as defined in any of the preceding embodiments, followed by administration of Envelope Dimer Epitopes or EDE compounds from the other two serotypes.

It is also envisaged that a patient which has received a vaccination according to the present invention may still require subsequent treatment with a compound or composition according to the present invention for use in treating or preventing dengue infection.

Thus the compound of the present invention is for use in treating or preventing dengue infection in a patient which has previously received a dengue vaccination, or in a patient which has not previously received a dengue vaccination.

The vaccine is preferably administered prior to symptoms of dengue infection, or before the patient is known to have dengue infection, though the vaccination is still considered to be useful if the patient already has dengue infection, as the vaccination is considered to offer protection to more than one serotype of dengue virus, preferably offer protection to all four serotypes of dengue virus.

Thus the vaccination is for use in a patient which has not been previously infected with dengue, and is not currently, at the time of the administration of the vaccine, infected with dengue. Alternatively, the vaccination is for use in a patient which has previously been infected with one or more serotypes of dengue infection, but is not infected at the time of administration of the vaccine, or the vaccination is for use in a patient which has previously been infected with one or more serotypes of dengue virus, and is currently, at the time of administration, infected with one or more serotypes of dengue virus.

The vaccination is also for use in a patient which has previously been treated with a compound of the invention but is not currently being treated with a compound of the invention, and is also for use in a patient which has previously been treated with a compound of the invention and is currently being treated with a compound of the invention. The vaccination is also for use in a patient which is being treated with a compound of the invention for the first time.

The present invention also provides an EDE compound, for example a stabilized recombinant sE dimer or an immunogenic composition as defined above for use as a medicament, preferably for preventing and/or treating a dengue virus infection.

The present invention also provides the use of an EDE compound, for example a stabilized recombinant sE dimer or an immunogenic composition as defined above for the manufacturing of a medicament, preferably of a preventive or therapeutic vaccine against a dengue virus infection in a subject.

The present invention also provides a method for preventing and/or treating a dengue virus infection, comprising administering to a subject in need thereof an EDE compound, for example a stabilized recombinant sE dimer or an immunogenic composition as defined above, in an amount effective to inhibit dengue virus infection of susceptible cells so as to thereby prevent or treat the infection.

The present invention also provides a diagnostic agent comprising or consisting of an EDE compound of the invention, for example a stabilized recombinant sE dimer, or a compound of the invention, for example an antibody or fragment thereof according to the present invention.

In an embodiment of said diagnostic agent, the compound, for example antibody or fragment thereof according to the present invention is linked, directly or indirectly, covalently or non-covalently to a detectable marker.

The detectable marker can be directly and covalently linked to the compound, for example antibody or fragment thereof, either to one of the terminal ends (N or C terminus) of said antibody or fragment thereof, or to the side chain of one of the amino acids of said antibody or fragment thereof. The detectable marker can also be indirectly and covalently linked to said antibody or fragment thereof through a connecting arm (i.e., a cross-linking reagent) either to one of the terminal ends of said antibody or fragment thereof, or to a side chain of one of the amino acids of said antibody or fragment thereof. Linking methods of a compound of interest to a peptide or antibody are well-known in the art.

Advantageously, said detectable marker is selected from the group consisting of:

enzymes such as horseradish peroxidase, alkaline phosphatase, glucose-6-phosphatase or beta-galactosidase;

fluorophores such as green fluorescent protein (GFP), blue fluorescent dyes excited at wavelengths in the ultraviolet (UV) part of the spectrum (e.g. AMCA (7-amino-4-methylcoumarin-3-acetic acid); Alexa Fluor 350), green fluorescent dyes excited by blue light (e.g. FITC, Cy2, Alexa Fluor 488), red fluorescent dyes excited by green light (e.g. rhodamines, Texas Red, Cy3, Alexa Fluor dyes 546, 564 and 594), or dyes excited with far-red light (e.g. Cy5) to be visualized with electronic detectors (CCD cameras, photomultipliers); —heavy metal chelates such as europium, lanthanum or yttrium; —radioisotopes such as [$^{18}$F] fluorodeoxyglucose, $^{11}$C-, $^{125}$I-, $^{131}$I-, $^{3}$H-, $^{14}$C-, $^{35}$S, or 99Tc-labelled compounds.

The present invention also provides the use of an EDE compound, for example a stabilized recombinant sE dimer, an antibody or fragment thereof, or a diagnostic agent according to the present invention for diagnosing or monitoring a dengue virus infection in a subject.

The present invention also provides an in vitro method for diagnosing a dengue virus infection in a subject, comprising the steps of:

a) contacting in vitro an appropriate biological sample from said subject with an antibody or fragment thereof, or a diagnostic agent comprising or consisting of an antibody or fragment thereof according to the present invention, and b) determining the presence or the absence of a dengue virus envelope glycoprotein E in said biological sample, the presence of said dengue virus envelope glycoprotein E indicating that said subject has dengue virus infection. Step b) can be carried out by determining the presence or the absence of the antibody-antigen complex (i.e., antibody directed to the dengue virus envelope glycoprotein E—dengue virus envelope glycoprotein E complex).

The present invention also provides an in vitro method for determining the presence of dengue virus envelope glycoprotein E in an appropriate biological sample from a subject, comprising the steps of a) contacting in vitro said appropriate biological sample from said subject with an antibody or fragment thereof, or a diagnostic agent comprising or consisting of an antibody or fragment thereof according to the present invention, and b) determining the presence or the absence of a dengue virus envelope glycoprotein E in said biological sample.

The present invention also provides an in vitro method for diagnosing a dengue virus infection in a subject, comprising the steps of:

a) contacting in vitro an appropriate biological sample from said subject with a stabilized recombinant sE dimer according to the present invention, and b) determining the presence or the absence of antibodies directed to said dimer in said biological sample, the presence of said antibodies indicating that said subject has dengue virus infection.

The present invention also provides an in vitro method for determining the presence of antibodies directed to dengue virus envelope glycoprotein E in an appropriate biological sample from a subject, comprising the steps of:

a) contacting in vitro said appropriate biological sample from said subject with a stabilized recombinant sE dimer according to the present invention, and b) determining the presence or the absence of antibodies directed to said dimer in said biological sample.

The present invention also provides an in vitro method for monitoring the progression or regression of a dengue virus infection in a subject, comprising the steps of:

a) contacting in vitro an appropriate biological sample from said subject with an antibody or fragment thereof, a diagnostic agent comprising or consisting of an antibody or fragment thereof according to the present invention, b) determining the amount of dengue virus envelope glycoprotein E in said biological sample, and c) comparing the amount determined in step (b) with the amount of dengue virus envelope glycoprotein E previously obtained for said subject, a significant increase in amount of dengue virus envelope glycoprotein E constituting a marker of the progression of said dengue virus infection and a significant decrease of dengue virus envelope glycoprotein E constituting a marker of the regression of said dengue virus infection.

As used herein the terms "significant increase" and "significant decrease" refer to a higher amount or lower amount respectively of dengue virus envelope glycoprotein E in an appropriate biological sample with respect to the amount of dengue virus envelope glycoprotein E in an appropriate biological sample from said subject, that was previously determined and used as a reference amount. Step b) can be carried out by determining the presence or the absence of the antibody-antigen complex (i.e., antibody directed to the dengue virus envelope glycoprotein E—dengue virus envelope glycoprotein E complex).

The present invention also provides an in vitro method for predicting a favourable prognosis of the evolution of a dengue virus infection in a subject, comprising the steps of:

a) contacting in vitro an appropriate biological sample from said subject with a stabilized recombinant sE dimer according to the present invention,
b) determining the amount of neutralizing antibodies directed to said dimer in said biological sample, and
c) comparing the amount determined in step (b) with the amount of antibodies directed to said dimer previously obtained for said subject, a significant increase in amount of neutralizing antibodies directed to said dimer constituting a marker of favourable prognosis of the evolution of said dengue virus infection.

The present invention also provides an in vitro method for monitoring the success of a vaccination protocol against a dengue virus infection in a subject vaccinated against dengue virus, comprising the steps of:

a) contacting in vitro an appropriate biological sample from said subject with a stabilized recombinant sE dimer according to the present invention,
b) determining the amount of neutralizing antibodies directed to said dimer in said biological sample, and
c) comparing the amount determined in step (b) with the amount of antibodies directed to said dimer previously obtained for said subject, a significant increase in amount of neutralizing antibodies directed to said dimer constituting a marker of success of said vaccination protocol. Said appropriate biological sample can be blood, serum, urine or a liver biopsy, preferably blood.

Immunological methods for detecting and determining the amount of proteins or antibodies are well known in the art. By way of examples, EIA, ELISA, RIA or immunofluorescence tests can be used.

The present invention also provides an isolated polynucleotide encoding a mutant sE as defined above or a polypeptide of SEQ ID NO: 28, 142, 140, 143, 144, 145, 146 or 147.

Polynucleotides according to the present invention may be obtained by well-known methods of recombinant DNA technology and/or of chemical DNA synthesis.

The invention also provides several kits of parts. One embodiment provides a kit for diagnosing or monitoring, in a subject, a dengue virus infection, comprising a stabilized recombinant sE dimer, or an antibody or fragment thereof according to the present invention and an appropriate diagnostic reagent.

The appropriate diagnostic reagent is necessary for performing an assay for diagnosing or monitoring, in a subject, a dengue virus infection. The appropriate diagnostic reagent can be a solvent, a buffer, a dye, an anticoagulant.

The kit can also comprise a micro-titre plate.

In one embodiment the kit of parts comprises the means to identify patients requiring treatment with the compound of the invention, or requiring a higher dose of the compound of the invention, according to the preceding embodiments. The kit may provide means to identify the presence or absence of anti-EDE and anti-FL antibodies, for example the kit may comprise a micro-titre plate, optionally wherein the micro-titre plate is coated with linear or denatured envelope protein, and separately coated with the EDE epitope according to any of the preceding embodiments, and/or may also include reagents to carry out an ELISA test, optionally a colourimetric test on a stick. Preferably the kit contains means to simply identify the presence or absence of the antibodies, preferably on a solid support. The kit may also further comprise a compound or composition of the present invention for use in treating or preventing dengue infection.

A further kit of parts comprising means to identify patients requiring vaccination is also provided. A patient is deemed to require vaccination based on the presence and absence, and level of, anti-EDE antibodies and anti-FL antibodies. The kit may therefore provide means to identify the presence or absence of anti-EDE and anti-FL antibodies, for example the kit may comprise a micro-titre plate, optionally wherein the micro-titre plate is coated with linear or denatured envelope protein, and separately coated with the EDE epitope according to any of the preceding embodiments, and/or may also include reagents to carry out an ELISA test, optionally a colourimetric test on a stick. Preferably the kit contains means to simply identify the presence or absence of the antibodies, preferably on a solid support. The kit may also further comprise a composition for use in vaccination, as described in the preceding embodiments.

A further kit comprises the means to treat or prevent dengue infection, and includes one or more compounds of the invention that bind to the EDE, or the composition comprising a compound of the invention that binds to the EDE, and optionally includes a further therapeutic agent, for example a further anti-viral agent.

It will be appreciated that any compound or composition or antigen or antibody mentioned herein may be part of a composition. The composition may comprise stabilising agents, such a PEG. It will be appreciated that a polypeptide component, for example, may be covalently modified or conjugated, for example PEGylated, as will be well known in the art Thus, for example, any compound or antibody for use in treating or preventing dengue infection, or any polypeptide or antigen, or nucleic acid or vector encoding the antigen or antibody, may be conjugated to one or more further entities, for example may be conjugated to a reporter moiety, or may be conjugated to one or more further therapeutic agents.

One such further therapeutic agent is an agent to prevent Fc receptor binding. It is well known that dengue virus causes antibody dependent enhancement, and this is thought to be due to the production of certain antibodies that can bind to, but not neutralise the virus. This leads to internalisation of the antigen via the Fc receptor, leading to a heightened response upon reinfection. It is believed that agents which can block Fc receptor binding may prevent antibody dependent enhancement. Examples of such agents are and such agents are considered to be useful when administered along with (or separately to) the compounds of the invention for use in treating or preventing dengue infection, and the antigen for use in vaccination. It may also be useful to modify or select the antibody molecule such that interaction with Fc receptor is lessened, as will be known to those skilled in the art.

It will be appreciated that administration of any agent described herein is typically administered as part of a pharmaceutical composition together with a pharmaceutically acceptable excipient, diluent, adjuvant, or carrier. Thus, any mention of a compound, polypeptide, antibody, antigen binding portion thereof, composition, nucleic acid, vector, antigen, host cell, and any mention of a further therapeutic agent, equally applies to a pharmaceutically acceptable composition comprising that compound, composition, nucleic acid, vector, antigen, host cell, and/or further therapeutic agent (e.g. a formulation).

The compound, polypeptide, antibody, antigen binding portion thereof, composition, nucleic acid, can be part of a nanoparticle.

Routes of administration will be known to those skilled in the art. For example, the agents of the invention (compound, polypeptide, antibody, antigen binding portion thereof, composition, nucleic acid, vector, antigen, host cell, further therapeutic agent) can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection. The compound polypeptide, antibody, antigen binding portion thereof, composition, nucleic acid, vector, antigen, host cell, further therapeutic agent according to the present invention can be orally administered to a mammal subject, preferably a human. They can also be administered to said subject by injection, such as intravenous, intraperitoneal, intramuscular, intradermal or subcutaneous injection.

The agents may be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the subject to be treated, as well as the route of administration, the agents may be administered at varying doses.

Preferably, the formulation is a unit dosage containing a daily dose or unit, daily sub-dose or an appropriate fraction thereof, a weekly dose, a monthly dose, or a 6 monthly dose of the agent or active ingredient.

In human therapy, the agents (compound, polypeptide, antibody, antigen binding portion thereof, composition, nucleic acid, vector, antigen, host cell, further therapeutic agent) can be administered alone but will generally be administered in admixture with a suitable pharmaceutical excipient diluent or carrier selected with regard to the intended route of administration and standard pharmaceutical practice.

Tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included. Capsules or tablets may also be enteric coated to enhance gastric stability.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The agents (compound, polypeptide, antibody, antigen binding portion thereof, composition, nucleic acid, vector, antigen, host cell, further therapeutic agent, vaccine) can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral Formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the Formulation isotonic with the blood of the intended recipient; and aqueous and non-aqueous sterile suspensions which may include suspending agents and thickening agents. The Formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human subjects, the daily dosage level of the agents (compound, polypeptide, antibody, antigen binding portion thereof, composition, nucleic acid, vector, antigen, host cell, further therapeutic agent, vaccine) will usually be from 1 to 5000 mg per adult, administered in single or divided doses.

Thus, for example, the tablets or capsules comprising the compound, polypeptide, antibody, antigen binding portion thereof, composition, nucleic acid, vector, antigen, host cell, further therapeutic agent, vaccine of the invention may contain from 1 mg to 1000 mg (i.e. from about 60-120 $mg/m^2$) of active compound for administration singly or two or more at a time, as appropriate. The physician in any event will determine the actual dosage which will be most suitable for any individual subject and it will vary with the age, weight and response of the particular subject. The above dosages are exemplary of the average case. There can, of course, be individual instances where higher or lower dosage ranges are merited and such are within the scope of this invention.

The agents (compound, polypeptide, antibody, antigen binding portion thereof, composition, nucleic acid, vector, antigen, host cell, further therapeutic agent, vaccine) can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the compound, polypeptide, antibody, antigen binding portion thereof, composition, nucleic acid, vector, antigen, host cell, further therapeutic agent, vaccine, e.g. using a mixture of ethanol and the propellant as the solvent, which may additionally contain a lubricant, e.g. sorbitan trioleate. Capsules and cartridges (made, for example, from gelatin) for use in an inhaler or insufflator may be Formulated to contain a powder mix of a compound of the invention and a suitable powder base such as lactose or starch.

Aerosol or dry powder formulations are preferably arranged so that each metered dose or "puff" contains at least 1 mg of an agent (compound, polypeptide, antibody, antigen binding portion thereof, composition, nucleic acid, vector, antigen, host cell, further therapeutic agent, vaccine) for delivery to the subject. It will be appreciated that the overall daily dose with an aerosol will vary from subject to subject, and may be administered in a single dose or, more usually, in divided doses throughout the day.

Alternatively, the agents (compound, polypeptide, antibody, antigen binding portion thereof, composition, nucleic acid, vector, antigen, host cell, further therapeutic agent, vaccine) can be administered in the form of a suppository or pessary, or they may be applied topically in the form of a lotion, solution, cream, ointment or dusting powder. The compound, polypeptide, antibody, antigen binding portion thereof, composition, nucleic acid, vector, antigen, host cell, further therapeutic agent, vaccine of the invention may also be transdermally administered, for example, by the use of a skin patch. They may also be administered by the ocular route, particularly for treating diseases of the eye.

For ophthalmic use, the agents (compound, polypeptide, antibody, antigen binding portion thereof, composition, nucleic acid, vector, antigen, host cell, further therapeutic agent, vaccine), can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agents (compound, polypeptide, antibody, antigen binding portion thereof, composition, nucleic acid, vector, antigen, host cell, further therapeutic agent, vaccine), can be formulated as a suitable ointment containing the active compound, polypeptide, antibody, antigen binding portion thereof, composition, nucleic acid, vector, antigen, host cell, further therapeutic agent, vaccine suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or topical administration of the agents (compound, polypeptide, antibody, antigen binding portion thereof, composition, nucleic acid, vector, antigen, host cell, further therapeutic agent, vaccine) is the preferred route, being the most convenient. In circumstances where the recipient suffers from a swallowing disorder or from impairment of drug absorption after oral administration, the drug may be administered parenterally, e.g. sublingually or buccally.

For veterinary use, the agent (compound, polypeptide, antibody, antigen binding portion thereof, composition, nucleic acid, vector, antigen, host cell, further therapeutic agent, vaccine) is administered as a suitably acceptable formulation in accordance with normal veterinary practice and the veterinary surgeon will determine the dosing regimen and route of administration which will be most appropriate for a particular animal.

Conveniently, the formulation is a pharmaceutical formulation. The formulation may be a veterinary formulation.

It will be appreciated that the term administration is not restricted to a one time administration. The term administration is taken to cover all of, but not limited to, a single dose administration, multiple administrations over a period of time, variable dosage administrations over a period of time, variable means of administration over a period of time, administration in conjunction with one or more further therapeutic agents. Administration can be by any means known in the art and includes, but is not limited to, oral, intravenous, topically direct to a tumour, sublingually or suppository.

The listing or discussion of an apparently prior-published document in this specification should not necessarily be taken as an acknowledgement that the document is part of the state of the art or is common general knowledge.

Preferences and options for a given aspect, feature or parameter of the invention should, unless the context indicates otherwise, be regarded as having been disclosed in combination with any and all preferences and options for all other aspects, features and parameters of the invention. For example, the various definitions for the VDE are relevant to all aspects of the invention, for example an epitope comprising the VDE for use in vaccination against dengue virus infection could comprise any one or more of: an epitope-scaffold protein, wherein the scaffold protein comprises a heterologous scaffold protein covalently linked to the Virion Dependent Epitope; at least Q77, W101, N153, T155, K310 of the envelope protein; or domain II of the envelope protein, optionally further comprising any one or more of the following features of domain II; the b strain (residues 67-74), the fusion loop and residues immediately upstream (residues 97-106) and the ij loop (residues 246-249).

REFERENCES

1. Bhatt, S et al 2013 The global distribution and burden of dengue. Nature 496: 504-507
2. Lindenbach et al 2007 Flaviviridae: the viruses and their replication. 5th edn, Vol. 1 1101-1152 (Lippincott Williams & Wilkins)

3. Guzman et al 2000. Epidemiologic studies on Dengue in Santiago de Cuba, 1997. Am J Epidemio 1152: 793-799
4. Sangkawibha et al 1984 Risk factors in dengue shock syndrome: a prospective epidemiologic study in Rayong, Thailand. I. The 1980 outbreak. Am J Epidemio 1120: 653-669
5. Simmons et al 2012 Dengue. N Engl j Med 366: 1423-1432
6. World Health Organization. Dengue and dengue haemorrhagic fever. Fact sheet no. 117. www.who.intimediacentre/factsheets/fs117/en/_(2009).
7. Mongkolsapaya et al 2003 Original antigenic sin and apoptosis in the pathogenesis of dengue hemorrhagic fever Nat Med 9: 921-927
8. Kuhn et al 2002 Structure of dengue virus: implications for flavivirus organization, maturation, and fusion Cell 108: 717-725
9. Zhang et al 2013 Cryo-EM structure of the mature dengue virus at 3.5-A resolution. Nat Struct Mol Biol 20: 105-110
10. Dejnirattisai et al 2008 A complex interplay among virus, dendritic cells, T cells, and cytokines in dengue virus infections. The Journal of Immunology 181: 5865-5874
11. Kuhn et al 2002 Structure of dengue virus: implications for flavivirus organization, maturation, and fusion. Cell 108: 717-725
12. Mukhopadhyay et al 2005 A structural perspective of the flavivirus life cycle Nat Rev Micro biol 3: 13-22
13. Li et al 2008 The flavivirus precursor membrane-envelope protein complex: structure and maturation Science 319: 1830-1834
14. Yu et al 2008 Structure of the immature dengue virus at low pH primes proteolytic maturation Science 319: 1834-1837
15. Junjhon et al 2010 Influence of pr-M cleavage on the heterogeneity of extracellular dengue virus particles Journal of virology 84: 8353-8358
16. Fibriansah et al 2013 Structural Changes in Dengue Virus When Exposed to a Temperature of 37C J Virol 87: 7585-7592
17. Zhang et al 2013 Dengue structure differs at the temperatures of its human and mosquito hosts. Proc Natl Acad Sci USA 110: 6795-6799
18. Bressanelli, S. et al 2004 Structure of a flavivirus envelope glycoprotein in its low-pH-induced membrane fusion conformation. EMBO J 23: 728-738
19. Modis et al 2004 Structure of the dengue virus envelope protein after membrane fusion. Nature 427: 313-319
20. Plevka et al 2011 Maturation of flaviviruses starts from one or more icosahedrally independent nucleation centres. EMBO reports 12: 602-606
21. odenhuis-Zybert, et al 2010 Immature dengue virus: a veiled pathogen? PLoS Pathog 6: e1000718
22. Dejnirattisai et al 2010 Cross-reacting antibodies enhance dengue virus infection in humans. Science 328: 745-748
23. Halstead 2003 Neutralization and antibody-dependent enhancement of dengue viruses. Advances in virus research 60: 421-467
24. Mantel et al 2011 Vaccine 29:6629-6635
25. Osorio et al 2011 Vaccine 29:7251-7260
26. Sittisombut et al 1995 Lack of augmenting effect of interferon-gamma on dengue virus multiplication in human peripheral blood monocytes. J Med Virol 45: 43-49.
27. de Alwis et al 2012 Identification of human neutralizing antibodies that bind to complex epitopes on dengue virions. Proc Natl Acad Sci USA 109: 7439-7444
28. Wengler & Rey 1999 The isolation of the ectodomain of the alphavirus E1 protein as a soluble hemagglutinin and its crystallization. Virology 257: 472-482
29. Cockburn et al 2012 Structural insights into the neutralization mechanism of a higher primate antibody against dengue virus. Embo J 31: 767-779
30. Wu & Kabat 1970 An analysis of the sequences of the variable regions of Bence Jones proteins and myeloma light chains and their implications for antibody complementarity. The Journal of experimental medicine 132: 211-250
31. Lefranc et al 2009 IMGT, the international ImMunoGeneTics information system. Nucleic Acids Res 37: D1006-1012
32. Smith et al 2009 Rapid generation of fully human monoclonal antibodies specific to a vaccinating antigen. Nat Protoc 4: 372-384
33. Tiller et al 2008 Efficient generation of monoclonal antibodies from single human B cells by single cell RT-PCR and expression vector cloning Immunol Methods 329: 112-124
34. Balakrishnan et al 2011 Dengue virus activates polyreactive, natural IgG B cells after primary and secondary infection PLoS One 6: e29430
35. Wrammert et al 2012 Rapid and massive virus-specific plasmablast responses during acute dengue virus infection in humans Virol 86: 2911-2918
36. Lin et al 2012 Analysis of epitopes on dengue virus envelope protein recognized by monoclonal antibodies and polyclonal human sera by a high throughput assay PLoS Negl Trop Dis 6: e1447
37. Beltramello et al 2010 The human immune response to Dengue virus is dominated by highly cross-reactive antibodies endowed with neutralizing and enhancing activity. Cell Host Microbe 8: 271-283
38. Tsai et al 2013 High-avidity and potently neutralizing cross-reactive human monoclonal antibodies derived from secondary dengue virus infection. J Virol 87: 12562-12575
39. Cherrier et al 2009 Structural basis for the preferential recognition of immature flaviviruses by a fusion-loop antibody. EMBO J 28: 3269-3276
40. Smith et al. 2013 The potent and broadly neutralizing human dengue virus-specific monoclonal antibody 1C19 reveals a unique cross-reactive epitope on the be loop of domain II of the envelope protein. mBio 4: e00873-00813
41. Wu et al 2000 Human skin Langerhans cells are targets of dengue virus infection. Nat Med 6: 816-820
42. Allison et al 1995 Oligomeric rearrangement of tick-borne encephalitis virus envelope proteins induced by an acidic pH. J Virol 69: 695-700
43. Nelson et al 2008 Maturation of West Nile virus modulates sensitivity to antibody-mediated neutralization. PLoS Pathog 4: e1000060
44. Backovic et al 2010 Efficient method for production of high yields of Fab fragments in *Drosophila* S2 cells. Protein Eng Des Sel 23: 169-174
45. Gilmartin et al 2012 High-level secretion of recombinant monomeric murine and human single-chain Fv antibodies from *Drosophila* S2 cells. Protein Eng Des Sel 25: 59-66
46. Yu et al 2008 Structure of the immature dengue virus at low pH primes proteolytic maturation. Science 319: 1834-1837

47. Cockburn et al 2012 Mechanism of dengue virus broad cross-neutralization by a monoclonal antibody. Structure 20: 303-314
48. Lok et al 2008 Binding of a neutralizing antibody to dengue virus alters the arrangement of surface glycoproteins. Nat Struct Mol Biol 15: 312-317
49. Pokidysheva et al 2006 Cryo-EM reconstruction of dengue virus in complex with the carbohydrate recognition domain of DC-SIGN. Cell 124: 485-493
50. de Alwis et al 2012 Identification of human neutralizing antibodies that bind to complex epitopes on dengue virions. Proc Natl Acad Sci USA 109: 7439-7444
51. Kaufmann, B. et al. Neutralization of West Nile virus by cross-linking of its surface proteins with Fab fragments of the human monoclonal antibody CR4354. Proc Natl Acad Sci USA 107, 18950-18955, doi:10.1073/pnas.1011036107 (2010).
52. Fibriansah, G. et al. Structural changes of dengue virus when exposed to 37° C. J Virol, doi:10.1128/JVI.00757-13 (2013).
53. Zhang, X. et al. Dengue structure differs at the temperatures of its human and mosquito hosts. Proc Natl Acad Sci USA 110, 6795-6799, doi:10.1073/pnas.1304300110 (2013).
54. McLellan, J. S. et al. Structure-based design of a fusion glycoprotein vaccine for respiratory syncytial virus. Science 342, 592-598, doi:10.1126/science.1f67283 (2013).
55. Aricescu, A. R., Lu, W. & Jones, E. Y. A time- and cost-efficient system for high-level protein production in mammalian cells. Acta Crystallogr D Biol Crystallogr 62, 1243-1250 (2006).
56. Rodenhuis-Zybert et al 2011 A fusion-loop antibody enhances the infectious properties of immature flavivirus particles. J Virol 85: 11800-11808
57. McLellan et al 2013 Structure of RSV fusion glycoprotein trimer bound to a prefusion-specific neutralizing antibody. Science 340: 1113-1117
58. Whittle et al 2011 Broadly neutralizing human antibody that recognizes the receptor-binding pocket of influenza virus hemagglutinin. Proc Natl Acad Sci USA 108: 14216-14221
59. Ekiert et al 2011 A highly conserved neutralizing epitope on group 2 influenza A viruses. Science 333: 843-850
60. Zhou et al 2007 Structural definition of a conserved neutralization epitope on HIVi gp120. Nature 44: 732-737
61. Zhou et al 2010 Structural basis for broad and potent neutralization of HIV-1 by antibody VRCO1. Science 329: 811-817
62. Papworth et al 1996 Site-directed mutagenesis in one day with >80% efficiency. Strategies 9:3-4
63. WO 2011/050168
64. ittisombut et al 1995 Lack of augmenting effect of interferon-gamma on dengue virus multiplication in human peripheral blood monocytes. Journal of medical virology 45: 43-49
65. Kabsch et al 2010 Acta Crystallogr D Biol Crystallogr 66: 125-132
66. Evans & Murshudov 2013 How good are my data and what is the resolution? Acta Crystallogr D Biol Crystallogr 69, 1204-1214
67. Winn et al 2011 Overview of the CCP4 suite and current developments. Acta Crystallogr D Biol Crystallogr 67: 235-242
68. McCoy et al 2007 Phaser crystallographic software. J Appl Crystallogr 40, 658674
69. Navaza, 2001 Implementation of molecular replacement in AMoRe. Acta Crystallogr D iol Crystallogr 57: 1367-1372
70. Emsley et al 2010. Features and development of Coot. Acta Crystallogr D Biol Crystallogr 66 486-501
71. Blanc et al. 2004 Refinement of severely incomplete structures with maximum likelihood in BUSTER-TNT. Acta Crystallogr D Biol Crystallogr 60: 2210-2221
72. Winn et al 2003 Macromolecular TLS refinement in REFMAC at moderate resolutions. Methods in enzymology 374: 300-321
73. Afonine et al 2012 Towards automated crystallographic structure refinement with phenix.refine. Acta Crystallogr D Biol Crystallogr 68: 352-367
74. Larkin et al 2007 Clustal W and Clustal X version 2.0. Bioinformatics 23: 2947-2948
75. Goujon et al 2010 A new bioinformatics analysis tools framework at EMBL-EBI. Nucleic Acids Res 38: W695-699
76. Klungthong et al 2008 Molecular genotyping of dengue viruses by phylogenetic analysis of the sequences of individual genes. Journal of virological methods 154, 175-181
77. Tamura et al MEGA5: molecular evolutionary genetics analysis using maximum likelihood, evolutionary distance, and maximum parsimony methods. Mol Biol Evol 28: 2731-2739
78. Gouet et al 1999 ESPript: analysis of multiple sequence alignments in PostScript. Bioinformatics 15: 305-308
79. Baker et al 2001 Electrostatics of nanosystems: application to microtubules and the ribosome. Proc Natl Acad Sci USA 98: 10037-10041
80. Dolinsky et al 2004 PDB2PQR: an automated pipeline for the setup of Poisson-Boltzmann electrostatics calculations. Nucleic Acids Res 32, W665-667
81. Rey 2013 Nature 497: 443-444
82. Ofek et al 2010 PNAS 107: 17880-17887
83. Burton 2010 PNAS 107:17859-17860
84. Bommakanti et al 2010 PNAS 13701-13706
85. Lee et al Clinical and Experimental Vaccine Research 2014 3: 12-28

OTHER REFERENCES

86. Coller & Clements 20111 Dengue vaccines: progress and challenges. Current opinion in immunology 23: 391-398
87. Murphy & Whitehead 2011 Immune response to dengue virus and prospects for a vaccine. Annual review of immunology 29: 587-619
88. Sabchareon et al 2012 Protective efficacy of the recombinant, live-attenuated, CYD tetravalent dengue vaccine in Thai schoolchildren: a randomised, controlled phase 2b trial. The Lancet 380: 1559-1567
89. Oliphant et al 2006 Antibody recognition and neutralization determinants on domains I and II of West Nile Virus envelope protein. J Vi rot 80: 12149-12159
90. Sukupolvi-Petty et al 2010 Structure and function analysis of therapeutic monoclonal antibodies against dengue virus type 2. J Virol 84: 9227-9239
91. Goncalvez & Lai 2004 Epitope determinants of a chimpanzee Fab antibody that efficiently cross-neutralizes dengue type 1 and type 2 viruses map to inside and in close proximity to fusion loop of the dengue type 2 virus envelope glycoprotein. J Vi rot 78: 12919-12928
92. Lai et al 2008 Antibodies to envelope glycoprotein of dengue virus during the natural course of infection are predominantly cross-reactive and recognize epitopes containing highly conserved residues at the fusion loop of domain II. J Virol 82: 6631-6643

93. Costin et al 2013 Mechanistic Study of Broadly Neutralizing Human Monoclonal Antibodies against Dengue Virus That Target the Fusion Loop. J Vi rot 87: 52-66

94. Teoh et al 2012 The Structural Basis for Serotype-Specific Neutralization of Dengue Virus by a Human Antibody. Science translational medicine 4: 139ra83

95. Lawrence & Colman 1993 Shape complementarity at protein/protein interfaces. J Mol Biol 234: 946-950

96. Tran et al 2012 Structural mechanism of trimeric HIV-1 envelope glycoprotein activation. PLoS Pathog 8: e1002797

97. McLellan et al 2011 Structure of HIV-1 gp120 V1/V2 domain with broadly neutralizing antibody PG9. Nature 480: 336-343

98. Chen et al 2010 Mol Probity: all-atom structure validation for macromolecular crystallography. Acta Crystallogr D Biol Crystallogr 66: 12-21

99. Millward et al 2007 Design of cyclic peptides that bind protein surfaces with antibody-like affinity", ACS CHEMICAL BIOLOGY, vol. 2, no. 9, pages 625-634, 100. Heinis Christian et al 2009 Phage-encoded combinatorial chemical libraries based on bicyclic peptides" NATURE CHEMICAL BIOLOGY, vol. 5, no. 7, pages 502-507

101. WO2009098450

REFERENCES

Afonine, P. V. et al., *Acta Crystallogr D Biol Crystallogr* 68, 352-367 (2012).

Backovic, M. et al., *Protein Eng Des Sel* 23, 169-174 (2010).

Bhatt, S. et al., *Nature* 496, 504-507 (2013).

Blanc, E. et al., *Acta Crystallogr D Biol Crystallogr* 60, 2210-2221 (2004).

Chen, V. B. et al. *Acta Crystallogr D Biol Crystallogr* 66, (2010).

Cockburn, J. J. et al., *Structure* 20, 303-314 (2012a).

Cockburn, J. J. et al., *Embo J* 31, 767-779 (2012b).

Coppieters, K. T. et al., *Arthritis Rheum* 54, 1856-66 (2006).

de Alwis, R. et al., *Proc Natl Acad Sci USA* 109, 7439-7444 (2012).

Dejnirattisai, W. et al., *Science* 328, 745-748 (2010).

Emsley, P. et al., *Acta Crystallogr D Biol Crystallogr* 66, 486-501 (2010).

Evans, P. R. & Murshudov, G. N., *Acta Crystallogr D Biol Crystallogr* 69, 1204-1214 (2013).

Fan S. Q. et al., *J Biol Chem* 287, 11272-81 (2012).

Gilmartin, A. A. et al., *Protein Eng Des Sel* 25, 59-66 (2012).

Goujon, M. et al., *Nucleic Acids Res* 38, W695-699 (2010).

Haberz P. et al., *Organic Letters,* 2006, 8, 1275-1278.

Hemaprabha E., *Journal of Pharmaceutical and Scientific Innovation* 1, 22-26 (2012).

Hermanson G. T., Bioconjugate Techniques, 3rd Edition. Academic Press (2013).

Harmsen, M. et al., Vaccine 23, 4926-34 (2005).

Kabsch, W. Xds., *Acta Crystallogr D Biol Crystallogr* 66, 125-132 (2010).

Kaufmann, B. et al., *Proc Natl Acad Sci USA* 107, 18950-18955 (2010).

Khakshoor, O. et al., *Org. Lett.* 11, 3000-3003 (2009).

Klungthong, C. et al., *Journal of virological methods* 154, 175-181 (2008).

Kuhn, R. J. et al., *Cell* 108, 717-725 (2002).

Laughlin, S. T. et al., *Nat Protoc* 2, 2930-44 (2007).

Larkin, M. A. et al., *Bioinformatics* 23, 2947-2948 (2007).

Lawrence, M. C. & Colman, P. M. *J Mol Biol* 234, 946-950 (1993).

Lefranc, M. P. et al., *Nucleic Acids Res* 37, D1006-1012 (2009).

Lindenbach, B., Thiel, H. & Rice, C. *Flaviviridae: the viruses and their replication.* 5th edn, Vol. 1 1101-1152 (Lippincott Williams & Wilkins, 2007).

Lok, S. M. et al., *Nat Struct Mol Biol* 15, 312-317 (2008).

McCoy, A. J. et al., *J Appl Crystallogr* 40, 658-674 (2007).

McLellan, J. S. et al., *Science* 342, 592-598 (2013).

Modis, Y. et al., *Proc Natl Acad Sci USA* 100, 6986-6991 (2003).

Navaza, *J., Acta Crystallogr D Biol Crystallogr* 57, 1367-1372 (2001).

Pokidysheva, E. et al., *Cell* 124, 485-493 (2006).

Rey, F. A. et al., *Nature* 375, 291-298 (1995).

Sabchareon, A. et al., *Lancet* 380, 1559-1567 (2012).

Sittisombut, N. et al., *Journal of medical virology* 45, 43-49 (1995).

Speers, A. E., et al., *J Am Chem Soc* 125, 4686-7 (2003).

Tamura, K. et al., *Mol Biol Evol* 28, 2731-2739 (2011).

Vincke, C. et al., *J Biol Chem* 284, 3273-84 (2009).

Winn, M. D. et al., *Methods in enzymology* 374, 300-321 (2003).

Winn, M. D. et al., *Acta Crystallogr D Biol Crystallogr* 67, 235-242 (2011).

Wu, T. T. & Kabat, E. A. *The Journal of experimental medicine* 132, 211-250 (1970).

Yu, I. M. et al., *Science* 319, 1834-1837 (2008).

Zhang, Y. et al., *Structure* 12, 1607-1618 (2004).

Zhang, X. et al., *Nat Struct Mol Biol* 20, 105-110 (2013).

FIGURE LEGENDS

Figure 1B:
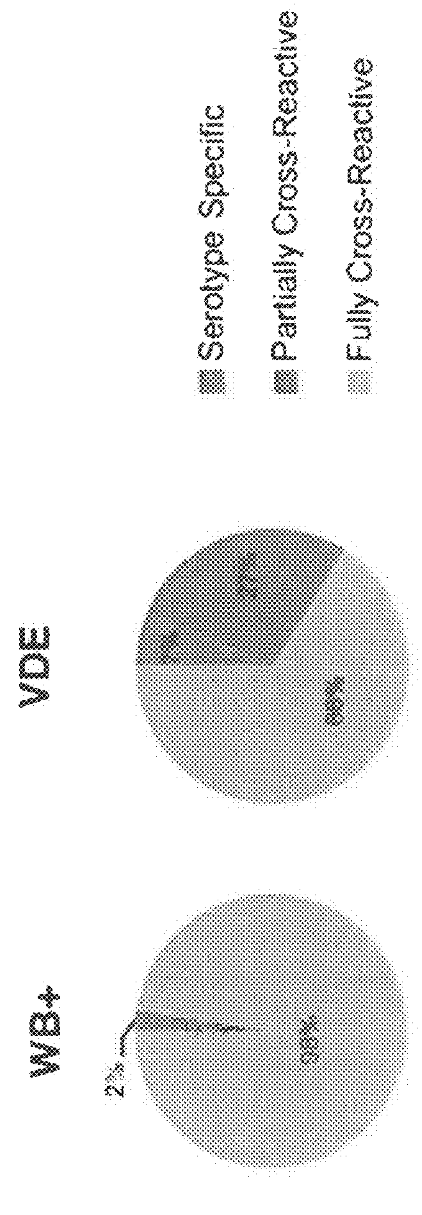
Figure 1C:
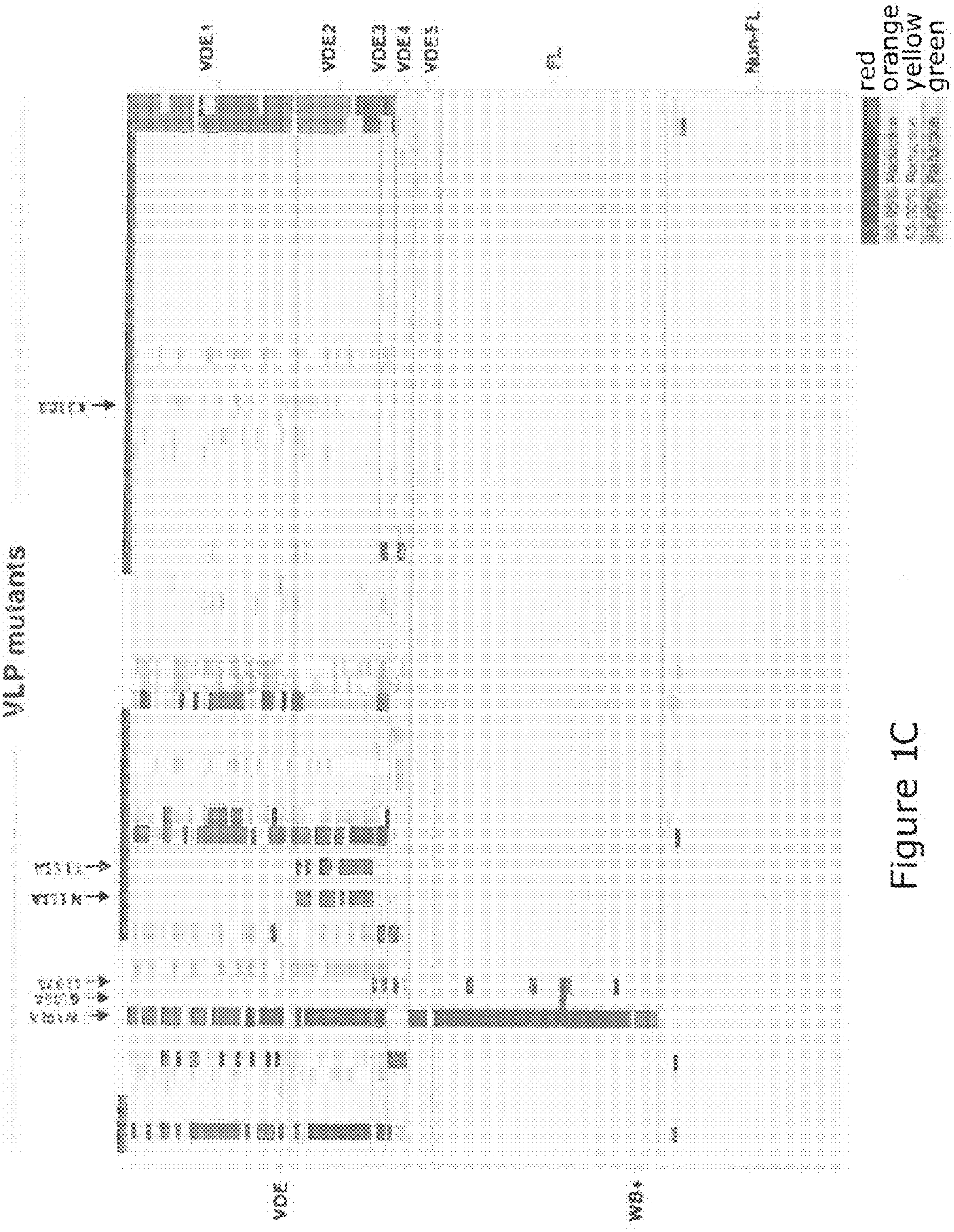

FIGS. 1A-C. Characterization of human anti-DENV monoclonal antibodies. (FIG. 1A) Serotype specificity and reaction to DENV envelope protein by Western Blot (WB) of 145 DENV mAbs. (FIG. 1B) Serotype specificity of WB positive and EDE (WB negative) antibodies. (FIG. 1C) Schematic of epitope mapping using a panel of mutant VLPs. The position of mutations are shown relative to the domain structure of dengue envelope protein with red, yellow and blue representing domain I, II and III, respectively. Positions of mutations marking the fusion loop around W101 and disrupting the N153 glycosylation motif are shown.

Figure 2:
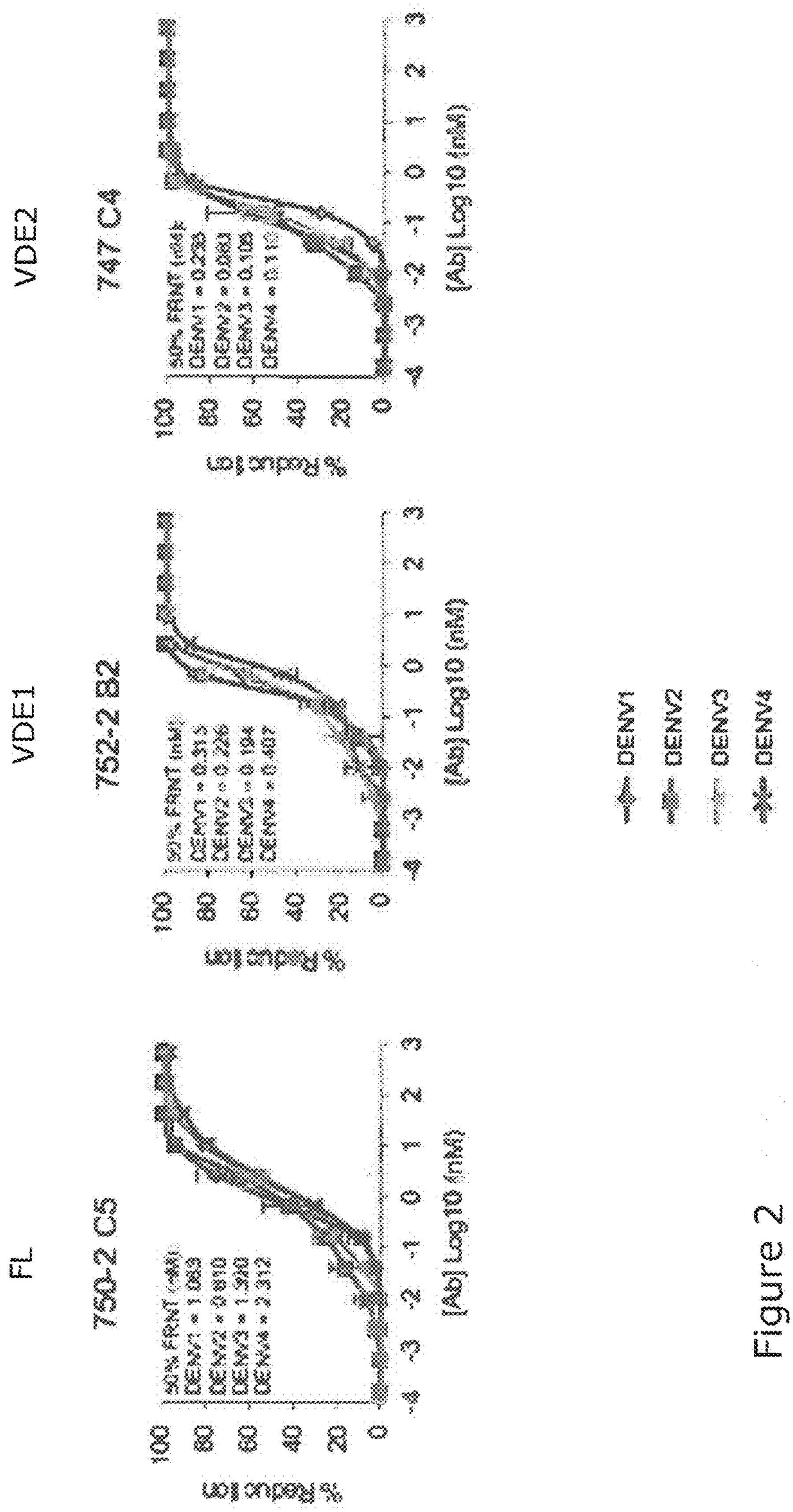
Figure 2:
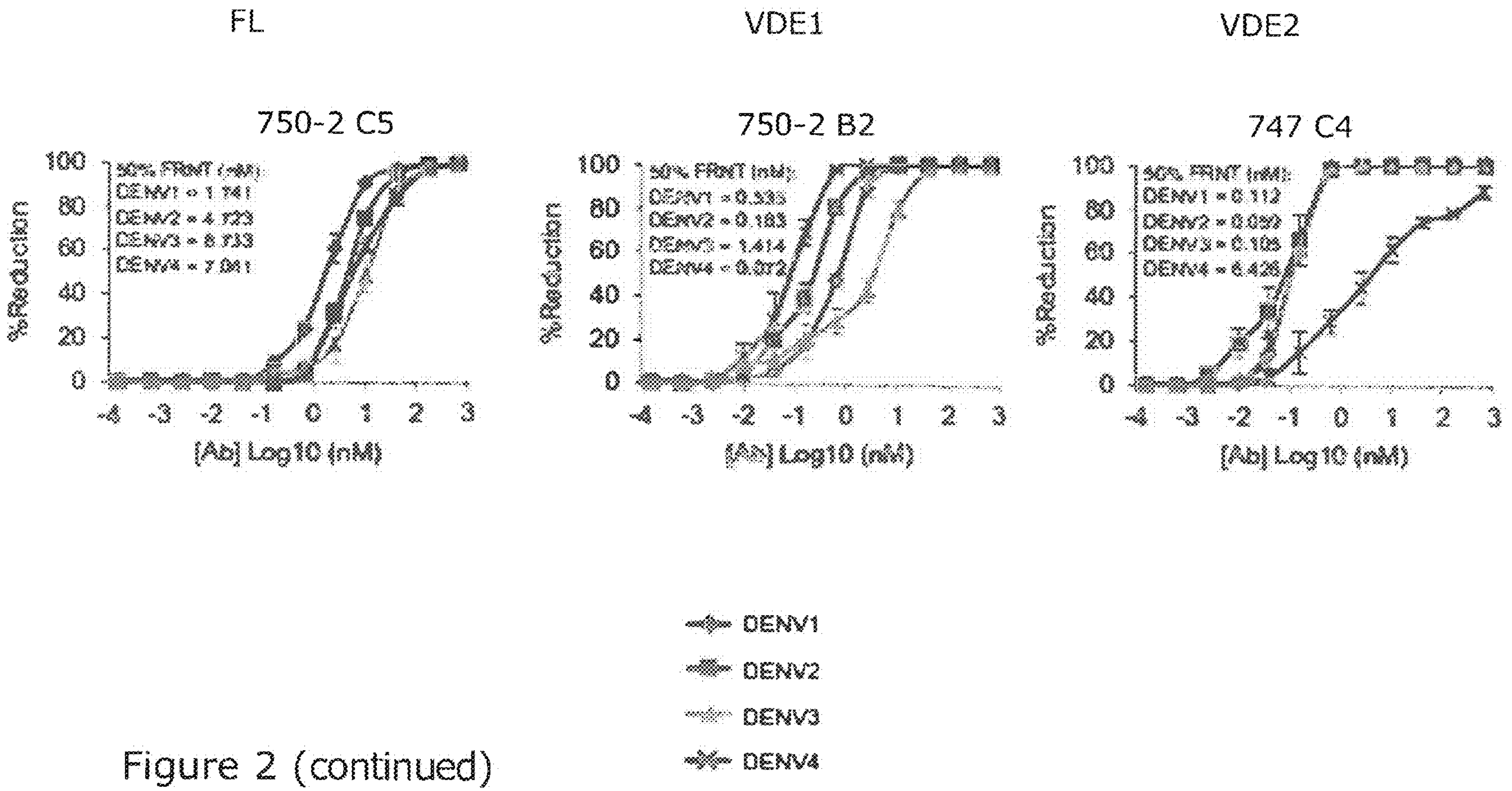
Figure 2:
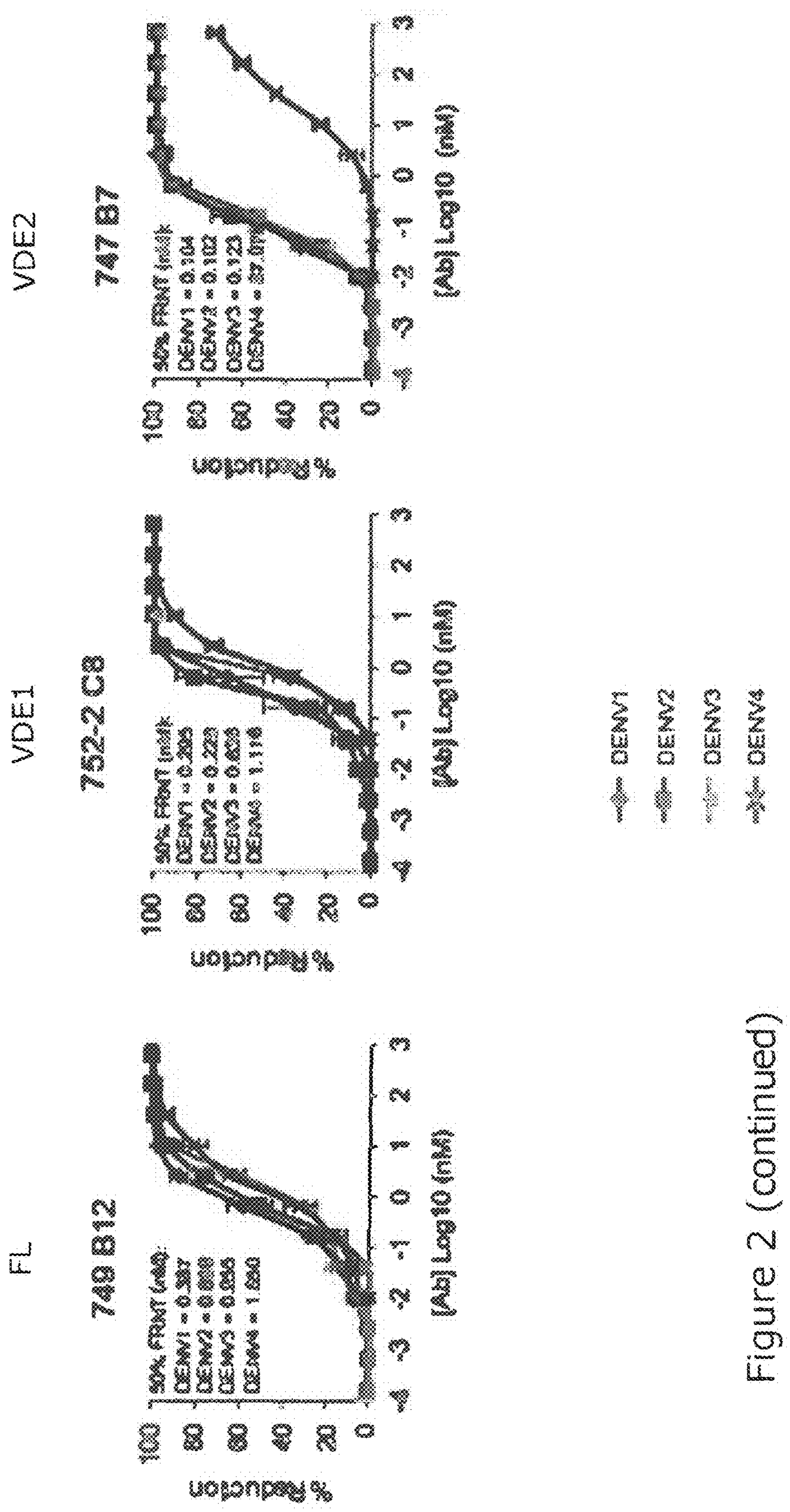

FIG. 2. EDE antibodies are potent and highly crossreactive in neutralization assays.

Neutralization assays performed on Vero cells for 9 representative mAbs against all four DENV serotypes produced in C6/36 insect cells (3 each of FL, EDE1 and EDE2). The data were from 3 independent experiments.

Figure 3A:
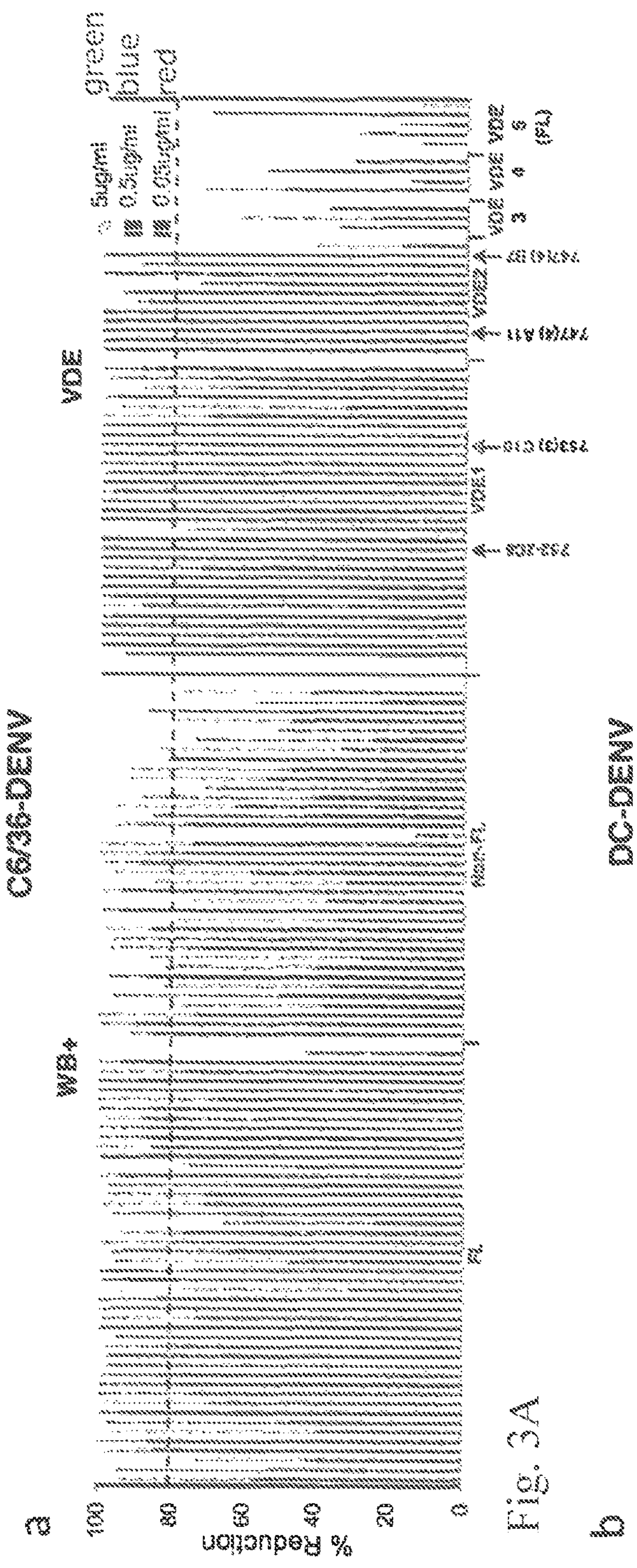
Figure 3B:
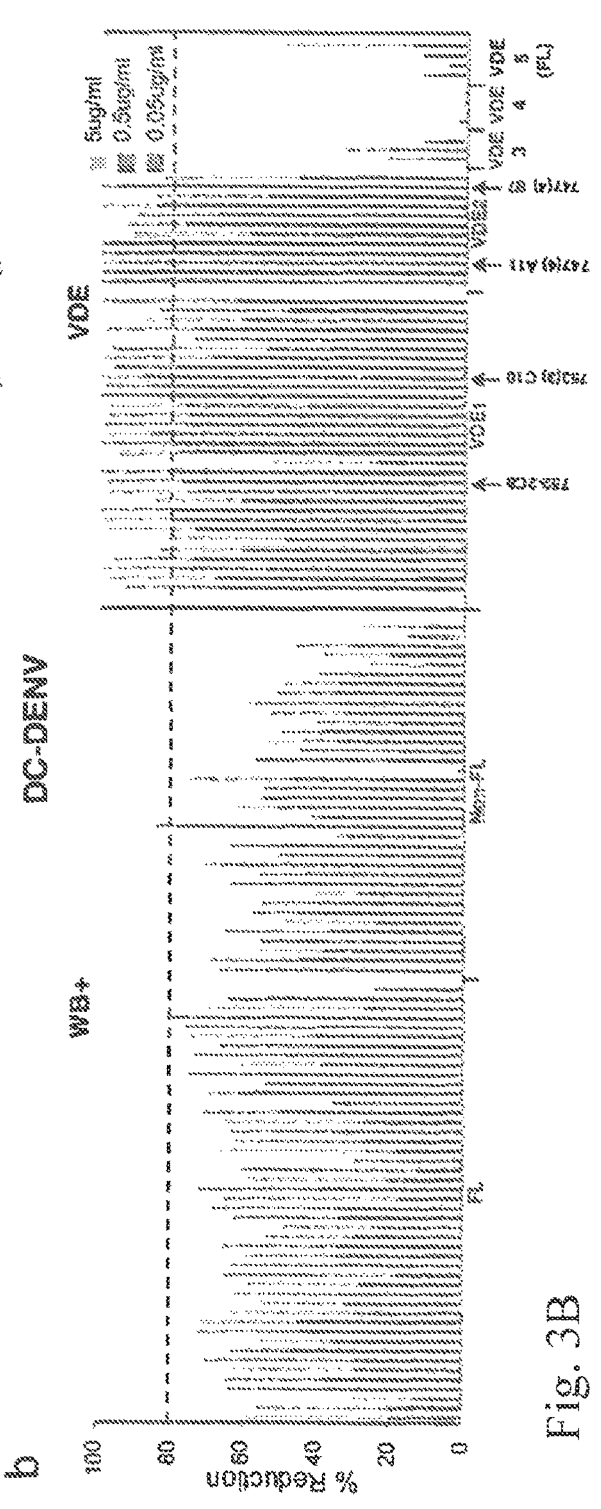

FIGS. 3A-B. EDE-specific antibodies have superior neutralizing activities. Neutralization assays using Vero as the target cell were performed on DENV2 generated from C6/36 insect cells C6/36-DENV. (FIG. 3A) or dendritic cells DC-DENV (FIG. 3B). Red, blue and green bars represented FRNT (% reduction) for mAbs at 0.05, 0.5 and 5 μg/ml (final concentration), respectively. The EDE mAbs used in the accompanying paper are marked below the histograms. Antibodies are classified into FL and EDE whereas antibodies positive by WB, which failed to map on the VLPs are termed non-FL. Based on the results of VLP mapping five subgroups of the EDE were identified referred to as EDE15. Titration curves for binding, measure by capture ELISA, and neutralization of DC and C6/36 produced viruses with 2 representative antibodies from the FL and EDE1&2 groups.

The data were from 2 independent experiments and are representative of the results from 9 each of anti-FL and anti-EDE1 antibodies and 7 anti-EDE2 antibodies.

Figure 4A:
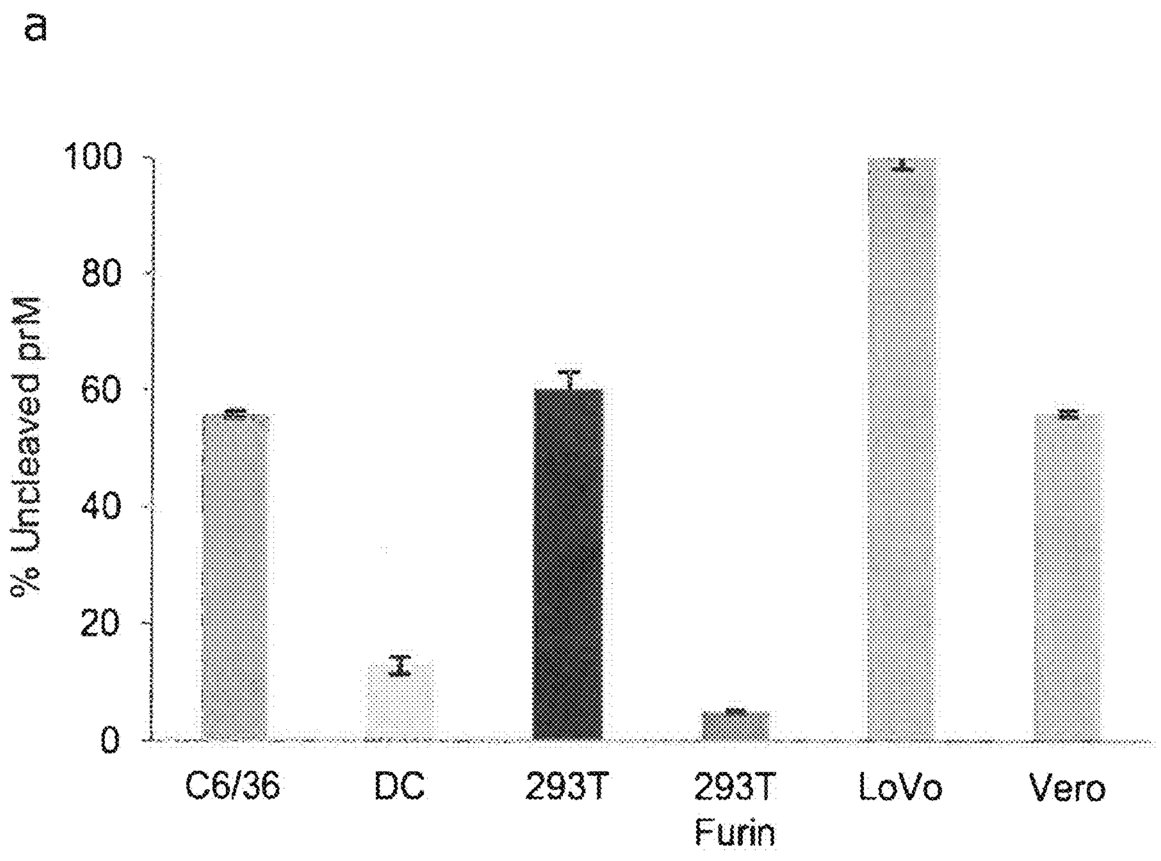
Figure 4B:
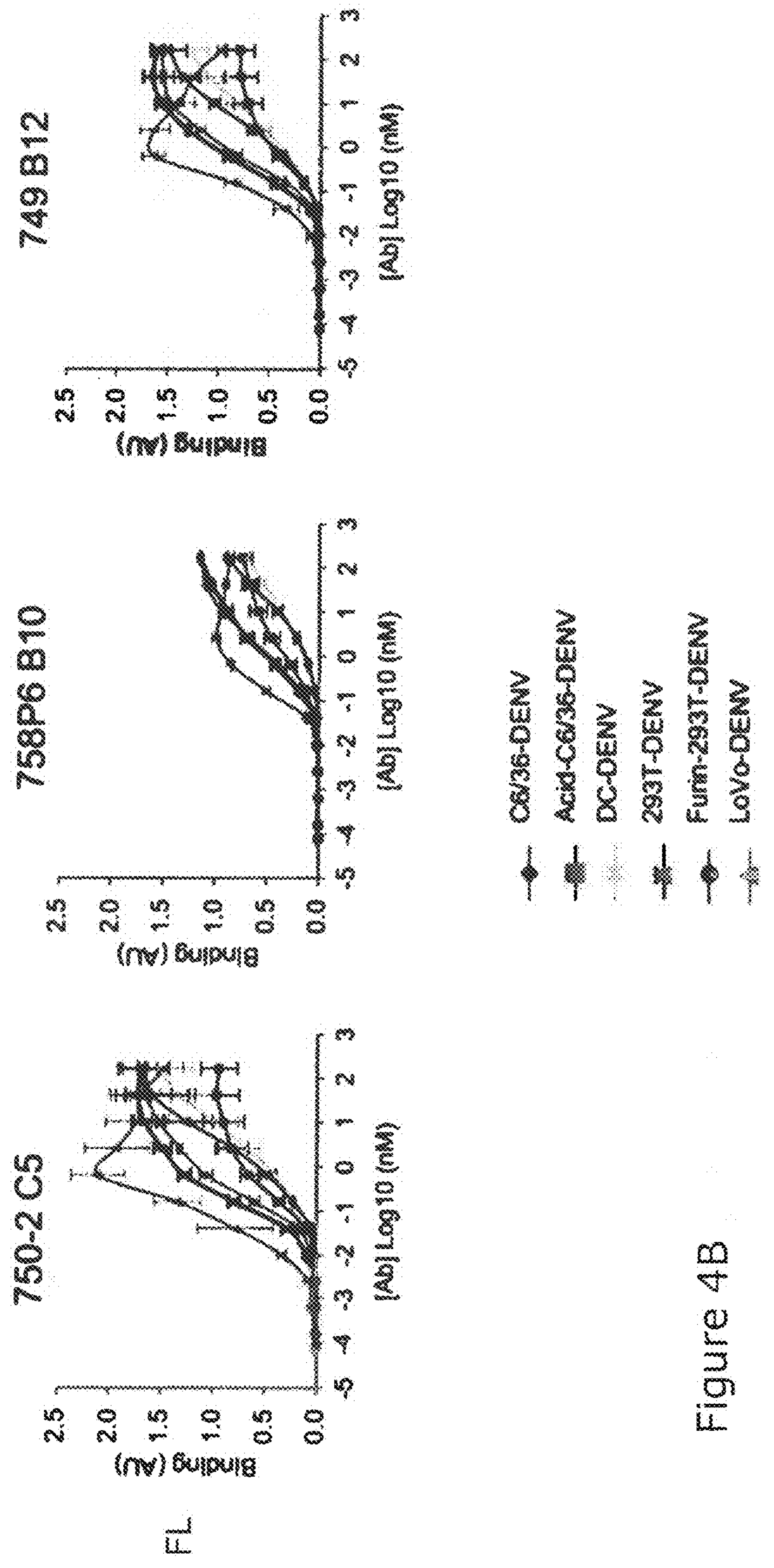
Figure 4B:
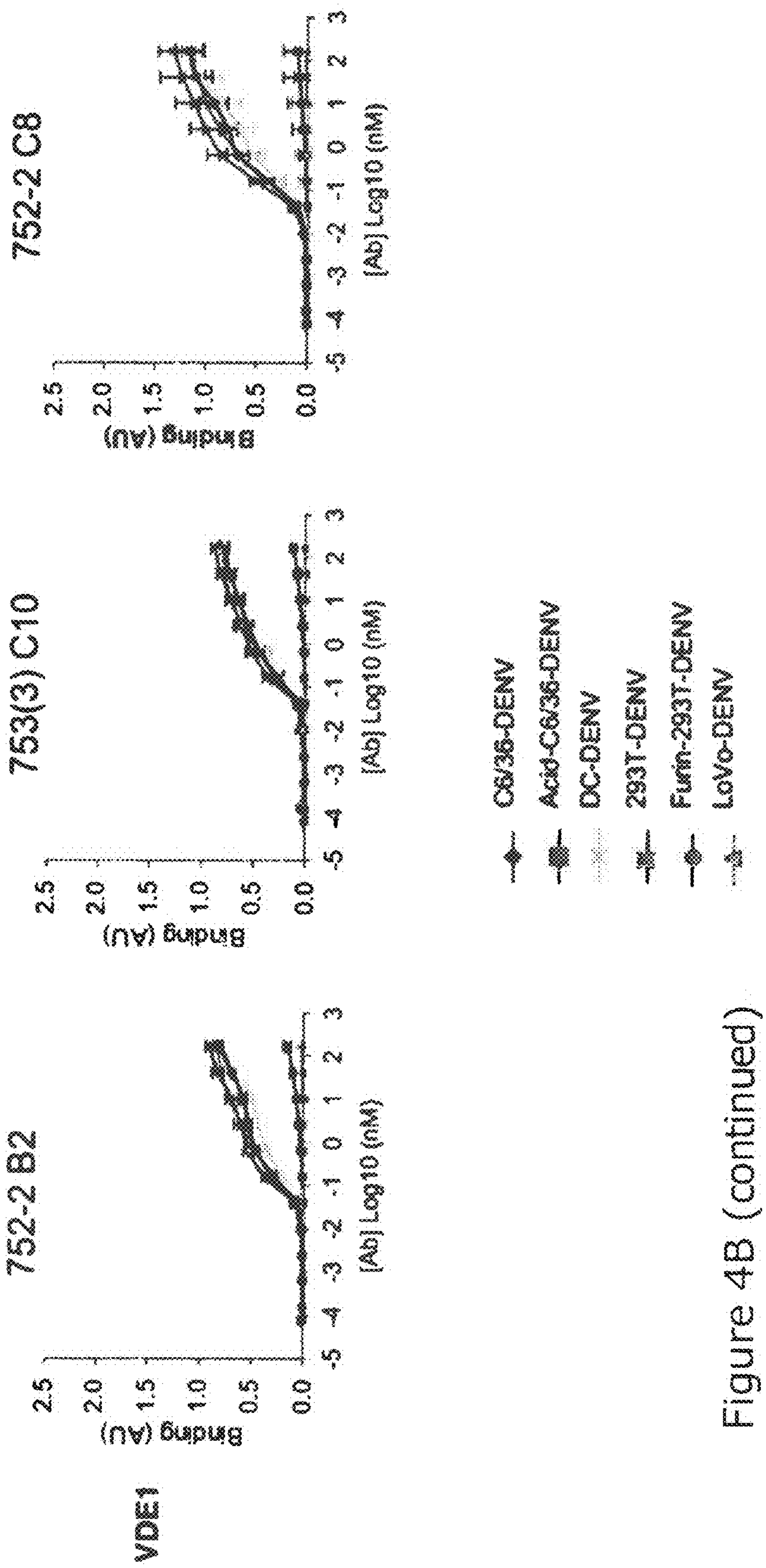
Figure 4B:
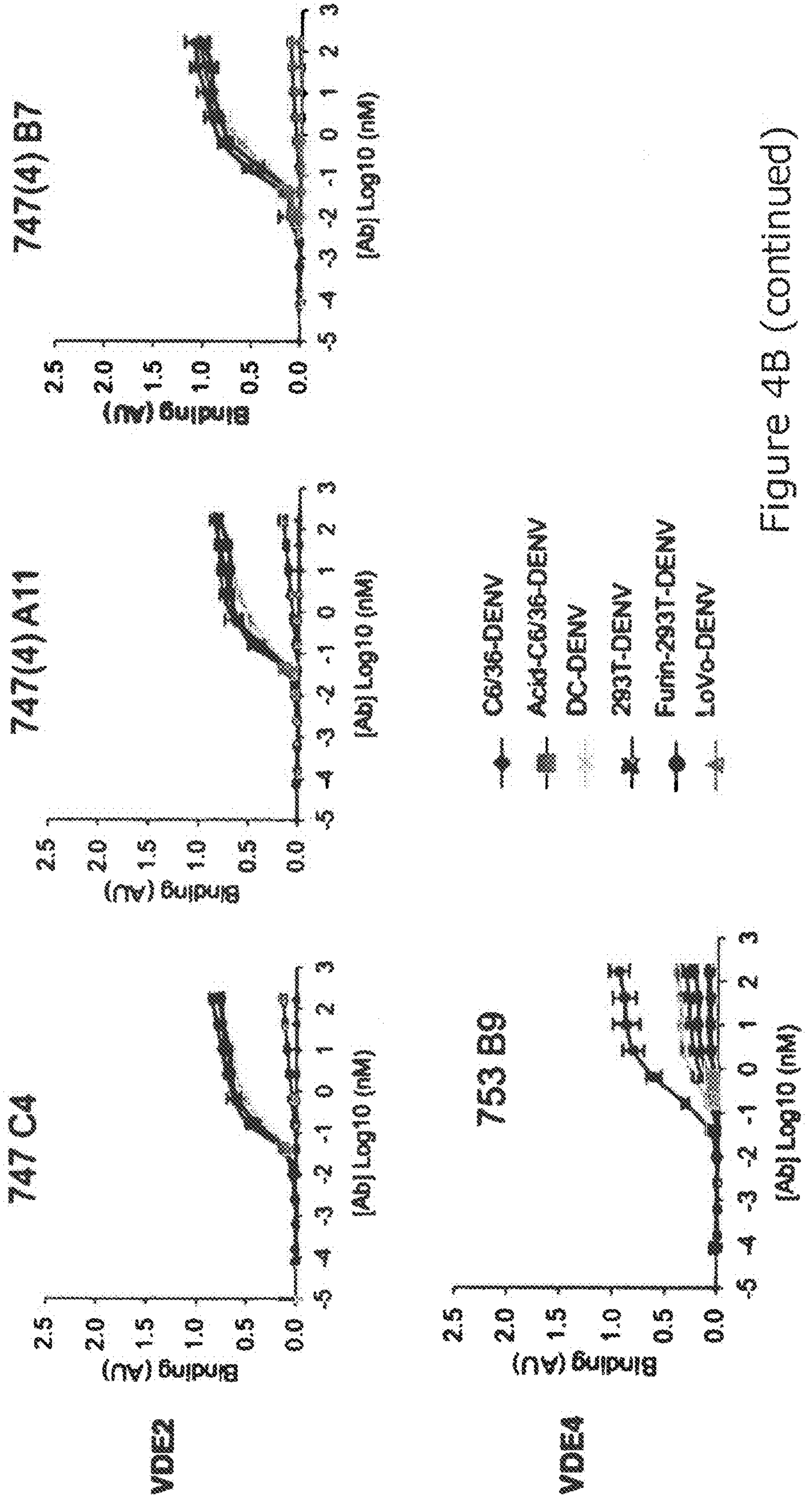

FIG. 4A-B. Antibody binding to viral particles in differing states of maturation. (FIG. 4A) Anti-prM and anti-E ELISAs were used to calculate a ratio of prM:E on the various viral particles and compared to virus from LoVo cells which was defined as 100% prM content. (FIG. 4B) Antibody binding to viral particles in differing states of maturation. Binding of representative mAbs to DENV2 produced from C6/36, DC, 293T, furin-transfected 293T, LoVo cells or acid-treated DENV2 were measured by capture ELISA. Two each of FL, VDE1 and VDE2 mAbs are shown together with a VDE4 mAb sensitive to acid treated virus. The data were from 2 independent experiments and are representative of the results from 8 anti-FL, 10 anti-VDE1 and 8 anti-VDE2 antibodies.

Figure 5A:
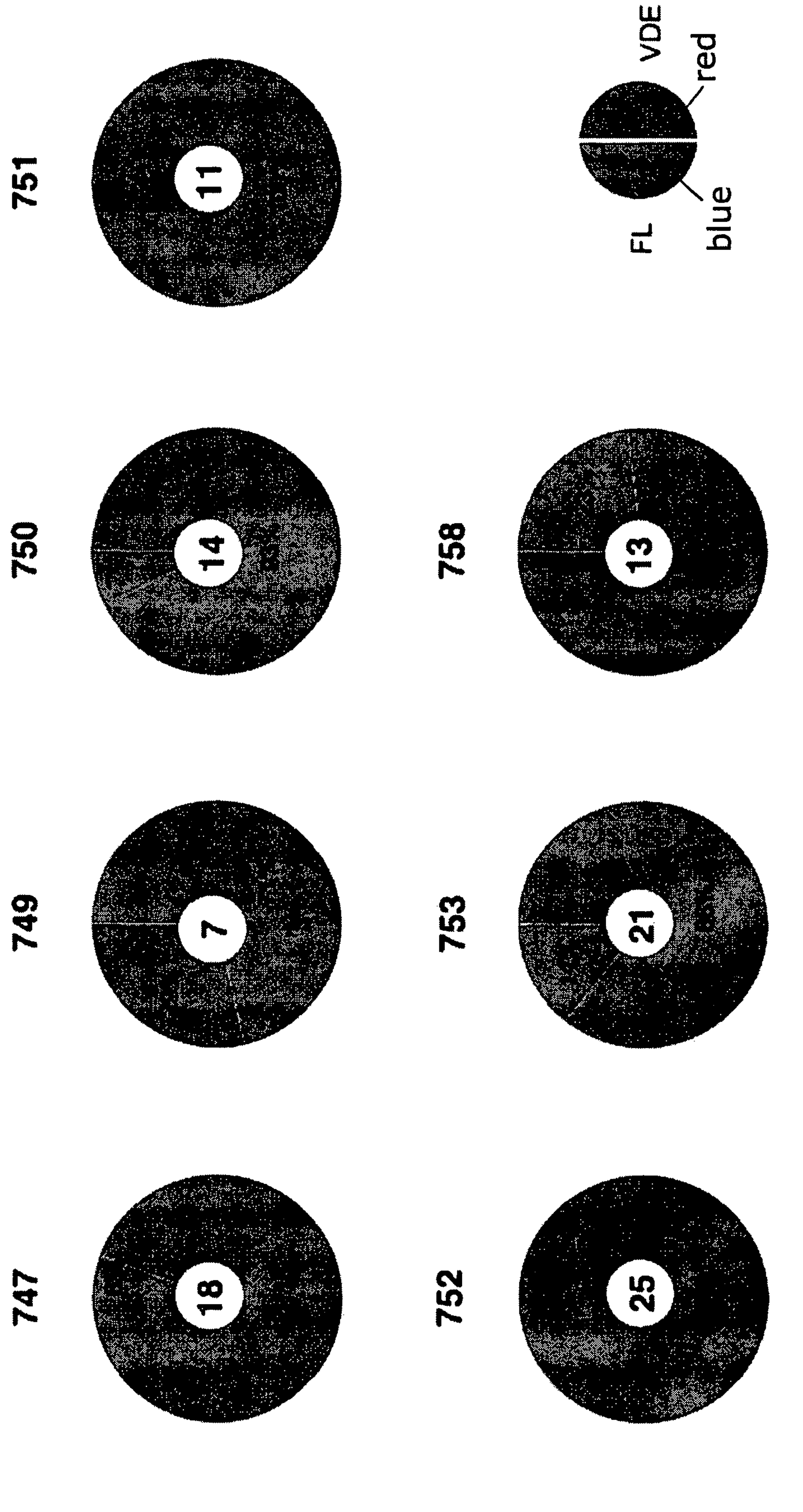
Figure 5B:
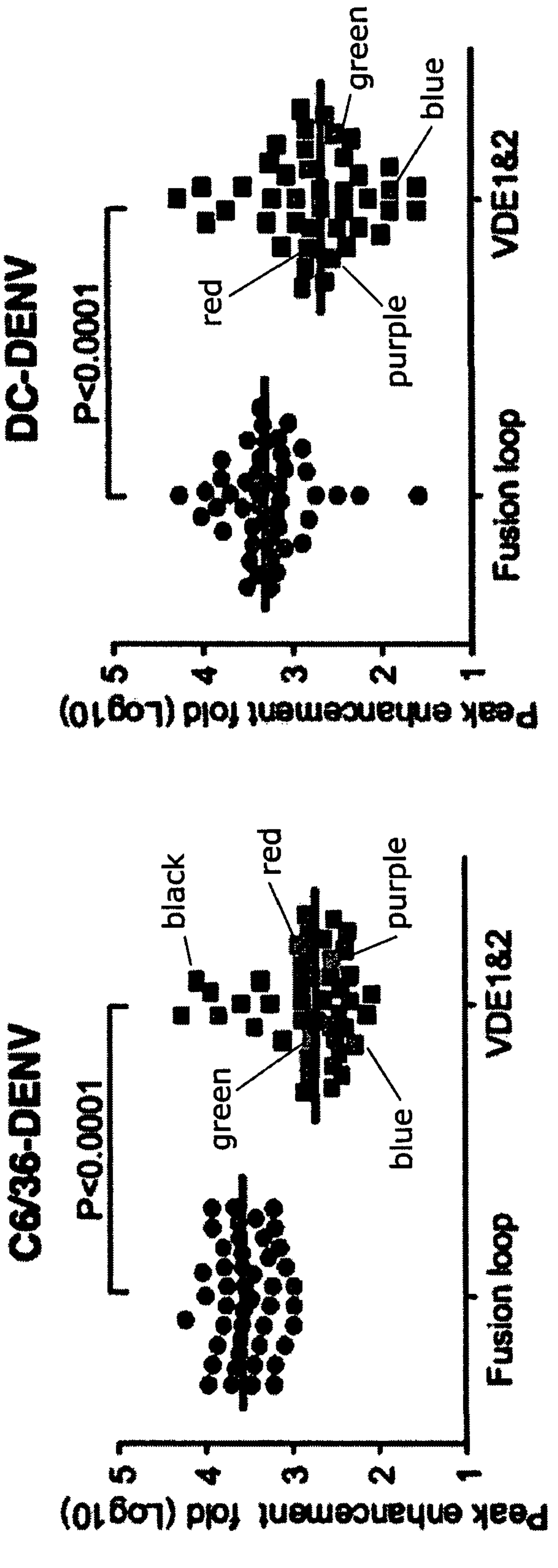
Figure 5C:
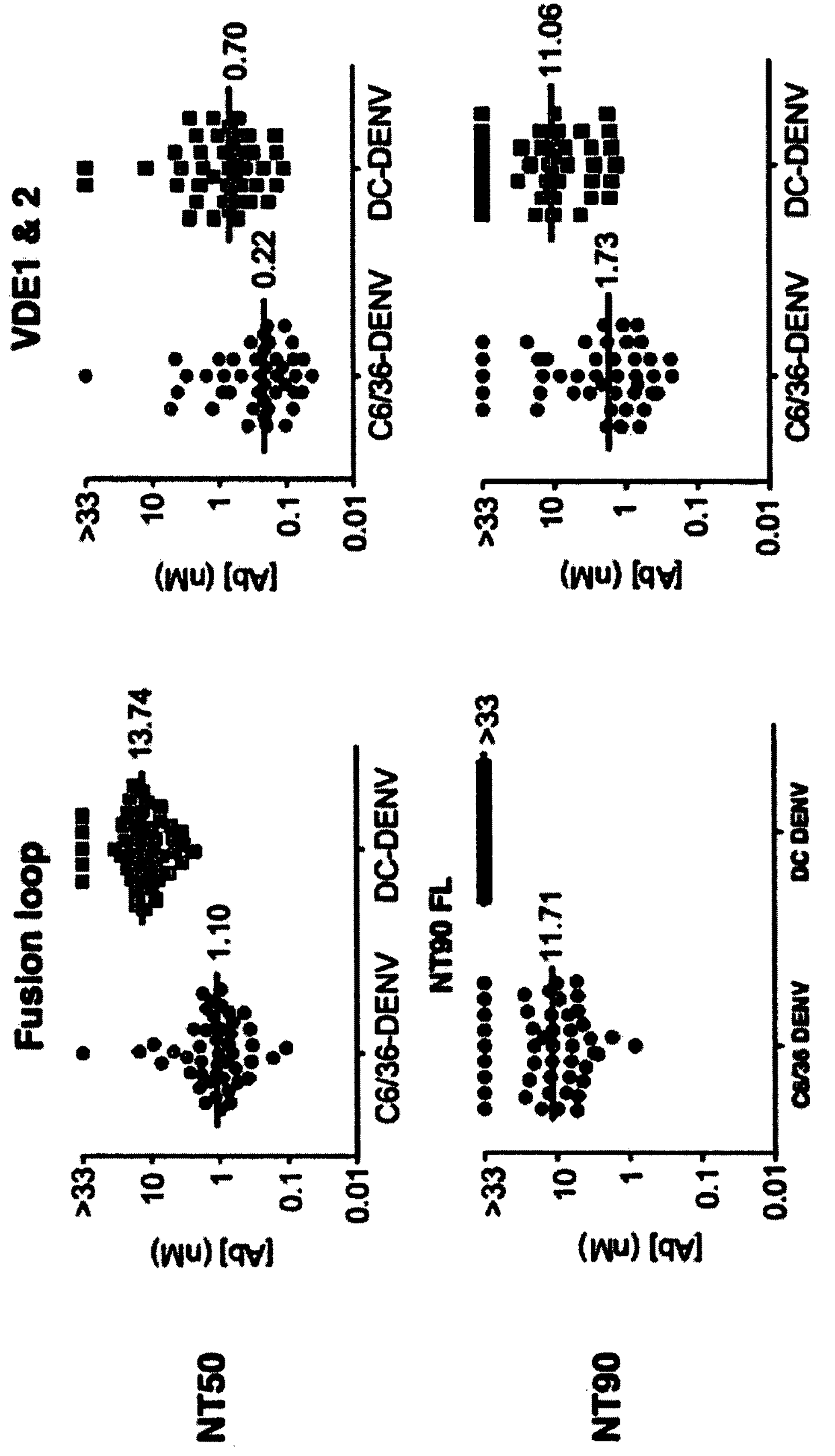

FIG. 5A-C. FL vs. EDE mAbs from individual patients. (FIG. 5A) Distribution of the FL and EDE responses between patients are shown, FL and EDE. The number in the centre indicates the number of Abs from each patient, one copy of three duplicate antibodies (1 EDE1 and 2 EDE2) from patient 752 which have identical amino acid sequences were excluded from this and all other analyses. (FIG. 5B). FL vs. EDE mAbs from individual patients. ADE, U937 cells were infected with DENV2, grown in either C6/36 cells or DC in the presence of titrations of anti-E mAbs reacting to the FL or EDE. The results are expressed as median peak enhancement (fold) from two independent experiments. 752-2C8, 753 (3) C10, 747 (4) A11 and 747 (4) B7 mAbs used in the accompanying paper. (FIG. 5C). FL vs. EDE mAbs from individual patients. NT50 and NT90 titres between the FL and EDE mAbs are compared on C6/36 and DC virus.

Figure 6:
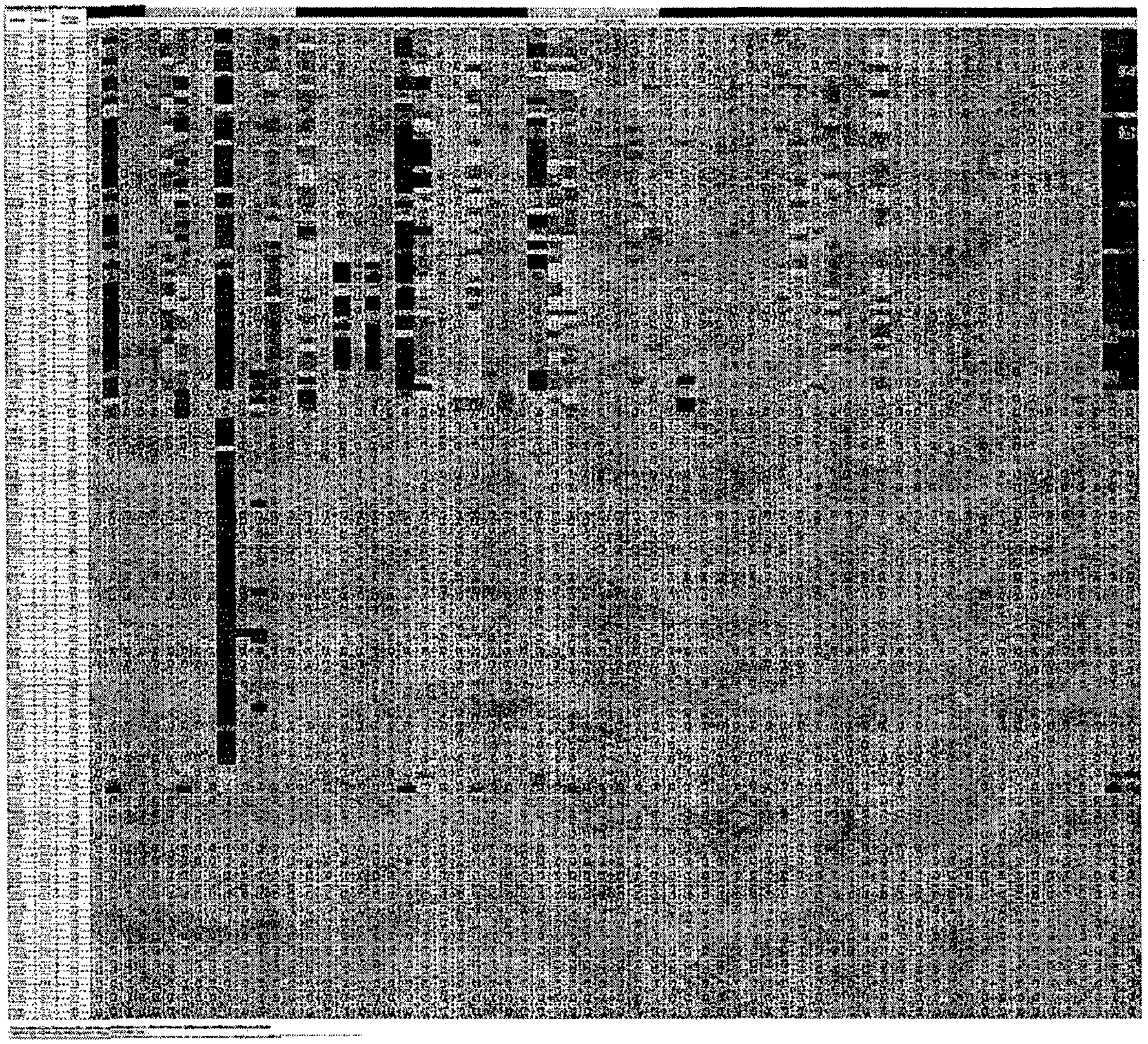

FIG. 6. Schematic of epitope mapping using a panel of mutant VLPs. The position of mutations are shown relative to the domain structure of dengue envelope protein with red, yellow and blue representing domain I, II and III, respectively. Positions of mutations marking the fusion loop around W101 and disrupting the N153 glycosylation motif are shown.

FIG. 7. Germline analysis of EDE1 and EDE2 anti-EDE antibodies.

Figure 8A:
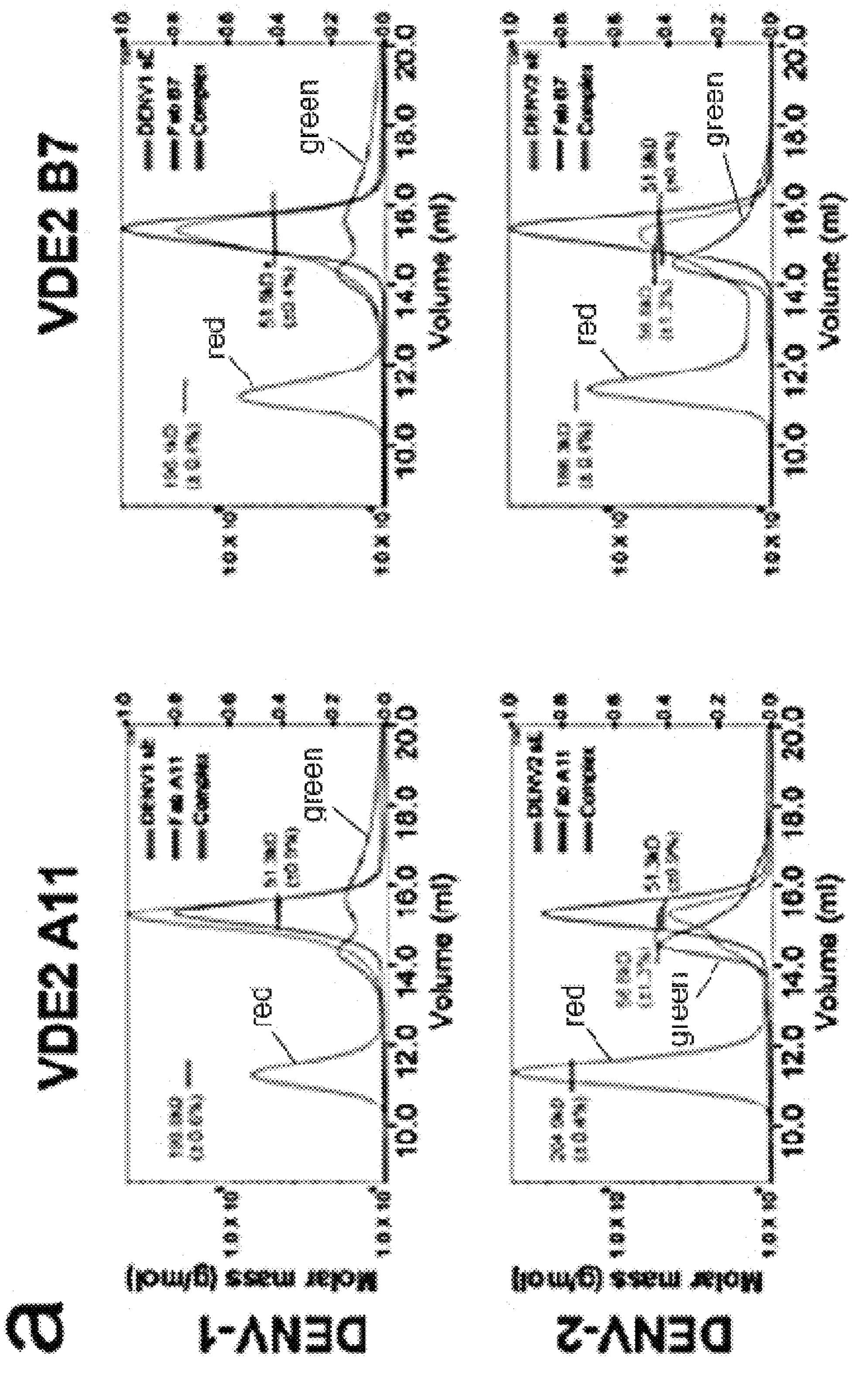
Figure 8A:
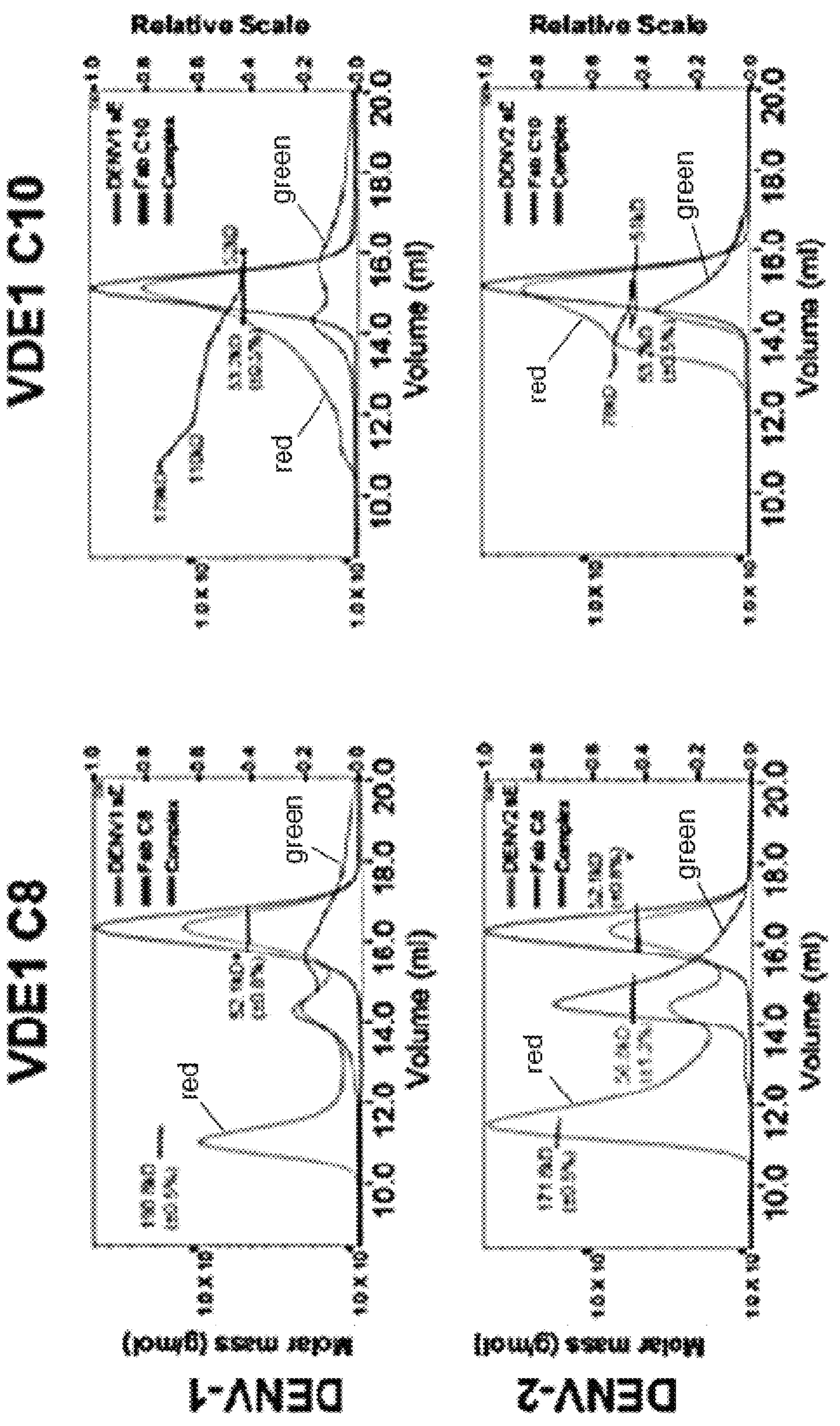
Figure 8A:
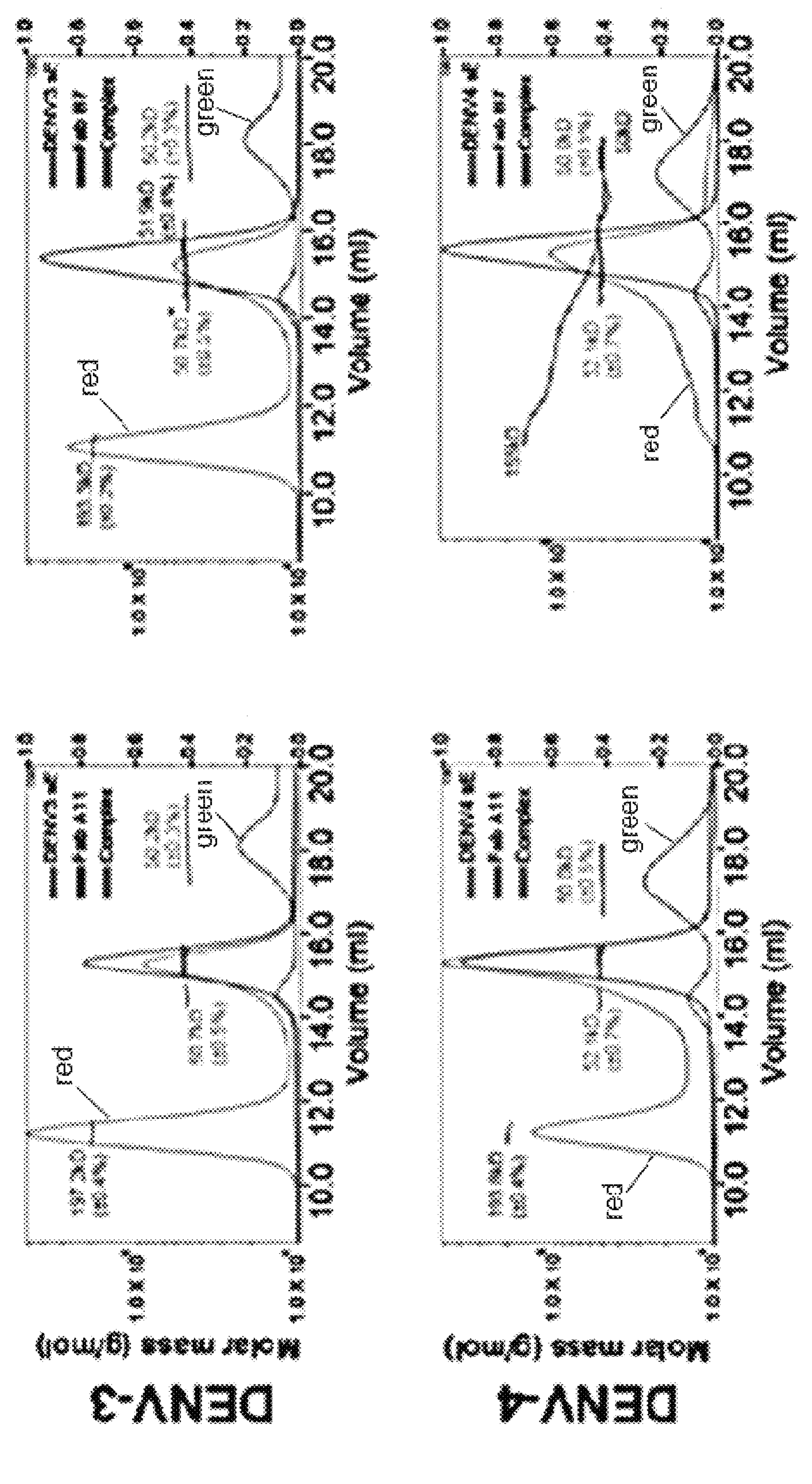
Figure 8A:
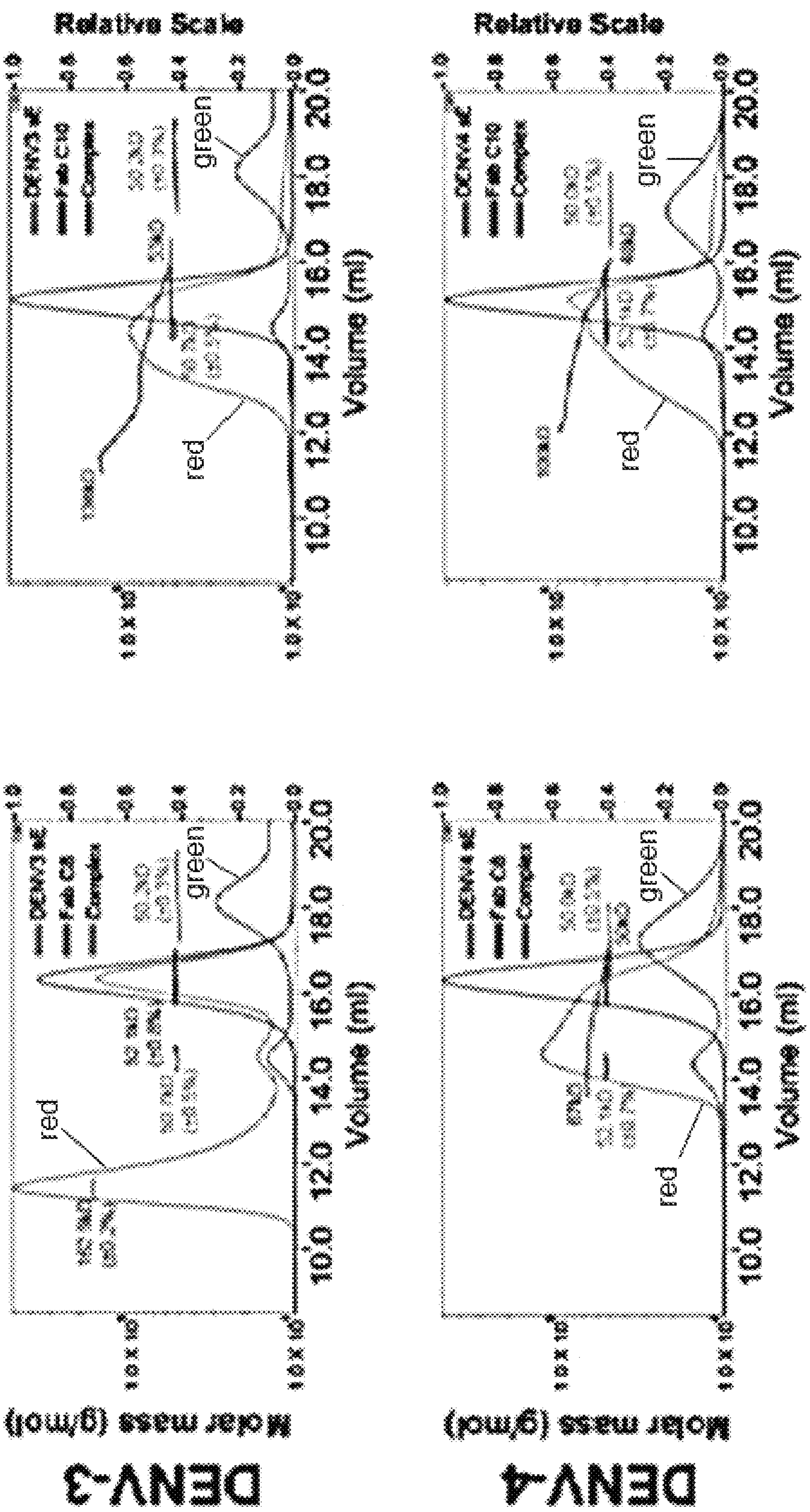
Figure 8B:
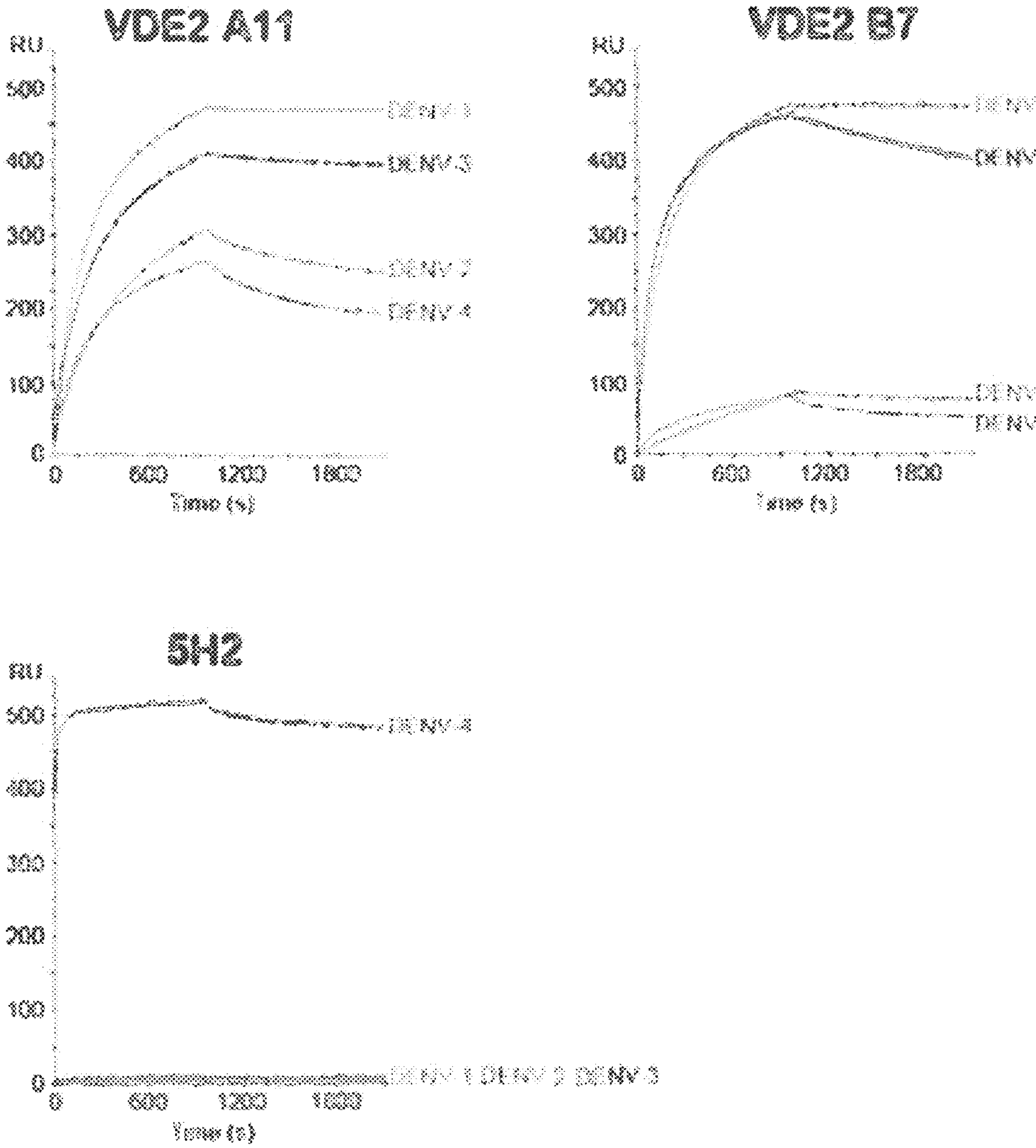
Figure 8B:
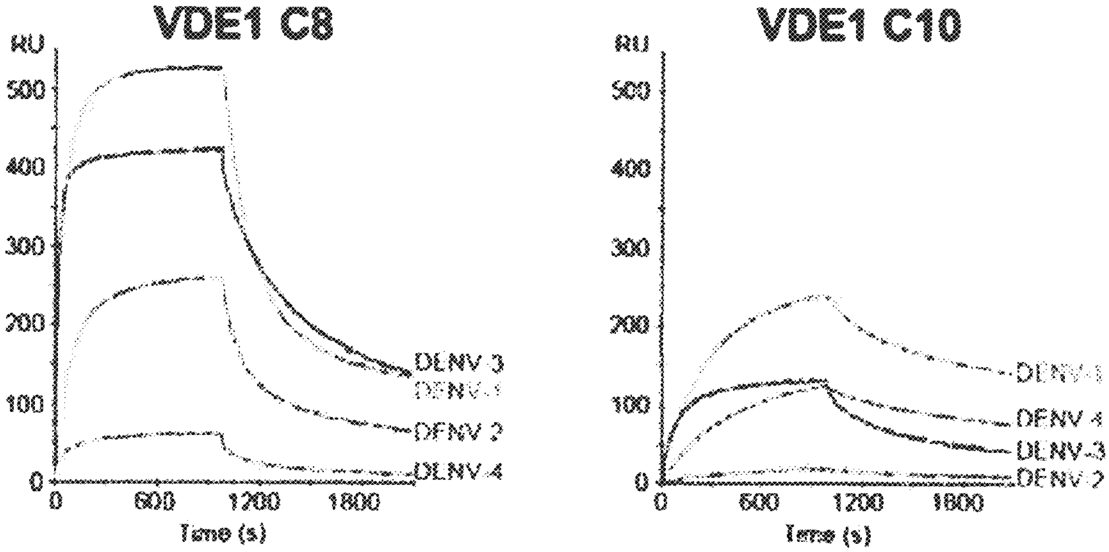

FIG. 8A-B. Recombinant E dimers bind both EDE1 and EDE2 antibodies. (FIG. 8A) SEC/MALS analysis of recombinant sE protein from the four dengue serotypes in complex or not with the BNA (broadly neutralizing antibodies) Fab fragments. MALS showed that the SEC chromatograms of sE protein (green curves) correspond only to the monomer fraction, and the dimer is not detected. The two peaks observed for sE serotypes 1, 3 and 4 correspond to monomers. The most likely explanation is that the dimer affinity is not high enough, and the dimer-monomer equilibrium is disrupted in the gel filtration column, such that the dimer dissociates. The complex with the Fab fragments clearly stabilizes the dimeric form, allowing the elution of a sE dimer in complex with two Fab fragments (red curves). We noted that only the sE monomer fraction eluting late is converted to complex, whereas the other peak remains unchanged (this was most clear with DENV-3 sE, but it also holds for the other serotypes). For DENV-2 sE, there is a single sE peak with a tail towards the small molecular weights, which disappears upon complex formation. Our explanation for this behavior is that the exposed fusion loop of the fraction containing sE competent to form dimers has a tendency to interact with the support, which is why it elutes so late, similar to our previous information with the alphavirus fusion protein EI[28]. (FIG. 8B). Recombinant E dimers bind both EDE1 and EDE2 antibodies. Real-time SPR profiles corresponding to the interactions of sE with tethered Fab fragments of EDE2 A11, EDE2 B7, EDE1 C8, EDE1 C10. The binding of Fab 5H2, which is specific for DENV-4, is shown as a positive control, given that its well-characterized epitope[29] is not at the dimer interface and does not require dimer formation for binding. The Fab fragments were immobilized to similar densities on a Proteon XPR36 chip. 2 μM solutions of DENV sE proteins from four serotypes (as indicated), were injected simultaneously over all the Fabs (see the Online Extended Methods section). SPR signal is presented in response unit (RU) as a function of time in seconds (s). Note that the level of binding is in general agreement with the SEC/MALS plots of the corresponding antibodies in panel FIG. 8A.

FIG. 9. Crystallographic statistics

Figure 10A:
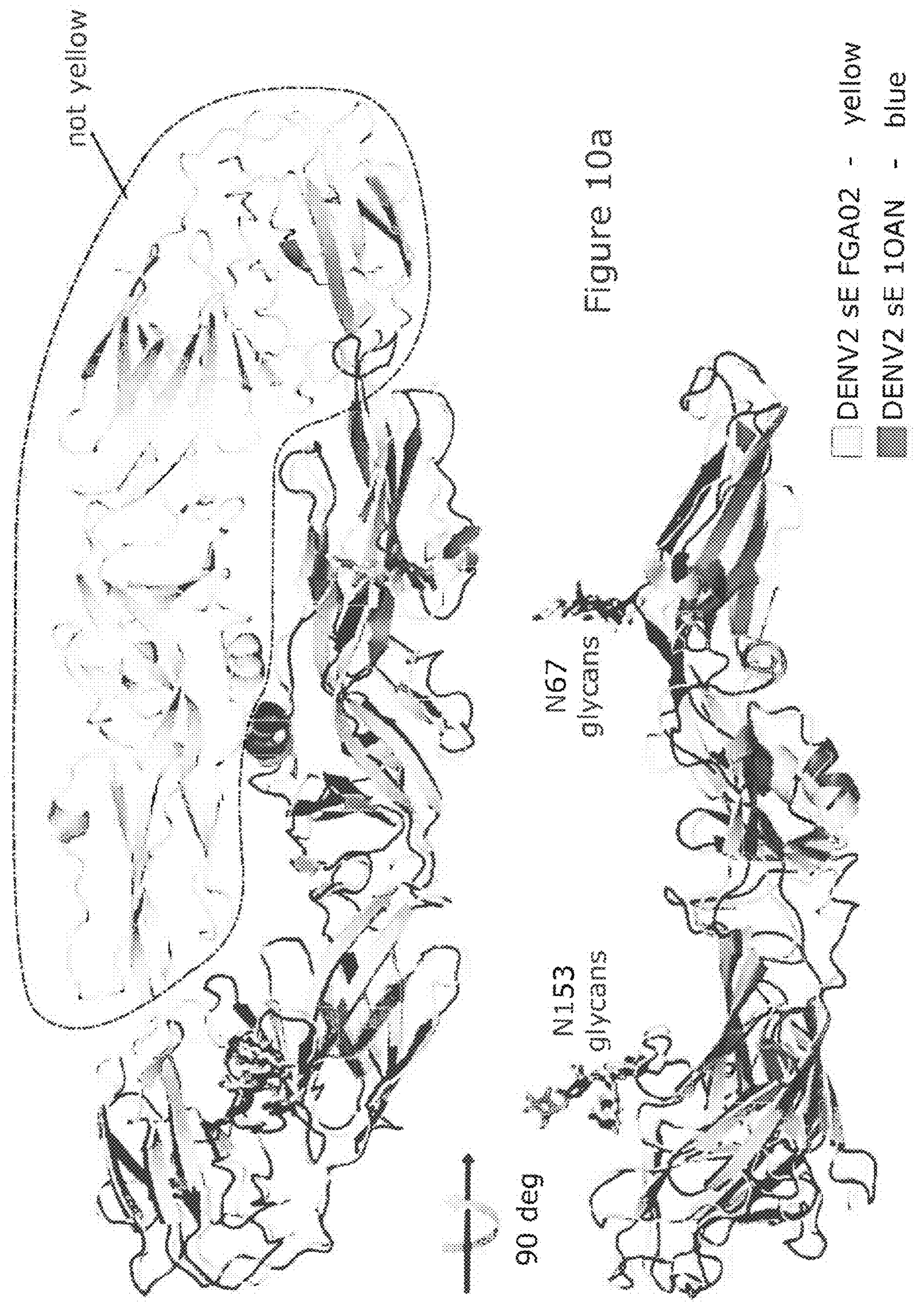
Figure 10B:
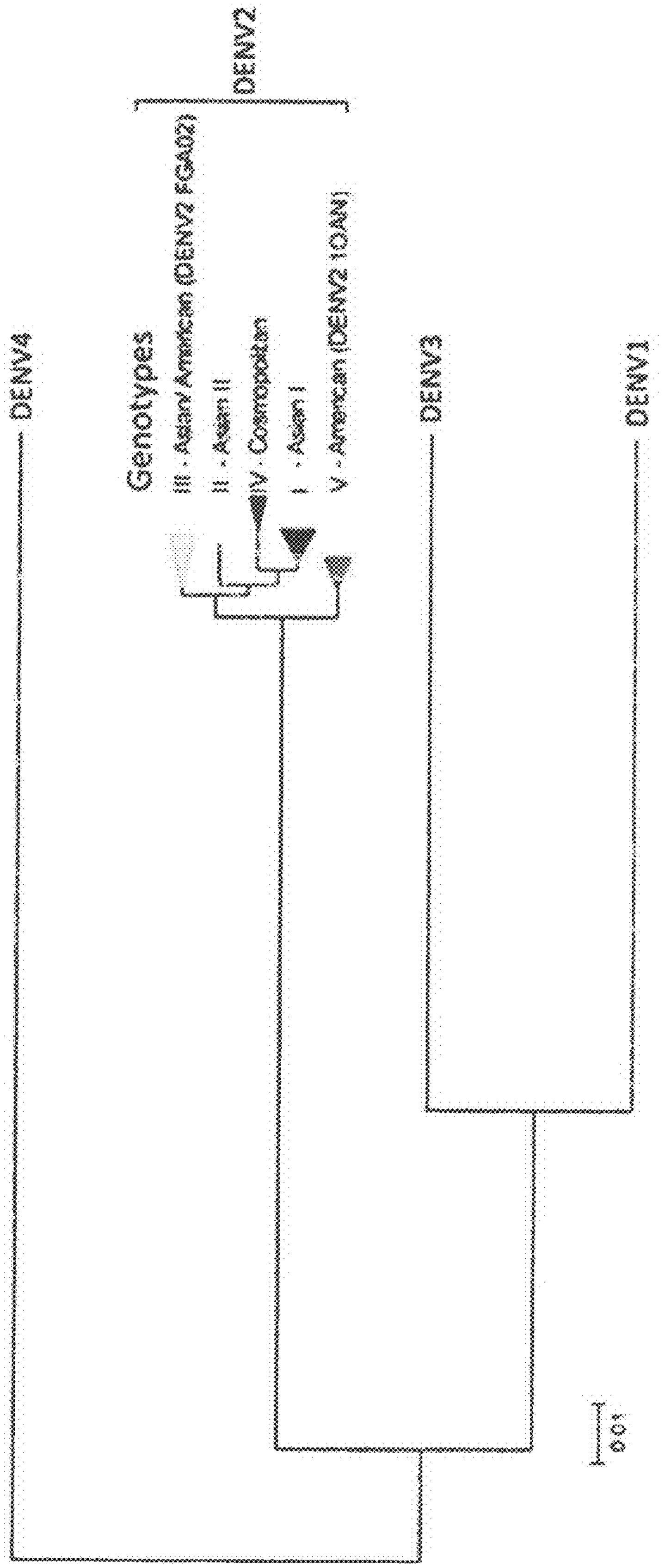

FIGS. 10A-B. Crystal structure of the unliganded DENV-2 FGA02 sE dimer. (FIG. 10A) Comparison with the available structure of sE. Of the three available structures of sE in its pre-fusion form (PDB codes 10AN, 10KE, 1TG8), the one with the PDB code 10AN displayed the smaller root mean square deviation with the unliganded FGA02 sE structure. (FIG. 10B). Crystal structure of the unliganded DENV-2 FGA02 sE dimer. Phylogenetic tree to position the two genotypes of DENV-2 represented by the structures.

Figure 11A:
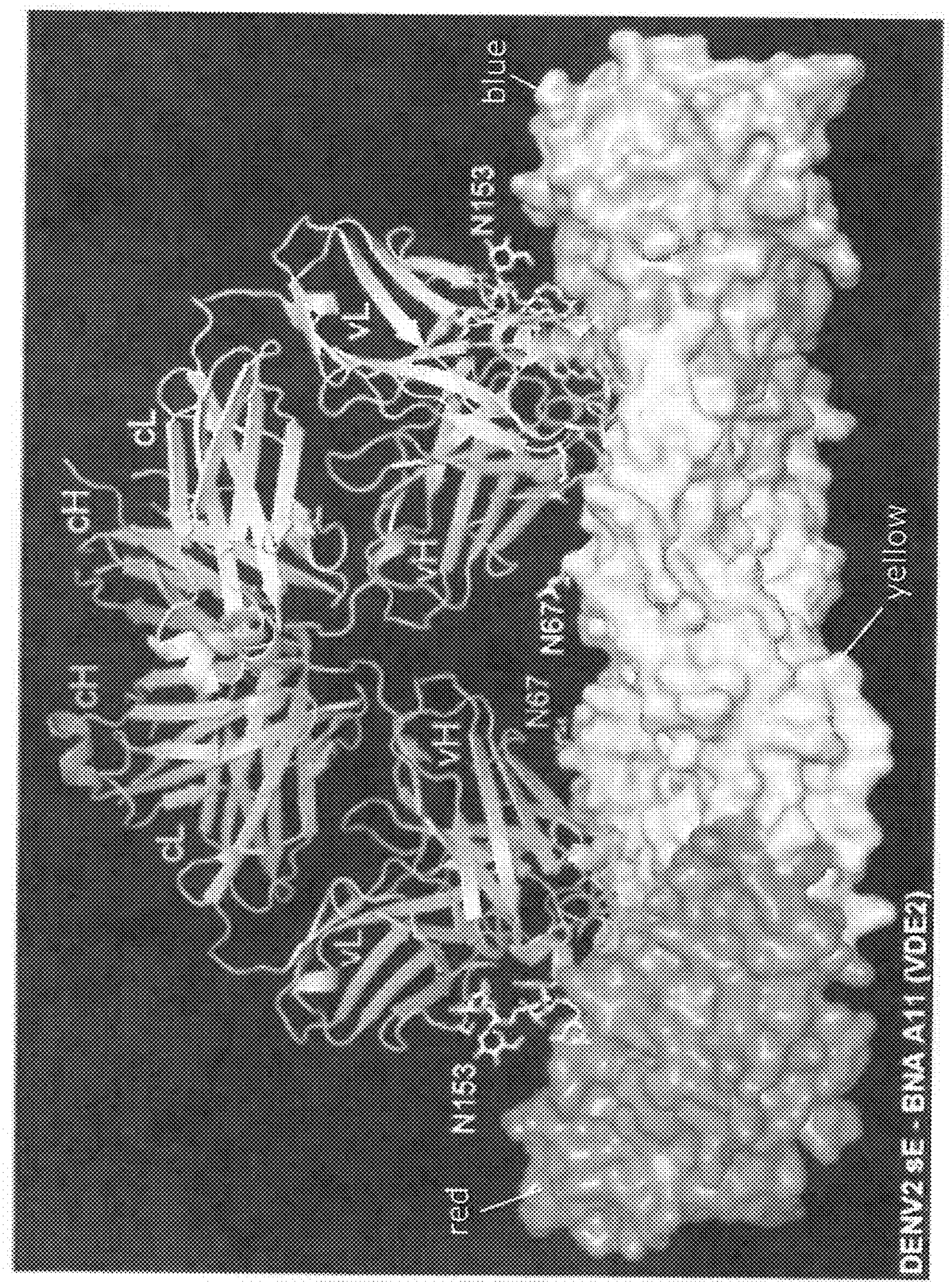
Figure 11B:
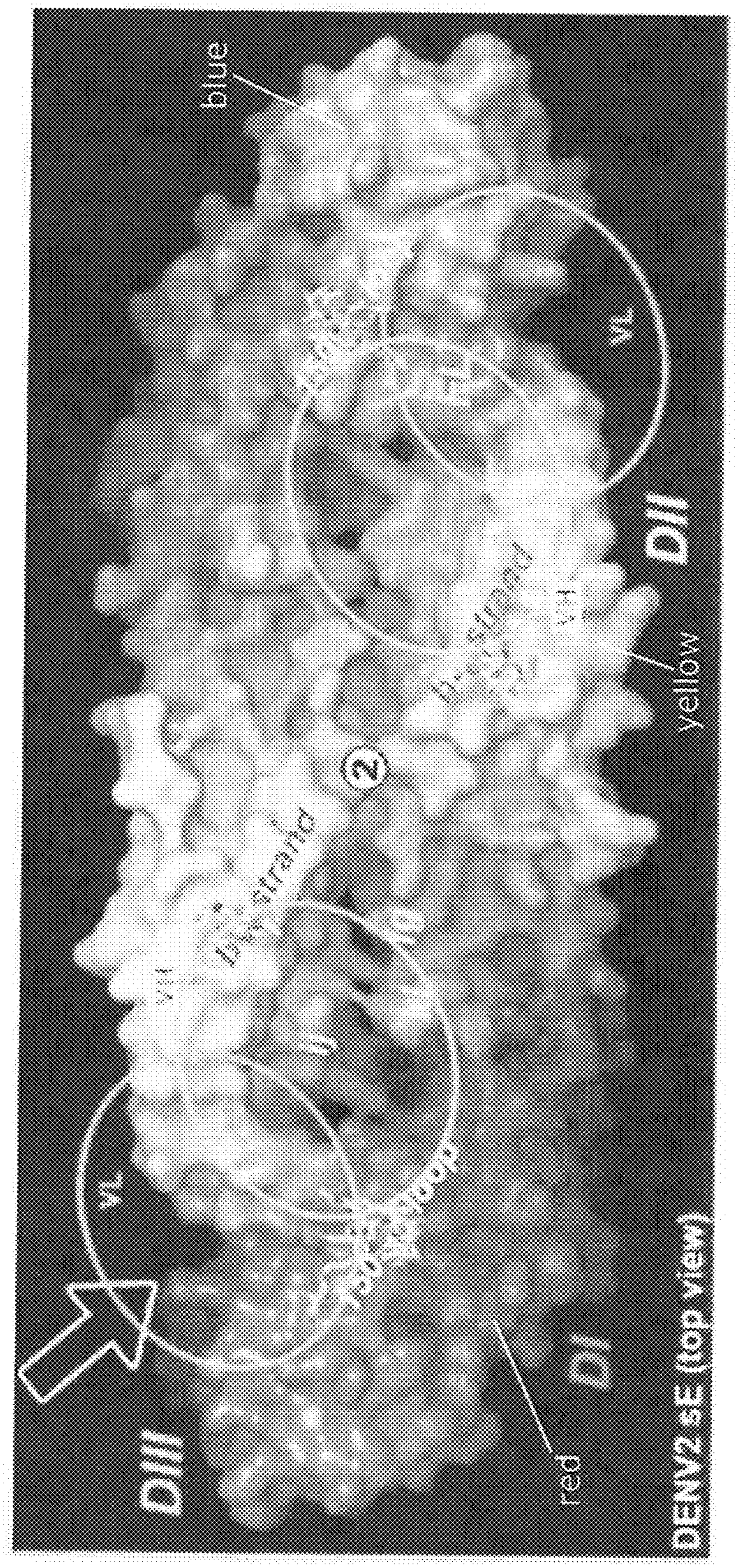
Figure 11C:
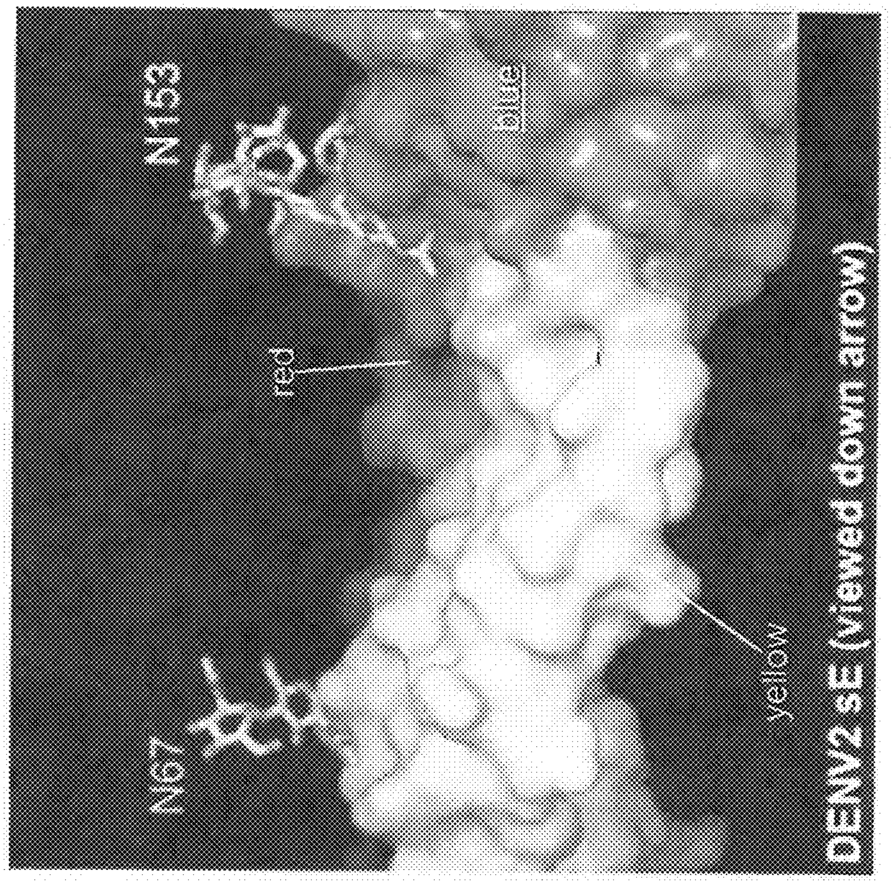
Figure 11D:
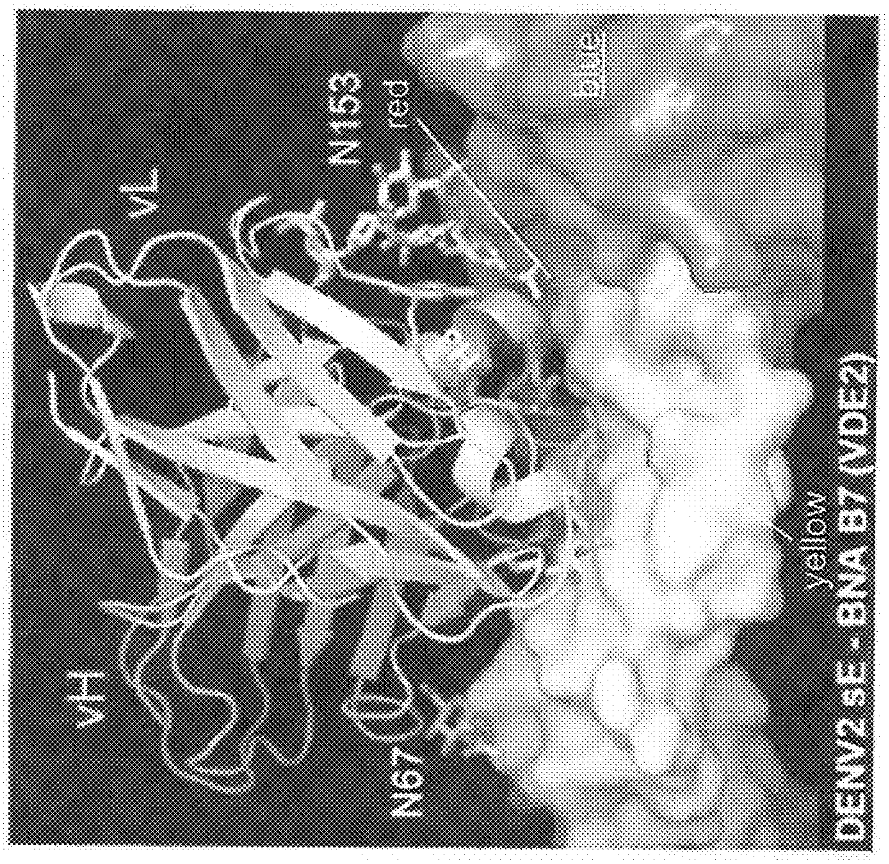
Figure 11F:
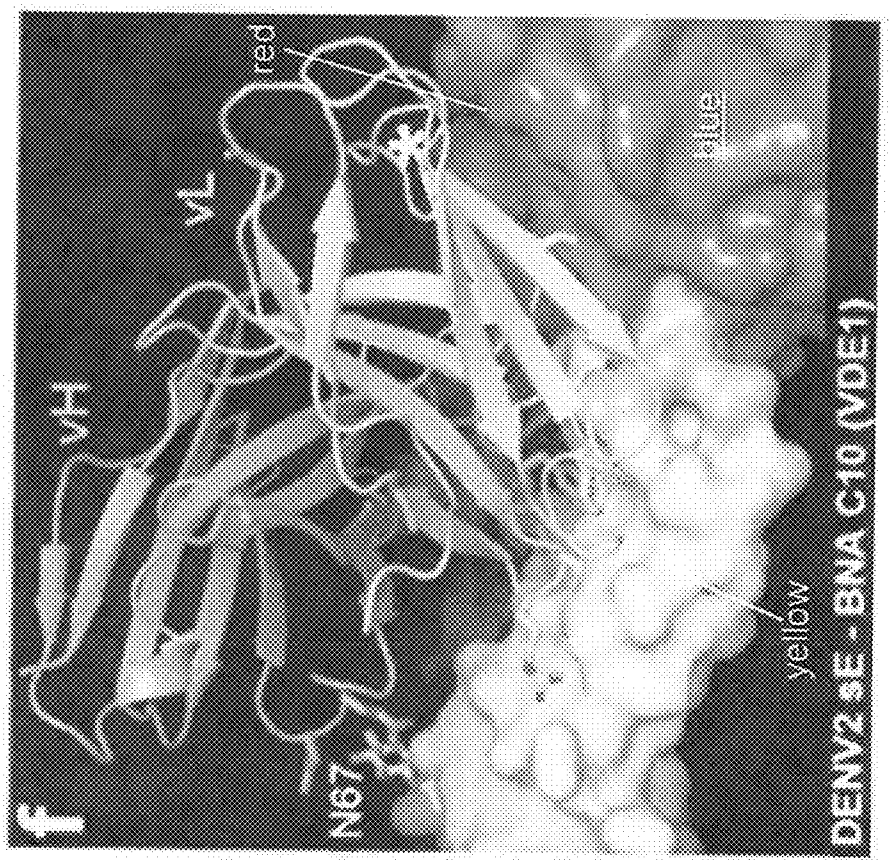
Figure 11E:
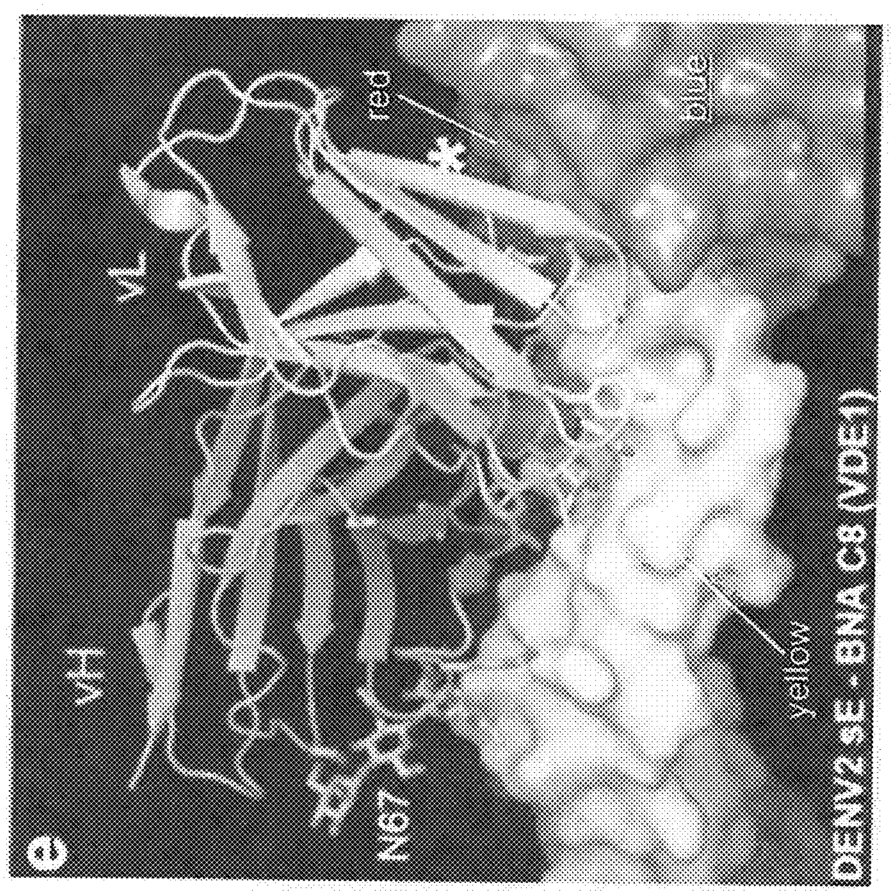

FIGS. 11A-F. DENV2 sE in complex with four EDE anti-EDE antibodies. (FIG. 11A) Complex with the EDE2 A11 Fab fragment. The sE dimer is oriented with the 2-fold molecular axes vertical and with the viral membrane-facing side below. The sE protomers are shown as surfaces according to domains (I, II and III respectively), and the fusion loop (labeled for one protomer in 11b). Foreground and background sE subunits are distinguished in bright and pale colors. The two N-linked glycan chains (not included in the surface) are shown as ball-and-stick according to atom type (carbon, oxygen, nitrogen) and labeled (N67 and N153). The All Fab is shown in ribbon representation with heavy and light chains, respectively. (FIG. 11B). DENV2 sE in complex with four EDE anti-EDE antibodies. The unliganded DENV2 FGA02 sE dimer seen down the 2-fold axis (labeled "2" at the center). Ovals (labeled VH and VL) show roughly the contact sites of heavy and light chains, respectively, with the VHs closer to the 2-fold molecular axis. Polypeptide segments and loops relevant to the description of the epitopes are labeled. (FIG. 11C). DENV2 sE in complex with four EDE anti-EDE antibodies. View down the empty arrow shown in FIG. 11 B, highlighting the fusion loop "valley" encased between two ridges, the b strand on one subunit and the 150 loop on the other. (FIG. 11D-F). DENV2 sE in complex with four EDE anti-EDE antibodies. The same view as in FIG. 11C, showing the complexes with anti-EDE antibodies EDE2 B7 (FIG. 11D), EDE1 C8 (FIG. 11E) and EDE1 C10 (FIG. 11F) (only the variable domains are shown). A star in FIG. 11E and FIG. 11F mark the region of the 150 loop, which is disordered in those complexes. Note that in the B7 and All complexes, the light chain is too far from domain III to interact with it, in contrast to the C8 and C10 complexes.

FIGS. 12A-E. Overall complexes and imprint of the anti-EDE antibodies on the sE dimer.

Each row corresponds to a different sE/BNA (broadly neutralizing antibody) complex (except for the first one, which shows the unliganded sE dimer) and each column displays the same orientation, as labeled. In the first two columns the sE dimer is depicted as ribbons and the BNA variable domains as surface colored as in FIGS. 11A-F. In the side view (left column) the viral membrane would be underneath, whereas the bottom view (middle column) corresponds to the sE dimer seen from the viral membrane, with the antibodies visible across the sE ribbons. The top view (right column) shows the sE surface as presented to the immune system on the viral particle, showing the imprint of the antibodies (green) with a white depth-cuing fog. For clarity, a white outline delimits the green imprint on the blue surface of domain III. As a guide, in the top-left panel the glycan chains of foreground and background subunits are labeled in red and black, respectively. The fusion loop and if the loop are labeled on the top-middle panel, and can be seen in the other rows in contact with the anti-EDE antibodies. A red star in the left panels of FIGS. 12C-E mark the location of the 150 loop, which is disordered in the complexes with the EDE1 anti-EDE antibodies. This loop bears the N153 glycan recognized by the EDE2 anti-EDE antibodies, as seen in FIG. 12B, left panel (glycan shown as sticks with carbon atoms colored red). In contrast, all the anti-EDE antibodies are seen contacting the N67 glycan, with C8 displaying the most contacts (row c, left panel, N67 glycan as sticks with carbon atoms yellow). A blue star in FIG. 12C shows a disordered loop in domain III. Note that EDE2 C10 (FIGS. 12D and 12 E) inserts deeper into the sE dimer than the other anti-EDE antibodies.

FIG. 13. Buried surface areas in the various BNA complexes

Figure 14:
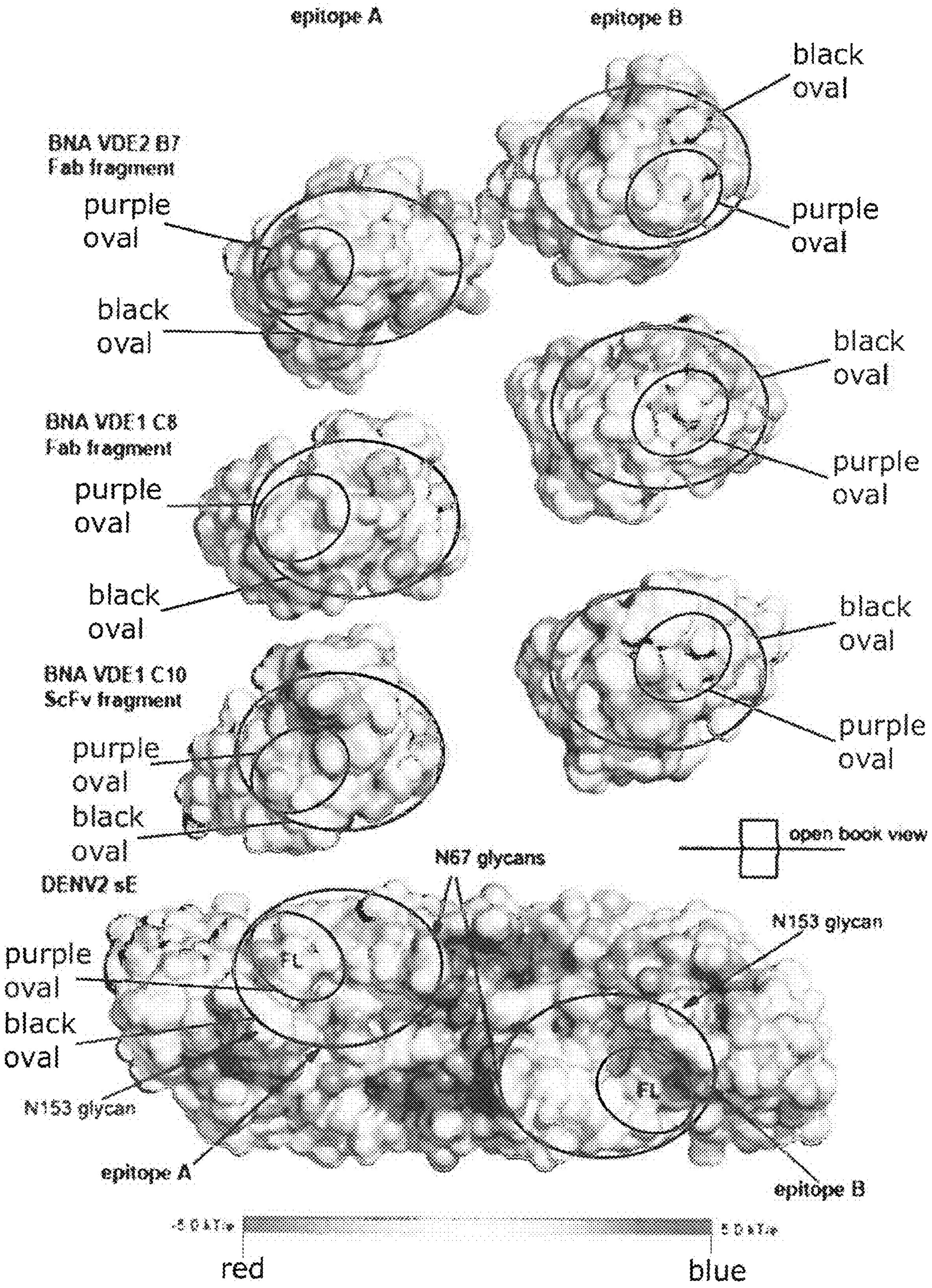

FIG. 14. Electrostatic potential of DENV-2 sE complex, epitopes and paratopes. Open book representation of the complexes, with negative and positive potential displayed and colored according to the bar underneath. Because certain regions are disordered in the complexes, the DENV-2 sE dimer model, generated as described in the Online Methods section, was used to calculate the surface electrostatic potential of the sE dimer. Corresponding areas in contact are indicated by same colored ovals.

Figure 15B:
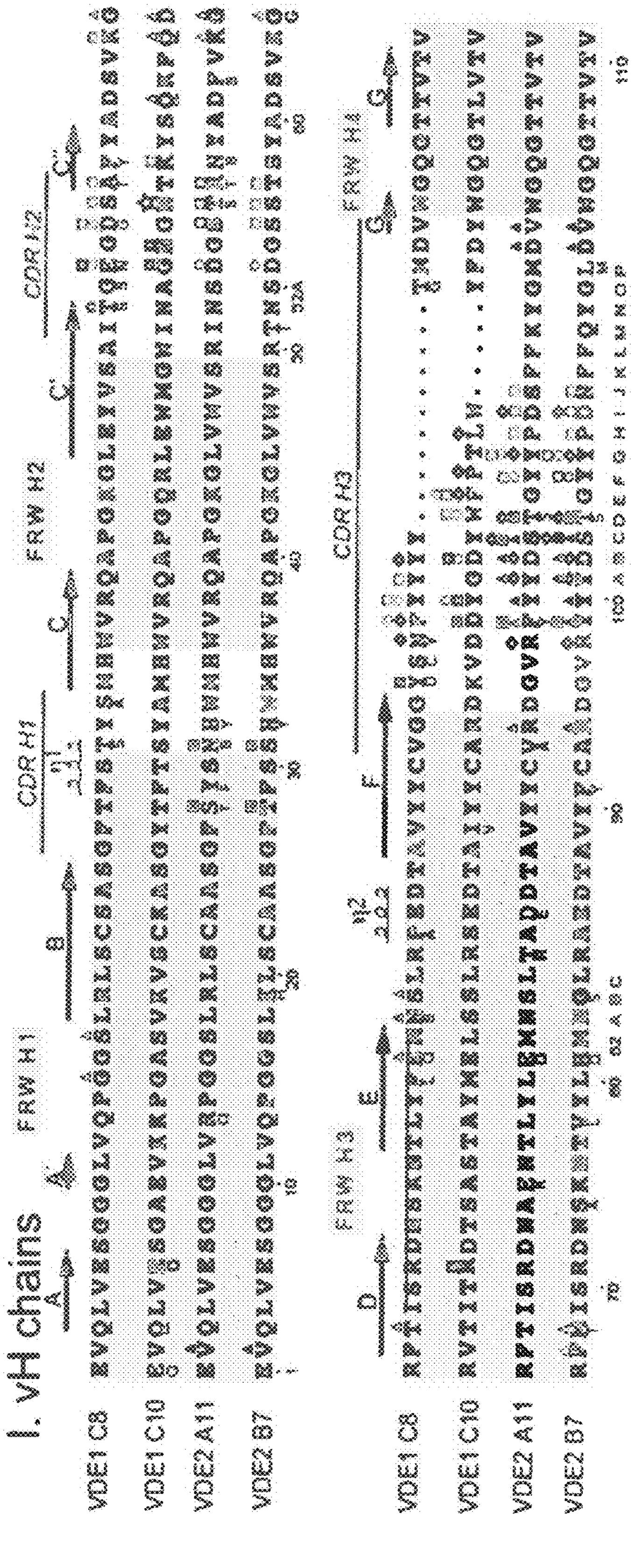
Figure 15B:
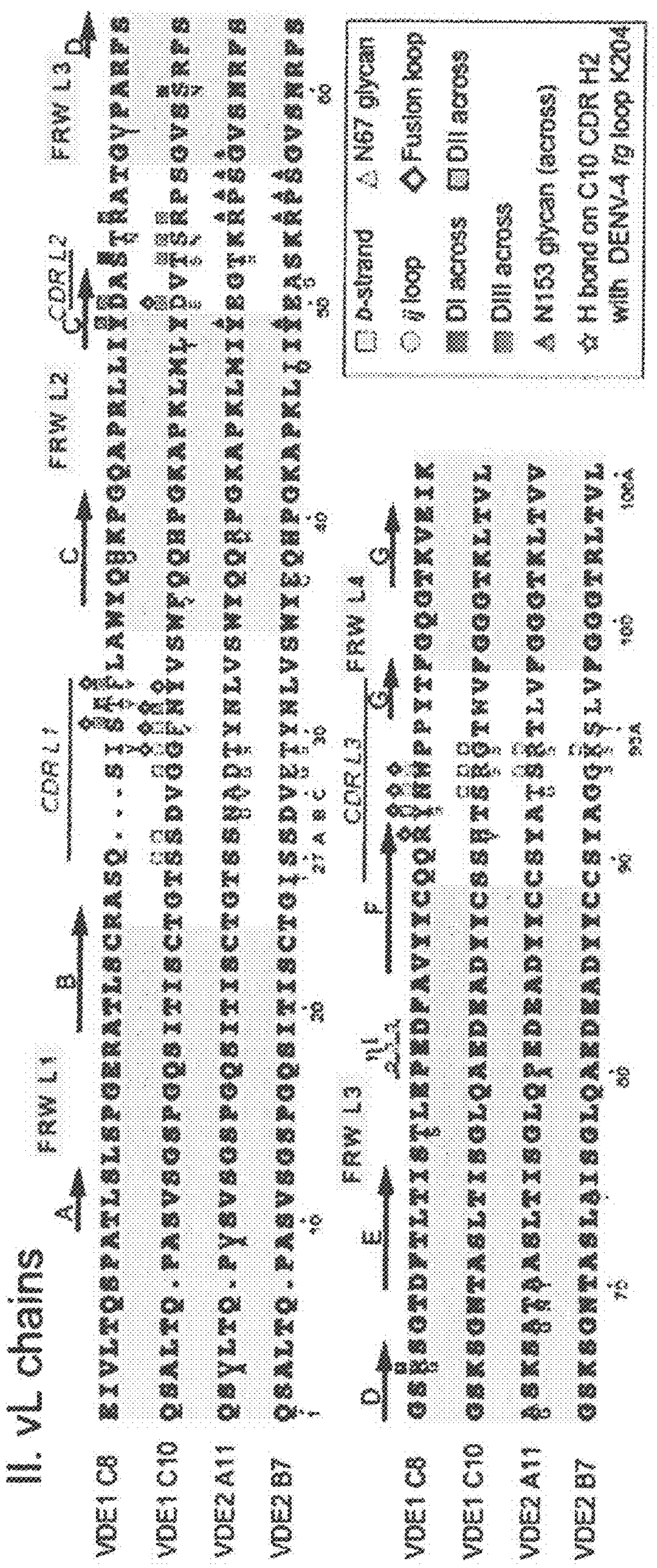
Figure 24A:
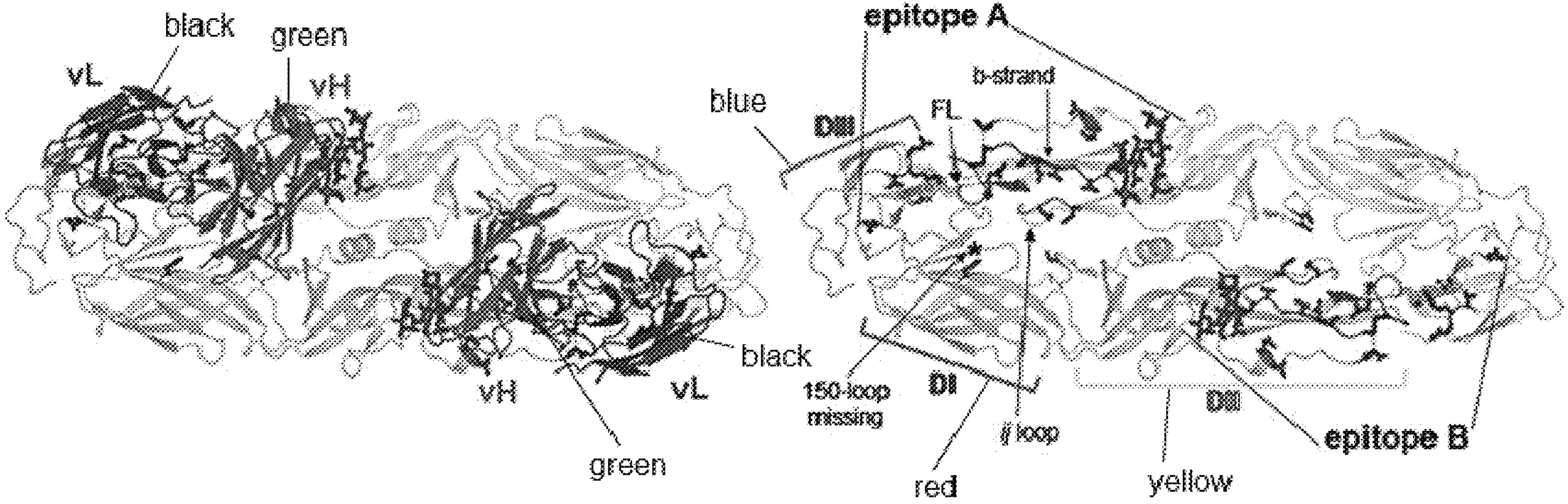
Figure 24A:
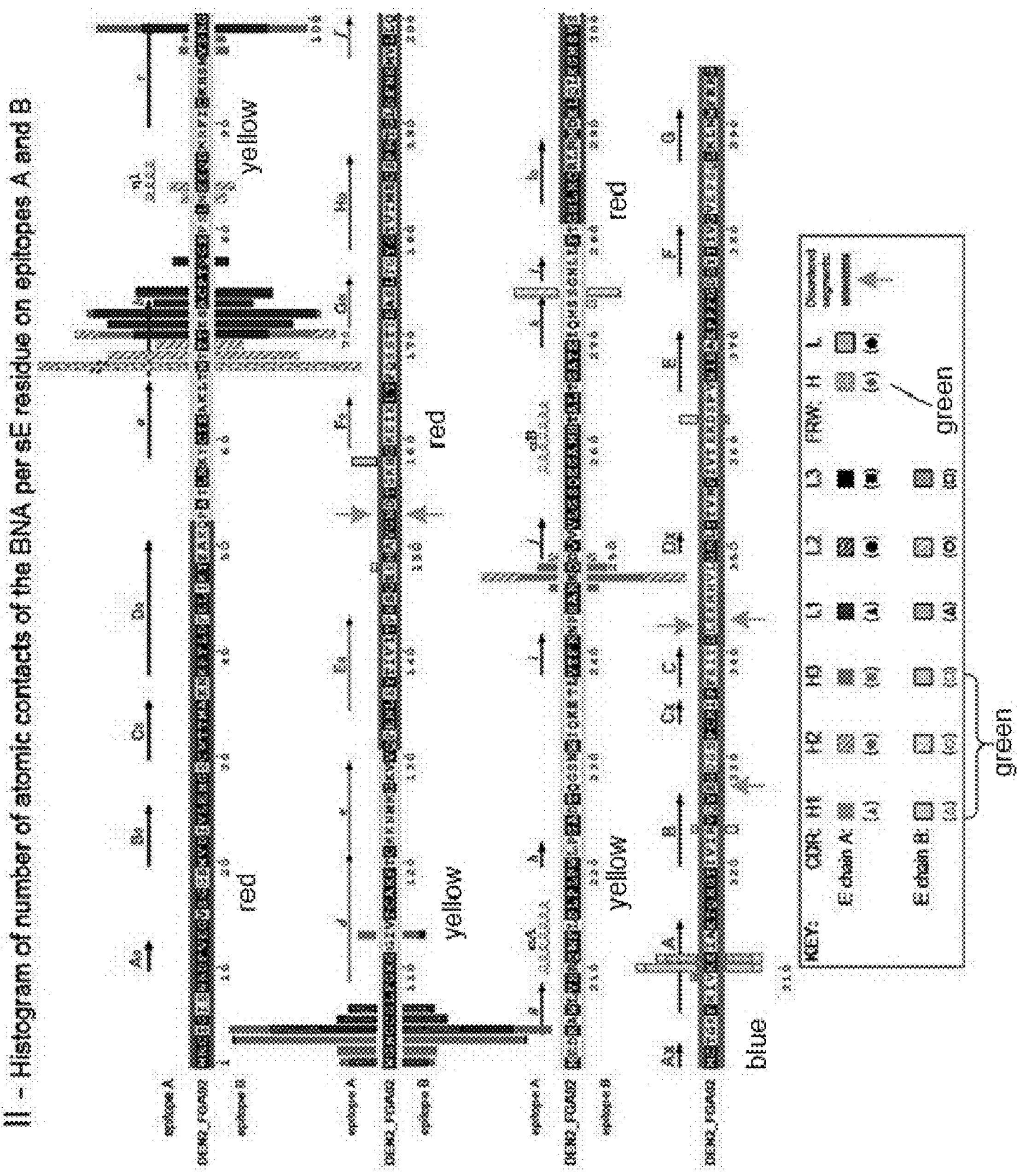
Figure 24B:
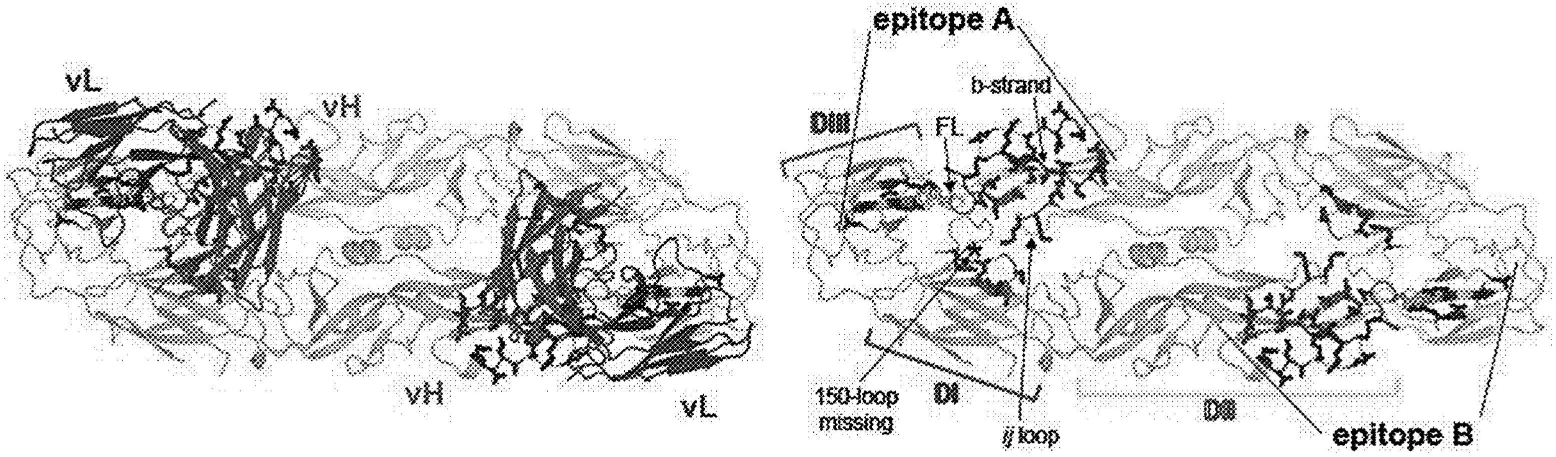
Figure 24B:
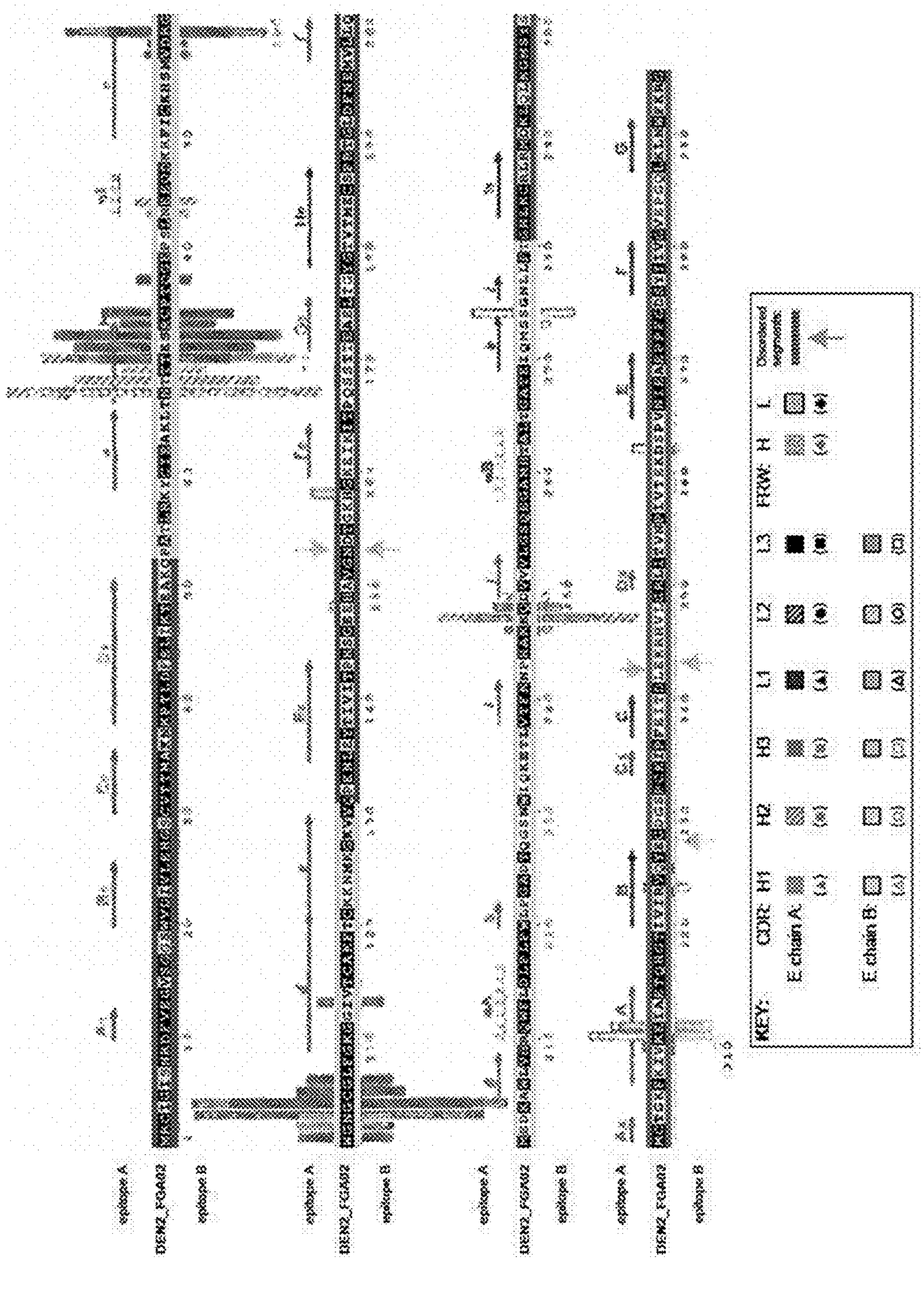
Figure 24B:
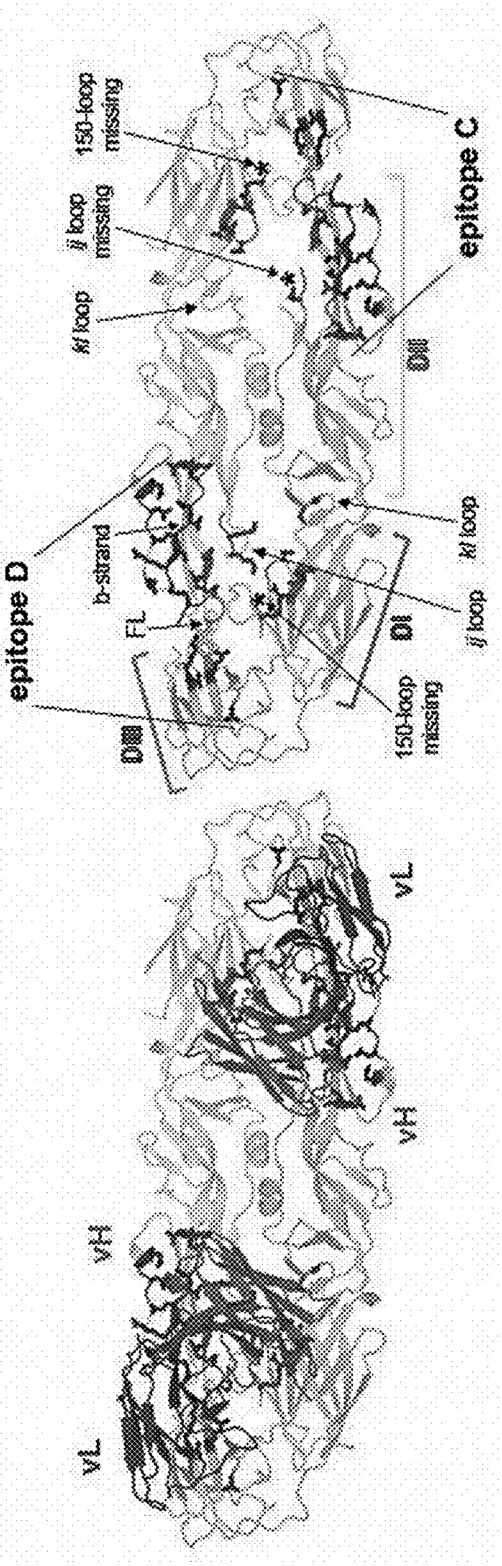
Figure 24B:
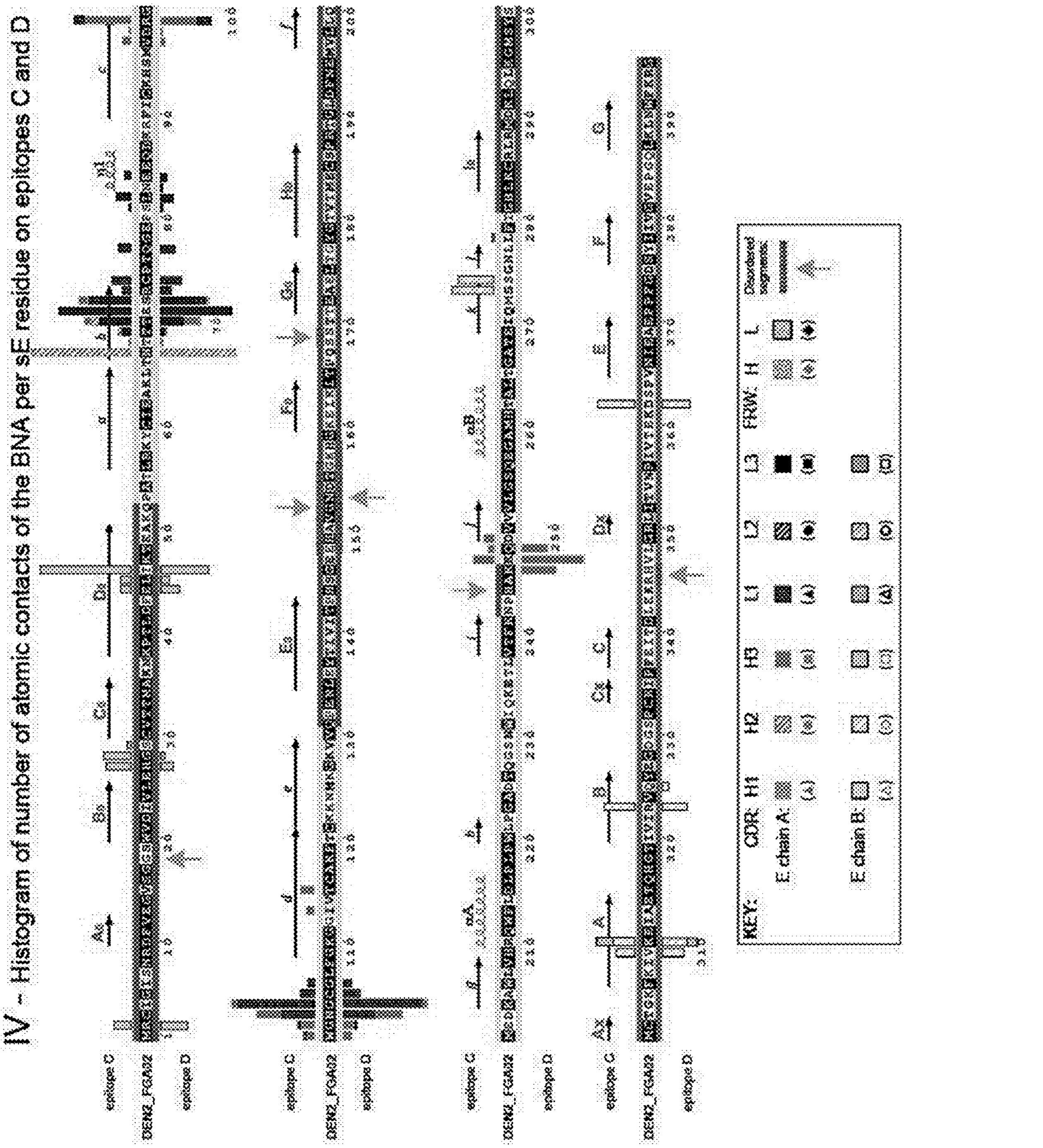
Figure 24C:
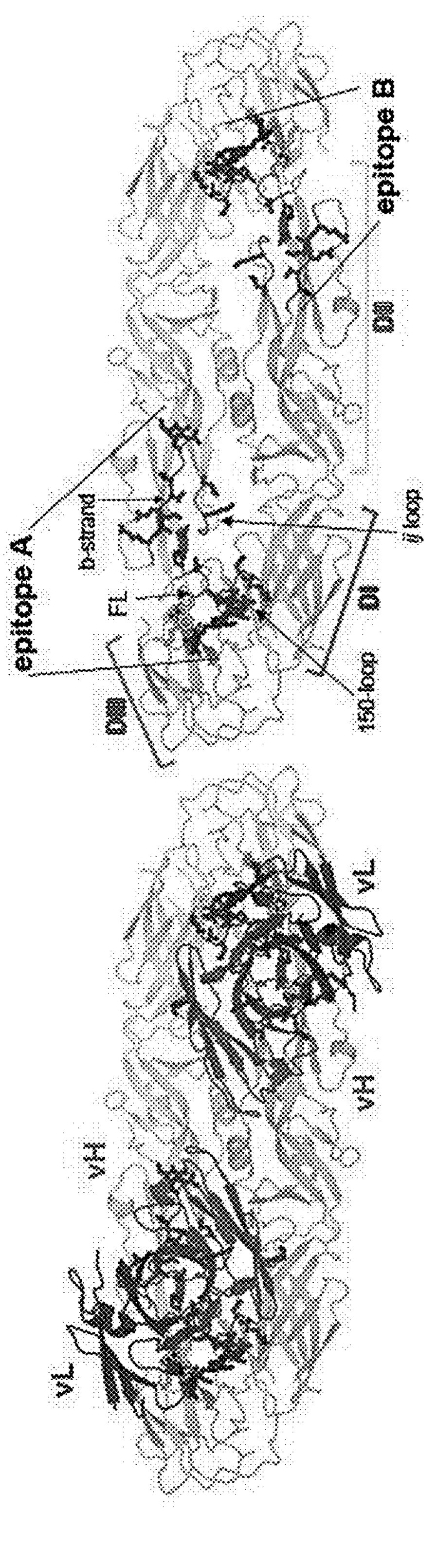
Figure 24C:
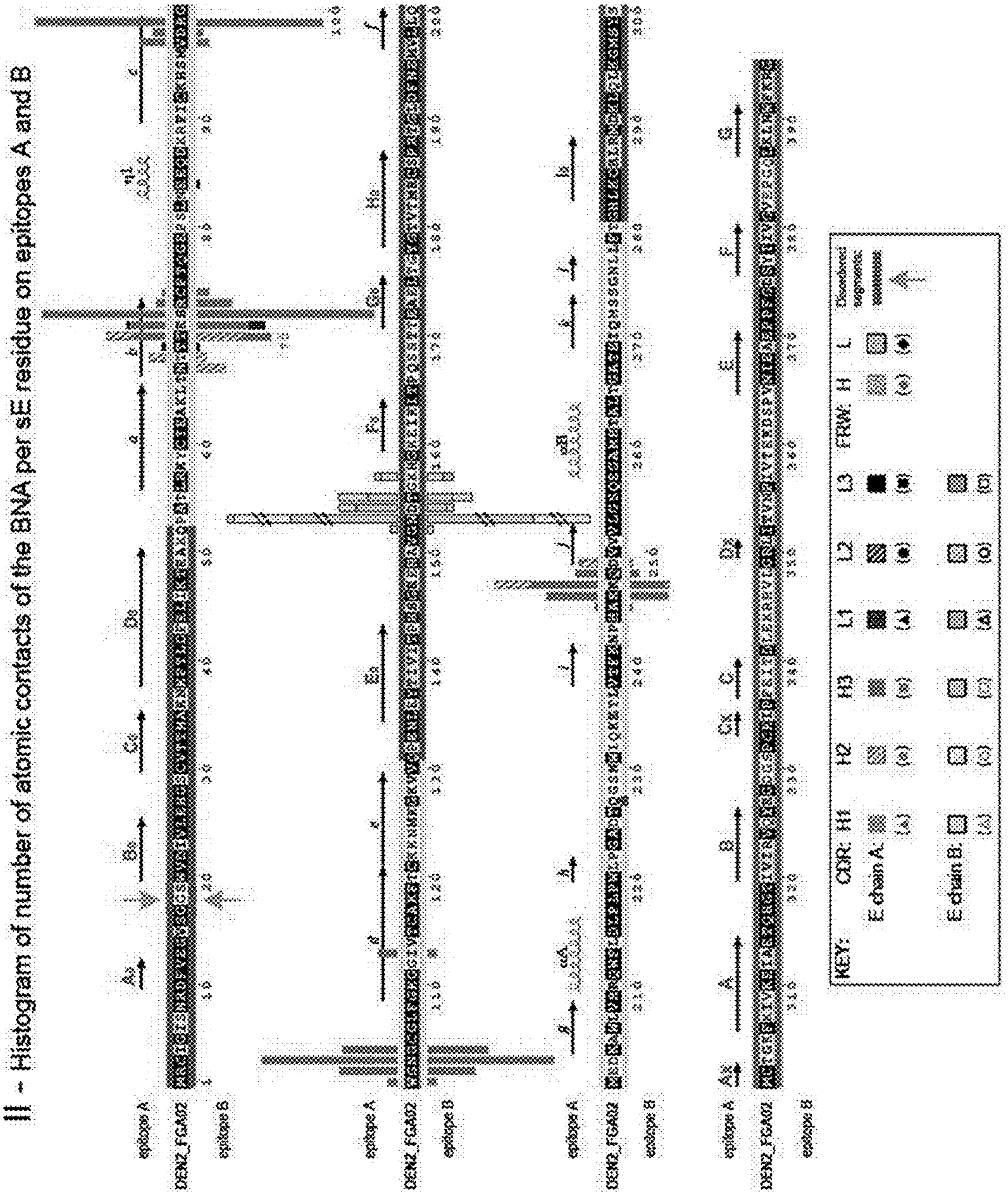
Figure 24D:
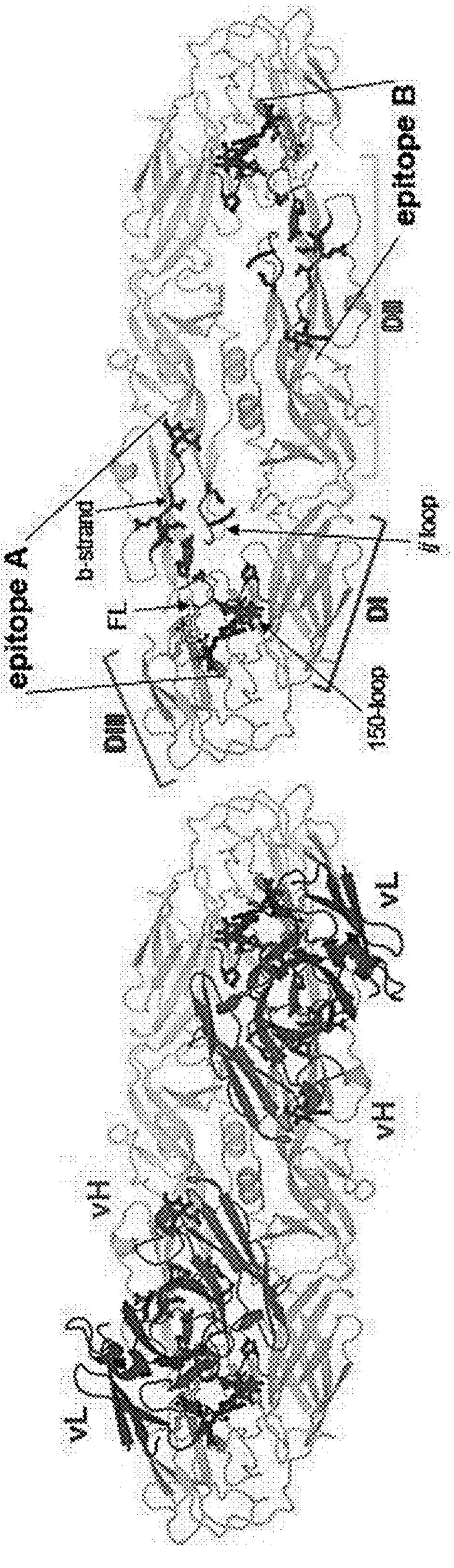
Figure 24D:
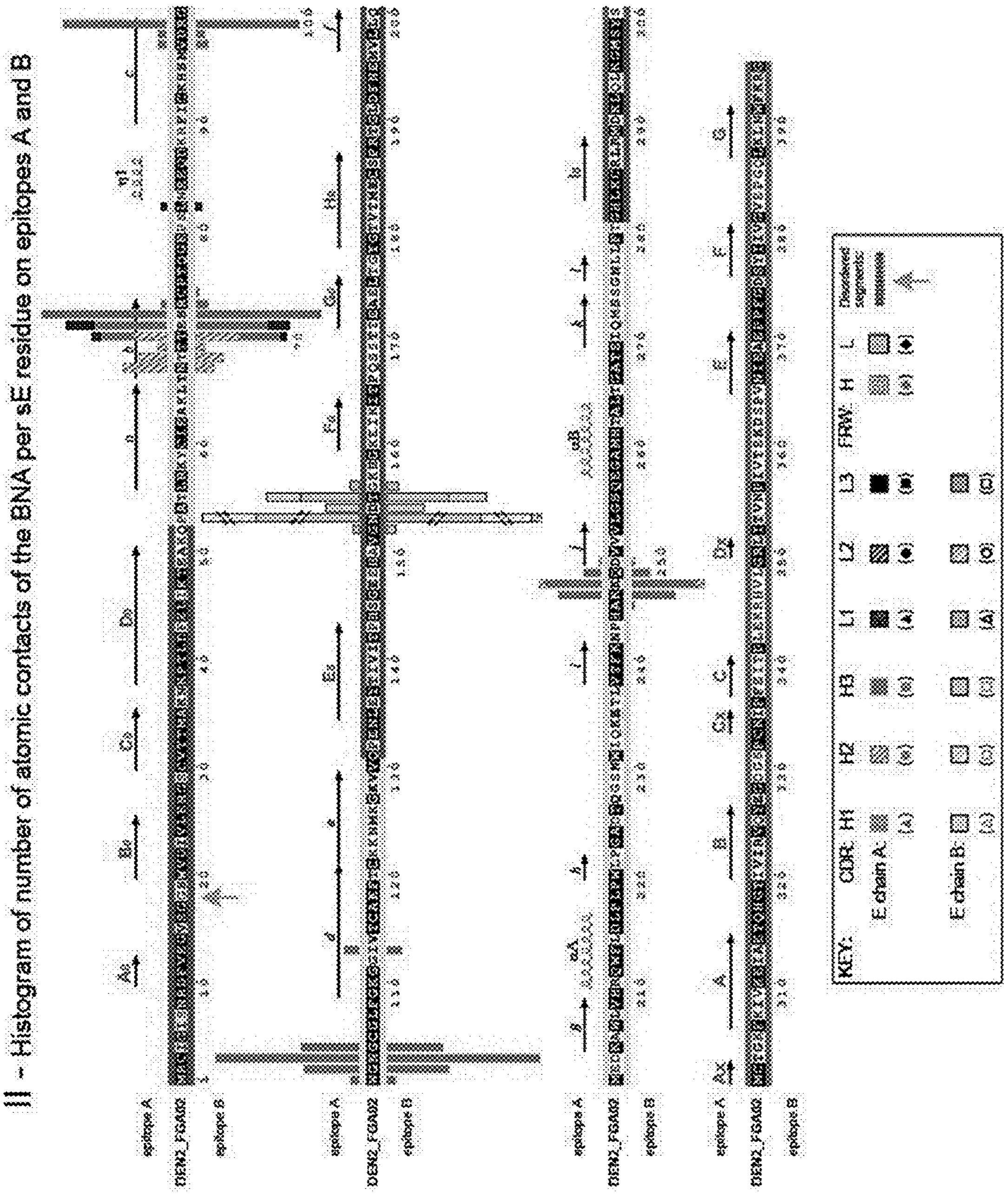
Figure 24E:
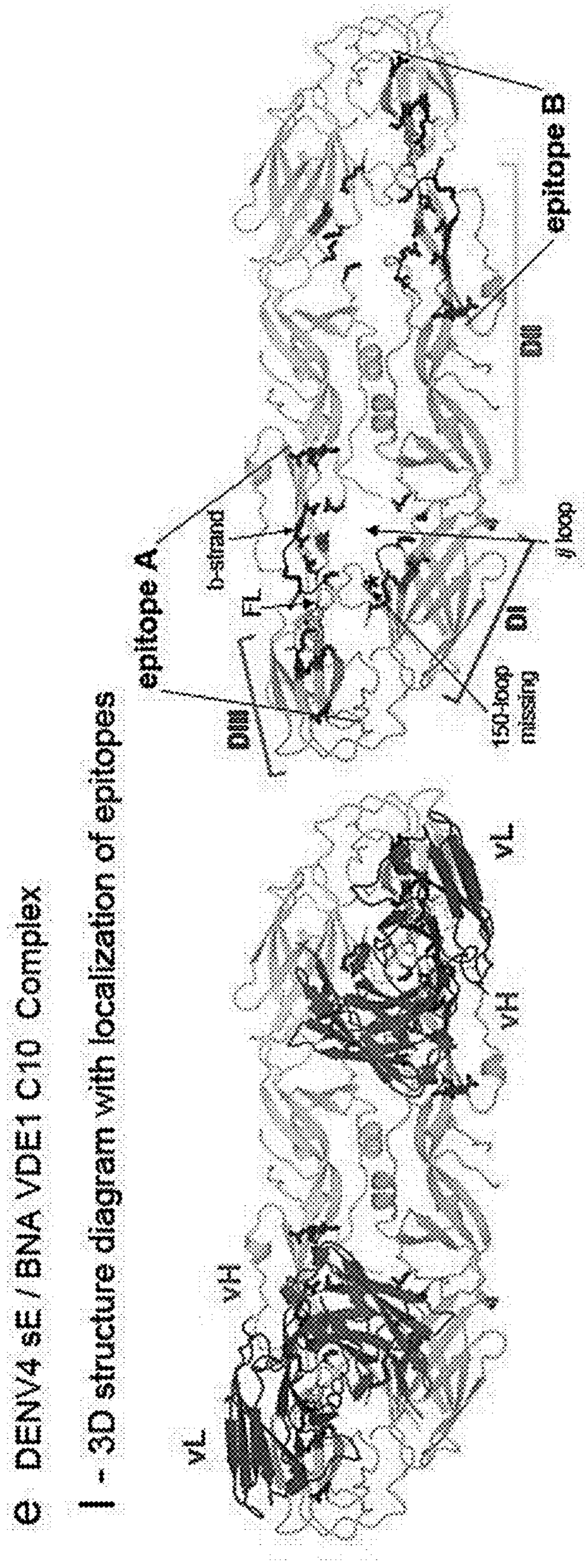
Figure 24E:
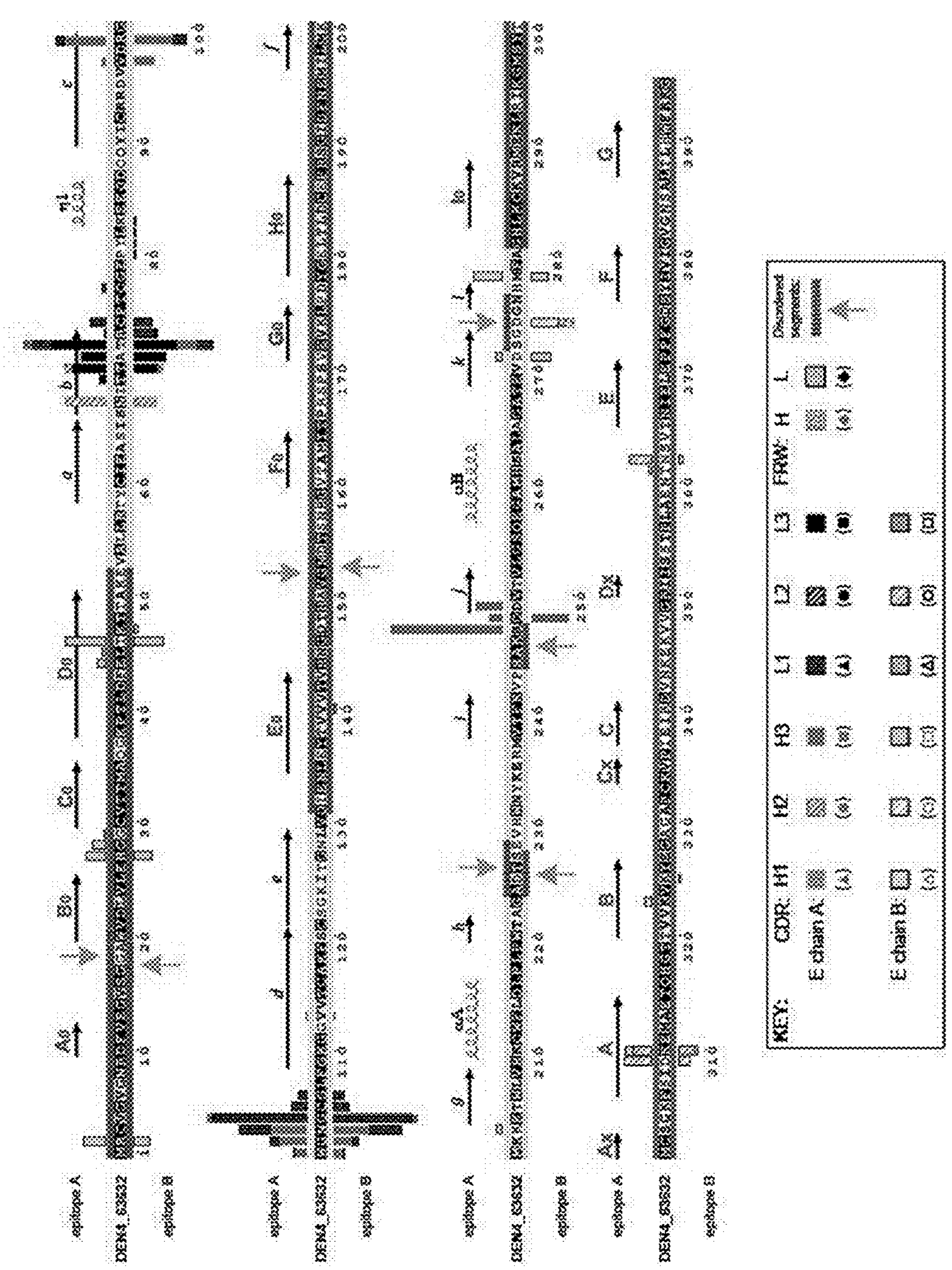
Figure 26A:
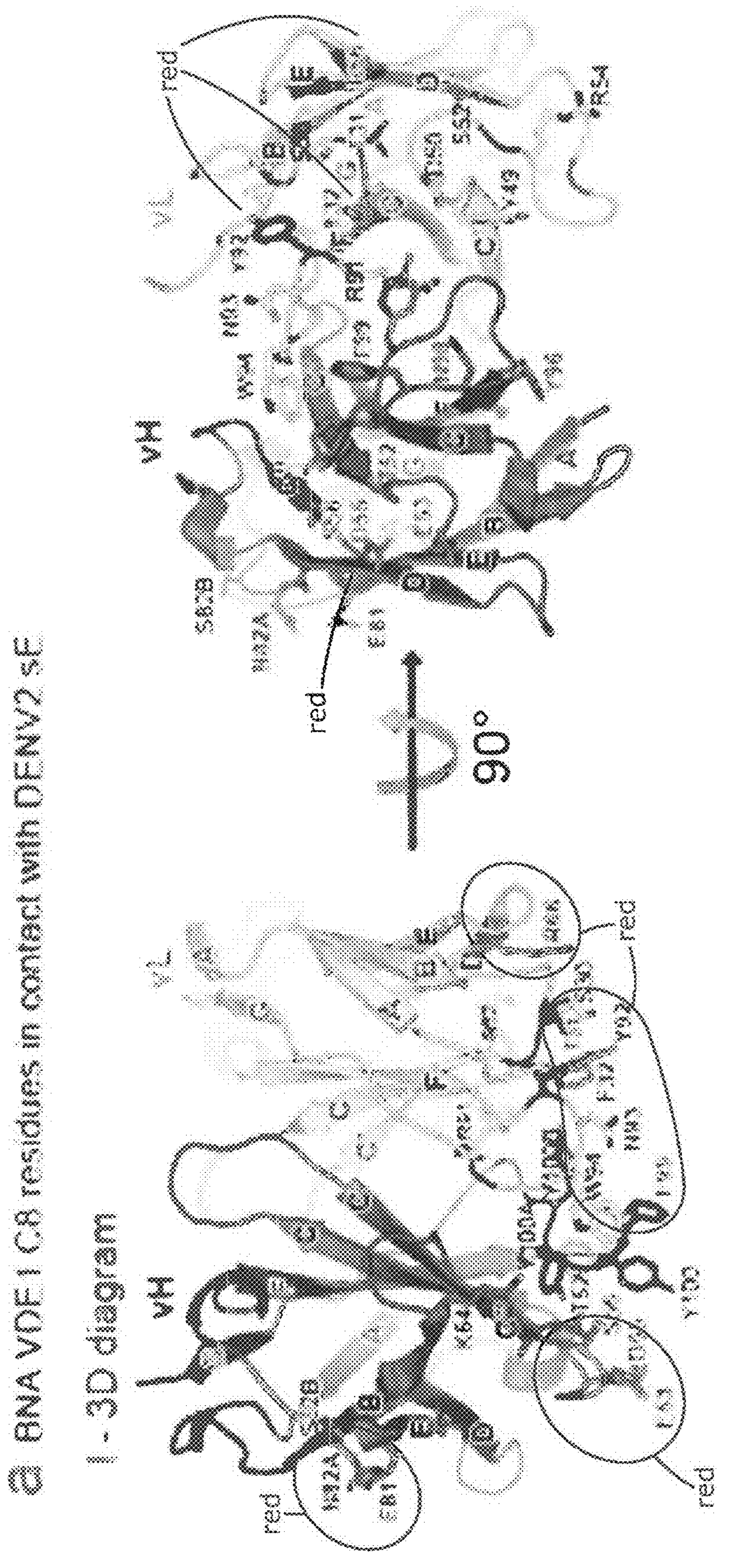
Figure 26A:
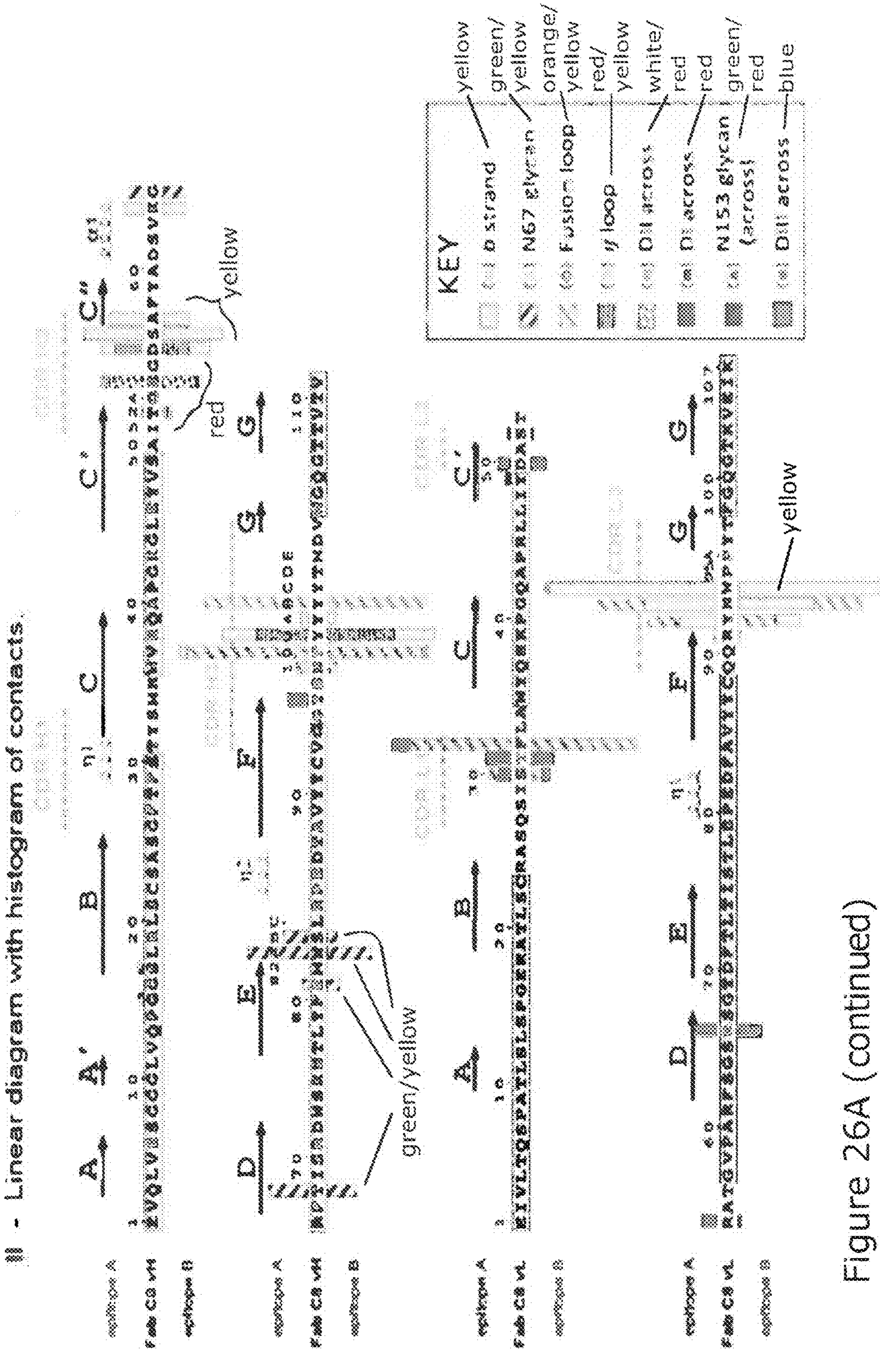
Figure 26B:
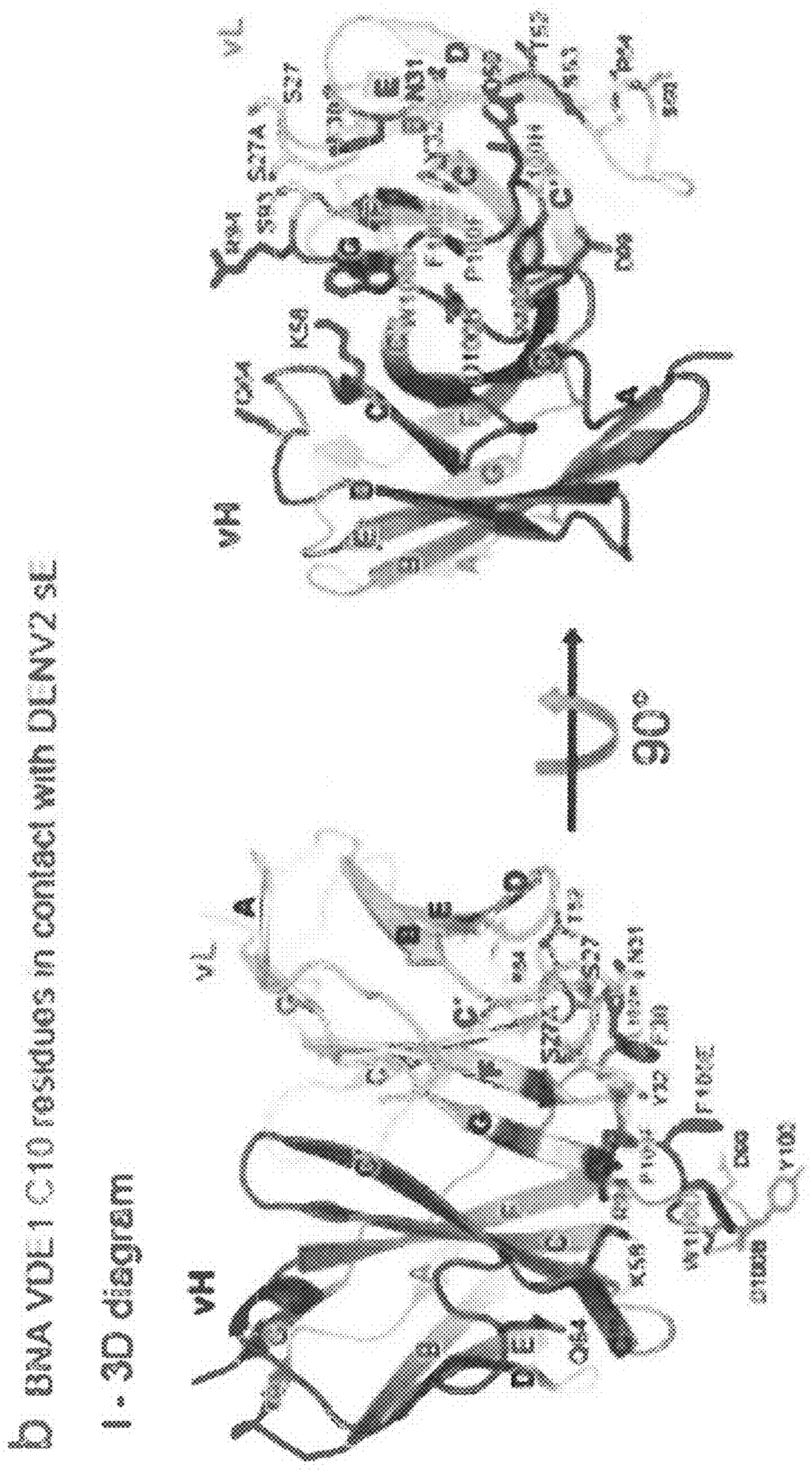
Figure 26B:
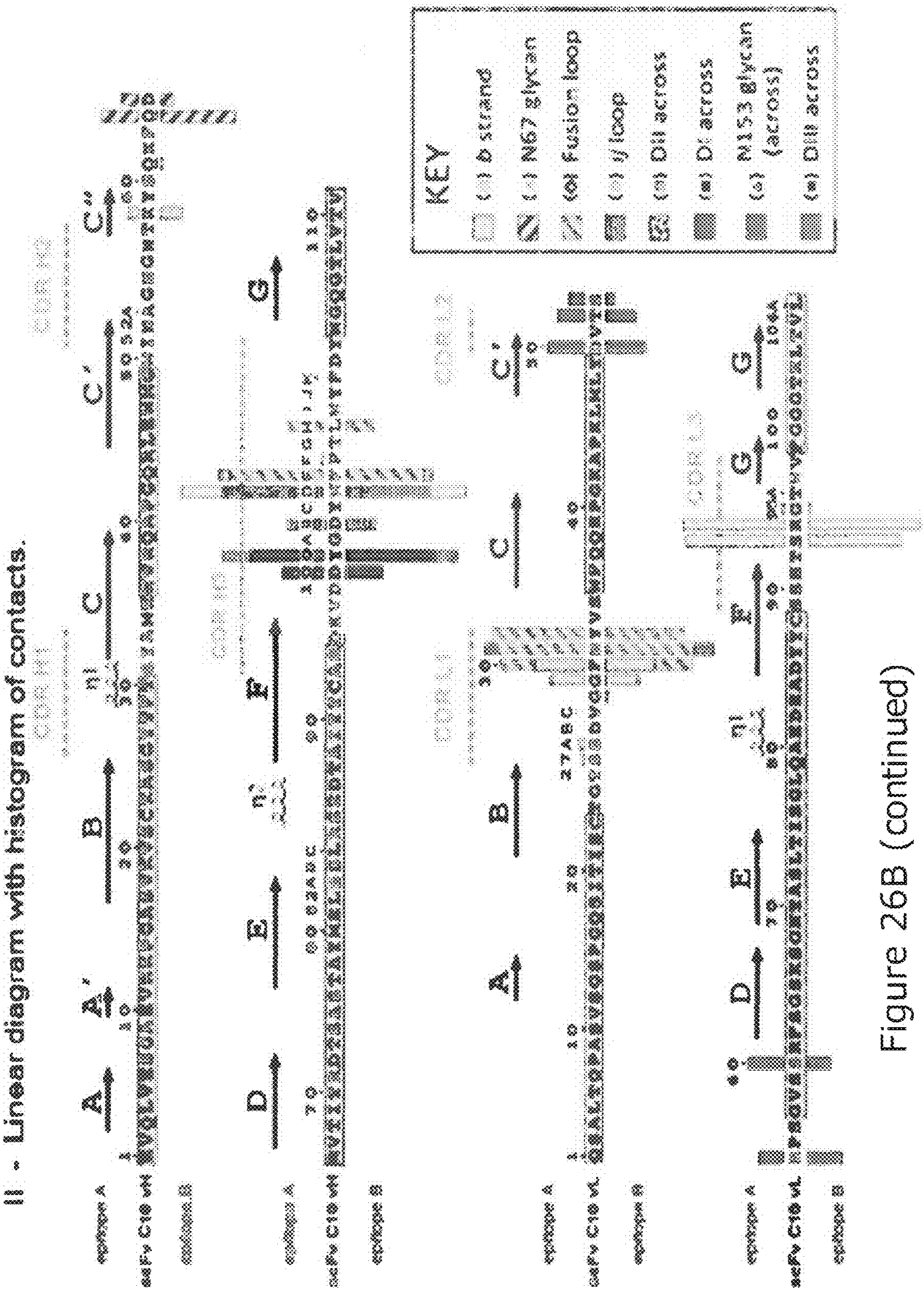
Figure 26B:
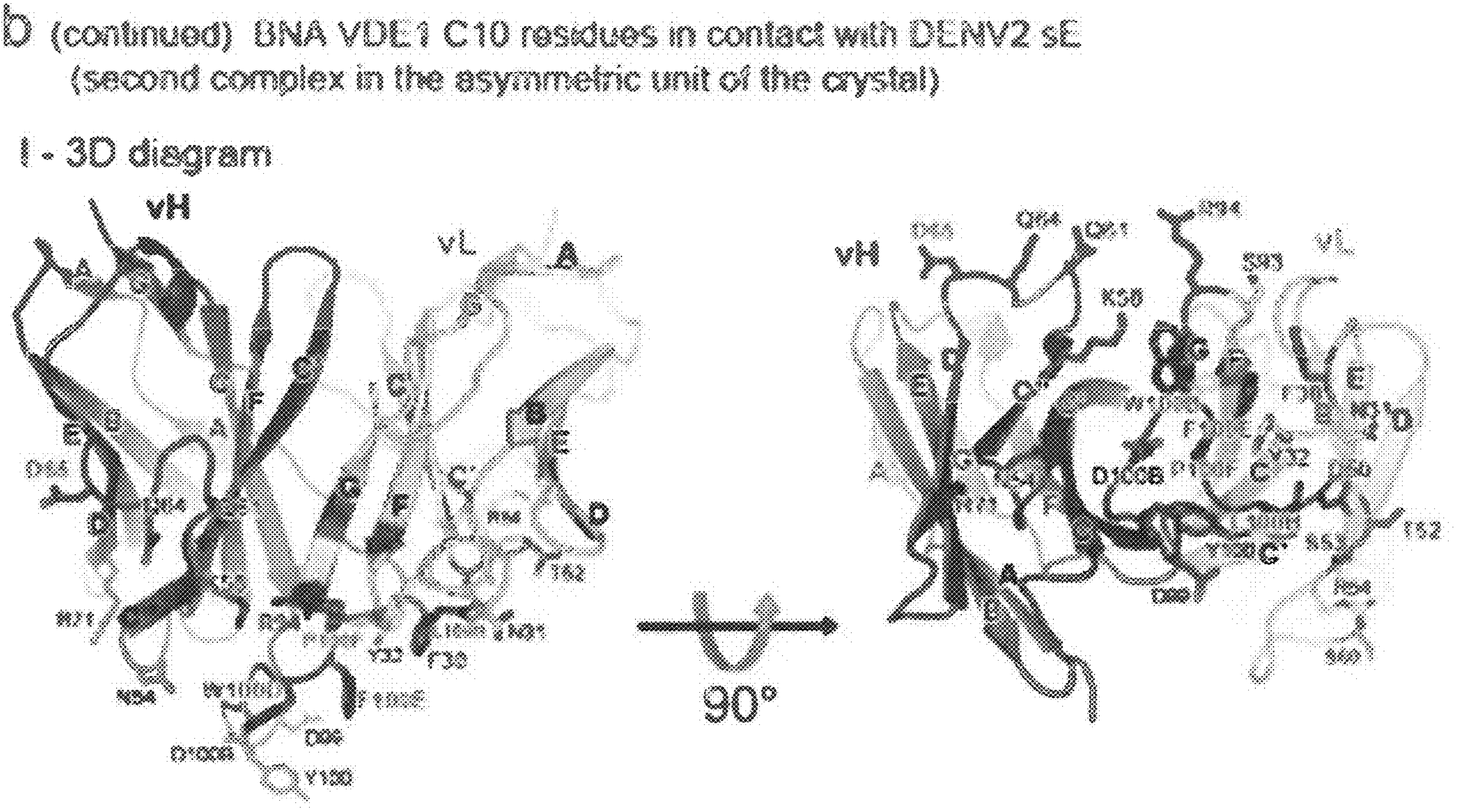
Figure 26B:
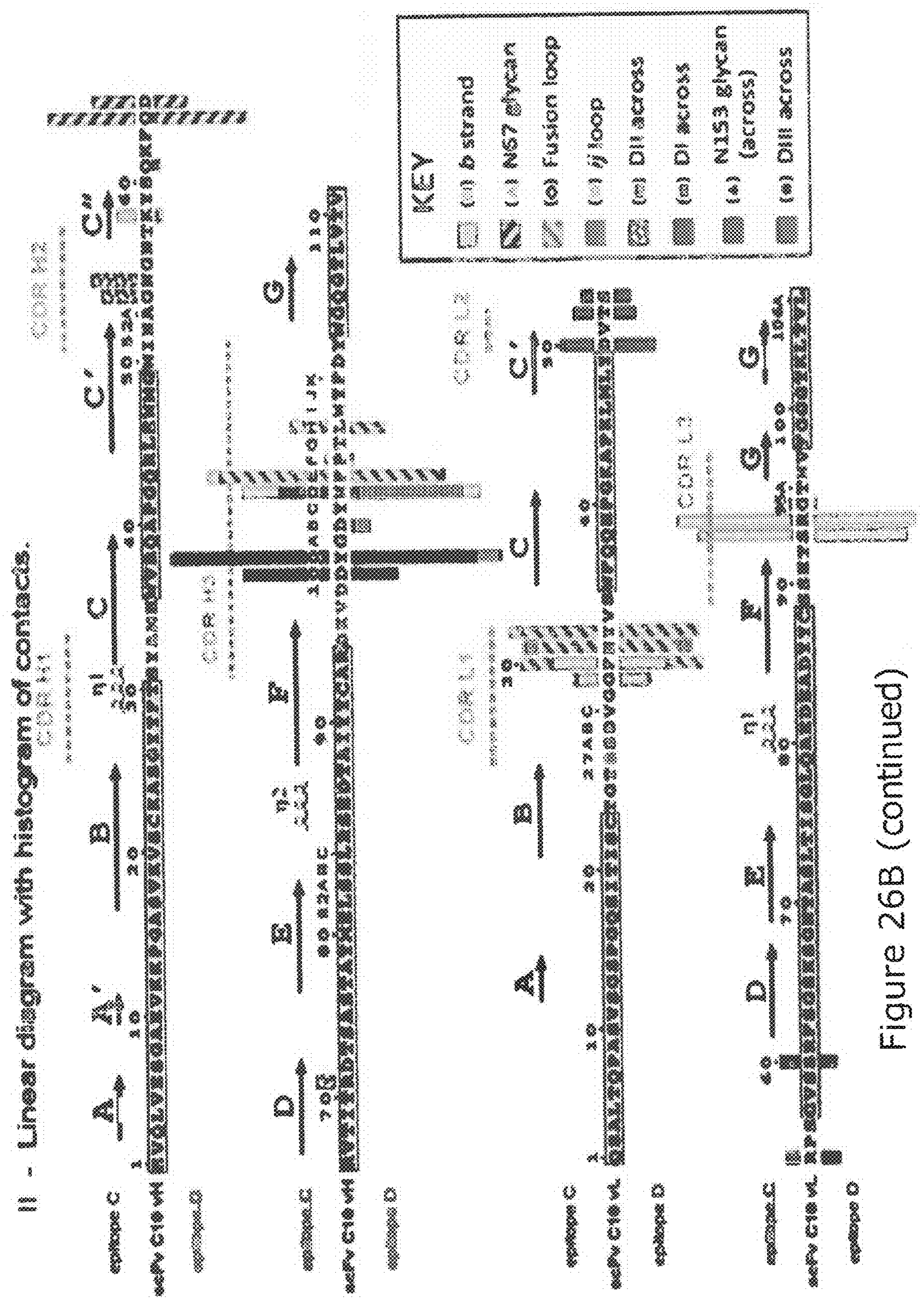
Figure 26C:
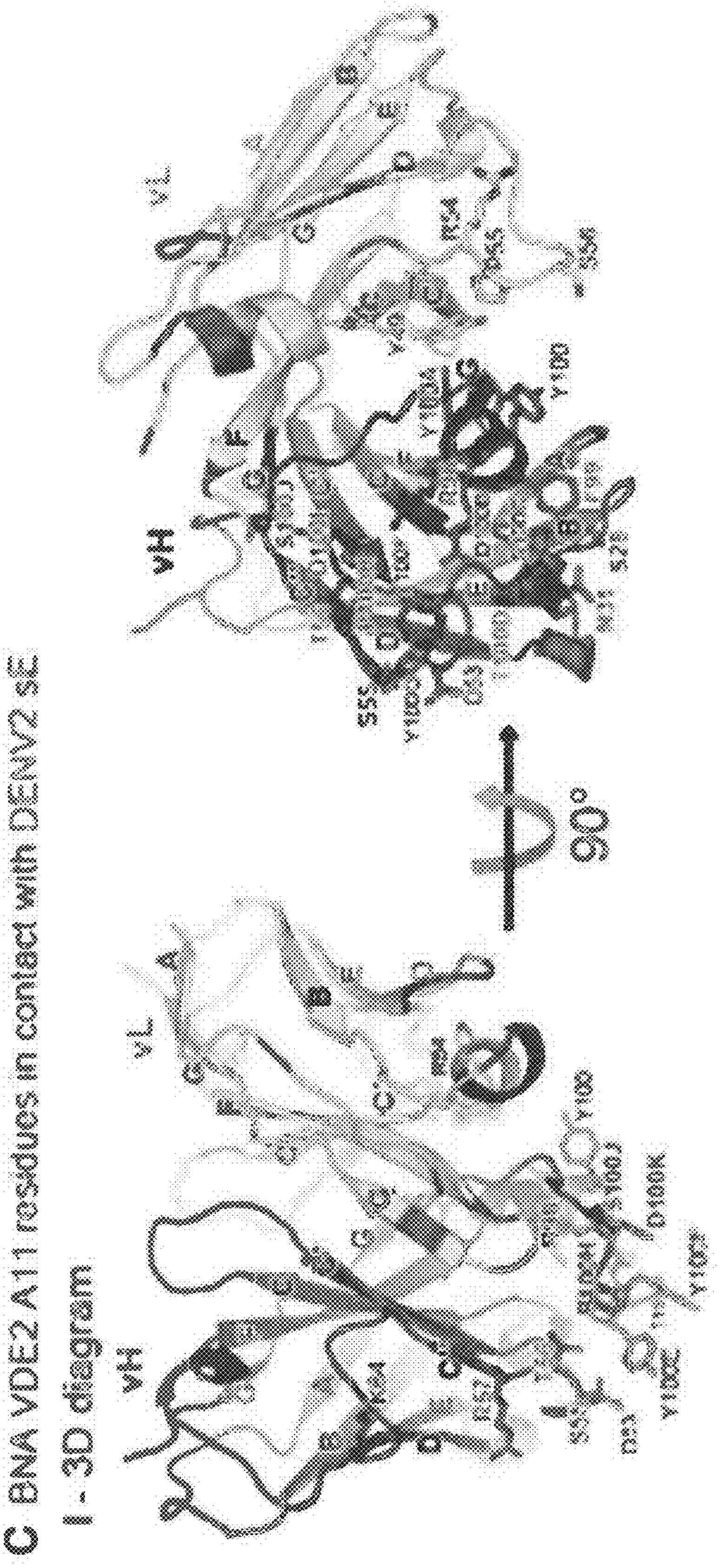
Figure 26C:
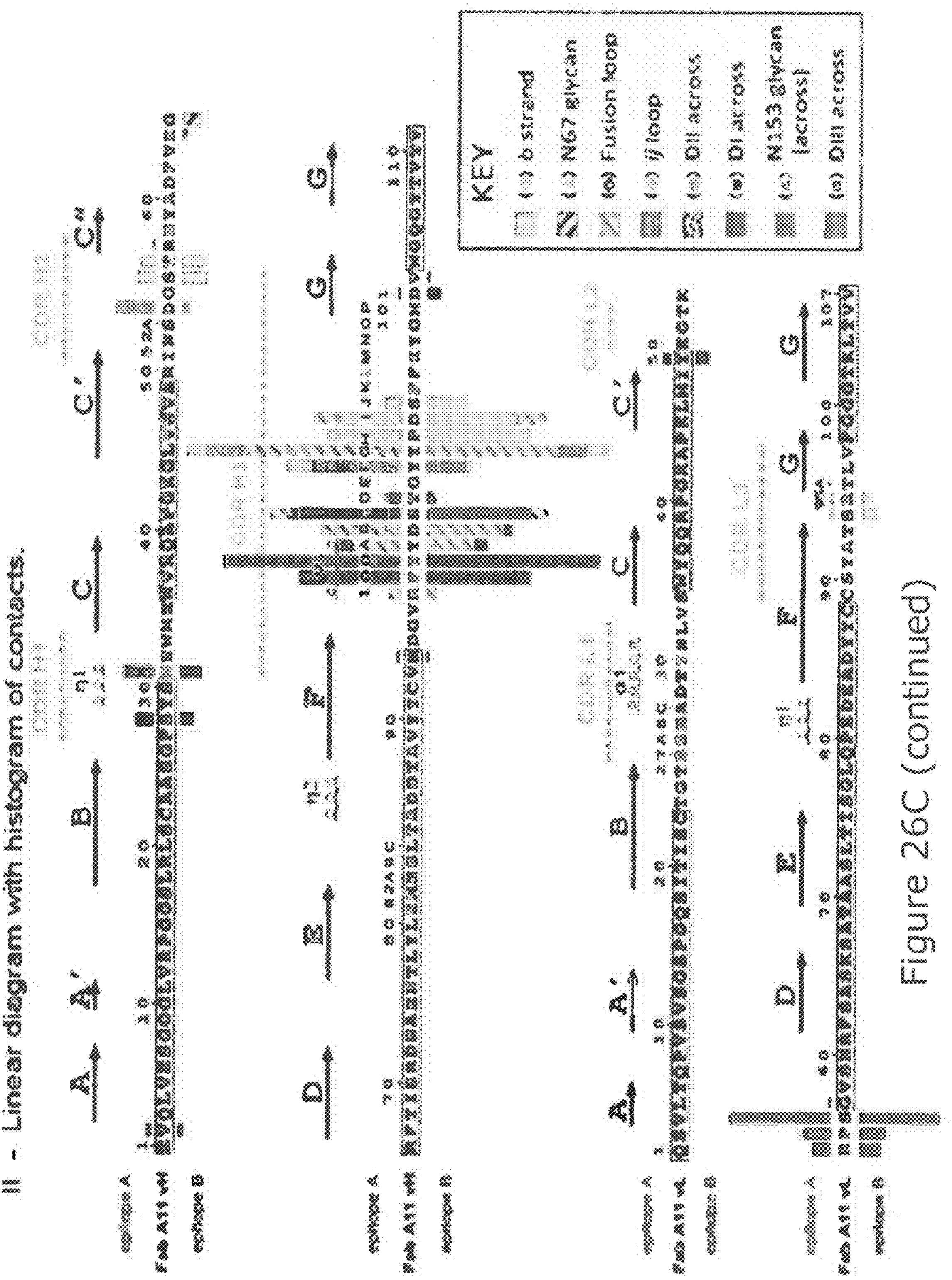
Figure 26D:
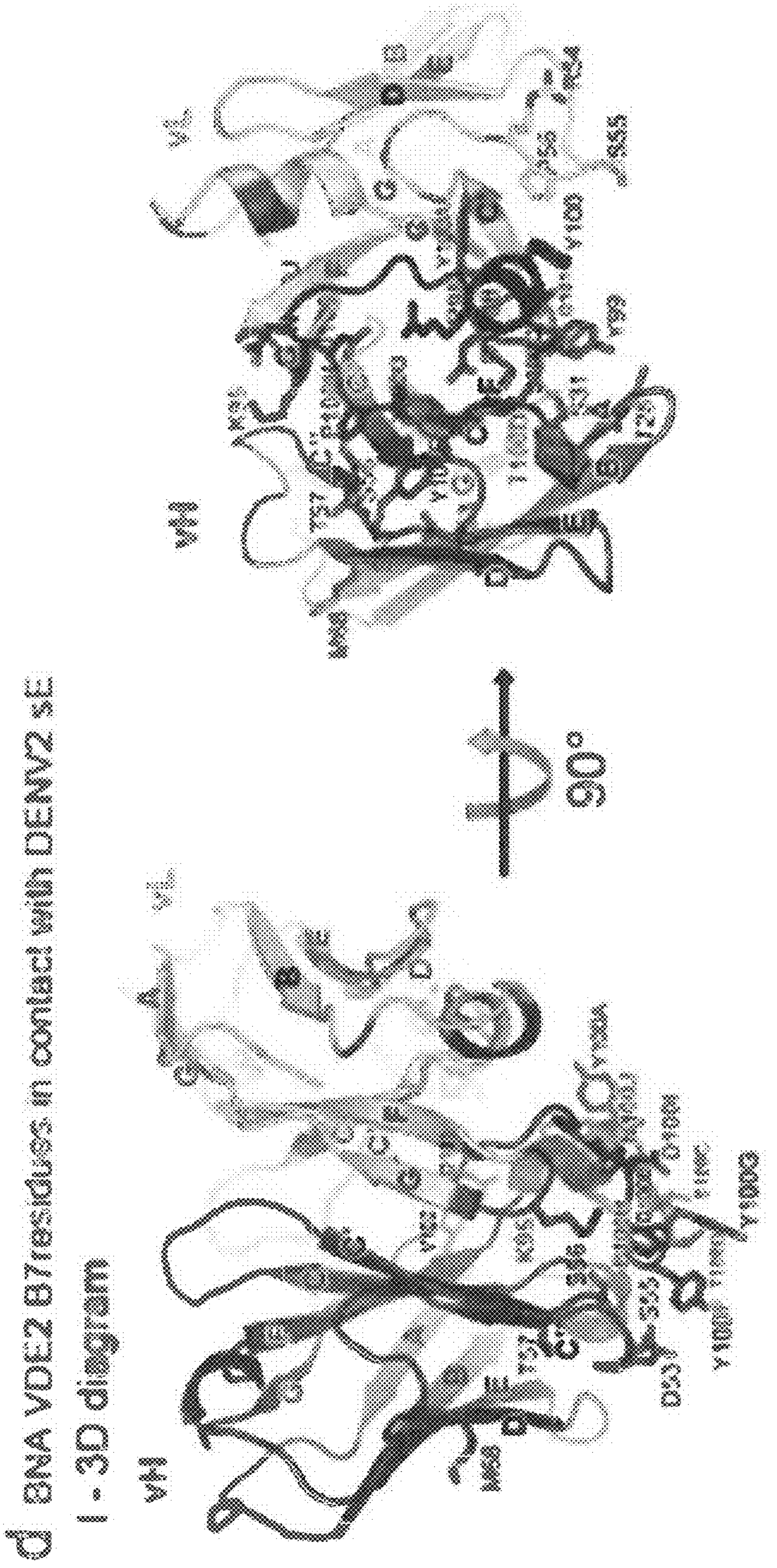
Figure 26D:
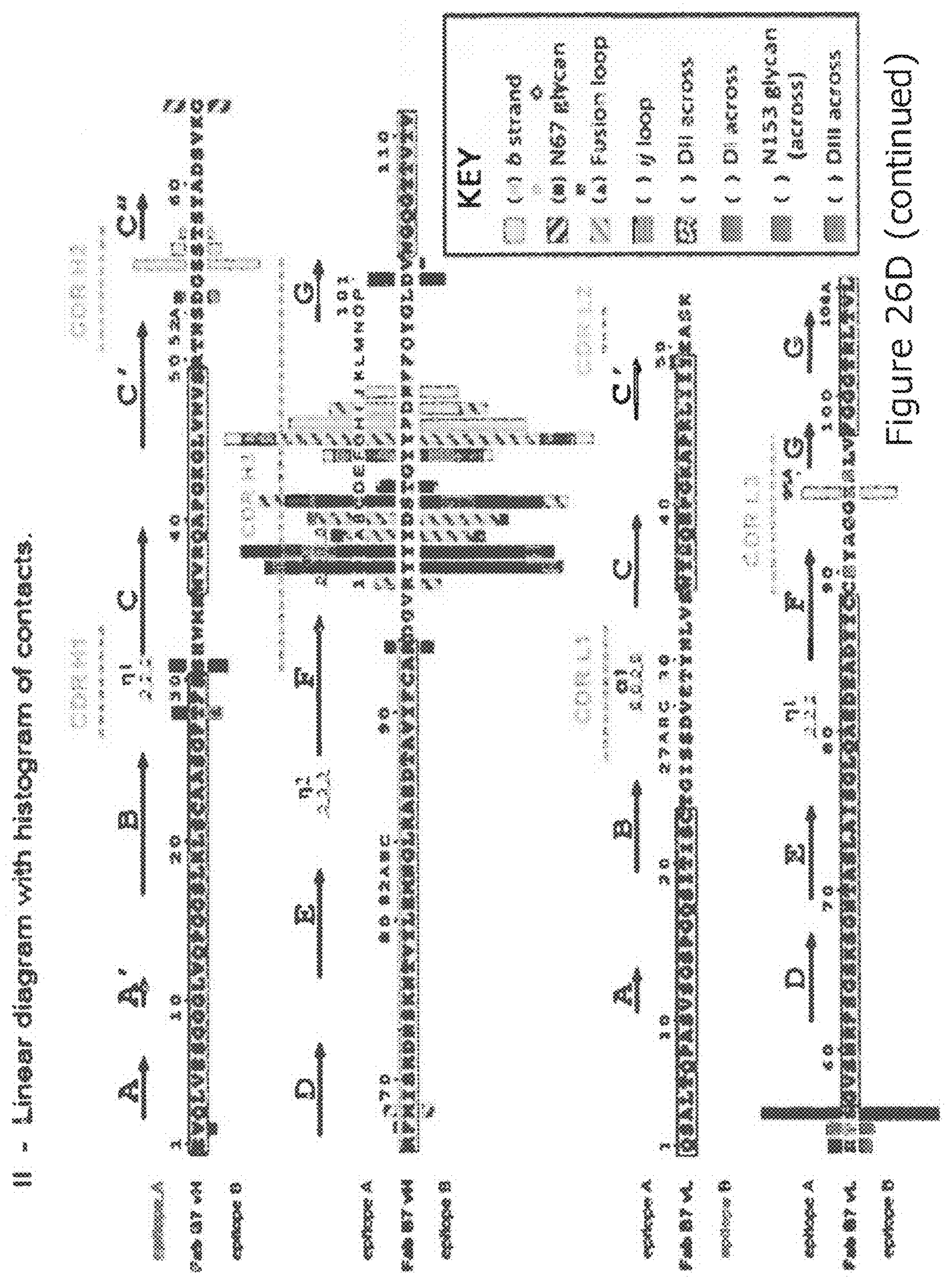
Figure 26E:
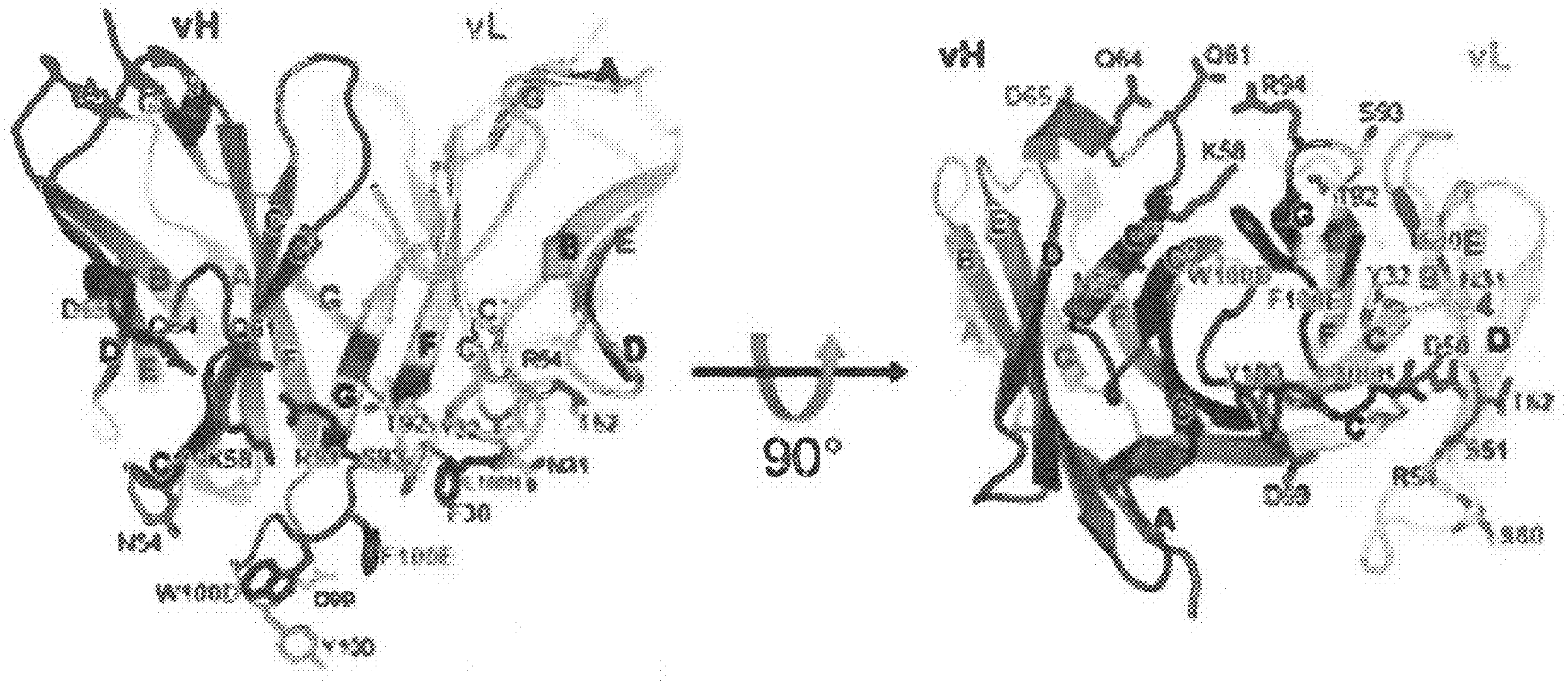
Figure 26E:
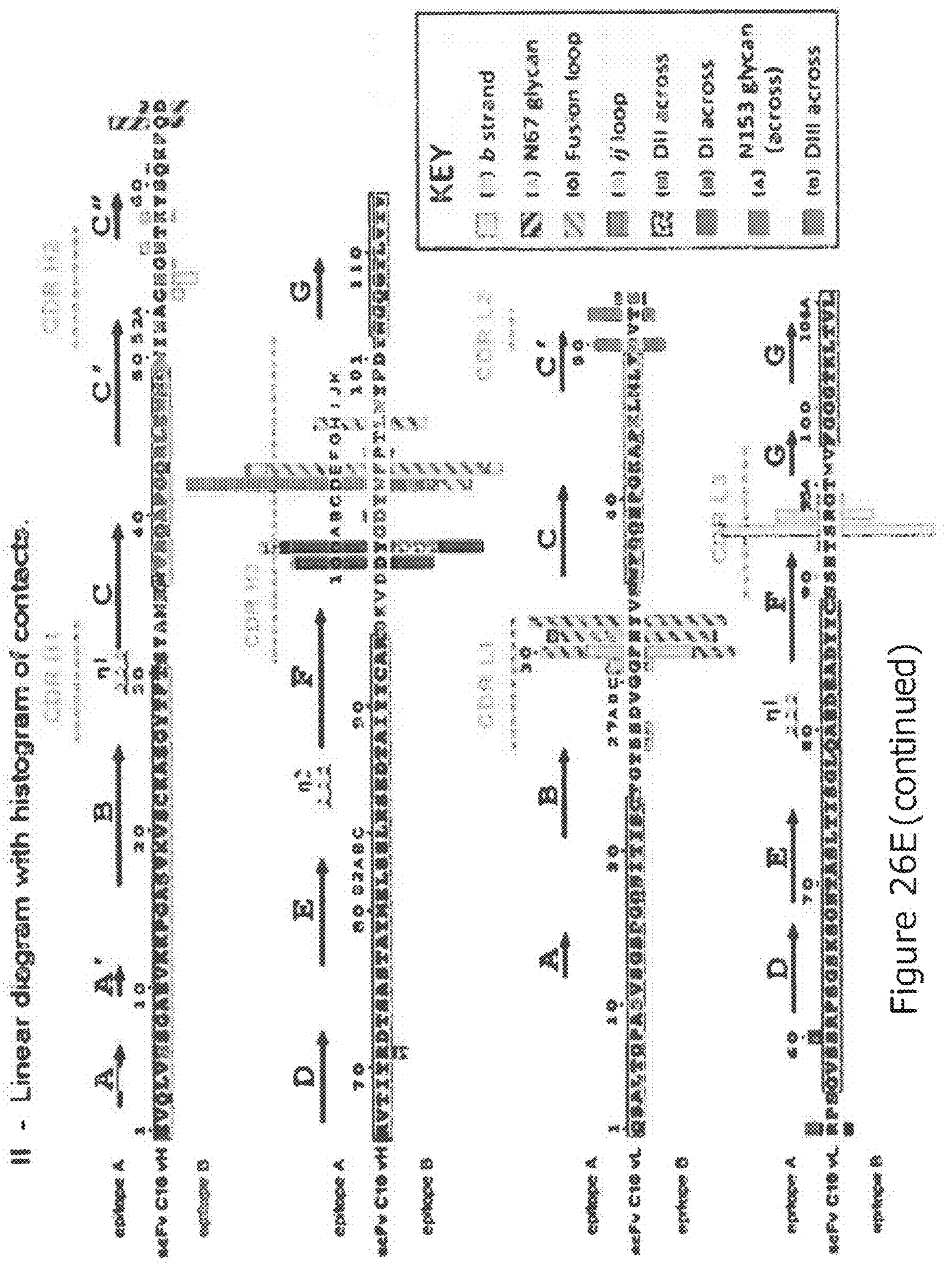
Figure 30A:
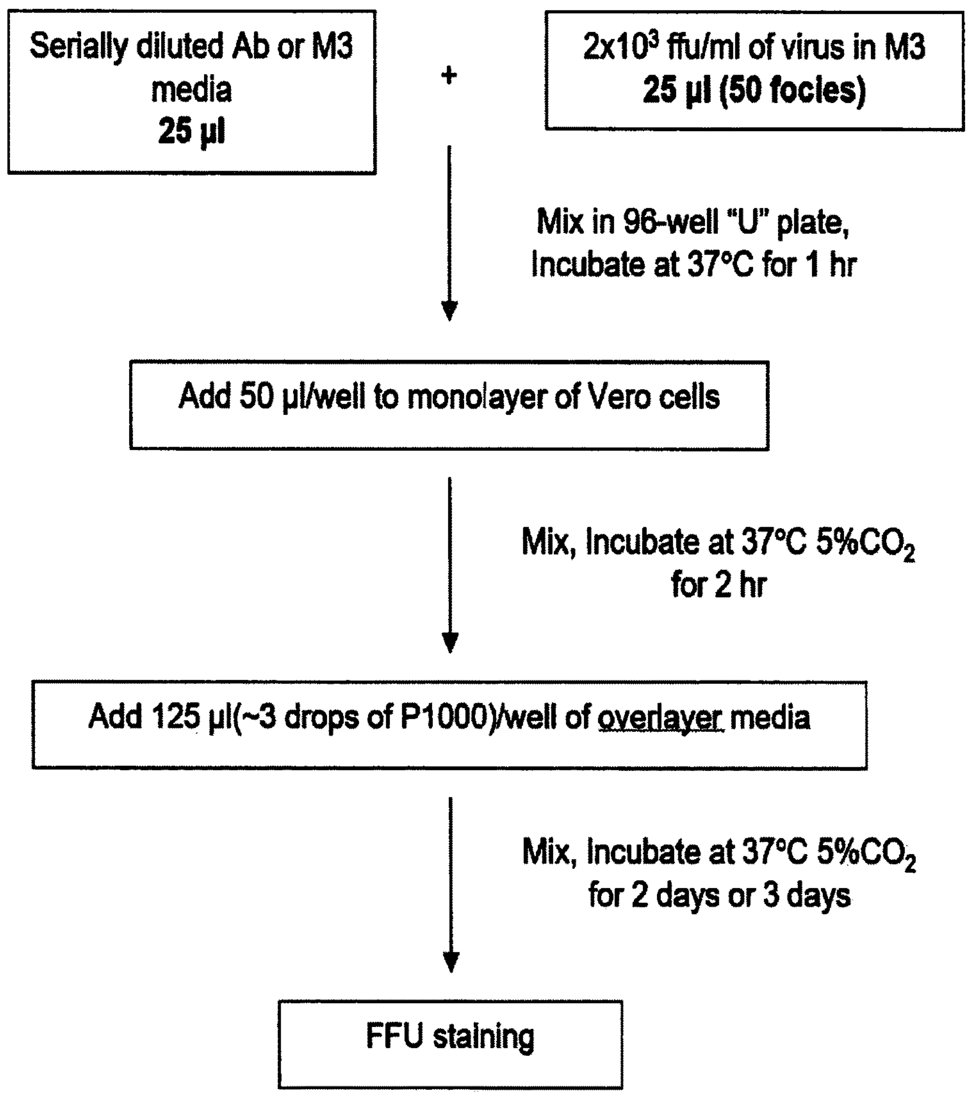
Figure 30B:
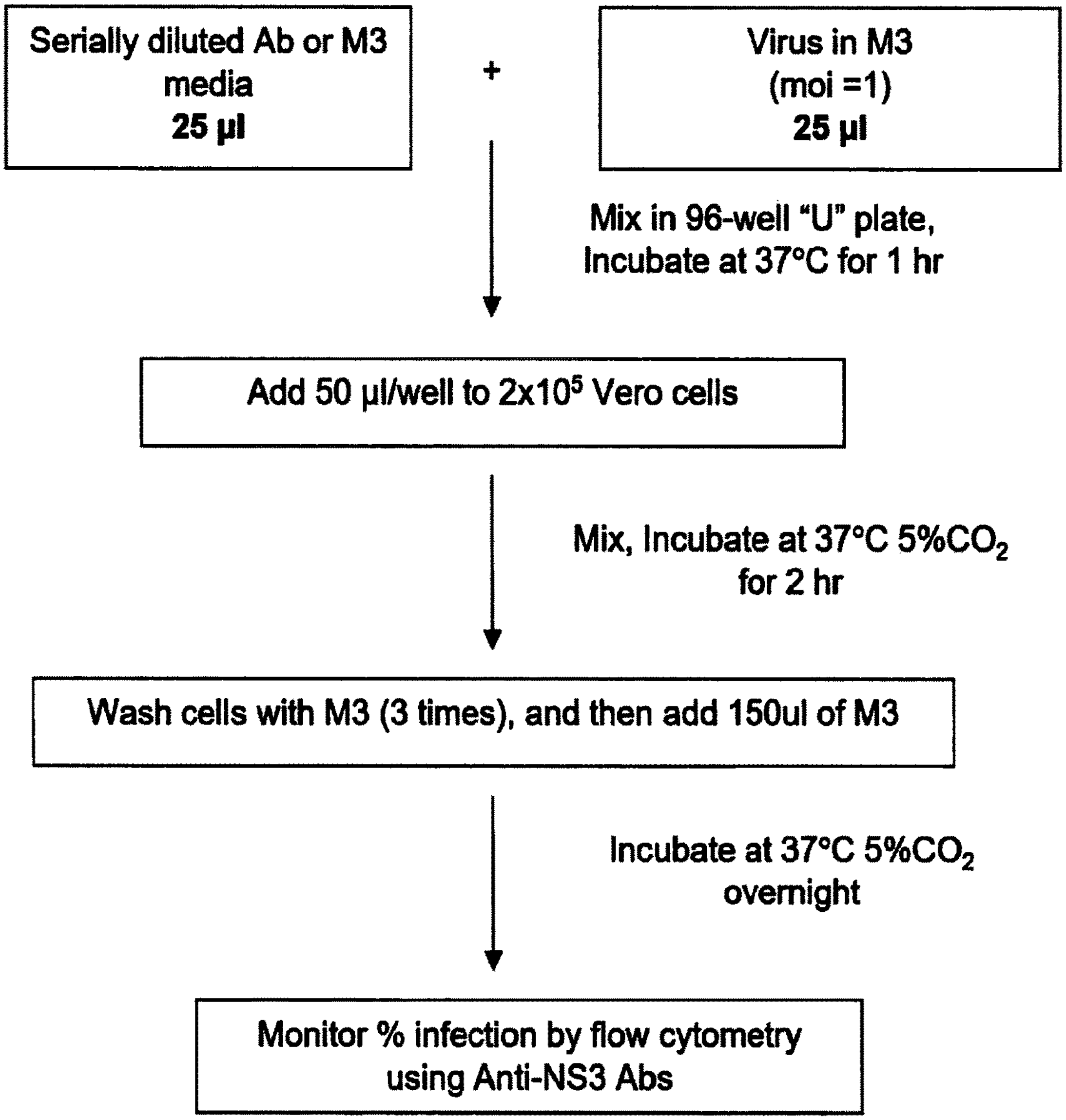
Figure 30C:
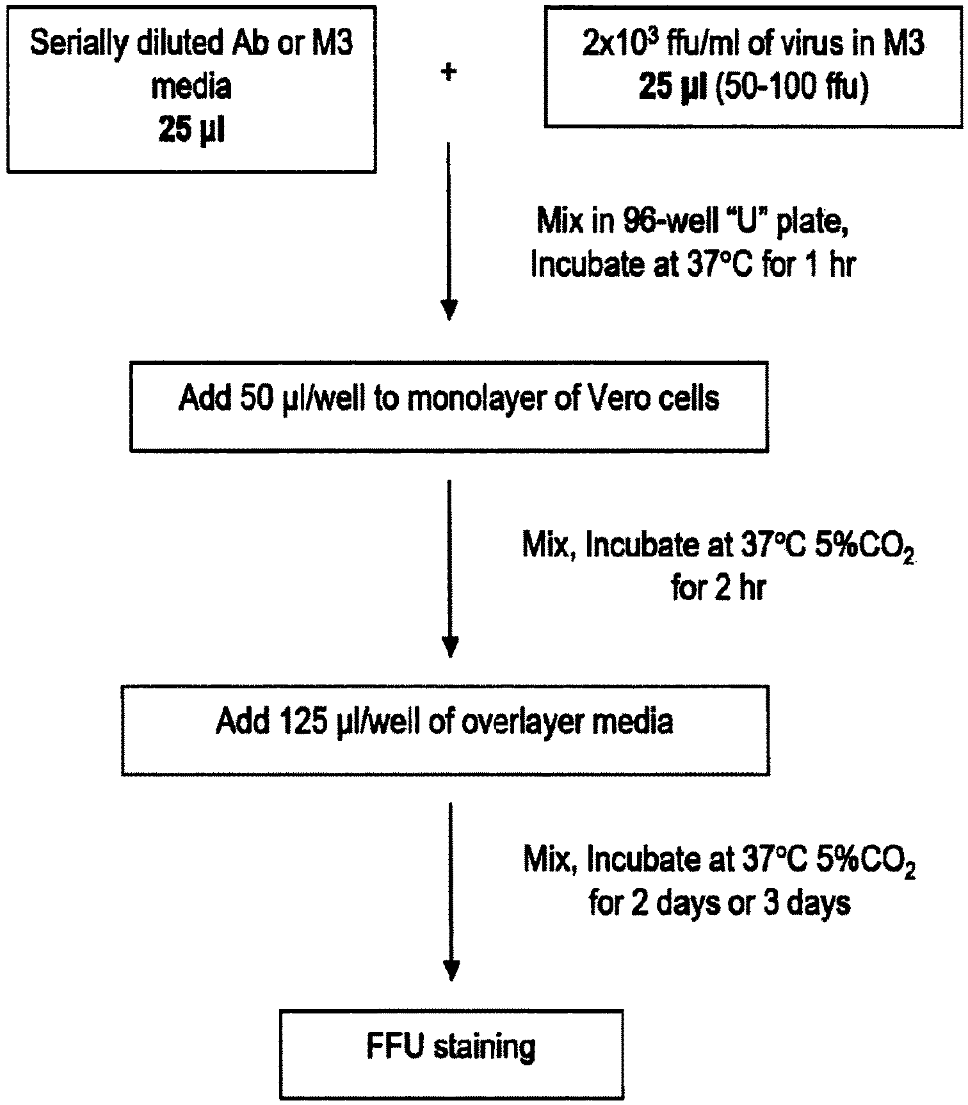
Figure 30D:
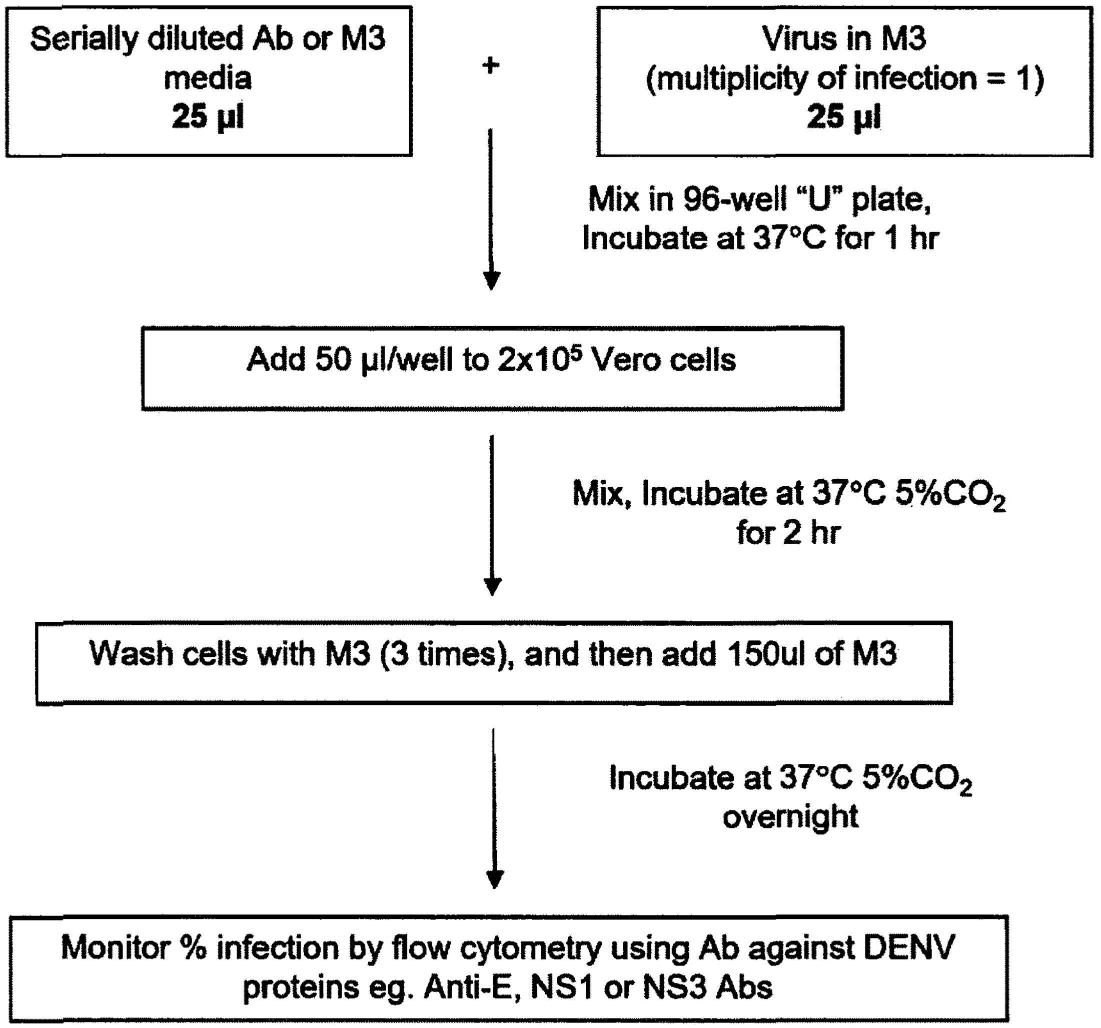

FIG. 15A-B. Residues involved in BNA/antigen interactions. (FIG. 15A) Amino acid sequence alignment of sE from the four DENV serotypes, with residues in black or light blue background highlighting identity and similarity, respectively, across serotypes. The secondary structure elements are displayed and labeled underneath the alignment, with the tertiary structure arrangement indicated by colors as in FIG. 11A-F. DENV2 sE residues contacted by the various anti-EDE antibodies are indicated above the alignment, indicating the BNA region in contact by the code provided in the key. Full symbols correspond to contacts in the reference subunit (defined as the one contributing the fusion loop to the epitope), and empty symbols to contacts across the dimer interface. Colored boxes on the sequence highlight the 5 distinct regions of sE making up the epitopes. FIG. 24A provides a histogram with the number of atomic contacts per sE residue in the complex with each BNA. Because the EDE2 B7 and A11 contacts are very similar, only the B7 contacts are shown here. The question mark on the 150 loop indicates that these residues are likely to contact the EDE1 anti-EDE antibodies, but are not visible in the structure because the loop is disordered. (FIG. 15B) Alignment of the four anti-EDE antibodies crystallized, numbered according to the Kabat definition[30] and with the FRW and CDR regions in grey and white background, respectively. The CDRs corresponding to the IMGT convention[31] are marked with a blue line over the sequence and labeled. Somatic mutations are in red with the corresponding residue in the germ-line written in smaller font underneath. Residues arising from the VDJ (or VJ) recombination process are in green. The sE segment contacted (corresponding to the colored boxes in FIG. 15A is indicated above each sequence, coded as indicated in the key. The secondary structure elements of the EDE2 C8 Ig β-barrels are indicated above the sequence, as a guide. The histograms of number of contacts per BNA residue for each crystallized complex are provided in FIG. 26A.

Figure 16A:
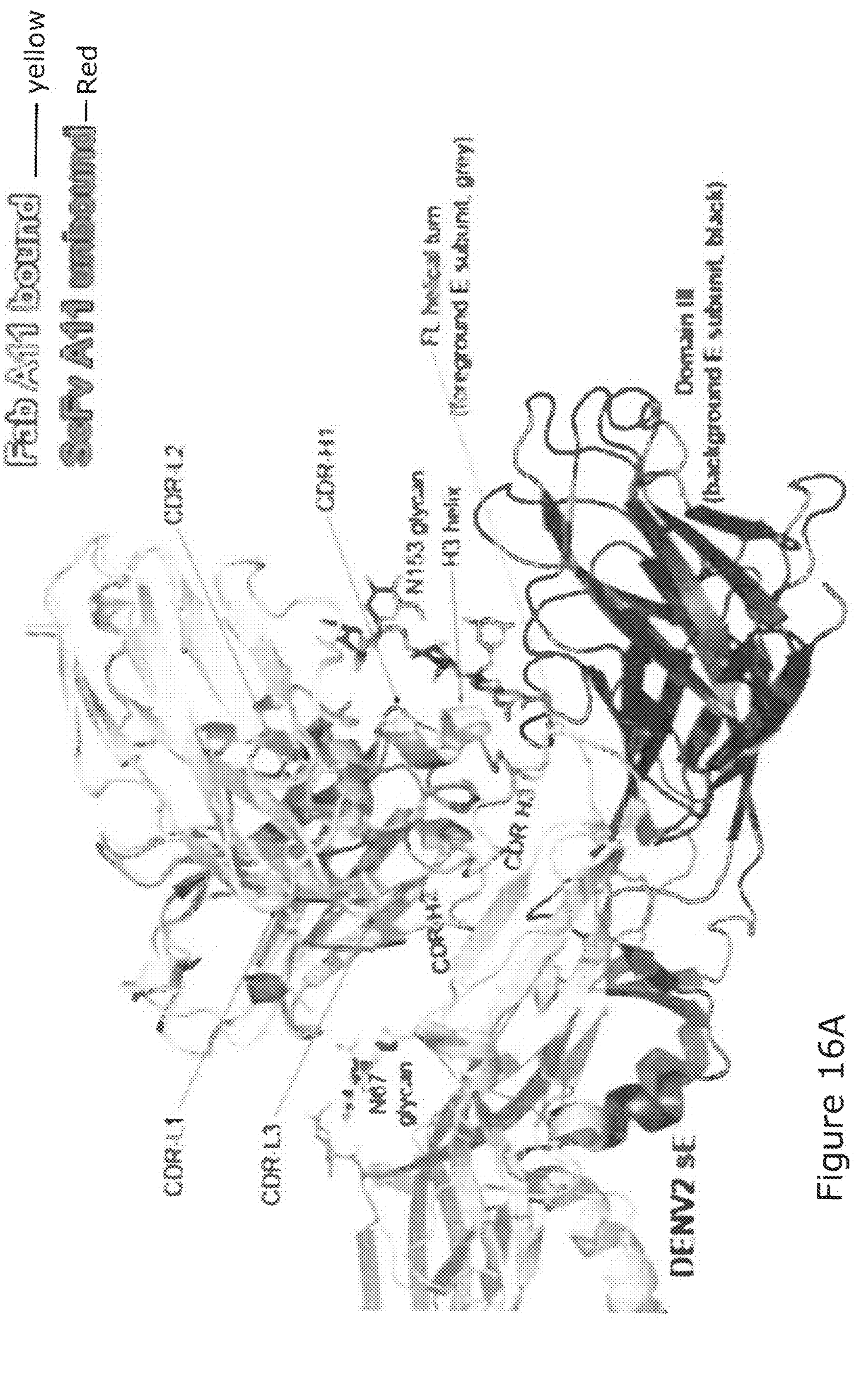
Figure 16B:
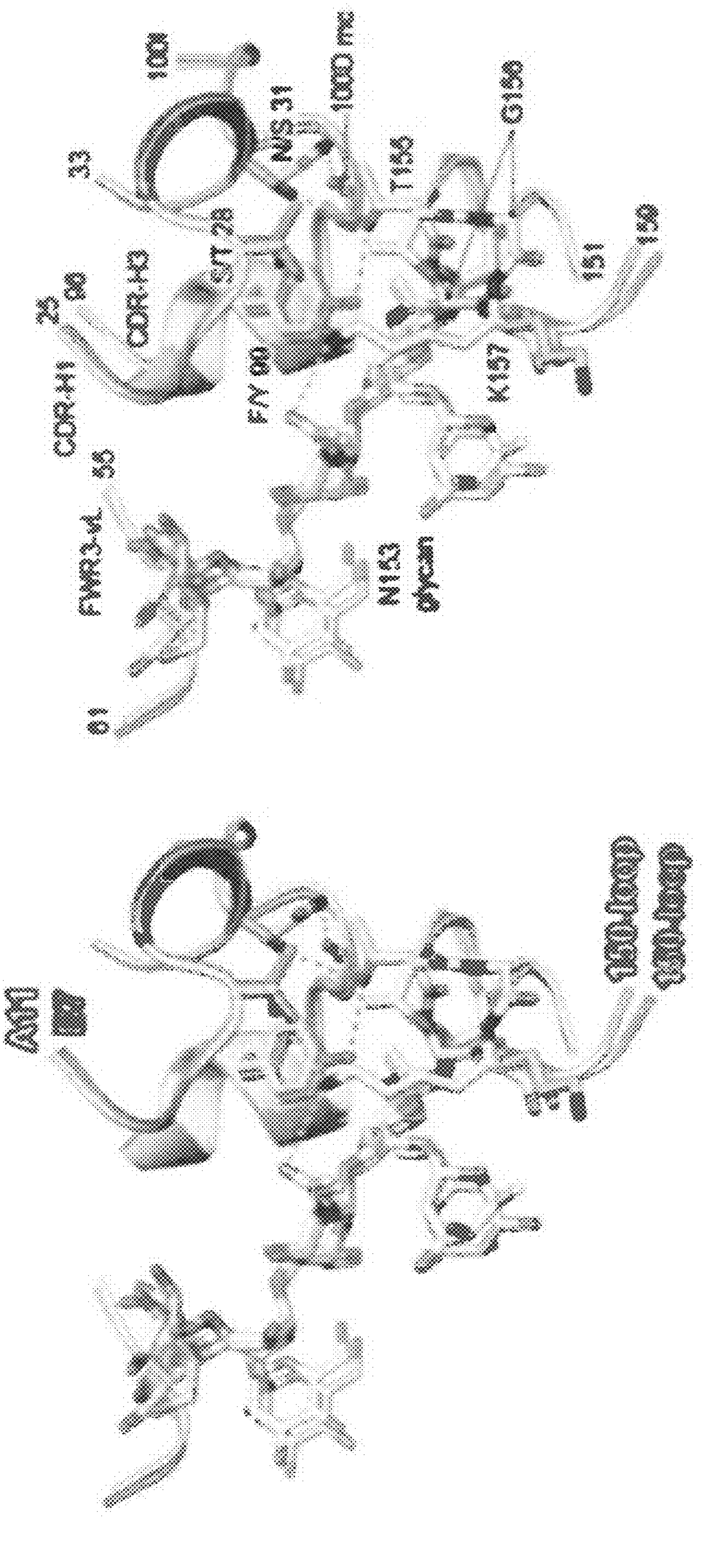
Figure 16C:
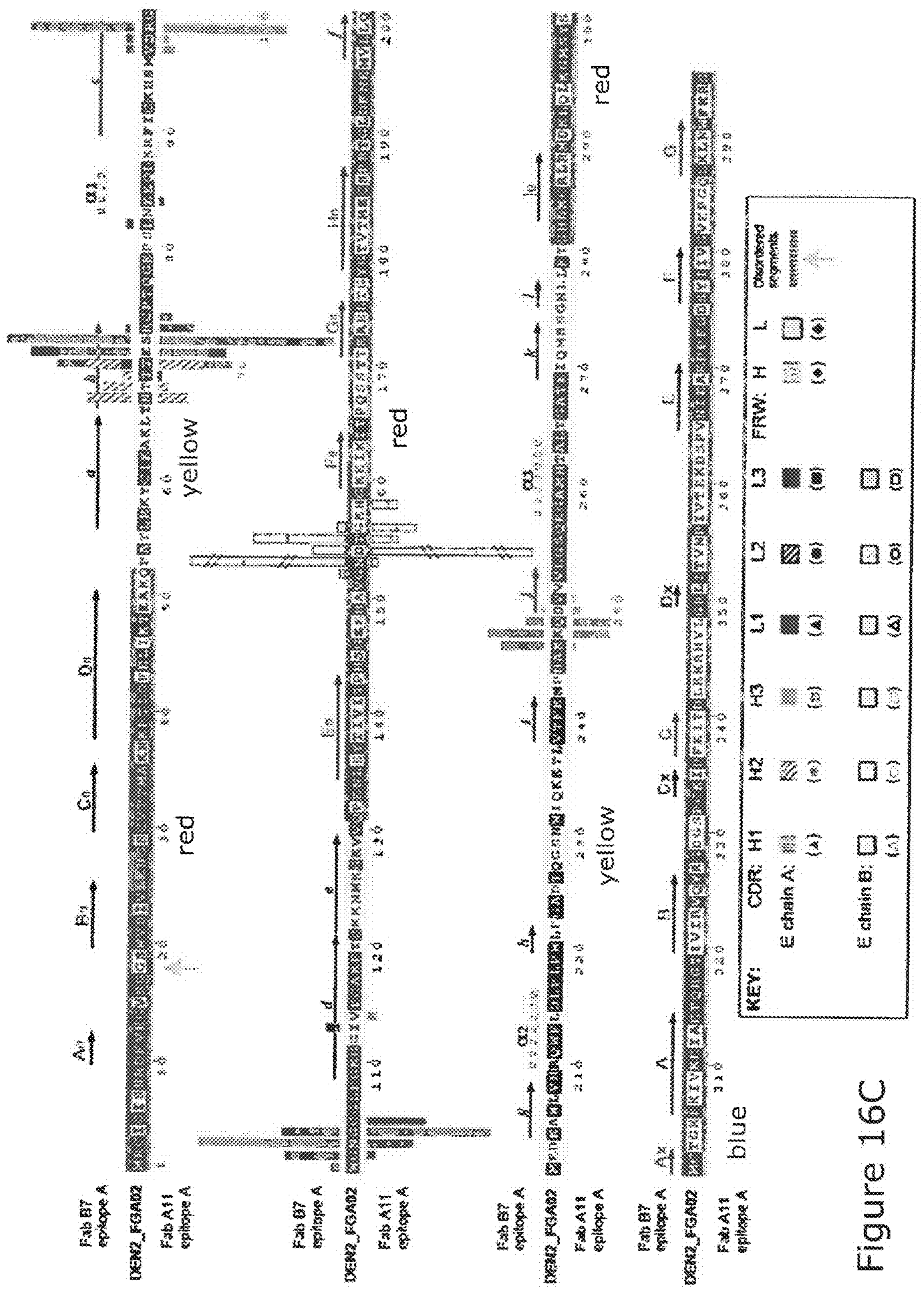
Figure 16D:
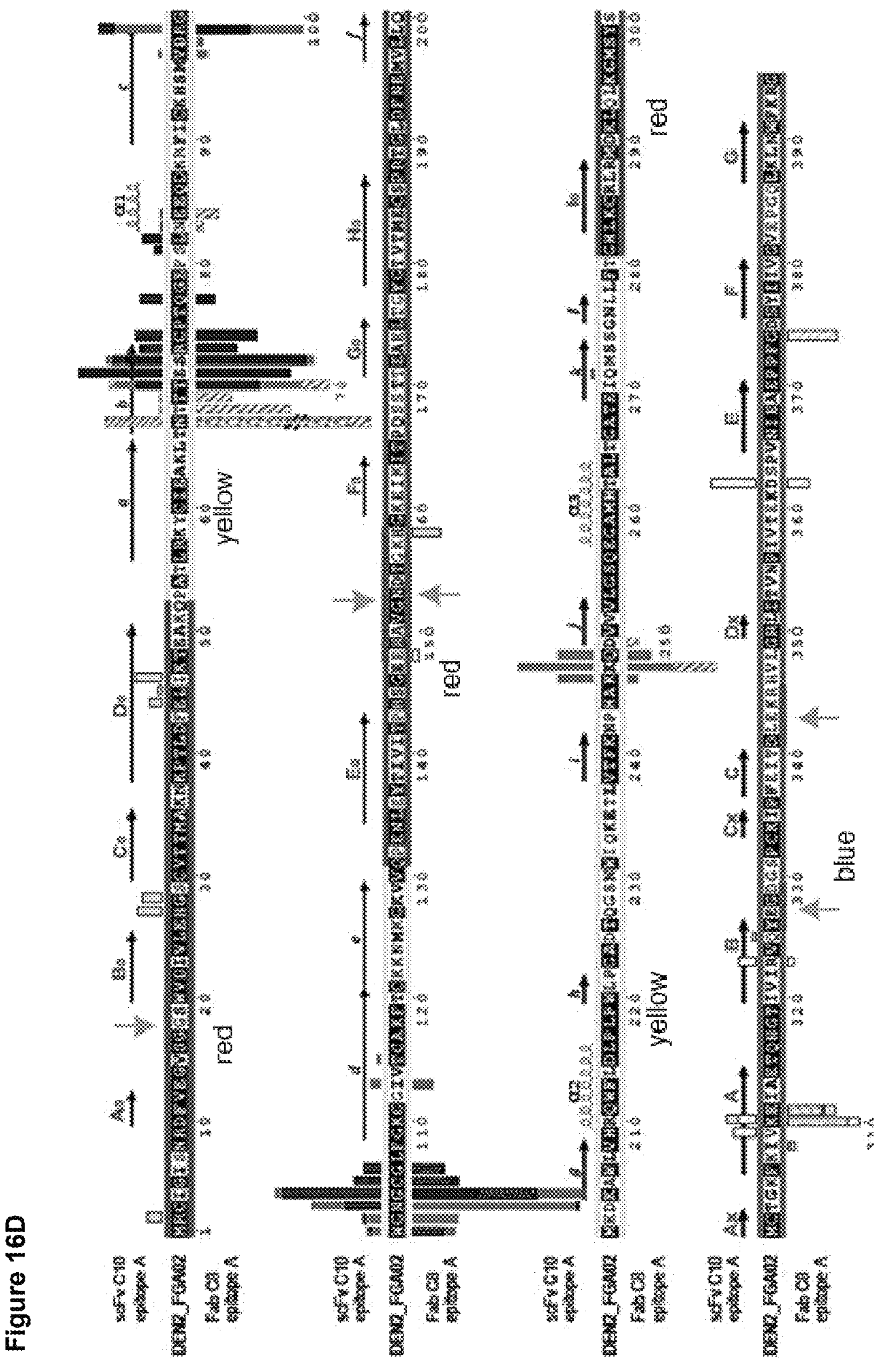
Figure 16E:
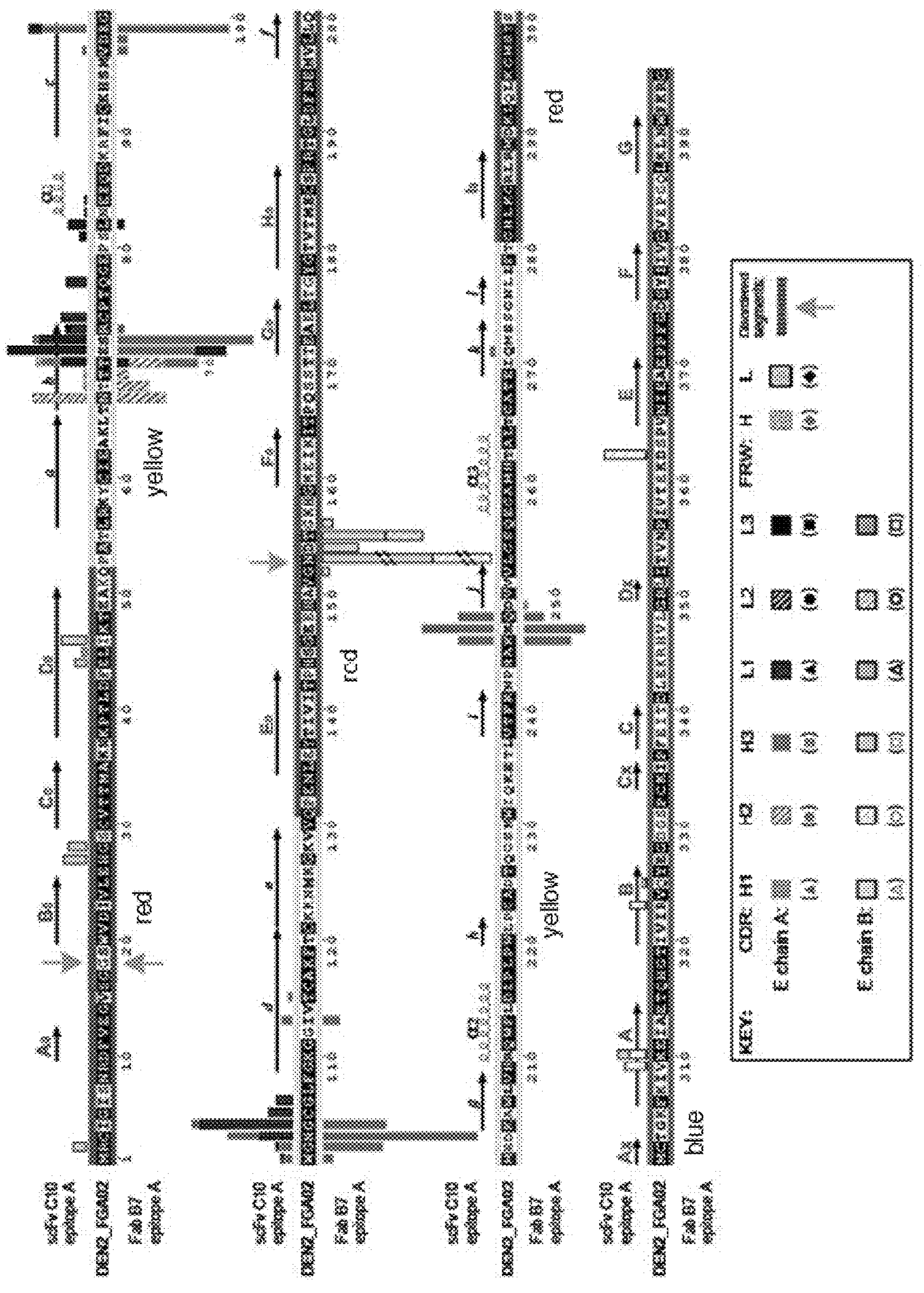

FIGS. 16A-E. Comparison of the various BNA interactions with DENV-2 sE. (FIG. 16A) The structure of the unliganded EDE2 A11 scFv (red, unbound, 1.7 A resolution) superposed to the variable domain of Fab A11 in complex with DENV-2 sE (yellow, 3.8 A resolution), to show that the same conformation is retained in the sE/Fab fragment complex. (FIG. 16B) Stereo view showing the superposed B7 (green) and A11 (yellow) variable domains, together with the 150 loop extracted from the structures of the corresponding Fab/DENV-2 sE complexes. Note that the main chain of the 150 loop adopts different conformations in the two complexes, mainly because of the hydroxyl group of the Y99 side chain in the CDR H3 of B7 makes a hydrogen bond with sE T155. All has a phenylalanine at this position, and so lacks the hydroxyl group. The sE protein in the complex with A11 displays the same conformation as the unliganded sE (not shown). (FIG. 16C) Histograms of the atomic contacts of B7 (above the sE sequence) and A11 (below the sequence). (FIG. 16D) As in FIG. 16C, but showing the pattern of contacts made by BNA C10 (above the sequence) and C8 (below) on the sE protein primary structure. (FIG. 16E). As in FIG. 16C but comparing C10 (EDE1) and B7 (EDE2) along the E protein sequence.

Figure 17:
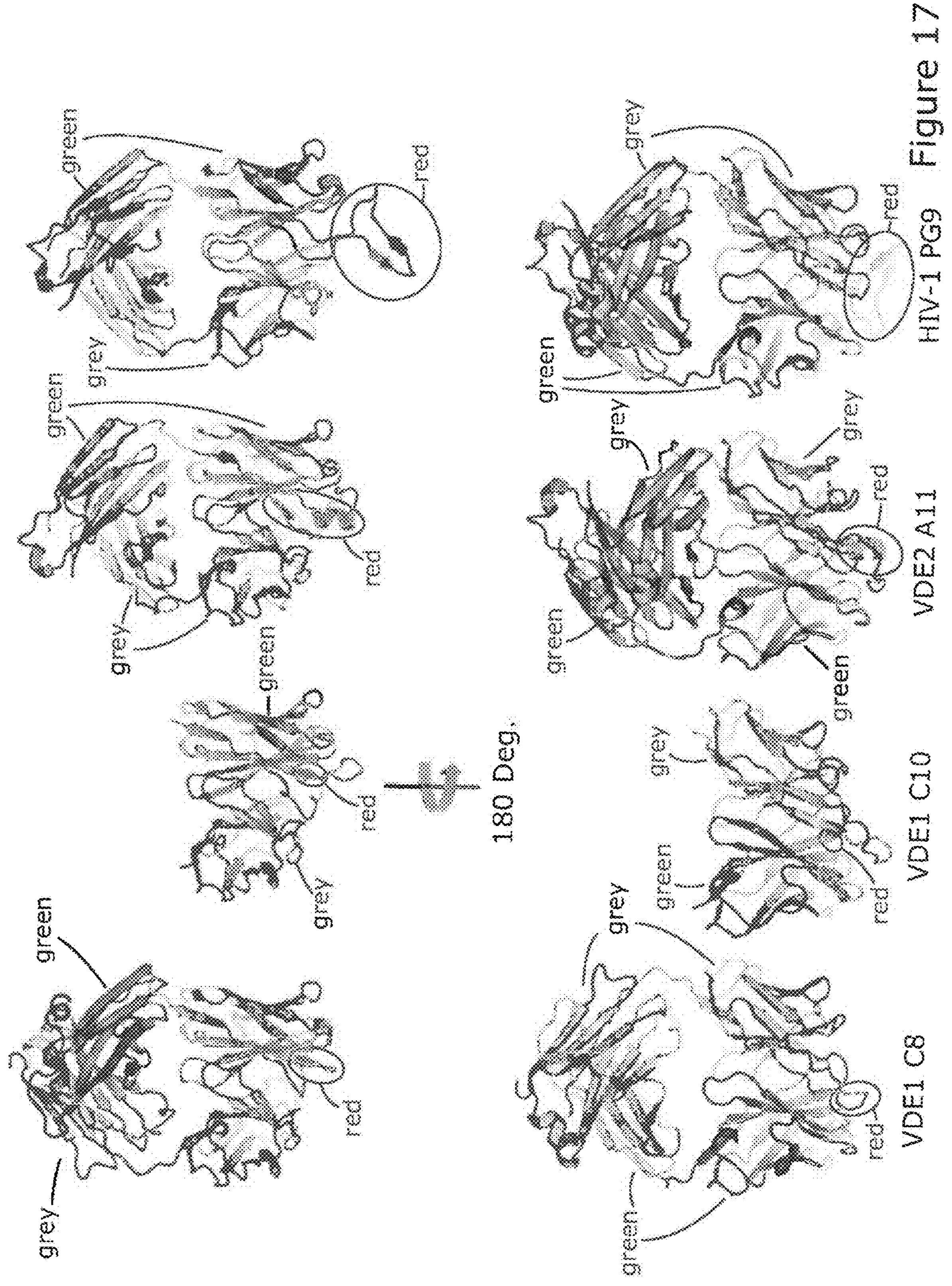

FIG. 17. The H3 loop in the EDE anti-EDE antibodies and in anti-HIV broadly neutralizing antibody PG9. The Fab or scFv fragments are oriented identically, with the light chain in grey and the heavy chain in green, with the H3 loop highlighted in red. For comparison, the Fab fragment of the potent anti HIV-1 BNA PG9[51], which recognizes the glycan chains to a large extent and has a very long H3 loop (30 aa as calculated by IMGT) is displayed in the same way.

Figure 18A:
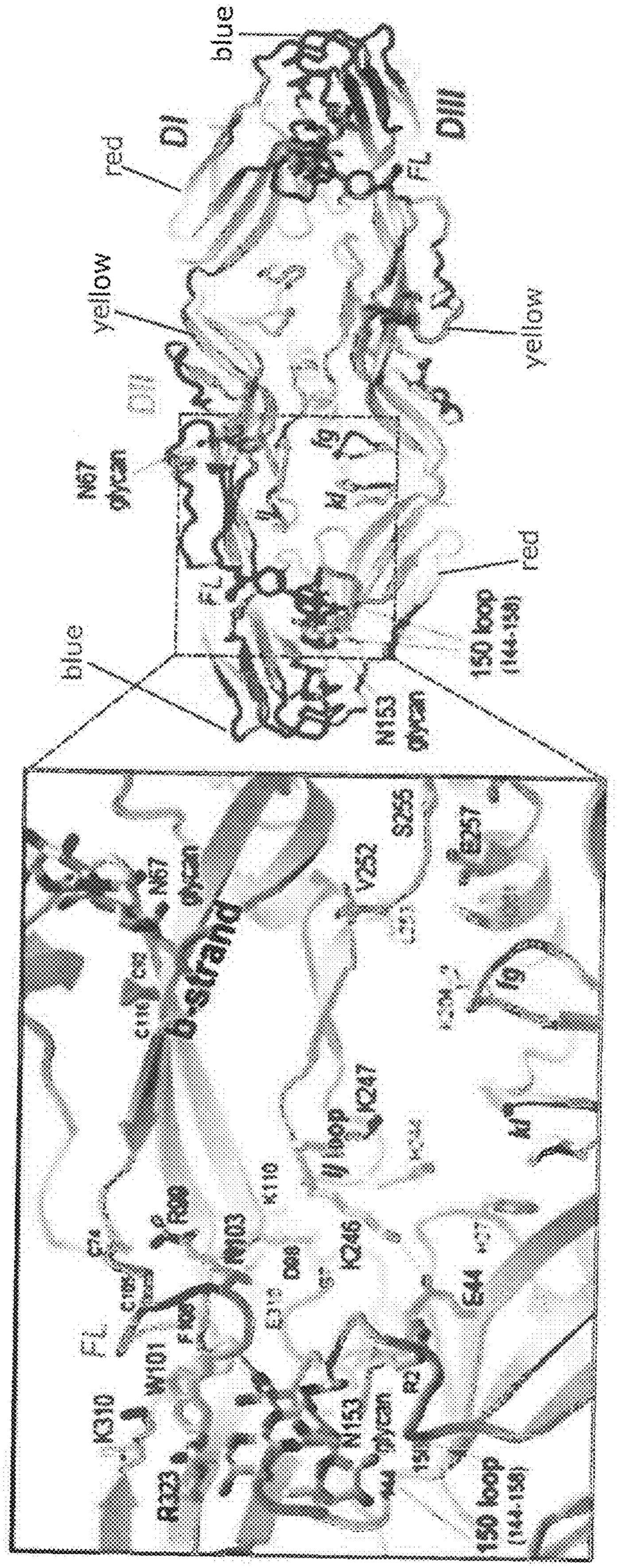
Figure 18B:
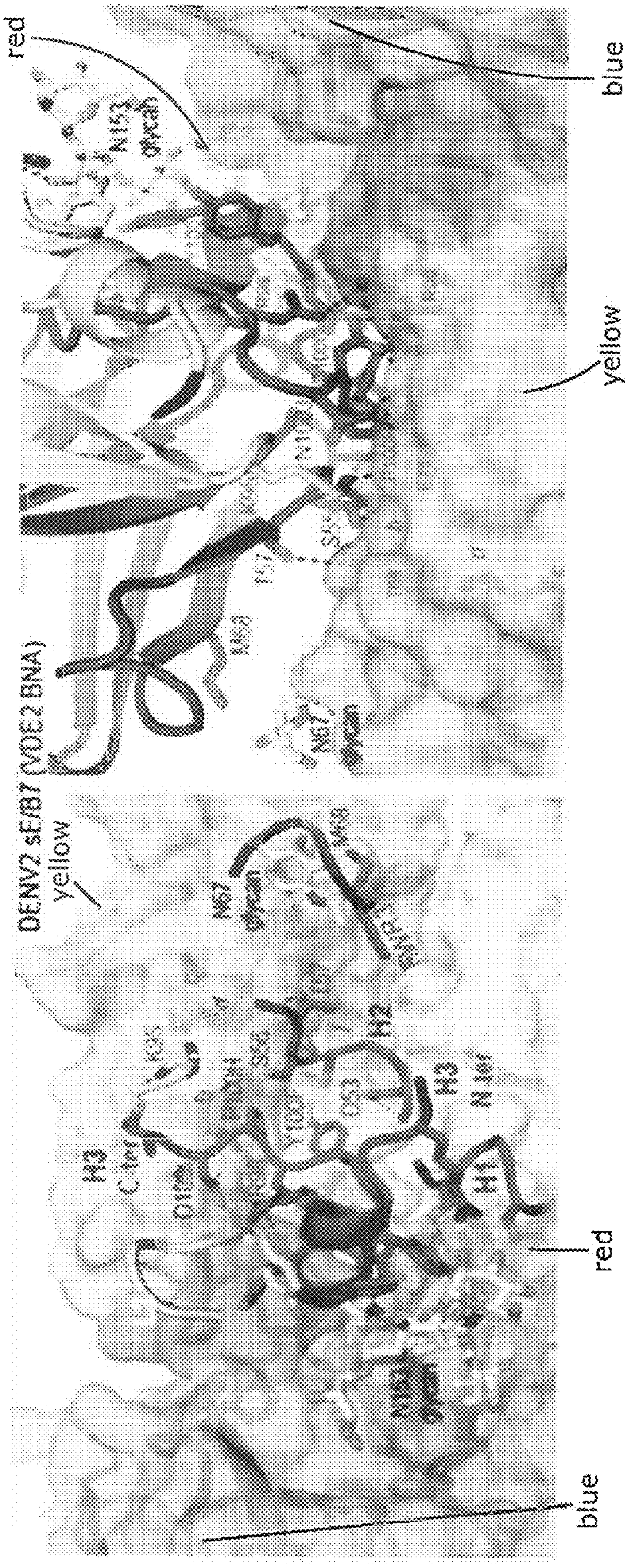
Figure 18C:
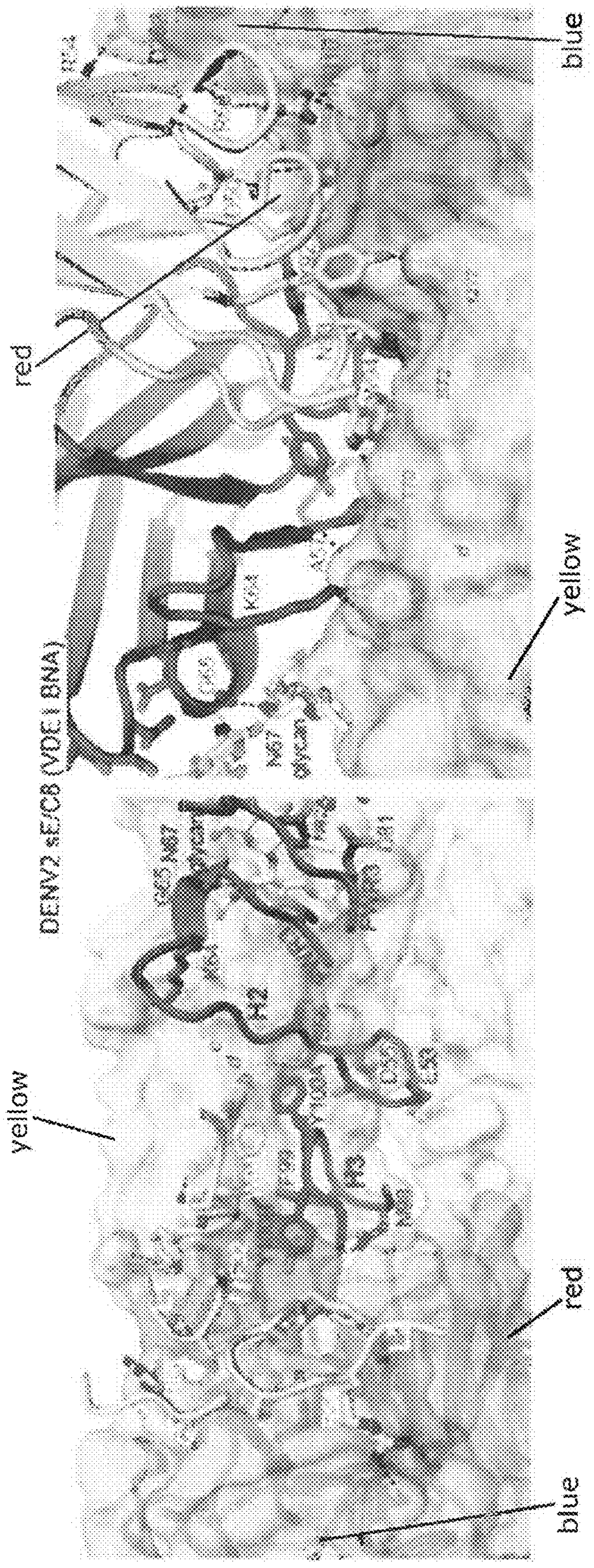
Figure 18D:
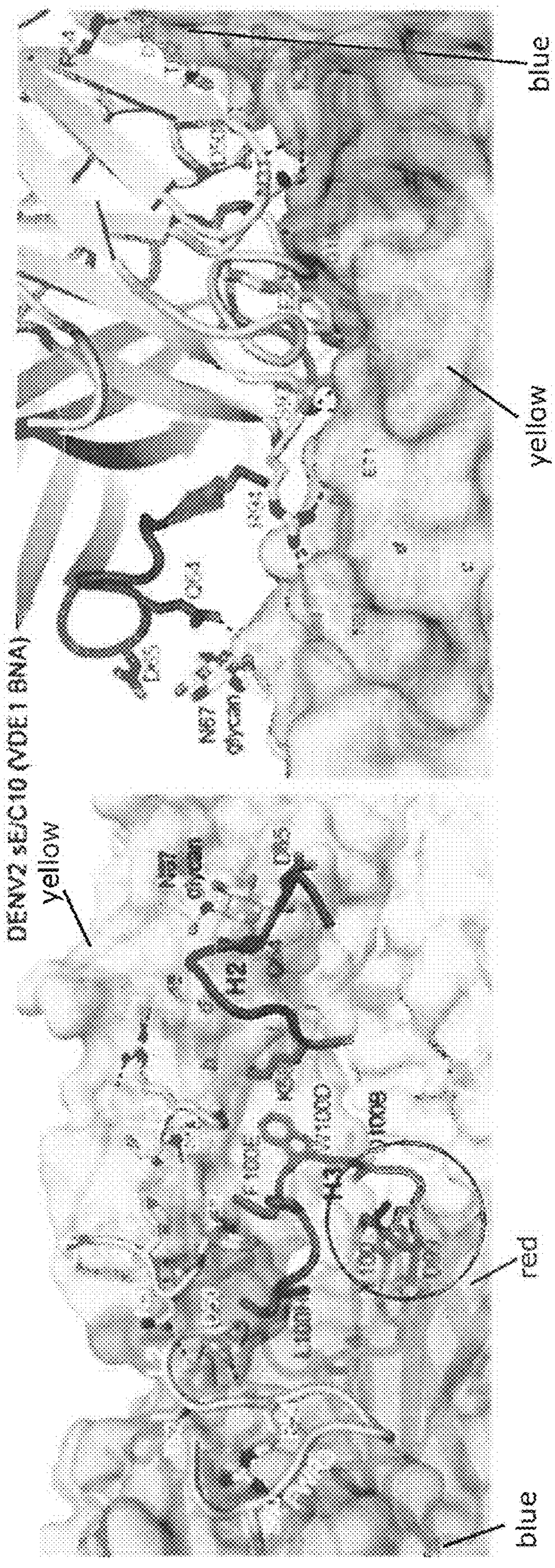

FIGS. 18A-D. Interactions of the BNA CDRs at sE dimer interface. (FIG. 18A) The right panel shows the sE dimer as ribbon, with the epitope area enlarged in the left panel, with main features labeled. FIGS. 18B-D show the sE surface in a semi-transparent representation with the ribbons visible through. The glycan residues are displayed as sticks (and were not included in the calculation of the surface). The relevant CDR loops of the anti-EDE antibodies are shown as ribbons with side chains as sticks on top of the sE protein, colored as in FIGS. 11A-F. The orientation of the left panel in FIGS. 18B-D corresponds to the left panel of FIG. 18A, and the right panel is a view along the arrow in FIG. 11B. Hydrogen bonds are displayed as dotted lines.

FIGS. 19A-E. Interactions with the glycan chains. (FIG. 19A) The EDE1 C8/DENV-2 sE complex shown as ribbons with selected side chains as sticks, with the sE surface in semi-transparent representation, highlighting the interactions with the N67 glycan. A few hydrogen bonds are displayed as dotted lines. The 150 loop is disordered (labeled at the density break). In both FIG. 19 A and FIG. 19 B, the right panel is a view down the arrow of the left panel, through the glycan chain. (FIG. 19B) The EDE2 B7 BNA/DENV-2 sE complex shown with B7 in the same orientation as C8 in FIG. 19A to highlight that EDE1 and EDE2 anti-EDE antibodies bind in a similar way. EDE2 B7 inserts its long CDR H3 into the fusion loop valley, while its sides contact the two glycan chains, as seen in the left panel. The H3 α-helix packs against the N153 glycan. Also shown are a number of hydrogen bonds between anti-EDE antibodies and sE, which are listed in FIG. 21. (FIG. 19C) to the sugar connectivity and nomenclature used in the text and in FIGS. 19 A and 19 B. (FIG. 19D) Contacts of the sugar residues with the antibodies, coded according to the key (same as in FIG. 24A-E). (FIG. 19E) Dengue variants lacking the N153 glycan are more readily neutralized by EDE1 anti-EDE antibodies, whereas they are more resistant to neutralization by EDE2 anti-EDE antibodies. Mean and s.e.m. values were estimated from three independent experiments.

Figure 20A:
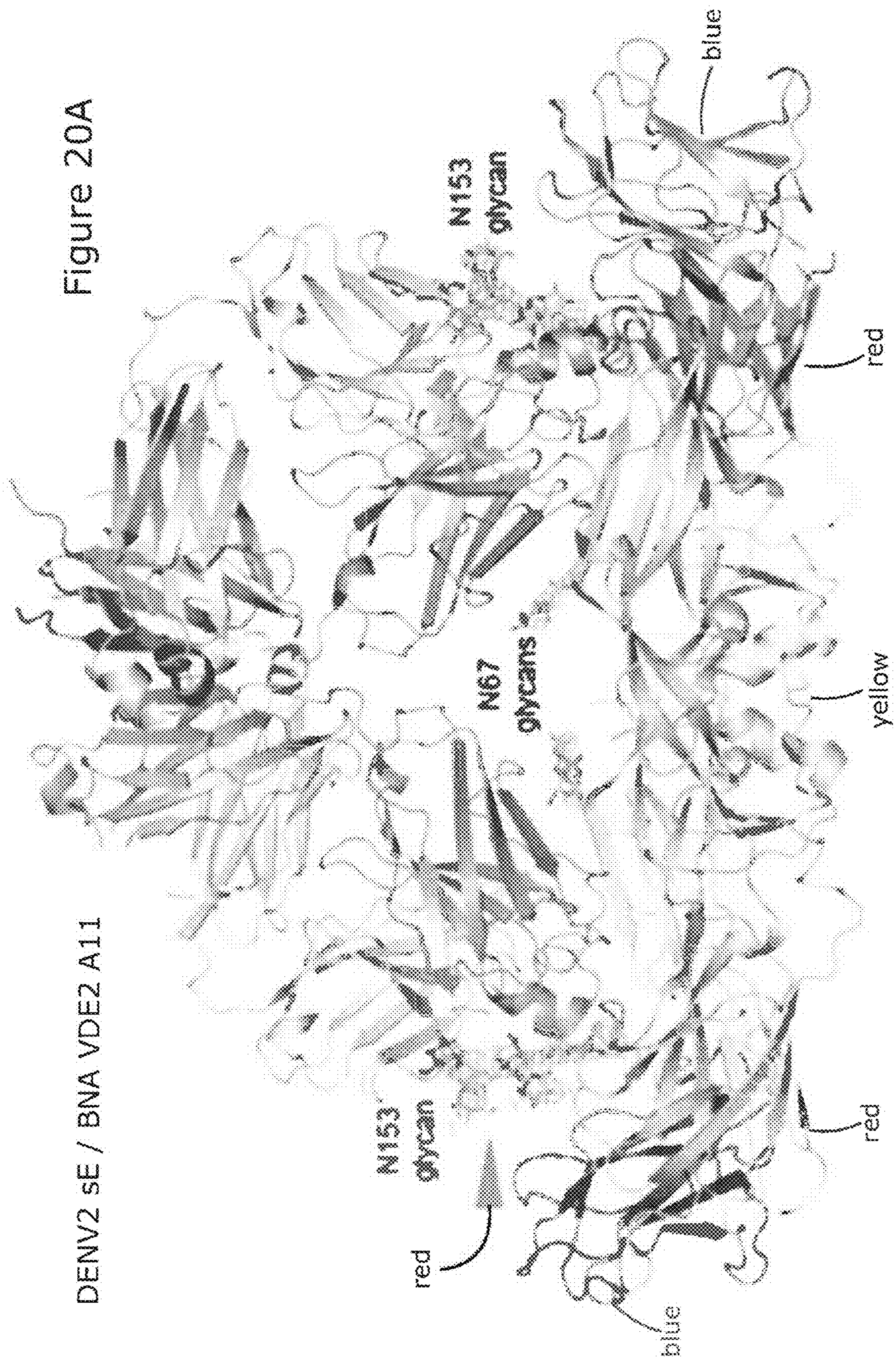
Figure 20B:
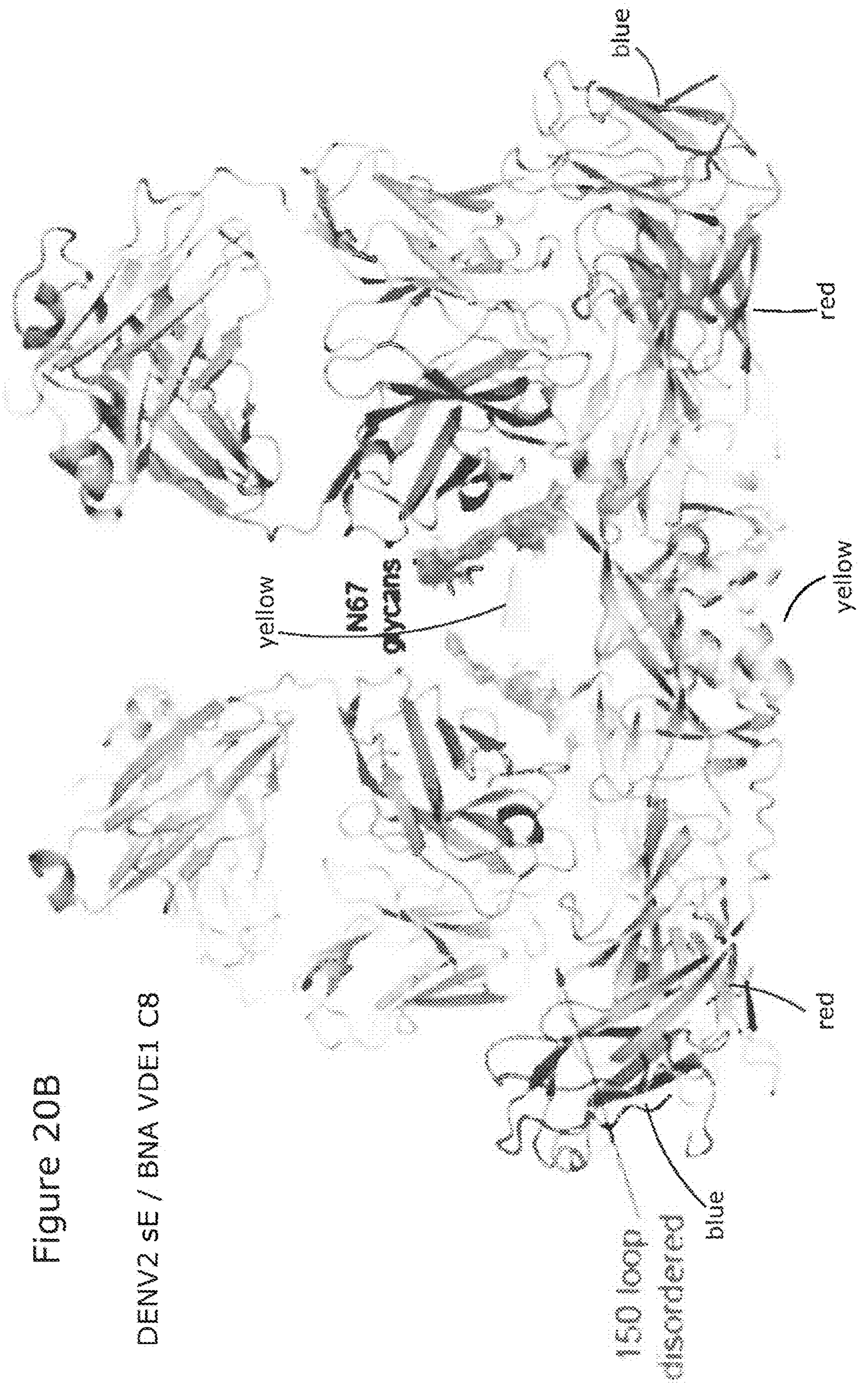
Figure 20C:
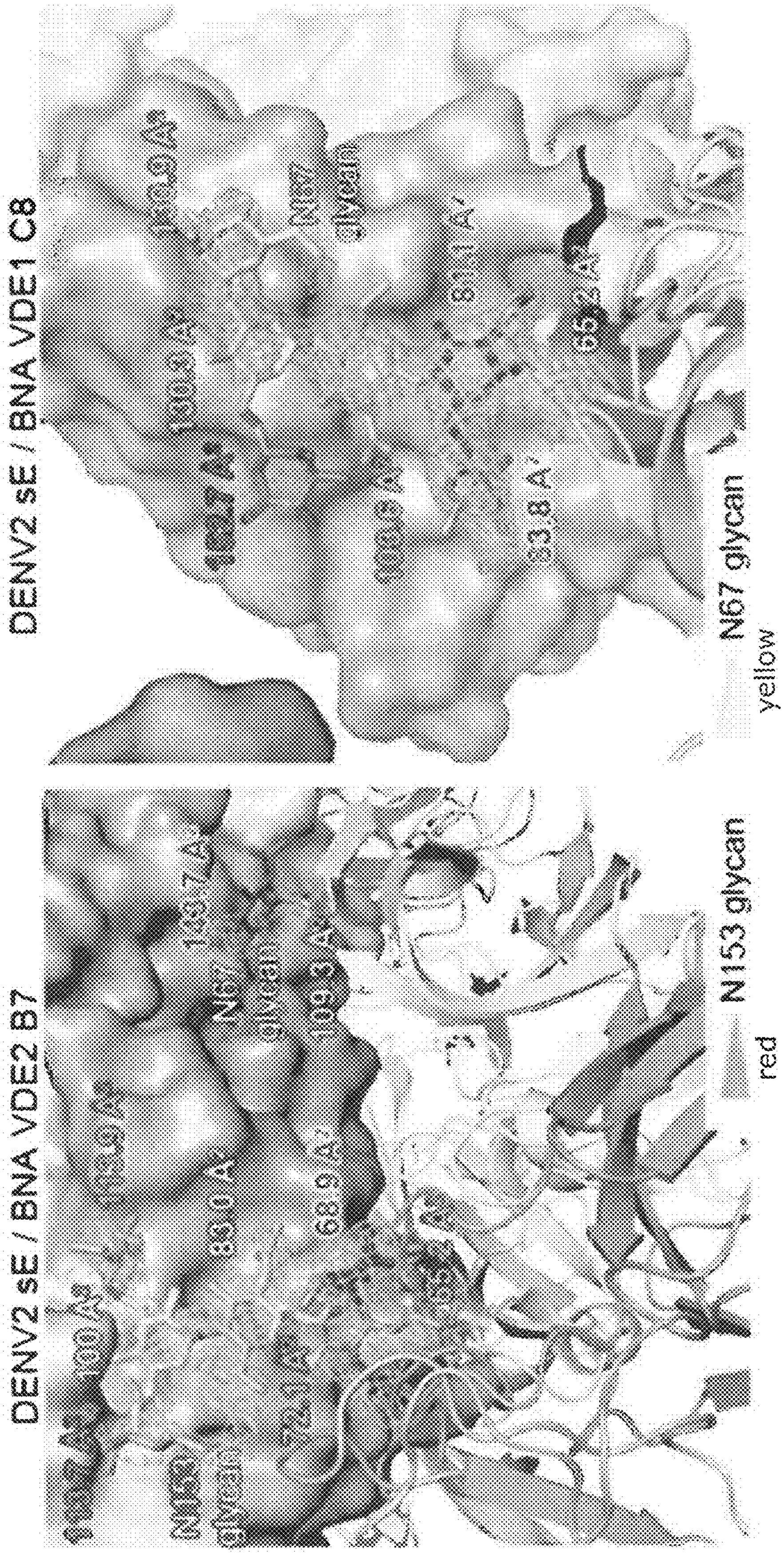

FIGS. 20A-C. Experimental electron density for the glycan chains. Ribbon representation of (FIG. 20A) the EDE2 A11 Fab and (FIG. 20B) the EDE2 C8 EDE1 Fab in complex with DENV2 sE, colored as in FIG. 11A-F. The simulated annealing omit maps contoured at 1 sigma (cyan) or 0.6 sigma (gold) show clear density for the N153 (in FIG. 20A) and N67 glycans (in FIGS. 20A and 20B) (red and yellow arrowheads, respectively). To create an unbiased map, all glycan atoms were removed from the structures, all B factors were reset to 20 $A^2$ and the structures were re-refined using torsion dynamics simulated annealing. Note that the antibody footprint spans the two glycans across the dimer interface (as also shown in FIG. 11A-F). (FIG. 20C) Zoom of complex viewed down the red (left panel) and yellow (right panel) arrowheads of FIGS. 20A and 20B respectively for DENV-2/B7 (left panel) and DENV-2/C8 (right panel). Heavy and light chains are shown as surfaces and the glycans (together with the corresponding asparagine) are labeled with the average B factor for each residue. Also, the glycans are ramp-colored from blue (cold) to red (hot). Note that, in order to show the omit map for the glycans in the three complexes, we have displayed in FIG. 20C the electron density for DENV-2/B7 instead of DENV-2/A11 as in FIG. 20A.

FIG. 21. Polar interactions between antibody and antigen.

Figure 22A:
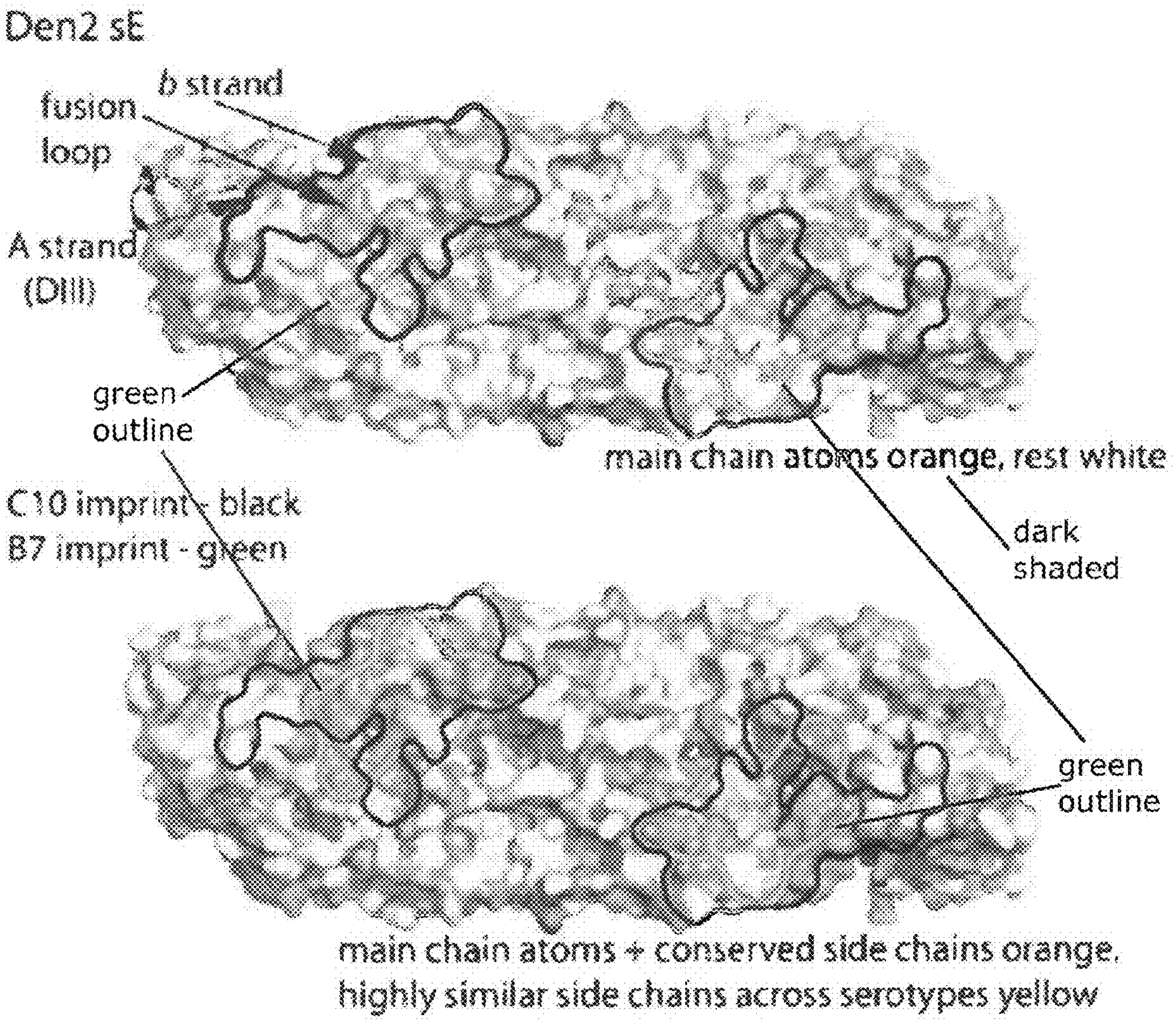
Figure 22B:
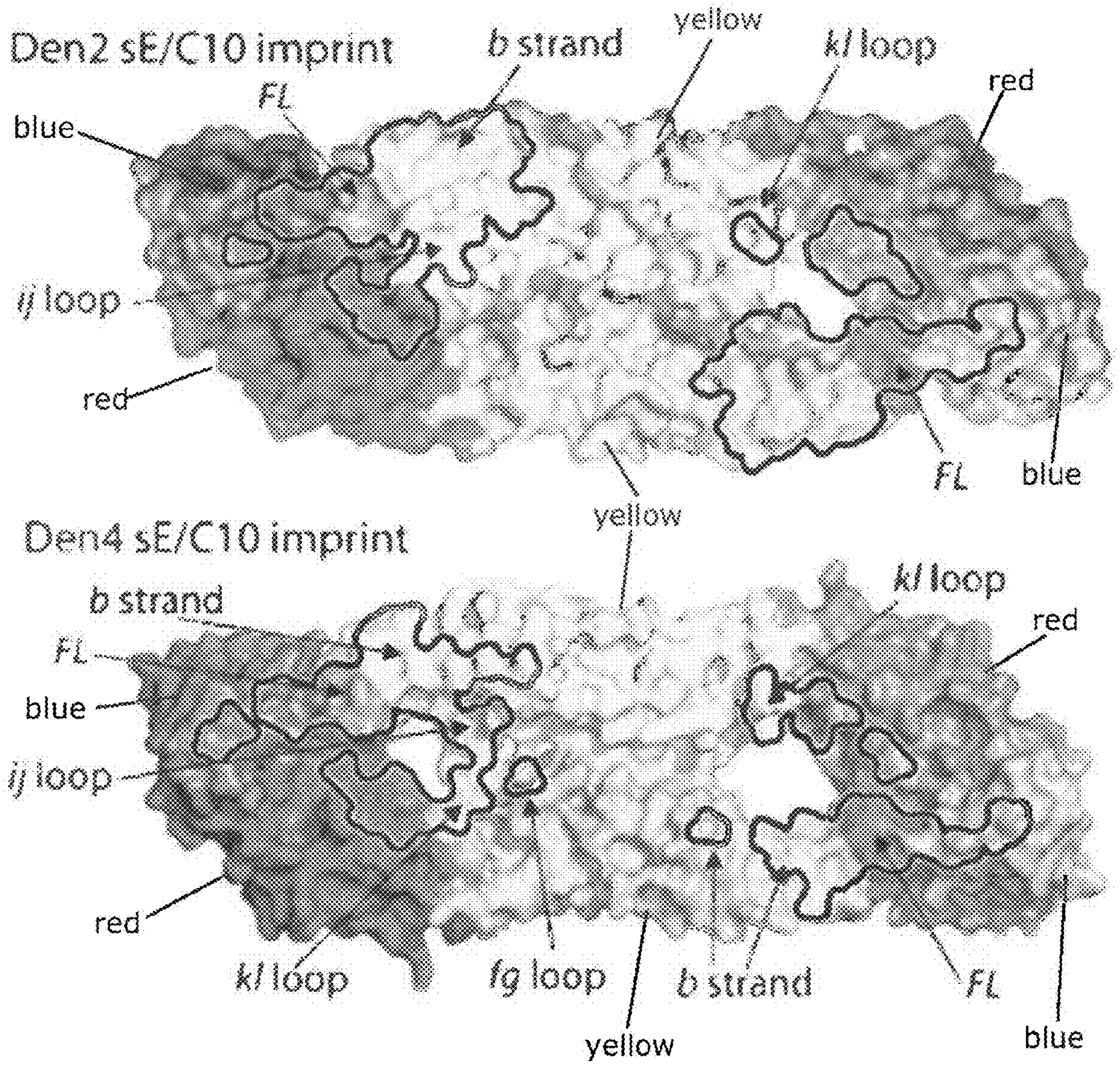

FIGS. 22A-B. C10 BNA imprints on sE dimers of dengue serotypes 2 and 4. (FIG. 22A) Surface representation of DENV-2 sE as viewed from outside the virion, with exposed main chain atoms orange (top panel) or with main chain atoms+strictly conserved side chains in orange, and highly conserved side chains in yellow (bottom panel). The epitopes of EDE1 BNA C10 (black outline) and a EDE2 BNA B7 (green outline) are indicated. (FIG. 22B) The surface of the DENV-2 (top panel) and DENV-4 (bottom) sE dimer extracted from the complex with C10, color-coded by domains as in FIG. 11A-F. The C10 footprint is shown in each case. Note the asymmetry in conformation. The bigger "hole" on the right hand side of the dimer (in both panels) is due to the ij loop being disordered, and the smaller one on the left (bottom panel, DENV-4 sE/C10) is due to the kl loop disordered.

Figure 23A:
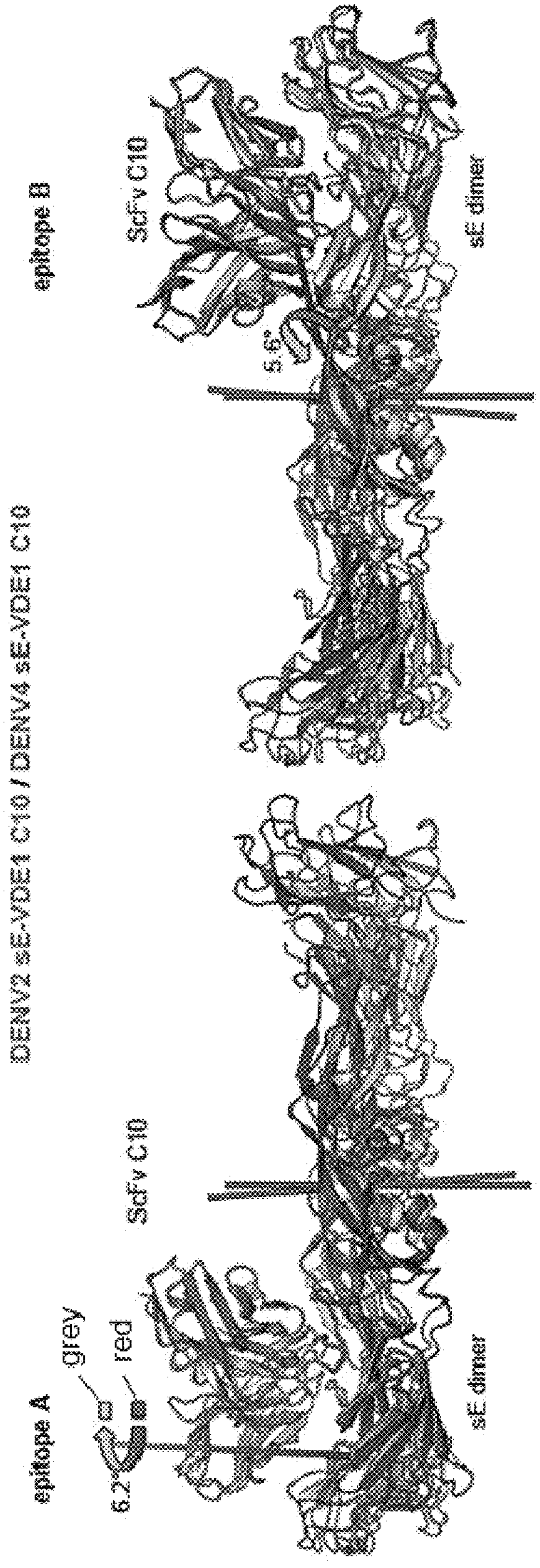
Figure 23B:
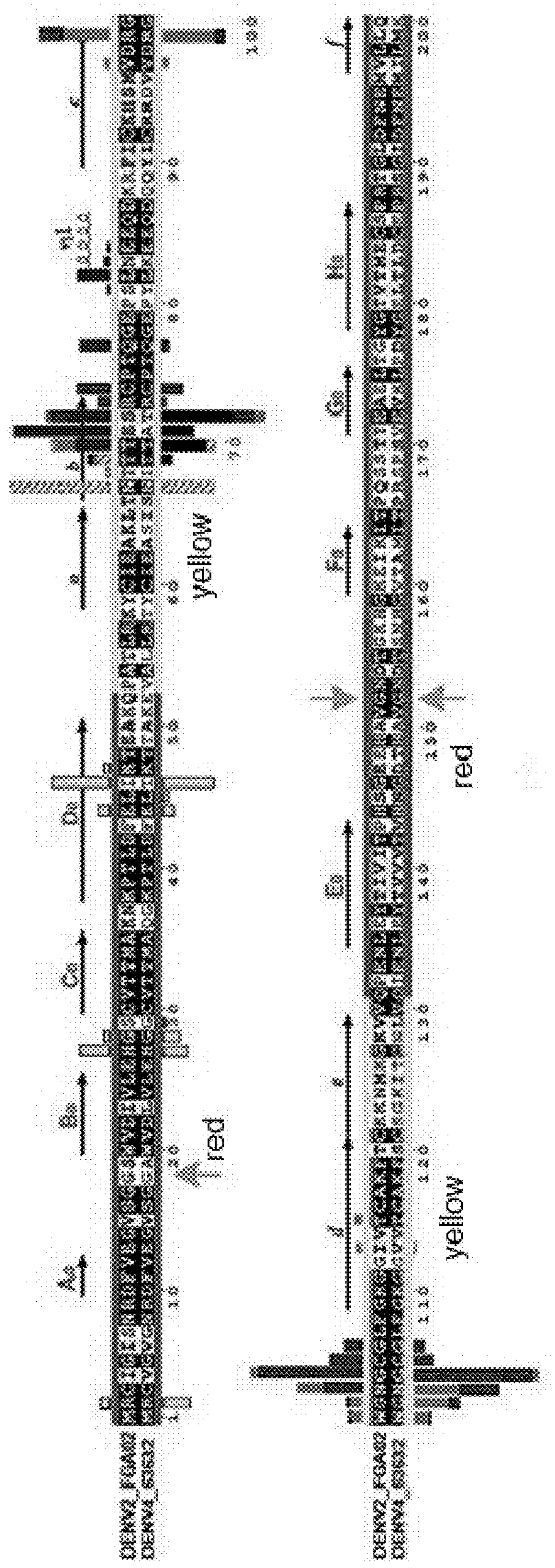

FIG. 23A-B—Comparison of the C10 interactions with DENV-2 and DENV-4 sE. FIG. 23A) The structures of DENV-2 (red) and DENV-4 (grey) sE dimers in complex with C10 were superposed on the C10 moiety. The axes of the sE dimers are drawn at the center, colored accordingly. For clarity, only the C10 scFv on which the superposition was made is displayed per complex. Upon superimposing the antibodies, the sE dimers match only locally, resulting in slightly different orientations of the dimer axes, as drawn. The sE dimers become rotated with respect to each other by about 6 degrees about the axes drawn in blue (labeled with a grey/red curved arrow), which have strikingly different orientations when the superposition is done on the scFv on the left (bound to epitope A) than on the one on the right (bound to epitope B), highlighting the asymmetry of C10 binding to the sE dimer. FIG. 23B) The C10 contacts plotted on an alignment of DENV-2 (above) and DENV-4 sE (below), showing that there is a very similar pattern of contacts in the two complexes. The background of the sequence corresponds to that of FIG. 15A in the main text, showing the conservation on the four serotypes.

FIGS. 24A-E. Detected asymmetry of BNA binding to the sE dimer. These Figures provide the histograms of number of contacts per sE residue in the structures of all of the independent complexes analyzed here, in FIGS. 24A-E: (FIG. 24A) EDE1 C8/DENV-2 sE; (FIG. 24B) EDE1 C10/DENV-2 sE; (FIG. 24C) EDE2 A11/DENV-2 sE; (FIG. 24D) EDE2 B7/DENV-2 sE; (FIG. 24E) EDE1 C10/DENV-4 sE. Each panel is divided in two portions: part (I) displays the immune complex viewed down the 2-fold axis of the sE dimer on the left (for clarity, the constant domain of the Fab fragments was removed), and on the right with the antibody removed altogether, to show the epitope. This part also defines epitopes A and B used in II. Part (II) shows the histogram of contacts corresponding to the A and B epitopes in the dimer, with the histogram bars color-coded as indicated in the key, to map the antibody region involved in the contact (in parenthesis is the symbol used in FIG. 15 A to mark the corresponding contact). Note that the contacts pattern remains the same, but the number of contacts is not identical on the two epitopes of the sE dimer. The crystals of DENV-2 sE/EDE2 C10 had two complexes in the asymmetric unit (i.e., two sE dimers, each with two C10 scFv), so that in total there are 4 independent views of the epitope, labeled A-D, described in FIG. 24 B.

Figures 25, 25A, 25B, 25C:
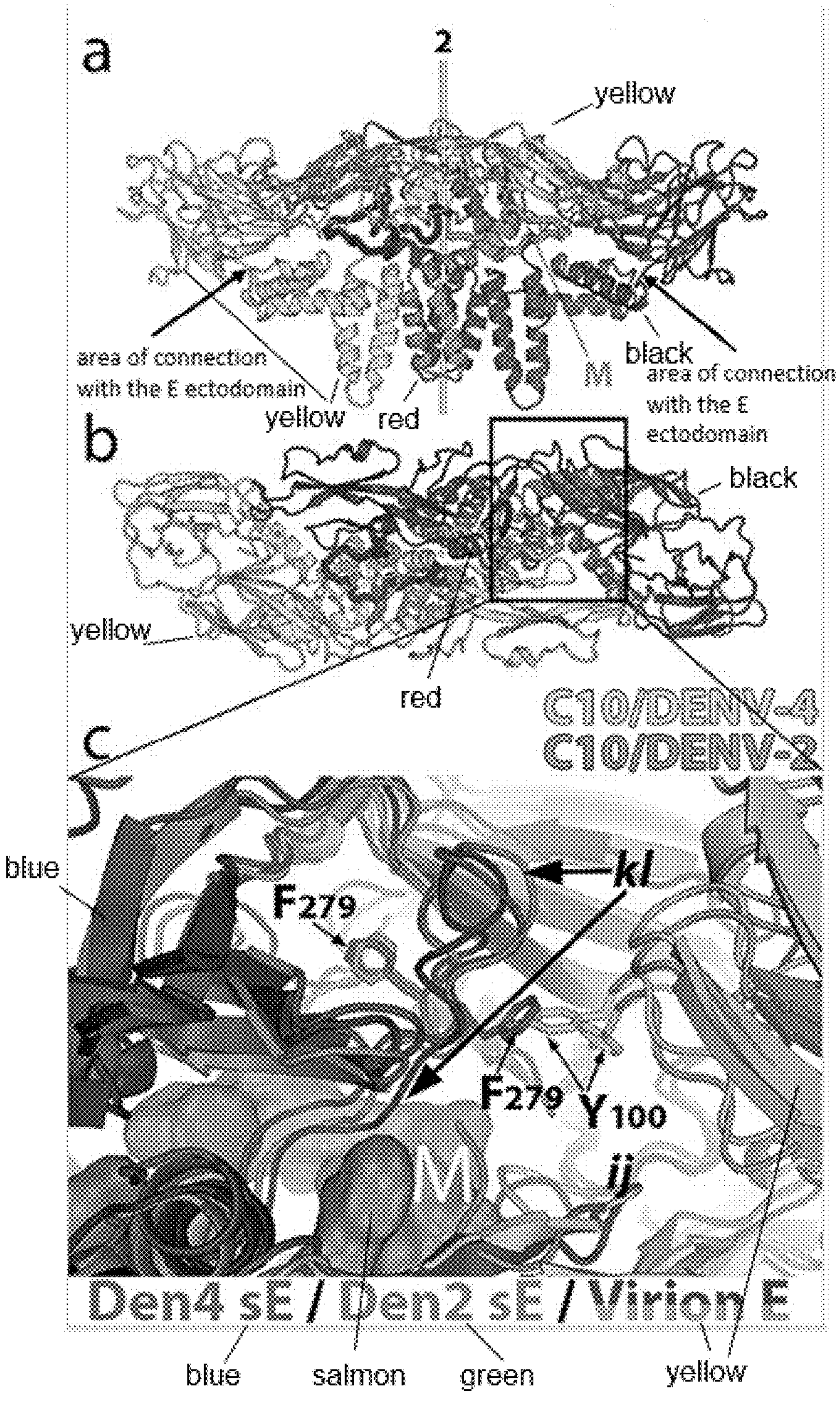

FIGS. 25A-C. EDE1 C10 residue Y100 (CDR H3) is likely to interact with F279 on mature dengue virions. (FIG. 25A) One of the 90 E/M heterotetramers that compose the mature DENV-2 particle was extracted from the 3.5 Å cryo-EM reconstruction[9], and is displayed in side view (2-fold axis vertical, drawn as a white rod labeled "2") with the two E subunits in grey and yellow and the two M subunits in red and salmon. The two black arrows indicate the connection between the E ectodomain (which corresponds to sE) with the α-helical membrane interacting region (the horizontal "stem" α-helices and the vertical TM αhelices). The N-terminal segment of M is seen interacting underneath the E dimer (pink arrow). (FIG. 25B) View down the 2-fold axis, with the region magnified in FIG. 25C framed. (FIG. 25C) The view has been slightly tilted, for clarity, with respect to the view in FIG. 25 B, with the structures of both C10 complexes (DENV-2 and -4 sE) superposed onto virion E. The labels match the color of the corresponding structures (DENV-2 sE/C10 green/mustard; DENV-4 sE/C10 blue/beige, and virion E as in FIGS. 25A and 25B. The M protein is shown as a salmon surface (labeled in white). It lies underneath the E dimer, where it buttresses the base of the kl hairpin (comprised between the arrows, labeled)) and also the ij hairpin across the dimer interface, inducing a different conformation of the kl hairpin, such that F279 (labeled) points away from the hydrophobic core of the E protomer (dark grey sticks), whereas in the sE protein structures (including unliganded sE, not shown) it is part of the hydrophobic core (green and blue sticks, labeled). The side chain of Y100 (labeled) in CDR H3 of C10 has alternative conformations because it doesn't find its partner in sE (Y100 is also illustrated in FIG. 18 D, left panel). The CDR H3 loop is flexible enough so that the Y100 could make a stacking interaction with F279 (which is conserved across serotypes, see FIG. 15 A) in the conformation observed on the virion.

FIGS. 26A-E. Histogram of contacts on the antibody residues. This Figure mirrors FIG. 24A-E, this time showing the contacts on the antibody side. (FIG. 26A) C8; (FIG. 26B) C10 (from the complex with DENV-2 sE) (FIG. 26C) A11;

(FIG. 26 D), B7; (FIG. 26 E) C10 (from complex with DENV-4 sE). In each panel, Part I shows the BNA variable domain extracted from the corresponding complex, colored grey (VH dark grey, VL light grey) with somatic mutations in red and junction residues arising from recombination in green. Side chains involved in contacts are displayed in ball and stick and labeled. Part II shows the histogram of the number of atomic contacts per residue, color-coded according to the key to indicate the region of sE that is contacted (in parenthesis, the symbol used in FIG. 15B to mark the corresponding contact). The sequence numbering and the background corresponds to Kabat convention (as in FIG. 15B). The CDRs corresponding to the IMGT convention are displayed as dotted orange lines above the sequences. Somatic mutations are in red, residues arising from VDJ (or VI) recombination are in green.

FIG. 27. Comparison with the binding properties of potent anti-EDE antibodies targeting other viruses.

FIG. 28. Sequences of the Dengue envelope protein from serotypes 1 to 4 FIG. 29. Sequences of the EDE1 and EDE2 type antibodies identified in Example 1.

FIGS. 30A-D. Methods of performing a neutralisation test.

FIG. 31. Contact residues in the envelope protein derived from crystal structures.

FIG. 32. Covalently cross-linked DV2 E dimers.

Figure 33:
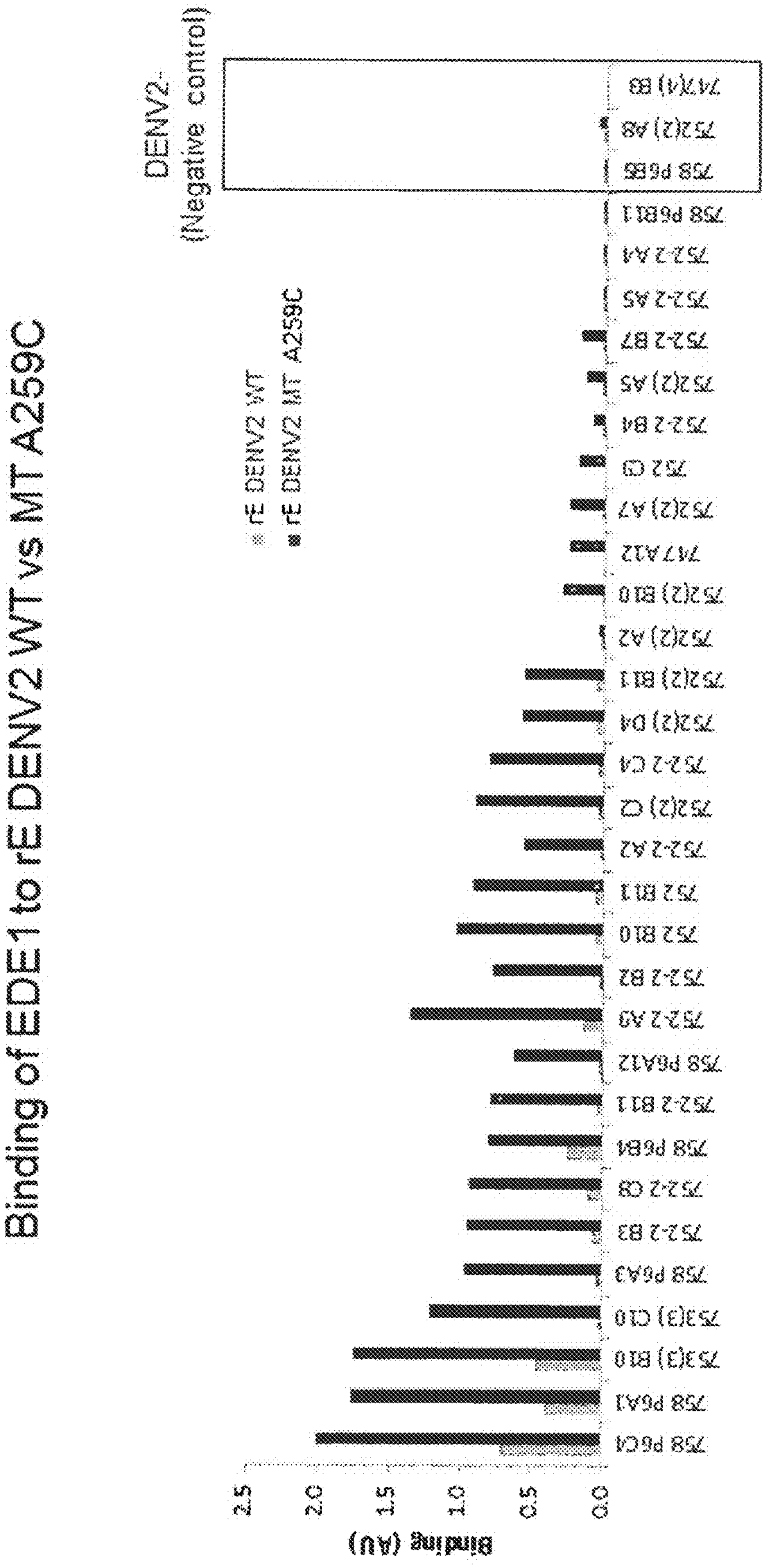

FIG. 33. Binding of EDE1 to rE DENV2 WT vs MT A259C

Figure 34:
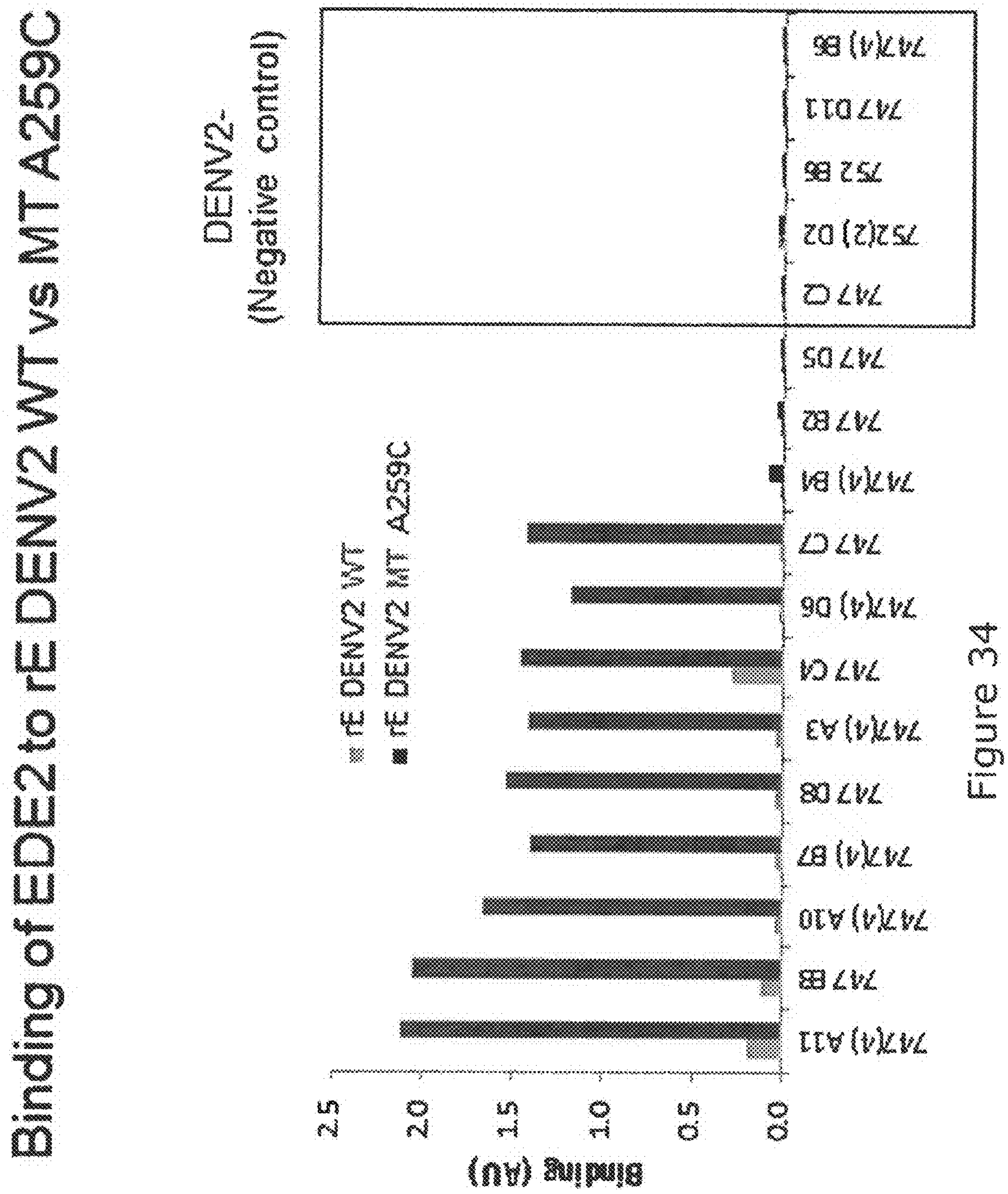

FIG. 34. Binding of EDE2 to rE DENV2 WT vs MT A259C

Figure 35:
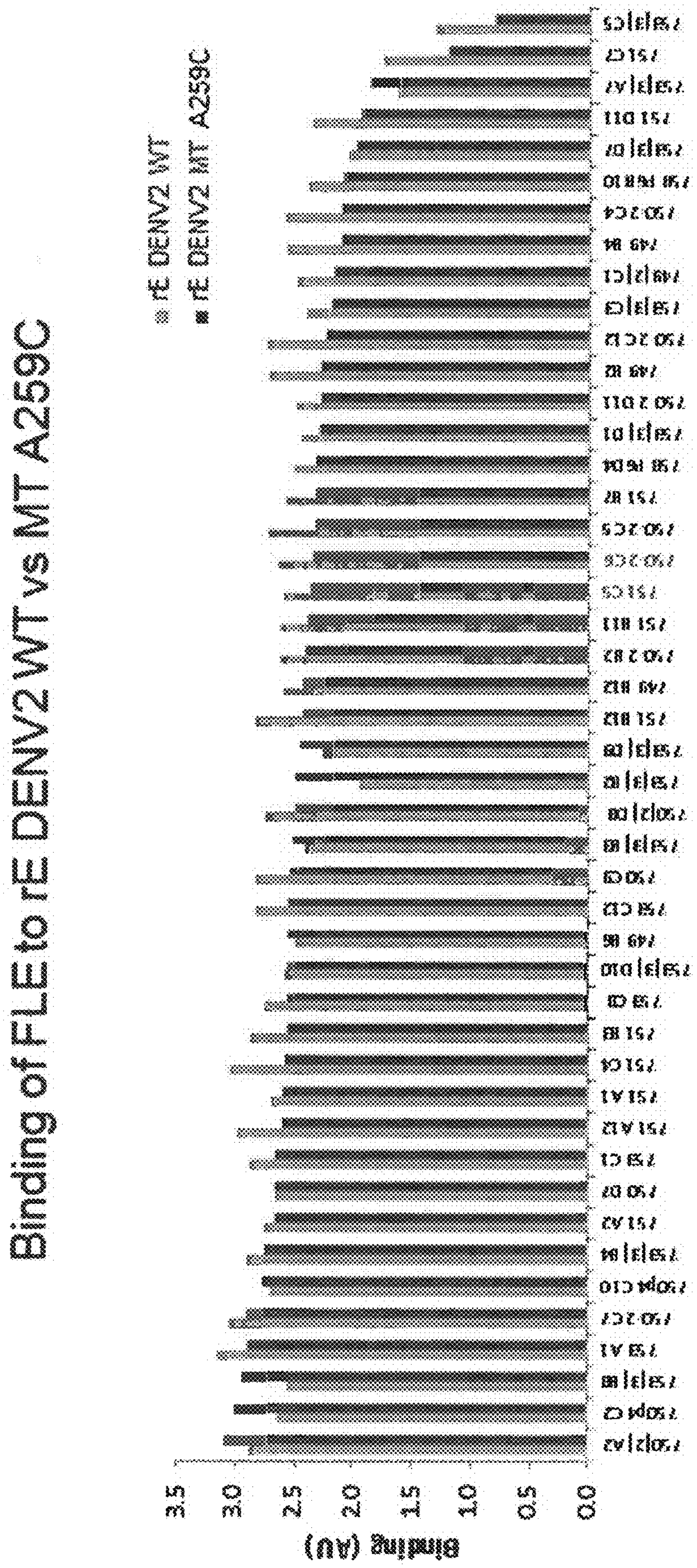

FIG. 35. Binding of FLE to rE DENV2 WT vs MT A259C

Figure 36:
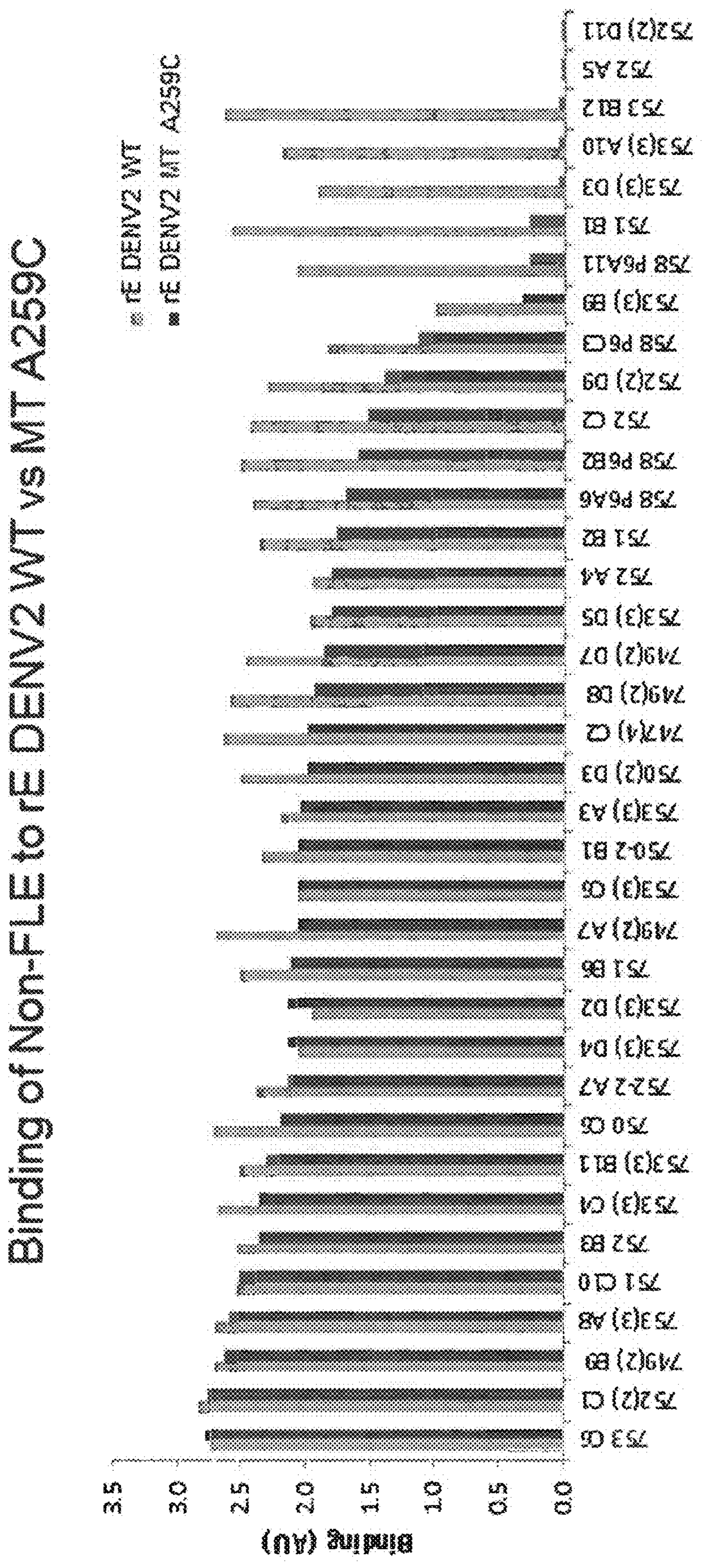

FIG. 36. Binding of Non-FLE to rE DENV2 WT vs MT A259C

Figure 37:
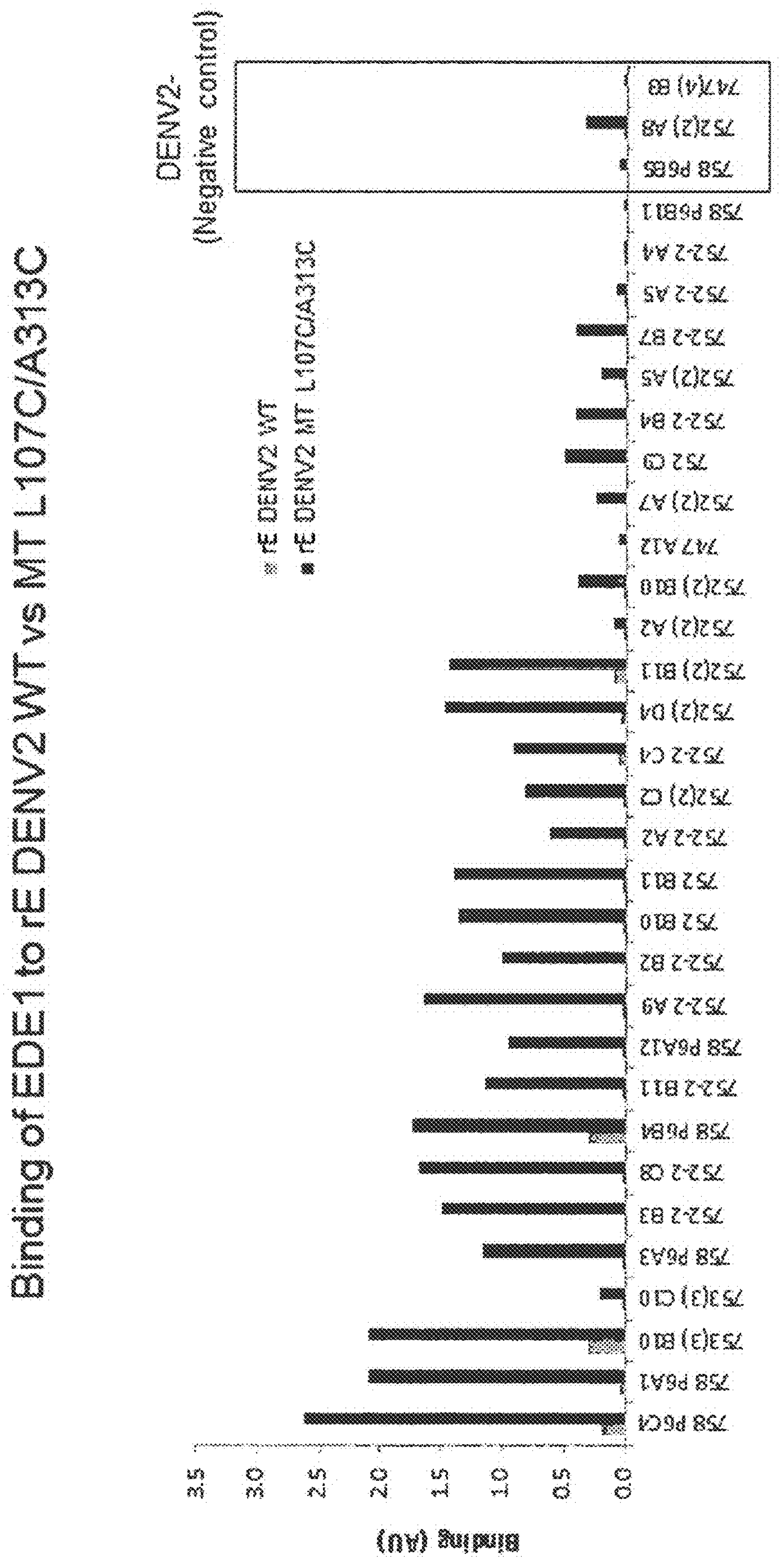

FIG. 37. Binding of EDE1 to rE DENV2 WT vs MT L107C, A313C

Figure 38:
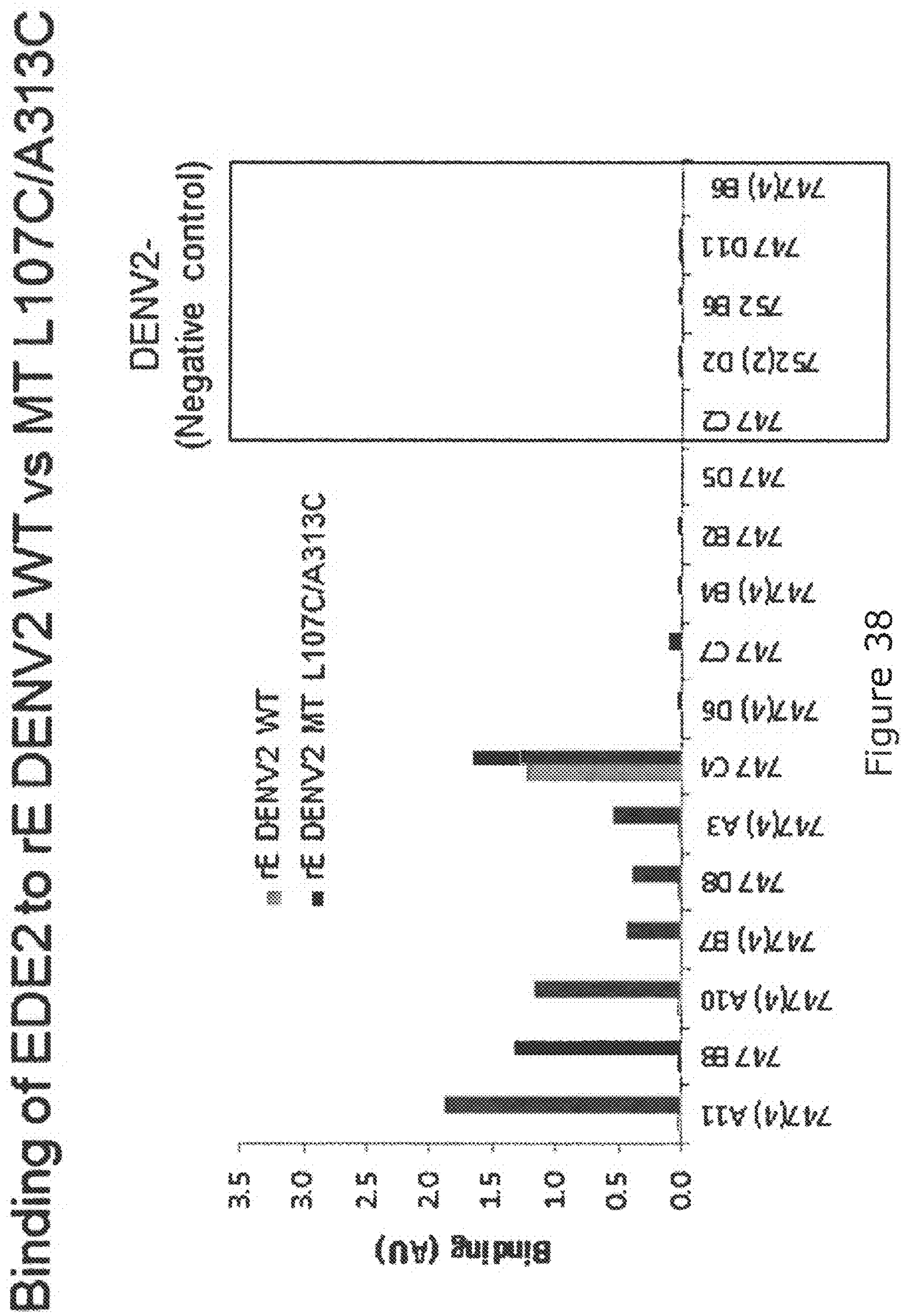

FIG. 38. Binding of EDE2 to rE DENV2 WT vs MT L107C, A313C

Figure 39:
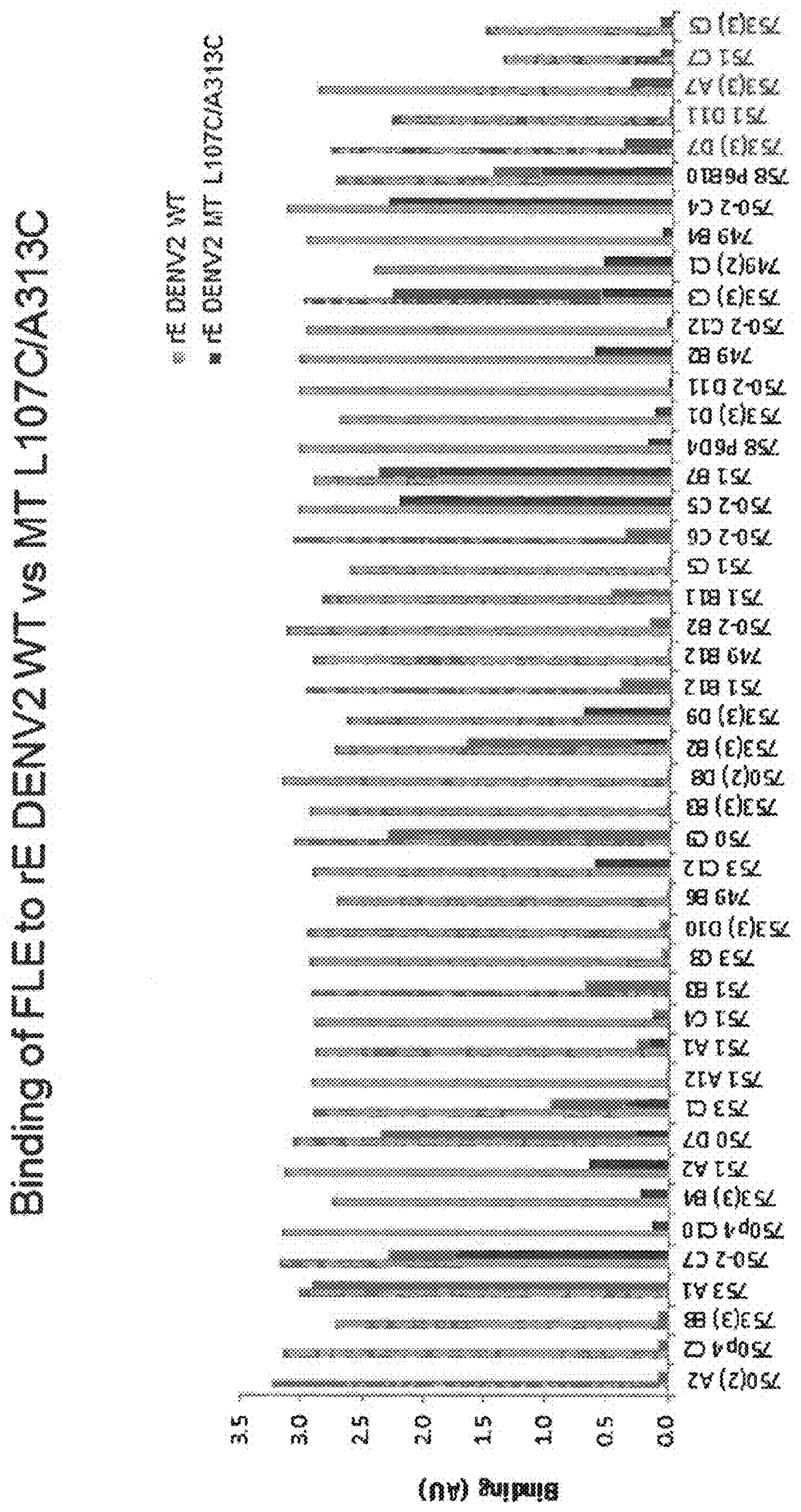

FIG. 39. Binding of FLE to rE DENV2 WT vs MT L107C, A313C

Figure 40:
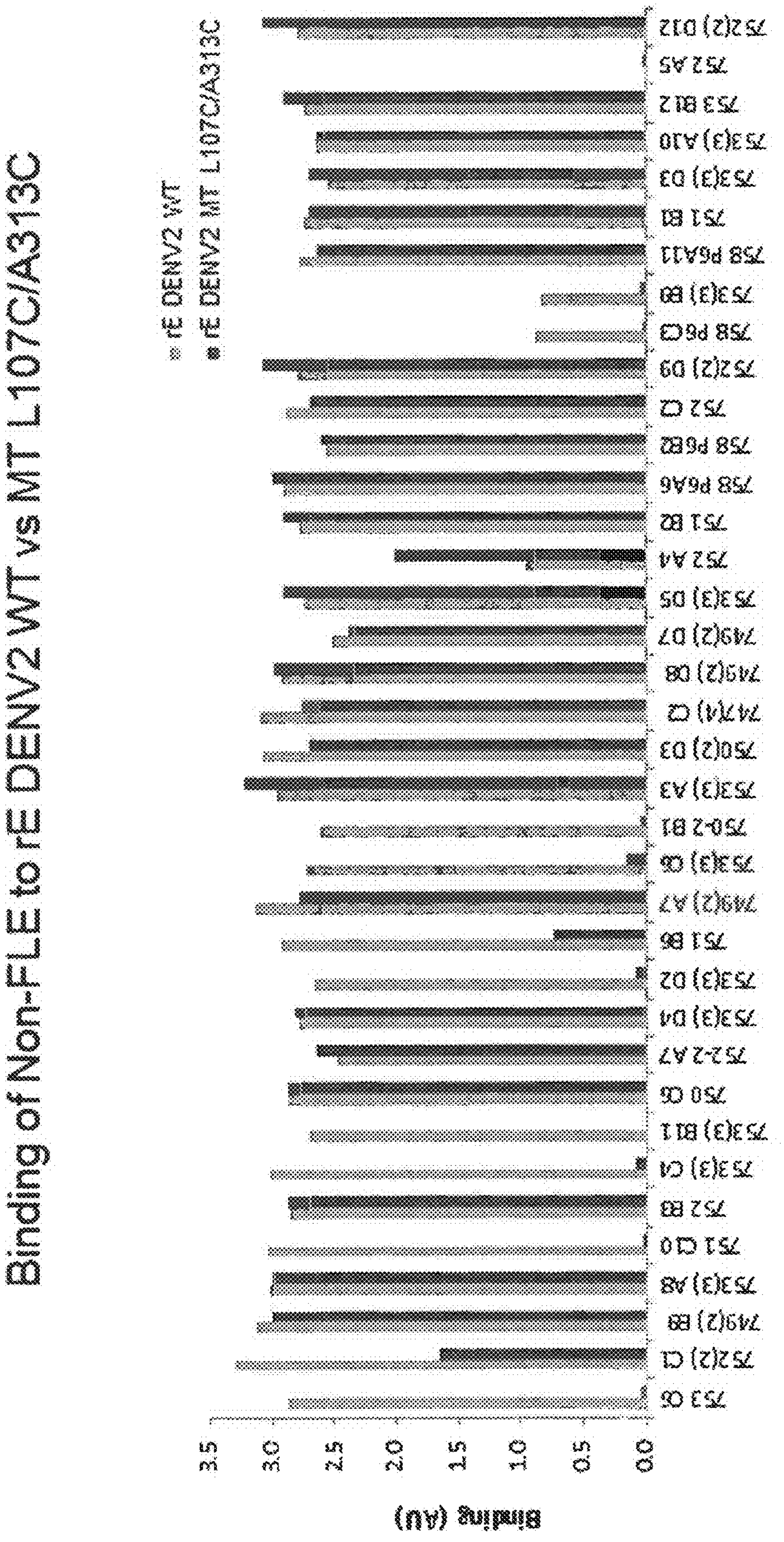

FIG. 40. Binding of non-FLE to rE DENV2 WT vs MT L107C, A313C

Figure 41:
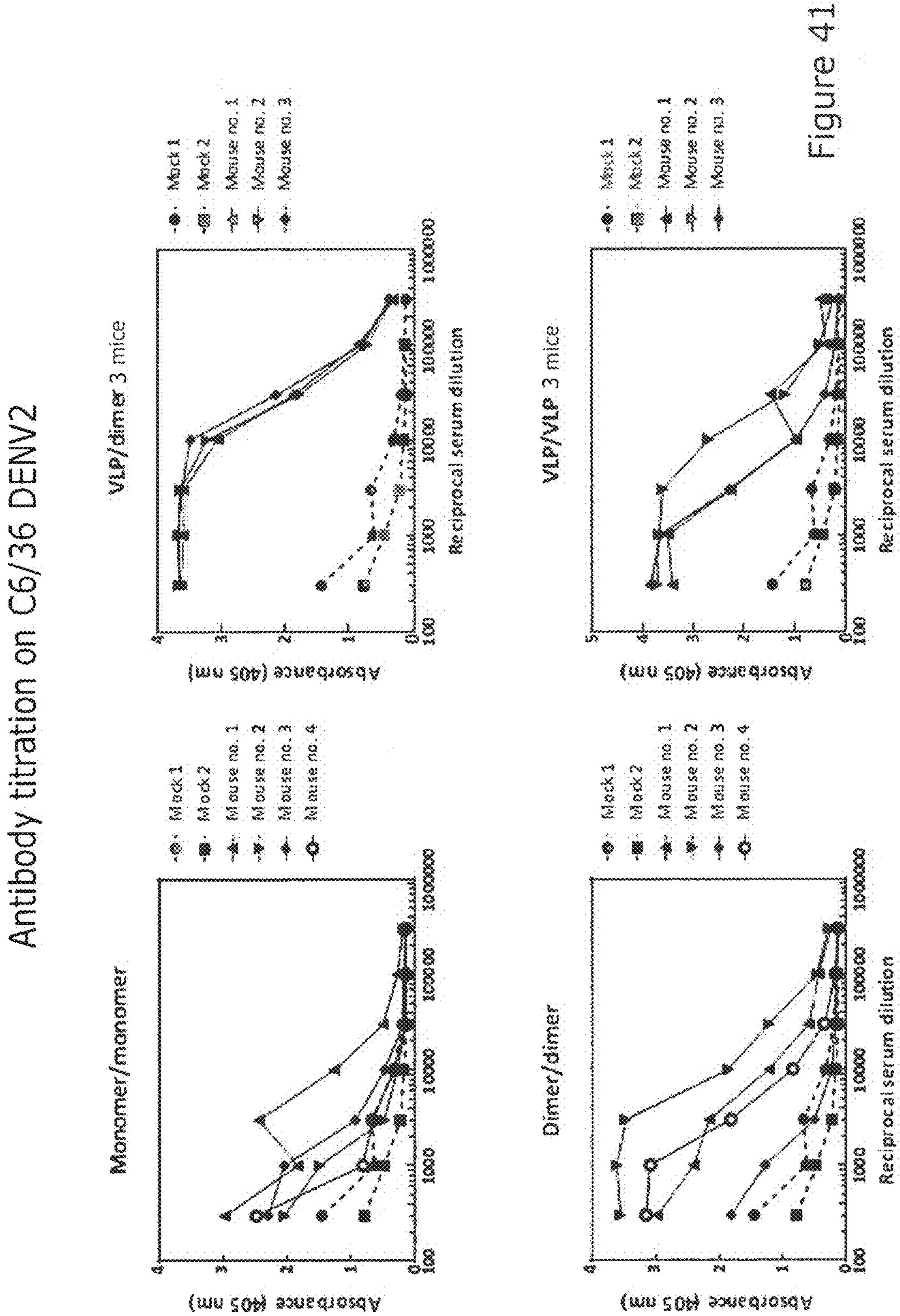

FIG. 41. Antibody titration on C6/36 DENV2

Group 1 Monomer/Monomer
 prime and boost with E WT. E WT
Group 2 Dimer/Dimer
 prime and boost with E A259C mutant
Group 3 VLP/VLP
 prime and boost with prM/E viral like particle (VLP)
Group 4 Dimer/VLP
 prime with E A259C mutant followed by boosting with VLP
Group 5 VLP/Dimer
 prime with VLP followed by boosting with E A259C mutant
Group 6 mock
 non immunisation FIG. 42. Cross reactivity: Binding to live virus (pooled serum)

Group 1 Monomer/Monomer
 prime and boost with E WT. E WT
Group 2 Dimer/Dimer
 prime and boost with E A259C mutant
Group 3 VLP/VLP
 prime and boost with prM/E viral like particle (VLP)
Group 4 Dimer/VLP
 prime with E A259C mutant followed by boosting with VLP
Group 5 VLP/Dimer
 prime with VLP followed by boosting with E A259C mutant
Group 6 Mock
 non immunisation FIG. 43. Neutralisation of mouse serum: C6/36 DENV2

Figure 44:
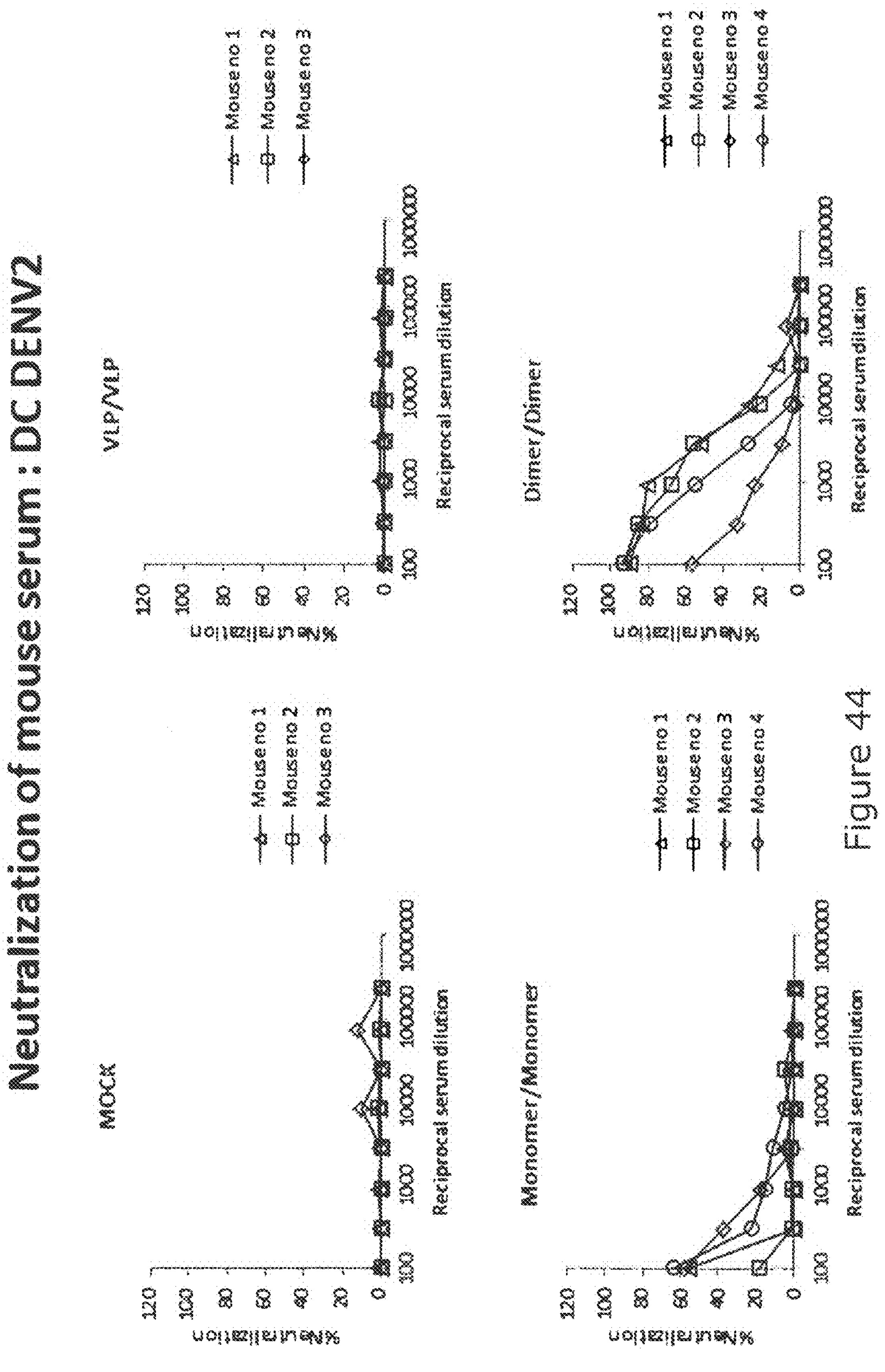
Figure 44:
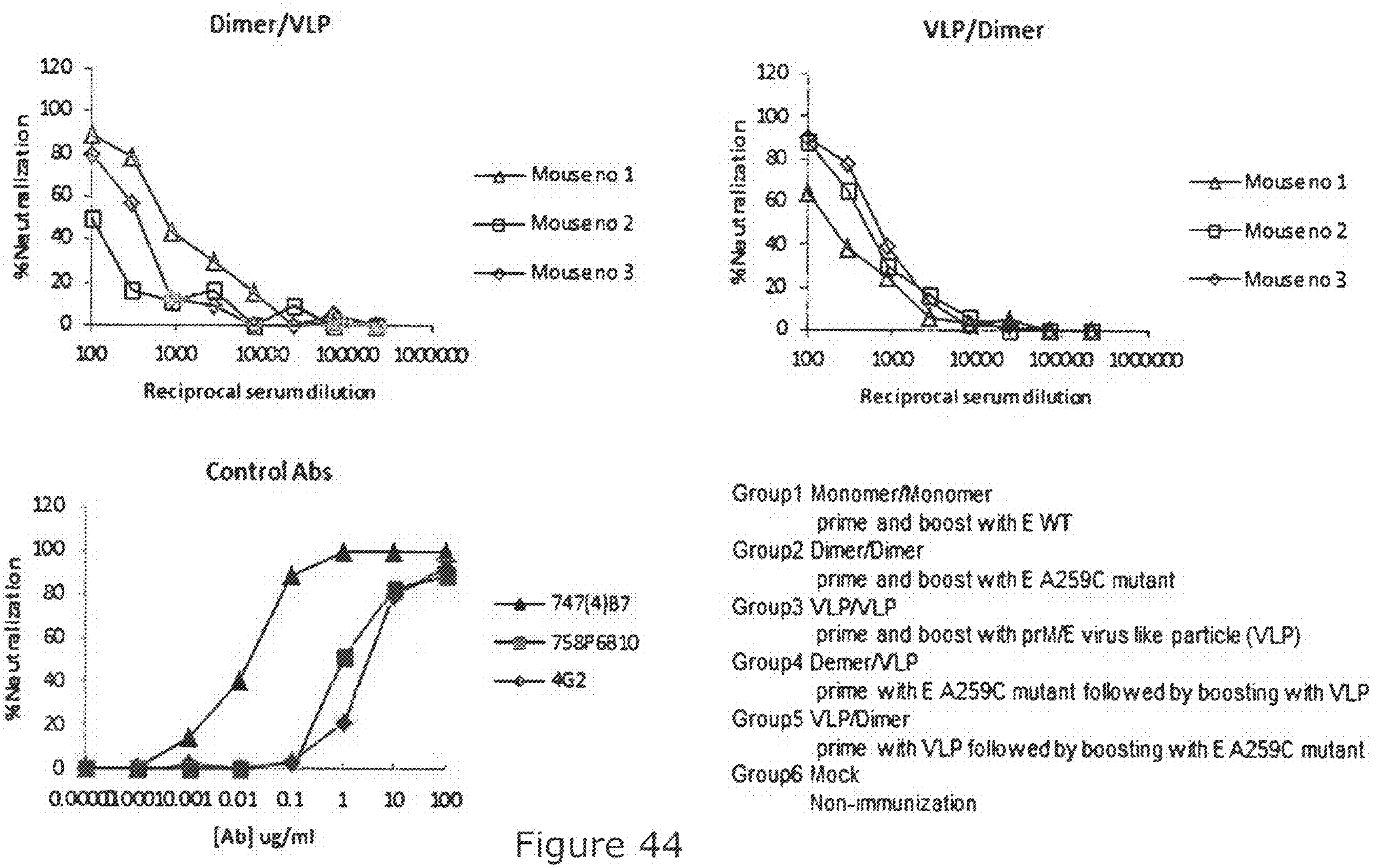

Group 1 Monomer/Monomer
 prime and boost with E WT
Group 2 Dimer/Dimer
 prime and boost with E A259C mutant
Group 3 VLP/VLP
 prime and boost with prM/E viral like particle (VLP)
Group 4 Dimer/VLP
 prime with E A259C mutant followed by boosting with VLP
Group 5 VLP/Dimer
 prime with VLP followed by boosting with E A259C mutant
Group 6 Mock
 non immunisation FIG. 44. Neutralisation of mouse serum: DC DENV2

Group 1 Monomer/Monomer
 prime and boost with E WT. E WT
Group 2 Monomer/Monomer
 prime and boost with E A259C mutant (dimer/dimer)
Group 3 VLP/VLP
 prime and boost with prM/E viral like particle (VLP)
Group 4 Dimer/VLP
 prime with E A259C mutant followed by boosting with VLP
Group 5 VLP/Dimer
 prime with VLP followed by boosting with E A259C mutant
Group 6 Mock
 non immunisation FIG. 45. ADE: Pooled mouse serum: U937

Group 1 Monomer/Monomer
 prime and boost with E WT. E WT
Group 2 Monomer/Monomer
 prime and boost with E A259C mutant (dimer/dimer)
Group 3 VLP/VLP
 prime and boost with prM/E viral like particle (VLP)
Group 4 Dimer/VLP
 prime with E A259C mutant followed by boosting with VLP
Group 5 VLP/Dimer
 prime with VLP followed by boosting with E A259C mutant
Group 6 Mock
 non immunisation

EXAMPLES

Example 1—Human DENV Antibodies Form Two Distinct Groups Based on their Ability to Bind to Dengue Envelope Protein on a Western Blot Samples from 7 patients (Table 1) were used to produce 145 human monoclonal antibodies reacting to the DENV envelope protein[32,33]. Plasmablasts ($CD3^-$, $CD20^{lo/-}$, $CD19^+$, $CD27^{hi}$, $CD38^{hi}$) were sorted from peripheral blood; Elispot demonstrated 5090% of these cells secreted anti-DENV antibodies, consistent with frequencies reported by others[34,35]. 84% of these antibodies reacted against all four DENV serotypes, 13% reacted to 2 or 3 serotypes and only 3% reacted to a single serotype (FIG. 1*a*).

TABLE 1

Summary of DENV-infected patients enrolled in the study

| Patient id | Severity | Serotype of infection | Serology | Day of illness | Frequency of plasmablasts vs. total CD19+ cells (%) | Frequency of DENV-specific B cells vs. total IgG + IgM secreting cells (%) | No. of anti-E Abs | κ/λ |
|---|---|---|---|---|---|---|---|---|
| 747 | DHF | DENV2 | Secondary | 6 | 64.9 | 76.9 | 18 | 7/11 |
| 749 | DF | DENV1 | Secondary | 4 | 56.7 | 62.4 | 11 | 1/10 |
| 750 | DHF | DENV1 | Secondary | 5 | 67.9 | 71.5 | 17 | 5/12 |
| 751 | DF | DENV1 | Secondary | 4 | 32.7 | 75.6 | 15 | 8/7 |
| 752 | DHF | Unknown | Primary | 4 | 68.3 | 47.0 | 32 | 31/1 |
| 753 | DHF | DENV1 | Secondary | 5 | 74 | 89.9 | 35 | 17/18 |
| 758 | DHF | Unknown | Secondary | 5 | ND | ND | 17 | 6/11 |

The initial antibody screen was performed by ELISA using captured whole virions, rather than recombinant protein or fixed cells, to make sure we obtained a fully representative panel of antibodies. Only 57% of the antibodies reacted to DENV envelope by Western Blot (FIG. 1*a*), the WB negative mAbs also failed to react to recombinant E by ELISA. This allowed us to group the antibodies into two broad groups, WB reactive and those which only recognize an epitope present on the intact virion; from hereon we refer to these antibodies as reactive to virion dependent epitopes or Envelope Dimer Epitope (VDE or EDE). Most of the WB positive antibodies were fully crossreactive between the four virus serotypes whilst for the EDEEDE mAbs 41/62 were fully crossreactive with a further 17/62 reacting against DENV-1, 2&3 (FIG. 1*b*). Neutralization assays on virus produced in C6/36 insect cells for three antibodies from each group are shown in FIG. 2. The fusion loop and EDEEDE antibodies were broadly neutralising against all four virus serotypes. For EDE2 747(4)A11 and 747(4)B7 there was lower activity to Den4, which relates to the lack of N-linked glycan at position N153 in the Den4 strain H241.

Methods Relevant to this and Other Examples

Samples. Blood samples were collected from inpatients following written informed consent. The study protocol was approved by the Scientific and Ethical Committee of the Hospital for Tropical Diseases, the Oxford Tropical Research Ethical Committee and the Riverside Ethics Committee in the UK. Laboratory confirmation of dengue infection was determined by RT-PCR detection of DENV nucleic acid (which also confirmed the infecting serotype), NS1 antigen lateral flow test or seroconversion in an IgM ELISA test. Disease severity was classified according to 1997 World Health Organization criteria. Of the patients enrolled in the study, 2 patients were classified as mild symptom Dengue Fever (DF) and 5 patients were classified as severe symptom with plasma leakage and bleeding Dengue Heamorrhagic Fever (DHF) (Table 1). Secondary infection were defined based on the ratio of dengue specific IgM to IgG less than 1.8 7. Blood samples for B cell sorting were collected during the hospitalization period at time points where the blood plasmablast population was apparent. PBMCs were isolated from whole blood by Ficoll-Hypaque density gradient centrifugation and resuspended in 10% FCS/RPMI for immediate use.

Cells and Antibodies. The C6/36 cell line, derived from the mosquito *Aedes albopictus*, was cultured in Leibovitz L-15 at 28° C. Vero, U937 and 293T or furin-transfected 293T cells were grown at 37° C. in MEM, RPMI 1640 and DMEM respectively. All media was supplemented with 10% heat-inactivated foetal bovine serum (FBS), 100 units/ml penicillin, 100 μg/ml streptomycin and 2 mM L-Glutamine. The furin-deficient LoVo cell line was purchased from ATCC and maintained in F-12 as recommended. Monocytederived dendritic cells (DC) were prepared as previously described[10].

Antibodies against human CD3, CD19, CD20, CD27 and CD38 (BD Pharmingen), AntiHuman IgG-ALP (Sigma) and anti-Human or mouse IgG-HRP (DAKO) were used in the experiments. anti-DENV envelope, 4G2, and anti-DENV prM, 1H10, murine monoclonal Abs were gifts from Dr C. Puttikhunt and Dr W. Kasinrerk (Puttikhunt, 2003). anti-DENV NS3, E1D8 was a gift from Prof. Eva Harris.

Virus Stock. Dengue virus serotype 1 (Hawaii), serotype 2 (16681), serotype 3 (H87) and serotype 4 (H241) were grown in C6/36 cells. In addition, DENV2 was propagated in DC, LoVo, 293T and Furin-transfected 293T and cell-free supernatants were collected and stored at −80° C. Viral titres were determined by a focus-forming assay on Vero cells and expressed as focus-forming units (FFU) per ml[26]

Generation of DENV-Specific Human Monoclonal Abs. DENV-specific human mAbs were generated from activated B cells/plasmablasts[32,33]. Briefly, PBMC were stained with anti-CD3, CD19, CD20, CD27 and CD38. Activated antibody secreting cells (ASCs) were then gated as $CD19^{+}$, $CD3^{-}$, $CD20^{lo/-}$, $CD27^{high}$, $CD38^{high}$. Single ASCs were sorted into each well of 96 well PCR plates containing RNase inhibitor (Promega). Plates were centrifuged briefly and frozen on dry ice before storage at −80° C. RT-PCR and nested PCR were then performed to amplify Gamma, Lambda and Kappa genes using cocktails of primers specific for IgG. PCR products of heavy and light chains were then digested with the appropriate restriction endonuclease and cloned into IgG1, Igκ or Igλ expression Vectors; gifts from Dr Hedda Wardemann. To express antibodies, heavy and light chain plasmids were co-transfected into the 293T cell line by Polyethylenimine method and antibody supernatant was harvested for further characterization.

ELISPOT Assay. Elispot plates (Millipore) were coated with either anti-human Ig (Invitrogen) or UV inactivated DENV1-4. Plates were washed with RPMI and blocked with 1% BSA/RPMI for 1 hour. Sorted ASCs were added at 500 cells to the anti-Ig and the DENV coated wells and incubated overnight at 37° C. in 5% $CO_2$. Plates were washed and incubated with biotinylated anti-human IgG and IgM (Sigma) for 2 hrs at room temperature, followed by Streptavidin-ALP (Sigma). The reaction was developed and spots were counted using an AID Elispot plate reader.

Detection of DENV-Specificity and Serotype Cross-Reactivity by ELISA. DENV1-4 and mock uninfected supernatant were captured separately onto a MAXISORP immunoplate (NUNC) coated anti-E Abs (4G2). DENV captured wells were then incubated with 1 μg/ml of human mAbs followed by ALP-conjugated anti-human IgG. The reaction was visualized by the addition of PNPP substrate and stopped with NaOH. The absorbance was measured at 405 nm.

Recombinant Soluble DENV Envelope Protein ELISA. Plates were directly coated with 150 ng recombinant soluble E and bovine serum albumin (BSA) was used as negative control antigen. Protein coated wells were then incubated with 1 μg/ml of human monoclonal Abs followed by ALP-conjugated anti-human IgG. PNPP substrate was finally added and the reaction was measured at 405 nM.

Western Blot Analysis. For western blot analysis, DENV supernatant from C6/36 cells was prepared in non-heated and non-reducing conditions and run on 12% SDS polyacryramide gels and electroblotted onto nitrocellulose membranes (Amersham). The membranes were then blocked with 5% skimmed milk and probed with DENV-specific human mAbs followed by HRP-conjugated anti-human IgG Abs, membranes were developed with enhanced chemiluminescence substrate (Amersham).

Example 2—Mutational Analysis Reveals that the EDE Antibodies and the WB Reactive Antibodies Bind Distinct Epitopes To gain more insight into the epitopes recognized by the mAbs, we created 65 virus like particles (VLP's) containing alanine substitutions at solvent exposed residues predicted to be on the virion surface. These were taken from the 3D structure of the mature virus particles[4, 7, 8]. These mutant VLP's were screened against the 145 monoclonal antibodies by ELISA[22, 36]. Mutations that resulted in >80% reduction of antibody binding were deemed significant. Using this panel 112 of the 145 mAbs were assigned an epitope on the envelope protein. Thirty three antibodies, all of which react to E by WB, remained unmapped using the mutant VLP panel. The epitope mapping results are shown in FIGS. 1*c* and 1*n* more detail in FIG. 6. These epitopes can be broadly clustered into two groups:

Group 1: Fusion Loop; a restricted set of residues in and around 101W defining the previously described or classical fusion loop epitope (FL). 46 of the 83 antibodies, which bound to envelope on WB, were sensitive to mutation at position 101W, which has been previously shown to be a key residue for the binding of a number of anti-DENV mAbs[37,38]. Of the FL specific mAbs, 40 of the 46 were sensitive to the W101 mutation only whilst other epitopes contained combinations of the residues W101, G106, and L107. The crystal structure of FL mAb E53 bound to the envelope protein from West Nile virus showed contacts with residues 104-110, but not 101W and with resides 74-79 in the bcloop[39]. Only two of the FL specific mAbs were sensitive to changes in the bc-loop where binding was lost when amino acids 76-79 were changed to alanine similar to the 1C19 mAb[40].

Group 2: The EDE antibodies; these could be subdivided into five distinct subgroups based upon the pattern of reactivity to the VLP mutants (FIG. 1*c* and FIG. 6). The majority of the EDE antibodies were sensitive to changes in fusion loop residue 101, but are not to be confused with the classical "Fusion Loop" specific antibodies described above as the epitope is much more extensive, with additional determinants on domains I, II and III. The majority of EDE antibodies can be divided between two distinct subgroups, EDE1 and EDE2, differentiated by sensitivity to changes at residues 153 and 155 in EDE2, which will disrupt an N-linked glycosylation site. Twelve antibodies constituted three further subgroups with different epitopes and function; EDE3 mAbs were similar to EDE1 mAbs but also sensitive to changes at 107L and 295K. EDE4 were not sensitive to changes at 101W and reacted best to acidified virus particles (FIG. 4B). Finally, EDE5 mAbs constitutes a group of 5 mAbs, which bind to the fusion loop 101W only, but the epitope is only recapitulated on intact virions, EDE3, 4 and 5 are all poorly neutralizing antibodies FIGS. 3A and 3B.

The VLP mutagenesis experiments suggest the EDE is a complex quaternary epitope encompassing more than one envelope protomer.

Methods

Antibody Epitope Mapping Using Virus-Like Particle (VLP) Mutants. Full length prM/E of DENV1 was cloned into the expression vector pHLsec to generate VLP (constructed by Dr Aleksandra Flanagan)[55]. VLP mutants were generated by PCR-based site-directed mutagenesis[62]. Mutagenic PCR was performed to substitute selected amino acid residues in the E protein with alanine using Pfx DNA polymerase (Invitrogen), if already alanine, mutation was made to glycine. After DpnI (NEB) treatment, PCR products were transformed into *E. coli*. All mutations were confirmed by sequencing. Plasmids were transfected into the 293T cell lines by Polyethylenimine method and culture supernatants were harvested for epitope mapping.

To identify the epitope-specific Ab, WT and mutant VLPs were captured with mouse anti-prM (1H10). DENV-specific human anti-E Abs were then added at 1-5 μg/ml followed by anti-human IgG-ALP. Finally, PNPP substrate was added and the reaction was stopped with NaOH and absorbance measured at 405 nm. The relative recognition index was calculated as [absorbance of mutant VLP/absorbance of WT VLP] (recognized by the test mAb)/[absorbance of mutant VLP/Absorbance of WT VLP] (recognized by a group of 4 mixed mAbs).

Example 3—the WB Reactive Antibodies are Incapable of Fully Neutralising Virus Made in Human Dendritic Cells, Unlike the EDE Antibodies During a DENV infection, the host is presented with two forms of virus; the initial exposure is to virus produced in insect cells, whilst virus produced in human cells drives subsequent rounds of infection and represents the vast bulk of virus encountered during infection. To look at these two different viral forms we compared neutralization of DENV-2 virus produced in C6/36 insect cells (C6/36-DENV) or in monocyte derived dendritic cells (DC-DENV), which are thought to be infected following injection of virus into the skin from the mosquito bite and to be a site of virus replication in the infected human host[20].

Of the 83 WB positive mAbs, 46 were mapped to the FL and 37 recognised an as yet unmapped binding site. Surprisingly, all 83 WB positive antibodies were incapable of fully neutralizing DC-DENV, even at high concentration, with only one neutralizing to >80% at 5 μg/ml (FIG. 3*a*&*b*). On the other hand, most of the EDE1&2 antibodies were able to neutralize DC-DENV to >80% with a number reaching 100% neutralization. Full binding and neutralization curves for representative mAbs, demonstrate that anti-FL mAbs have reduced binding by ELISA to DC-DENV and fail to fully neutralize DC virus infection, whereas the neutralization and binding curves for the EDE mAbs are more closely opposed for C6/36 and DC-DENV.

Methods

Neutralization and Enhancement Assays. The neutralization potential of mAbs was determined using the Focus Reduction Neutralization Test (FRNT), where the reduction in the number of the infected foci is compared to control (no antibody)[22]. Briefly, serially-diluted Ab was mixed with virus and incubated for 1 hr at 37° C. The mixtures were then transferred to Vero cells and incubated for 3 days. The focus-forming assay was then performed using anti-E mAb (4G2) followed by rabbit anti-mouse IgG, conjugated with HRP. The reaction was visualized by the addition of DAB substrate. The percentage focus reduction was calculated for each antibody dilution. 50% FRNT values were determined from graphs of percentage reduction versus concentration of Abs using the probit program from the SPSS package.

Example 4—Anti-EDE Antibodies Cannot Bind to Virus with a High Proportion of prM or where the Envelope Protein has Adopted the Trimer Conformation To represent these different virus forms, we compared antibody binding to 6 DENV-2 preparations. To assess the degree of prM cleavage, we measured the ratio of prM:E by ELISA and normalized this to DENV produced in LoVo cells, which lack furin activity and produce almost completely non-infectious mature virus particles with a full complement of prM[17] (FIG. 4A). The virus preparations were as follows: 1) C6/36-DENV which has a relatively high prM content of 56%, 2) DC-DENV which has a prM content of 13%, 3) virus produced in furin deficient LoVo cells (LoVo-DENV) which have a prM content approaching 100%[22], 4) Virus produced in 293T cells overexpressing furin (Furin-293T-DENV) which have a prM content of 5%, 5) virus produced in native 293T cells having 60% prM (293T-DENV) and 6) Virus incubated at pH 5.5 which irreversibly adopts the E trimer conformation (acid-DENV)[42].

The EDE1&2 mAbs could not bind to acid-DENV, presumably because trimerization destroys the conformational epitope, or bind to LoVo-DENV likely because a full complement of prM supports prM/E spikes, which may again disrupt the mature envelope dimer epitope or may sterically interfere with access to the EDE (FIG. 4B). The antiFL mAbs showed reduced binding to the low-prM content viruses; binding curves for DC-DENV and 293T-Furin-DENV were shifted 1.5-2 logs to the right of C6/36 produced DENV. Additionally, binding to LoVo-DENV was even more efficient than C6/36DENV, underscoring the importance of prM for the exposure and efficient binding of fusion loop antibodies 39,43. The four EDE4 antibodies, which were isolated from three separate individuals, bound most efficiently to acid-treated virus, but showed negligible neutralization (FIG. 4B).

Methods

DENV Binding ELISA. To determine the binding affinity of Ab to DENV generated from different cell types, Mock, DENV2 produced from C6/36, DC, 293T, furintransfected 293T or LoVo cells and acid-treated C6/36 DENV2 was captured onto plates coated with 4G2 and then incubated with serial dilutions of DENV-specific human monoclonal Abs followed by ALP-conjugated anti-human IgG. The reaction was developed by the addition of PNPP substrate and stopped with NaOH. The absorbance was measured at 405 nm. Antigen loading of the different viral forms and inter-day variation in OD readings between experiments was normalised by a control ELISA using a humanised version of the well described 3H5 mAb, which is specific to Domain III of DENV2.

Example 5—the Antibodies within a Particular Patient Show Immunodominance

The anti-DENV mAbs described here are a complex ensemble of overlapping specificities where the EDE overlaps with the more restricted epitope of FL antibodies. When we compared these antibody groups (FL vs. EDE) within the individual patients we found skewed repertoires showing a preference to pick either the FL or EDE epitopes (FIG. 5A). This immunodominance of recognition within an individual was surprising. As the epitopes are overlapping, it is possible that the most avid antibody would compete off other antibodies, affinity mature and hence dominate the response leading to a stochastic choice between FL and EDE. However, the responses to the EDE or FL are polyclonal (different VDJ recombinations) within individuals, making this less likely as an explanation.

Example 6—Anti-EDE Antibodies Cause a Reduced Level of Antibody Dependent Enhancement of Infection We tested the ability of the antibodies to enhance DENV infection in Fc receptor expressing U937 cells. All antibodies tested caused ADE, however it was around 4-8 fold less in the EDE group when compared to FL group; the median peak enhancement for the FL vs. the EDE groups were 3745:545 on C6/36-DENV and 2070:480 on DC-DENV (FIG. 5B).

Methods

Or the ADE assay, serially-diluted Ab was pre-incubated with virus for 1 hr at 37° C., then transferred to U937 cells (Fc receptor-bearing human monocyte cell lines) and incubated for 4 days. Supernatants were harvested and titrated on Vero cells by a focus forming assay. The titres of virus were expressed as focus-forming units (FFU) per ml and the fold increment was calculated by comparing the viral titre in the absence of antibody.

Example 7—the Anti-EDE Antibodies Bind Recombinant sE Dimer

For the structural studies we selected four of the most potent anti-EDE antibodies identified: 747(4) A11 and 747 B7 (EDE2) and 752-2 C8 and 753(3) C10 (EDE1), from hereon referred to as A11, B7, C8 and C10. Both EDE2 anti-EDE antibodies were isolated from the same patient (who had a secondary infection with DENV-2), and are somatic variants of the same IgG clone, derived from the IGHV3-74 and IGLV2-23 germ lines. The heavy chain has a very long (26 amino acids) complementarity-determining region 3 (CDR H3). The EDE1 anti-EDE antibodies were isolated from different patients and the corresponding germ lines derive from VH and VL genes IGHV3-64 and IGKV3-11, (EDE1 C8, the patient had a primary infection of undetermined serotype) and IGHV1-3* and IGLV2-14 (EDE1 C10, from a patient with secondary DENV-1 infection). The analysis of the genes for these antibodies is summarized in FIG. 7.

Recombinant sE protein (the 400 amino terminal residues of the ectodomain of Envelope protein, termed "sE" for "soluble E") and the antigen binding portions (Fab) as well as single-chain variable domains (scFv) of the anti-EDE antibodies were produced in *Drosophila* S2 cells[44, 45]. Because the anti-EDE antibodies did not react with recombinant sE protein in standard ELISA assays, we tested the interaction of the antibody fragments with purified recombinant DENV sE in solution at high concentrations to favour dimer formation. Size exclusion chromatography (SEC) combined with multi-angle light scattering (MALS) experiments showed that the dimer/monomer equilibrium of recombinant DENV-1, -2, -3 and -4 sE was shifted to dimer by the antibody fragments, eluting as a complex corresponding an sE dimer with two antibody fragments in most cases, in spite of the size-exclusion induced dissociation effect upon separation of the various species, as shown in FIG. 8A. This was further confirmed by surface plasmon resonance (SPR) analysis (FIG. 8B).

Example 8—Crystal Structures

We determined in total 7 crystal structures, including the DENV-2 sE dimer in complex with fragments of the four selected anti-EDE antibodies and DENV-4 sE in complex with EDE1 C10 in order to confirm the determinants of cross-reactivity. Because the DENV-2 sE dimer used belongs to a different strain from the one for which structures are already available, we also crystallized the unliganded sE dimer to detect possible changes in conformation induced by the antibodies. In addition, we determined the structure of the unliganded A11 scFv, because it was not clear whether its long CDR H3 maintained the same conformation in the absence of antigen. The crystallization procedures are described Example 15 and the crystallographic statistics are listed in FIG. 9.

DENV-2 sE Strain FGA02, Genotype III

We did most of the structural studies with recombinant sE from DENV-2 field strain FGA02 (isolated in 2002 in French Guiana), which belongs to the Asian/American genotype III[11] within serotype 2. FGA02 sE displays 13 amino acid differences compared to the previously crystallized DENV-2 sE[5, 7], scattered over the 394 residues (3%) of the ectodomain. As expected, the 3 Å resolution structure of FGA02 sE shows only small differences with the already available structure of DENV-2 sE in its prefusion form (FIGS. 10A and 10B), fitting within the range of conformations observed in the various structures deposited in the PDB (accessions 1OAN, 1OKE, 1TG8). The structure of unliganded FGA02 sE was useful in assessing regions in which antibody binding induces disorder—in particular, the 150 loop (see below)—by showing that it is not due to the specific amino acid sequence of the E protein of this strain.

Example 9—the Envelope Dimer Epitope

The Anti-EDE Antibodies Bind at the sE Dimer Interface

The crystal structures of the FGA02 sE immune complexes show that the four anti-EDE antibodies bind in a similar way (FIGS. 11A-F), interacting with both subunits of the dimer, (see also ED FIGS. 12A-E, which provides the imprints of each anti-EDE antibody on the sE dimer). The heavy chain binds closer to the 2-fold axis (i.e., the center of the dimer) while the light chain is positioned peripherally. The epitopes largely overlap with the imprint of the prM protein on the E dimer in immature DENV particles exposed to low pH[46]. They are centered in a valley lined by the b strand on the domain II side, and the "150 loop" on the domain I side (across the dimer interface, FIG. 11C). The 150 loop spans residues 148159, connecting β-strands $E_0$ and $F_0$ of domain I, and carries the N153 glycan, which lies above the fusion loop of the partner subunit in the dimer. The heavy chains span the distance between the two glycan chains, N67 and N153, across the dimer interface (FIG. 11C-F). The total buried surface per epitope ranges between 1050 $Å^2$ and 1400 $Å^2$, and the surface complementarity coefficient[13] is between 0.67 and 0.74, which are values typical for antibody/antigen complexes (FIG. 13). The surface electrostatic potentials of epitope and paratopes are mildly charged, with a relatively complementary charge distribution (FIG. 14).

Conserved Residues Make Up the Epitopes

The anti-EDE antibody contacts cluster essentially on highly conserved residues across the four serotypes (FIGS. 15A and 15B), explaining their cross-reactivity. The 26-residue long CDR H3 of B7 and A11 accounts for the vast majority of the EDE2 anti-EDE antibody contacts on both sE subunits forming the epitope. The H3 loop makes a protrusion in the paratope, adopting a convex shape complementary to the concave surface of the antigen (FIG. 11D). The H3 protrusion is pre-formed in the antibody, as shown by the 1.7 Å resolution structure of the unliganded EDE2 A11 scFv (FIGS. 9, 16A-E and 17), indicating that there is no entropic cost for binding. On the reference subunit, defined as the one contributing the fusion loop to the epitope, both EDE1 and EDE2 anti-EDE antibodies target the same serotype invariant residues, which cluster in three main polypeptide segments of domain II (boxed in FIG. 15A): the b strand (residues 67-74, bearing the N67 glycan), the fusion loop and residues immediately upstream (aa 97-106), and the ij loop (aa 246-249). Whereas both light and heavy chains of the EDE1 anti-EDE antibodies interact with the reference subunit via all three CDRs, the EDE2 anti-EDE antibodies interact essentially with the heavy chain, with only a few light chain contacts from CDR L3 (FIGS. 18A-D). On the opposite subunit, across the interface, the sE segments targeted are different for the two EDE groups. The EDE2 anti-EDE antibodies interact with the 150 loop and the N153 glycan chain (see below), whereas EDE1 anti-EDE antibodies induce disorder of the 150 loop upon binding. This allows the light chain in EDE1 anti-EDE antibodies to come closer to sE and to interact with domain III in the region of the "A strand" epitope, which has been structurally characterized previously for murine DENV cross-reactive antibodies[47, 48]. These domain III contacts are centred on the conserved sE residue K310, the side chain of which makes a lid covering the indole ring of W101 of the fusion loop, in an important stabilizing sE dimer contact (FIGS. 18A-D). Although the light chains derive from different VL genes (FIG. 7), both EDE1 C10 and C8 use CDR L1 and L2 residues to contact domain III (FIGS. 15A-B and FIGS. 18A-D). In domain I, EDE1 C10 inserts its relatively long CDR H3 (21 aa, FIG. 7) such that it interacts with conserved residues underneath the 150 loop (scattered in the N-terminal 50 amino acids of the E protein, see FIG. 15A—also circled in FIG. 18D, left panel), whereas the shorter H3 loop of EDE1 C8 cannot reach this region.

Example 10—Antibody Recognition of the Glycan Chains

The anti-EDE antibodies make extensive contact with the glycan chains, both at positions N67 and N153 of E (FIGS. 19A-E and FIGS. 20A-C). All four anti-EDE antibodies interact with the N67 glycan via CDR H2 contacts, and will therefore interfere with binding to the DC-SIGN receptor of dendritic cells, which was shown to interact specifically with the N67 glycan[49]. The DENV-2 sE/EDE1 C8 complex displays the highest ordered N67 glycan structure, with the distant mannose residues contacting the framework region 3 of the heavy chain (FRW H3, FIG. 15B and FIG. 18C). Except for EDE1 C10 (which is very close to its germ line, FIG. 7), a number of the FRW H3 residues have undergone changes (FIG. 15B), suggesting affinity maturation to recognize the sugars. It is possible that if more glycan residues were visible in the structures, they would be seen interacting with the same FRW H3 residues of the other anti-EDE antibodies as well.

Although the N150 loop and N153 glycan are disordered in the EDE1 complexes, the limited space between the antibody and the remainder of domain I (FIG. 19A, left panel) suggests that this glycopeptide segment does make contacts with the antibody (as indicated by the question mark over the 150 loop in FIG. 15A), but adopting variable local conformations in each complex such that it averages out to no resolved electron density in the crystal. If the 150 loop remained in place, the CDR H3 loop of the EDE1 anti-EDE antibodies would collide with the N153 glycan, e.g. with the first GlcNAc residue in DENV-2 sE/EDE1 C10 (sugar 1 in FIG. 19C).

The electron density is clear for the core 6 sugar residues of the N153 glycan of sE in the crystals of the complexes with the EDE2 anti-EDE antibodies (including in omit maps, as shown in FIGS. 20A-C). The CDR H3 of EDE2 anti-EDE antibodies makes a 2-turn $\alpha$-helix (termed H3 helix, FIG. 11D), with one of the carbonyl groups at its C-terminal end capped by a hydrogen bond donated by the N2 atom of the first N153 GlcNAc residue (FIG. 21). The H3 helix projects laterally the aromatic side chains of Y99 (F99 in EDE2 A11) and Y100 to pack against the sugar residues 1, 3 and 4 of the N153 glycan. The most distant residues of the glycan, mannoses 4, 5 and 6, are in contact with the light chain, via residues from CDR L2, including several hydrogen bonds (FIGS. 19A-E and FIG. 21).

The different type of interactions that EDE1 and EDE2 anti-EDE antibodies make with the 150 loop and N153 glycan is reflected in the contrasting effects of the absence of glycan in their neutralization potency. For instance, a DENV-4 isolate having isoleucine at position 155 (i.e., a natural glycosylation mutant, lacking the 153-NDT-155 glycosylation motif), is more sensitive to neutralization by EDE1 anti-EDE antibodies, as there no collision of CDR H3 with the glycan chain. In contrast, this variant is more resistant to neutralization by the EDE2 anti-EDE antibodies (FIG. 19E), highlighting the importance of the observed specific recognition of the N153 glycan.

Example 11—the Main Chain Conformation of the Fusion Loop as Binding Determinant In the fusion loop, residues 101-WGNG-104 make a distorted $\alpha$-helical turn that projects the W101 side chain towards domain III across the dimer interface. In the complexes with EDE2 anti-EDE antibodies the helical turn of the fusion loop is under the H3 helix, such that the carbonyl groups at the C-terminal sides of the two helices face each other. Furthermore, S100C of the CDR H3 caps the helical turn by making main chain and side chain hydrogen bonds to the carbonyl group of G102 in the fusion loop. In the complexes with EDE1 anti-EDE antibodies, the fusion loop lies right underneath the VH/VL interface, with the side chains of several aromatic residues of both heavy and light chains packing against it. In particular, the VL main chain runs very close by, donating a hydrogen bond to the main chain carbonyl group of G104. In EDE1 C8, the main chain amide proton donor belongs to N93 from CDR L3, while in EDE1 C10 it belongs to N31 from CDR L1. Residue D50 in the CDR L2 of both C10 and C8 makes a salt bridge with K310 (FIG. 19A and FIG. 18D), which is part of an extensive network of polar interactions in this area (listed in FIG. 21).

The conformation of the glycine rich fusion loop in the E dimer is such that it essentially exposes the main chain, while the side chains are mostly buried. Together with the main chain of the ij loop, main chain atoms make a large surface patch that is augmented by one edge of the b strand, resulting in an invariant exposed surface recognized by the anti-EDE antibodies. The invariant side chains in this region, together with the exposed main chain atoms at the E dimer surface (FIG. 22A, lower panel), result in a core region of the epitope that is serotype invariant, with non-conserved residues essentially at the periphery. The reason of this conservation is likely to be related to the interaction with prM during particle maturation[46]. The least conserved region is the surface of domain III within the EDE1 epitope.

Example 12—Structure of DENV-4 sE in Complex with EDE1 C10

Figure 19A:
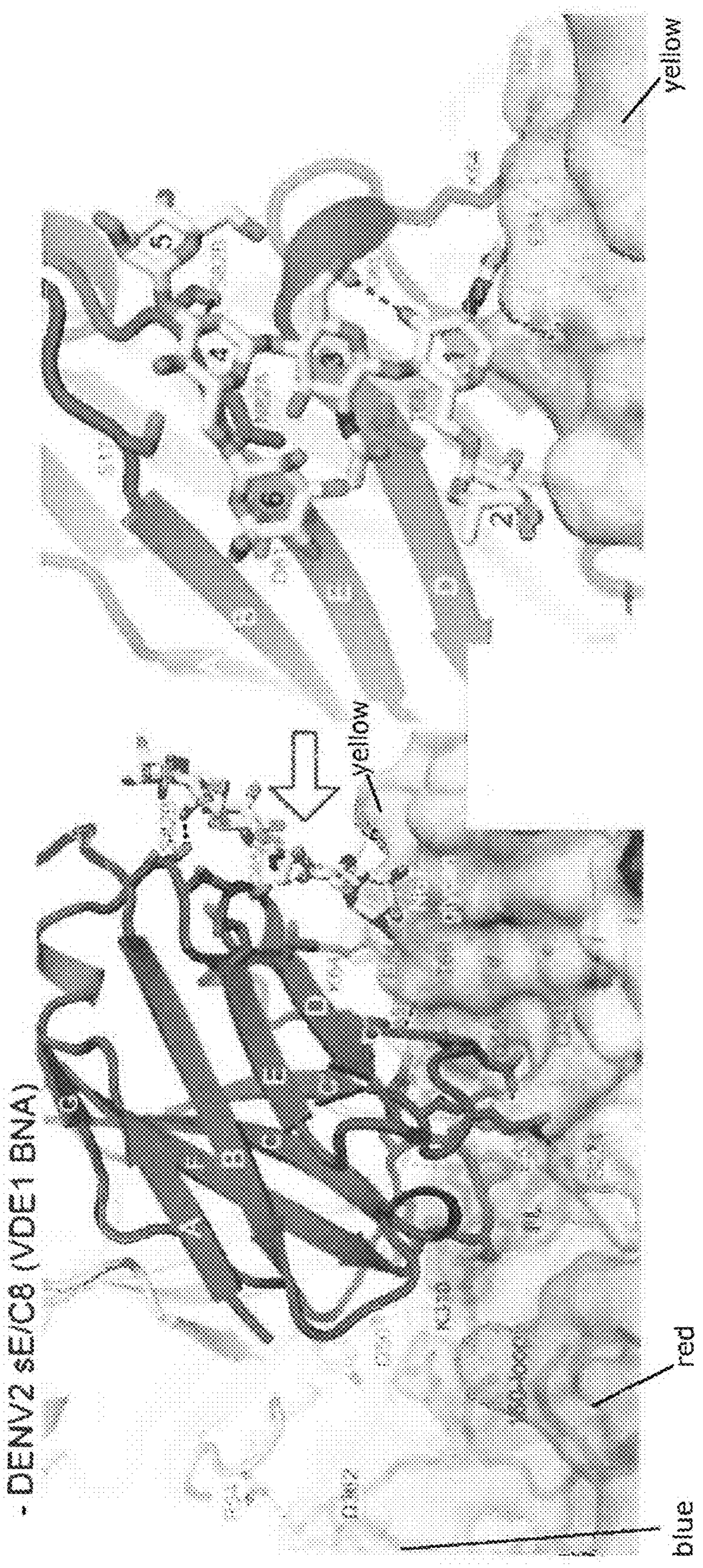
Figure 19B:
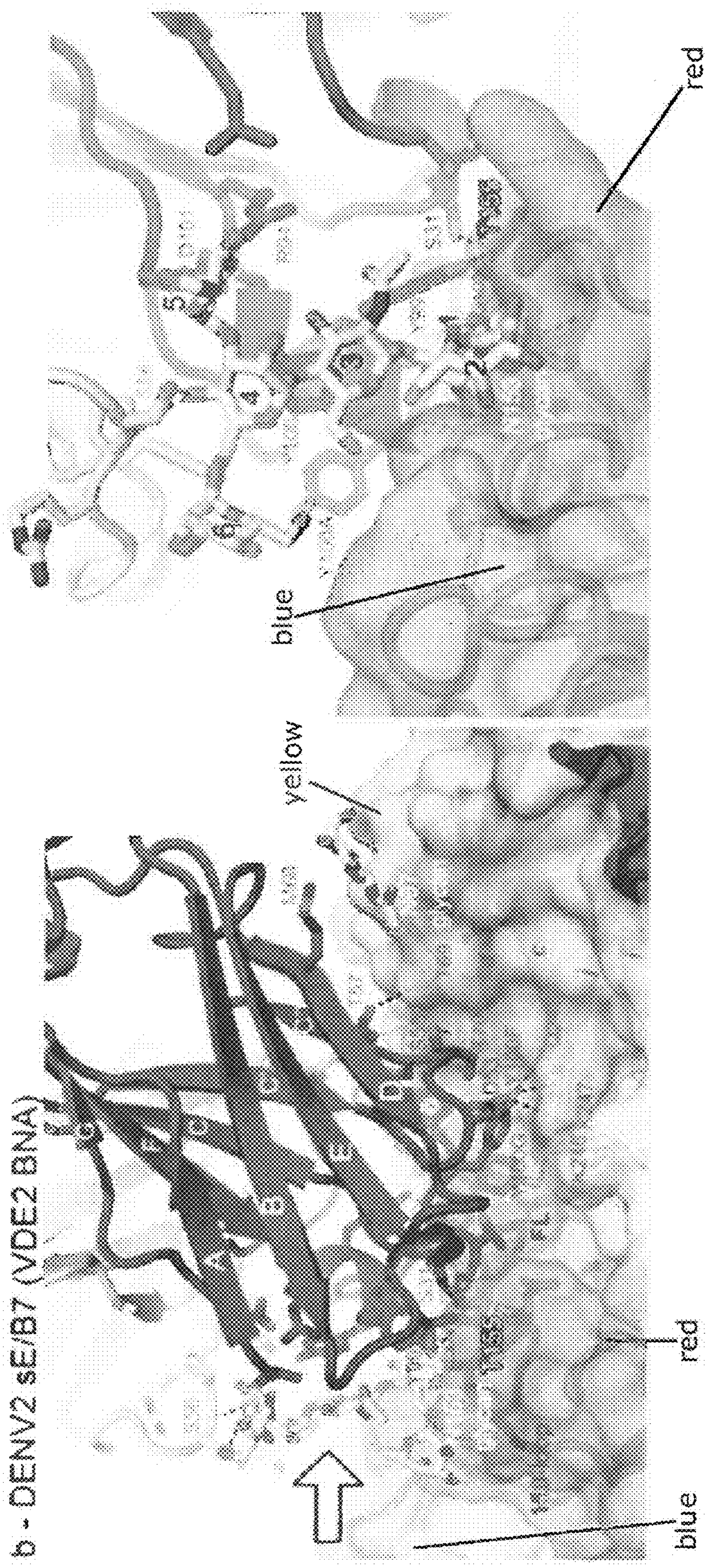
Figure 19C:
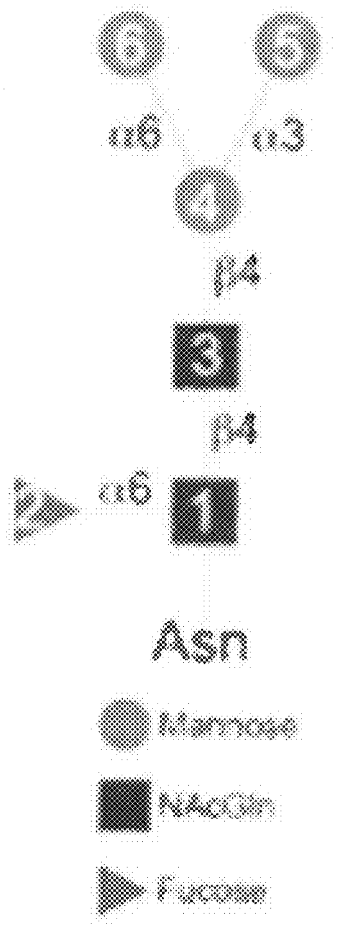
Figure 19D:
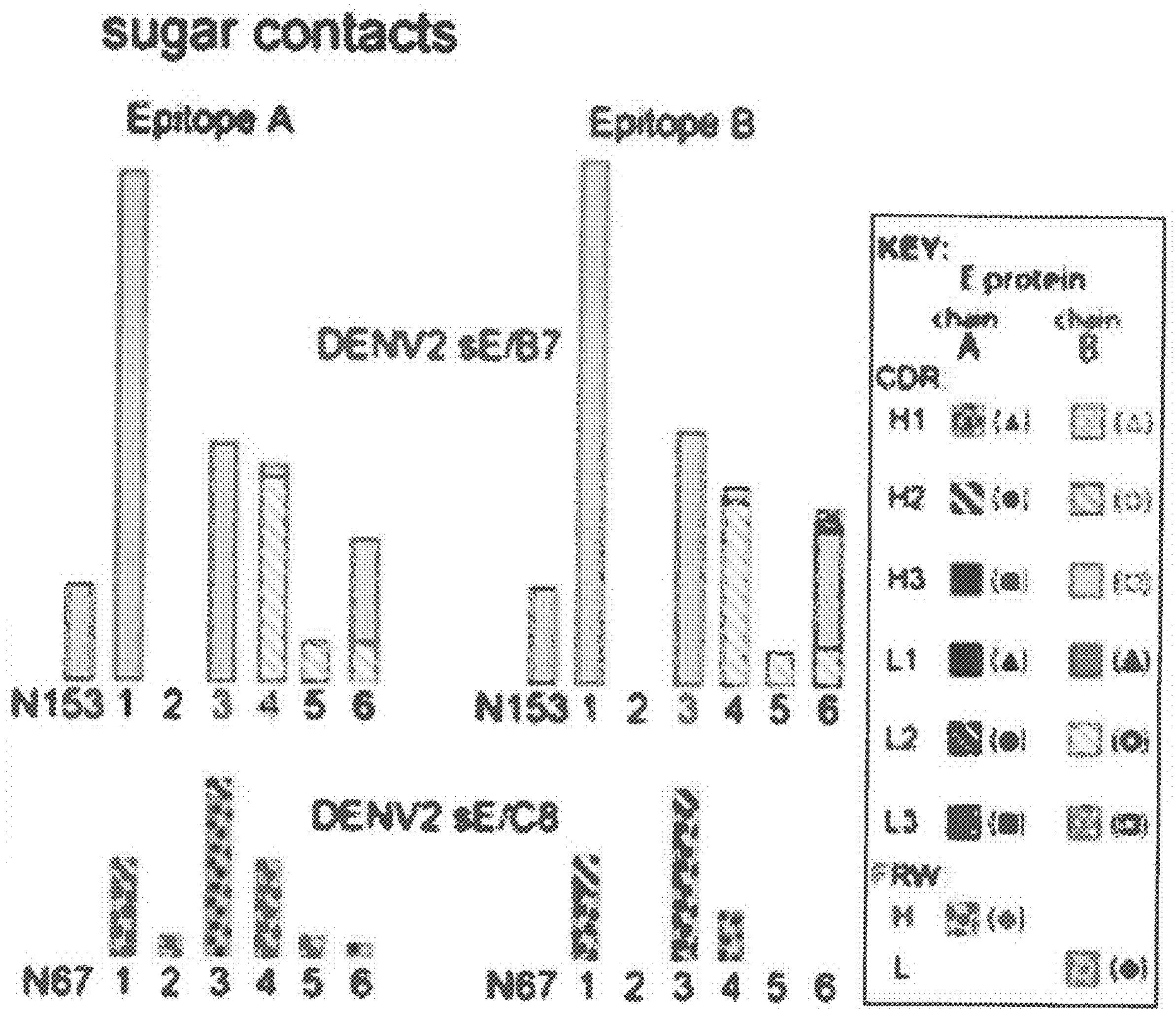
Figure 19E:
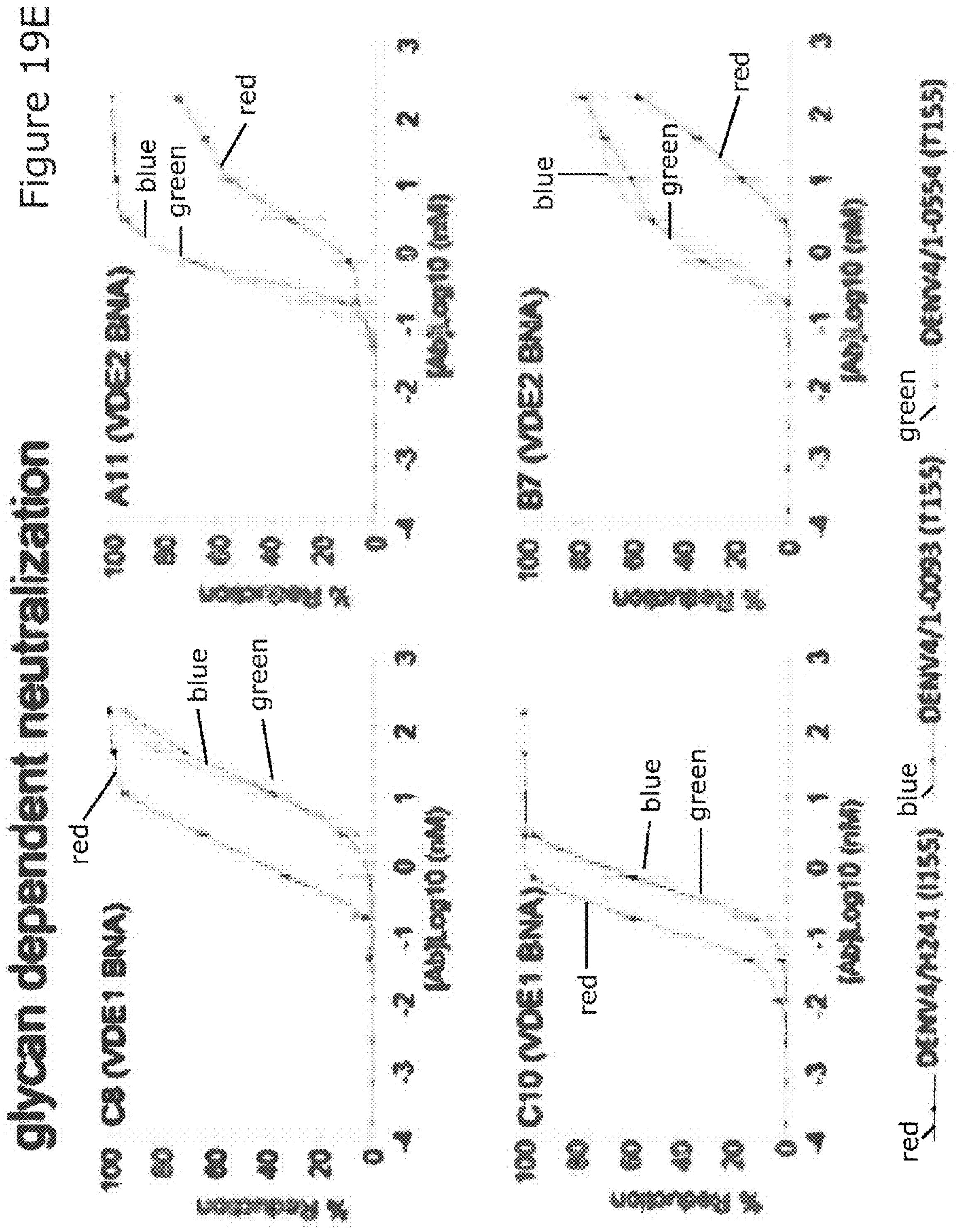
Figure 23B:
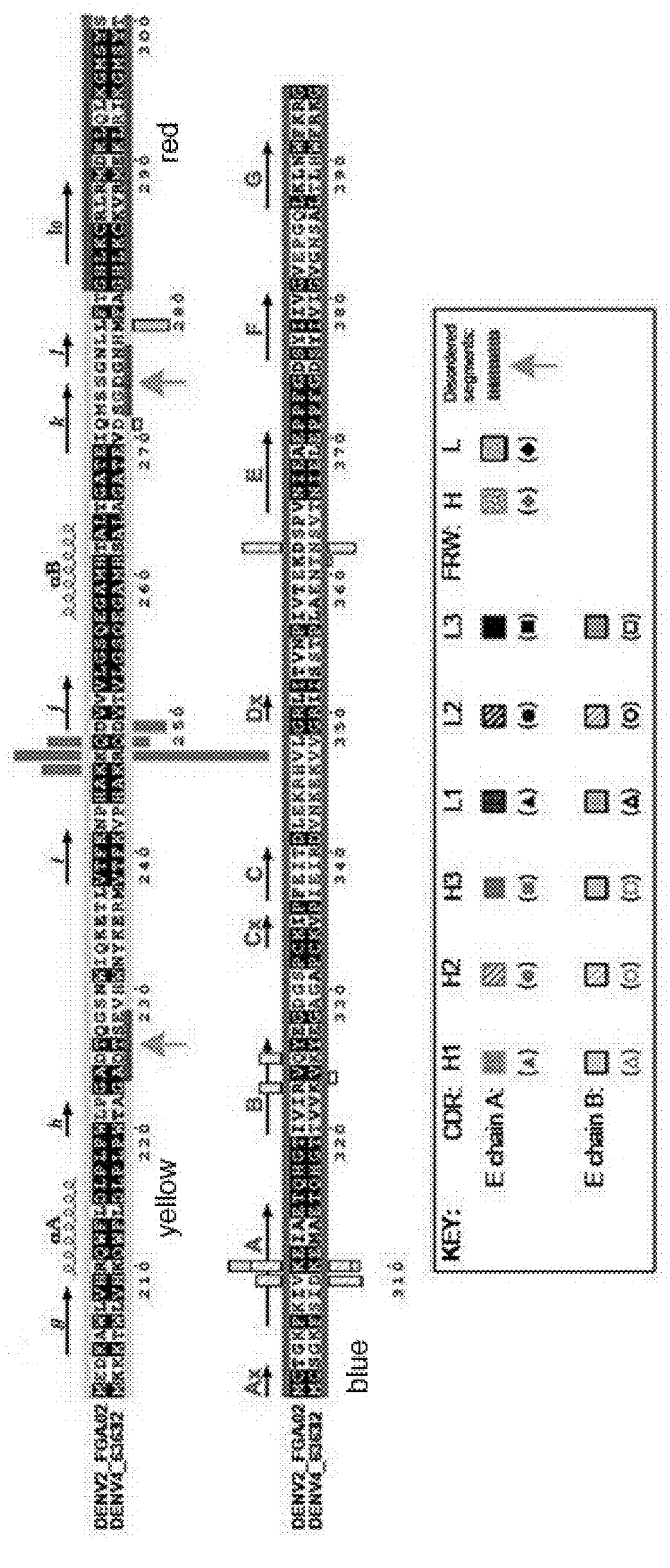

To understand in detail how the anti-EDE antibodies can efficiently recognize multiple viral serotypes, we turned to DENV-4, since it differs most from the other dengue serotypes in amino acid sequence (FIG. 15A), and is also potently neutralized by the EDE anti-EDE antibodies (FIG. 19E). The 2.7 Å resolution crystal structure of DENV-4 sE in complex with the C10 scFv confirmed the general pattern observed in the complex with DENV-2 sE (FIG. 22B and FIGS. 23A and B), with the 150 loop disordered. As expected, the anti-EDE antibody displays the same interactions with the main chain and with the conserved side chains of the epitope. In the more variable lateral region of the EDE1 epitope, on domain III (FIG. 22A), the contact site includes the side chain of residue 309, which is aspartic acid in DENV-4 but valine in DENV-2 (FIG. 15A). In the latter complex there is Van der Waals packing between the side chains V309 and T52 of CDR L2, while in the former there is a polar interaction, with D309 accepting a hydrogen bond from the T52 side chain (FIG. 23 and FIG. 21). The other contacts with domain III are also maintained, in particular the one at position 362, which involves a hydrogen bond to the main chain carbonyl (FIG. 21).

EDE1 C10 clearly induces disorder of the 150 loop in DENV-2 sE, but in the case of DENV-4 sE this loop appears to display an intrinsic higher mobility, as suggested by its crystal structure in complex with the Fab fragment of an unrelated chimpanzee antibody termed 5H2 (ref.[17]). Indeed, although the 5H2 epitope is also in domain I, it is at the side of the sE dimer and does not overlap with the anti-EDE antibody epitopes described here, yet the 150 loop was disordered in that structure. In addition, the structure of the DENV-4 sE/EDE1 C10 complex highlighted a non-negligible degree of asymmetry in the contacts of the anti-EDE antibodies with the two epitopes of the dimer (FIGS. 23A and B, FIG. 13 and FIG. 21). This asymmetry was also detectable in the complexes with DENV-2 sE, as displayed in FIGS. 24A-E. It is likely that stochastically, the binding of the first antibody fragment induces an asymmetric conformational adjustment of the sE dimer, which affects the second site such that when the second one binds it accommodates to the available conformation of the second epitope. Taken together, these observations strongly suggest that the binding determinants of the EDE1 anti-EDE antibodies lie at the conserved core of the epitope, in the region shared with the EDE2 anti-EDE antibodies, and that the contacts at either edge adapt to the particular side chains present in each serotype, which do not compromise binding. This observed plasticity of the E dimer is in line with reports of conformational breathing of the E dimers on virions, exposing normally hidden epitopes for interaction with antibodies.

Example 13—Putative Additional EDE1 C10/E Dimer Interactions on Mature Virions A close examination of the structure shows that the tip of the CDR H3 of EDE1 C10 reaches the "bottom" of the sE dimer (circled in FIG. 18D, left panel; see also FIG. 15D and FIGS. 12D-E), a region which, in the context of the intact virion, is buttressed by protein M underneath (FIGS. 25A-C). The 3.5 Å resolution cryo-EM structure of the intact mature particle of DENV-2 (ref.[9]) shows that the interaction with M results in conserved residue F279, at the base of the kl hairpin of E (FIG. 15A), to be exposed at the dimer interface instead of being buried in the hydrophobic core of domain II (FIG. 25C). Superposition with DENV-2 sE/C10 structure shows that, when in the context of the virion, the exposed F279 side chain could interact with Y100 in the H3 loop. Y100 is seen making different interactions with DENV-2 sE compared to DENV-4 (FIG. 25C; compare also panels b and e in ED FIGS. 26A-E), suggesting that it does not find its right partner. Thus the EDE1 C10 binding site on the E dimer in mature virions appears not to be completely recapitulated by the recombinant sE dimer. This observation likely explains the apparent discrepancy between the weak binding of EDE1 C10 to the sE dimer (FIGS. 8A and B) and its potent binding and neutralization of viruses from the four dengue serotypes (NT 50 in the low nM range, see accompanying manuscript). Importantly, we note that the conformation of F279 on the mature virion is similar to that observed in sE bound to a hydrophobic ligand[4], suggesting that it is possible to induce the right conformation of this region of the recombinant sE dimer as immunogen.

Example 14

We have provided snapshots of anti-EDE antibodies interacting with a major new epitope targeted by human monoclonal antibodies elicited in dengue infected patients. These antibodies appear to have converged toward the same specificity via totally different evolutionary pathways: acquiring a heavy chain with a very long CDR H3 that makes most of the interactions, as in the EDE2 examples, or a fine-tuned combination of light and heavy chains, with the light chain making main-chain contacts to the fusion loop and to domain III for the EDE1 anti-EDE antibodies analyzed here. EDE1 and EDE2 anti-EDE antibodies comprise nearly one third of the antibodies isolated from dengue patients in the accompanying study, and constitute the vast majority of those that recognize conformation-specific quaternary epitopes at the virion surface. Their common signature from the alanine scanning experiments (accompanying manuscript) strongly indicates that they all target the same quaternary epitopes described here.

Importantly, the binding determinants of the EDE anti-EDE antibodies are totally circumscribed to the E dimer, and do not depend on a higher order arrangement of dimers at the virion surface, as recently suggested for the quaternary epitopes on the DENV particle[50] based on studies on a different flavivirus, the West Nile virus[51]. Recent cryo-EM analyses of DENV-2 particles suggest that the herringbone pattern may be disrupted at physiological temperatures in humans, with the dimers reorienting with respect to each other, loosing the symmetric arrangement and/or presenting a different surface pattern[52, 53]. The epitopes described here will therefore be accessible in the E dimers independent of swelling or not of the particles and may be the favored target for next generation vaccines. As a corollary, our results indicate that it is feasible to design potent immunogens by stabilizing the dimer contacts in such a way that only E dimers are presented to the immune system, as proposed recently for the respiratory syncytial virus (RSV)[54], thus avoiding eliciting antibodies against poorly immunogenic regions that are normally not accessible at the surface of an infectious virion.

The principal binding determinant of the EDE anti-EDE antibodies appears to be the conformation of the main chain of the fusion loop and its immediate neighbors in the context of an intact E dimer. This is in stark contrast with the other major class of antibodies isolated from humans in the accompanying manuscript, which recognize the fusion loop sequence in a context independent of the quaternary organization. The latter antibodies are cross reactive but poorly neutralizing and have a strong infection enhancing potential[56]. A notable feature of the epitopes described here is the number of exposed main chain atoms, which accounts for approximately 30% of the total surface area buried in the complex in the case of EDE1 and 20% for the EDE2 anti-EDE antibodies (this lower EDE2 percentage is largely compensated with 40% of invariant glycan composition) (FIG. 13), whereas in general main chain atoms contribute between 5% to 15% for most immune complexes that we have analyzed. We note that certain very potent neutralizing antibodies also recognize a high percentage (around 30%) of main chain atoms in the antigen (FIG. 27), such as the D25 antibody against the respiratory syncytial virus (RSV), which binds to the "antigenic site 0" present exclusively in the pre-fusion form of the RSV fusion protein, stabilizing it in that conformation[57] as do the EDE anti-EDE antibodies. A similar pattern is found with BNA CH65, which neutralizes a broad range of H1 influenza virus isolates by binding to the receptor binding pocket of hemagglutinin (HA)[58] or CR8020, a potent group 2 reactive anti influenza human BNA with neutralization activity against H3, H7 and H10 isolates, by binding to the base of the stem of H1[59]. CR8020 also recognizes the main chain conformation of the fusion peptide within the context of the quaternary structure, similar to the EDE anti-EDE antibodies described here, in the pre-fusion trimer conformation. Finally, two of the very broad anti HIV-1 anti-EDE antibodies, B12 (ref.[60]) and VRCO1 (ref.[61]), which recognize the CD4 binding site in the envelope (ENV) protein, display 36% and 33% of main chain atoms in the epitope (FIG. 27), suggesting that recognition of the main chain conformation is an important aspect shared by many (but not all) anti-EDE antibodies. These anti-HIV-1 broadly neutralising antibodies, which also require the correct quaternary structure of the ENV trimer for efficient binding[29], undergo a long affinity maturation process, displaying more than 20% divergence from the germ line, whereas the EDE anti-EDE antibodies against dengue are at most 9% divergent from the germ line (FIG. 27), indicating that they are relatively easy to develop within individuals if an appropriate immunogen is used for vaccination.

In conclusion, we described a highly conserved binding site for potent highly cross-reactive antibodies against dengue viruses. The poor efficacy of a recent live attenuated polyvalent dengue vaccine has created a pressing need to better understand protective responses in humans and to design a next generation of efficacious vaccines. Serotype specific immunity has often been the goal of dengue vaccines mandating their tetravalent formulation. Our results suggest that a subunit vaccine comprising a stabilized E dimer should be evaluated, that a single optimized universal immunogen may be possible and that the elicitation of anti-EDE antibodies should be considered as a realizable goal for a successful vaccine.

Example 15—Additional Methods

The recombinant sE proteins from DENV serotypes 1 through 4, as well as Fab and scFv BNA fragments, were produced in *Drosophila melanogaster* Schneider 2 using previously described protocols[44,45,29]. The binding of the BNA fragments to the sE proteins was monitored by SEC/MALS and by SPR (FIGS. 8A and B). Crystals of the sE/BNA complexes were obtained by isolating the complex from a mixture by SEC, or by mixing the two in a 1:2 sE:antibody stoichiometric ratio in the case of EDE1 C10. Crystallization trials were made using a robotized facility. Diffraction data were collected at the synchrotron sources SOLEIL and ESRF, and the structures were determined by molecular replacement using the search models listed in FIG. 9, which also provides the relevant crystallographic statistics. The neutralization tests on the DENV-4 variants were carried out using the same procedures outlined in the accompanying paper.

Recombinant sE Protein Production

Recombinant DENV-1 FGA/89 sE (1-395), DENV-2 FGA02 sE (1-395) and DENV-3 PAH881 sE (1-393) were produced in *Drosophila* S2 cells essentially as described earlier for DENV-4 sE (Den4_Burma/63632/1976) 29, with some modifications. Briefly, sE expression was driven by the metallothionein promoter and was induced by 5 μM of $CdCl_2$ in Insect-XPRESS medium (Lonza). The constructs had a *Drosophila* BiP signal sequence fused at the N-terminal end of a prM-sE construct for efficient translocation into the ER of the transfected S2 cells. prM was present N-terminal to sE, as in the DENV polyprotein precursor, with the N-termini of prM and sE generated by signalase cleavage in the ER, where prM (which remains membrane-anchored) plays a chaperone role by masking the fusion loop of sE. The prM/sE complex is transported across the acidic compartments, where prM is cleaved by furin into pr (N-terminal half, bound to sE) and M (membrane-anchored C-terminal half). Upon reaching the external milieu, sE and pr dissociate, and the sE component is purified by affinity chromatography from the cells' supernatant fluid. While the DENV-3 and 4 sE constructs had C-terminal fusion with a twin-strep-tag (IBA, www.iba-lifesciences.com/twin-strep-tag.html), DENV-1 and 2 sE had a 6×His C-terminal tag. Clarified cell supernatants were concentrated 20-fold using Vivaflow tangential filtration cassettes (Sartorius, cut-off 10 kDa) and adjusted to 0.5M NaCl before purification in an AKTA FPLC system with either StrepTactin affinity purification or HisTrap-HP chromatography after buffer exchange to remove divalent ions, depending on the construct. The His-tagged proteins (DENV-1 and 2 sE) were desalted after elution of the HisTrap column and further purified by ion exchange chromatography on MonoQ. A final purification SEC step using a Superdex 200 10/300 GL column equilibrated in 50 mM Tris pH8, 500 mM NaCl was done with all constructs.

Production of Fabs and ScFvs

The BNA fragments were cloned into plasmids for expression as Fab[62] and scFv[63] in *Drosophila* S2 cells. The constructs contain a twin strep tag fused at the C-terminus (only of the heavy chain in the case of the Fab) for affinity purification. The purification protocol included the same steps described above for the strep tagged sE proteins, and the same buffers were used.

Immune Complex Formation and Isolation

The purified DENV sE proteins were mixed with Fabs or ScFvs (in ~2-fold molar excess) in standard buffer (500 mM NaCl, Tris 50 mM pH 8.0 buffer). The volume was brought to 0.2 ml by centrifugation in a Vivaspin 10 kDa cutoff, after 30 min incubation at 4° C., the complex was separated from excess Fab or scFv by SEC, except when a clear peak for the complex was not obtained (as with BNA C10, see FIGS. 8A and B). In this case, a molar ratio 1:2 antigen:antibody mixture (i.e., with an excess of antibody) was directly used for crystallization. In all cases, the buffer was exchanged to 150 mM NaCl, 15 mM Tris, pH 8 for crystallization trials. The protein concentrations used for crystallization, determined by measuring the optical density at 280 nm and using an extinction coefficient estimated from the amino acid sequences, are listed in FIG. 9.

MALS Analysis

150 μg of purified DENV-1, -2, -3 and -4 sE were mixed with 300 μg of A11, B7, C8 and C10 Fab fragments and adjusted to a total volume of 100p. The individual proteins (DENV sE or Fabs) were also run separately as controls at the same concentration. Samples were incubated for 15 min at RT, and analyzed by MALS as they eluted from an SDX200 10/300 GL gel filtration column run at a flow rate 0.4 ml/min. The elution was followed by refractometry and MALS detection with a DAWN Heleos-Optilab T-rEX setup (Wyatt Technology).

Surface Plasmon Resonance

Real-time SPR measurements of the binding of sE dimers to captured Fab fragments of the anti-EDE antibodies were performed using a ProteOn XPR36 instrument (BioRad).

The Fab fragment of the DENV-4 specific neutralizing antibody 5H2 was used as control. Biotinylated anti-human CH1 specific antibody (Life Technologies) was immobilized on a Neutravidin ProteOn NLC sensor chip, and used to capture similar densities (400-500 RU) of the different Fab fragments. This anti-CH1 antibody recognizes all IgG subclasses (1, 2, 3 and 4) independently of the light chain subclass (Kappa/Lambda). We found that this anti-CH1 antibody also cross reacts with 5H2, a chimpanzee antibody, although with a lower affinity. The Fab fragment of an anti-HCV E2 antibody was used as a negative control. The chip was rotated 90° following Fab capture, and sE of the four DENV serotypes was injected at a concentration of 2 μM. Blank injections with running buffer (50 mM Tris pH8, 500 mM NaCl, 0.01% Tween20) were used for double referencing. SPR signals were normalized to the amount of Fab captured. A control injection of the ectodomain of Rubella virus E1 glycoprotein at a similar concentration over all the Fabs showed no apparent binding (data not shown).

Neutralization Assays with DENV-4 Glycosylation Variants

The neutralization potential of the anti-EDE antibodies was determined using the Focus Reduction Neutralization Test (FRNT)[22], where the reduction in the number of infected foci is compared to control (no antibody). DENV-4 strains H241 (with Ile at position 155), 1-0093 and 1-0554 (both with Thr at position 155—thus restoring glycosylation at Asn153) were grown in C6/36 cells. Viral titres were determined by a focus-forming assay on Vero cells[64]. Briefly, serially-diluted anti-EDE antibodies were mixed with virus and incubated for 1 hr at 37° C. The mixtures were then transferred to Vero cells and incubated for 3 days. The focus-forming assay was then performed using the murine monoclonal 4G2 antibody (which cross-reacts with E protein from all flaviviruses) followed by rabbit anti-mouse IgG, conjugated with horse radish peroxidase. The reaction was visualized by the addition of diaminobenzidine substrate. The percentage foci reduction was calculated for each antibody dilution. 50% FRNT were determined from graphs of percentage reduction versus concentration of Abs using "probit" (www.statisticalassociates.com/probitregression.htm) with the statistical package SPSS.

Crystallization and 3D Structure Determinations

Crystallization trials were carried out in sitting drops of 400 nl. Drops were formed by mixing equal volumes of the protein and reservoir solution in the format of 96 Greiner plates, using a Mosquito robot, and monitored by a Rock-Imager. Crystals were optimized with a robotized Matrix Maker and Mosquito setups on 400 nl sitting drops, or manually in 24 well plates using 2-3 μl hanging drops (FIG. 9). The crystallization and cryo-cooling conditions for diffraction data collection are listed in FIG. 9.

X-ray diffraction data were collected at beam lines PROXIMA-1 and PROXIMA-2 at the SOLEIL synchrotron (St Aubin, France), and ID23-2 and ID29 at the European Synchrotron Radiation Facility (Grenoble, France) (FIG. 9). Diffraction data were processed using the XDS package[65] and scaled with SCALA or AIMLESS[66] in conjunction with other programs of the CCP4 suite[67]. The structures were determined by molecular replacement with PHASER[68] and/or AMoRe[69] using the search models listed in FIG. 9.

Subsequently, careful model building with COOT[70], alternating with cycles of crystallographic refinement with program BUSTER/TNT[71], led to a final model. Refinement was constrained to respect non crystallographic symmetry, and also used target restraints (with high resolution structures of parts of the complexes) and TLS refinement[72] depending on the resolution of the crystal (see FIG. 9). Final omit maps were calculated using Phenix.Refine[73].

Analysis of the Atomic Models and Illustrations

Each complex was analyzed with the CCP4 suite of programs[67]. For intermolecular interactions, the maximal cutoff distance used for the interactions was 4.75 Å. Then the contacts of each residue of the Fab/ScFv or of DENV sE proteins were counted and plotted as a proportional bar above the corresponding residue.

The Ab sequences were analyzed by Abysis (www.bioinf.org.uk/software) and IMGT (www.imgt.org)[31] websites for mapping CDR/FWR regions according to Kabat[30] and IMGT[31] conventions, respectively. The analysis of the putative germline and somatic maturation events was done with the IMGT website (www.imgt.org).

Multiple sequence alignments and phylogenetic trees were calculated using ClustalW (ClustalW and ClustalX version 2 (ref.[74]) on the EBI server[75]. The tree was calculated using amino acid sequences of sE proteins used in this study: DENV-1 FGA/89 (1-395), DENV-2 FGA02, DENV-3 PAH881 (1-393) and DENV-4 (DEN_Burma/63632/1976). For mapping DENV-2 genotypes, the database from[76] was used to extract amino acid sequences of sE ectodomains and extended to include DENV2 FGA02 sE and DENV-2 10AN sE. For simplicity of representation sub-roots were collapsed to the level of individual genotype for DENV-2. The tree was then rooted with the DENV-4 sE sequence and drawn to scale using the MEGA5 software package[77].

For FIG. 22A and FIG. 14 and for analysis purposes, a model of DENV-2 sE dimer without gaps in the sequence was used. The model was built using the complete protomer A of the DENV-2 sE/B7 complex.

Figures were prepared using Program ESPript[78] and the PyMOL Molecular Graphics System, Version 1.5.0.4 Schradinger, LLC. (pymol.sourceforge.net) with APBS[79] and PDB2PQR tools[80].

Finally, current vaccine strategies employ a tetravalent formulation with the aim of raising a balanced type specific response against all four serotypes. The description here of such potent and crossreactive antibodies points the way for subunit vaccines containing the desired epitope and possibly heterologous prime boost strategies to recapitulate responses seen in natural sequential infections. Per Karen line off seperate Example 16: Sequence Information

| SEQ ID NO's |
|---|
| SEQ ID NO: 1<br>Full seq of antibody C8 Heavy chain<br>EVQLVESGGGLVQPGGSLRLSCSASGFTFSTYSMHWVRQAPGKGLEYVSA<br>ITGEGDSAFYADSVKGRFTISRDNSKNTLYFEMNSLRPEDTAVYYCVGGY<br>SNFYYYYTMDVWGQGTTVTV |
| SEQ ID NO: 2<br>Full seq of antibody C10 Heavy chain<br>EVQLVESGAEVKKPGASVKVSCKASGYTFTSYAMHWVRQAPGQRLEWMGW<br>INAGNGNTKYSQKFQDRVTITRDTSASTAYMELSSLRSEDTAIYYCARDK<br>VDDYGDYWFPTLWYFDYWGQGTLVTV |
| SEQ ID NO: 3<br>Full seq of antibody A11 Heavy<br>EVQLVESGGGLVRPGGSLRLSCAASGFSYSNHWMHWVRQAPGKGLVWVSR<br>INSDGSTRNYADFVKGRFTISRDNAENTLYLEMNSLTADDTAVYYCVRDG<br>VRFYYDSTGYYPDSFFKYGMDVWGQGTTVTV |
| SEQ ID NO: 4<br>Full seq of antibody B7 Heavy chain<br>EVQLVESGGGLVQPGGSLKLSCAASGFTFSSHWMHWVRQAPGKGLVWVSR<br>TNSDGSSTSYADSVKGRFMISRDNSKNTVYLHMNGLRAEDTAVYFCARDG<br>VRYYYDSTGYYPDNFFQYGLDVWGQGTT |
| SEQ ID NO: 5<br>C8 CDR H1<br>TYSMH |
| SEQ ID NO: 6<br>C8 CDR H2<br>AITGEGDSAFYADSVKG |
| SEQ ID NO: 7<br>C8 CDR H3<br>GYSNFYYY |
| SEQ ID NO: 8<br>C10 CDR H1<br>SYAMH |
| SEQ ID NO: 9<br>C10 CDR H2<br>WINAGNGNTKYSQKFQD |
| SEQ ID NO: 10<br>C10 CDR H3<br>DKVDDYGDYWFPTLW |
| SEQ ID NO: 11<br>A11 CDR H1<br>NHWMH |

-continued

SEQ ID NO's

SEQ ID NO: 12
A11 CDR H2
RINSDGSTRNYADFVKG

SEQ ID NO: 13
A11 CDR H3
DGVRFYYDSTGYYPDSFFKY

SEQ ID NO: 14
B7 CDR H1
SHWMH

SEQ ID NO: 15
B7 CDR H2
RTNSDGSSTSYADSVKG

SEQ ID NO: 16
B7 CDR H3
DGVRYYYDSTGYYPDNFFQY

SEQ ID NO: 17
C8-CDR L1
RASQSISTFLA

SEQ ID NO: 18
C8 CDR L2
DASTRAT

SEQ ID NO: 19
C8 CDR L3
QQRYNWPPYT

SEQ ID NO: 20
C10 CDR L1
TGTSSDVGGFNYVS

SEQ ID NO: 21
C10 CDR L2
DVTSRPS

SEQ ID NO: 22
SSHTSRGTWVF

SEQ ID NO: 23
A11 CDR L1
TGTSSNADTYNLVS

SEQ ID NO: 24
A11 CDR L2
EGTKRPS

SEQ ID NO: 25
A11 CDR L3
CSYATSRTLVF

SEQ ID NO: 26
B7 CDR L1
TGISSDVETYNLVS

SEQ ID NO: 27
B7 CDR L2
EASKRPS

SEQ ID NO: 28
B7 CDR L3
CSYAGGKSLV

SEQ ID NO: 29
Full length envelope protein sequence DENV1
>DENV1 strain Hawaii
MRCVGIGNRDFVEGLSGGTWVDVVLEHGSCVTTMAKDKPTLDIELLKTEV
TNPAVLRKLCIEAKISNTTTDSRCPTQGEATLVEEQDANFVCRRTFVDRG
WGNGCGLFGKGSLITCAKFKCVTKLEGKIVQYENLKYSVIVTVHTGDQHQ
VGNETTEHGTIATITPQAPTSEIQLTDYGALTLDCSPRTGLDFNEMVLLT
MKEKSWLVHKQWFLDLPLPWTSGASTPQETWNREDLLVTFKTAHAKKQEV
VVLGSQEGAMHTALTGATEIQTSGTTKIFAGHLKCRLKMDKLTLKGMSYV
MCTGSFKLEKEVAETQHGTVLVQVKYEGTDAPCKIPFSTQDEKGVTQNGR -continued SEQ ID NO's LITANPIVTDKEKPVNIEAEPPFGESYIVVGAGEKALKLSWFKKGSSIGK
MLEATARGARRMAILGDTAWDFGSIGGVFTSVGKLVHQIFGTAYGVLFSG
VSWTMKIGIGILLTWLGLNSRSTSLSMTCIAVGMVTLYLGVMVQA SEQ ID NO: 30
full length envelope nucleotide sequence DENV1

SEQ ID NO: 31
full length envelope protein sequence DENV2
>DENV2 strain 16681
MRCIGMSNRDFVEGVSGGSWVDIVLEHGSCVTTMAKNKPTLDFELIKTEA
KQPATLRKYCIEAKLTNTTTESRCPTQGEPSLNEEQDKRFVCKHSMVDRG
WGNGCGLFGKGGIVTCAMFRCKKNMEGKVVQPENLEYTIVITPHSGEEHA
VGNDTGKHGKEIKITPQSSITEAELTGYGTVTMECSPRTGLDFNEMVLLQ
MENKAWLVHRQWFLDLPLPWLPGADTQGSNWIQKETLVTFKNPHAKKQDV
VVLGSQEGAMHTALTGATEIQMSSGNLLFTGHLKCRLRMDKLQLKGMSYS
MCTGKFKVVKEIAETQHGTIVIRVQYEGDGSPCKIPFEIMDLEKRHVLGR
LITVNPIVTEKDSPVNIEAEPPFGDSYIIIGVEPGQLKLNWFKKGSSIGQ
MFETTMRGAKRMAILGDTAWDFGSLGGVFTSIGKALHQVFGAIYGAAFSG
VSWTMKILIGVIITWIGMNSRSTSLSVTLVLVGIVTLYLGVMVQA SEQ ID NO: 32
full length envelope nucleotide sequence DENV2

SEQ ID NO: 33
full length envelope protein sequence DENV3
>DENV3 stain H87
MRCVGVGNRDFVEGLSGATWVDVVLEHGGCVTTMAKNKPTLDIELQKTEA
TQLATLRKLCIEGKITNITTDSRCPTQGEAILPEEQDQNYVCKHTYVDRG
WGNGCGLFGKGSLVTCAKFQCLESIEGKVVQHENLKYTVIITVHTGDQHQ
VGNETQGVTAEITSQASTAEAILPGYGTLGLECSPRTGLDFNEMILLTMK
NKAWMVHRQWFFDLPLPWTSGATTETPTWNRRELLVTFKNAHAKKQEVVV
LGSQEGAMHTALTGATEIQTSGGTSIFAGHLKCRLKMDKLELKGMSYAMC
LNTFVLKKEVSETQHGTILIKVEYKGEDAPCKIPFSTEDGQGKAHNGRLI
TANPVVTKKEEPVNIEAEPPFGESNIVIGIGDKALKINWYRKGSSIGKMF
EATARGARRMAILGDTAWDFGSVGGVLNSLGKMVHQIFGSAYTALFSGVS
WIMKIGIGVLLTWIGLNSKNTSMSFSCIAIGIITLYLGVVVQA SEQ ID NO: 34
full length envelope nucleotide sequence DENV3

SEQ ID NO: 35
full length envelope protein sequence DENV4
>DENV4 strain 241
MRCVGVGNRDFVEGVSGGAWVDLVLEHGGCVTTMAQGKPTLDFELIKTTA
KEVALLRTYCIEASISNITTATRCPTQGEPYLKEEQDQQYICRRDVVDRG
WGNGCGLFGKGGVVTCAKFSCSGKITGNLVQIENLEYTVVVTVHNGDTHA
VGNDIPNHGVTATITPRSPSVEVKLPDYGELTLDCEPRSGIDFNEMILMK
MKKKTWLVHKQWFLDLPLPWAAGADTSEVHWNYKERMVTFKVPHAKRQDV
IVLGSQEGAMHSALTGATEVDSGDGNHMFAGHLKCKVRMEKLRIKGMSYT
MCSGKFSIDKEMAETQHGTTVVKVKYEGAGAPCKVPIEIRDVNKEKVVGR
IISSTPFAEYTNSVTNIELEPPFGDSYIVIGVGDSALTLHWFRKGSSIGK
MLESTYRGVKRMAILGETAWDFGSVGGLFTSLGKAVHQVFGSVYTTMFGG
VSWMVRILIGFLVLWIGTNSRNTSMAMTCIAVGGITLFLGFTVHA SEQ ID NO: 36-full length envelope nucleotide sequence DENV4

SEQ ID NO: 37
C8 light chain-See table below

SEQ ID NO: 38
Full seq of antibody C10 light chain-See table below

SEQ ID NO: 39
Full seq of antibody A11 light chain-See table below

SEQ ID NO: 40
B7 light chain See table below

SEQ ID NO: 37--131 antibody light and heavy chain sequences from the table below

| Sequence ID | epitope | SEQ ID NO: | Sequence AA (H chain) | SEQ ID NO: | Sequence AA (L chain) |
|---|---|---|---|---|---|
| 747(4) B3 | EDE 1 | 40 | QVQLQESGPGLMKPSETLSLTCSVSGVSISTHYWSWIRQPPGKGLEWIGFIYNSGGTHYNPSLKSRVTISADTSKNQFALTLSSVTAADTAVYYCARGRRAYDSSGYVKYYYFYGVDVWGQGTTVTVSS | 86 | QTVVTQEPSLTVSPGGTVTLTCGSNTGPVTNGHYPYWFQQKSGQAPRTLIYDTTNRQSWTPVRFSGSLLGGKAALTLSGAQPEDEADYHCLLSYSDGLVFGGGTKLTVL |
| 747 A12 | EDE 1 | 41 | EVQLVESGSELKKPGASVKVSCRASGFTFTSYTFNVVVRQAPGQGLEWMGWIDTKSGRPTYAQGFTGRFVLSLDTSVSTAYLQINSLKVEDTAMYYCARVHTGGYPPELRYYYYGMDVWGQGTTVTVSS | 87 | CMTPAPSTLAVTPGEPASISCRSTQSLLHSDGYNYLDWYLQKPGQSPHLLIYLGSHRASGVPDRFSGSGSDTDFTLKISRVEAEDVGVYYCMQPLRTPPTFGQGTKLEIK |
| 752 B10 | EDE 1 | 42 | EVQLVESGGGLVQPGGSLRLSCSASGFTFSTYSMHVVVRQAPGKGLEYVSAITTDGNSAFYADSVKGRFTISRDNSKNTMYFHMNSLRPEDTAVYYCVGGYSSFYYYYTMDVWGQGTTVTVSS | 88 | EIVLTQSPATLSLSAGDRATLSCRASQDISSFLAWYQQKPGQAPRLLMYDTSNRATGVPARFSGSRSGTDFTLTISTLEPEDVAVYYCQHRYNWPPYTFGQGTKVEIK |
| 752 B11 | EDE 1 | 43 | QVQLVESGGGLVQPGGSLRLSCSASGFTFSTYSMHVVVRQAPGKGLEYVSAITTDGDSAFYADSVKGRFTISRDNSKNTMFFHMSNLRPEDTAVYYCVGGYSSFYYYYTLDVWGQGTTVTVSS | 89 | EIVLTQSPATLSLSPGERATLSCRASQSISSFLAWYQQKPGQAPRLLIYDASNRVTGVPARFSGSRSGTDFTLTISTLEPEDFAVYYCQHRYNWPPYTFGQGTKVEIK |
| 752 C9 | EDE 1 | 44 | EVQLVESEGGLVQPGGSLRLSCSASGFTFSTYSMHVVVRQAPGKGLEYVSAITTNGDSTFYADSVKGRFTISRDNSKNTLYFQMSSLRAEDTGVYYCVGGYSSFYYYYTMDVWGQGTTVTVSS | 90 | EIVLTQSPATLSLSPGERATLSCRASQSISTYLAWYQQKPGQAPRLLIYDASNRATGVPARFSGSRSGTDFTLTISTLEPEDFAVYYCQQRYNWPPYTFGQGTKVEIK |
| 752(2) A2 | EDE 1 | 45 | EVQLVQSGPEMRKPGASVKVSCKASGYTFTSHGINWVRQVPGQGPEWMGWSSSYTDNTNYAQKFKGRVTMTTDPSTSTAYMELRSLRSDDTAIYFCARGFYSGSYYPTAPFDIWGQGTLVTVSS | 91 | DIQMTQSPSSLSASVGDRVTITCRASQTISGSLSWYQHKPGKAPKLLIYAASSLQSGVPSRFSGSGSGTDFTLTISSLQPEDFATFYCQQSYSTPYTFGQGTKVEIK |
| 752(2) A5 | EDE 1 | 46 | EVQLVQSGAEVKKPGASVKVSCKASGYTFTTYGLSWVRQAPGQGLEWMGWCSSYNDNTNYAQKFKGRVTMTTDTSTNTAYMELRSLRSDDTAVYYCARVFYSGSYYPNSPFDYWGQGTLVTVSS | 92 | DIQMTQSPSSLSASIGDRVTITCRASESISSQLHWYQQKPGKAPRLLIYAASSLQGGVPSRFSGSGSGTDFTLTISGLQPEDFATYCCQQSFTTPYTFGQGTKVEIK |
| 752(2) A7 | EDE 1 | 47 | QVQLQESGPGLVKPSQTLSLTCTVSGDSISSNNYQWNWIRQPAGKGLEWLGRIDTTGSTNYNPSLKSRISISIDTSKKQFSLRLNSVTAADTAVYYCARSLWSGELWGGPLGYWGQGTLVTVSS | 93 | EIVMTQSPATLSASPGERATLSCRASQDVSTFVAWFQQNPGQAPRLLIYDASTRAPGIPARFSGSRSGTEFTLTINSLQSEDFAVYYCQQYYNWPPWTFGQGTKVEIK |
| 752(2) A8 | EDE 1 | 48 | EVQLVESGAEVKNPGASVKVSCKASGYTFIGYYIHWVRQAPGQGLEWMGWINPNSGATYSAQKFQGRVTLTGDASPSTVYMELSSLRSDDTAIYYCAGRSYNWNDVFYYYYMDVWGQGTTVTVSS | 94 | DIQMTQSPSSVSASVGDRVTISCRASQDISASLGWYQQKPGKAPKLLIYRASNLEGGVPSRFRGSGSGTDFTLTISSLQPEDFATYYCLQANSFPLTFGGGTKVEIK |

-continued

| Sequence ID | epitope | SEQ ID NO: | Sequence AA (H chain) | SEQ ID NO: | Sequence AA (L chain) |
|---|---|---|---|---|---|
| 752(2) B10 | EDE 1 | 49 | EVQLVESGPGLVKPSETLSLTCTISGVSISDYYWT WIRQPPGKGLEWIGNIYNTGSTNYNPSLKSRVAI WMDTSKNKFSLRLTSVTSADTAVYYCARVEGGP KYYFGSGDFYNLWGRGSLVTVSS | 95 | DIQMTQSPSSLSASVG DSVTVACRASQPIYRN LNWYQQKPGKAPKLL IYDASTLQSGVPARFS GSGSGTDFTLTISSLQ AEDFATYYCQQSYSS PRTFGQGTKVEIK |
| 752(2) C2 | EDE 1 | 50 | SQVQLVQSGAELKKPGASVKVSCKTSGYTFSYYI HWVRQAPGQGLEWMAMINPTSGSTSYAQRFQG RVTMTRDTPTNTVYMEVRSLRSDDTAVYFCASR GYNWNDVQYYYTMDVWGQGTTVTVSS | 96 | DIQMTQSPSTLSASVG DRVTITCRASQSISTYL AWYQQKPGKAPKLLI YKASSLEIGVPSRFSG SGSGTEFTLTISSLQPD DFAIYYCQQYNNYSP PVTFGGGTKVEIK |
| 752(2) D4 | EDE 1 | 51 | SEVQLVQSGAELKKPGASVKVSCKASGYTFSYYI HWVRQAPGQGLEWMAIINPTSGSTSYAQRFQGR VTMTRDTSTNTVYMELSSLISEDTAVYYCASRG YNWNDVHYYYTMDVWGQGTTVTVSS | 97 | DIQMTQSPSTLSASVG DRVTITCRASQSISTYL AWYQQKPGKAPKLLI YKASTLESGVPLRFSG SGSGTEFTLTISSLQPD DFAIYYCQQYNNYSP PVTFGGGTKVEIK |
| 752(2) B11 | EDE 1 | 52 | QVQLVESGAEVKKPGSSVKVSCKASGYTFTTYG LSWVRQAPGQGLEWMGWCSSYEDNTNYAPRFK GRVTMTTDTSTNTAYMELRSLRFDDTAVYYCAR VFYSGSYYPNSPFDSW | 98 | DIQMTQSPSSLSASVG DAVSITCRASESVSRQ LNWYQQKPGKAPNLL IYAASSLQGGVPSRFS GSGSGTDFTLTISGLQ PEDFATYYCQQGYST PYSFGQGTKVEIK |
| 752-2 A2 | EDE 1 | 53 | QVQLVESGGGLVQPGGSLRLSCSASGFTFSTYSM HWVRQAPGKGLEYISAITTDGDSAFYADSVKGR FTISRDNSKNTMYFHMNSLRPEDTAVYYCVGGY SSFYYYYTMDVWGQGTTVTVSS | 99 | EIVLTQSPATLSLSAG ERATLSCRASQSISSY LAWYQQKPGQAPRLL IYDASNRATGVPARFS GSQSGTDFTLTISTLEP EDFAVYYCQLRYNWP PYTFGQGTKVEIK |
| 752-2 A4 | EDE 1 | 54 | EVQLVESGAEVKKPGASVKVSCKASGYTFTSYGI NWVRQAPGQGLEWMGWISSDSGHTNYARKLK GRVTMTTDTSTTTAYMELRSLRSDDTAVYYCAR GLYSVSYYPTSPFDYWGQGSTVTVSS | 100 | DIQMTQSPSPLSASVG DRVTITCRASQSISSHL NWYQQKSGKVPKLLI YAASSLQSGVPSRFSG SGSGTDFTLTITSLQPE DFATYYCQQSDTTPY TFGQGTKVEIK |
| 752-2 A5 | EDE 1 | 55 | QVQLVESGAEVKKPGSSVKVSCRASGYTFTTYG LSWVRQAPGQGLEWMGWCSSYNDNTNYAQKF KGRVTMTTDTSTNTAYMELRSLRSDDTAVYYC ARVFYSGSYYPNSPFDSWGQGTLVTVSS | 101 | DIQMTQSPSSLSASVG DAVSITCRASESIARQ LNWYQQKPGKAPNLL IYAASSLQGGVPSRFS GSGSGADFTLTISGLQ PEDFATYYCQQGYST PYTFGQGTKVEIK |
| 752-2 A9 | EDE 1 | 56 | EVQLVESGGGLVQPGGSLRLSCSASGFTFSTYSM HWVRQAPGKGLEYVSAITTDGDSAFYADSVKGR FTISRDNSKNTMYFHMNSVRPEDTAVYYCVGGY SSFYYYYTMDVWGQGTTVTVSS | 102 | EIVLTQSPATLSLSAG ERATLSCRASQDISTF LAWYQQKPGQAPRLL IYDTSTRATGVPARFS GSRSGTDFTLTITTLEP EDFAVYYCQHRYNW PPYTFGQGTKVEIK |
| 752-2 B2 | EDE 1 | 57 | EVQLVESGGGLVQPGGSLRLSCSASGFTFSTYSM HWVRQAPGKGLEYVSAITTDGDSAFYADSVKGR FTISRDNSKNTMYFHMNSLRPEDTAVYYCVGGY SSFYYYYTMDVWGQGTTVTVSS | 103 | EIVLTQSPATLSLSAG ERATLSCRASQSISSY LAWYQQKPGQAPRLL IYDASNRATGVPARFS GSRSGTDFTLTISTLEP EDFAVYYCQHRYNW PPYTFGQGTKVEIK |

-continued

| Sequence ID | epitope | SEQ ID NO: | Sequence AA (H chain) | SEQ ID NO: | Sequence AA (L chain) |
|---|---|---|---|---|---|
| 752-2 B3 | EDE 1 | 58 | EVQLLESGGGLVQPGGSLRLSCSASGFTFSTYSM HWVRQAPGKGLEYVSAISTDGDSAFYADSVKGR FTISRDNSKNTLYFHMSSLRAEDTAVYYCLGGYS TFYYYYTMDVWGQGTTVTVSS | 104 | EIVLTQSPATLSLSPGE RATLSCRASHSISTFL AWYQQKPGQAPRLLI YDTSTRATGVPARFS GSRSGTDFTLTINTLEP EDFAVYYCQQRYNW PPYTFGQGTKVEIK |
| 752-2 B4 | EDE 1 | 59 | QVQLVESGGGLVQPGGSLRLSCSASGFPFSTYSM HWVRQAPGKGLEYVSAITTNGDSTFYADSVKGR FTISRDNSKNTVYFQLSSLRAEDTAVYYCVGGYS SFYFYYTMDVW | 105 | EIVLTQSPATLSLSPGE RATLSCRASQSISSFLA WYQQKPGQAPRLLIY DTSNRATGVPARFSGS RSGTDFTLTISTLEPED FAIYYCQHRYNWPPY TFGQGTKVEIK |
| 752-2 B7 | EDE 1 | 60 | EVQLVQSGAEVKKPGASVKVSCKASGYTYTNY GLSWVRQAPGQGLEWMGWMSSYNDNTNYSQK FKGRVTMTTDPSTTTAYMELRSLRSDDTAVYYC ARGLYSGSHYPTSPLDYWGQGTLVTVSS | 106 | DIQMTQSPSSLSASVG DRVTITCRASQSISRSL NWYQQKPGKAPKLLI YAASTLQSGVPSRFSG SGSGTDFALTISSLQPE DFATYSCQQSDRTPY TFGQGTKVEIK |
| 752-2 B11 | EDE 1 | 61 | EVQLVESGGGLVQPGGSLRLSCSASGFTFTTYSL HWVRQTPGKGLEYVSAITTDGDSAFYADSVKGR FTISRDNSKNTMYFHMSSLRPEDTAVYYCVGGY SSFYYFYTVDVWGQGTTVTVSF | 107 | EIVLTQSPATLSLSPGE RATLSCRASQSISTYL VWYQQKPGQAPRLLI YDASTRATGVPARFS GSRSGTDFTLTISTLEP EDFAVYYCQHRYNW PPYTFGRGTKVEIK |
| 752-2 C4 | EDE 1 | 62 | SQVQLVESGAELKKPGASVKVSCKASGYTFSYY MHWVRQAPGQGLEWMAIINPTSGSTTYAQRFQ GRVTMTRDTSTSTVYMELSSLRSEDTAVYYCAS RGYNWNDVHYYYTMDVWGQGTTVTVSS | 108 | DIQMTQSPSTLSASVG DRVTITCRASQSISTYL AWYQQKVGKAPKLLI YKASTLEGGVPSRFSG SGSGTEFTLTISSLQPE DFAIYYCQQYNNYSP PVTFGGGTKVEIK |
| 752-2 C8 | EDE 1 | 1 | EVQLVESGGGLVQPGGSLRLSCSASGFTFSTYSM HWVRQAPGKGLEYVSAITGEGDSAFYADSVKGR FTISRDNSKNTLYFEMNSLRPEDTAVYYCVGGYS NFYYYYTMDVWGQGTTVTVSS | 37 | EIVLTQSPATLSLSPGE RATLSCRASQSISTFL AWYQHKPGQAPRLLI YDASTRATGVPARFS GSRSGTDFTLTISTLEP EDFAVYYCQQRYNW PPYTFGQGTKVEIK |
| 753(3) C10 | EDE 1 | 2 | EVQLVESGAEVKKPGASVKVSCKASGYTFTSYA MHWVRQAPGQRLEWMGWINAGNGNTKYSQKF QDRVTITRDTSASTAYMELSSLRSEDTAIYYCAR DKVDDYGDYWFPTLWYFDYWGQGTLVTVSS | 38 | QSALTQPASVSGSPGQ SITISCTGTSSDVGGFN YVSWFQQHPGKAPKL MLYDVTSRPSGVSSRF SGSKSGNTASLTISGL QAEDEADYYCSSHTS RGTWVFGGGTKLTVL |
| 753(3) B10 | EDE 1 | 63 | EVQLVESGPEVKKPGASVKVSCKTSGYTFINYYI HWVRQAPGQGLEWLGLINPRGGNTNYAEKFED RVTMTRDTSTSTVNMELSSLTSEDTAVYYCARP LAHTYDFWSGYHRATGYGMDVWGQGTTVTVS S | 109 | DIVMTQSPLSLSVTPG EPASISCRSSQSLVYSD GNKYLDWYVQKPGQ SPQLLIYLTSTRASGV PDRFSGSASGTDFTLK ISRVEAEDVGLYYCM QALQTPFTFGPGTKV DIK |
| 758 P6A1 | EDE 1 | 64 | EVQLVESGGGLVQPGGSLRLSCAAFGFTFVNYA MNWVRQAPGKGPEWVAVIYAAGDGANYGDSV KGRFTISRDNSRNTLYLQMNSLRAEDTAIYYCAK PAHYDDSGYPYMAYFDSWGQGTLVTVSS | 110 | EIVMTQSPATLSVSPG ERATLTCRASQTISTF LAWYQQKPGQPPRLL IYDTSTRATGIPGRFSG SRSGTEFTLTISSLQSE DVAVYYCQHYYNWP PWTFGQGTKVEIK |

-continued

| Sequence ID | epitope | SEQ ID NO: | Sequence AA (H chain) | SEQ ID NO: | Sequence AA (L chain) |
|---|---|---|---|---|---|
| 758 P6A3 | EDE 1 | 65 | QVQLVQSGAEVKKPGSSVKVSCKASGGFFSSYAITWVRQAPGQGLEWMGGIIPDYDSAKYAQKFQGRVTITADESTSTAYLELRSLRSEDTAVYYCARRHCSSTSCSDPWTFFPSWGQGTLVTSPQ | 111 | QSALTQPPSASGSPGQSVTISCTGSSSDIGGNEYVSWYQLQPGKAPKLMIYEVTKRPSGVPNRFSGSKSGNTASLTVSGLQSEDEGDYYCSSYADNSVLFGGGTTLTVL |
| 758 P6A1 2 | EDE 1 | 66 | EVQLVESGAEMKKPGSSVKVSCKASGATFTSFAMYWVRQAPGQGLEWMGRIIPMFASAEYAQKFQGRLTMTADESTTTAYMELSSLRSDDTAVYYCAGRYCSSTSCSDPWTYFPHWGQGTLVTVSS | 112 | QSVLTQPPSASGSPGQSVTISCTGTSSDVGAYYYVSWYQQHPGKAPKLIIYEVNKRPSGVPARFSGSKSGNTASLTVSGLQGEDEADYYCTSYAGSNTVIFGGGTKLTVL |
| 758 P6B4 | EDE 1 | 67 | EVQLVQSGATVRKPGASVTISCKTSGYTFTDYALHWVRQAPGQRLEWMGWLIPGSGYTKFAENFQGRVTITRATSAHTAYMELSNLRSEDTAVYYCARWGGDCNAGSCYGPYQYRGLDAWGQGTTVTVSS | 113 | EIVLTQSPVTLSLSPGERATLSCRASQTVDSTYLAWYQQKPGRAPRLLIYGASNRAIGVPSRFTGSGSGTDFTLTISRLEPEDFALYYCQQSDGSLFTFGPGTKVDIK |
| 758 P6B5 | EDE 1 | 68 | EVQLVQSGAEVKKPGASVKVSCKASGYSFIGYYLHWVRQAPGQGLEWMGRINPNSGGIDYGQTFQGRVTMTRDMSSSTVYLELTRLRSDDTARYYCAGRSDNWNDVYYNYALDVWGQGTTVTVSS | 114 | DIQMTQSPASVSASVGDRVTISCRASQGIASWLAWYQQKPGKAPRLLIYGASSLQSGVPSRFRGSGSGTDFTLTISSLQPEDFATYYCQQANSFPFTFGPGTKVDIK |
| 758 P6B1 1 | EDE 1 | 69 | EVQLLESGGGVVQPGRSLKLSCAASGFTFSGYAMHWVRQAPGKGLEWLAVISYDATTTYYTPSVKGRFTISRDNSKNTLYLQINSLRAEDAAVYYCAKEISYCGGDCQNFFFYYNMDVWGQGTTVTVSS | 115 | QSALTQPASVSGSPGQSITISCTGTSSDVGRYNVVSWYQQHPGKAPKLIIYGSTKRPSGVSYRFSASKSGNTASLTISGLQAEDEAEYHCCSYASGSVWVFGGGTKLTVL |
| 758 P6C4 | EDE 1 | 70 | QVQLVQSGAEVKKPGASVKVSCKASGYTFTAYYIHWVRQAPGQGLEWMGSINPNNGGTNYAQGFQGRVTMTRDTSIRTVYMELSKLRSDDTALYYCARDLGAMGYYLCSAGNCPFDYWGQGTLVTVSS | 116 | QSALTQPPSASGSPGQSVTISCTGTSSDVGGYNYVSWYQHHPGKAPKLIIYEVSKRPSGVPHRFSGSKSGNTASLTVSGLQAEDEAEYYCSSYAGSNTFTFGGGTKLTVL |
| 747 B8 | EDE 2 | 71 | QVQLVESGGALVKPGGSLRLSCAASGFTFRSHWMHWVRQAPGKGLVWVSRINSDGSSTNYADFVKGRFTTSRDNAENTLYLEMNSLTADDTAVYYCVRDGVRYYYDSSGYYPDSFFKYGMDVWGQGTTVTVSS | 117 | QSALTQTASVSGSPGQSITISCTGTSSDAEIYNLVSWYQQHPGKAPKLIIYEGSKRPSGVSNRFSASKSAGAASLRISGLQPEDEADYYCCSYATSKTLVFGGGTKLTVV |
| 747 C2 | EDE 2 | 72 | EVQLVESGGGLVQPGGSLRLSCAASGFTFRSSAMYWVRQAPGKGLEFVSCIRSNGVTHYADSVKGRFTISRDNSKNTLHLQMGGLRPDDMAVYYCTRDDGPYSGYDWPWASSMDVWGQGTTVTVSS | 118 | DVVMTQSPLSLPVTLGQPASISCRSSRSLLNSDGNTYLNWFHQRPGQSPRRLIFKLSNRDSGVPDRFSGSGSGTDFTLKISRVEAEDVGIYYCMQGTHWPVTFGGGTKVEIK |
| 747 D8 | EDE 2 | 73 | EVQLVESGGGLVQPGGSLRLSCAASGFIFSNHWMHWVRQAPGKGLVWVSRTNSDGSSTSYADFVKGRFTISRDNAKNTLHLQINSLRADDTAVYYCARDGVRYYYDSTGYYPDSYYEYGLDVWGQGTTVTVSS | 119 | QSALTQPASVSGSPGQSITISCTGTSSGVGSYNLVSWYQQHPGKAPKFIIYEGSKRPSGVSNRFSGSNSGNTASLTISGLQAEDEADYYCCSYAGSKTLVFGGGTKVTVL |

-continued

| Sequence ID | epitope | SEQ ID NO: | Sequence AA (H chain) | SEQ ID NO: | Sequence AA (L chain) |
|---|---|---|---|---|---|
| 747(4) A3 | EDE 2 | 74 | EVQLVESGGGLVQPGGSLRLSCAASGFIFNRHWMHWVRQGPGKGLVWVSRINSDGSSTSYADSVKGRFTISRDNAKNTLHLQINSLRAEDTAVYYCARDGVRYYYDSTGYYPDSYYEYGMDVWGQGTTVTVSS | 120 | QSVLTQPASVSGSPGQSITISCTGTSSDVGSYNLVSWYQQHPGKAPKFIIYEGSKRPSGVSNRFSGSNSGNTASLTISGLQAEDEADYYCCSYAGSKTLVFGGGTKVTVL |
| 747(4) A10 | EDE 2 | 75 | QVQLVQSGGALVKPGGSLRLSCVASGFTFGSHWMHWVRQAPGKGLVWVSRVNSDGSSTNYADFVKGRFTTSRDNAENTLYLEMNSLTADDTAVYYCVRDGVRYYYDSSGYYPDSFFKYGMDVWGQGTTVTVSS | 121 | QSALTQPASVSGSPGQSITISCTGTSSDIGIYNLVSWYQQHPGKAPKLIIYEGSKRPSGVSNRFSASKSAGAASLTISGLQPEDEADYYCCSYATSKTLVFGGGTKLTVV |
| 747(4) A11 | EDE 2 | 3 | EVQLVESGGGLVRPGGSLRLSCAASGFSYSNHWMHWVRQAPGKGLVWVSRINSDGSTRNYADFVKGRFTISRDNAENTLYLEMNSLTADDTAVYYCVRDGVRFYYDSTGYYPDSFFKYGMDVWGQGTTVTVSS | 39 | QSVLTQPASVSGSPGQSITISCTGTSSNADTYNLVSWYQQRPGKAPKLMIYEGTKRPSGVSNRFSASKSATAASLTISGLQPEDEADYYCCSYATSRTLVFGGGTKLTVV |
| 747(4) B4 | EDE 2 | 76 | QVQLQESGPGLVRPSETLSLTCTVSGLSVSTYYWSWIRQPPGKGLEWIAYVYSRGGTNYNPSLESRVTISVDTATNQFSLRLRSVTAADTAVYFCARATNYFDSSGYFFAPWFDPWGQGILVTVSS | 122 | EIVMTQSPATLSVSPGERATLSCRASQSVKSNLAWYQQKPGQAPRLLMYGASTRVVTIPARFSGSGSGTEFTLTISSLQSEDFAVYYCQQYNKWPLTFGGGTKVEIK |
| 747(4) B6 | EDE 2 | 77 | QVQLVQSGAEVKKPGSSVKVSCKASGGTRSSYAISWVRRAPGRGLEWMGVIIPFFGTANYAQIFQGRLTITADESTSIANMELTSLTPEDTAIYYCASGGGGYAGYNWFDPWGQGTLVTVSS | 123 | QSALTQPASVSGSPGQSITISCTGTSSDIGGFNYVSWYQQHPGKAPKVMIFDVSNRPSGVSNRFSGSKSGNTASLTISGLQAEDEADYYCSSYTTRTTYVFGTGTKVTVL |
| 747(4) B7 | EDE 2 | 4 | EVQLVESGGGLVQPGGSLKLSCAASGFTFSSHWMHWVRQAPGKGLVWVSRTNSDGSSTSYADSVKGRFMISRDNSKNTVYLHMNGLRAEDTAVYFCARDGVRYYYDSTGYYPDNFFQYGLDVWGQGTTVTVSS | 40 | QSALTQPASVSGSPGQSITISCTGISSDVETYNLVSWYEQHPGKAPKLIIYEASKRPSGVSNRFSGSKSGNTASLAISGLQAEDEADYYCCSYAGGKSLVFGGGTRLTVL |
| 747(4) D6 | EDE 2 | 78 | EVQLVQSGGGLIQPGGSLKLSCAASGFSFRNHWMHWVRQAPGKGLVWVSRVNSDGYSTSYADSVKGRFTISRDNAKNTLYLQMNSLRPEDTAVYFCARDGVRFYSDSTGYYPDNYFPYGMDVWGQGTTVTVSS | 124 | QSALTQPASVSGSPGQSITISCSGFSSDVGGDKVVSWYEQHPGKVPKLIIYEGSKRPSGVSNRFSGSKSGNTASLTISGLQAEDEADYYCCSYAGPKTLVFGGGTKVTVL |
| 747 B2 | EDE 2 | 79 | EVQLVESGGGLVQPGGSLRLSCKVSGFTFKAYWMHWVRQAPGKGLVWVSRINGLGSSRDYADSVRGRFTISRDDAENTVYLQMNSLTAEDTAMYYCARDVXFHDSSGYYRXGFXAPWG | 125 | NSPLSLSASVGDRVTITCRASRTIDNFLHWYQQKPGKAPNLLIYAASSLQSGVPSRFRGSGSGTDFTLTINSVQPEDFATYYCQQSYTIPPTFGGGTKVEIR |
| 747 C4 | EDE 2 | 80 | EVQLVESGGGLVQPGGSLRLSCAASGFAFSNHWMHWVRQAPGKGLVWVSRINSDGSSTTYADSVKGRFTISRDNAKNTLSLELNSLRAEDTAIYYCARDGVRFYYDSTGYYPDPYFQYGLDVWGQGTTVTVSS | 126 | QSALTQPASVSGSLGQSITISYTGTAIDVGSYNLVSWYQQHPGKVPKLMIYEGSKRPSGVSNRFFGSKSGNTASLTISGLQSEDEAEYYCCSYGGSRTLLFGGGTKLTVL |

-continued

| Sequence ID | epitope | SEQ ID NO: | Sequence AA (H chain) | SEQ ID NO: | Sequence AA (L chain) |
|---|---|---|---|---|---|
| 747 C7 | EDE 2 | 81 | EVQLVESGGGLVQPGASLRVSCAASGFTFSTYN MNWVRQAPGKGLEWVSYISSRSSTIYYADSVQG RFTISRDNAKNSLYLQMNSLRAEDTAVYYCARD IGHYYDSSGYFHYSFGMDVWGQGTTVTVSS | 127 | DIVMTQSPLSLPVTLG EPASISCRSSRSLLHSN GYNYLDWYLQKPGQ SPQLLIYLGSNRASGV PDRFSGSGSGTDFTLK ISRVEAEDVGVYYCM QARQTPVTFGGGTKV EIK |
| 747 D5 | EDE 2 | 82 | EVQLVESGGGLVQPGGSLRLSCAASGFIFRNYW MHWVRQAPGKGLVWVSRINGLGSTTTYADSVE GRFTITRDDAKNTIFLQMNSLRAEDTAVYYCAR DVNFYDSSGYYREGWFDSWGPGTTVTVSS | 128 | GPFTLSASVGDRVTIT CRASRSINTFLNWYQ QKTGSAPKLLIYGAST LQSGVPSRFSGSGSGT DFALTITSLQPDDFAA YYCQQSYTTPLTFGG GTRVEIK |
| 747 D11 | EDE 2 | 83 | EVQLLESGAEVKKPGSSVKISCKASGGTFSNYAIS WVRQAPGRGLEWLGGIIPIFGTPNYAQRFQGRVT ITADESTSTAYMELNSLTSDDTAIYYCARDHPTVI NPTFVGSWFDPWGQGTLVTVSS | 129 | SYELTQPPSVSVAPGK TATITCGGDNIGSKTV HWYQQKPGQAPLLVI YYNGDRPPGIPERFSG SNSGNTATLTITRVEA GDEADYCCQIWDSRS SHPVFGGGTKLTVL |
| 752 B6 | EDE 2 | 84 | QVQLVESGAEVKKPGASVKVSCKASGFTFTSYYI HWVRQAPGQGLEWMGVINPSGGTTIYARNLQG RVTMTRDTSTTTVYMELSSLKSEDTAVYYCARA HSGNYDFWSGSNYHYYYGMDVWGQGTTVTVS S | 130 | DIVMTQSPLSLPVTPG EPASISCRSSQSLLHTN GYNFLDWYVQKPGQ SPQLLIYLGSSRASGV PDRFSGSGSGTDFTLK ISRVEAEDVGLYYCM QALHTPRTFGQGTKV EIK |
| 752(2) D2 | EDE 2 | 85 | EVQLVESGAEVKKPGASVKVSCKASGFTFTSYYI HWVRQAPGQGLEWMGVINPSGGTTIYAQNFQG RVTMTRDTSTTTVYMELSSLKSEDTAVYYCARA HSGNYDFWSGSNYHYYYGMDVWGQGTTVTVS S | 131 | DIVMTQSPLSLPVTPG EPASISCRSSQSLLHTN GYNFLDWYVQKPGQ SPQLLIYLGSSRASGV PDRFSGSGSGTDFTLK ISRVEAEDVGLYYCM QALQTPRTFGQGTKV EIK |

envelope ectodomain protein sequence DENV1

SEQ ID NO: 132

FHLTTRGGEPHMIVSKQERGKSLLFKTSAGVNMCTLIAMDLGELCEDTMTYKCP

RITEAEPDDVDCWCNATDTWVTYGTCSQTGEHRRDKRSVALAPHVGLGLETRT

ETWMSSEGAWKQIQKVETWALRHPGFTVIALFLAHAIGTSITQKGIIFILLMLVTP

SMAMRCVGIGNRDFVEGLSGATWVDVVLEHGSCVTTMAKNKPTLDIELLKTEV

TNPAVLRKLCIEAKISNTTTDSRCPTQGEATLVEEQDANFVCRRTVVDRGWGNG

CGLFGKGSLLTCAKFKCVTKLEGKIVQYENLKYSVIVTVHTGDQHQVGNETTEH

GTIATITPQAPTSEIQLTDYGTLTLDCSPRTGLDFNEVVLLTMKEKSWLVHKQWF

LDLPLPWTSGASTSQETWNRQDLLVTFKTAHAKKQEVVVLGSQEGAMHTALTG

ATEIQTSGTTTIFAGHLKCRLKMDKLTLKGMSYVMCTGSFKLEKEVAETQHGTV

LVQVKYEGTDAPCKIPFSTQDEKGVTQNGRLITANPIVTDKEKPINIETEPPFGESY

IIVGAGEKALKLSWFKKG envelope ectodomain protein sequence DENV2

SEQ ID NO: 133

MRCIGISNRDFVEGVSGGSWVDIVLEHGSCVTTMAKNKPTLDFELIKTEAKQPAT

LRKYCIEAKLTNTTTESRCPTQGEPSLNEEQDKRFICKHSMVDRGWGNGCGLFG

-continued

KGGIVTCAKFTCKKNMEGKIVQPENLEYTIVITPHSGEEHAVGNDTGKHGKEIKIT

PQSSTTEAELTGYGTVTMECSPRTGLDFNEMVLLQMEDKAWLVHRQWFLDLPL

PWLPGADTQGSNWIQKETLVTFKNPHAKKQDVVVLGSQEGAMHTALTGATEIQ

MSS GNLLFTGHLKCRLRMDKLQLKGMSYSMCTGKFKIVKEIAETQHGTIVIRVQ

YEGDGSPCKIPFEITDLEKRHVLGRLITVNPIVTEKDSPVNIEAEPPFGDSYIIVGVE

PGQLKLNWFKRG envelope ectodomain protein sequence DENV3

SEQ ID NO: 134

FHLTSRDGEPRMIVGKNERGKSLLFKTASGINMCTLIAMDLGEMCDDTVTYKCP

HITEVEPEDIDCWCNLTSTWVTYGTCNQAGEHRRDKRSVALAPHVGMGLDTRT

QTWMSAEGAWRQVEKVETWALRHPGFTILALFLAHYIGTSLTQKVVIFILLMLV

TPSMTMRCVGVGNRDFVEGLSGATWVDVVLEHGGCVTTMAKNKPTLDIELQKT

EATQLATLRKLCIEGKITNITTDSRCPTQGEAILPEEQDQNYVCKHTYVDRGWGN

GCGLFGKGSLVTCAKFQCLESIEGKVVQHENLKYTVIITVHTGDQHQVGNETQG

VTAEITSQASTAEAILPEYGTLGLECSPRTGLDFNEMILLTMKNKAWMVHRQWFF

DLPLPWTSGATTKTPTWNRKELLVTFKNAHAKKQEVVVLGSQEGAMHTALTGA

TEIQTSGGTSIFAGHLKCRLKMDKLKLKGMSYAMCLNTFVLKKEVSETQHGTILI

KVEYKGEDAPCKIPFSTEDGQGKAHNGRLITANPVVTKKEEPVNIEAEPPFGESNI

VIGIGDKALKINWYRKG envelope ectodomain protein sequence DENV4

SEQ ID NO: 135

FSLSTRDGEPLMIVAKHERGRPLLFKTTEGINKCTLIAMDLGEMCEDTVTYKCPL

LVNTEPEDIDCWCNLTSTWVMYGTCTQSGERRREKRSVALTPHSGMGLETRAET

WMSSEGAWKHAQRVESWILRNPGFALLAGFMAYMIGQTGIQRTVFFVLMMLVA

PSYGMRCVGVGNRDFVEGVSGGAWVDLVLEHGGCVTTMAQGKPTLDFELTKT

TAKEVALLRTYCIEASISNITTATRCPTQGEPYLKEEQDQQYICRRDVVDRGWGN

GCGLFGKGGVVTCAKFSCSGKITGNLVQIENLEYTVVVTVHNGDTHAVGNDTSN

HGVTAMITPRSPSVEVKLPDYGELTLDCEPRSGIDFNEMILMKMKKKTWLVHKQ

WFLDLPLPWTAGADTSEVHWNYKERMVTFKVPHAKRQDVTVLGSQEGAMHSA

LAGATEVDS GDGNHMFAGHLKCKVRMEKLRIKGMSYTMCSGKFSIDKEMAETQ

HGTTVVKVKYEGAGAPCKVPIEIRDVNKEKVVGRIISSTPLAENTNSVTNIELEPPF

GDSYIVIGVGNSALTLHWFRKG envelope ectodomain nucleotide sequence DENV1

SEQ ID NO: 136 ttccatttga ccacacgagg gggagagcca cacatgatag ttagtaagca ggaaagagga aagtcactct tgttcaagac ctctgcaggt gtcaatatgt gcactctcat tgcgatggat ttgggagagt tatgtgagga cacaatgact tacaaatgcc cccggatcac tgaggcggaa ccagatgacg ttgactgctg gtgcaatgcc acagacacat gggtgaccta tgggacgtgt tctcaaaccg gtgaacaccg acgagacaaa cgttccgtgg cactggcccc acacgtggga cttggtctag aaacaagaac cgaaacatgg atgtcctctg aaggcgcctg gaaacaaata caaaaagtgg agacttgggc tttgagacac ccaggattca cggtgatagc tcttttttta gcacatgcca taggaacatc catcactcag aaagggatca ttttcattct gctgatgctg gtaacaccat caatggccat gcgatgcgtg ggaataggca acagagactt cgttgaagga -continued ctgtcaggag caacgtgggt ggacgtggta ttggagcatg gaagctgcgt caccaccatg gcaaaaaata aaccaacatt ggacattgaa ctcttgaaga cggaggtcac gaaccctgcc gtcttgcgca aattgtgcat tgaagctaaa atatcaaaca ccaccaccga ttcaagatgt ccaacacaag gagaggctac actggtggaa gaacaagacg cgaactttgt gtgtcgacga acggttgtgg acagaggctg gggcaatggc tgcggactat ttggaaaagg aagcctactg acgtgtgcta agttcaagtg tgtgacaaaa ctggaaggaa agatagttca atatgaaaac ttaaaatatt cagtgatagt cactgtccac acaggggacc agcaccaggt gggaaacgag actacagaac atggaacaat tgcaaccata acacctcaag ctcctacgtc ggaaatacag ttgacagact acggaaccct tacactggac tgctcaccca gaacagggct ggactttaat gaggtggtgc tattgacaat gaaagaaaaa tcatggcttg tccacaaaca atggtttcta gacttaccac tgccttggac ttcgggggct tcaacatccc aagagacttg gaacagacaa gatttgctgg tcacattcaa gacagctcat gcaaagaagc aggaagtagt cgtactggga tcacaggaag gagcaatgca cactgcgttg accggggcga cagaaatcca gacgtcagga acgacaacaa tctttgcagg acacctgaaa tgcagattaa aaatggataa actgacttta aaagggatgt catatgtgat gtgcacaggc tcatttaagc tagagaagga agtggctgag acccagcatg gaactgtcct agtgcaggtt aaatacgaag gaacagatgc gccatgcaag atcccctttt cgacccaaga tgagaaagga gtgacccaga atgggagatt gataacagcc aatcccatag ttactgacaa agaaaaacca atcaacattg agacagaacc accttttggt gagagctaca tcatagtagg ggcaggtgaa aaagctttga aactaagctg gttcaagaaa gga envelope ectodomain nucleotide sequence DENV2

SEQ ID NO: 137 ttccatttaa ccacacgtaa cggagaacca cacatgatcg tcagtagaca agagaaaggg aaaagtcttc tgtttaaaac agaggatggt gtgaacatgt gtaccctcat ggccatggac cttggtgaat tgtgtgaaga tacaatcacg tacaagtgtc cttttctcag gcagaatgaa ccagaagaca tagattgttg gtgcaactct acgtccacat gggtaactta tgggacgtgt accaccacag gagaacacag aagagaaaaa agatcagtgg cactcgttcc acatgtggga atgggactgg agacacgaac tgaaacatgg atgtcatcag aaggggcctg gaaacatgcc cagagaattg aaacttggat cttgagacat ccaggcttta ccataatggc agcaatcctg gcatacacca taggaacgac acatttccaa agagccctga ttttcatctt actgacagct gtcgctcctt caatgacaat gcgttgcata ggaatatcaa atagagactt tgtagaaggg gtttcaggag gaagctgggt tgacatagtc ttagaacatg gaagctgtgt gacgacgatg gcaaaaaaca aaccaacatt ggattttgaa ctgataaaaa cagaagccaa acaacctgcc actctaagga agtactgtat agaggcaaag ctgaccaaca caacaacaga ttctcgctgc ccaacacaag gagaacccag cctaaatgaa gagcaggaca aaaggttcgt ctgcaaacac tccatggtgg acagaggatg gggaaatgga tgtggattat ttggaaaagg aggcattgtg acctgtgcta tgttcacatg caaaaagaac atgaaaggaa aagtcgtgca accagaaaac ttggaataca ccattgtgat aacacctcac tcaggggaag agcatgcagt cggaaatgac acaggaaaac atggcaagga aatcaaaata acaccacaga gttccatcac agaagcagag ttgacaggct atggcactgt cacgatggag tgctctccga gaacgggcct cgacttcaat gagatggtgt tgctgcaaat ggaaaataaa gcttggctgg tgcacaggca atggttccta gacctgccgt tgccatggct gcccggagcg gacacacaag gatcaaattg gatacagaaa -continued gagacattgg tgactttcaa aaatccccat gcgaagaaac aggatgttgt tgttttggga
tcccaagaag ggccatgca cacagcactc acaggggcca cagaaatcca gatgtcatca
ggaaacttac tgttcacagg acatctcaag tgcaggctga ggatggacaa actacagctc
aaaggaatgt catactctat gtgcacagga aagtttaaag ttgtgaagga aatagcagaa
acacaacatg gaacaatagt tatcagagta caatatgaag gggacggttc tccatgtaag
atcccttttg agataatgga tttggaaaaa agacatgttt taggtcgcct gattacagtc
aacccaatcg taacagaaaa agatagccca gtcaacatag aagcagaacc tccattcgga
gacagctaca tcatcatagg agtagagccg ggacaattga agctcaactg gtttaagaaa
gga envelope ectodomain nucleotide sequence DENV3

SEQ ID NO: 138 ttccacttaa cttcacgaga tggagagccg cgcatgattg tggggaagaa tgaaagagga
aaatccctac tttttaagac agcctctgga atcaacatgt gcacactcat agccatggat
ttgggagaga tgtgtgatga cacggtcact tacaaatgcc cccacattac cgaagtggag
cctgaagaca ttgactgttg gtgcaacctt acatcgacat gggtgactta tggaacatgc
aatcaagctg gagagcatag acgcgataag agatcagtgg cgttagctcc ccatgtcggc
atgggactgg acacacgcac tcaaacctgg atgtcggctg aaggagcttg gagacaagtc
gagaaggtag agacatgggc ccttaggcac ccagggttta ccatactagc cctatttctt
gcccattaca taggcacttc cttgacccag aaagtggtta tttttatact attaatgctg
gttaccccat ccatgacaat gagatgtgtg ggagtaggaa acagagattt tgtggaaggc
ctatcgggag ctacgtgggt tgacgtggtg ctcgagcacg gtgggtgtgt gactaccatg
gctaagaaca agcccacgct ggacatagag cttcagaaga ctgaggccac tcagctggcg
accctaagga agctatgcat tgagggaaaa attaccaaca taacaaccga ctcaagatgt
cccacccaag gggaagcgat tttacctgag gagcaggacc agaactacgt gtgtaagcat
acatacgtgg acagaggctg gggaaacggt tgtggtttgt ttggcaaggg aagcttggtg
acatgcgcga aatttcaatg tttagaatca atagagggaa aagtggtgca acatgagaac
ctcaaataca ccgtcatcat cacagtgcac acaggagacc aacaccaggt gggaaatgaa
acgcagggag ttacggctga gataacatcc caggcatcaa ccgctgaagc cattttacct
gaatatggaa ccctcgggct agaatgctca ccacggacag gtttggattt caatgaaatg
attttattga caatgaagaa caaagcatgg atggtacata gacaatggtt ctttgactta
cccctaccat ggacatcagg agctacaaca aaaacaccaa cttggaacag gaaagagctt
cttgtgacat ttaaaaatgc acatgcaaaa aagcaagaag tagttgtcct tggatcacaa
gagggagcaa tgcatacagc actgacagga gctacagaga tccaaacctc aggaggcaca
agtatttttg cggggcactt aaaatgtaga ctcaagatgg acaaattgaa actcaagggg
atgagctatg caatgtgctt gaatacccttt gtgttgaaga aagaagtctc cgaaacgcag
catgggacaa tactcattaa ggttgagtac aaaggggaag atgcaccctg caagattcct
ttctccacgg aggatggaca agggaaagct cacaatggca gactgatcac agccaatcca
gtggtgacca agaaggagga gcctgtcaac attgaggctg aacctccttt tggggaaagt
aatatagtaa ttggaattgg agacaaagcc ctgaaaatca actggtacag gaagggaa -continued envelope ectodomain nucleotide sequence DENV4

SEQ ID NO: 139 ttttccctca gcacaagaga tggcgaaccc ctcatgatag tggcaaaaca tgaaaggggg agacctctct tgtttaagac aacagagggg atcaacaaat gcactctcat tgccatggac ttgggtgaaa tgtgtgagga cactgtcacg tataaatgcc ccctactggt caataccgaa cctgaagaca ttgattgctg gtgcaacctc acgtctacct gggtcatgta tgggacatgc acccagagcg gagaacggag acgagagaag cgctcagtag ctttaacacc acattcagga atgggattgg aaacaagagc tgagacatgg atgtcatcgg aaggggcttg gaagcatgct cagagagtag agagctggat actcagaaac ccaggattcg cgctcttggc aggatttatg gcttatatga ttgggcaaac aggaatccag cgaactgtct tctttgtcct aatgatgctg gtcgccccat cctacggaat gcgatgcgta ggagtaggaa acagagactt tgtggaagga gtctcaggtg gagcatgggt cgacctggtg ctagaacatg gaggatgcgt cacaaccatg gcccagggaa aaccaacctt ggattttgaa ctgactaaga caacagccaa ggaagtggct ctgttaagaa cctattgcat tgaagcctca atatcaaaca taactacggc aacaagatgt ccaacgcaag gagagcctta tctgaaagag gaacaggacc aacagtacat ttgccggaga gatgtggtag acagagggtg gggcaatggc tgtggcttgt ttggaaaagg aggagttgtg acatgtgcga agttttcatg ttcggggaag ataacaggca atttggtcca aattgagaac cttgaataca cagtggttgt aacagtccac aatggagaca cccatgcagt aggaaatgac acatccaatc atggagttac agccatgata actcccaggt caccatcggt ggaagtcaaa ttgccggact atggagaact aacactcgat tgtgaaccca ggtctggaat tgactttaat gagatgattc tgatgaaaat gaaaaagaaa acatggctcg tgcataagca atggtttttg gatctgcctc ttccatggac agcaggagca gacacatcag aggttcactg gaattacaaa gagagaatgg tgacatttaa ggttcctcat gccaagagac aggatgtgac agtgctggga tctcaggaag gagccatgca ttctgccctc gctggagcca cagaagtgga ctccggtgat ggaaatcaca tgtttgcagg acatcttaag tgcaaagtcc gtatggagaa attgagaatc aagggaatgt catacacgat gtgttcagga aagttttcaa ttgacaaaga gatggcagaa acacagcatg ggacaacagt ggtgaaagtc aagtatgaag gtgctggagc tccgtgtaaa gtccccatag agataagaga tgtaaacaag gaaaaagtgg ttgggcgtat catctcatcc accccttttgg ctgagaatac caacagtgta accaacatag aattagaacc ccccttttggg gacagctaca tagtgatagg tgttggaaac agcgcattaa cactccattg gttcaggaaa ggg A11 Light chain

SEQ ID NO: 140

QSVLTQPVSVSGSPGQSITISCTGTSSNADTYNLVSWYQQRPGKAPKLMIYEGTK

RPSGVSNRFSASKSATAASLTISGLQPEDEADYYCCSYATSRTLVFGGGTKLTVV

B7 Light chain

SEQ ID NO: 141

RSQSALTQPASVSGSPGQSITISCTGISSDVETYNLVSWYEQHPGKAPKLIIYEASK

RPSGVSNRFSGSKSGNTASLAISGLQAEDEADYYCCSYAGGKSLVFGGGTRLTVL

GQPKAAPSVTLFPPSSEELQANKATLVCLISDFYPGAVTVAWKADSSPVKAGVET

TTPSKQSNNKYAASSYLSLTPEQWKSHRSYSCQVTHEGSTVEKTVAPTECS

-continued vH chain of A11

SEQ ID NO: 142

EVQLVESGGGLVRPGGSLRLSCAASGFSYSNHWMHWVRQAPGKGLVWVSRINS

DGSTRNYADFVKGRFTISRDNAENTLYLEMNSLTADDTAVYYCVRDGVRFYYD

STGYYPDSFFKYGMDVWGQGTTVTV vH B7

SEQ ID NO: 143

EVQLVESGGGLVQPGGSLKLSCAASGFTFSSHWMHWVRQAPGKGLVWVSRTNS

DGSSTSYADSVKGRFMISRDNSKNTVYLHMNGLRAEDTAVYFCARDGVRYYYD

STGYYPDNFFQYGLDVWGQGTTVTV vH C8

SEQ ID NO: 144

EVQLVESGGGLVQPGGSLRLSCSASGFTFSTYSMHWVRQAPGKGLEYVSAITGE

GDSAFYADSVKGRFTISRDNSKNTLYFEMNSLRPEDTAVYYCVGGYSNFYYYYT

MDVWGQGTTVTV vLight C8

SEQ ID NO: 145

EIVLTQSPATLSLSPGERATLSCRASQSISTFLAWYQHKPGQAPRLLIYDASTRATG

VPARFSGSRSGTDFTLTISTLEPEDFAVYYCQQRYNWPPYTFGQGTKVEIK vH C10

SEQ ID NO: 146

EVQLVESGAEVKKPGASVKVSCKASGYTFTSYAMHWVRQAPGQRLEWMGWIN

AGNGNTKYSQKFQDRVTITRDTSASTAYMELSSLRSEDTAIYYCARDKVDDYGD

YWFPTLWYFDYWGQGTLVTV vL C10

SEQ ID NO: 147

QSALTQPASVSGSPGQSITISCTGTSSDVGGFNYVSWFQQHPGKAPKLMLYDVTS

RPSGVSSRFSGSKSGNTASLTISGLQAEDEADYYCSSHTSRGTWVFGGGTKLTVL 150 loop of Denv-1

SEQ ID NO: 148

QHQVGNETTEHG 150 loop of Denv 2

SEQ ID NO: 149

EHAVGNDTGKHG 150 loop of Denv 3

SEQ ID NO: 150

QHQVGNETQG 150 loop of Denv 4

SEQ ID NO: 151

THAVGNDIPNHG

Example 17. Site-Directed Mutagenesis of the DV2 E Protein in Order to Obtain Stable E Dimers Based on the 3D structure, we generated 3 different E mutants in order to create disulphide bonds to stabilise the E dimer. The first had A259C, the second S255C and the third had two simultaneous changes: L107C and A313C (FIG. 32). The mutants were expressed in insect S2 cells using the same procedure that we had developed for wild-type DV-2 E protein, as described above. Mutant A259C gave the highest yields of purified dimeric protein, but the other two constructs also yielded reasonable amounts of cross-linked dimers. The mutants were compared to wild type in antibody-binding and in mice immunization experiments.

1. Binding of FLE and EDE mAbs to the Mutants.

A panel of FLE (fusion loop epitope), EDE (envelope dimer epitope) and other (non FLE) mAbs were tested on the mutant and WT protein by ELISA. FIGS. 33-36 show the binding activity of FLE and EDE mAbs on the A259C mutant and WT.

FIG. 37-40 shows the binding activity of FLE and EDE mAbs on the L107/A313 mutant and WT 2 Mice Immunisation with the A259C Mutant Mice were set into 6 groups and immunised as prime followed by boost as describe below

- Group 1 prime and boost with E WT. E WT (monomer/monomer)
- Group 2, prime and boost with E A259C mutant (dimer/dimer)
- Group 3 prime and boost with prM/E viral like particle (VLP) (VLP/VLP)

Group 4 prime with E A259C mutant followed by boosting with VLP (dimer/VLP)

Group 5 prime with VLP followed by boosting with E A259C mutant (VLP/dimer)

Group 6 control mice (mock)

FIGS. 41-45 shows the anti E antibody titre, binding to yeast expressing E domain 1 to 3 (all 3 domains), domain 1-2 and domain 3, serotype cross reactivity, neutralisation on insect and DC virus and ADE on insect virus.

Methods

Recombinant Soluble DENV Envelope Protein Binding ELISA

To determine the binding affinity of human monoclonal Abs to recombinant soluble DENV envelope protein (rE), the Nunc Immobilizer Amino plates (436006, Thermo Scientific) were directly coated with 50 µl of 10 µg/ml rE DENV2 wild type monomer (WT), mutant dimer (A259C or L107C/A313C) or bovine serum albumin (BSA; negative control) in 50 mM carbonate buffer pH 9.6 (C3041, Sigma). Following overnight incubation at 4° C., plates were washed 3 times with wash buffer (PBS+0.1% Tween-20) and blocked with 200 µl blocking buffer (PBS+3% BSA) for 1 hr at the room temperature followed by 50 µl of 1-10 µg/ml human monoclonal Abs in blocking buffer at 37° C. for 1 hr. Afterwards, Plates were washed again 3 times and further incubated with 50 µl of ALP-conjugated anti-human IgG at 1:10,000 dilutions in blocking buffer (A9544, Sigma) for 1 hr at 37° C. Finally, after 3× washing, 100 µl of PNPP substrate (N2770, Sigma) was added and left for 1 hr at the room temperature. The reaction was measured at 405 nm.

Mice

Female C57BL/6 mice were obtained from Harlan UK (Bicester, UK). Mice were used at 6-8 weeks of age. All animal experiments were performed in accordance with United Kingdom governmental regulations (Animal Scientific Procedures Act 1986) and were approved by the United Kingdom Home Office.

Immunization Experiment

Mice were intra-peritoneally administered with 1% v/v of antigen (5 µg) co-adsorbed on 2% alhydrogel (Invivogen). The antigen-alum mix was allowed to stand for about 5 min prior to injection. At 3 weeks post priming, a booster injection was given with 5 µg antigen similarly adsorbed on alum. Serum samples were collected at 3 weeks following the boost and tested in various assays. DV2-VLP supernatant was generated by PEI mediated transfection of HEK293T cells with pHLsec-prM-E plasmid DNA. The VLP supernatant collected in UltraDoma protein free medium (Lonza, USA) was concentrated and buffer exchanged to PBS using Centricon (100 KDa cut-off). E-protein was estimated using capture ELISA. Briefly VLP supernatant was captured using mouse anti-FL (4G2) and detected using DENV-specific human antibody to E protein, 30-E2 (from patients); followed by AP-conjugated antibody to human IgG (A9544; Sigma). The colorimetric reaction was developed using PNPP substrate and absorbance measured at 405 nm. E-protein in the VLP supernatant was quantified based on non-linear regression analysis of standard curve generated with purified E-protein monomer. The E-protein equivalent used for immunization was ~7 ng/mouse corresponding to a total protein concentration of ~5 mg/mouse. The total protein concentration for VLP preparation was performed by Bradford method using BSA as standard.

Measurement of Anti E Antibody Titre on Live Virus

Virus from supernatants of C636 cells infected with various Dengue serotypes was captured on Maxisorp immunoplate (442404; NUNC) coated with 10 µg/ml human anti-prM antibody, 3-147. Wells were then incubated with various dilutions of mouse serum diluted in 1% BSA, followed by 1:2000 dilution of Fc-specific goat anti-mouse IgG-alkaline phosphatase conjugate (A2429, Sigma). Reaction was visualized by the addition of PNPP substrate and read for absorbance at 405 nm after the reaction was stopped with 0.4N NaOH. Data was plotted and analysed using GraphPad prism v6.03.

Neutralization Assay

The neutralization potential of mouse sera was determined using the Focus Reduction Neutralization Test (FRNT), where the reduction in the number of the infected foci is compared to control (no antibody). For FRNT, Fifty-five microlitres of DENV-derived C6/36 cells (C6/36 DENV) or DENV-derived DC (DC-DENV) were mixed with an equal volume of serial 3-fold dilutions of mouse sera (from 1:50 to 1:36450 and incubated for 1 hr at 37° C. Fifty microlitres of the mixtures were then transferred to Vero cell monolayer in duplicate in 96-well plate and incubated for 3 days at 37° C. The focus-forming assay was then performed by washing the cell monolayer with 200 µl of PBS twice. Cells were then fixed with 100 µl of 3.7% formaldehyde in PBS for 10 min at the room temperature and then permeabilized with 100 µl of 2% TritonX-100 in PBS for 10 min at the room temperature. Following 2 times wash with PBS, 50 µl of mouse monoclonal anti-DENV envelope Ab (4G2) was added to each well and incubated for 2 hrs, at 37° C. Cells were washed again with PBS and incubated for 1 hr at 37° C. with 50 µl of HRP-conjugated goat anti-mouse IgG (P0447, Dako) at 1:1,000 dilutions in 0.05% tween-20/2% FBS in PBS. The reaction was visualized by the addition of DAB substrate (PBS+0.05 g/ml DAB+0.03% $H_2O_2$+0.32% $NiCl_2$). The percentage focus reduction was calculated for each antibody dilution.

Antibody Dependent Enhancement Assay

Serially diluted heat-inactivated mouse serum or control antibody (anti FL: 4G2) was pre-incubated with DV2-virus for 1 h at 37° C. The virus-antibody complexes were then transferred to U937 cells (Fc receptor-bearing human monocyte cell lines) plated at $1\times10^5$ cells/well. Cells were incubated with virus-antibody complexes for 4 days and viral titres determined by titration on Vero cells by a focus-forming assay using anti-FL, 4G2 antibody for detection. The virus titres were read out as focus-forming units per ml and fold enhancement of infection calculated based on the titres observed in the absence of antibody. Data was plotted and analysed using GraphPad prism v6.03.

CONCLUSIONS

The further data in this Example shows that we can make dimer; that it is correctly folded; binds to the EDE antibodies and is immunogenic.

FIG. 32 shows the locations of single and double site mutations. The A259C mutant binds to the panel of EDE 1 antibodies (FIG. 33). Likewise EDE2 panel antibodies bind also bind to the A259C mutant (FIG. 34). However (FIG. 35) FLE panel antibodies also bind (which is considered less desirable) probably because the E monomers can pivot around the central cysteine link allowing access to the FLE. The "non-FLE" panel of antibodies (antibodies which have not been mapped, termed non-fusion loop epitope (non FLE) mAb)) likewise bind to the A259C dimer (FIG. 36).

The double mutant L107C and A313C likewise forms a stable dimer which binds EDE1 antibodies (FIG. 37) and EDE2 antibodies (FIG. 38). However, this double mutant is locked at both ends and is much less recognised by the FLE antibodies (FIG. 39), which is ideal as one would prefer an immunogen that did not promote the generation of a FLE response. There is also less non-FLE recognition (FIG. 40) which is also good.

A series of mouse immunisations with different combinations of monomer, dimer and vlp are shown in FIG. 41. Dimer+/−VLP generate good serum antibodies recognising DENV2 virus particles (FIG. 41). Combinations with VLP initiate good cross reactive binding responses (FIG. 42), and are expected to provide good neutralisation. A tetravalent or prime boost approach may be required to generate broad neutralisation.

VLP was used at 5 μg E protein equivalent ie amount of E WT, mutant and VLP were 5 μg. E WT and mutant were protein and measured concentration based on OD whereas E conc on VLP prep was measured by ELISA and WT E protein was used for setting up a standard curve. Thus, E-protein was estimated using capture ELISA. Briefly VLP supernatant was captured using mouse anti-FL (4G2) and detected using DENV-specific human antibody to E protein, 30-E2 (from patients); followed by AP-conjugated antibody to human IgG (A9544; Sigma). The colorimetric reaction was developed using PNPP substrate and absorbance measured at 405 nm. E-protein in the VLP supernatant was quantified based on non-linear regression analysis of standard curve generated with purified E-protein monomer. 5 μg of VLP is considered to correspond to total protein containing about 7 ng of E protein equivalent.

The VLP may induce anti-prM activity that will not have been induced by monomer or dimer. The anti-prM activity induced by the VLP may contribute to the virion binding, cross reactivity, ADE and neutralisation results.

Neutralisation results of DENV2 show superior response from the dimer above the monomer on both insect (high prM; FIG. 43) and DC virus (low prM; FIG. 44) viruses.

FIG. 45 indicates that antibodies raised to the A259C dimer can still cause ADE (Antibody dependent enhancement of DENV infection). The A259C dimer also reacts with FL-Abs and thus could elicit FL-like Abs which cause strong ADE and displace EDE Abs. It is not yet known whether the L107C/A313C dimer induces ADE.

One possibility to test which component is important for ADE is to deplete serum from DIII binding Abs and to perform ADE tests again.

We are also performing other cavity filling approaches to the stable dimer in order to enhance the desired EDE response and minisise the less desirable FLE and nonFLE/nonEDE responses. Extensive mutagenic resurfacing of the dimer is also performed to further reduce the generation of non-EDE suboptimal responses by mutation of residues or addition of glycan (to assist in masking the less desirable FLE and nonFLE/nonEDE epitopes/responses).

Modelling and optimisation of the core EDE epitope is also performed to produce an optimal sequence to induce BNA's (broadly neutralising antibodies).

Priming and boosting with a variety of heterologous techniques may be required to focus in on the EDE.

A further dimer that is considered to be useful is a A259C/S255C double mutant, which may (similarly to the L107C/T313C double mutant) provide a dimer in which the FLE is less accessible.

A further mutation that is considered to reshape the kl-loop and to mimick the virion-like conformation is L278F as discussed above. Combinations of such a mutation and one or more mutations to establish cysteine links between monomers to form a dimer may be useful.

As noted above, a molecule displaying the EDE, for example a stabilised dimer, may be useful in screening for broadly neutralising antibodies, for example.

Example 18

Further Strategies for Optimising EDE Constructs or Binding Compounds

Protein Folding

In order to promote proper folding and assembly of stabilised dimer molecules, it may be useful to co-express EDE-binding compounds, for example Fabs or scFv in the same cells as the E protein. This is considered to aid protein folding and may assist in eliminating or reducing protein aggregates.

Reduction in prM Level

It may be desirable and possible to produce VLPs that lack prM, thereby potentially increasing their immunogenicity.

scFv Optimisation

A yeast display screen, for example, could be used to screen for optimised scFvs. Already-identified scFvs, for example, can be randomly (or non-randomly) mutated and expressed in yeast. Recombinant stabilised E dimers from the four serotypes can be prepared and each tagged with a different colour. The scFv-expressing yeast can be stained using these tagged proteins, and yeast cells that carry all four colours selected (as the scFvs are able to bind to the stabilised E dimer from each of the four serotypes.

Yeast staining may be carried based on the following. Yeast cells expressing E-protein domain 1+2 or domain 3 or all 3 domains were washed with PBS. Cells were resuspended in FACS buffer (PBS containing 1% FCS, 0.5% BSA) and aliquoted in 96-well U bottom plates. Mouse serum samples (diluted to 1:300) were added to cells and cells were incubated overnight at 4 degrees. Cells were washed and stained with 1:150 dilution of PE-conjugated $(F_{ab})_2$ fragment of rabbit anti-mouse Ig (Dako R0439). Cells were stained for 30 min at 4 degrees, washed well in PBS and fixed using 1% PFA in PBS. Data were acquired using a FACSVERSE (Becton-Dickinson, Mountain View, Calif.) and analysed using FlowJo software, (TreeStar, Ashland, Oreg.).

The invention claimed is:

1. A composition comprising an adjuvant and a compound that binds to an E-Dimer Epitope (EDE), wherein the compound is an antibody comprising a heavy chain comprising CDR regions and light chain comprising CDR regions, or antigen binding portion thereof, wherein the antibody, or antigen binding portion thereof, comprises:

a) a heavy chain variable region comprising the amino acid sequences SEQ ID NO: 5, 6 and 7 and a light chain variable region comprising the amino acid sequences SEQ ID NO: 17, 18 and 19; or b) a heavy chain variable region comprising the amino acid sequences SEQ ID NO: 8, 9 and 10 and a light chain variable region comprising the amino acid sequences SEQ ID NO: 20, 21 and 22; or c) a heavy chain variable region comprising the amino acid sequences SEQ ID NO: 11, 12 and 13 and a light chain variable region comprising the amino acid sequences SEQ ID NO: 23, 24 and 25; or d) a heavy chain variable region comprising the amino acid sequences SEQ ID NO: 14, 15, and 16 and a light chain variable region comprising the amino acid sequences SEQ ID NO: 26, 27 and 28;

wherein the EDE comprises a stabilized recombinant dengue virus envelope glycoprotein E ectodomain (sE) dimer, a dimer of Envelope proteins, or the antigenic portion thereof, or consecutive or non-consecutive residues of the envelope polypeptide dimer, held within a heterologous scaffold protein, and wherein said antibody or fragment thereof binds the five polypeptide segments of the dengue virus glycoprotein E ectodomain consisting of the residues 67-74, residues 97-106, residues 307-314, residues 148-159 and residues 243-251, wherein the amino acid residue position of each sE monomer is numbered according to SEQ ID NO: 132, SEQ ID NO: 133, SEQ ID NO: 134, and SEQ ID NO: 135.

2. The composition according to claim 1, wherein the stabilised EDE is any one or more of:

a) a dimer wherein the monomer is selected from the group consisting of: the DENV-1 sE of SEQ ID NO: 132, the DENV-2 SE of SEQ ID NO: 133 the DENV-3 SE of SEQ ID NO: 134, the DENV-4 sE of SEQ ID NO: 135 and a mutant sE thereof having at least one mutation selected among H27F, H27W, L107C, F108C, H244F, H244W, S255C, A259C, T/S262C, T/A265C, L278F, L292F, L294N, A313C and T315C and optionally at least one additional mutation selected from the group consisting of Q227N, E174N and D329N;

b) a homodimer of two identical recombinant sE or a heterodimer of two different recombinant sE;

c) a dimer which is glycosylated at position 67, at position 153 of each sE monomer, or both;

d) a dimer which is covalently stabilized with at least one, two or three disulphide inter-chain bonds between the two sE monomers;

e) a homodimer of mutant sE having each the mutation A259C or S255C and wherein the residues 259C or 255C are linked together through a disulphide inter-chain bond;

f) a dimer which is a heterodimer of a mutant sE having the mutation A259C and a mutant sE having the mutation S255C, wherein the residues 259C and 255C are linked together through a disulphide inter-chain bond;

g a homodimer of mutant sE having each the mutations F108C and T315C or a homodimer of mutants sE having each the mutations L107C and A313C wherein the residues 108C and 315C or the residues 107C and 313C are linked together through a disulphide inter-chain bond;

h) a heterodimer of a mutant sE having the mutations F108C and A313C and a mutant sE having the mutations L107C and T315C wherein the residues 108C and 313C are linked respectively to the residues 315C and 107C through a disulphide inter-chain bond between the two sE monomers;

i) a dimer, selected from the group consisting of a homodimer of mutants sE having each the mutations A259C, F108C and T315C, a homodimer of mutants sE having each the mutations S255C, F108C and T315C, a homodimer of mutants sE having each the mutations A259C, L107C and A313C, and a homodimer of mutants sE having each the mutations A255C, L107C and A313C as defined above, wherein the residues 259C, 255C, 108C, 315C, 107C and 313C are linked respectively to the residues 259C, 255C, 315C, 108C, 313C and 107C through disulphide inter-chain bonds;

j) a heterodimer of a mutant sE having the mutations A259C, F108C and T315C and a mutant sE having the mutations S255C, F108C and T315C as defined above, wherein the residues 259C, 108C and 315C are linked respectively to the residues 255C, 315C and 108C through disulphide inter-chain bonds;

k) a heterodimer of a mutant sE having the mutations S255C, L107C and A313C and a mutant sE having the mutations A259C, L107C and A313C, wherein the residues 255C, 107C and 313C are linked respectively to the residues 259C, 313C and 107C through disulphide inter-chain bonds;

l) a dimer which is covalently stabilized with at least one, two or three, sulfhydryl-reactive crosslinkers (also called thiol-reactive crosslinkers) between the sE monomers;

m) is a homodimer of mutant sE having each the mutation T/S262C or T/A265C, wherein the residues 262C or 265C are linked together through a sulfhydryl-reactive crosslinker;

n) a heterodimer of a mutant sE having the mutation T/S262C as defined above and a mutant sE having the mutation T/A265C, wherein the residues 262C and 265C are linked together through a sulfhydryl-reactive crosslinker;

o) a homodimer or a heterodimer of a mutant sE wherein at least one of the amino acid residues 1-9, 25-30, 238-282, 96-111 311-318 of sE is mutated to cysteine and a mutant sE wherein at least one of the amino acid residues 1-9, 25-30, 238-282, 96-111 311-318 of sE is mutated to cysteine, and wherein the mutated cysteine residues are linked together through a sulfhydryl-reactive crosslinker;

p) a dimer which is covalently stabilized by linking the two monomers through modified sugars;

q) a homodimer or heterodimer of mutant sE, wherein:

one sE monomer has at least one mutation which introduces a glycosylation site, and wherein the mutated amino acid residue is glycosylated with a modified sugar bearing an X functional group, and the other sE monomer has at least one mutation which introduces a glycosylation site, and wherein the mutated amino acid residue is glycosylated with a modified sugar bearing a Y functional group, and wherein both mutated residues are joined together through the modified sugars by reacting, specifically by click chemistry, the X functional group of the sugar of the first sE monomer with the Y functional group of the sugar of the other sE monomer;

r) a dimer which is non-covalently stabilized by filling the cavities of said dimer at the dimer interface by substituting at least one amino acid in the amino acid sequence of one or the two monomers, with bulky side chain amino acids;

s) a dimer which is non-covalently stabilized by substituting at least one amino acid residue in the amino acid sequence of at least one sE monomer with at least one bulky side chain amino acid within regions forming cavities at the dimer interface or in domain 1 (D1)/domain 3 (D3) linker of each monomer increasing hydrophobic interactions between the two sE monomers;

t) a homodimer or heterodimer of two recombinant sE as defined above, wherein one of the recombinant sE or the two recombinant sE have at least one mutation selected from the group consisting of H27F, H27W, H244F, H244W, and L278F;

u) a dimer which is non-covalently stabilized in domain 1 (D1)/domain 3 (D3) linker of each monomer, by substituting amino acids in the amino acid sequence of one or the two monomers with at least one bulky side chain amino acid;

v) a dimer which is a homodimer or heterodimer of two recombinant sE as defined above, wherein one of the recombinant sE or the two recombinant sE have at least one mutation selected from the group consisting of L292F and L294N, wherein the amino acid residue position of each sE monomer is numbered according to SEQ ID NO: 132, SEQ ID NO: 133, SEQ ID NO: 134, and SEQ ID NO: 135.

3. The composition according to claim 1 wherein the compound does not bind:

a) only to the fusion loop; or b) to the Envelope protein when in a denatured form; or c) made in cells lacking furin activity, and/or at low pH.

4. The composition according to claim 1 wherein the compound neutralises one or more serotypes of Dengue virus to 80% or 90% or 98% or 100%.

5. The composition according to claim 1, wherein the compound neutralises one or more serotypes of Dengue virus to 80% or 90% or 100% at a concentration of 0.5 μg/ml.

6. The composition according to claim 1 wherein the compound neutralises virus made in C6/36 insect cells and human dendritic cells to the same level.

7. The composition according to claim 1 wherein the compound is conjugated to a further agent, optionally wherein the further agent is a therapeutic agent, optionally an anti-viral agent; or wherein the further agent is a stabilising agent, optionally PEG.

8. The composition according to claim 1, wherein the antibody, or antigen binding portion thereof, comprises:
 a) heavy chain comprising SEQ ID NO: 1 and the light chain comprising SEQ ID NO: 37; or
 b) heavy chain comprising SEQ ID NO: 2 and the light chain comprising SEQ ID NO: 38; or
 c) heavy chain comprising SEQ ID NO: 3 and the light chain comprising SEQ ID NO: 39; or
 d) heavy chain comprising SEQ ID NO: 4 and the light chain comprising SEQ ID NO: 40; or comprises a sequence with at least 90% homology to the said sequences.

9. The composition according to claim 2 wherein the mutant sE having at least one mutation selected among H27F, H27W, L107C, F108C, H244F, H244W, S255C, A259C, T/S262C, T/A265C, L278F, L292F, L294N, A313C and T315C comprises the three mutations Q227N, E174N and D329N, wherein the amino acid residue position of each sE monomer is numbered according to SEQ ID NO: 132, SEQ ID NO: 133, SEQ ID NO: 134, and SEQ ID NO: 135.

10. The composition of claim 7, wherein the compound is conjugated to a therapeutic agent, an anti-viral agent; or a stabilising agent.

11. The composition of claim 10, wherein the stabilizing agent comprises PEG.

12. A composition comprising an adjuvant and a compound that binds to an E-Dimer Epitope (EDE), wherein the compound is an antibody, or an antigen binding portion thereof, comprising:
 a) heavy chain comprising SEQ ID NO: 42 and the light chain comprising SEQ ID NO: 88; or
 b) heavy chain comprising SEQ ID NO: 56 and the light chain comprising SEQ ID NO: 102; or
 c) heavy chain comprising SEQ ID NO: 57 and the light chain comprising SEQ ID NO: 103; or
 d) heavy chain comprising SEQ ID NO: 58 and the light chain comprising SEQ ID NO: 104; or
 e) heavy chain comprising SEQ ID NO: 61 and the light chain comprising SEQ ID NO: 107; or
 f) heavy chain comprising SEQ ID NO: 64 and the light chain comprising SEQ ID NO: 110; or
 g) heavy chain comprising SEQ ID NO: 65 and the light chain comprising SEQ ID NO: 111; or
 h) heavy chain comprising SEQ ID NO: 70 and the light chain comprising SEQ ID NO: 116;

wherein the EDE comprises a stabilized recombinant dengue virus envelope glycoprotein E ectodomain (sE) dimer, a dimer of Envelope proteins, or the antigenic portion thereof, or consecutive or non-consecutive residues of the envelope polypeptide dimer, held within a heterologous scaffold protein.

* * * * *

SEQUENCE LISTING

```
<160> NUMBER OF SEQ ID NOS: 160

<210> SEQ ID NO 1
<211> LENGTH: 120
<212> TYPE: PRT
<213> ORGANISM: Artificial Sequence
<220> FEATURE:
```

<223> OTHER INFORMATION: Full sequence of antibody C8 heavy chain

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Gly Glu Gly Asp Ser Ala Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Phe Glu Met Asn Ser Leu Arg Pro Glu Asp Thr Ala Val Tyr Tyr Cys
                85                  90                  95

Val Gly Gly Tyr Ser Asn Phe Tyr Tyr Tyr Tyr Thr Met Asp Val Trp
            100                 105                 110

Gly Gln Gly Thr Thr Val Thr Val
        115                 120

<210> SEQ ID NO 2
<211> LENGTH: 126
<212> TYPE: PRT
<213> ORGANISM: Artificial Sequence
<220> FEATURE:
<223> OTHER INFORMATION: Full sequence of antibody C10 heavy chain

<400> SEQUENCE: 2

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Lys Val Asp Asp Tyr Gly Asp Tyr Trp Phe Pro Thr Leu
            100                 105                 110

Trp Tyr Phe Asp Tyr Trp Gly Gln Gly Thr Leu Val Thr Val
        115                 120                 125

<210> SEQ ID NO 3
<211> LENGTH: 131
<212> TYPE: PRT
<213> ORGANISM: Artificial Sequence
<220> FEATURE:
<223> OTHER INFORMATION: Full sequence of antibody A11 heavy chain

<400> SEQUENCE: 3

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Ser Tyr Ser Asn His
            20                  25                  30

Trp Met His Trp Val Arg Gln Ala Pro Gly Lys Gly Leu Val Trp Val

```
        35                  40                  45

Ser Arg Ile Asn Ser Asp Gly Ser Thr Arg Asn Tyr Ala Asp Phe Val
    50                  55                  60

Lys Gly Arg Phe Thr Ile Ser Arg Asp Asn Ala Glu Asn Thr Leu Tyr
65                  70                  75                  80

Leu Glu Met Asn Ser Leu Thr Ala Asp Asp Thr Ala Val Tyr Tyr Cys
                85                  90                  95

Val Arg Asp Gly Val Arg Phe Tyr Tyr Asp Ser Thr Gly Tyr Tyr Pro
            100                 105                 110

Asp Ser Phe Phe Lys Tyr Gly Met Asp Val Trp Gly Gln Gly Thr Thr
        115                 120                 125

Val Thr Val
    130


<210> SEQ ID NO 4
<211> LENGTH: 128
<212> TYPE: PRT
<213> ORGANISM: Artificial Sequence
<220> FEATURE:
<223> OTHER INFORMATION: Full sequence of antibody B7 heavy chain

<400> SEQUENCE: 4

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser His
            20                  25                  30

Trp Met His Trp Val Arg Gln Ala Pro Gly Lys Gly Leu Val Trp Val
        35                  40                  45

Ser Arg Thr Asn Ser Asp Gly Ser Ser Thr Ser Tyr Ala Asp Ser Val
    50                  55                  60

Lys Gly Arg Phe Met Ile Ser Arg Asp Asn Ser Lys Asn Thr Val Tyr
65                  70                  75                  80

Leu His Met Asn Gly Leu Arg Ala Glu Asp Thr Ala Val Tyr Phe Cys
                85                  90                  95

Ala Arg Asp Gly Val Arg Tyr Tyr Tyr Asp Ser Thr Gly Tyr Tyr Pro
            100                 105                 110

Asp Asn Phe Phe Gln Tyr Gly Leu Asp Val Trp Gly Gln Gly Thr Thr
        115                 120                 125


<210> SEQ ID NO 5
<211> LENGTH: 5
<212> TYPE: PRT
<213> ORGANISM: Artificial Sequence
<220> FEATURE:
<223> OTHER INFORMATION: C8 CDR H1

<400> SEQUENCE: 5

Thr Tyr Ser Met His
1               5


<210> SEQ ID NO 6
<211> LENGTH: 17
<212> TYPE: PRT
<213> ORGANISM: Artificial Sequence
<220> FEATURE:
<223> OTHER INFORMATION: C8 CDR H2

<400> SEQUENCE: 6

Ala Ile Thr Gly Glu Gly Asp Ser Ala Phe Tyr Ala Asp Ser Val Lys
1               5                   10                  15
```

Gly

<210> SEQ ID NO 7
<211> LENGTH: 8
<212> TYPE: PRT
<213> ORGANISM: Artificial Sequence
<220> FEATURE:
<223> OTHER INFORMATION: C8 CDR H3

<400> SEQUENCE: 7

Gly Tyr Ser Asn Phe Tyr Tyr Tyr
1 5

<210> SEQ ID NO 8
<211> LENGTH: 5
<212> TYPE: PRT
<213> ORGANISM: Artificial Sequence
<220> FEATURE:
<223> OTHER INFORMATION: C10 CDR H1

<400> SEQUENCE: 8

Ser Tyr Ala Met His
1 5

<210> SEQ ID NO 9
<211> LENGTH: 17
<212> TYPE: PRT
<213> ORGANISM: Artificial Sequence
<220> FEATURE:
<223> OTHER INFORMATION: C10 CDR H2

<400> SEQUENCE: 9

Trp Ile Asn Ala Gly Asn Gly Asn Thr Lys Tyr Ser Gln Lys Phe Gln
1 5 10 15

Asp

<210> SEQ ID NO 10
<211> LENGTH: 15
<212> TYPE: PRT
<213> ORGANISM: Artificial Sequence
<220> FEATURE:
<223> OTHER INFORMATION: C10 CDR H3

<400> SEQUENCE: 10

Asp Lys Val Asp Asp Tyr Gly Asp Tyr Trp Phe Pro Thr Leu Trp
1 5 10 15

<210> SEQ ID NO 11
<211> LENGTH: 5
<212> TYPE: PRT
<213> ORGANISM: Artificial Sequence
<220> FEATURE:
<223> OTHER INFORMATION: A11 CDR H1

<400> SEQUENCE: 11

Asn His Trp Met His
1 5

<210> SEQ ID NO 12
<211> LENGTH: 17
<212> TYPE: PRT
<213> ORGANISM: Artificial Sequence
<220> FEATURE:
<223> OTHER INFORMATION: A11 CDR H2

<400> SEQUENCE: 12

Arg Ile Asn Ser Asp Gly Ser Thr Arg Asn Tyr Ala Asp Phe Val Lys
1 5 10 15

Gly

<210> SEQ ID NO 13
<211> LENGTH: 20
<212> TYPE: PRT
<213> ORGANISM: Artificial Sequence
<220> FEATURE:
<223> OTHER INFORMATION: A11 CDR H3

<400> SEQUENCE: 13

Asp Gly Val Arg Phe Tyr Tyr Asp Ser Thr Gly Tyr Tyr Pro Asp Ser
1 5 10 15

Phe Phe Lys Tyr
20

<210> SEQ ID NO 14
<211> LENGTH: 5
<212> TYPE: PRT
<213> ORGANISM: Artificial Sequence
<220> FEATURE:
<223> OTHER INFORMATION: B7 CDR H1

<400> SEQUENCE: 14

Ser His Trp Met His
1 5

<210> SEQ ID NO 15
<211> LENGTH: 17
<212> TYPE: PRT
<213> ORGANISM: Artificial Sequence
<220> FEATURE:
<223> OTHER INFORMATION: B7 CDR H2

<400> SEQUENCE: 15

Arg Thr Asn Ser Asp Gly Ser Ser Thr Ser Tyr Ala Asp Ser Val Lys
1 5 10 15

Gly

<210> SEQ ID NO 16
<211> LENGTH: 20
<212> TYPE: PRT
<213> ORGANISM: Artificial Sequence
<220> FEATURE:
<223> OTHER INFORMATION: B7 CDR H3

<400> SEQUENCE: 16

Asp Gly Val Arg Tyr Tyr Tyr Asp Ser Thr Gly Tyr Tyr Pro Asp Asn
1 5 10 15

Phe Phe Gln Tyr
20

<210> SEQ ID NO 17
<211> LENGTH: 11
<212> TYPE: PRT
<213> ORGANISM: Artificial Sequence
<220> FEATURE:
<223> OTHER INFORMATION: C8-CDR L1

<400> SEQUENCE: 17

Arg Ala Ser Gln Ser Ile Ser Thr Phe Leu Ala
1 5 10

-continued

<210> SEQ ID NO 18
<211> LENGTH: 7
<212> TYPE: PRT
<213> ORGANISM: Artificial Sequence
<220> FEATURE:
<223> OTHER INFORMATION: C8 CDR L2

<400> SEQUENCE: 18

Asp Ala Ser Thr Arg Ala Thr
1               5

<210> SEQ ID NO 19
<211> LENGTH: 10
<212> TYPE: PRT
<213> ORGANISM: Artificial Sequence
<220> FEATURE:
<223> OTHER INFORMATION: C8 CDR L3

<400> SEQUENCE: 19

Gln Gln Arg Tyr Asn Trp Pro Pro Tyr Thr
1               5                   10

<210> SEQ ID NO 20
<211> LENGTH: 14
<212> TYPE: PRT
<213> ORGANISM: Artificial Sequence
<220> FEATURE:
<223> OTHER INFORMATION: C10 CDR L1

<400> SEQUENCE: 20

Thr Gly Thr Ser Ser Asp Val Gly Gly Phe Asn Tyr Val Ser
1               5                   10

<210> SEQ ID NO 21
<211> LENGTH: 7
<212> TYPE: PRT
<213> ORGANISM: Artificial Sequence
<220> FEATURE:
<223> OTHER INFORMATION: C10 CDR L2

<400> SEQUENCE: 21

Asp Val Thr Ser Arg Pro Ser
1               5

<210> SEQ ID NO 22
<211> LENGTH: 11
<212> TYPE: PRT
<213> ORGANISM: Artificial Sequence
<220> FEATURE:
<223> OTHER INFORMATION: no description

<400> SEQUENCE: 22

Ser Ser His Thr Ser Arg Gly Thr Trp Val Phe
1               5                   10

<210> SEQ ID NO 23
<211> LENGTH: 14
<212> TYPE: PRT
<213> ORGANISM: Artificial Sequence
<220> FEATURE:
<223> OTHER INFORMATION: A11 CDR L1

<400> SEQUENCE: 23

Thr Gly Thr Ser Ser Asn Ala Asp Thr Tyr Asn Leu Val Ser
1               5                   10

<210> SEQ ID NO 24
<211> LENGTH: 7
<212> TYPE: PRT
<213> ORGANISM: Artificial Sequence
<220> FEATURE:
<223> OTHER INFORMATION: A11 CDR L2

<400> SEQUENCE: 24

Glu Gly Thr Lys Arg Pro Ser
1               5

<210> SEQ ID NO 25
<211> LENGTH: 11
<212> TYPE: PRT
<213> ORGANISM: Artificial Sequence
<220> FEATURE:
<223> OTHER INFORMATION: A11 CDR L3

<400> SEQUENCE: 25

Cys Ser Tyr Ala Thr Ser Arg Thr Leu Val Phe
1               5                   10

<210> SEQ ID NO 26
<211> LENGTH: 14
<212> TYPE: PRT
<213> ORGANISM: Artificial Sequence
<220> FEATURE:
<223> OTHER INFORMATION: B7 CDR L1

<400> SEQUENCE: 26

Thr Gly Ile Ser Ser Asp Val Glu Thr Tyr Asn Leu Val Ser
1               5                   10

<210> SEQ ID NO 27
<211> LENGTH: 7
<212> TYPE: PRT
<213> ORGANISM: Artificial Sequence
<220> FEATURE:
<223> OTHER INFORMATION: B7 CDR L2

<400> SEQUENCE: 27

Glu Ala Ser Lys Arg Pro Ser
1               5

<210> SEQ ID NO 28
<211> LENGTH: 10
<212> TYPE: PRT
<213> ORGANISM: Artificial Sequence
<220> FEATURE:
<223> OTHER INFORMATION: B7 CDR L3

<400> SEQUENCE: 28

Cys Ser Tyr Ala Gly Gly Lys Ser Leu Val
1               5                   10

<210> SEQ ID NO 29
<211> LENGTH: 495
<212> TYPE: PRT
<213> ORGANISM: Artificial Sequence
<220> FEATURE:
<223> OTHER INFORMATION: Full length envelope protein sequence DENV1

<400> SEQUENCE: 29

Met Arg Cys Val Gly Ile Gly Asn Arg Asp Phe Val Glu Gly Leu Ser
1               5                   10                  15

Gly Gly Thr Trp Val Asp Val Val Leu Glu His Gly Ser Cys Val Thr
            20                  25                  30

-continued

```
Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Pro Gln Glu Thr Trp Asn Arg Glu Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Lys Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
    370                 375                 380

Lys Ala Leu Lys Leu Ser Trp Phe Lys Lys Gly Ser Ser Ile Gly Lys
385                 390                 395                 400

Met Leu Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
            420                 425                 430

Gly Lys Leu Val His Gln Ile Phe Gly Thr Ala Tyr Gly Val Leu Phe
        435                 440                 445
```

-continued

```
Ser Gly Val Ser Trp Thr Met Lys Ile Gly Ile Gly Ile Leu Leu Thr
    450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495


<210> SEQ ID NO 30

<400> SEQUENCE: 30

000


<210> SEQ ID NO 31
<211> LENGTH: 495
<212> TYPE: PRT
<213> ORGANISM: Artificial Sequence
<220> FEATURE:
<223> OTHER INFORMATION: Full length envelope protein sequence DENV2

<400> SEQUENCE: 31

Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Arg Cys Lys Lys Asn Met Glu Gly Lys
        115                 120                 125

Val Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285
```

```
Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
        435                 440                 445

Ser Gly Val Ser Trp Thr Met Lys Ile Leu Ile Gly Val Ile Ile Thr
    450                 455                 460

Trp Ile Gly Met Asn Ser Arg Ser Thr Ser Leu Ser Val Thr Leu Val
465                 470                 475                 480

Leu Val Gly Ile Val Thr Leu Tyr Leu Gly Val Met Val Gln Ala
                485                 490                 495


<210> SEQ ID NO 32

<400> SEQUENCE: 32

000


<210> SEQ ID NO 33
<211> LENGTH: 493
<212> TYPE: PRT
<213> ORGANISM: Artificial Sequence
<220> FEATURE:
<223> OTHER INFORMATION: Full length envelope protein sequence DENV3

<400> SEQUENCE: 33

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Ile Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Ser Ile Glu Gly Lys
```

```
        115                 120                 125

Val Val Gln His Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Ser Gln Ala Ser Thr Ala Glu Ala Ile Leu Pro Gly Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Arg Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Thr Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Ala Met Cys Leu Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Lys Ala
    370                 375                 380

Leu Lys Ile Asn Trp Tyr Arg Lys Gly Ser Ser Ile Gly Lys Met Phe
385                 390                 395                 400

Glu Ala Thr Ala Arg Gly Ala Arg Arg Met Ala Ile Leu Gly Asp Thr
                405                 410                 415

Ala Trp Asp Phe Gly Ser Val Gly Gly Val Leu Asn Ser Leu Gly Lys
            420                 425                 430

Met Val His Gln Ile Phe Gly Ser Ala Tyr Thr Ala Leu Phe Ser Gly
        435                 440                 445

Val Ser Trp Ile Met Lys Ile Gly Ile Gly Val Leu Leu Thr Trp Ile
    450                 455                 460

Gly Leu Asn Ser Lys Asn Thr Ser Met Ser Phe Ser Cys Ile Ala Ile
465                 470                 475                 480

Gly Ile Ile Thr Leu Tyr Leu Gly Val Val Val Gln Ala
                485                 490
```

<210> SEQ ID NO 34

<400> SEQUENCE: 34

000

<210> SEQ ID NO 35
<211> LENGTH: 495
<212> TYPE: PRT
<213> ORGANISM: Artificial Sequence
<220> FEATURE:
<223> OTHER INFORMATION: Full length envelope protein sequence DENV4

<400> SEQUENCE: 35

```
Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Ile Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Val Thr Val His
    130                 135                 140

Asn Gly Asp Thr His Ala Val Gly Asn Asp Ile Pro Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Lys Thr Trp Leu Val
        195                 200                 205

His Lys Gln Trp Phe Leu Asp Leu Pro Leu Pro Trp Ala Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Ile Val Leu Gly Ser Gln
                245                 250                 255

Glu Gly Ala Met His Ser Ala Leu Thr Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Phe Ala Glu Tyr Thr Asn Ser Val Thr Asn Ile Glu
        355                 360                 365

Leu Glu Pro Pro Phe Gly Asp Ser Tyr Ile Val Ile Gly Val Gly Asp
```

```
    370                 375                 380

Ser Ala Leu Thr Leu His Trp Phe Arg Lys Gly Ser Ser Ile Gly Lys
385                 390                 395                 400

Met Leu Glu Ser Thr Tyr Arg Gly Val Lys Arg Met Ala Ile Leu Gly
                405                 410                 415

Glu Thr Ala Trp Asp Phe Gly Ser Val Gly Gly Leu Phe Thr Ser Leu
            420                 425                 430

Gly Lys Ala Val His Gln Val Phe Gly Ser Val Tyr Thr Thr Met Phe
        435                 440                 445

Gly Gly Val Ser Trp Met Val Arg Ile Leu Ile Gly Phe Leu Val Leu
    450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val His Ala
                485                 490                 495


<210> SEQ ID NO 36

<400> SEQUENCE: 36

000


<210> SEQ ID NO 37
<211> LENGTH: 108
<212> TYPE: PRT
<213> ORGANISM: Artificial Sequence
<220> FEATURE:
<223> OTHER INFORMATION: C8 light chain

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Phe
            20                  25                  30

Leu Ala Trp Tyr Gln His Lys Pro Gly Gln Ala Pro Arg Leu Leu Ile
        35                  40                  45

Tyr Asp Ala Ser Thr Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln Gln Arg Tyr Asn Trp Pro Pro
                85                  90                  95

Tyr Thr Phe Gly Gln Gly Thr Lys Val Glu Ile Lys
            100                 105


<210> SEQ ID NO 38
<211> LENGTH: 110
<212> TYPE: PRT
<213> ORGANISM: Artificial Sequence
<220> FEATURE:
<223> OTHER INFORMATION: C10 light chain

<400> SEQUENCE: 38

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Phe
            20                  25                  30

Asn Tyr Val Ser Trp Phe Gln Gln His Pro Gly Lys Ala Pro Lys Leu
        35                  40                  45
```

```
Met Leu Tyr Asp Val Thr Ser Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser His Thr Ser Arg
                85                  90                  95

Gly Thr Trp Val Phe Gly Gly Gly Thr Lys Leu Thr Val Leu
            100                 105                 110


<210> SEQ ID NO 39
<211> LENGTH: 110
<212> TYPE: PRT
<213> ORGANISM: Artificial Sequence
<220> FEATURE:
<223> OTHER INFORMATION: A11 light chain

<400> SEQUENCE: 39

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asn Ala Asp Thr Tyr
            20                  25                  30

Asn Leu Val Ser Trp Tyr Gln Gln Arg Pro Gly Lys Ala Pro Lys Leu
        35                  40                  45

Met Ile Tyr Glu Gly Thr Lys Arg Pro Ser Gly Val Ser Asn Arg Phe
    50                  55                  60

Ser Ala Ser Lys Ser Ala Thr Ala Ala Ser Leu Thr Ile Ser Gly Leu
65                  70                  75                  80

Gln Pro Glu Asp Glu Ala Asp Tyr Tyr Cys Cys Ser Tyr Ala Thr Ser
                85                  90                  95

Arg Thr Leu Val Phe Gly Gly Gly Thr Lys Leu Thr Val Val
            100                 105                 110


<210> SEQ ID NO 40
<211> LENGTH: 110
<212> TYPE: PRT
<213> ORGANISM: Artificial Sequence
<220> FEATURE:
<223> OTHER INFORMATION: B7 light chain

<400> SEQUENCE: 40

Gln Ser Ala Leu Thr Gln Pro Ala Ser Val Ser Gly Ser Pro Gly Gln
1               5                   10                  15

Ser Ile Thr Ile Ser Cys Thr Gly Ile Ser Ser Asp Val Glu Thr Tyr
            20                  25                  30

Asn Leu Val Ser Trp Tyr Glu Gln His Pro Gly Lys Ala Pro Lys Leu
        35                  40                  45

Ile Ile Tyr Glu Ala Ser Lys Arg Pro Ser Gly Val Ser Asn Arg Phe
    50                  55                  60

Ser Gly Ser Lys Ser Gly Asn Thr Ala Ser Leu Ala Ile Ser Gly Leu
65                  70                  75                  80

Gln Ala Glu Asp Glu Ala Asp Tyr Tyr Cys Cys Ser Tyr Ala Gly Gly
                85                  90                  95

Lys Ser Leu Val Phe Gly Gly Gly Thr Arg Leu Thr Val Leu
            100                 105                 110


<210> SEQ ID NO 41
<211> LENGTH: 128
<212> TYPE: PRT
```

```
<213> ORGANISM: Artificial Sequence
<220> FEATURE:
<223> OTHER INFORMATION: A12 heavy chain

<400> SEQUENCE: 41

Glu Val Gln Leu Val Glu Ser Gly Ser Glu Leu Lys Lys Pro Gly Ala
1               5                   10                  15

Ser Val Lys Val Ser Cys Arg Ala Ser Gly Phe Thr Phe Thr Ser Tyr
            20                  25                  30

Thr Phe Asn Trp Val Arg Gln Ala Pro Gly Gln Gly Leu Glu Trp Met
        35                  40                  45

Gly Trp Ile Asp Thr Lys Ser Gly Arg Pro Thr Tyr Ala Gln Gly Phe
    50                  55                  60

Thr Gly Arg Phe Val Leu Ser Leu Asp Thr Ser Val Ser Thr Ala Tyr
65                  70                  75                  80

Leu Gln Ile Asn Ser Leu Lys Val Glu Asp Thr Ala Met Tyr Tyr Cys
                85                  90                  95

Ala Arg Val His Thr Gly Gly Tyr Pro Pro Glu Leu Arg Tyr Tyr Tyr
            100                 105                 110

Tyr Gly Met Asp Val Trp Gly Gln Gly Thr Thr Val Thr Val Ser Ser
        115                 120                 125


<210> SEQ ID NO 42
<211> LENGTH: 122
<212> TYPE: PRT
<213> ORGANISM: Artificial Sequence
<220> FEATURE:
<223> OTHER INFORMATION: B10 heavy chain

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Thr Asp Gly Asn Ser Ala Phe Tyr Ala Asp Ser Val
    50                  55                  60

Lys Gly Arg Phe Thr Ile Ser Arg Asp Asn Ser Lys Asn Thr Met Tyr
65                  70                  75                  80

Phe His Met Asn Ser Leu Arg Pro Glu Asp Thr Ala Val Tyr Tyr Cys
                85                  90                  95

Val Gly Gly Tyr Ser Ser Phe Tyr Tyr Tyr Tyr Thr Met Asp Val Trp
            100                 105                 110

Gly Gln Gly Thr Thr Val Thr Val Ser Ser
        115                 120


<210> SEQ ID NO 43
<211> LENGTH: 122
<212> TYPE: PRT
<213> ORGANISM: Artificial Sequence
<220> FEATURE:
<223> OTHER INFORMATION: B11 heavy chain

<400> SEQUENCE: 43

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30
```

```
Ser Met His Trp Val Arg Gln Ala Pro Gly Lys Gly Leu Glu Tyr Val
        35                  40                  45

Ser Ala Ile Thr Thr Asp Gly Asp Ser Ala Phe Tyr Ala Asp Ser Val
    50                  55                  60

Lys Gly Arg Phe Thr Ile Ser Arg Asp Asn Ser Lys Asn Thr Met Phe
65                  70                  75                  80

Phe His Met Ser Asn Leu Arg Pro Glu Asp Thr Ala Val Tyr Tyr Cys
                85                  90                  95

Val Gly Gly Tyr Ser Ser Phe Tyr Tyr Tyr Tyr Thr Leu Asp Val Trp
            100                 105                 110

Gly Gln Gly Thr Thr Val Thr Val Ser Ser
        115                 120


<210> SEQ ID NO 44
<211> LENGTH: 122
<212> TYPE: PRT
<213> ORGANISM: Artificial Sequence
<220> FEATURE:
<223> OTHER INFORMATION: C9 heavy chain

<400> SEQUENCE: 44

Glu Val Gln Leu Val Glu Ser Glu Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Thr Asn Gly Asp Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Phe Gln Met Ser Ser Leu Arg Ala Glu Asp Thr Gly Val Tyr Tyr Cys
                85                  90                  95

Val Gly Gly Tyr Ser Ser Phe Tyr Tyr Tyr Tyr Thr Met Asp Val Trp
            100                 105                 110

Gly Gln Gly Thr Thr Val Thr Val Ser Ser
        115                 120


<210> SEQ ID NO 45
<211> LENGTH: 124
<212> TYPE: PRT
<213> ORGANISM: Artificial Sequence
<220> FEATURE:
<223> OTHER INFORMATION: A2 heavy chain

<400> SEQUENCE: 45

Glu Val Gln Leu Val Gln Ser Gly Pro Glu Met Arg Lys Pro Gly Ala
1               5                   10                  15

Ser Val Lys Val Ser Cys Lys Ala Ser Gly Tyr Thr Phe Thr Ser His
            20                  25                  30

Gly Ile Asn Trp Val Arg Gln Val Pro Gly Gln Gly Pro Glu Trp Met
        35                  40                  45

Gly Trp Ser Ser Ser Tyr Thr Asp Asn Thr Asn Tyr Ala Gln Lys Phe
    50                  55                  60

Lys Gly Arg Val Thr Met Thr Thr Asp Pro Ser Thr Ser Thr Ala Tyr
65                  70                  75                  80

Met Glu Leu Arg Ser Leu Arg Ser Asp Asp Thr Ala Ile Tyr Phe Cys
```

```
                85                  90                  95

Ala Arg Gly Phe Tyr Ser Gly Ser Tyr Tyr Pro Thr Ala Pro Phe Asp
            100                 105                 110

Ile Trp Gly Gln Gly Thr Leu Val Thr Val Ser Ser
        115                 120


<210> SEQ ID NO 46
<211> LENGTH: 124
<212> TYPE: PRT
<213> ORGANISM: Artificial Sequence
<220> FEATURE:
<223> OTHER INFORMATION: A5 heavy chain

<400> SEQUENCE: 46

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Leu Ser Trp Val Arg Gln Ala Pro Gly Gln Gly Leu Glu Trp Met
        35                  40                  45

Gly Trp Cys Ser Ser Tyr Asn Asp Asn Thr Asn Tyr Ala Gln Lys Phe
    50                  55                  60

Lys Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Val Phe Tyr Ser Gly Ser Tyr Tyr Pro Asn Ser Pro Phe Asp
            100                 105                 110

Tyr Trp Gly Gln Gly Thr Leu Val Thr Val Ser Ser
        115                 120


<210> SEQ ID NO 47
<211> LENGTH: 124
<212> TYPE: PRT
<213> ORGANISM: Artificial Sequence
<220> FEATURE:
<223> OTHER INFORMATION: A7 heavy chain

<400> SEQUENCE: 47

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Ser Ser Asn
            20                  25                  30

Asn Tyr Gln Trp Asn Trp Ile Arg Gln Pro Ala Gly Lys Gly Leu Glu
        35                  40                  45

Trp Leu Gly Arg Ile Asp Thr Thr Gly Ser Thr Asn Tyr Asn Pro Ser
    50                  55                  60

Leu Lys Ser Arg Ile Ser Ile Ser Ile Asp Thr Ser Lys Lys Gln Phe
65                  70                  75                  80

Ser Leu Arg Leu Asn Ser Val Thr Ala Ala Asp Thr Ala Val Tyr Tyr
                85                  90                  95

Cys Ala Arg Ser Leu Trp Ser Gly Glu Leu Trp Gly Gly Pro Leu Gly
            100                 105                 110

Tyr Trp Gly Gln Gly Thr Leu Val Thr Val Ser Ser
        115                 120


<210> SEQ ID NO 48
<211> LENGTH: 125
```

<212> TYPE: PRT
<213> ORGANISM: Artificial Sequence
<220> FEATURE:
<223> OTHER INFORMATION: A8 heavy chain

<400> SEQUENCE: 48

```
Glu Val Gln Leu Val Glu Ser Gly Ala Glu Val Lys Asn Pro Gly Ala
1               5                   10                  15

Ser Val Lys Val Ser Cys Lys Ala Ser Gly Tyr Thr Phe Ile Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Ala Thr Tyr Ser Ala Gln Lys Phe
    50                  55                  60

Gln Gly Arg Val Thr Leu Thr Gly Asp Ala Ser Pro Ser Thr Val Tyr
65                  70                  75                  80

Met Glu Leu Ser Ser Leu Arg Ser Asp Asp Thr Ala Ile Tyr Tyr Cys
                85                  90                  95

Ala Gly Arg Ser Tyr Asn Trp Asn Asp Val Phe Tyr Tyr Tyr Tyr Met
            100                 105                 110

Asp Val Trp Gly Gln Gly Thr Thr Val Thr Val Ser Ser
        115                 120                 125
```

<210> SEQ ID NO 49
<211> LENGTH: 125
<212> TYPE: PRT
<213> ORGANISM: Artificial Sequence
<220> FEATURE:
<223> OTHER INFORMATION: B10 heavy chain

<400> SEQUENCE: 49

```
Glu Val Gln Leu Val Glu Ser Gly Pro Gly Leu Val Lys Pro Ser Glu
1               5                   10                  15

Thr Leu Ser Leu Thr Cys Thr Ile Ser Gly Val Ser Ile Ser Asp Tyr
            20                  25                  30

Tyr Trp Thr Trp Ile Arg Gln Pro Pro Gly Lys Gly Leu Glu Trp Ile
        35                  40                  45

Gly Asn Ile Tyr Asn Thr Gly Ser Thr Asn Tyr Asn Pro Ser Leu Lys
    50                  55                  60

Ser Arg Val Ala Ile Trp Met Asp Thr Ser Lys Asn Lys Phe Ser Leu
65                  70                  75                  80

Arg Leu Thr Ser Val Thr Ser Ala Asp Thr Ala Val Tyr Tyr Cys Ala
                85                  90                  95

Arg Val Glu Gly Gly Pro Lys Tyr Tyr Phe Gly Ser Gly Asp Phe Tyr
            100                 105                 110

Asn Leu Trp Gly Arg Gly Ser Leu Val Thr Val Ser Ser
        115                 120                 125
```

<210> SEQ ID NO 50
<211> LENGTH: 125
<212> TYPE: PRT
<213> ORGANISM: Artificial Sequence
<220> FEATURE:
<223> OTHER INFORMATION: C2 heavy chain

<400> SEQUENCE: 50

```
Ser Gln Val Gln Leu Val Gln Ser Gly Ala Glu Leu Lys Lys Pro Gly
1               5                   10                  15

Ala Ser Val Lys Val Ser Cys Lys Thr Ser Gly Tyr Thr Phe Ser Tyr
```

```
            20                  25                  30

Tyr Ile His Trp Val Arg Gln Ala Pro Gly Gln Gly Leu Glu Trp Met
        35                  40                  45

Ala Met Ile Asn Pro Thr Ser Gly Ser Thr Ser Tyr Ala Gln Arg Phe
    50                  55                  60

Gln Gly Arg Val Thr Met Thr Arg Asp Thr Pro Thr Asn Thr Val Tyr
65                  70                  75                  80

Met Glu Val Arg Ser Leu Arg Ser Asp Asp Thr Ala Val Tyr Phe Cys
                85                  90                  95

Ala Ser Arg Gly Tyr Asn Trp Asn Asp Val Gln Tyr Tyr Tyr Thr Met
            100                 105                 110

Asp Val Trp Gly Gln Gly Thr Thr Val Thr Val Ser Ser
        115                 120                 125


<210> SEQ ID NO 51
<211> LENGTH: 125
<212> TYPE: PRT
<213> ORGANISM: Artificial Sequence
<220> FEATURE:
<223> OTHER INFORMATION: D4 heavy chain

<400> SEQUENCE: 51

Ser Glu Val Gln Leu Val Gln Ser Gly Ala Glu Leu Lys Lys Pro Gly
1               5                   10                  15

Ala Ser Val Lys Val Ser Cys Lys Ala Ser Gly Tyr Thr Phe Ser Tyr
            20                  25                  30

Tyr Ile His Trp Val Arg Gln Ala Pro Gly Gln Gly Leu Glu Trp Met
        35                  40                  45

Ala Ile Ile Asn Pro Thr Ser Gly Ser Thr Ser Tyr Ala Gln Arg Phe
    50                  55                  60

Gln Gly Arg Val Thr Met Thr Arg Asp Thr Ser Thr Asn Thr Val Tyr
65                  70                  75                  80

Met Glu Leu Ser Ser Leu Ile Ser Glu Asp Thr Ala Val Tyr Tyr Cys
                85                  90                  95

Ala Ser Arg Gly Tyr Asn Trp Asn Asp Val His Tyr Tyr Tyr Thr Met
            100                 105                 110

Asp Val Trp Gly Gln Gly Thr Thr Val Thr Val Ser Ser
        115                 120                 125


<210> SEQ ID NO 52
<211> LENGTH: 114
<212> TYPE: PRT
<213> ORGANISM: Artificial Sequence
<220> FEATURE:
<223> OTHER INFORMATION: B11 heavy chain

<400> SEQUENCE: 52

Gln Val Gln Leu Val Glu Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Gly Leu Ser Trp Val Arg Gln Ala Pro Gly Gln Gly Leu Glu Trp Met
        35                  40                  45

Gly Trp Cys Ser Ser Tyr Glu Asp Asn Thr Asn Tyr Ala Pro Arg Phe
    50                  55                  60

Lys Gly Arg Val Thr Met Thr Thr Asp Thr Ser Thr Asn Thr Ala Tyr
65                  70                  75                  80
```

-continued

```
Met Glu Leu Arg Ser Leu Arg Phe Asp Asp Thr Ala Val Tyr Tyr Cys
                85                  90                  95

Ala Arg Val Phe Tyr Ser Gly Ser Tyr Tyr Pro Asn Ser Pro Phe Asp
            100                 105                 110

Ser Trp


<210> SEQ ID NO 53
<211> LENGTH: 122
<212> TYPE: PRT
<213> ORGANISM: Artificial Sequence
<220> FEATURE:
<223> OTHER INFORMATION: A2 heavy chain

<400> SEQUENCE: 53

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Ile
        35                  40                  45

Ser Ala Ile Thr Thr Asp Gly Asp Ser Ala Phe Tyr Ala Asp Ser Val
    50                  55                  60

Lys Gly Arg Phe Thr Ile Ser Arg Asp Asn Ser Lys Asn Thr Met Tyr
65                  70                  75                  80

Phe His Met Asn Ser Leu Arg Pro Glu Asp Thr Ala Val Tyr Tyr Cys
                85                  90                  95

Val Gly Gly Tyr Ser Ser Phe Tyr Tyr Tyr Tyr Thr Met Asp Val Trp
            100                 105                 110

Gly Gln Gly Thr Thr Val Thr Val Ser Ser
        115                 120


<210> SEQ ID NO 54
<211> LENGTH: 124
<212> TYPE: PRT
<213> ORGANISM: Artificial Sequence
<220> FEATURE:
<223> OTHER INFORMATION: A4 heavy chain

<400> SEQUENCE: 54

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Gly Leu Glu Trp Met
        35                  40                  45

Gly Trp Ile Ser Ser Asp Ser Gly His Thr Asn Tyr Ala Arg Lys Leu
    50                  55                  60

Lys Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Leu Tyr Ser Val Ser Tyr Tyr Pro Thr Ser Pro Phe Asp
            100                 105                 110

Tyr Trp Gly Gln Gly Ser Thr Val Thr Val Ser Ser
        115                 120


<210> SEQ ID NO 55
<211> LENGTH: 124
```

<212> TYPE: PRT
<213> ORGANISM: Artificial Sequence
<220> FEATURE:
<223> OTHER INFORMATION: A5 heavy chain

<400> SEQUENCE: 55

```
Gln Val Gln Leu Val Glu Ser Gly Ala Glu Val Lys Lys Pro Gly Ser
1               5                   10                  15

Ser Val Lys Val Ser Cys Arg Ala Ser Gly Tyr Thr Phe Thr Thr Tyr
            20                  25                  30

Gly Leu Ser Trp Val Arg Gln Ala Pro Gly Gln Gly Leu Glu Trp Met
        35                  40                  45

Gly Trp Cys Ser Ser Tyr Asn Asp Asn Thr Asn Tyr Ala Gln Lys Phe
    50                  55                  60

Lys Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Val Phe Tyr Ser Gly Ser Tyr Tyr Pro Asn Ser Pro Phe Asp
            100                 105                 110

Ser Trp Gly Gln Gly Thr Leu Val Thr Val Ser Ser
        115                 120
```

<210> SEQ ID NO 56
<211> LENGTH: 122
<212> TYPE: PRT
<213> ORGANISM: Artificial Sequence
<220> FEATURE:
<223> OTHER INFORMATION: A9 heavy chain

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Thr Asp Gly Asp Ser Ala Phe Tyr Ala Asp Ser Val
    50                  55                  60

Lys Gly Arg Phe Thr Ile Ser Arg Asp Asn Ser Lys Asn Thr Met Tyr
65                  70                  75                  80

Phe His Met Asn Ser Val Arg Pro Glu Asp Thr Ala Val Tyr Tyr Cys
                85                  90                  95

Val Gly Gly Tyr Ser Ser Phe Tyr Tyr Tyr Tyr Thr Met Asp Val Trp
            100                 105                 110

Gly Gln Gly Thr Thr Val Thr Val Ser Ser
        115                 120
```

<210> SEQ ID NO 57
<211> LENGTH: 122
<212> TYPE: PRT
<213> ORGANISM: Artificial Sequence
<220> FEATURE:
<223> OTHER INFORMATION: B2 heavy chain

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
```

```
            20                  25                  30

Ser Met His Trp Val Arg Gln Ala Pro Gly Lys Gly Leu Glu Tyr Val
        35                  40                  45

Ser Ala Ile Thr Thr Asp Gly Asp Ser Ala Phe Tyr Ala Asp Ser Val
    50                  55                  60

Lys Gly Arg Phe Thr Ile Ser Arg Asp Asn Ser Lys Asn Thr Met Tyr
65                  70                  75                  80

Phe His Met Asn Ser Leu Arg Pro Glu Asp Thr Ala Val Tyr Tyr Cys
                85                  90                  95

Val Gly Gly Tyr Ser Ser Phe Tyr Tyr Tyr Tyr Thr Met Asp Val Trp
            100                 105                 110

Gly Gln Gly Thr Thr Val Thr Val Ser Ser
        115                 120


<210> SEQ ID NO 58
<211> LENGTH: 122
<212> TYPE: PRT
<213> ORGANISM: Artificial Sequence
<220> FEATURE:
<223> OTHER INFORMATION: B3 heavy chain

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Ser Thr Asp Gly Asp Ser Ala Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Phe His Met Ser Ser Leu Arg Ala Glu Asp Thr Ala Val Tyr Tyr Cys
                85                  90                  95

Leu Gly Gly Tyr Ser Thr Phe Tyr Tyr Tyr Tyr Thr Met Asp Val Trp
            100                 105                 110

Gly Gln Gly Thr Thr Val Thr Val Ser Ser
        115                 120


<210> SEQ ID NO 59
<211> LENGTH: 112
<212> TYPE: PRT
<213> ORGANISM: Artificial Sequence
<220> FEATURE:
<223> OTHER INFORMATION: B4 heavy chain

<400> SEQUENCE: 59

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Pro Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Thr Asn Gly Asp Ser Thr Phe Tyr Ala Asp Ser Val
    50                  55                  60

Lys Gly Arg Phe Thr Ile Ser Arg Asp Asn Ser Lys Asn Thr Val Tyr
65                  70                  75                  80
```

```
Phe Gln Leu Ser Ser Leu Arg Ala Glu Asp Thr Ala Val Tyr Tyr Cys
                85                  90                  95

Val Gly Gly Tyr Ser Ser Phe Tyr Phe Tyr Tyr Thr Met Asp Val Trp
            100                 105                 110


<210> SEQ ID NO 60
<211> LENGTH: 124
<212> TYPE: PRT
<213> ORGANISM: Artificial Sequence
<220> FEATURE:
<223> OTHER INFORMATION: B7 heavy chain

<400> SEQUENCE: 60

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Tyr Thr Asn Tyr
            20                  25                  30

Gly Leu Ser Trp Val Arg Gln Ala Pro Gly Gln Gly Leu Glu Trp Met
        35                  40                  45

Gly Trp Met Ser Ser Tyr Asn Asp Asn Thr Asn Tyr Ser Gln Lys Phe
    50                  55                  60

Lys Gly Arg Val Thr Met Thr Thr Asp Pro Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Leu Tyr Ser Gly Ser His Tyr Pro Thr Ser Pro Leu Asp
            100                 105                 110

Tyr Trp Gly Gln Gly Thr Leu Val Thr Val Ser Ser
        115                 120


<210> SEQ ID NO 61
<211> LENGTH: 122
<212> TYPE: PRT
<213> ORGANISM: Artificial Sequence
<220> FEATURE:
<223> OTHER INFORMATION: B11 heavy chain

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Thr Thr Tyr
            20                  25                  30

Ser Leu His Trp Val Arg Gln Thr Pro Gly Lys Gly Leu Glu Tyr Val
        35                  40                  45

Ser Ala Ile Thr Thr Asp Gly Asp Ser Ala Phe Tyr Ala Asp Ser Val
    50                  55                  60

Lys Gly Arg Phe Thr Ile Ser Arg Asp Asn Ser Lys Asn Thr Met Tyr
65                  70                  75                  80

Phe His Met Ser Ser Leu Arg Pro Glu Asp Thr Ala Val Tyr Tyr Cys
                85                  90                  95

Val Gly Gly Tyr Ser Ser Phe Tyr Tyr Phe Tyr Thr Val Asp Val Trp
            100                 105                 110

Gly Gln Gly Thr Thr Val Thr Val Ser Phe
        115                 120


<210> SEQ ID NO 62
<211> LENGTH: 125
<212> TYPE: PRT
<213> ORGANISM: Artificial Sequence
```

```
<220> FEATURE:
<223> OTHER INFORMATION: C4 heavy chain

<400> SEQUENCE: 62

Ser Gln Val Gln Leu Val Glu Ser Gly Ala Glu Leu Lys Lys Pro Gly
1               5                   10                  15

Ala Ser Val Lys Val Ser Cys Lys Ala Ser Gly Tyr Thr Phe Ser Tyr
            20                  25                  30

Tyr Met His Trp Val Arg Gln Ala Pro Gly Gln Gly Leu Glu Trp Met
        35                  40                  45

Ala Ile Ile Asn Pro Thr Ser Gly Ser Thr Thr Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Arg Gly Tyr Asn Trp Asn Asp Val His Tyr Tyr Tyr Thr Met
            100                 105                 110

Asp Val Trp Gly Gln Gly Thr Thr Val Thr Val Ser Ser
        115                 120                 125


<210> SEQ ID NO 63
<211> LENGTH: 131
<212> TYPE: PRT
<213> ORGANISM: Artificial Sequence
<220> FEATURE:
<223> OTHER INFORMATION: B10 heavy chain

<400> SEQUENCE: 63

Glu Val Gln Leu Val Glu Ser Gly Pro Glu Val Lys Lys Pro Gly Ala
1               5                   10                  15

Ser Val Lys Val Ser Cys Lys Thr Ser Gly Tyr Thr Phe Ile Asn Tyr
            20                  25                  30

Tyr Ile His Trp Val Arg Gln Ala Pro Gly Gln Gly Leu Glu Trp Leu
        35                  40                  45

Gly Leu Ile Asn Pro Arg Gly Gly Asn Thr Asn Tyr Ala Glu Lys Phe
    50                  55                  60

Glu Asp Arg Val Thr Met Thr Arg Asp Thr Ser Thr Ser Thr Val Asn
65                  70                  75                  80

Met Glu Leu Ser Ser Leu Thr Ser Glu Asp Thr Ala Val Tyr Tyr Cys
                85                  90                  95

Ala Arg Pro Leu Ala His Thr Tyr Asp Phe Trp Ser Gly Tyr His Arg
            100                 105                 110

Ala Thr Gly Tyr Gly Met Asp Val Trp Gly Gln Gly Thr Thr Val Thr
        115                 120                 125

Val Ser Ser
    130


<210> SEQ ID NO 64
<211> LENGTH: 126
<212> TYPE: PRT
<213> ORGANISM: Artificial Sequence
<220> FEATURE:
<223> OTHER INFORMATION: P6A1 heavy chain

<400> SEQUENCE: 64

Glu Val Gln Leu Val Glu Ser Gly Gly Gly Leu Val Gln Pro Gly Gly
1               5                   10                  15
```

```
Ser Leu Arg Leu Ser Cys Ala Ala Phe Gly Phe Thr Phe Val Asn Tyr
            20                  25                  30

Ala Met Asn Trp Val Arg Gln Ala Pro Gly Lys Gly Pro Glu Trp Val
        35                  40                  45

Ala Val Ile Tyr Ala Ala Gly Asp Gly Ala Asn Tyr Gly Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Pro Ala His Tyr Asp Asp Ser Gly Tyr Pro Tyr Met Ala Tyr
            100                 105                 110

Phe Asp Ser Trp Gly Gln Gly Thr Leu Val Thr Val Ser Ser
        115                 120                 125


<210> SEQ ID NO 65
<211> LENGTH: 126
<212> TYPE: PRT
<213> ORGANISM: Artificial Sequence
<220> FEATURE:
<223> OTHER INFORMATION: P6A3 heavy chain

<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Phe Ser Ser Tyr
            20                  25                  30

Ala Ile Thr Trp Val Arg Gln Ala Pro Gly Gln Gly Leu Glu Trp Met
        35                  40                  45

Gly Gly Ile Ile Pro Asp Tyr Asp Ser Ala Lys Tyr Ala Gln Lys Phe
    50                  55                  60

Gln Gly Arg Val Thr Ile Thr Ala Asp Glu Ser Thr Ser Thr Ala Tyr
65                  70                  75                  80

Leu Glu Leu Arg Ser Leu Arg Ser Glu Asp Thr Ala Val Tyr Tyr Cys
                85                  90                  95

Ala Arg Arg His Cys Ser Ser Thr Ser Cys Ser Asp Pro Trp Thr Phe
            100                 105                 110

Phe Pro Ser Trp Gly Gln Gly Thr Leu Val Thr Ser Pro Gln
        115                 120                 125


<210> SEQ ID NO 66
<211> LENGTH: 126
<212> TYPE: PRT
<213> ORGANISM: Artificial Sequence
<220> FEATURE:
<223> OTHER INFORMATION: P6A12 heavy chain

<400> SEQUENCE: 66

Glu Val Gln Leu Val Glu Ser Gly Ala Glu Met Lys Lys Pro Gly Ser
1               5                   10                  15

Ser Val Lys Val Ser Cys Lys Ala Ser Gly Ala Thr Phe Thr Ser Phe
            20                  25                  30

Ala Met Tyr Trp Val Arg Gln Ala Pro Gly Gln Gly Leu Glu Trp Met
        35                  40                  45

Gly Arg Ile Ile Pro Met Phe Ala Ser Ala Glu Tyr Ala Gln Lys Phe
    50                  55                  60

Gln Gly Arg Leu Thr Met Thr Ala Asp Glu Ser Thr Thr Thr Ala Tyr
65                  70                  75                  80
```

```
Met Glu Leu Ser Ser Leu Arg Ser Asp Asp Thr Ala Val Tyr Tyr Cys
                85                  90                  95

Ala Gly Arg Tyr Cys Ser Ser Thr Ser Cys Ser Asp Pro Trp Thr Tyr
            100                 105                 110

Phe Pro His Trp Gly Gln Gly Thr Leu Val Thr Val Ser Ser
        115                 120                 125


<210> SEQ ID NO 67
<211> LENGTH: 130
<212> TYPE: PRT
<213> ORGANISM: Artificial Sequence
<220> FEATURE:
<223> OTHER INFORMATION: P6B4 heavy chain

<400> SEQUENCE: 67

Glu Val Gln Leu Val Gln Ser Gly Ala Thr Val Arg Lys Pro Gly Ala
1               5                   10                  15

Ser Val Thr Ile Ser Cys Lys Thr Ser Gly Tyr Thr Phe Thr Asp Tyr
            20                  25                  30

Ala Leu His Trp Val Arg Gln Ala Pro Gly Gln Arg Leu Glu Trp Met
        35                  40                  45

Gly Trp Leu Ile Pro Gly Ser Gly Tyr Thr Lys Phe Ala Glu Asn Phe
    50                  55                  60

Gln Gly Arg Val Thr Ile Thr Arg Ala Thr Ser Ala His Thr Ala Tyr
65                  70                  75                  80

Met Glu Leu Ser Asn Leu Arg Ser Glu Asp Thr Ala Val Tyr Tyr Cys
                85                  90                  95

Ala Arg Trp Gly Gly Asp Cys Asn Ala Gly Ser Cys Tyr Gly Pro Tyr
            100                 105                 110

Gln Tyr Arg Gly Leu Asp Ala Trp Gly Gln Gly Thr Thr Val Thr Val
        115                 120                 125

Ser Ser
    130


<210> SEQ ID NO 68
<211> LENGTH: 125
<212> TYPE: PRT
<213> ORGANISM: Artificial Sequence
<220> FEATURE:
<223> OTHER INFORMATION: P6B5 heavy chain

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ile Gly Tyr
            20                  25                  30

Tyr Leu His Trp Val Arg Gln Ala Pro Gly Gln Gly Leu Glu Trp Met
        35                  40                  45

Gly Arg Ile Asn Pro Asn Ser Gly Gly Ile Asp Tyr Gly Gln Thr Phe
    50                  55                  60

Gln Gly Arg Val Thr Met Thr Arg Asp Met Ser Ser Ser Thr Val Tyr
65                  70                  75                  80

Leu Glu Leu Thr Arg Leu Arg Ser Asp Asp Thr Ala Arg Tyr Tyr Cys
                85                  90                  95

Ala Gly Arg Ser Asp Asn Trp Asn Asp Val Tyr Tyr Asn Tyr Ala Leu
            100                 105                 110

Asp Val Trp Gly Gln Gly Thr Thr Val Thr Val Ser Ser
```

```
        115                 120                 125


<210> SEQ ID NO 69
<211> LENGTH: 129
<212> TYPE: PRT
<213> ORGANISM: Artificial Sequence
<220> FEATURE:
<223> OTHER INFORMATION: P6B11 heavy chain

<400> SEQUENCE: 69

Glu Val Gln Leu Leu Glu Ser Gly Gly Gly Val Val Gln Pro Gly Arg
1               5                   10                  15

Ser Leu Lys Leu Ser Cys Ala Ala Ser Gly Phe Thr Phe Ser Gly Tyr
            20                  25                  30

Ala Met His Trp Val Arg Gln Ala Pro Gly Lys Gly Leu Glu Trp Leu
        35                  40                  45

Ala Val Ile Ser Tyr Asp Ala Thr Thr Thr Tyr Tyr Thr Pro Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Ala Ala Val Tyr Tyr Cys
                85                  90                  95

Ala Lys Glu Ile Ser Tyr Cys Gly Gly Asp Cys Gln Asn Phe Phe Phe
            100                 105                 110

Tyr Tyr Asn Met Asp Val Trp Gly Gln Gly Thr Thr Val Thr Val Ser
        115                 120                 125

Ser


<210> SEQ ID NO 70
<211> LENGTH: 128
<212> TYPE: PRT
<213> ORGANISM: Artificial Sequence
<220> FEATURE:
<223> OTHER INFORMATION: P6C4 heavy chain

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Ile His Trp Val Arg Gln Ala Pro Gly Gln Gly Leu Glu Trp Met
        35                  40                  45

Gly Ser Ile Asn Pro Asn Asn Gly Gly Thr Asn Tyr Ala Gln Gly Phe
    50                  55                  60

Gln Gly Arg Val Thr Met Thr Arg Asp Thr Ser Ile Arg Thr Val Tyr
65                  70                  75                  80

Met Glu Leu Ser Lys Leu Arg Ser Asp Asp Thr Ala Leu Tyr Tyr Cys
                85                  90                  95

Ala Arg Asp Leu Gly Ala Met Gly Tyr Tyr Leu Cys Ser Ala Gly Asn
            100                 105                 110

Cys Pro Phe Asp Tyr Trp Gly Gln Gly Thr Leu Val Thr Val Ser Ser
        115                 120                 125


<210> SEQ ID NO 71
<211> LENGTH: 133
<212> TYPE: PRT
<213> ORGANISM: Artificial Sequence
<220> FEATURE:
<223> OTHER INFORMATION: B8 heavy chain
```

<400> SEQUENCE: 71

Gln Val Gln Leu Val Glu Ser Gly Gly Ala Leu Val Lys Pro Gly Gly
1               5                   10                  15

Ser Leu Arg Leu Ser Cys Ala Ala Ser Gly Phe Thr Phe Arg Ser His
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Asn Tyr Ala Asp Phe Val
    50                  55                  60

Lys Gly Arg Phe Thr Thr Ser Arg Asp Asn Ala Glu Asn Thr Leu Tyr
65                  70                  75                  80

Leu Glu Met Asn Ser Leu Thr Ala Asp Asp Thr Ala Val Tyr Tyr Cys
                85                  90                  95

Val Arg Asp Gly Val Arg Tyr Tyr Tyr Asp Ser Ser Gly Tyr Tyr Pro
            100                 105                 110

Asp Ser Phe Phe Lys Tyr Gly Met Asp Val Trp Gly Gln Gly Thr Thr
        115                 120                 125

Val Thr Val Ser Ser
    130

<210> SEQ ID NO 72
<211> LENGTH: 126
<212> TYPE: PRT
<213> ORGANISM: Artificial Sequence
<220> FEATURE:
<223> OTHER INFORMATION: C2 heavy chain

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Ser
            20                  25                  30

Ala Met Tyr Trp Val Arg Gln Ala Pro Gly Lys Gly Leu Glu Phe Val
        35                  40                  45

Ser Cys Ile Arg Ser Asn Gly Val Thr His Tyr Ala Asp Ser Val Lys
    50                  55                  60

Gly Arg Phe Thr Ile Ser Arg Asp Asn Ser Lys Asn Thr Leu His Leu
65                  70                  75                  80

Gln Met Gly Gly Leu Arg Pro Asp Asp Met Ala Val Tyr Tyr Cys Thr
                85                  90                  95

Arg Asp Asp Gly Pro Tyr Ser Gly Tyr Asp Trp Pro Trp Ala Ser Ser
            100                 105                 110

Met Asp Val Trp Gly Gln Gly Thr Thr Val Thr Val Ser Ser
        115                 120                 125

<210> SEQ ID NO 73
<211> LENGTH: 133
<212> TYPE: PRT
<213> ORGANISM: Artificial Sequence
<220> FEATURE:
<223> OTHER INFORMATION: D8 heavy chain

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Asn His
            20                  25                  30

```
Trp Met His Trp Val Arg Gln Ala Pro Gly Lys Gly Leu Val Trp Val
        35                  40                  45

Ser Arg Thr Asn Ser Asp Gly Ser Ser Thr Ser Tyr Ala Asp Phe Val
    50                  55                  60

Lys Gly Arg Phe Thr Ile Ser Arg Asp Asn Ala Lys Asn Thr Leu His
65                  70                  75                  80

Leu Gln Ile Asn Ser Leu Arg Ala Asp Asp Thr Ala Val Tyr Tyr Cys
                85                  90                  95

Ala Arg Asp Gly Val Arg Tyr Tyr Tyr Asp Ser Thr Gly Tyr Tyr Pro
            100                 105                 110

Asp Ser Tyr Tyr Glu Tyr Gly Leu Asp Val Trp Gly Gln Gly Thr Thr
        115                 120                 125

Val Thr Val Ser Ser
    130


<210> SEQ ID NO 74
<211> LENGTH: 133
<212> TYPE: PRT
<213> ORGANISM: Artificial Sequence
<220> FEATURE:
<223> OTHER INFORMATION: A3 heavy chain

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Asn Arg His
            20                  25                  30

Trp Met His Trp Val Arg Gln Gly Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu His
65                  70                  75                  80

Leu Gln Ile Asn Ser Leu Arg Ala Glu Asp Thr Ala Val Tyr Tyr Cys
                85                  90                  95

Ala Arg Asp Gly Val Arg Tyr Tyr Tyr Asp Ser Thr Gly Tyr Tyr Pro
            100                 105                 110

Asp Ser Tyr Tyr Glu Tyr Gly Met Asp Val Trp Gly Gln Gly Thr Thr
        115                 120                 125

Val Thr Val Ser Ser
    130


<210> SEQ ID NO 75
<211> LENGTH: 133
<212> TYPE: PRT
<213> ORGANISM: Artificial Sequence
<220> FEATURE:
<223> OTHER INFORMATION: A10 heavy chain

<400> SEQUENCE: 75

Gln Val Gln Leu Val Gln Ser Gly Gly Ala Leu Val Lys Pro Gly Gly
1               5                   10                  15

Ser Leu Arg Leu Ser Cys Val Ala Ser Gly Phe Thr Phe Gly Ser His
            20                  25                  30

Trp Met His Trp Val Arg Gln Ala Pro Gly Lys Gly Leu Val Trp Val
        35                  40                  45

Ser Arg Val Asn Ser Asp Gly Ser Ser Thr Asn Tyr Ala Asp Phe Val
```

```
    50                  55                  60

Lys Gly Arg Phe Thr Thr Ser Arg Asp Asn Ala Glu Asn Thr Leu Tyr
65                  70                  75                  80

Leu Glu Met Asn Ser Leu Thr Ala Asp Asp Thr Ala Val Tyr Tyr Cys
                85                  90                  95

Val Arg Asp Gly Val Arg Tyr Tyr Tyr Asp Ser Ser Gly Tyr Tyr Pro
            100                 105                 110

Asp Ser Phe Phe Lys Tyr Gly Met Asp Val Trp Gly Gln Gly Thr Thr
        115                 120                 125

Val Thr Val Ser Ser
    130


<210> SEQ ID NO 76
<211> LENGTH: 126
<212> TYPE: PRT
<213> ORGANISM: Artificial Sequence
<220> FEATURE:
<223> OTHER INFORMATION: B4 heavy chain

<400> SEQUENCE: 76

Gln Val Gln Leu Gln Glu Ser Gly Pro Gly Leu Val Arg Pro Ser Glu
1               5                   10                  15

Thr Leu Ser Leu Thr Cys Thr Val Ser Gly Leu Ser Val Ser Thr Tyr
            20                  25                  30

Tyr Trp Ser Trp Ile Arg Gln Pro Pro Gly Lys Gly Leu Glu Trp Ile
        35                  40                  45

Ala Tyr Val Tyr Ser Arg Gly Gly Thr Asn Tyr Asn Pro Ser Leu Glu
    50                  55                  60

Ser Arg Val Thr Ile Ser Val Asp Thr Ala Thr Asn Gln Phe Ser Leu
65                  70                  75                  80

Arg Leu Arg Ser Val Thr Ala Ala Asp Thr Ala Val Tyr Phe Cys Ala
                85                  90                  95

Arg Ala Thr Asn Tyr Phe Asp Ser Ser Gly Tyr Phe Phe Ala Pro Trp
            100                 105                 110

Phe Asp Pro Trp Gly Gln Gly Ile Leu Val Thr Val Ser Ser
        115                 120                 125


<210> SEQ ID NO 77
<211> LENGTH: 122
<212> TYPE: PRT
<213> ORGANISM: Artificial Sequence
<220> FEATURE:
<223> OTHER INFORMATION: B6 heavy chain

<400> SEQUENCE: 77

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Arg Ser Ser Tyr
            20                  25                  30

Ala Ile Ser Trp Val Arg Arg Ala Pro Gly Arg Gly Leu Glu Trp Met
        35                  40                  45

Gly Val Ile Ile Pro Phe Phe Gly Thr Ala Asn Tyr Ala Gln Ile Phe
    50                  55                  60

Gln Gly Arg Leu Thr Ile Thr Ala Asp Glu Ser Thr Ser Ile Ala Asn
65                  70                  75                  80

Met Glu Leu Thr Ser Leu Thr Pro Glu Asp Thr Ala Ile Tyr Tyr Cys
                85                  90                  95
```

```
Ala Ser Gly Gly Gly Gly Tyr Ala Gly Tyr Asn Trp Phe Asp Pro Trp
            100                 105                 110

Gly Gln Gly Thr Leu Val Thr Val Ser Ser
        115                 120


<210> SEQ ID NO 78
<211> LENGTH: 133
<212> TYPE: PRT
<213> ORGANISM: Artificial Sequence
<220> FEATURE:
<223> OTHER INFORMATION: D6 heavy chain

<400> SEQUENCE: 78

Glu Val Gln Leu Val Gln Ser Gly Gly Gly Leu Ile Gln Pro Gly Gly
1               5                   10                  15

Ser Leu Lys Leu Ser Cys Ala Ala Ser Gly Phe Ser Phe Arg Asn His
            20                  25                  30

Trp Met His Trp Val Arg Gln Ala Pro Gly Lys Gly Leu Val Trp Val
        35                  40                  45

Ser Arg Val Asn Ser Asp Gly Tyr Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Phe Cys
                85                  90                  95

Ala Arg Asp Gly Val Arg Phe Tyr Ser Asp Ser Thr Gly Tyr Tyr Pro
            100                 105                 110

Asp Asn Tyr Phe Pro Tyr Gly Met Asp Val Trp Gly Gln Gly Thr Thr
        115                 120                 125

Val Thr Val Ser Ser
    130


<210> SEQ ID NO 79
<211> LENGTH: 118
<212> TYPE: PRT
<213> ORGANISM: Artificial Sequence
<220> FEATURE:
<223> OTHER INFORMATION: B2 heavy chain
<220> FEATURE:
<221> NAME/KEY: UNSURE
<222> LOCATION: 101
<220> FEATURE:
<221> NAME/KEY: UNSURE
<222> LOCATION: 111
<220> FEATURE:
<221> NAME/KEY: UNSURE
<222> LOCATION: 114

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Lys Val Ser Gly Phe Thr Phe Lys Ala Tyr
            20                  25                  30

Trp Met His Trp Val Arg Gln Ala Pro Gly Lys Gly Leu Val Trp Val
        35                  40                  45

Ser Arg Ile Asn Gly Leu Gly Ser Ser Arg Asp Tyr Ala Asp Ser Val
    50                  55                  60

Arg Gly Arg Phe Thr Ile Ser Arg Asp Asp Ala Glu Asn Thr Val Tyr
65                  70                  75                  80

Leu Gln Met Asn Ser Leu Thr Ala Glu Asp Thr Ala Met Tyr Tyr Cys
                85                  90                  95
```

```
Ala Arg Asp Val Xaa Phe His Asp Ser Ser Gly Tyr Tyr Arg Xaa Gly
            100                 105                 110

Phe Xaa Ala Pro Trp Gly
        115


<210> SEQ ID NO 80
<211> LENGTH: 133
<212> TYPE: PRT
<213> ORGANISM: Artificial Sequence
<220> FEATURE:
<223> OTHER INFORMATION: C4 heavy chain

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asn His
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Thr Tyr Ala Asp Ser Val
    50                  55                  60

Lys Gly Arg Phe Thr Ile Ser Arg Asp Asn Ala Lys Asn Thr Leu Ser
65                  70                  75                  80

Leu Glu Leu Asn Ser Leu Arg Ala Glu Asp Thr Ala Ile Tyr Tyr Cys
                85                  90                  95

Ala Arg Asp Gly Val Arg Phe Tyr Tyr Asp Ser Thr Gly Tyr Tyr Pro
            100                 105                 110

Asp Pro Tyr Phe Gln Tyr Gly Leu Asp Val Trp Gly Gln Gly Thr Thr
        115                 120                 125

Val Thr Val Ser Ser
    130


<210> SEQ ID NO 81
<211> LENGTH: 129
<212> TYPE: PRT
<213> ORGANISM: Artificial Sequence
<220> FEATURE:
<223> OTHER INFORMATION: C7 heavy chain

<400> SEQUENCE: 81

Glu Val Gln Leu Val Glu Ser Gly Gly Gly Leu Val Gln Pro Gly Ala
1               5                   10                  15

Ser Leu Arg Val Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Tyr Ile Ser Ser Arg Ser Ser Thr Ile Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly His Tyr Tyr Asp Ser Ser Gly Tyr Phe His Tyr
            100                 105                 110

Ser Phe Gly Met Asp Val Trp Gly Gln Gly Thr Thr Val Thr Val Ser
        115                 120                 125

Ser
```

<210> SEQ ID NO 82
<211> LENGTH: 127
<212> TYPE: PRT
<213> ORGANISM: Artificial Sequence
<220> FEATURE:
<223> OTHER INFORMATION: D5 heavy chain

<400> SEQUENCE: 82

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Arg Asn Tyr
            20                  25                  30

Trp Met His Trp Val Arg Gln Ala Pro Gly Lys Gly Leu Val Trp Val
        35                  40                  45

Ser Arg Ile Asn Gly Leu Gly Ser Thr Thr Thr Tyr Ala Asp Ser Val
    50                  55                  60

Glu Gly Arg Phe Thr Ile Thr Arg Asp Asp Ala Lys Asn Thr Ile Phe
65                  70                  75                  80

Leu Gln Met Asn Ser Leu Arg Ala Glu Asp Thr Ala Val Tyr Tyr Cys
                85                  90                  95

Ala Arg Asp Val Asn Phe Tyr Asp Ser Ser Gly Tyr Tyr Arg Glu Gly
            100                 105                 110

Trp Phe Asp Ser Trp Gly Pro Gly Thr Thr Val Thr Val Ser Ser
        115                 120                 125
```

<210> SEQ ID NO 83
<211> LENGTH: 126
<212> TYPE: PRT
<213> ORGANISM: Artificial Sequence
<220> FEATURE:
<223> OTHER INFORMATION: D11 heavy chain

<400> SEQUENCE: 83

```
Glu Val Gln Leu Leu Glu Ser Gly Ala Glu Val Lys Lys Pro Gly Ser
1               5                   10                  15

Ser Val Lys Ile Ser Cys Lys Ala Ser Gly Gly Thr Phe Ser Asn Tyr
            20                  25                  30

Ala Ile Ser Trp Val Arg Gln Ala Pro Gly Arg Gly Leu Glu Trp Leu
        35                  40                  45

Gly Gly Ile Ile Pro Ile Phe Gly Thr Pro Asn Tyr Ala Gln Arg Phe
    50                  55                  60

Gln Gly Arg Val Thr Ile Thr Ala Asp Glu Ser Thr Ser Thr Ala Tyr
65                  70                  75                  80

Met Glu Leu Asn Ser Leu Thr Ser Asp Asp Thr Ala Ile Tyr Tyr Cys
                85                  90                  95

Ala Arg Asp His Pro Thr Val Ile Asn Pro Thr Phe Val Gly Ser Trp
            100                 105                 110

Phe Asp Pro Trp Gly Gln Gly Thr Leu Val Thr Val Ser Ser
        115                 120                 125
```

<210> SEQ ID NO 84
<211> LENGTH: 131
<212> TYPE: PRT
<213> ORGANISM: Artificial Sequence
<220> FEATURE:
<223> OTHER INFORMATION: B6 heavy chain

<400> SEQUENCE: 84

```
Gln Val Gln Leu Val Glu Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Met
        35                  40                  45

Gly Val Ile Asn Pro Ser Gly Gly Thr Thr Ile Tyr Ala Arg Asn Leu
    50                  55                  60

Gln Gly Arg Val Thr Met Thr Arg Asp Thr Ser Thr Thr Thr Val Tyr
65                  70                  75                  80

Met Glu Leu Ser Ser Leu Lys Ser Glu Asp Thr Ala Val Tyr Tyr Cys
                85                  90                  95

Ala Arg Ala His Ser Gly Asn Tyr Asp Phe Trp Ser Gly Ser Asn Tyr
            100                 105                 110

His Tyr Tyr Tyr Gly Met Asp Val Trp Gly Gln Gly Thr Thr Val Thr
        115                 120                 125

Val Ser Ser
    130
```

<210> SEQ ID NO 85
<211> LENGTH: 131
<212> TYPE: PRT
<213> ORGANISM: Artificial Sequence
<220> FEATURE:
<223> OTHER INFORMATION: D2 heavy chain

<400> SEQUENCE: 85

```
Glu Val Gln Leu Val Glu Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Met
        35                  40                  45

Gly Val Ile Asn Pro Ser Gly Gly Thr Thr Ile Tyr Ala Gln Asn Phe
    50                  55                  60

Gln Gly Arg Val Thr Met Thr Arg Asp Thr Ser Thr Thr Thr Val Tyr
65                  70                  75                  80

Met Glu Leu Ser Ser Leu Lys Ser Glu Asp Thr Ala Val Tyr Tyr Cys
                85                  90                  95

Ala Arg Ala His Ser Gly Asn Tyr Asp Phe Trp Ser Gly Ser Asn Tyr
            100                 105                 110

His Tyr Tyr Tyr Gly Met Asp Val Trp Gly Gln Gly Thr Thr Val Thr
        115                 120                 125

Val Ser Ser
    130
```

<210> SEQ ID NO 86
<211> LENGTH: 109
<212> TYPE: PRT
<213> ORGANISM: Artificial Sequence
<220> FEATURE:
<223> OTHER INFORMATION: B3 light chain

<400> SEQUENCE: 86

```
Gln Thr Val Val Thr Gln Glu Pro Ser Leu Thr Val Ser Pro Gly Gly
1               5                   10                  15

Thr Val Thr Leu Thr Cys Gly Ser Asn Thr Gly Pro Val Thr Asn Gly
            20                  25                  30
```

```
His Tyr Pro Tyr Trp Phe Gln Gln Lys Ser Gly Gln Ala Pro Arg Thr
        35                  40                  45

Leu Ile Tyr Asp Thr Thr Asn Arg Gln Ser Trp Thr Pro Val Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Asp Tyr His Cys Leu Leu Ser Tyr Ser Asp
                85                  90                  95

Gly Leu Val Phe Gly Gly Gly Thr Lys Leu Thr Val Leu
            100                 105


<210> SEQ ID NO 87
<211> LENGTH: 110
<212> TYPE: PRT
<213> ORGANISM: Artificial Sequence
<220> FEATURE:
<223> OTHER INFORMATION: A12 light chain

<400> SEQUENCE: 87

Cys Met Thr Pro Ala Pro Ser Thr Leu Ala Val Thr Pro Gly Glu Pro
1               5                   10                  15

Ala Ser Ile Ser Cys Arg Ser Thr Gln Ser Leu Leu His Ser Asp Gly
            20                  25                  30

Tyr Asn Tyr Leu Asp Trp Tyr Leu Gln Lys Pro Gly Gln Ser Pro His
        35                  40                  45

Leu Leu Ile Tyr Leu Gly Ser His Arg Ala Ser Gly Val Pro Asp Arg
    50                  55                  60

Phe Ser Gly Ser Gly Ser Asp Thr Asp Phe Thr Leu Lys Ile Ser Arg
65                  70                  75                  80

Val Glu Ala Glu Asp Val Gly Val Tyr Tyr Cys Met Gln Pro Leu Arg
                85                  90                  95

Thr Pro Pro Thr Phe Gly Gln Gly Thr Lys Leu Glu Ile Lys
            100                 105                 110


<210> SEQ ID NO 88
<211> LENGTH: 108
<212> TYPE: PRT
<213> ORGANISM: Artificial Sequence
<220> FEATURE:
<223> OTHER INFORMATION: B10 light chain

<400> SEQUENCE: 88

Glu Ile Val Leu Thr Gln Ser Pro Ala Thr Leu Ser Leu Ser Ala Gly
1               5                   10                  15

Asp Arg Ala Thr Leu Ser Cys Arg Ala Ser Gln Asp Ile Ser Ser Phe
            20                  25                  30

Leu Ala Trp Tyr Gln Gln Lys Pro Gly Gln Ala Pro Arg Leu Leu Met
        35                  40                  45

Tyr Asp Thr Ser Asn Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Val Ala Val Tyr Tyr Cys Gln His Arg Tyr Asn Trp Pro Pro
                85                  90                  95

Tyr Thr Phe Gly Gln Gly Thr Lys Val Glu Ile Lys
            100                 105
```

<210> SEQ ID NO 89
<211> LENGTH: 108
<212> TYPE: PRT
<213> ORGANISM: Artificial Sequence
<220> FEATURE:
<223> OTHER INFORMATION: B11 light chain

<400> SEQUENCE: 89

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Val Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln His Arg Tyr Asn Trp Pro Pro
                85                  90                  95

Tyr Thr Phe Gly Gln Gly Thr Lys Val Glu Ile Lys
            100                 105
```

<210> SEQ ID NO 90
<211> LENGTH: 108
<212> TYPE: PRT
<213> ORGANISM: Artificial Sequence
<220> FEATURE:
<223> OTHER INFORMATION: C9 light chain

<400> SEQUENCE: 90

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln Gln Arg Tyr Asn Trp Pro Pro
                85                  90                  95

Tyr Thr Phe Gly Gln Gly Thr Lys Val Glu Ile Lys
            100                 105
```

<210> SEQ ID NO 91
<211> LENGTH: 107
<212> TYPE: PRT
<213> ORGANISM: Artificial Sequence
<220> FEATURE:
<223> OTHER INFORMATION: A2 light chain

<400> SEQUENCE: 91

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Gly Ser
            20                  25                  30

Leu Ser Trp Tyr Gln His Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Phe Tyr Cys Gln Gln Ser Tyr Ser Thr Pro Tyr
                85                  90                  95

Thr Phe Gly Gln Gly Thr Lys Val Glu Ile Lys
            100                 105


<210> SEQ ID NO 92
<211> LENGTH: 107
<212> TYPE: PRT
<213> ORGANISM: Artificial Sequence
<220> FEATURE:
<223> OTHER INFORMATION: A5 light chain

<400> SEQUENCE: 92

Asp Ile Gln Met Thr Gln Ser Pro Ser Ser Leu Ser Ala Ser Ile Gly
1               5                   10                  15

Asp Arg Val Thr Ile Thr Cys Arg Ala Ser Glu Ser Ile Ser Ser Gln
            20                  25                  30

Leu His Trp Tyr Gln Gln Lys Pro Gly Lys Ala Pro Arg Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Cys Cys Gln Gln Ser Phe Thr Thr Pro Tyr
                85                  90                  95

Thr Phe Gly Gln Gly Thr Lys Val Glu Ile Lys
            100                 105


<210> SEQ ID NO 93
<211> LENGTH: 108
<212> TYPE: PRT
<213> ORGANISM: Artificial Sequence
<220> FEATURE:
<223> OTHER INFORMATION: A7 light chain

<400> SEQUENCE: 93

Glu Ile Val Met Thr Gln Ser Pro Ala Thr Leu Ser Ala Ser Pro Gly
1               5                   10                  15

Glu Arg Ala Thr Leu Ser Cys Arg Ala Ser Gln Asp Val Ser Thr Phe
            20                  25                  30

Val Ala Trp Phe Gln Gln Asn Pro Gly Gln Ala Pro Arg Leu Leu Ile
        35                  40                  45

Tyr Asp Ala Ser Thr Arg Ala Pro Gly Ile Pro Ala Arg Phe Ser Gly
    50                  55                  60

Ser Arg Ser Gly Thr Glu Phe Thr Leu Thr Ile Asn Ser Leu Gln Ser
65                  70                  75                  80

Glu Asp Phe Ala Val Tyr Tyr Cys Gln Gln Tyr Tyr Asn Trp Pro Pro
                85                  90                  95

Trp Thr Phe Gly Gln Gly Thr Lys Val Glu Ile Lys
            100                 105


<210> SEQ ID NO 94
<211> LENGTH: 107
<212> TYPE: PRT
```

-continued

<213> ORGANISM: Artificial Sequence
<220> FEATURE:
<223> OTHER INFORMATION: A8 light chain

<400> SEQUENCE: 94

Asp Ile Gln Met Thr Gln Ser Pro Ser Ser Val Ser Ala Ser Val Gly
1               5                   10                  15

Asp Arg Val Thr Ile Ser Cys Arg Ala Ser Gln Asp Ile Ser Ala Ser
            20                  25                  30

Leu Gly Trp Tyr Gln Gln Lys Pro Gly Lys Ala Pro Lys Leu Leu Ile
        35                  40                  45

Tyr Arg Ala Ser Asn Leu Glu Gly Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Asn Ser Phe Pro Leu
                85                  90                  95

Thr Phe Gly Gly Gly Thr Lys Val Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: B10 light chain

<400> SEQUENCE: 95

Asp Ile Gln Met Thr Gln Ser Pro Ser Ser Leu Ser Ala Ser Val Gly
1               5                   10                  15

Asp Ser Val Thr Val Ala Cys Arg Ala Ser Gln Pro Ile Tyr Arg Asn
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Ser Gly Val Pro Ala Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Ser Pro Arg
                85                  90                  95

Thr Phe Gly Gln Gly Thr Lys Val Glu Ile Lys
            100                 105

<210> SEQ ID NO 96
<211> LENGTH: 109
<212> TYPE: PRT
<213> ORGANISM: Artificial Sequence
<220> FEATURE:
<223> OTHER INFORMATION: C2 light chain

<400> SEQUENCE: 96

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ile Gly Val Pro Ser Arg Phe Ser Gly
    50                  55                  60

```
Ser Gly Ser Gly Thr Glu Phe Thr Leu Thr Ile Ser Ser Leu Gln Pro
65                  70                  75                  80

Asp Asp Phe Ala Ile Tyr Tyr Cys Gln Gln Tyr Asn Asn Tyr Ser Pro
                85                  90                  95

Pro Val Thr Phe Gly Gly Gly Thr Lys Val Glu Ile Lys
            100                 105


<210> SEQ ID NO 97
<211> LENGTH: 109
<212> TYPE: PRT
<213> ORGANISM: Artificial Sequence
<220> FEATURE:
<223> OTHER INFORMATION: D4 light chain

<400> SEQUENCE: 97

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ile Tyr Tyr Cys Gln Gln Tyr Asn Asn Tyr Ser Pro
                85                  90                  95

Pro Val Thr Phe Gly Gly Gly Thr Lys Val Glu Ile Lys
            100                 105


<210> SEQ ID NO 98
<211> LENGTH: 107
<212> TYPE: PRT
<213> ORGANISM: Artificial Sequence
<220> FEATURE:
<223> OTHER INFORMATION: B11 light chain

<400> SEQUENCE: 98

Asp Ile Gln Met Thr Gln Ser Pro Ser Ser Leu Ser Ala Ser Val Gly
1               5                   10                  15

Asp Ala Val Ser Ile Thr Cys Arg Ala Ser Glu Ser Val Ser Arg Gln
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Gly Tyr Ser Thr Pro Tyr
                85                  90                  95

Ser Phe Gly Gln Gly Thr Lys Val Glu Ile Lys
            100                 105


<210> SEQ ID NO 99
<211> LENGTH: 108
<212> TYPE: PRT
<213> ORGANISM: Artificial Sequence
<220> FEATURE:
<223> OTHER INFORMATION: A2 light chain
```

<400> SEQUENCE: 99

Glu Ile Val Leu Thr Gln Ser Pro Ala Thr Leu Ser Leu Ser Ala Gly
1 5 10 15

Glu Arg Ala Thr Leu Ser Cys Arg Ala Ser Gln Ser Ile Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Val Pro Ala Arg Phe Ser Gly
50 55 60

Ser Gln Ser Gly Thr Asp Phe Thr Leu Thr Ile Ser Thr Leu Glu Pro
65 70 75 80

Glu Asp Phe Ala Val Tyr Tyr Cys Gln Leu Arg Tyr Asn Trp Pro Pro
85 90 95

Tyr Thr Phe Gly Gln Gly Thr Lys Val Glu Ile Lys
100 105

<210> SEQ ID NO 100
<211> LENGTH: 107
<212> TYPE: PRT
<213> ORGANISM: Artificial Sequence
<220> FEATURE:
<223> OTHER INFORMATION: A4 light chain

<400> SEQUENCE: 100

Asp Ile Gln Met Thr Gln Ser Pro Ser Pro Leu Ser Ala Ser Val Gly
1 5 10 15

Asp Arg Val Thr Ile Thr Cys Arg Ala Ser Gln Ser Ile Ser Ser His
20 25 30

Leu Asn Trp Tyr Gln Gln Lys Ser Gly Lys Val Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Thr Ser Leu Gln Pro
65 70 75 80

Glu Asp Phe Ala Thr Tyr Tyr Cys Gln Gln Ser Asp Thr Thr Pro Tyr
85 90 95

Thr Phe Gly Gln Gly Thr Lys Val Glu Ile Lys
100 105

<210> SEQ ID NO 101
<211> LENGTH: 107
<212> TYPE: PRT
<213> ORGANISM: Artificial Sequence
<220> FEATURE:
<223> OTHER INFORMATION: A5 light chain

<400> SEQUENCE: 101

Asp Ile Gln Met Thr Gln Ser Pro Ser Ser Leu Ser Ala Ser Val Gly
1 5 10 15

Asp Ala Val Ser Ile Thr Cys Arg Ala Ser Glu Ser Ile Ala Arg Gln
20 25 30

Leu Asn Trp Tyr Gln Gln Lys Pro Gly Lys Ala Pro Asn Leu Leu Ile
35 40 45

Tyr Ala Ala Ser Ser Leu Gln Gly Gly Val Pro Ser Arg Phe Ser Gly
50 55 60

Ser Gly Ser Gly Ala Asp Phe Thr Leu Thr Ile Ser Gly Leu Gln Pro
65 70 75 80

```
Glu Asp Phe Ala Thr Tyr Tyr Cys Gln Gln Gly Tyr Ser Thr Pro Tyr
                85                  90                  95

Thr Phe Gly Gln Gly Thr Lys Val Glu Ile Lys
            100                 105


<210> SEQ ID NO 102
<211> LENGTH: 108
<212> TYPE: PRT
<213> ORGANISM: Artificial Sequence
<220> FEATURE:
<223> OTHER INFORMATION: A9 light chain

<400> SEQUENCE: 102

Glu Ile Val Leu Thr Gln Ser Pro Ala Thr Leu Ser Leu Ser Ala Gly
1               5                   10                  15

Glu Arg Ala Thr Leu Ser Cys Arg Ala Ser Gln Asp Ile Ser Thr Phe
            20                  25                  30

Leu Ala Trp Tyr Gln Gln Lys Pro Gly Gln Ala Pro Arg Leu Leu Ile
        35                  40                  45

Tyr Asp Thr Ser Thr Arg Ala Thr Gly Val Pro Ala Arg Phe Ser Gly
    50                  55                  60

Ser Arg Ser Gly Thr Asp Phe Thr Leu Thr Ile Thr Thr Leu Glu Pro
65                  70                  75                  80

Glu Asp Phe Ala Val Tyr Tyr Cys Gln His Arg Tyr Asn Trp Pro Pro
                85                  90                  95

Tyr Thr Phe Gly Gln Gly Thr Lys Val Glu Ile Lys
            100                 105


<210> SEQ ID NO 103
<211> LENGTH: 108
<212> TYPE: PRT
<213> ORGANISM: Artificial Sequence
<220> FEATURE:
<223> OTHER INFORMATION: B2 light chain

<400> SEQUENCE: 103

Glu Ile Val Leu Thr Gln Ser Pro Ala Thr Leu Ser Leu Ser Ala Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln His Arg Tyr Asn Trp Pro Pro
                85                  90                  95

Tyr Thr Phe Gly Gln Gly Thr Lys Val Glu Ile Lys
            100                 105


<210> SEQ ID NO 104
<211> LENGTH: 108
<212> TYPE: PRT
<213> ORGANISM: Artificial Sequence
<220> FEATURE:
<223> OTHER INFORMATION: B3 light chain

<400> SEQUENCE: 104
```

-continued

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser His Ser Ile Ser Thr Phe
            20                  25                  30

Leu Ala Trp Tyr Gln Gln Lys Pro Gly Gln Ala Pro Arg Leu Leu Ile
        35                  40                  45

Tyr Asp Thr Ser Thr Arg Ala Thr Gly Val Pro Ala Arg Phe Ser Gly
    50                  55                  60

Ser Arg Ser Gly Thr Asp Phe Thr Leu Thr Ile Asn Thr Leu Glu Pro
65                  70                  75                  80

Glu Asp Phe Ala Val Tyr Tyr Cys Gln Gln Arg Tyr Asn Trp Pro Pro
                85                  90                  95

Tyr Thr Phe Gly Gln Gly Thr Lys Val Glu Ile Lys
            100                 105


<210> SEQ ID NO 105
<211> LENGTH: 108
<212> TYPE: PRT
<213> ORGANISM: Artificial Sequence
<220> FEATURE:
<223> OTHER INFORMATION: B4 light chain

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Phe
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Ile Tyr Tyr Cys Gln His Arg Tyr Asn Trp Pro Pro
                85                  90                  95

Tyr Thr Phe Gly Gln Gly Thr Lys Val Glu Ile Lys
            100                 105


<210> SEQ ID NO 106
<211> LENGTH: 107
<212> TYPE: PRT
<213> ORGANISM: Artificial Sequence
<220> FEATURE:
<223> OTHER INFORMATION: B7 light chain

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Ser
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Ala Leu Thr Ile Ser Ser Leu Gln Pro
65                  70                  75                  80

Glu Asp Phe Ala Thr Tyr Ser Cys Gln Gln Ser Asp Arg Thr Pro Tyr
                85                  90                  95
```

```
Thr Phe Gly Gln Gly Thr Lys Val Glu Ile Lys
            100                 105


<210> SEQ ID NO 107
<211> LENGTH: 108
<212> TYPE: PRT
<213> ORGANISM: Artificial Sequence
<220> FEATURE:
<223> OTHER INFORMATION: B11 light chain

<400> SEQUENCE: 107

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Tyr
            20                  25                  30

Leu Val Trp Tyr Gln Gln Lys Pro Gly Gln Ala Pro Arg Leu Leu Ile
        35                  40                  45

Tyr Asp Ala Ser Thr Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln His Arg Tyr Asn Trp Pro Pro
                85                  90                  95

Tyr Thr Phe Gly Arg Gly Thr Lys Val Glu Ile Lys
            100                 105


<210> SEQ ID NO 108
<211> LENGTH: 109
<212> TYPE: PRT
<213> ORGANISM: Artificial Sequence
<220> FEATURE:
<223> OTHER INFORMATION: C4 light chain

<400> SEQUENCE: 108

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Ala Trp Tyr Gln Gln Lys Val Gly Lys Ala Pro Lys Leu Leu Ile
        35                  40                  45

Tyr Lys Ala Ser Thr Leu Glu Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ile Tyr Tyr Cys Gln Gln Tyr Asn Asn Tyr Ser Pro
                85                  90                  95

Pro Val Thr Phe Gly Gly Gly Thr Lys Val Glu Ile Lys
            100                 105


<210> SEQ ID NO 109
<211> LENGTH: 112
<212> TYPE: PRT
<213> ORGANISM: Artificial Sequence
<220> FEATURE:
<223> OTHER INFORMATION: B10 light chain

<400> SEQUENCE: 109

Asp Ile Val Met Thr Gln Ser Pro Leu Ser Leu Ser Val Thr Pro Gly
1               5                   10                  15
```

-continued

```
Glu Pro Ala Ser Ile Ser Cys Arg Ser Ser Gln Ser Leu Val Tyr Ser
            20                  25                  30

Asp Gly Asn Lys Tyr Leu Asp Trp Tyr Val Gln Lys Pro Gly Gln Ser
        35                  40                  45

Pro Gln Leu Leu Ile Tyr Leu Thr Ser Thr Arg Ala Ser Gly Val Pro
    50                  55                  60

Asp Arg Phe Ser Gly Ser Ala Ser Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Leu Gln Thr Pro Phe Thr Phe Gly Pro Gly Thr Lys Val Asp Ile Lys
            100                 105                 110


<210> SEQ ID NO 110
<211> LENGTH: 108
<212> TYPE: PRT
<213> ORGANISM: Artificial Sequence
<220> FEATURE:
<223> OTHER INFORMATION: P6A1 ligth chain

<400> SEQUENCE: 110

Glu Ile Val Met Thr Gln Ser Pro Ala Thr Leu Ser Val Ser Pro Gly
1               5                   10                  15

Glu Arg Ala Thr Leu Thr Cys Arg Ala Ser Gln Thr Ile Ser Thr Phe
            20                  25                  30

Leu Ala Trp Tyr Gln Gln Lys Pro Gly Gln Pro Pro Arg Leu Leu Ile
        35                  40                  45

Tyr Asp Thr Ser Thr Arg Ala Thr Gly Ile Pro Gly Arg Phe Ser Gly
    50                  55                  60

Ser Arg Ser Gly Thr Glu Phe Thr Leu Thr Ile Ser Ser Leu Gln Ser
65                  70                  75                  80

Glu Asp Val Ala Val Tyr Tyr Cys Gln His Tyr Tyr Asn Trp Pro Pro
                85                  90                  95

Trp Thr Phe Gly Gln Gly Thr Lys Val Glu Ile Lys
            100                 105


<210> SEQ ID NO 111
<211> LENGTH: 109
<212> TYPE: PRT
<213> ORGANISM: Artificial Sequence
<220> FEATURE:
<223> OTHER INFORMATION: P6A3 light chain

<400> SEQUENCE: 111

Gln Ser Ala Leu Thr Gln Pro Pro Ser Ala Ser Gly Ser Pro Gly Gln
1               5                   10                  15

Ser Val Thr Ile Ser Cys Thr Gly Ser Ser Ser Asp Ile Gly Gly Asn
            20                  25                  30

Glu Tyr Val Ser Trp Tyr Gln Leu Gln Pro Gly Lys Ala Pro Lys Leu
        35                  40                  45

Met Ile Tyr Glu Val Thr Lys Arg Pro Ser Gly Val Pro Asn Arg Phe
    50                  55                  60

Ser Gly Ser Lys Ser Gly Asn Thr Ala Ser Leu Thr Val Ser Gly Leu
65                  70                  75                  80

Gln Ser Glu Asp Glu Gly Asp Tyr Tyr Cys Ser Ser Tyr Ala Asp Asn
                85                  90                  95

Ser Val Leu Phe Gly Gly Gly Thr Thr Leu Thr Val Leu
            100                 105
```

<210> SEQ ID NO 112
<211> LENGTH: 110
<212> TYPE: PRT
<213> ORGANISM: Artificial Sequence
<220> FEATURE:
<223> OTHER INFORMATION: P6A12 light chain

<400> SEQUENCE: 112

```
Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
            20                  25                  30

Tyr Tyr Val Ser Trp Tyr Gln Gln His Pro Gly Lys Ala Pro Lys Leu
        35                  40                  45

Ile Ile Tyr Glu Val Asn Lys Arg Pro Ser Gly Val Pro Ala Arg Phe
    50                  55                  60

Ser Gly Ser Lys Ser Gly Asn Thr Ala Ser Leu Thr Val Ser Gly Leu
65                  70                  75                  80

Gln Gly Glu Asp Glu Ala Asp Tyr Tyr Cys Thr Ser Tyr Ala Gly Ser
                85                  90                  95

Asn Thr Val Ile Phe Gly Gly Gly Thr Lys Leu Thr Val Leu
            100                 105                 110
```

<210> SEQ ID NO 113
<211> LENGTH: 108
<212> TYPE: PRT
<213> ORGANISM: Artificial Sequence
<220> FEATURE:
<223> OTHER INFORMATION: P6B4 light chain

<400> SEQUENCE: 113

```
Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Thr Val Asp Ser Thr
            20                  25                  30

Tyr Leu Ala Trp Tyr Gln Gln Lys Pro Gly Arg Ala Pro Arg Leu Leu
        35                  40                  45

Ile Tyr Gly Ala Ser Asn Arg Ala Ile Gly Val Pro Ser Arg Phe Thr
    50                  55                  60

Gly Ser Gly Ser Gly Thr Asp Phe Thr Leu Thr Ile Ser Arg Leu Glu
65                  70                  75                  80

Pro Glu Asp Phe Ala Leu Tyr Tyr Cys Gln Gln Ser Asp Gly Ser Leu
                85                  90                  95

Phe Thr Phe Gly Pro Gly Thr Lys Val Asp Ile Lys
            100                 105
```

<210> SEQ ID NO 114
<211> LENGTH: 107
<212> TYPE: PRT
<213> ORGANISM: Artificial Sequence
<220> FEATURE:
<223> OTHER INFORMATION: P6B5 light chain

<400> SEQUENCE: 114

```
Asp Ile Gln Met Thr Gln Ser Pro Ala Ser Val Ser Ala Ser Val Gly
1               5                   10                  15

Asp Arg Val Thr Ile Ser Cys Arg Ala Ser Gln Gly Ile Ala Ser Trp
            20                  25                  30
```

-continued

```
Leu Ala Trp Tyr Gln Gln Lys Pro Gly Lys Ala Pro Arg Leu Leu Ile
        35                  40                  45

Tyr Gly Ala Ser Ser Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105


<210> SEQ ID NO 115
<211> LENGTH: 110
<212> TYPE: PRT
<213> ORGANISM: Artificial Sequence
<220> FEATURE:
<223> OTHER INFORMATION: P6B11 light chain

<400> SEQUENCE: 115

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr
            20                  25                  30

Asn Val Val Ser Trp Tyr Gln Gln His Pro Gly Lys Ala Pro Lys Leu
        35                  40                  45

Ile Ile Tyr Gly Ser Thr Lys Arg Pro Ser Gly Val Ser Tyr Arg Phe
    50                  55                  60

Ser Ala Ser Lys Ser Gly Asn Thr Ala Ser Leu Thr Ile Ser Gly Leu
65                  70                  75                  80

Gln Ala Glu Asp Glu Ala Glu Tyr His Cys Cys Ser Tyr Ala Ser Gly
                85                  90                  95

Ser Val Trp Val Phe Gly Gly Gly Thr Lys Leu Thr Val Leu
            100                 105                 110


<210> SEQ ID NO 116
<211> LENGTH: 110
<212> TYPE: PRT
<213> ORGANISM: Artificial Sequence
<220> FEATURE:
<223> OTHER INFORMATION: P6C4 light chain

<400> SEQUENCE: 116

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45

Ile Ile Tyr Glu Val Ser Lys Arg Pro Ser Gly Val Pro His Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Ala Gly Ser
                85                  90                  95

Asn Thr Phe Thr Phe Gly Gly Gly Thr Lys Leu Thr Val Leu
            100                 105                 110


<210> SEQ ID NO 117
```

<211> LENGTH: 110
<212> TYPE: PRT
<213> ORGANISM: Artificial Sequence
<220> FEATURE:
<223> OTHER INFORMATION: B8 light chain

<400> SEQUENCE: 117

```
Gln Ser Ala Leu Thr Gln Thr Ala Ser Val Ser Gly Ser Pro Gly Gln
1               5                   10                  15

Ser Ile Thr Ile Ser Cys Thr Gly Thr Ser Ser Asp Ala Glu Ile Tyr
            20                  25                  30

Asn Leu Val Ser Trp Tyr Gln Gln His Pro Gly Lys Ala Pro Lys Leu
        35                  40                  45

Ile Ile Tyr Glu Gly Ser Lys Arg Pro Ser Gly Val Ser Asn Arg Phe
    50                  55                  60

Ser Ala Ser Lys Ser Ala Gly Ala Ala Ser Leu Arg Ile Ser Gly Leu
65                  70                  75                  80

Gln Pro Glu Asp Glu Ala Asp Tyr Tyr Cys Cys Ser Tyr Ala Thr Ser
                85                  90                  95

Lys Thr Leu Val Phe Gly Gly Gly Thr Lys Leu Thr Val Val
            100                 105                 110
```

<210> SEQ ID NO 118
<211> LENGTH: 112
<212> TYPE: PRT
<213> ORGANISM: Artificial Sequence
<220> FEATURE:
<223> OTHER INFORMATION: C2 light chain

<400> SEQUENCE: 118

```
Asp Val Val Met Thr Gln Ser Pro Leu Ser Leu Pro Val Thr Leu Gly
1               5                   10                  15

Gln Pro Ala Ser Ile Ser Cys Arg Ser Ser Arg Ser Leu Leu Asn Ser
            20                  25                  30

Asp Gly Asn Thr Tyr Leu Asn Trp Phe His Gln Arg Pro Gly Gln Ser
        35                  40                  45

Pro Arg Arg Leu Ile Phe Lys Leu Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Val Thr Phe Gly Gly Gly Thr Lys Val Glu Ile Lys
            100                 105                 110
```

<210> SEQ ID NO 119
<211> LENGTH: 110
<212> TYPE: PRT
<213> ORGANISM: Artificial Sequence
<220> FEATURE:
<223> OTHER INFORMATION: D8 light chain

<400> SEQUENCE: 119

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Gly Val Gly Ser Tyr
            20                  25                  30

Asn Leu Val Ser Trp Tyr Gln Gln His Pro Gly Lys Ala Pro Lys Phe
        35                  40                  45
```

-continued

Ile Ile Tyr Glu Gly Ser Lys Arg Pro Ser Gly Val Ser Asn Arg Phe
50 55 60

Ser Gly Ser Asn Ser Gly Asn Thr Ala Ser Leu Thr Ile Ser Gly Leu
65 70 75 80

Gln Ala Glu Asp Glu Ala Asp Tyr Tyr Cys Cys Ser Tyr Ala Gly Ser
85 90 95

Lys Thr Leu Val Phe Gly Gly Gly Thr Lys Val Thr Val Leu
100 105 110

<210> SEQ ID NO 120
<211> LENGTH: 110
<212> TYPE: PRT
<213> ORGANISM: Artificial Sequence
<220> FEATURE:
<223> OTHER INFORMATION: A3 light chain

<400> SEQUENCE: 120

Gln Ser Val Leu Thr Gln Pro Ala Ser Val Ser Gly Ser Pro Gly Gln
1 5 10 15

Ser Ile Thr Ile Ser Cys Thr Gly Thr Ser Ser Asp Val Gly Ser Tyr
20 25 30

Asn Leu Val Ser Trp Tyr Gln Gln His Pro Gly Lys Ala Pro Lys Phe
35 40 45

Ile Ile Tyr Glu Gly Ser Lys Arg Pro Ser Gly Val Ser Asn Arg Phe
50 55 60

Ser Gly Ser Asn Ser Gly Asn Thr Ala Ser Leu Thr Ile Ser Gly Leu
65 70 75 80

Gln Ala Glu Asp Glu Ala Asp Tyr Tyr Cys Cys Ser Tyr Ala Gly Ser
85 90 95

Lys Thr Leu Val Phe Gly Gly Gly Thr Lys Val Thr Val Leu
100 105 110

<210> SEQ ID NO 121
<211> LENGTH: 110
<212> TYPE: PRT
<213> ORGANISM: Artificial Sequence
<220> FEATURE:
<223> OTHER INFORMATION: A10 light chain

<400> SEQUENCE: 121

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Ile Gly Ile Tyr
20 25 30

Asn Leu Val Ser Trp Tyr Gln Gln His Pro Gly Lys Ala Pro Lys Leu
35 40 45

Ile Ile Tyr Glu Gly Ser Lys Arg Pro Ser Gly Val Ser Asn Arg Phe
50 55 60

Ser Ala Ser Lys Ser Ala Gly Ala Ala Ser Leu Thr Ile Ser Gly Leu
65 70 75 80

Gln Pro Glu Asp Glu Ala Asp Tyr Tyr Cys Cys Ser Tyr Ala Thr Ser
85 90 95

Lys Thr Leu Val Phe Gly Gly Gly Thr Lys Leu Thr Val Val
100 105 110

<210> SEQ ID NO 122
<211> LENGTH: 107
<212> TYPE: PRT
<213> ORGANISM: Artificial Sequence

```
<220> FEATURE:
<223> OTHER INFORMATION: B4 light chain

<400> SEQUENCE: 122

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Lys Ser Asn
            20                  25                  30

Leu Ala Trp Tyr Gln Gln Lys Pro Gly Gln Ala Pro Arg Leu Leu Met
        35                  40                  45

Tyr Gly Ala Ser Thr Arg Val Val Thr Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Leu
                85                  90                  95

Thr Phe Gly Gly Gly Thr Lys Val Glu Ile Lys
            100                 105


<210> SEQ ID NO 123
<211> LENGTH: 110
<212> TYPE: PRT
<213> ORGANISM: Artificial Sequence
<220> FEATURE:
<223> OTHER INFORMATION: B6 light chain

<400> SEQUENCE: 123

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Phe
            20                  25                  30

Asn Tyr Val Ser Trp Tyr Gln Gln His Pro Gly Lys Ala Pro Lys Val
        35                  40                  45

Met Ile Phe Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Thr Thr Tyr Val Phe Gly Thr Gly Thr Lys Val Thr Val Leu
            100                 105                 110


<210> SEQ ID NO 124
<211> LENGTH: 110
<212> TYPE: PRT
<213> ORGANISM: Artificial Sequence
<220> FEATURE:
<223> OTHER INFORMATION: D6 light chain

<400> SEQUENCE: 124

Gln Ser Ala Leu Thr Gln Pro Ala Ser Val Ser Gly Ser Pro Gly Gln
1               5                   10                  15

Ser Ile Thr Ile Ser Cys Ser Gly Phe Ser Ser Asp Val Gly Gly Asp
            20                  25                  30

Lys Val Val Ser Trp Tyr Glu Gln His Pro Gly Lys Val Pro Lys Leu
        35                  40                  45

Ile Ile Tyr Glu Gly Ser Lys Arg Pro Ser Gly Val Ser Asn Arg Phe
    50                  55                  60
```

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Cys Ser Tyr Ala Gly Pro
85 90 95

Lys Thr Leu Val Phe Gly Gly Gly Thr Lys Val Thr Val Leu
100 105 110

<210> SEQ ID NO 125
<211> LENGTH: 102
<212> TYPE: PRT
<213> ORGANISM: Artificial Sequence
<220> FEATURE:
<223> OTHER INFORMATION: B2 light chain

<400> SEQUENCE: 125

Asn Ser Pro Leu Ser Leu Ser Ala Ser Val Gly Asp Arg Val Thr Ile
1 5 10 15

Thr Cys Arg Ala Ser Arg Thr Ile Asp Asn Phe Leu His Trp Tyr Gln
20 25 30

Gln Lys Pro Gly Lys Ala Pro Asn Leu Leu Ile Tyr Ala Ala Ser Ser
35 40 45

Leu Gln Ser Gly Val Pro Ser Arg Phe Arg Gly Ser Gly Ser Gly Thr
50 55 60

Asp Phe Thr Leu Thr Ile Asn Ser Val Gln Pro Glu Asp Phe Ala Thr
65 70 75 80

Tyr Tyr Cys Gln Gln Ser Tyr Thr Ile Pro Pro Thr Phe Gly Gly Gly
85 90 95

Thr Lys Val Glu Ile Arg
100

<210> SEQ ID NO 126
<211> LENGTH: 110
<212> TYPE: PRT
<213> ORGANISM: Artificial Sequence
<220> FEATURE:
<223> OTHER INFORMATION: C4 light chain

<400> SEQUENCE: 126

Gln Ser Ala Leu Thr Gln Pro Ala Ser Val Ser Gly Ser Leu Gly Gln
1 5 10 15

Ser Ile Thr Ile Ser Tyr Thr Gly Thr Ala Ile Asp Val Gly Ser Tyr
20 25 30

Asn Leu Val Ser Trp Tyr Gln Gln His Pro Gly Lys Val Pro Lys Leu
35 40 45

Met Ile Tyr Glu Gly Ser Lys Arg Pro Ser Gly Val Ser Asn Arg Phe
50 55 60

Phe Gly Ser Lys Ser Gly Asn Thr Ala Ser Leu Thr Ile Ser Gly Leu
65 70 75 80

Gln Ser Glu Asp Glu Ala Glu Tyr Tyr Cys Cys Ser Tyr Gly Gly Ser
85 90 95

Arg Thr Leu Leu Phe Gly Gly Gly Thr Lys Leu Thr Val Leu
100 105 110

<210> SEQ ID NO 127
<211> LENGTH: 112
<212> TYPE: PRT
<213> ORGANISM: Artificial Sequence
<220> FEATURE:
<223> OTHER INFORMATION: C7 light chain

<400> SEQUENCE: 127

Asp Ile Val Met Thr Gln Ser Pro Leu Ser Leu Pro Val Thr Leu Gly
1               5                   10                  15

Glu Pro Ala Ser Ile Ser Cys Arg Ser Ser Arg Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Val Thr Phe Gly Gly Gly Thr Lys Val Glu Ile Lys
            100                 105                 110

<210> SEQ ID NO 128
<211> LENGTH: 101
<212> TYPE: PRT
<213> ORGANISM: Artificial Sequence
<220> FEATURE:
<223> OTHER INFORMATION: D5 light chain

<400> SEQUENCE: 128

Gly Pro Phe Thr Leu Ser Ala Ser Val Gly Asp Arg Val Thr Ile Thr
1               5                   10                  15

Cys Arg Ala Ser Arg Ser Ile Asn Thr Phe Leu Asn Trp Tyr Gln Gln
            20                  25                  30

Lys Thr Gly Ser Ala Pro Lys Leu Leu Ile Tyr Gly Ala Ser Thr Leu
        35                  40                  45

Gln Ser Gly Val Pro Ser Arg Phe Ser Gly Ser Gly Ser Gly Thr Asp
    50                  55                  60

Phe Ala Leu Thr Ile Thr Ser Leu Gln Pro Asp Asp Phe Ala Ala Tyr
65                  70                  75                  80

Tyr Cys Gln Gln Ser Tyr Thr Thr Pro Leu Thr Phe Gly Gly Gly Thr
                85                  90                  95

Arg Val Glu Ile Lys
            100

<210> SEQ ID NO 129
<211> LENGTH: 108
<212> TYPE: PRT
<213> ORGANISM: Artificial Sequence
<220> FEATURE:
<223> OTHER INFORMATION: D11 light chain

<400> SEQUENCE: 129

Ser Tyr Glu Leu Thr Gln Pro Pro Ser Val Ser Val Ala Pro Gly Lys
1               5                   10                  15

Thr Ala Thr Ile Thr Cys Gly Gly Asp Asn Ile Gly Ser Lys Thr Val
            20                  25                  30

His Trp Tyr Gln Gln Lys Pro Gly Gln Ala Pro Leu Leu Val Ile Tyr
        35                  40                  45

Tyr Asn Gly Asp Arg Pro Pro Gly Ile Pro Glu Arg Phe Ser Gly Ser
    50                  55                  60

Asn Ser Gly Asn Thr Ala Thr Leu Thr Ile Thr Arg Val Glu Ala Gly
65                  70                  75                  80

```
Asp Glu Ala Asp Tyr Cys Cys Gln Ile Trp Asp Ser Arg Ser Ser His
                85                  90                  95

Pro Val Phe Gly Gly Gly Thr Lys Leu Thr Val Leu
            100                 105


<210> SEQ ID NO 130
<211> LENGTH: 112
<212> TYPE: PRT
<213> ORGANISM: Artificial Sequence
<220> FEATURE:
<223> OTHER INFORMATION: B6 light chain

<400> SEQUENCE: 130

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Phe Leu Asp Trp Tyr Val Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Leu His Thr Pro Arg Thr Phe Gly Gln Gly Thr Lys Val Glu Ile Lys
            100                 105                 110


<210> SEQ ID NO 131
<211> LENGTH: 112
<212> TYPE: PRT
<213> ORGANISM: Artificial Sequence
<220> FEATURE:
<223> OTHER INFORMATION: D2 light chain

<400> SEQUENCE: 131

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Phe Leu Asp Trp Tyr Val Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Leu Gln Thr Pro Arg Thr Phe Gly Gln Gly Thr Lys Val Glu Ile Lys
            100                 105                 110


<210> SEQ ID NO 132
<211> LENGTH: 561
<212> TYPE: PRT
<213> ORGANISM: Artificial Sequence
<220> FEATURE:
<223> OTHER INFORMATION: Envelope ectodomain protein sequence DENV1

<400> SEQUENCE: 132

Phe His Leu Thr Thr Arg Gly Gly Glu Pro His Met Ile Val Ser Lys
```

-continued

```
1               5                   10                  15

Gln Glu Arg Gly Lys Ser Leu Leu Phe Lys Thr Ser Ala Gly Val Asn
            20                  25                  30

Met Cys Thr Leu Ile Ala Met Asp Leu Gly Glu Leu Cys Glu Asp Thr
        35                  40                  45

Met Thr Tyr Lys Cys Pro Arg Ile Thr Glu Ala Glu Pro Asp Asp Val
    50                  55                  60

Asp Cys Trp Cys Asn Ala Thr Asp Thr Trp Val Thr Tyr Gly Thr Cys
65                  70                  75                  80

Ser Gln Thr Gly Glu His Arg Arg Asp Lys Arg Ser Val Ala Leu Ala
                85                  90                  95

Pro His Val Gly Leu Gly Leu Glu Thr Arg Thr Glu Thr Trp Met Ser
            100                 105                 110

Ser Glu Gly Ala Trp Lys Gln Ile Gln Lys Val Glu Thr Trp Ala Leu
        115                 120                 125

Arg His Pro Gly Phe Thr Val Ile Ala Leu Phe Leu Ala His Ala Ile
    130                 135                 140

Gly Thr Ser Ile Thr Gln Lys Gly Ile Ile Phe Ile Leu Leu Met Leu
145                 150                 155                 160

Val Thr Pro Ser Met Ala Met Arg Cys Val Gly Ile Gly Asn Arg Asp
                165                 170                 175

Phe Val Glu Gly Leu Ser Gly Ala Thr Trp Val Asp Val Val Leu Glu
            180                 185                 190

His Gly Ser Cys Val Thr Thr Met Ala Lys Asn Lys Pro Thr Leu Asp
        195                 200                 205

Ile Glu Leu Leu Lys Thr Glu Val Thr Asn Pro Ala Val Leu Arg Lys
    210                 215                 220

Leu Cys Ile Glu Ala Lys Ile Ser Asn Thr Thr Thr Asp Ser Arg Cys
225                 230                 235                 240

Pro Thr Gln Gly Glu Ala Thr Leu Val Glu Glu Gln Asp Ala Asn Phe
                245                 250                 255

Val Cys Arg Arg Thr Val Val Asp Arg Gly Trp Gly Asn Gly Cys Gly
            260                 265                 270

Leu Phe Gly Lys Gly Ser Leu Leu Thr Cys Ala Lys Phe Lys Cys Val
        275                 280                 285

Thr Lys Leu Glu Gly Lys Ile Val Gln Tyr Glu Asn Leu Lys Tyr Ser
    290                 295                 300

Val Ile Val Thr Val His Thr Gly Asp Gln His Gln Val Gly Asn Glu
305                 310                 315                 320

Thr Thr Glu His Gly Thr Ile Ala Thr Ile Thr Pro Gln Ala Pro Thr
                325                 330                 335

Ser Glu Ile Gln Leu Thr Asp Tyr Gly Thr Leu Thr Leu Asp Cys Ser
            340                 345                 350

Pro Arg Thr Gly Leu Asp Phe Asn Glu Val Val Leu Leu Thr Met Lys
        355                 360                 365

Glu Lys Ser Trp Leu Val His Lys Gln Trp Phe Leu Asp Leu Pro Leu
    370                 375                 380

Pro Trp Thr Ser Gly Ala Ser Thr Ser Gln Glu Thr Trp Asn Arg Gln
385                 390                 395                 400

Asp Leu Leu Val Thr Phe Lys Thr Ala His Ala Lys Lys Gln Glu Val
                405                 410                 415

Val Val Leu Gly Ser Gln Glu Gly Ala Met His Thr Ala Leu Thr Gly
            420                 425                 430
```

```
Ala Thr Glu Ile Gln Thr Ser Gly Thr Thr Thr Ile Phe Ala Gly His
        435                 440                 445

Leu Lys Cys Arg Leu Lys Met Asp Lys Leu Thr Leu Lys Gly Met Ser
    450                 455                 460

Tyr Val Met Cys Thr Gly Ser Phe Lys Leu Glu Lys Glu Val Ala Glu
465                 470                 475                 480

Thr Gln His Gly Thr Val Leu Val Gln Val Lys Tyr Glu Gly Thr Asp
                485                 490                 495

Ala Pro Cys Lys Ile Pro Phe Ser Thr Gln Asp Glu Lys Gly Val Thr
            500                 505                 510

Gln Asn Gly Arg Leu Ile Thr Ala Asn Pro Ile Val Thr Asp Lys Glu
        515                 520                 525

Lys Pro Ile Asn Ile Glu Thr Glu Pro Pro Phe Gly Glu Ser Tyr Ile
    530                 535                 540

Ile Val Gly Ala Gly Glu Lys Ala Leu Lys Leu Ser Trp Phe Lys Lys
545                 550                 555                 560

Gly


<210> SEQ ID NO 133
<211> LENGTH: 395
<212> TYPE: PRT
<213> ORGANISM: Artificial Sequence
<220> FEATURE:
<223> OTHER INFORMATION: Envelope ectodomain protein sequence DENV2

<400> SEQUENCE: 133

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Ile Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Lys Phe Thr Cys Lys Lys Asn Met Glu Gly Lys
        115                 120                 125

Ile Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Thr Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asp Lys Ala Trp Leu Val
        195                 200                 205

His Arg Gln Trp Phe Leu Asp Leu Pro Leu Pro Trp Leu Pro Gly Ala
    210                 215                 220
```

Asp Thr Gln Gly Ser Asn Trp Ile Gln Lys Glu Thr Leu Val Thr Phe
225 230 235 240

Lys Asn Pro His Ala Lys Lys Gln Asp Val Val Val Leu Gly Ser Gln
245 250 255

Glu Gly Ala Met His Thr Ala Leu Thr Gly Ala Thr Glu Ile Gln Met
260 265 270

Ser Ser Gly Asn Leu Leu Phe Thr Gly His Leu Lys Cys Arg Leu Arg
275 280 285

Met Asp Lys Leu Gln Leu Lys Gly Met Ser Tyr Ser Met Cys Thr Gly
290 295 300

Lys Phe Lys Ile Val Lys Glu Ile Ala Glu Thr Gln His Gly Thr Ile
305 310 315 320

Val Ile Arg Val Gln Tyr Glu Gly Asp Gly Ser Pro Cys Lys Ile Pro
325 330 335

Phe Glu Ile Thr Asp Leu Glu Lys Arg His Val Leu Gly Arg Leu Ile
340 345 350

Thr Val Asn Pro Ile Val Thr Glu Lys Asp Ser Pro Val Asn Ile Glu
355 360 365

Ala Glu Pro Pro Phe Gly Asp Ser Tyr Ile Ile Val Gly Val Glu Pro
370 375 380

Gly Gln Leu Lys Leu Asn Trp Phe Lys Arg Gly
385 390 395

<210> SEQ ID NO 134
<211> LENGTH: 559
<212> TYPE: PRT
<213> ORGANISM: Artificial Sequence
<220> FEATURE:
<223> OTHER INFORMATION: Envelope ectodomain protein sequence DENV3

<400> SEQUENCE: 134

Phe His Leu Thr Ser Arg Asp Gly Glu Pro Arg Met Ile Val Gly Lys
1 5 10 15

Asn Glu Arg Gly Lys Ser Leu Leu Phe Lys Thr Ala Ser Gly Ile Asn
20 25 30

Met Cys Thr Leu Ile Ala Met Asp Leu Gly Glu Met Cys Asp Asp Thr
35 40 45

Val Thr Tyr Lys Cys Pro His Ile Thr Glu Val Glu Pro Glu Asp Ile
50 55 60

Asp Cys Trp Cys Asn Leu Thr Ser Thr Trp Val Thr Tyr Gly Thr Cys
65 70 75 80

Asn Gln Ala Gly Glu His Arg Arg Asp Lys Arg Ser Val Ala Leu Ala
85 90 95

Pro His Val Gly Met Gly Leu Asp Thr Arg Thr Gln Thr Trp Met Ser
100 105 110

Ala Glu Gly Ala Trp Arg Gln Val Glu Lys Val Glu Thr Trp Ala Leu
115 120 125

Arg His Pro Gly Phe Thr Ile Leu Ala Leu Phe Leu Ala His Tyr Ile
130 135 140

Gly Thr Ser Leu Thr Gln Lys Val Val Ile Phe Ile Leu Leu Met Leu
145 150 155 160

Val Thr Pro Ser Met Thr Met Arg Cys Val Gly Val Gly Asn Arg Asp
165 170 175

Phe Val Glu Gly Leu Ser Gly Ala Thr Trp Val Asp Val Val Leu Glu
180 185 190

-continued

His Gly Gly Cys Val Thr Thr Met Ala Lys Asn Lys Pro Thr Leu Asp
195 200 205

Ile Glu Leu Gln Lys Thr Glu Ala Thr Gln Leu Ala Thr Leu Arg Lys
210 215 220

Leu Cys Ile Glu Gly Lys Ile Thr Asn Ile Thr Thr Asp Ser Arg Cys
225 230 235 240

Pro Thr Gln Gly Glu Ala Ile Leu Pro Glu Glu Gln Asp Gln Asn Tyr
245 250 255

Val Cys Lys His Thr Tyr Val Asp Arg Gly Trp Gly Asn Gly Cys Gly
260 265 270

Leu Phe Gly Lys Gly Ser Leu Val Thr Cys Ala Lys Phe Gln Cys Leu
275 280 285

Glu Ser Ile Glu Gly Lys Val Val Gln His Glu Asn Leu Lys Tyr Thr
290 295 300

Val Ile Ile Thr Val His Thr Gly Asp Gln His Gln Val Gly Asn Glu
305 310 315 320

Thr Gln Gly Val Thr Ala Glu Ile Thr Ser Gln Ala Ser Thr Ala Glu
325 330 335

Ala Ile Leu Pro Glu Tyr Gly Thr Leu Gly Leu Glu Cys Ser Pro Arg
340 345 350

Thr Gly Leu Asp Phe Asn Glu Met Ile Leu Leu Thr Met Lys Asn Lys
355 360 365

Ala Trp Met Val His Arg Gln Trp Phe Phe Asp Leu Pro Leu Pro Trp
370 375 380

Thr Ser Gly Ala Thr Thr Lys Thr Pro Thr Trp Asn Arg Lys Glu Leu
385 390 395 400

Leu Val Thr Phe Lys Asn Ala His Ala Lys Lys Gln Glu Val Val Val
405 410 415

Leu Gly Ser Gln Glu Gly Ala Met His Thr Ala Leu Thr Gly Ala Thr
420 425 430

Glu Ile Gln Thr Ser Gly Gly Thr Ser Ile Phe Ala Gly His Leu Lys
435 440 445

Cys Arg Leu Lys Met Asp Lys Leu Lys Leu Lys Gly Met Ser Tyr Ala
450 455 460

Met Cys Leu Asn Thr Phe Val Leu Lys Lys Glu Val Ser Glu Thr Gln
465 470 475 480

His Gly Thr Ile Leu Ile Lys Val Glu Tyr Lys Gly Glu Asp Ala Pro
485 490 495

Cys Lys Ile Pro Phe Ser Thr Glu Asp Gly Gln Gly Lys Ala His Asn
500 505 510

Gly Arg Leu Ile Thr Ala Asn Pro Val Val Thr Lys Lys Glu Glu Pro
515 520 525

Val Asn Ile Glu Ala Glu Pro Pro Phe Gly Glu Ser Asn Ile Val Ile
530 535 540

Gly Ile Gly Asp Lys Ala Leu Lys Ile Asn Trp Tyr Arg Lys Gly
545 550 555

<210> SEQ ID NO 135
<211> LENGTH: 561
<212> TYPE: PRT
<213> ORGANISM: Artificial Sequence
<220> FEATURE:
<223> OTHER INFORMATION: Envelope ectodomain protein sequence DENV4

<400> SEQUENCE: 135

-continued

```
Phe Ser Leu Ser Thr Arg Asp Gly Glu Pro Leu Met Ile Val Ala Lys
1               5                   10                  15

His Glu Arg Gly Arg Pro Leu Leu Phe Lys Thr Thr Glu Gly Ile Asn
            20                  25                  30

Lys Cys Thr Leu Ile Ala Met Asp Leu Gly Glu Met Cys Glu Asp Thr
        35                  40                  45

Val Thr Tyr Lys Cys Pro Leu Leu Val Asn Thr Glu Pro Glu Asp Ile
    50                  55                  60

Asp Cys Trp Cys Asn Leu Thr Ser Thr Trp Val Met Tyr Gly Thr Cys
65                  70                  75                  80

Thr Gln Ser Gly Glu Arg Arg Arg Glu Lys Arg Ser Val Ala Leu Thr
                85                  90                  95

Pro His Ser Gly Met Gly Leu Glu Thr Arg Ala Glu Thr Trp Met Ser
            100                 105                 110

Ser Glu Gly Ala Trp Lys His Ala Gln Arg Val Glu Ser Trp Ile Leu
        115                 120                 125

Arg Asn Pro Gly Phe Ala Leu Leu Ala Gly Phe Met Ala Tyr Met Ile
    130                 135                 140

Gly Gln Thr Gly Ile Gln Arg Thr Val Phe Phe Val Leu Met Met Leu
145                 150                 155                 160

Val Ala Pro Ser Tyr Gly Met Arg Cys Val Gly Val Gly Asn Arg Asp
                165                 170                 175

Phe Val Glu Gly Val Ser Gly Gly Ala Trp Val Asp Leu Val Leu Glu
            180                 185                 190

His Gly Gly Cys Val Thr Thr Met Ala Gln Gly Lys Pro Thr Leu Asp
        195                 200                 205

Phe Glu Leu Thr Lys Thr Thr Ala Lys Glu Val Ala Leu Leu Arg Thr
    210                 215                 220

Tyr Cys Ile Glu Ala Ser Ile Ser Asn Ile Thr Thr Ala Thr Arg Cys
225                 230                 235                 240

Pro Thr Gln Gly Glu Pro Tyr Leu Lys Glu Glu Gln Asp Gln Gln Tyr
                245                 250                 255

Ile Cys Arg Arg Asp Val Val Asp Arg Gly Trp Gly Asn Gly Cys Gly
            260                 265                 270

Leu Phe Gly Lys Gly Gly Val Val Thr Cys Ala Lys Phe Ser Cys Ser
        275                 280                 285

Gly Lys Ile Thr Gly Asn Leu Val Gln Ile Glu Asn Leu Glu Tyr Thr
    290                 295                 300

Val Val Val Thr Val His Asn Gly Asp Thr His Ala Val Gly Asn Asp
305                 310                 315                 320

Thr Ser Asn His Gly Val Thr Ala Met Ile Thr Pro Arg Ser Pro Ser
                325                 330                 335

Val Glu Val Lys Leu Pro Asp Tyr Gly Glu Leu Thr Leu Asp Cys Glu
            340                 345                 350

Pro Arg Ser Gly Ile Asp Phe Asn Glu Met Ile Leu Met Lys Met Lys
        355                 360                 365

Lys Lys Thr Trp Leu Val His Lys Gln Trp Phe Leu Asp Leu Pro Leu
    370                 375                 380

Pro Trp Thr Ala Gly Ala Asp Thr Ser Glu Val His Trp Asn Tyr Lys
385                 390                 395                 400

Glu Arg Met Val Thr Phe Lys Val Pro His Ala Lys Arg Gln Asp Val
                405                 410                 415

Thr Val Leu Gly Ser Gln Glu Gly Ala Met His Ser Ala Leu Ala Gly
```

```
            420                 425                 430

Ala Thr Glu Val Asp Ser Gly Asp Gly Asn His Met Phe Ala Gly His
        435                 440                 445

Leu Lys Cys Lys Val Arg Met Glu Lys Leu Arg Ile Lys Gly Met Ser
    450                 455                 460

Tyr Thr Met Cys Ser Gly Lys Phe Ser Ile Asp Lys Glu Met Ala Glu
465                 470                 475                 480

Thr Gln His Gly Thr Thr Val Val Lys Val Lys Tyr Glu Gly Ala Gly
                485                 490                 495

Ala Pro Cys Lys Val Pro Ile Glu Ile Arg Asp Val Asn Lys Glu Lys
            500                 505                 510

Val Val Gly Arg Ile Ile Ser Ser Thr Pro Leu Ala Glu Asn Thr Asn
        515                 520                 525

Ser Val Thr Asn Ile Glu Leu Glu Pro Pro Phe Gly Asp Ser Tyr Ile
    530                 535                 540

Val Ile Gly Val Gly Asn Ser Ala Leu Thr Leu His Trp Phe Arg Lys
545                 550                 555                 560

Gly


<210> SEQ ID NO 136
<211> LENGTH: 1683
<212> TYPE: DNA
<213> ORGANISM: Artificial Sequence
<220> FEATURE:
<223> OTHER INFORMATION: Envelope ectodomain nucleotide sequence DENV1

<400> SEQUENCE: 136

ttccatttga ccacacgagg gggagagcca cacatgatag ttagtaagca ggaaagagga     60

aagtcactct tgttcaagac ctctgcaggt gtcaatatgt gcactctcat tgcgatggat    120

ttgggagagt tatgtgagga cacaatgact tacaaatgcc cccggatcac tgaggcggaa    180

ccagatgacg ttgactgctg gtgcaatgcc acagacacat gggtgaccta tgggacgtgt    240

tctcaaaccg gtgaacaccg acgagacaaa cgttccgtgg cactggcccc acacgtggga    300

cttggtctag aaacaagaac cgaaacatgg atgtcctctg aaggcgcctg gaaacaaata    360

caaaaagtgg agacttgggc tttgagacac ccaggattca cggtgatagc tcttttttta    420

gcacatgcca taggaacatc catcactcag aaagggatca ttttcattct gctgatgctg    480

gtaacaccat caatggccat gcgatgcgtg ggaataggca acagagactt cgttgaagga    540

ctgtcaggag caacgtgggt ggacgtggta ttggagcatg gaagctgcgt caccaccatg    600

gcaaaaaata aaccaacatt ggacattgaa ctcttgaaga cggaggtcac gaaccctgcc    660

gtcttgcgca aattgtgcat tgaagctaaa atatcaaaca ccaccaccga ttcaagatgt    720

ccaacacaag gagaggctac actggtggaa gaacaagacg cgaactttgt gtgtcgacga    780

acggttgtgg acagaggctg gggcaatggc tgcggactat ttggaaaagg aagcctactg    840

acgtgtgcta agttcaagtg tgtgacaaaa ctggaaggaa agatagttca atatgaaaac    900

ttaaaatatt cagtgatagt cactgtccac acaggggacc agcaccaggt gggaaacgag    960

actacagaac atggaacaat tgcaaccata acacctcaag ctcctacgtc ggaaatacag   1020

ttgacagact acggaaccct tacactggac tgctcaccca gaacagggct ggactttaat   1080

gaggtggtgc tattgacaat gaaagaaaaa tcatggcttg tccacaaaca atggtttcta   1140

gacttaccac tgccttggac ttcgggggct tcaacatccc aagagacttg gaacagacaa   1200

gatttgctgg tcacattcaa gacagctcat gcaaagaagc aggaagtagt cgtactggga   1260
```

tcacaggaag gagcaatgca cactgcgttg accggggcga cagaaatcca gacgtcagga 1320
acgacaacaa tctttgcagg acacctgaaa tgcagattaa aaatggataa actgacttta 1380
aaagggatgt catatgtgat gtgcacaggc tcatttaagc tagagaagga agtggctgag 1440
acccagcatg gaactgtcct agtgcaggtt aaatacgaag gaacagatgc gccatgcaag 1500
atcccctttt cgacccaaga tgagaaagga gtgacccaga atgggagatt gataacagcc 1560
aatcccatag ttactgacaa agaaaaacca atcaacattg agacagaacc accttttggt 1620
gagagctaca tcatagtagg ggcaggtgaa aaagctttga aactaagctg gttcaagaaa 1680
gga 1683

<210> SEQ ID NO 137
<211> LENGTH: 1683
<212> TYPE: DNA
<213> ORGANISM: Artificial Sequence
<220> FEATURE:
<223> OTHER INFORMATION: Envelope ectodomain nucleotide sequence DENV2

<400> SEQUENCE: 137
ttccatttaa ccacacgtaa cggagaacca cacatgatcg tcagtagaca agagaaaggg 60
aaaagtcttc tgtttaaaac agaggatggt gtgaacatgt gtaccctcat ggccatggac 120
cttggtgaat tgtgtgaaga tacaatcacg tacaagtgtc cttttctcag gcagaatgaa 180
ccagaagaca tagattgttg gtgcaactct acgtccacat gggtaactta tgggacgtgt 240
accaccacag gagaacacag aagagaaaaa agatcagtgg cactcgttcc acatgtggga 300
atgggactgg agacacgaac tgaaacatgg atgtcatcag aaggggcctg gaaacatgcc 360
cagagaattg aaacttggat cttgagacat ccaggcttta ccataatggc agcaatcctg 420
gcatacacca taggaacgac acatttccaa agagccctga ttttcatctt actgacagct 480
gtcgctcctt caatgacaat gcgttgcata ggaatatcaa atagagactt tgtagaaggg 540
gtttcaggag gaagctgggt tgacatagtc ttagaacatg gaagctgtgt gacgacgatg 600
gcaaaaaaca aaccaacatt ggattttgaa ctgataaaaa cagaagccaa acaacctgcc 660
actctaagga agtactgtat agaggcaaag ctgaccaaca caacaacaga ttctcgctgc 720
ccaacacaag gagaacccag cctaaatgaa gagcaggaca aaaggttcgt ctgcaaacac 780
tccatggtgg acagaggatg gggaaatgga tgtggattat ttggaaaagg aggcattgtg 840
acctgtgcta tgttcacatg caaaaagaac atgaaaggaa aagtcgtgca accagaaaac 900
ttggaataca ccattgtgat aacacctcac tcaggggaag agcatgcagt cggaaatgac 960
acaggaaaac atggcaagga aatcaaaata acaccacaga gttccatcac agaagcagag 1020
ttgacaggct atggcactgt cacgatggag tgctctccga gaacgggcct cgacttcaat 1080
gagatggtgt tgctgcaaat ggaaaataaa gcttggctgg tgcacaggca atggttccta 1140
gacctgccgt tgccatggct gcccggagcg gacacacaag gatcaaattg gatacagaaa 1200
gagacattgg tgactttcaa aaatccccat gcgaagaaac aggatgttgt tgttttggga 1260
tcccaagaag ggccatgca cacagcactc acaggggcca cagaaatcca gatgtcatca 1320
ggaaacttac tgttcacagg acatctcaag tgcaggctga ggatggacaa actacagctc 1380
aaaggaatgt catactctat gtgcacagga aagtttaaag ttgtgaagga aatagcagaa 1440
acacaacatg gaacaatagt tatcagagta caatatgaag gggacggttc tccatgtaag 1500
atcccttttg agataatgga tttggaaaaa agacatgttt taggtcgcct gattacagtc 1560
aacccaatcg taacagaaaa agatagccca gtcaacatag aagcagaacc tccattcgga 1620
gacagctaca tcatcatagg agtagagccg ggacaattga agctcaactg gtttaagaaa 1680
gga 1683

<210> SEQ ID NO 138
<211> LENGTH: 1678
<212> TYPE: DNA
<213> ORGANISM: Artificial Sequence
<220> FEATURE:
<223> OTHER INFORMATION: Envelope ectodomain nucleotide sequence DENV3

<400> SEQUENCE: 138
ttccacttaa cttcacgaga tggagagccg cgcatgattg tggggaagaa tgaaagagga 60
aaatccctac tttttaagac agcctctgga atcaacatgt gcacactcat agccatggat 120
ttgggagaga tgtgtgatga cacggtcact tacaaatgcc cccacattac cgaagtggag 180
cctgaagaca ttgactgttg gtgcaacctt acatcgacat gggtgactta tggaacatgc 240
aatcaagctg gagagcatag acgcgataag agatcagtgg cgttagctcc ccatgtcggc 300
atgggactgg acacacgcac tcaaacctgg atgtcggctg aaggagcttg gagacaagtc 360
gagaaggtag agacatgggc ccttaggcac ccagggttta ccatactagc cctatttctt 420
gcccattaca taggcacttc cttgacccag aaagtggtta tttttatact attaatgctg 480
gttaccccat ccatgacaat gagatgtgtg ggagtaggaa acagagattt tgtggaaggc 540
ctatcgggag ctacgtgggt tgacgtggtg ctcgagcacg gtgggtgtgt gactaccatg 600
gctaagaaca agcccacgct ggacatagag cttcagaaga ctgaggccac tcagctggcg 660
accctaagga agctatgcat tgagggaaaa attaccaaca taacaaccga ctcaagatgt 720
cccacccaag gggaagcgat ttacctgag gagcaggacc agaactacgt gtgtaagcat 780
acatacgtgg acagaggctg ggaaacggt tgtggtttgt ttggcaaggg aagcttggtg 840
acatgcgcga aatttcaatg tttagaatca atagagggaa aagtggtgca acatgagaac 900
ctcaaataca ccgtcatcat cacagtgcac acaggagacc aacaccaggt gggaaatgaa 960
acgcagggag ttacggctga gataacatcc caggcatcaa ccgctgaagc cattttacct 1020
gaatatggaa ccctcgggct agaatgctca ccacggacag gtttggattt caatgaaatg 1080
attttattga caatgaagaa caaagcatgg atggtacata gacaatggtt ctttgactta 1140
cccctaccat ggacatcagg agctacaaca aaaacaccaa cttggaacag gaaagagctt 1200
cttgtgacat ttaaaaatgc acatgcaaaa aagcaagaag tagttgtcct tggatcacaa 1260
gagggagcaa tgcatacagc actgacagga gctacagaga tccaaacctc aggaggcaca 1320
agtatttttg cggggcactt aaaatgtaga ctcaagatgg acaaattgaa actcaagggg 1380
atgagctatg caatgtgctt gaataccttt gtgttgaaga aagaagtctc cgaaacgcag 1440
catgggacaa tactcattaa ggttgagtac aaaggggaag atgcaccctg caagattcct 1500
ttctccacgg aggatggaca agggaaagct cacaatggca gactgatcac agccaatcca 1560
gtggtgacca agaaggagga gcctgtcaac attgaggctg aacctccttt tggggaaagt 1620
aatatagtaa ttggaattgg agacaaagcc ctgaaaatca actggtacag gaagggaa 1678

<210> SEQ ID NO 139
<211> LENGTH: 1683
<212> TYPE: DNA
<213> ORGANISM: Artificial Sequence
<220> FEATURE:
<223> OTHER INFORMATION: Envelope ectodomain nucleotide sequence DENV4

<400> SEQUENCE: 139
ttttccctca gcacaagaga tggcgaaccc ctcatgatag tggcaaaaca tgaaaggggg 60
agacctctct tgtttaagac aacagagggg atcaacaaat gcactctcat tgccatggac 120
ttgggtgaaa tgtgtgagga cactgtcacg tataaatgcc ccctactggt caataccgaa 180
cctgaagaca ttgattgctg gtgcaacctc acgtctacct gggtcatgta tgggacatgc 240
acccagagcg gagaacggag acgagagaag cgctcagtag ctttaacacc acattcagga 300
atgggattgg aaacaagagc tgagacatgg atgtcatcgg aaggggcttg gaagcatgct 360
cagagagtag agagctggat actcagaaac ccaggattcg cgctcttggc aggatttatg 420
gcttatatga ttgggcaaac aggaatccag cgaactgtct tctttgtcct aatgatgctg 480
gtcgccccat cctacggaat gcgatgcgta ggagtaggaa acagagactt tgtggaagga 540
gtctcaggtg gagcatgggt cgacctggtg ctagaacatg gaggatgcgt cacaaccatg 600
gcccagggaa aaccaacctt ggattttgaa ctgactaaga caacagccaa ggaagtggct 660
ctgttaagaa cctattgcat tgaagcctca atatcaaaca taactacggc aacaagatgt 720
ccaacgcaag gagagcctta tctgaaagag gaacaggacc aacagtacat ttgccggaga 780
gatgtggtag acagagggtg gggcaatggc tgtggcttgt ttggaaaagg aggagttgtg 840
acatgtgcga agttttcatg ttcggggaag ataacaggca atttggtcca aattgagaac 900
cttgaataca cagtggttgt aacagtccac aatggagaca cccatgcagt aggaaatgac 960
acatccaatc atggagttac agccatgata actcccaggt caccatcggt ggaagtcaaa 1020
ttgccggact atggagaact aacactcgat tgtgaaccca ggtctggaat tgactttaat 1080
gagatgattc tgatgaaaat gaaaaagaaa acatggctcg tgcataagca atggtttttg 1140
gatctgcctc ttccatggac agcaggagca gacacatcag aggttcactg gaattacaaa 1200
gagagaatgg tgacatttaa ggttcctcat gccaagagac aggatgtgac agtgctggga 1260
tctcaggaag gagccatgca ttctgccctc gctggagcca cagaagtgga ctccggtgat 1320
ggaaatcaca tgtttgcagg acatcttaag tgcaaagtcc gtatggagaa attgagaatc 1380
aagggaatgt catacacgat gtgttcagga aagttttcaa ttgacaaaga gatggcagaa 1440
acacagcatg ggacaacagt ggtgaaagtc aagtatgaag gtgctggagc tccgtgtaaa 1500
gtccccatag agataagaga tgtaaacaag gaaaaagtgg ttgggcgtat catctcatcc 1560
accccctttgg ctgagaatac caacagtgta accaacatag aattagaacc cccctttggg 1620
gacagctaca tagtgatagg tgttggaaac agcgcattaa cactccattg gttcaggaaa 1680
ggg 1683

<210> SEQ ID NO 140
<211> LENGTH: 110
<212> TYPE: PRT
<213> ORGANISM: Artificial Sequence
<220> FEATURE:
<223> OTHER INFORMATION: A11 light chain

<400> SEQUENCE: 140

Gln Ser Val Leu Thr Gln Pro Val Ser Val Ser Gly Ser Pro Gly Gln
1               5                   10                  15

Ser Ile Thr Ile Ser Cys Thr Gly Thr Ser Ser Asn Ala Asp Thr Tyr
            20                  25                  30

Asn Leu Val Ser Trp Tyr Gln Gln Arg Pro Gly Lys Ala Pro Lys Leu
        35                  40                  45

```
Met Ile Tyr Glu Gly Thr Lys Arg Pro Ser Gly Val Ser Asn Arg Phe
    50                  55                  60

Ser Ala Ser Lys Ser Ala Thr Ala Ala Ser Leu Thr Ile Ser Gly Leu
65                  70                  75                  80

Gln Pro Glu Asp Glu Ala Asp Tyr Tyr Cys Cys Ser Tyr Ala Thr Ser
                85                  90                  95

Arg Thr Leu Val Phe Gly Gly Gly Thr Lys Leu Thr Val Val
            100                 105                 110
```

<210> SEQ ID NO 141
<211> LENGTH: 218
<212> TYPE: PRT
<213> ORGANISM: Artificial Sequence
<220> FEATURE:
<223> OTHER INFORMATION: B7 light chain

<400> SEQUENCE: 141

```
Arg Ser Gln Ser Ala Leu Thr Gln Pro Ala Ser Val Ser Gly Ser Pro
1               5                   10                  15

Gly Gln Ser Ile Thr Ile Ser Cys Thr Gly Ile Ser Ser Asp Val Glu
            20                  25                  30

Thr Tyr Asn Leu Val Ser Trp Tyr Glu Gln His Pro Gly Lys Ala Pro
        35                  40                  45

Lys Leu Ile Ile Tyr Glu Ala Ser Lys Arg Pro Ser Gly Val Ser Asn
    50                  55                  60

Arg Phe Ser Gly Ser Lys Ser Gly Asn Thr Ala Ser Leu Ala Ile Ser
65                  70                  75                  80

Gly Leu Gln Ala Glu Asp Glu Ala Asp Tyr Tyr Cys Cys Ser Tyr Ala
                85                  90                  95

Gly Gly Lys Ser Leu Val Phe Gly Gly Gly Thr Arg Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 142
<211> LENGTH: 131
<212> TYPE: PRT
<213> ORGANISM: Artificial Sequence
<220> FEATURE:
<223> OTHER INFORMATION: Variable heavy chain of A11

<400> SEQUENCE: 142

```
Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Ser Tyr Ser Asn His
```

```
            20                  25                  30

Trp Met His Trp Val Arg Gln Ala Pro Gly Lys Gly Leu Val Trp Val
        35                  40                  45

Ser Arg Ile Asn Ser Asp Gly Ser Thr Arg Asn Tyr Ala Asp Phe Val
    50                  55                  60

Lys Gly Arg Phe Thr Ile Ser Arg Asp Asn Ala Glu Asn Thr Leu Tyr
65                  70                  75                  80

Leu Glu Met Asn Ser Leu Thr Ala Asp Asp Thr Ala Val Tyr Tyr Cys
                85                  90                  95

Val Arg Asp Gly Val Arg Phe Tyr Tyr Asp Ser Thr Gly Tyr Tyr Pro
            100                 105                 110

Asp Ser Phe Phe Lys Tyr Gly Met Asp Val Trp Gly Gln Gly Thr Thr
        115                 120                 125

Val Thr Val
    130


<210> SEQ ID NO 143
<211> LENGTH: 131
<212> TYPE: PRT
<213> ORGANISM: Artificial Sequence
<220> FEATURE:
<223> OTHER INFORMATION: Variable heavy chain of B7

<400> SEQUENCE: 143

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser His
            20                  25                  30

Trp Met His Trp Val Arg Gln Ala Pro Gly Lys Gly Leu Val Trp Val
        35                  40                  45

Ser Arg Thr Asn Ser Asp Gly Ser Ser Thr Ser Tyr Ala Asp Ser Val
    50                  55                  60

Lys Gly Arg Phe Met Ile Ser Arg Asp Asn Ser Lys Asn Thr Val Tyr
65                  70                  75                  80

Leu His Met Asn Gly Leu Arg Ala Glu Asp Thr Ala Val Tyr Phe Cys
                85                  90                  95

Ala Arg Asp Gly Val Arg Tyr Tyr Tyr Asp Ser Thr Gly Tyr Tyr Pro
            100                 105                 110

Asp Asn Phe Phe Gln Tyr Gly Leu Asp Val Trp Gly Gln Gly Thr Thr
        115                 120                 125

Val Thr Val
    130


<210> SEQ ID NO 144
<211> LENGTH: 120
<212> TYPE: PRT
<213> ORGANISM: Artificial Sequence
<220> FEATURE:
<223> OTHER INFORMATION: Variable heavy chain of C8

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45
```

```
Ser Ala Ile Thr Gly Glu Gly Asp Ser Ala Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Phe Glu Met Asn Ser Leu Arg Pro Glu Asp Thr Ala Val Tyr Tyr Cys
                85                  90                  95

Val Gly Gly Tyr Ser Asn Phe Tyr Tyr Tyr Tyr Thr Met Asp Val Trp
            100                 105                 110

Gly Gln Gly Thr Thr Val Thr Val
        115                 120


<210> SEQ ID NO 145
<211> LENGTH: 108
<212> TYPE: PRT
<213> ORGANISM: Artificial Sequence
<220> FEATURE:
<223> OTHER INFORMATION: Variable light chain of C8

<400> SEQUENCE: 145

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Phe
            20                  25                  30

Leu Ala Trp Tyr Gln His Lys Pro Gly Gln Ala Pro Arg Leu Leu Ile
        35                  40                  45

Tyr Asp Ala Ser Thr Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln Gln Arg Tyr Asn Trp Pro Pro
                85                  90                  95

Tyr Thr Phe Gly Gln Gly Thr Lys Val Glu Ile Lys
            100                 105


<210> SEQ ID NO 146
<211> LENGTH: 126
<212> TYPE: PRT
<213> ORGANISM: Artificial Sequence
<220> FEATURE:
<223> OTHER INFORMATION: Variable heavy chain of C10

<400> SEQUENCE: 146

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Lys Val Asp Asp Tyr Gly Asp Tyr Trp Phe Pro Thr Leu
            100                 105                 110

Trp Tyr Phe Asp Tyr Trp Gly Gln Gly Thr Leu Val Thr Val
        115                 120                 125
```

<210> SEQ ID NO 147
<211> LENGTH: 110
<212> TYPE: PRT
<213> ORGANISM: Artificial Sequence
<220> FEATURE:
<223> OTHER INFORMATION: Variable light chain of C10

<400> SEQUENCE: 147

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Phe
            20                  25                  30

Asn Tyr Val Ser Trp Phe Gln Gln His Pro Gly Lys Ala Pro Lys Leu
        35                  40                  45

Met Leu Tyr Asp Val Thr Ser Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser His Thr Ser Arg
                85                  90                  95

Gly Thr Trp Val Phe Gly Gly Gly Thr Lys Leu Thr Val Leu
            100                 105                 110
```

<210> SEQ ID NO 148
<211> LENGTH: 12
<212> TYPE: PRT
<213> ORGANISM: Artificial Sequence
<220> FEATURE:
<223> OTHER INFORMATION: 150 loop of Denv-1

<400> SEQUENCE: 148

```
Gln His Gln Val Gly Asn Glu Thr Thr Glu His Gly
1               5                   10
```

<210> SEQ ID NO 149
<211> LENGTH: 12
<212> TYPE: PRT
<213> ORGANISM: Artificial Sequence
<220> FEATURE:
<223> OTHER INFORMATION: 150 loop of Denv-2

<400> SEQUENCE: 149

```
Glu His Ala Val Gly Asn Asp Thr Gly Lys His Gly
1               5                   10
```

<210> SEQ ID NO 150
<211> LENGTH: 10
<212> TYPE: PRT
<213> ORGANISM: Artificial Sequence
<220> FEATURE:
<223> OTHER INFORMATION: 150 loop of Denv-3

<400> SEQUENCE: 150

```
Gln His Gln Val Gly Asn Glu Thr Gln Gly
1               5                   10
```

<210> SEQ ID NO 151
<211> LENGTH: 12
<212> TYPE: PRT
<213> ORGANISM: Artificial Sequence
<220> FEATURE:
<223> OTHER INFORMATION: 150 loop of Denv-4

<400> SEQUENCE: 151

Thr His Ala Val Gly Asn Asp Ile Pro Asn His Gly
1               5                   10

<210> SEQ ID NO 152
<211> LENGTH: 122
<212> TYPE: PRT
<213> ORGANISM: Artificial Sequence
<220> FEATURE:
<223> OTHER INFORMATION: C8 heavy chain

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Gly Glu Gly Asp Ser Ala Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Phe Glu Met Asn Ser Leu Arg Pro Glu Asp Thr Ala Val Tyr Tyr Cys
                85                  90                  95

Val Gly Gly Tyr Ser Asn Phe Tyr Tyr Tyr Tyr Thr Met Asp Val Trp
            100                 105                 110

Gly Gln Gly Thr Thr Val Thr Val Ser Ser
        115                 120

<210> SEQ ID NO 153
<211> LENGTH: 128
<212> TYPE: PRT
<213> ORGANISM: Artificial Sequence
<220> FEATURE:
<223> OTHER INFORMATION: C10 heavy chain

<400> SEQUENCE: 153

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Lys Val Asp Asp Tyr Gly Asp Tyr Trp Phe Pro Thr Leu
            100                 105                 110

Trp Tyr Phe Asp Tyr Trp Gly Gln Gly Thr Leu Val Thr Val Ser Ser
        115                 120                 125

<210> SEQ ID NO 154
<211> LENGTH: 133
<212> TYPE: PRT
<213> ORGANISM: Artificial Sequence
<220> FEATURE:

<223> OTHER INFORMATION: A11 heavy chain

<400> SEQUENCE: 154

Glu Val Gln Leu Val Glu Ser Gly Gly Gly Leu Val Arg Pro Gly Gly
1 5 10 15

Ser Leu Arg Leu Ser Cys Ala Ala Ser Gly Phe Ser Tyr Ser Asn His
20 25 30

Trp Met His Trp Val Arg Gln Ala Pro Gly Lys Gly Leu Val Trp Val
35 40 45

Ser Arg Ile Asn Ser Asp Gly Ser Thr Arg Asn Tyr Ala Asp Phe Val
50 55 60

Lys Gly Arg Phe Thr Ile Ser Arg Asp Asn Ala Glu Asn Thr Leu Tyr
65 70 75 80

Leu Glu Met Asn Ser Leu Thr Ala Asp Asp Thr Ala Val Tyr Tyr Cys
85 90 95

Val Arg Asp Gly Val Arg Phe Tyr Tyr Asp Ser Thr Gly Tyr Tyr Pro
100 105 110

Asp Ser Phe Phe Lys Tyr Gly Met Asp Val Trp Gly Gln Gly Thr Thr
115 120 125

Val Thr Val Ser Ser
130

<210> SEQ ID NO 155
<211> LENGTH: 133
<212> TYPE: PRT
<213> ORGANISM: Artificial Sequence
<220> FEATURE:
<223> OTHER INFORMATION: B7 heavy chain

<400> SEQUENCE: 155

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Ser Ser His
20 25 30

Trp Met His Trp Val Arg Gln Ala Pro Gly Lys Gly Leu Val Trp Val
35 40 45

Ser Arg Thr Asn Ser Asp Gly Ser Ser Thr Ser Tyr Ala Asp Ser Val
50 55 60

Lys Gly Arg Phe Met Ile Ser Arg Asp Asn Ser Lys Asn Thr Val Tyr
65 70 75 80

Leu His Met Asn Gly Leu Arg Ala Glu Asp Thr Ala Val Tyr Phe Cys
85 90 95

Ala Arg Asp Gly Val Arg Tyr Tyr Tyr Asp Ser Thr Gly Tyr Tyr Pro
100 105 110

Asp Asn Phe Phe Gln Tyr Gly Leu Asp Val Trp Gly Gln Gly Thr Thr
115 120 125

Val Thr Val Ser Ser
130

<210> SEQ ID NO 156
<211> LENGTH: 129
<212> TYPE: PRT
<213> ORGANISM: Artificial Sequence
<220> FEATURE:
<223> OTHER INFORMATION: B7 light chain

<400> SEQUENCE: 156

Gln Val Gln Leu Gln Glu Ser Gly Pro Gly Leu Met Lys Pro Ser Glu

-continued

```
1               5                   10                  15

Thr Leu Ser Leu Thr Cys Ser Val Ser Gly Val Ser Ile Ser Thr His
            20                  25                  30

Tyr Trp Ser Trp Ile Arg Gln Pro Pro Gly Lys Gly Leu Glu Trp Ile
        35                  40                  45

Gly Phe Ile Tyr Asn Ser Gly Gly Thr His Tyr Asn Pro Ser Leu Lys
    50                  55                  60

Ser Arg Val Thr Ile Ser Ala Asp Thr Ser Lys Asn Gln Phe Ala Leu
65                  70                  75                  80

Thr Leu Ser Ser Val Thr Ala Ala Asp Thr Ala Val Tyr Tyr Cys Ala
                85                  90                  95

Arg Gly Arg Arg Ala Tyr Asp Ser Ser Gly Tyr Val Lys Tyr Tyr Tyr
            100                 105                 110

Phe Tyr Gly Val Asp Val Trp Gly Gln Gly Thr Thr Val Thr Val Ser
        115                 120                 125

Ser


<210> SEQ ID NO 157
<211> LENGTH: 395
<212> TYPE: PRT
<213> ORGANISM: Dengue virus
<220> FEATURE:
<223> OTHER INFORMATION: DENV1 envelope ectodomain Figure 15A

<400> SEQUENCE: 157

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asn Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Val
                85                  90                  95

Val Asp Arg Gly Trp Gly Asn Gly Cys Gly Leu Phe Gly Lys Gly Ser
            100                 105                 110

Leu Leu Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Thr Leu Thr Leu Asp Cys Ser Pro Arg Thr Gly Leu Asp
            180                 185                 190

Phe Asn Glu Val Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240
```

```
Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
            340                 345                 350

Thr Ala Asn Pro Ile Val Thr Asp Lys Glu Lys Pro Ile Asn Ile Glu
        355                 360                 365

Thr Glu Pro Pro Phe Gly Glu Ser Tyr Ile Ile Val Gly Ala Gly Glu
    370                 375                 380

Lys Ala Leu Lys Leu Ser Trp Phe Lys Lys Gly
385                 390                 395


<210> SEQ ID NO 158
<211> LENGTH: 395
<212> TYPE: PRT
<213> ORGANISM: Dengue virus
<220> FEATURE:
<223> OTHER INFORMATION: DENV2 envelope ectodomain Figure 15A

<400> SEQUENCE: 158

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Ile Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Lys Phe Thr Cys Lys Lys Asn Met Glu Gly Lys
        115                 120                 125

Ile Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Thr Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asp Lys Ala Trp Leu Val
        195                 200                 205
```

```
His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Thr Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Val Gly Val Glu Pro
    370                 375                 380

Gly Gln Leu Lys Leu Asn Trp Phe Lys Arg Gly
385                 390                 395


<210> SEQ ID NO 159
<211> LENGTH: 393
<212> TYPE: PRT
<213> ORGANISM: Dengue virus
<220> FEATURE:
<223> OTHER INFORMATION: DENV3 envelope ectodomain Figure 15A

<400> SEQUENCE: 159

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Ile Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Ser Ile Glu Gly Lys
        115                 120                 125

Val Val Gln His Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Ser Gln Ala Ser Thr Ala Glu Ala Ile Leu Pro Glu Tyr
                165                 170                 175
```

```
Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Lys Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Thr Ser Gly
            260                 265                 270

Gly Thr Ser Ile Phe Ala Gly His Leu Lys Cys Arg Leu Lys Met Asp
        275                 280                 285

Lys Leu Lys Leu Lys Gly Met Ser Tyr Ala Met Cys Leu Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Lys Ala
    370                 375                 380

Leu Lys Ile Asn Trp Tyr Arg Lys Gly
385                 390
```

<210> SEQ ID NO 160
<211> LENGTH: 395
<212> TYPE: PRT
<213> ORGANISM: Dengue virus
<220> FEATURE:
<223> OTHER INFORMATION: DENV4 envelope ectodomain Figure 15A

<400> SEQUENCE: 160

```
Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Val Thr Val His
    130                 135                 140
```

-continued

```
Asn Gly Asp Thr His Ala Val Gly Asn Asp Thr Ser Asn His Gly Val
145                 150                 155                 160

Thr Ala Met Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Leu Ala Glu Asn Thr Asn Ser Val Thr Asn Ile Glu
        355                 360                 365

Leu Glu Pro Pro Phe Gly Asp Ser Tyr Ile Val Ile Gly Val Gly Asn
    370                 375                 380

Ser Ala Leu Thr Leu His Trp Phe Arg Lys Gly
385                 390                 395
```